US010961537B2

(12) United States Patent
Ahlers et al.

(10) Patent No.: US 10,961,537 B2
(45) Date of Patent: Mar. 30, 2021

(54) COMPOSITIONS AND METHODS FOR TREATING BETA-HEMOGLOBINOPATHIES

(71) Applicants: CSL Behring Gene Therapy, Inc., Pasadena, CA (US); CSL Gene Therapy, Pty Ltd, Parkville (AU)

(72) Inventors: Jeffrey Ahlers, Winterville, NC (US); Jeffrey Bartlett, Columbus, OH (US); Chi-Lin Lee, Arcadia, CA (US); Gene-Errol Eugenio Ringpis, West Hollywood, CA (US); Geoffrey Phillip Symonds, Rose Bay (AU); Ming Yan, Encino, CA (US)

(73) Assignees: CSL Behring Gene Therapy, Inc., Pasadena, CA (US); CSL Gene Therapy Pty Ltd, Parkville (AU)

( * ) Notice: Subject to any disclaimer, the term of this patent is extended or adjusted under 35 U.S.C. 154(b) by 0 days.

(21) Appl. No.: 16/037,726

(22) Filed: Jul. 17, 2018

(65) Prior Publication Data

US 2019/0100759 A1    Apr. 4, 2019
US 2019/0256855 A9    Aug. 22, 2019

Related U.S. Application Data

(60) Provisional application No. 62/533,719, filed on Jul. 18, 2017, provisional application No. 62/541,931, filed on Aug. 7, 2017, provisional application No. 62/653,913, filed on Apr. 6, 2018.

(51) Int. Cl.
| | |
|---|---|
| *C12N 15/113* | (2010.01) |
| *A61K 35/28* | (2015.01) |
| *C07K 14/805* | (2006.01) |
| *C12N 15/86* | (2006.01) |
| *C12N 9/10* | (2006.01) |
| *A61P 7/00* | (2006.01) |

(52) U.S. Cl.
CPC .......... *C12N 15/1137* (2013.01); *A61K 35/28* (2013.01); *A61P 7/00* (2018.01); *C07K 14/805* (2013.01); *C12N 9/1077* (2013.01); *C12N 15/86* (2013.01); *C12Y 204/02008* (2013.01); *C12N 2310/122* (2013.01); *C12N 2310/14* (2013.01); *C12N 2310/20* (2017.05); *C12N 2310/531* (2013.01); *C12N 2330/51* (2013.01); *C12N 2740/15043* (2013.01); *C12N 2740/16043* (2013.01); *C12N 2830/008* (2013.01)

(58) Field of Classification Search
None
See application file for complete search history.

(56) References Cited

U.S. PATENT DOCUMENTS

| | | |
|---|---|---|
| 9,439,928 B2 | 9/2016 | Kasahara et al. |
| 10,138,495 B2 | 11/2018 | Lee et al. |
| 2003/0022303 A1 | 1/2003 | Sadelain |
| 2003/0059944 A1 | 3/2003 | Lois-Caballe |
| 2005/0255487 A1 | 11/2005 | Khvorova et al. |
| 2008/0120733 A1 | 5/2008 | Hafner et al. |
| 2011/0294114 A1 | 12/2011 | Van Der Loo et al. |
| 2012/0201794 A1 | 8/2012 | Chen et al. |
| 2013/0122591 A1 | 5/2013 | Cost et al. |
| 2013/0137104 A1 | 5/2013 | Cost et al. |
| 2014/0154225 A1 | 6/2014 | Kasahara et al. |
| 2015/0152435 A1 | 6/2015 | Lois-Caballe et al. |
| 2017/0145077 A1 | 5/2017 | Malik |
| 2017/0296630 A1 | 10/2017 | Uchida et al. |
| 2018/0008725 A1 | 1/2018 | Rivella et al. |
| 2018/0112233 A1 | 4/2018 | Lee et al. |
| 2018/0271895 A1 | 9/2018 | Iba et al. |

FOREIGN PATENT DOCUMENTS

| | | |
|---|---|---|
| EP | 1607482 A1 | 12/2005 |
| JP | WO2017057312 A1 | 7/2018 |
| WO | 2003022052 A1 | 3/2003 |
| WO | 2003002155 B1 | 5/2004 |
| WO | 2011008348 A2 | 1/2011 |
| WO | 2012145723 A1 | 10/2012 |
| WO | 2013063315 A2 | 5/2013 |
| WO | 2014036219 A2 | 3/2014 |
| WO | 2015117027 A1 | 8/2015 |
| WO | 2016039933 A1 | 3/2016 |
| WO | 2016118715 A1 | 7/2016 |
| WO | 2016183260 A1 | 11/2016 |
| WO | 2017057312 A1 | 4/2017 |
| WO | 2017143266 A1 | 8/2017 |
| WO | 2018106724 A1 | 6/2018 |

OTHER PUBLICATIONS

Askou et al. (Molecular Therapy—Methods & Clinical Development (2015) 2, 14064).*
Jorge Mansilla-Soto, Genetic strategies for the treatment of sickle cell anaemia, British Journal of Haematology, 154, 715-727 (2011).
Alessia Finotti, Recent trends in the gene therapy of β-thalassemia, Journal of Blood Medicine 2015:6 69-85 (2015).
Yongliang Huo, Humanized Mouse Model of Cooley's Anemia, The Journal of Biological Chemistry vol. 284, No. 8, pp. 4889-4896 (2009).
Rashmi Choudhary, Knockdown of HPRT for Selection of Genetically Modified Human Hematopoietic Progenitor Cells, PLOS ONE, vol. 8, Issue 3, e59594 (2013).

(Continued)

*Primary Examiner* — Kimberly Chong
(74) *Attorney, Agent, or Firm* — Charney IP Law LLC; Thomas M. Finetti

(57) ABSTRACT

The present disclosure provides expression vectors comprising at least two nucleic acid sequences, namely a nucleic acid sequence encoding an anti-HPRT RNAi, and a nucleic acid sequence encoding a gamma globin gene. In some embodiments, the viral vector is a self-inactivating lentiviral vector. In some embodiments, the gamma-globin gene is used to genetically correct sickle cell disease or β-thalassemia or to reduce symptoms thereof.

27 Claims, 54 Drawing Sheets

Specification includes a Sequence Listing.

(56) References Cited

OTHER PUBLICATIONS

Katrin Hacke, Genetic modification of mouse bone marrow by lentiviral vector-mediated delivery of HPRT shRNA confers chemoprotection against 6-thioguanine cytotoxicity, Transplant Proc., 45(5): 2040-2044, (2013).
International Search Report and Written Opinion, dated Oct. 22, 2018.
Aker et al., Extended core sequences from the cHS4 insulator are necessary for protecting retroviral vectors from silencing position effects. Hum Gene Ther. Apr. 2007;18(4):333-43.
Arumugam et al., Improved human beta-globin expression from self-inactivating lentiviral vectors carrying the chicken hypersensitive site-4 (cHS4) insulator element. Mol Ther. Oct. 2007;15(10):1863-71.
Arumugam et al., The 3' region of the chicken hypersensitive site-4 insulator has properties similar to its core and is required for full insulator activity. PLoS One. Sep. 10, 2009;4(9):e6995.
Azzouzi et al., MicroRNA-96 Directly Inhibits γ-Globin Expression in Human Erythropoiesis. PLoS ONE, 2011, vol. 6(7): e22838.
Baum et al., Side effects of retroviral gene transfer into hematopoietic stem cells. Blood. Mar. 15, 2003;101 (6)2099-114.
Bender et al., A majority of mice show long-term expression of a human beta-globin gene after retrovirus transfer into hematopoietic stem cells. Mol Cell Biol. Apr. 1989;9(4):1426-34.
Bernaudin et al., Long-term results of related myeloablative stem-cell transplantation to cure sickle cell disease. Blood. Oct. 1, 2007;110(7):2749-56.
Blouin et al., Genetic correction of sickle cell disease: insights using transgenic mouse models. Nat Med. Feb. 2000;6(2):177-82.
Burke et al., Engineering cellular resistance to HIV-1 infection in vivo using a dual therapeutic lentiviral vector. Mol Ther Nucleic Acids., 2015, 4, e236.
Chang et al., A 36-base-pair core sequence of locus control region enhances retrovirally transferred human beta-globin gene expression. Proc Natl Acad Sci USA. Apr. 1, 1992;89(7):3107-10.
Chung et al., Characterization of the chicken beta-globin insulator. Proc Natl Acad Sci USA Jan. 21, 1997;94(2):575-80.
Cone et al., Regulated expression of a complete human beta-globin gene encoded by a transmissible retrovirus vector. Mol Cell Biol. Feb. 1987; 7(2):887-97.
Crusselle-Davis et al., Antagonistic regulation of beta-globin gene expression by helix-loop-helix proteins USF and TFII-1. Mol Cell Biol. Sep. 2006; 26(18):6832-43.
Cui J., et al., Identification of three novel Hb F variants. Hemoglobin, 2012, 36(3), pp. 305-309.
Cui, J., et al., Application of Multiplex Ligation-Dependent Probe Amplification to Screen for β-Globin Cluster Deletions: Detection of Two Novel Deletions in a Multi Ethnic Population. Hemoglobin, 2013; 37(3): pp. 241-256.
Darbari et al., Circumstances of death in adult sickle cell disease patients. Am J Hematol. Nov. 2006; 81(I 1):858-63.
Emery et al., Development of virus vectors for gene therapy of beta chain hemoglobinopathies: flanking with a chromatin insulator reduces gamma-globin gene silencing in vivo. Blood. Sep. 15, 2002; 100(6):2012-9.
Fabry et al., Second generation knockout sickle mice: the effect of HbF. Blood. Jan. 15, 2001; 97(2): pp. 410-418.
Franco et al., Time-dependent changes in the density and hemoglobin F content of biotin-labeled sickle cells. J Clin Invest. Jun. 15, 1998; 101(12): pp. 2730-2740.
Kalberer et al., Preselection of retrovirally transduced bone marrow avoids subsequent stem cell gene silencing and age-dependent extinction of expression of human beta-globin in engrafted mice. Proc Natl Acad Sci USA. May 9, 2000; 97(10): pp. 5411-5415.
Kean et al., A cure for murine sickle cell disease through stable mixed chimerism and tolerance induction after nonmyeloablative conditioning and major histocompatibility complex-mismatched bone marrow transplantation. Blood. Mar. 1, 2002; 99(5):1840-9.
Kean et al., Chimerism and cure: hematologic and pathologic correction of murine sickle cell disease. Blood. Dec. 15, 2003; 102(13):4582-93. Epub Aug. 21, 2003.
Krishnamurti et al., Stable long-term donor engraftment following reduced-intensity hematopoietic cell transplantation for sickle cell disease. Biol Blood Marrow Transplant. Nov. 2008; 14(11): 1270-8.
Leboulch et al., Mutagenesis of retroviral vectors transducing human beta-globin gene and beta-globin locus control region derivatives results in stable transmission of an active transcriptional structure. EMBO J. Jul. 1, 1994; 13(13): pp. 3065-3076.
Ledger et al., Analysis and dissociation of anti-HIV effects of shRNA to CCR5 and the fusion inhibitor C46, J Gene Med., 2018, 20, e3006.
Levasseur et al., Correction of a mouse model of sickle cell disease: lentiviral/antisickling beta-globin gene transduction of unmobilized, purified hematopoietic stem cells. Blood. Dec. 15, 2003;102(13):4312-9. Epub Aug. 21, 2003.
Lunzen et al., "Transfer of Autologous Gene-modified T Cells in HIV-infected Patients with Advanced Immunodeficiency and Drug-resistant Virus," Mol Ther., 2007, 15(5):1024-1033.
Maier-Redelsperger et al., Fetal hemoglobin and F-cell responses to long-term hydroxyurea treatment in young sickle cell patients. The French Study Group on Sickle Cell Disease. Blood. Jun. 15, 1998;91(12):4472-9.
Maier-Redelsperger et al., Variation in fetal hemoglobin parameters and predicted hemoglobin S polymerization in sickle cell children in the first two years of life: Parisian Prospective Study on Sickle Cell Disease. Blood. Nov. 1, 1994; 84(9):3182-8.
Manci et al., Pathology of Berkeley sickle cell mice: similarities and differences with human sickle cell disease. Blood. Feb. 15, 2006; 107(4):1651-8. Epub Sep. 15, 2005.
Marcus et al., Physiologic decline in fetal hemoglobin parameters in infants with sickle cell disease: implications for pharmacological intervention. J Pediatr Hematol Oncol. Sep.-Oct. 1999; 21(5):407-11.
Novak et al., High-level beta-globin expression after retroviral transfer of locus activation region-containing human beta-globin gene derivatives into murine erythroleukemia cells. Proc Natl Acad Sci USA. May 1990; 87(9):3386-90.
Paszty et al., Transgenic knockout mice with exclusively human sickle hemoglobin and sickle cell disease. Science. Oct. 31, 1997; 278(5339):876-8.
Pawliuk et al., Correction of sickle cell disease in transgenic mouse models by gene therapy. Science. Dec. 14, 2001; 294(5550):2368-71.
Perumbeti et al., A novel human gamma-globin gene vector for genetic correction of sickle cell anemia in a humanized sickle mouse model: critical determinants for successful correction. Blood. Aug. 6, 2009;114(6):1174-85.
Pestina et al., Correction of murine sickle cell disease using gamma-globin lentiviral vectors to mediate high-level expression of fetal hemoglobin. Mol Ther. Feb. 2009;17(2):245-52.
Peterson, et al., Multi-lineage polyclonal engraftment of Cal-1 gene-modified cells and in vivo selection after SHIV infection in a nonhuman primate model of AIDS. Mol Ther Methods Clin Dev., 2016, 3, 16007.
Rivella et al., A novel murine model of Cooley anemia and its rescue by lentiviral-mediated human beta-globin gene transfer. Blood. Apr. 15, 2003; 101(8):2932-9. Epub Dec. 12, 2002.
Rivella et al., The cHS4 insulator increases the probability of retroviral expression at random chromosomal integration sites. J Virol. May 2000; 74(10):4679-87.
Rubin et al., Locus control region activity by 5'HS3 requires a functional interaction with beta-globin gene regulatory elements: expression of novel beta/gamma-globin hybrid transgenes. Blood. May 15, 2000; 95(10):3242-9.
Sabatino et al., Long-term expression of gamma-globin mRNA in mouse erythrocytes from retrovirus vectors containing the human gamma-globin gene fused to the ankyrin-1 promoter. Proc Natl Acad Sci USA Nov. 21, 2000; 97(24):13294-9.
Sadelain et al., Generation of a high-titer retroviral vector capable of expressing high levels of the human beta-globin gene. Proc Natl Acad Sci USA. Jul. 18, 1995; 92(15):6728-32.

(56) References Cited

OTHER PUBLICATIONS

Schambach et al., Improving transcriptional termination of self-inactivating gamma-retroviral and lentiviral vectors. Mol Ther. Jun. 2007; I5(6):1167-73. Epub Apr. 3, 2007.

Symonds et al., Cell-delivered entry inhibitors for HIV-1: CCR5 downregulation and blocking virus/membrane fusion in defending the host cell population. AIDS Patient Care STDS., 2016, (12):545-550.

Zhou, H. et al., An RNA polymerase II construct synthesizes short-hairpin RNA with a quantitative indicator and mediates highly efficient RNAi Nucleic Acids Research, 2005, vol. 33, No. 6, pp. 1-8.

\* cited by examiner

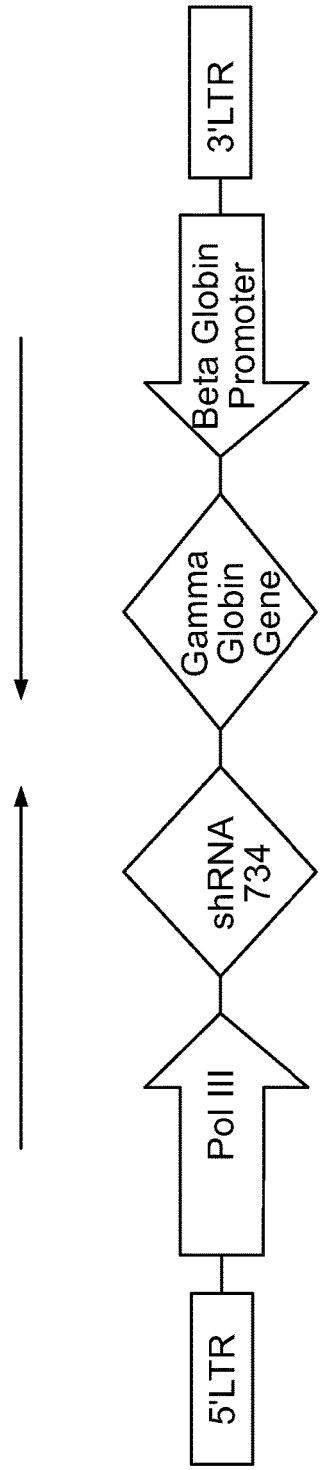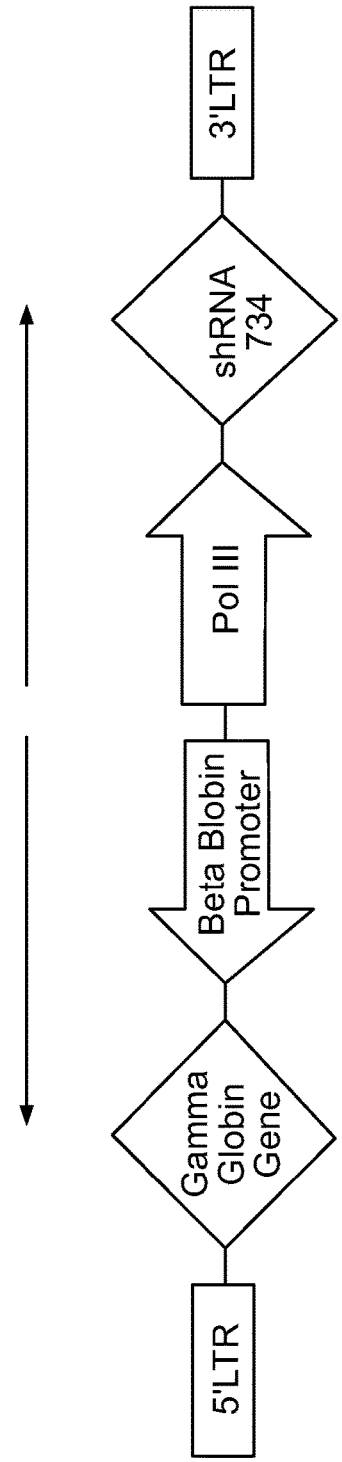
FIG. 1A
FIG. 1B

MFE Secondary Structure
-62.85 kcal/mol miRNA734-3G

Base-pair Probabilities

MFE Secondary Structure
-56.77 kcal/mol
miRNA211-3G

Base-pair Probabilities
0 1 sh734, Secondary Structure MFE -30.9 kcal/mol sh734.1 MFE= -36.16 kcal/mol; Freq. 65.95 %

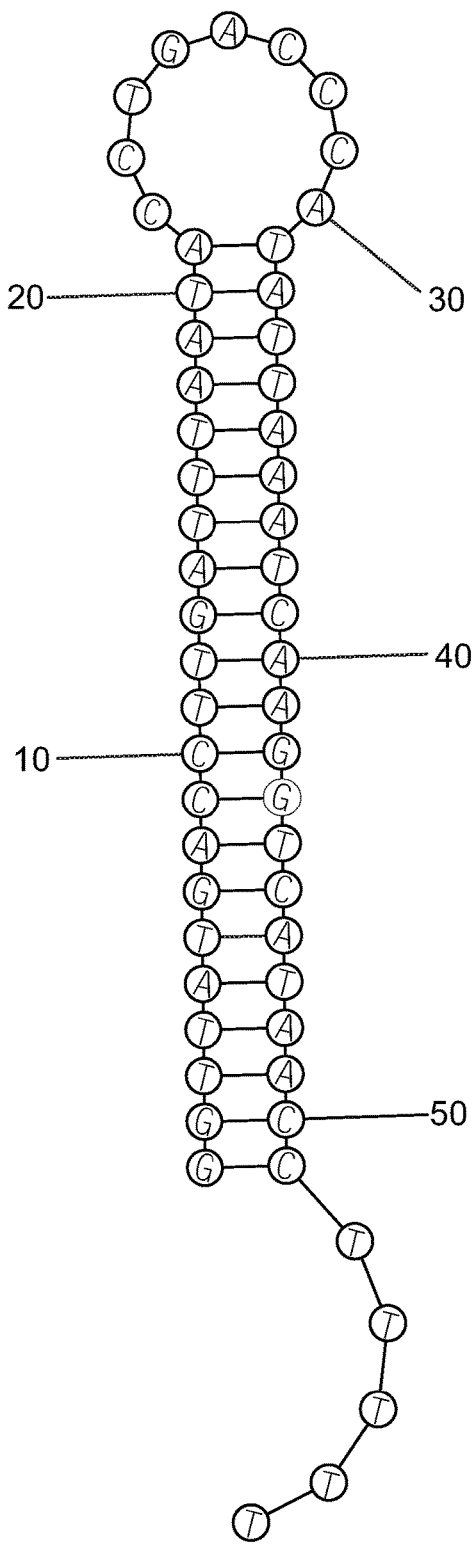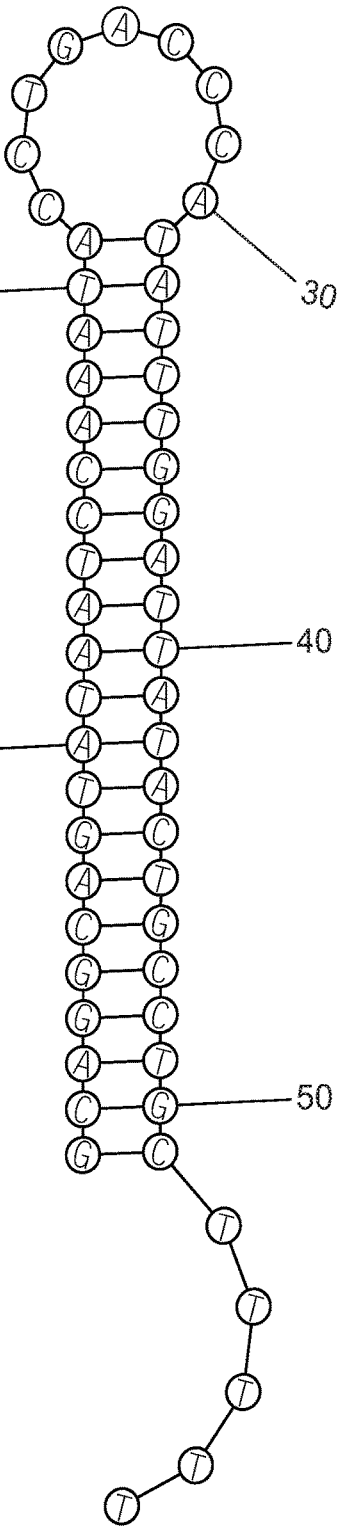

miRNA 734 de novo
SEQ ID NO: 23

Agosh 734 RNA, SEQ ID NO: 58

7SK RNA Promoter Region -- Corresponding to Nucleotides 7 through 248 of SEQ ID NO: 32

```
LENGTH = 242   COMBINED   P-VALUE = 1.52e-06   E-VALUE = 1.5e-06
DIAGRAM: 7- [+3] - [+2]-3-[+1]-17-[+1]-20-[+3]-50-[-1]-44-[-1]-15-[+2]-10

-232 Oct   CAC -214 Oct
              [+3]  [+2]       [+1]                          [+1]
              2.2e-05 2.9e-05  9.6e-06                       1.7e-06
     -242     TTTAGCAT CCCCGCC CAGCAGGAAAT                   CAGCAGGAAAT
              +++++++++++++++  ++++++++++                    +++++++++++
    1   tgcagtattttagcatgcccdaccdatctgcdaggcattct ggatagt gtcaaaacagccggaaatcaagtcc tt
                        DSE          Tal-1              GATA-1
                  [+3]                                                        [+3]
                  2.2e-05                                                     4.9e-07
                  TTTAGCAT                                                    ATTTCCT
                  +++++++                                                     +++++++
    76  tatctd aactttagcattttgggaataaatgatatttgctatgctggttaaattagattttagttaad ttttcct
        GATA-1
                                                    [-1]
                                                    3.9e-06                        [
               GCTG       -45                       ATTTCCTGCTG                    1
                                                    +++++++ +++                    G
    151 gctgaagatctag acgataagta acttgacctaagt gtaaagttgagatttcctt caggttta cat ad cttgtg
              PSE           GATA-1     T3R                              Tal-1 TATA
        [+2]                           Nuclear receptors
        3e-05
        CCCCGCC
        +++++++
    226 cgccgcctgggtacctc
```

7sKM1 promoter mutation. 7sKM1 Oct binding site mutations in the distal sequence enhancer (DSE) (dashed blue boxes) and predicted TAL-1 and GATA-1 binding sites.

FIG. 36

NM_000194.2 Homo sapiens hypoxanthine
phosphoribosyltransferase 1 (HPRT1), mRNA

SEQ ID NO: 59

```
   1 ggcggggcct gcttctcctc agcttcaggc ggctgcgacg agccctcagg cgaacctctc
  61 ggctttcccg cgcggcgccg cctcttgctg cgcctccgcc tcctcctctg ctccgccacc
 121 ggcttcctcc tcctgagcag tcagcccgcg cgccggccgg ctccgttatg gcgacccgca
 181 gccctggcgt cgtgattagt gatgatgaac caggttatga ccttgattta ttttgcatac
 241 ctaatcatta tgctgaggat ttggaaaggg tgtttattcc tcatggacta attatggaca
 301 ggactgaacg tcttgctcga gatgtgatga aggagatggg aggccatcac attgtagccc
 361 tctgtgtgct caagggggc tataaattct tgctgacct gctggattac atcaaagcac
 421 tgaatagaaa tagtgataga tccattccta tgactgtaga ttttatcaga ctgaagagct
 481 attgtaatga ccagtcaaca ggggacataa aagtaattgg tggagatgat ctctcaactt
 541 taactggaaa gaatgtcttg attgtggaag atataattga cactggcaaa acaatgcaga
 601 ctttgctttc cttggtcagg cagtataatc caaagatggt caaggtcgca agcttgctgg
 661 tgaaaaggac cccacgaagt gttggatata gccagactt tgttggattt gaaattccag
 721 acaagtttgt tgtgggtgt gcccttgct ataatgaata cttcagggat ttgaatcatg
 781 tttgtgtcat tagtgaaact ggaaaagcaa aatacaaagc ctaagatgag agttcaagtt
 841 gagtttggaa acatctggag tcctattgac atcgccagta aaattatcaa tgttctagtt
 901 ctgtggccat ctgcttagta gagcttttg catgtatctt ctaagaattt tatctgtttt
 961 gtactttaga aatgtcagtt gctgcattcc taaactgttt atttgcacta tgagcctata
1021 gactatcagt tcccttggg cggattgttg tttaacttgt aaatgaaaaa attctcttaa
1081 accacagcac tattgagtga acattgaac tcatatctgt aagaaataaa gagaagatat
1141 attagtttt taattggtat tttaatttt atatatgcag gaaagaatag aagtgattga
1201 atattgttaa ttataccacc gtgtgttaga aaagtaagaa gcagtcaatt ttcacatcaa
1261 agacagcatc taagaagttt tgttctgtcc tggaattatt ttagtagtgt ttcagtaatg
1321 ttgactgtat tttccaactt gttcaaatta ttaccagtga atctttgtca gcagttccct
1381 tttaaatgca aatcaataaa ttcccaaaaa tttaaaaaaa aaaaaaaaaa aaaaa
``` shHPRT734

5'- AGGATATGCCCTTGACTATtttgtccgacATAGTCAAGGG̲CATACCTTTTT - 3'

FIG. 37

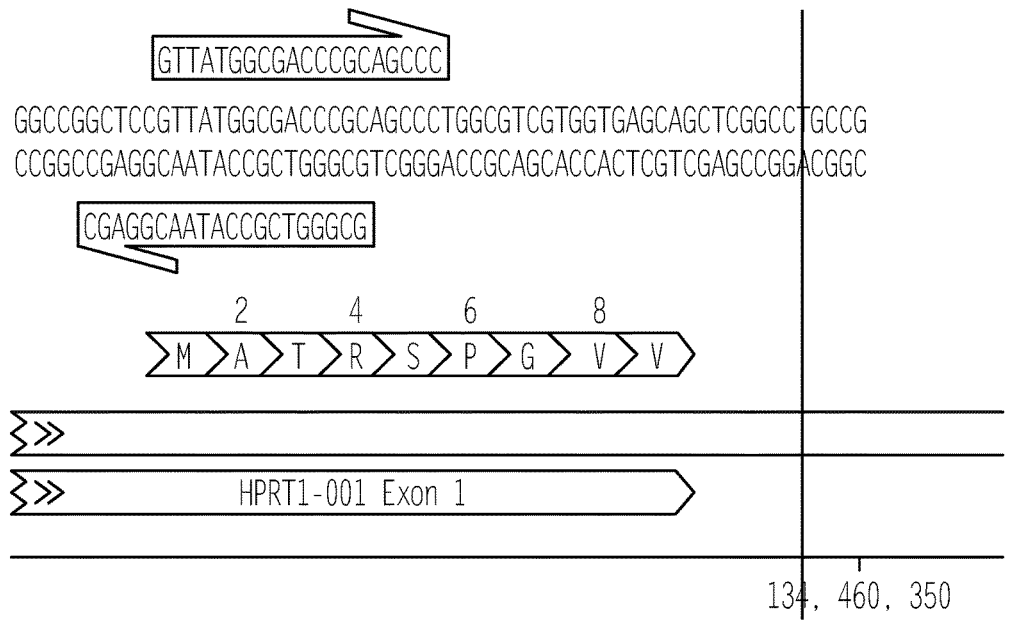

| Position | | Strand | SequencePAM | | Specificity Score | Efficiency Score |
|---|---|---|---|---|---|---|
| 134460326 | HPRT3 | 1 | GTTATGGCGACCCGCAGCCC | TGG | 89 | 51 |
| 134460307 | HPRT4 | -1 | GCGGGTCGCCATAACGGAGC | CGG | 98 | 50 |

FIG. 38 sGbGm exons 1-3

CAGACACCATGGGTCATTTCACAGAGGAGGACAAGGCTACTATCACAAGCCTGTGGGACA
AGGTGAATGTGGAAGATGCTGGAGGAAAACCCTGGGAAGGCTCCTGGTTGTCTACC
CATGGACCCAGAGGTTCTTTGACAGCTTTGGCAACCTGTCCTCTGCCTCTGCCAT
CATGGGCAACCCCAAAGTCAAGGCACATGGCAAGAAGGTGCTGACTTCCTTGGGA
GATGCCATAAAGCACCTGGATGATCTCAAGGGCACCTTTGCCCAGCTGAGTGAAC
TGCACTGTGACAAGCTGCATGTGGATCCTGAGAACTTCAAGCTCCTGGGCAACGT
GCTGGTCACCGTGCTGGCCATTCACTTTGGCAAAGAATTCACCCCTGAGGTGCAG
GCTTCCTGGCAGAAGATGGTGACTGCAGTGGCCAGTGCCCTGTCCTCCAGATACC
ACTGAGCCTCTTGCCCATGATTCAGAGCTTTCAAGGATAGGCTTTATTCTGCAAG
CAATACAAATAATAAATCTATTCTGCTGAGAGATCAC

FIG. 39

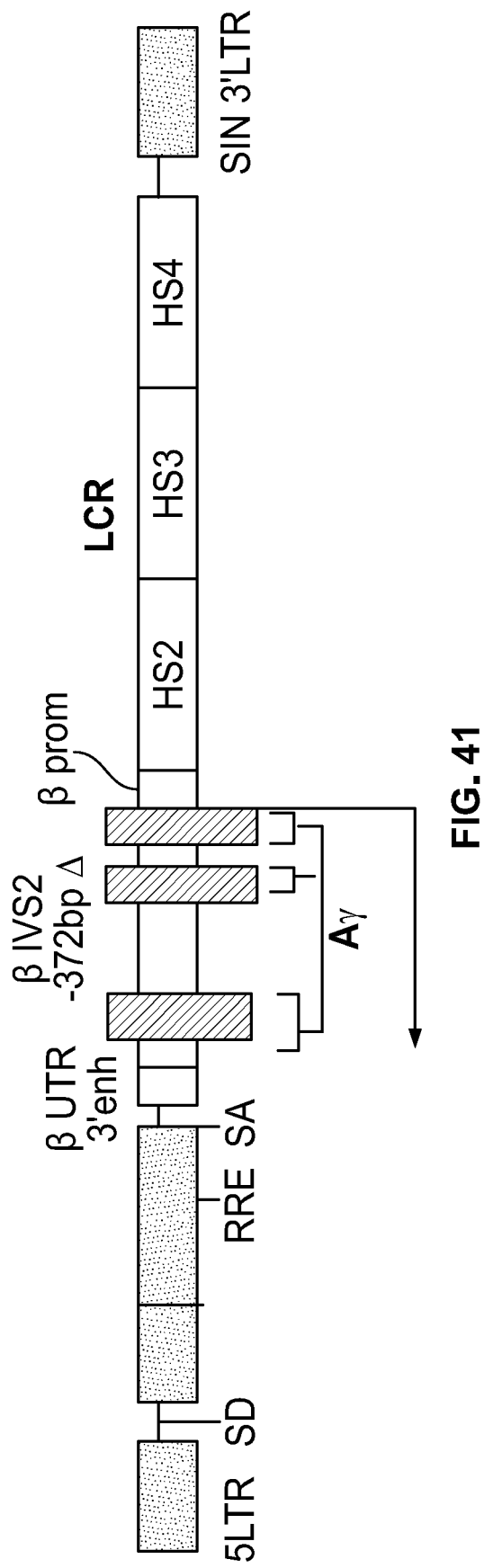

Titration of γ-globin Expression Vectors

| Name | Average Titer (TU/mL) | Stdev |
|---|---|---|
| sGbG$^M$ | $1.90 \times 10^5$ | $5.72 \times 10^4$ |
| TL20c-sGbG$^M$ | $7.32 \times 10^5$ | $7.71 \times 10^4$ |
| Cal-H | $6.94 \times 10^5$ | $3.18 \times 10^5$ |

| Vectors | Dilution | Day 0 | | | Day 35 | | |
|---|---|---|---|---|---|---|---|
| | | %GFP+ | sh734/%GFP+ | Rel.HPRT | %GFP+ | sh734/%GFP+ | Rel.HPRT |
| Mock | Mock | 0.4 | | 1 | 0.7 | | 1 |
| TL20cw-UbC/GFP | 1024 | 10.4 | ND | 0.95 | 9.1 | N/A | N/A |
| TL20cw-7SK/sh734-UbC/GFP | 1024 | 8.3 | 3.03 | 1.19 | 99.6 | 21.06 | 0.087 |
| TL20cw-r7SK/sh734-UbC/GFP | 1024 | 8.2 | 4.49 | 0.71 | 95.4 | 27.48 | 0.070 |
| TL20cw-UbC/GFP-7SK/sh734 | 1024 | 12.4 | 0.87 | 0.94 | 59.6 | 6.98 | 0.223 |
| TL20cw-UbC/GFP-r7SK/sh734 | 1024 | 10.1 | 0.27 | 0.72 | 98 | 15.17 | 0.163 |

FIG. 49K

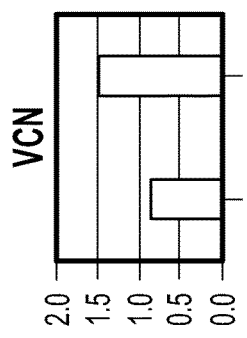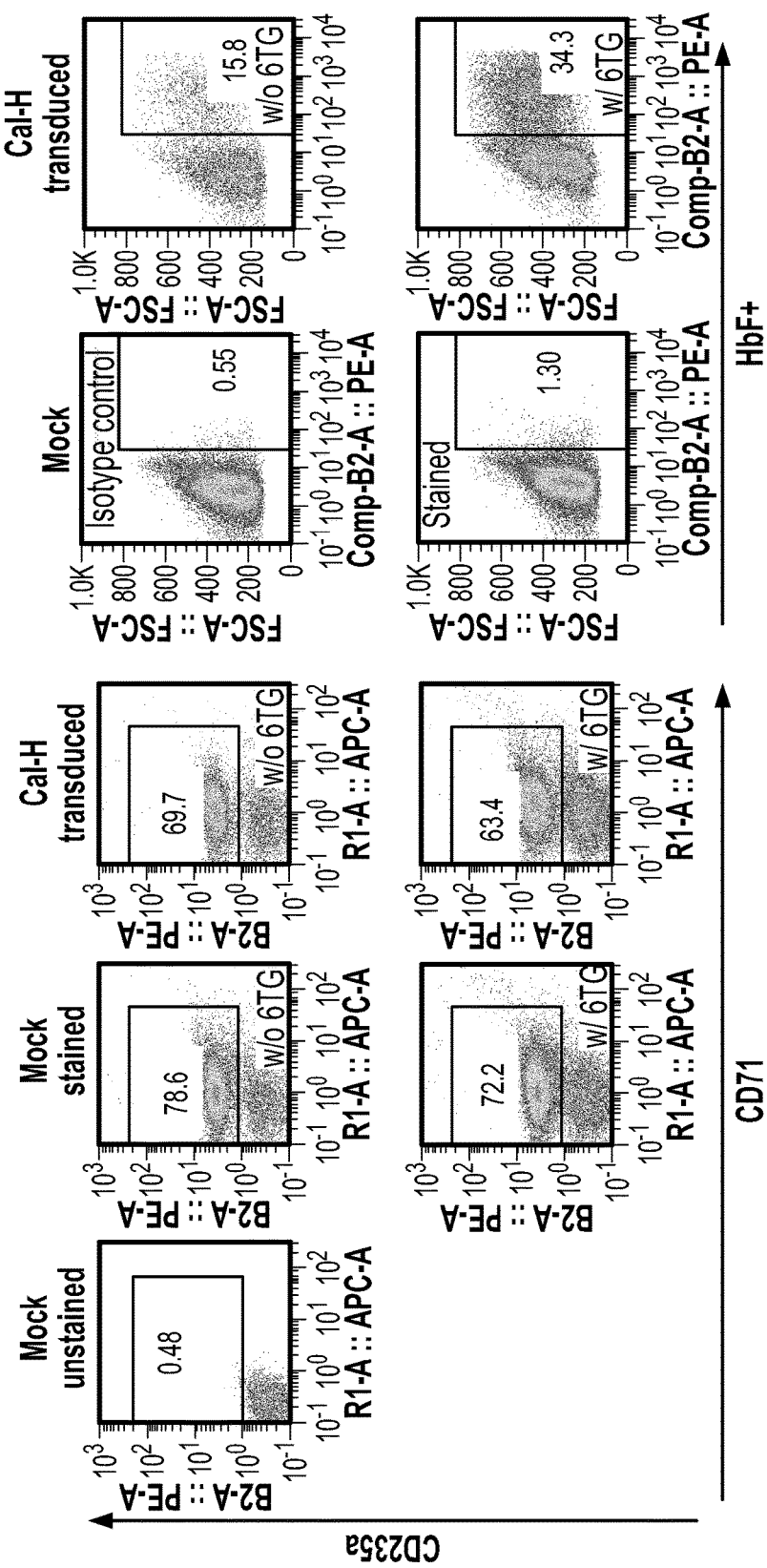
FIG. 52A
FIG. 52B
FIG. 52C

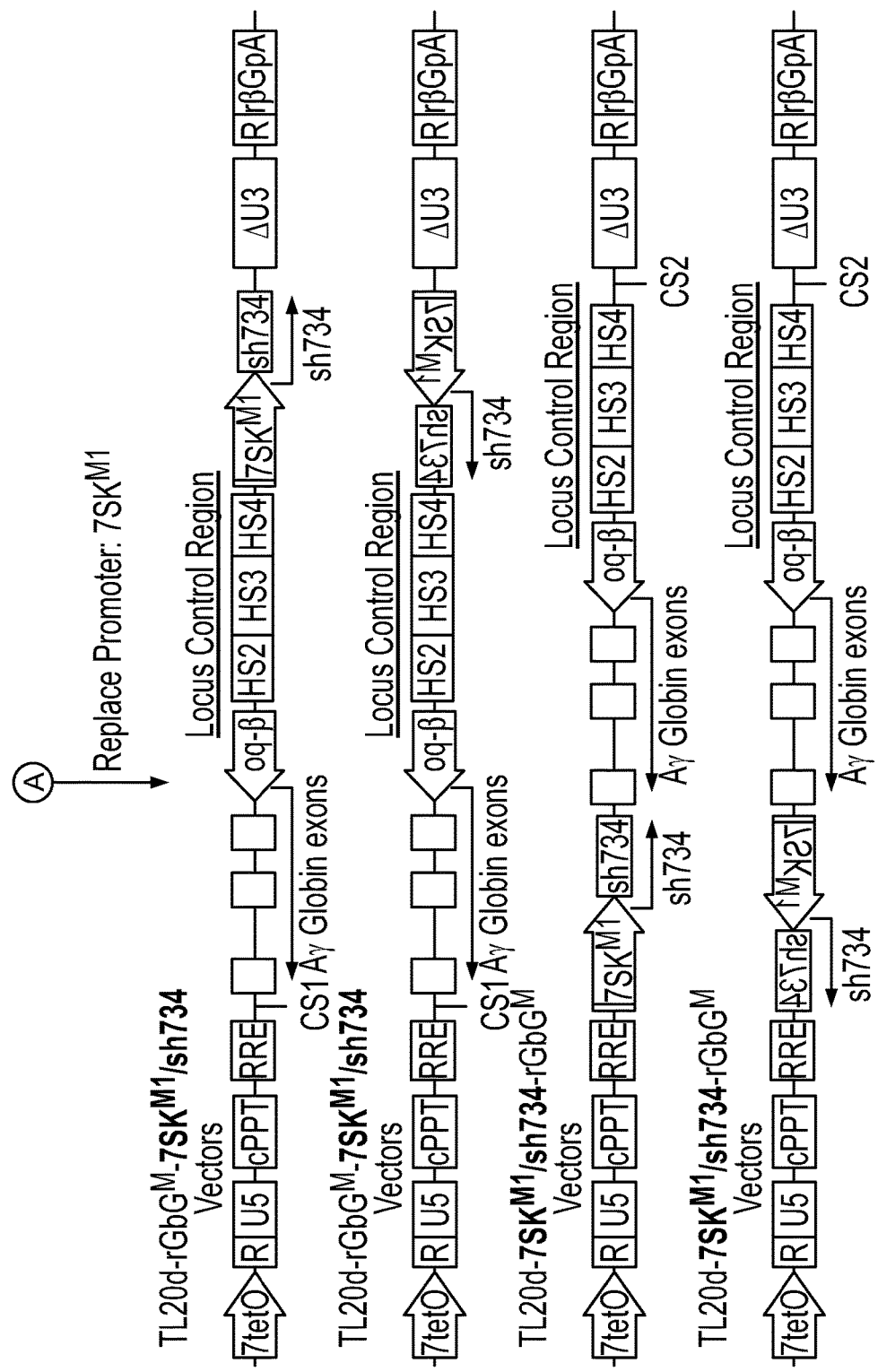
FIG. 53 (Cont..)

SEQUENCE LISTING

```
<160> NUMBER OF SEQ ID NOS: 69

<210> SEQ ID NO 1
<211> LENGTH: 46
<212> TYPE: DNA
<213> ORGANISM: Artificial Sequence
<220> FEATURE:
<223> OTHER INFORMATION: Synthetic: shRNA targeting an HPRT gene

<400> SEQUENCE: 1
aggatatgcc cttgactatt tgtccgacat agtcaagggc atatcc          46

<210> SEQ ID NO 2
<211> LENGTH: 46
<212> TYPE: DNA
<213> ORGANISM: Artificial Sequence
<220> FEATURE:
<223> OTHER INFORMATION: Synthetic: shRNA targeting an HPRT gene

<400> SEQUENCE: 2
tcctatacgg gaactgataa acaggctgta tcagttcccg tatagg          46

<210> SEQ ID NO 3
<211> LENGTH: 444
<212> TYPE: DNA
<213> ORGANISM: Artificial Sequence
<220> FEATURE:
<223> OTHER INFORMATION: Synthetic: sGbGm A gamma-globin translated
      sequence

<400> SEQUENCE: 3
atgggtcatt tcacagagga ggacaaggct actatcacaa gcctgtggga caaggtgaat      60
gtggaagatg ctggaggaga aaccctggga aggctcctgg ttgtctaccc atggacccag     120
aggttctttg acagctttgg caacctgtcc tctgcctctg ccatcatggg caaccccaaa     180
gtcaaggcac atggcaagaa ggtgctgact tccttgggag atgccataaa gcacctggat     240
gatctcaagg gcacctttgc ccagctgagt gaactgcact gtgacaagct gcatgtggat     300
cctgagaact tcaagctcct gggcaacgtg ctggtcaccg tgctggccat tcactttggc     360
```

```
aaagaattca ccctgaggt gcaggcttcc tggcagaaga tggtgactgc agtggccagt      420
gccctgtcct ccagatacca ctga                                            444

<210> SEQ ID NO 4
<211> LENGTH: 147
<212> TYPE: PRT
<213> ORGANISM: Artificial Sequence
<220> FEATURE:
<223> OTHER INFORMATION: Synthetic: sGbGM  HGB1 amino acid sequece

<400> SEQUENCE: 4

Met Gly His Phe Thr Glu Glu Asp Lys Ala Thr Ile Thr Ser Leu Trp
1               5                   10                  15

Asp Lys Val Asn Val Glu Asp Ala Gly Gly Glu Thr Leu Gly Arg Leu
            20                  25                  30

Leu Val Val Tyr Pro Trp Thr Gln Arg Phe Phe Asp Ser Phe Gly Asn
        35                  40                  45

Leu Ser Ser Ala Ser Ala Ile Met Gly Asn Pro Lys Val Lys Ala His
    50                  55                  60

Gly Lys Lys Val Leu Thr Ser Leu Gly Asp Ala Ile Lys His Leu Asp
65                  70                  75                  80

Asp Leu Lys Gly Thr Phe Ala Gln Leu Ser Glu Leu His Cys Asp Lys
                85                  90                  95

Leu His Val Asp Pro Glu Asn Phe Lys Leu Leu Gly Asn Val Leu Val
            100                 105                 110

Thr Val Leu Ala Ile His Phe Gly Lys Glu Phe Thr Pro Glu Val Gln
        115                 120                 125

Ala Ser Trp Gln Lys Met Val Thr Ala Val Ala Ser Ala Leu Ser Ser
    130                 135                 140

Arg Tyr His
145

<210> SEQ ID NO 5
<211> LENGTH: 12088
<212> TYPE: DNA
<213> ORGANISM: Artificial Sequence
<220> FEATURE:
<223> OTHER INFORMATION: Synthetic: TL20c-7SKM1/sh734-rGbGM

<400> SEQUENCE: 5
ggccgcctcg gccaaacagc ccttgagttt accactccct atcagtgata gagaaaagtg    60
aaagtcgagt ttaccactcc ctatcagtga tagagaaaag tgaaagtcga gtttaccact   120
ccctatcagt gatagagaaa agtgaaagtc gagtttacca ctccctatca gtgatagaga   180
aaagtgaaag tcgagtttac cagtccctat cagtgataga gaaaagtgaa agtcgagttt   240
accactccct atcagtgata gagaaaagtg aaagtcgagt ttaccactcc ctatcagtga   300
tagagaaaag tgaaagtcga gctcgccatg ggaggcgtgg cctgggcggg actgggagtg   360
ggcgagccct cagatcctgc atataagcag ctgcttttg cctgtactgg gtctctctgg   420
ttagaccaga tctgagcctg ggagctctct ggctaactag ggaacccact gcttaagcct   480
caataaagct tgccttgagt gcttcaagta gtgtgtgccc gtctgttgtg tgactctggt   540
aactagagat ccctcagacc cttttagtca gtgtggaaaa tctctagcag tggcgcccga   600
acagggactt gaaagcgaaa gggaaaccag aggagctctc tcgacgcagg actcggcttg   660
ctgaagcgcg cacggcaaga ggcgaggggc ggcgactggt gagtacgcca aaaatttga    720 ctagcggagg ctagaaggag agagatgggt gcgagagcgt cagtattaag cggggagaa    780
```

```
ttagatcgcg atgggaaaaa attcggttaa ggccaggggg aaagaaaaaa tataaattaa    840
aacatatagt atgggcaagc agggagctag aacgattcgc agttaatact ggcctgttag    900
aaacatcaga aggctgtaga caaatactgg gacagctaca accatcccct cagacaggat    960
cagaagaact tagatcatta tataatacag tagcaaccct ctattgtgtg catcaaagga   1020
tagagataaa agacaccaag gaagctttag acaagataga ggaagagcaa acaaaagta    1080 agaaaaaagc acagcaagca gcaggatctt cagacctgga aattccctac aatccccaaa   1140
gtcaaggagt agtagaatct atgaataaag aattaaagaa aattatagga caggtaagag   1200
atcaggctga acatcttaag acagcagtac aaatggcagt attcatccac aattttaaaa   1260 gaaaagggg  gattgggggg tacagtgcag gggaagaat  agtagacata atagcaacag    1320
acatacaaac taagaattac aaaaacaaa  ttacaaaaat tcaaaatttt cgggtttatt    1380
acagggacag cagaaatcca ctttggaaag gaccagcaaa gctcctctgg aaaggtgaag   1440
gggcagtagt aatacaagat aatagtgaca taaaagtagt gccaagaaga aaagcaaaga   1500
tcattaggga ttatggaaaa cagatggcag gtgatgattg tgtggcaagt agacaggatg   1560
aggattagaa catggaaaag tttagtaaaa caccataagg aggagatatg agggacaatt   1620
ggagaagtga attatataaa tataaagtag taaaaattga accattagga gtagcaccca   1680
ccaaggcaaa gagaagagtg gtgcagagag aaaaaagagc agtgggaata ggagctttgt   1740
tccttgggtt cttgggagca gcaggaagca ctatgggcgc agcgtcaatg acgctgacgg   1800
tacaggccag acaattattg tctggtatag tgcagcagca gaacaatttg ctgagggcta   1860
ttgaggcgca acagcatctg ttgcaactca cagtctgggg catcaagcag ctccaggcaa   1920
gaatcctggc tgtggaaaga tacctaaagg atcaacagct cctggggatt tggggttgct   1980
ctggaaaact catttgcacc actgctgtgc cttggaatgc tagttggagt aataaatctc   2040
tggaacagat ttggaatcac acgacctgga tggagtggga cagagaaatt aacaattaca   2100
caagcttaat acactcctta attgaagaat cgcaaaacca gcaagaaaag aatgaacaag   2160
aattattgga attagataaa tgggcaagtt tgtggaattg gtttaacata acaaattggc   2220
tgtggtatat aaaattattc ataatgatag taggaggctt ggtaggttta agaatagttt   2280
ttgctgtact ttctatagtg aatagagtta ggcagggata ttcaccatta tcgtttcaga   2340
cccacctccc aaccccgagg ggaccgagct caagcttcga agcggccgct cgacgtgcag   2400
tcgggctact gccccaccca tagtaccggc attctggata gtgtcaaaac agccggaaat   2460
caagtccgtt tatctcaaac tttagcattt tgggaataaa tgatatttgc tatgctggtt   2520
aaattagatt ttagttaaat ttcctgctga agctctagta cgataagtaa cttgacctaa   2580
gtgtaaagtt gagatttcct tcaggtttat atagcttgtg cgccgcctgg gtacctcagg   2640
atatgccctt gactatttgt ccgacatagt caagggcata tccttttta cgcgtgggga   2700 tcctctagag tcgagctcgc gaggatcatc accggtgcta gccggagcca gaagcaccat   2760
aagggacatg ataagggagc cagcagacct ctgatctctt cctgaatgct aatcttaaac   2820
atcctgagga agaatgggac ttccatttgg ggtgggccta tgatagggta ataagacagt   2880
agtgaatatc aagctacaaa aagcccccct tcaaattctt ctcagtccta acttttcata   2940
ctaagcccag tccttccaaa gcagactgtg aaagagtgat agttccggga gactagcacc   3000
ggctagccga gcttgaaca cttttccctt attaagaacc atccttgcta ctcagctgca    3060
atcaatccag cccccaggtc ttcactgaac cttttcccat ctcttccaaa acatctgttt   3120
```

```
ctgagaagtc ctgtcctata gaggtctttc ttcccaccgg atttctccta caccatttac    3180
tcccacttgc agaactcccg tgtacaagtg tctttactgc ttttatttgc tcaacaaaat    3240
gcacatctca tataaaaata aatgaggagc atgcacacac cacaaacaca aacaggcatg    3300
cagaaataca catacacact tccctcaata taaacccttt gtggctcata tatttaaaaa    3360
gatgtaaaaa aaagagctga agaaaatcat gtgtgatctc tcagcagaat agatttatta    3420
tttgtattgc ttgcagaata aagcctatcc ttgaaagctc tgaatcatgg gcaagaggct    3480
cagtggtatc tggaggacag ggcactggcc actgcagtca ccatcttctg ccaggaagcc    3540
tgcacctcag gggtgaattc tttgccaaag tgaatggcca gcacggtgac cagcacgttg    3600
cccaggagct gtgggaggaa gataagaggt atgaacatga ttagcaaaag ggcctagctt    3660
ggactcagaa taatccagcc ttatcccaac cataaaataa aagcagaatg gtagctggat    3720
tgtagctgct attagcaata tgaaacctct tacatcagtt acaatttata tgcagaaata    3780
tttatatgca gaaatattgc tattgcctta acccagaaat tatcactgtt attctttaga    3840
atggtgcaaa gaggcatgat acattgtatc attattgccc tgaaagaaag agattaggga    3900
aagtattaga aataagataa acaaaaaagt atattaaaag aagaaagcat ttttttaaaat    3960
tacaaatgca aaattaccct gatttggtca atatgtgtac cctgttactt ctccccttcc    4020
tatgacatga acttaaccat agaaaagaag gggaaagaaa acatcaaggg tcccatagac    4080
tcaccttgaa gttctcagga tccacatgca gcttgtcaca gtgcagttca ctcagctggg    4140
caaaggtgcc cttgagatca tccaggtgct ttatggcatc tcccaaggaa gtcagcacct    4200
tcttgccatg tgccttgact ttggggttgc ccatgatggc agaggcagag gacaggttgc    4260
caaagctgtc aaagaacctc tgggtccatg ggtagacaac caggagcctg tgagattgac    4320
aagaacagtt tgcagtcag aaggtgccac aaatcctgag aagcaacctg gacttttgcc    4380
aggcacaggg tccttccttc cctcccttgt cctggtcacc agagcctacc ttcccagggt    4440
ttctcctcca gcatcttcca cattcacctt gtcccacagg cttgtgatag tagccttgtc    4500
ctcctctgtg aaatgaccca tggtgtctgt ttgaggttgc tagtgaacac agttgtgtca    4560
gaagcaaatg taagcaatag atggctctgc cctgacttt atgcccagcc ctggctcctg    4620
ccctccctgc tcctgggagt agattggcca accctagggt gtggctccac agggtgaggt    4680
ctaagtgatg acagccgtac ctgtccttgg ctcttctggc actggcttag gagttggact    4740
tcaaaccctc agccctccct ctaagatata tctcttggcc ccataccatc agtacaaatt    4800
gctactaaaa acatcctcct ttgcaagtgt atttacgacg gtatcgatgt atgtgagcat    4860
gtgtcctcta acagcacagg ccttttgcca cctagctgtc caggggtgcc ttaaaatggc    4920
aaacaaggtt tgttttcttt tcctgttttc atgccttcct cttccatatc cttgtttcat    4980
attaatacat gtgtatagat cctaaaaatc tatacacatg tattaataaa gcctgattct    5040
gccgcttcta ggtatagagg ccacctgcaa gataaatatt tgattcacaa taactaatca    5100
ttctatggca attgataaca acaaatatat atatatatat atatatacgt atatgtgtat    5160
atatatatat atattcagga aataatatat tctagaatat gtcacattct gtctcaggca    5220
tccattttct ttatgatgcc gtttgagtg gagttttagt caggtggtca gcttctcctt    5280
tttttgcca tctgccctgt aagcatcctg ctggggaccc agataggagt catcactcta    5340
ggctgagaac atctgggcac acaccctaag cctcagcatg actcatcatg actcagcatt    5400
gctgtgcttg agccagaagg tttgcttaga aggttacaca gaaccagaag gcggggtgg    5460
ggcactgacc ccgacagggg cctggccaga actgctcatg cttggactat gggaggtcac    5520
```

```
taatggagac acacagaaat gtaacaggaa ctaagggaat tccggtgccc tgcttaggag    5580
cttaatcttt aatgaaagct aagctttcat taaaaaaagt ctaaccagct gcattcgact    5640
ttgactgcag cagctggtta gaaggttcta ctggaggagg gtcccagccc attgctaaat    5700
taacatcagg ctctgagact ggcagtatat ctctaacagt ggttgatgct atcttctgga    5760
acttgcctgc tacattgaga ccactgaccc atacatagga agcccatagc tctgtcctga    5820
actgttaggc cactggtcca gagagtgtgc atctcctttg atcctcataa taaccctatg    5880
agatagacac aattattact cttactttat agatgatgat cctgaaaaca taggagtcaa    5940
ggcacttgcc cctagctggg ggtatagggg agcagtccca tgtagtagta gaatgaaaaa    6000
tgctgctatg ctgtgcctcc cccacctttc ccatgtctgc cctctactca tggtctatct    6060
ctcctggctc ctgggagtca tggactccac ccagcaccac caacctgacc taaccaccta    6120
tctgagcctg ccagcctata acccatctgg gccctgatag ctggtggcca gccctgaccc    6180
caccccaccc tccctggaac ctctgataga cacatctggc acaccagctc gcaaagtcac    6240
cgtgagggtc ttgtgtttgc tgagtcaaaa ttccttgaaa tccaagtcct tagagactcc    6300
tgctcccaaa tttacagtca tagacttctt catggctgtc tcctttatcc acagaatgat    6360
tcctttgctt cattgcccca tccatctgat cctcctcatc agtgcagcac agggcccatg    6420
agcagtagct gcagagtctc ataggtct ggcactgcct ctgacatgtc cgaccttagg    6480
caaatgcttg actcttctga gctcggatcc cttgagctca ggaggtcaag gctgcagtga    6540
gacatgatct tgccactgca ctccagcctg gacagcagag tgaaaccttg cctcacgaaa    6600
cagaatacaa aaacaaacaa acaaaaaact gctccgcaat gcgcttcctt gatgctctac    6660
cacataggtc tgggtacttt gtacacatta tctcattgct gttcataatt gttagattaa    6720
ttttgtaata ttgatattat tcctagaaag ctgaggcctc aagatgataa cttttatttt    6780
ctggacttgt aatagctttc tcttgtattc accatgttgt aactttctta gagtagtaac    6840
aatataaagt tattgtgagt ttttgcaaac acagcaaaca caacgaccca tatagacatt    6900
gatgtgaaat tgtctattgt caatttatgg gaaaacaagt atgtacttt tctactaagc    6960 cattgaaaca ggaataacag aacaagattg aaagaataca ttttccgaaa ttacttgagt    7020
attatacaaa gacaagcacg tggacctggg aggagggtta ttgtccatga ctggtgtgtg    7080
gagacaaatg caggtttata atagatggga tggcatctag cgcaatgact ttgccatcac    7140
ttttagagag ctcttggggg ccccagtaca caagagggga cgcagggtat atgtagacat    7200
ctcattcttt ttcttagtgt gagaataaga atagccatga cctgagttta tagacaatga    7260
gcccttttct ctctcccact cagcagctat gagatggctt gccctgcctc tctactaggc    7320
tgactcactc caaggcccag caatgggcag ggctctgtca gggctttgat agcactatct    7380
gcagagccag ggccgagaag gggtggactc cagagactct ccctcccatt cccgagcagg    7440
gtttgcttat ttatgcattt aaatgatata tttattttaa aagaaataac aggagactgc    7500
ccagccctgg ctgtgacatg gaaactatgt agaatatttt gggttccatt ttttttttcct   7560 tctttcagtt agaggaaaag gggctcactg cacatacact agacagaaag tcaggagctt    7620
tgaatccaag cctgatcatt tccatgtcat actgagaaag tccccaccct tctctgagcc    7680
tcagtttctc ttttttataag taggagtctg gagtaaatga tttccaatgg ctctcatttc    7740
aatacaaaat ttccgtttat taaatgcatg agcttccgtt actccaagac tgagaaggaa    7800
attgaacctg agactcattg actggcaaga tgtccccaga ggctctcatt cagcaataaa    7860
```

-continued

```
attctcacct tcacccaggc ccactagtgt cagatttgca tgcgttaacg cggccgcatc      7920
gatgccgtag tacctttaag accaatgact tacaaggcag ctgtagatct tagccacttt      7980
ttaaaagaaa aggggggact ggaagggcta attcactccc aaagaagaca agatccctgc      8040
aggcattcaa ggccaggctg gatgtggctc tgggcagcct gggctgctgg ttgatgaccc      8100
tgcacatagc aggggttgg atctggatga gcactgtgct cctttgcaac ccaggccgtt       8160
ctatgattct gtcattctaa atctctcttt cagcctaaag cttttttcccc gtatcccccc     8220 aggtgtctgc aggctcaaag agcagcgaga agcgttcaga ggaaagcgat cccgtgccac      8280
cttccccgtg cccgggctgt ccccgcacgc tgccggctcg gggatgcggg gggagcgccg      8340
gaccggagcg gagccccggg cggctcgctg ctgcccccta gcggggagg gacgtaatta       8400 catccctggg ggctttgggg gggggctgtc cccgtgagct ccccagatct gcttttttgcc     8460 tgtactgggt ctctctggtt agaccagatc tgagcctggg agctctctgg ctaactaggg      8520
aacccactgc ttaagcctca ataaagcttc agctgtcga gctagcagat ctttttcccct     8580 ctgccaaaaa ttatgggac atcatgaagc ccccttgagca tctgacttct ggctaataaa      8640
ggaaatttat tttcattgca atagtgtgtt ggaatttttt gtgtctctca ctcggaagga     8700
catatgggag ggcaaatcat ttaaaacatc agaatgagta tttggtttag agtttggcaa     8760
catatgccca tatgctggct gccatgaaca aaggttggct ataaagaggt catcagtata     8820
tgaaacagcc ccctgctgtc cattccttat tccatagaaa agccttgact tgaggttaga     8880
ttttttttat attttgtttt gtgttatttt tttctttaac atccctaaaa ttttccttac      8940
atgttttact agccagattt ttcctcctct cctgactact cccagtcata gctgtccctc      9000
ttctcttatg gagatccctc gacctgcagc ccaagcttgg cgtaatcatg gtcatagctg      9060
tttcctgtgt gaaattgtta tccgctcaca attccacaca acatacgagc cggaagcata     9120
aagtgtaaag cctggggtgc ctaatgagtg agctaactca cattaattgc gttgcgctca     9180
ctgcccgctt tccagtcggg aaacctgtcg tgccagcgga tccgcatctc aattagtcag     9240
caaccatagt cccgccccta actccgccca tcccgcccct aactccgccc agttccgccc     9300
attctccgcc ccatggctga ctaattttttt ttatttatgc agaggccgag gccgcctcgg     9360
cctctgagct attccagaag tagtgaggag gcttttttgg aggcctaggc ttttgcaaaa     9420
agctgtcgac tgcagaggcc tgcatgcaag cttggcgtaa tcatggtcat agctgtttcc     9480
tgtgtgaaat tgttatccgc tcacaattcc acacaacata cgagccggaa gcataaagtg     9540
taaagcctgg ggtgcctaat gagtgagcta actcacatta attgcgttgc gctcactgcc     9600
cgctttccag tcgggaaacc tgtcgtgcca gctgcattaa tgaatcggcc aacgcgcggg     9660
gagaggcggt ttgcgtattg ggcgctcttc cgcttcctcg ctcactgact cgctgcgctc     9720
ggtcgttcgg ctgcggcgag cggtatcagc tcactcaaag gcggtaatac ggttatccac     9780
agaatcaggg gataacgcag gaaagaacat gtgagcaaaa ggccagcaaa aggccaggaa     9840
ccgtaaaaag gccgcgttgc tggcgttttt ccataggctc cgcccccctg acgagcatca     9900
caaaaatcga cgctcaagtc agaggtggcg aaacccgaca ggactataaa gataccaggc     9960
gtttccccct ggaagctccc tcgtgcgctc tcctgttccg accctgccgc ttaccggata     10020
cctgtccgcc tttctccctt cgggaagcgt ggcgctttct catagctcac gctgtaggta     10080
tctcagttcg gtgtaggtcg ttcgctccaa gctgggctgt gtgcacgaac cccccgttca     10140
gcccgaccgc tgcgccttat ccggtaacta tcgtcttgag tccaacccgg taagacacga     10200
cttatcgcca ctggcagcag ccactggtaa caggattagc agagcgaggt atgtaggcgg     10260
```

```
tgctacagag ttcttgaagt ggtggcctaa ctacggctac actagaagaa cagtatttgg    10320
tatctgcgct ctgctgaagc cagttacctt cggaaaaaga gttggtagct cttgatccgg    10380
caaacaaacc accgctggta gcggtggttt ttttgtttgc aagcagcaga ttacgcgcag    10440
aaaaaaagga tctcaagaag atcctttgat cttttctacg gggtctgacg ctcagtggaa    10500
cgaaaactca cgttaaggga ttttggtcat gagattatca aaaggatctt cacctagat     10560 cctttt aaat taaaaatgaa gttttaaatc aatctaaagt atatgagt aaacttggtc     10620 tgacagttac caatgcttaa tcagtgaggc acctatctca gcgatctgtc tatttcgttc    10680
atccatagtt gcctgactcc ccgtcgtgta gataactacg atacgggagg cttaccatc     10740 tggccccagt gctgcaatga taccgcgaga cccacgctca ccggctccag atttatcagc    10800
aataaaccag ccagccggaa gggccgagcg cagaagtggt cctgcaactt tatccgcctc    10860
catccagtct attaattgtt gccgggaagc tagagtaagt agttcgccag ttaatagttt    10920
gcgcaacgtt gttgccattg ctacaggcat cgtggtgtca cgctcgtcgt ttggtatggc    10980
ttcattcagc tccggttccc aacgatcaag gcgagttaca tgatccccca tgttgtgcaa    11040
aaaagcggtt agctccttcg gtcctccgat cgttgtcaga agtaagttgg ccgcagtgtt    11100
atcactcatg gttatggcag cactgcataa ttctcttact gtcatgccat ccgtaagatg    11160
cttttctgtg actggtgagt actcaaccaa gtcattctga atagtgta tgcggcgacc      11220 gagttgctct tgcccggcgt caatacggga taataccgcg ccacatagca gaactttaaa    11280
agtgctcatc attggaaaac gttcttcggg gcgaaaactc tcaaggatct taccgctgtt    11340
gagatccagt tcgatgtaac ccactcgtgc acccaactga tcttcagcat ctttactttt    11400
caccagcgtt tctgggtgag caaaaacagg aaggcaaaat gccgcaaaaa agggaataag    11460
ggcgacacgg aaatgttgaa tactcatact cttcctttt caatattatt gaagcattta     11520
tcagggttat tgtctcatga gcggatacat atttgaatgt atttagaaaa ataaacaaat    11580
aggggttccg cgcacatttc cccgaaaagt gccacctgac gtctaagaaa ccattattat    11640
catgacatta acctataaaa ataggcgtat cacgaggccc tttcgtctcg cgcgtttcgg    11700
tgatgacggt gaaaacctct gacacatgca gctcccggag acggtcacag cttgtctgta    11760
agcggatgcc gggagcagac aagcccgtca gggcgcgtca gcgggtgttg gcgggtgtcg    11820
gggctggctt aactatgcgg catcagagca gattgtactg agagtgcacc atatgcggtg    11880
tgaaataccg cacagatgcg taaggagaaa ataccgcatc aggcgccatt cgccattcag    11940
gctgcgcaac tgttgggaag ggcgatcggt gcgggcctct tcgctattac gccagctggc    12000
gaaaggggga tgtgctgcaa ggcgattaag ttgggtaacg ccagggtttt cccagtcacg    12060
acgttgtaaa acgacggcca gtgaattc                                       12088
```

<210> SEQ ID NO 6
<211> LENGTH: 12091
<212> TYPE: DNA
<213> ORGANISM: Artificial Sequence
<220> FEATURE:
<223> OTHER INFORMATION: Synthetic: TL20c-7SK/sh734-rGbGM

<400> SEQUENCE: 6

```
ggccgcctcg gccaaacagc ccttgagttt accactccct atcagtgata gagaaaagtg       60
aaagtcgagt ttaccactcc ctatcagtga tagagaaaag tgaaagtcga gtttaccact      120
ccctatcagt gatagagaaa agtgaaagtc gagtttacca ctccctatca gtgatagaga      180
```

```
aaagtgaaag tcgagtttac cagtccctat cagtgataga gaaaagtgaa agtcgagttt    240
accactccct atcagtgata gagaaaagtg aaagtcgagt ttaccactcc ctatcagtga    300
tagagaaaag tgaaagtcga gctcgccatg ggaggcgtgg cctgggcggg actggggagt    360
ggcgagccct cagatcctgc atataagcag ctgcttttg cctgtactgg gtctctctgg    420
ttagaccaga tctgagcctg ggagctctct ggctaactag gaacccact gcttaagcct    480 caataaagct tgccttgagt gcttcaagta gtgtgtgccc gtctgttgtg tgactctggt    540
aactagagat ccctcagacc cttttagtca gtgtggaaaa tctctagcag tggcgcccga    600
acagggactt gaaagcgaaa gggaaaccag aggagctctc tcgacgcagg actcggcttg    660
ctgaagcgcg cacggcaaga ggcgaggggc ggcgactggt gagtacgcca aaattttga    720 ctagcggagg ctagaaggag agagatgggt gcgagagcgt cagtattaag cggggagaa    780 ttagatcgcg atgggaaaaa attcggttaa ggccaggggg aaagaaaaaa tataaattaa    840
aacatatagt atgggcaagc agggagctag aacgattcgc agttaatact ggcctgttag    900
aaacatcaga aggctgtaga caaatactgg gacagctaca accatccctt cagacaggat    960
cagaagaact tagatcatta tataatacag tagcaaccct ctattgtgtg catcaaagga   1020
tagagataaa agacaccaag gaagctttag acaagataga ggaagagcaa acaaaagta   1080 agaaaaaagc acagcaagca gcaggatctt cagacctgga aattccctac aatccccaaa   1140
gtcaaggagt agtagaatct atgaataaag aattaaagaa aattatagga caggtaagag   1200
atcaggctga acatcttaag acagcagtac aaatggcagt attcatccac aattttaaaa   1260 gaaaagggg gattgggggg tacagtgcag gggaagaat agtagacata atagcaacag   1320
acatacaaac taagaatta caaaacaaa ttacaaaaat tcaaaatttt cgggttat   1380 acagggacag cagaaatcca ctttggaaag gaccagcaaa gctcctctgg aaaggtgaag   1440
gggcagtagt aatacaagat aatagtgaca taaagtagt gccaagaaga aagcaaaga   1500 tcattaggga ttatggaaaa cagatggcag gtgatgattg tgtggcaagt agacaggatg   1560
aggattagaa catggaaag tttagtaaaa caccataagg aggagatatg agggacaatt   1620
ggagaagtga attatataa tataagtag taaaattga accattagga gtagcaccca   1680
ccaaggcaaa gagaagagtg gtgcagagag aaaaagagc agtgggaata ggagctttgt   1740
tccttgggtt cttgggagca gcaggaagca ctatgggcgc agcgtcaatg acgctgacgg   1800
tacaggccag acaattattg tctggtatag tgcagcagca gaacaatttg ctgagggcta   1860
ttgaggcgca acagcatctg ttgcaactca cagtctgggg catcaagcag ctccaggcaa   1920
gaatcctggc tgtggaaaga tacctaaagg atcaacagct cctggggatt tggggttgct   1980
ctggaaaact catttgcacc actgctgtgc cttggaatgc tagttggagt aataaatctc   2040
tggaacagat ttggaatcac acgacctgga tggagtggga cagagaaatt aacaattaca   2100
caagcttaat acactcctta attgaagaat cgcaaaacca gcaagaaaag aatgaacaag   2160
aattattgga attagataaa tgggcaagtt tgtggaattg gtttaacata caaattggc   2220 tgtggtatat aaaattattc ataatgatag taggaggctt ggtaggttta agaatagttt   2280
ttgctgtact ttctatagtg aatagagtta ggcaggata ttcaccatta tcgtttcaga   2340
cccacctccc aaccccgagg ggaccgagct caagcttcga agcggccgca tcgacgtgca   2400
gtatttagca tgccccaccc atctgcaagg cattctggat agtgtcaaaa cagccggaaa   2460
tcaagtccgt ttatctcaaa ctttagcatt ttgggaataa atgatattg ctatgctggt   2520 taaattagat tttagttaaa tttcctgctg aagctctagt acgataagta acttgaccta   2580
```

```
agtgtaaagt tgagatttcc ttcaggttta tatagcttgt gcgccgcctg ggtacctcag  2640
gatatgccct tgactatttg tccgacatag tcaagggcat atccttttt gtacgcgtgg   2700 ggatcctcta gagtcgagct cgcgaggatc atcaccggtg ctagccggag ccagaagcac  2760
cataagggac atgataaggg agccagcaga cctctgatct cttcctgaat gctaatctta  2820
aacatcctga ggaagaatgg gacttccatt tggggtgggc ctatgatagg gtaataagac  2880
agtagtgaat atcaagctac aaaaagcccc ctttcaaatt cttctcagtc ctaacttttc  2940
atactaagcc cagtccttcc aaagcagact gtgaaagagt gatagttccg ggagactagc  3000
accggctagc cgagcttgga acactttccc ttcattaaga accatccttg ctactcagct  3060
gcaatcaatc cagccccag gtcttcactg aacctttcc catctcttcc aaaacatctg    3120
tttctgagaa gtcctgtcct atagaggtct ttcttcccac cggatttctc ctacaccatt  3180
tactcccact tgcagaactc ccgtgtacaa gtgtctttac tgcttttatt tgctcaacaa  3240
aatgcacatc tcatataaaa ataaatgagg agcatgcaca caccacaaac acaaacaggc  3300
atgcagaaat acacatacac acttccctca atataaaccc tttgtggctc atatatttaa  3360
aaagatgtaa aaaaagagc tgaagaaaat catgtgtgat ctctcagcag aatagattta   3420
ttatttgtat tgcttgcaga ataaagccta tccttgaaag ctctgaatca tgggcaagag  3480
gctcagtggt atctggagga cagggcactg gccactgcag tcaccatctt ctgccaggaa  3540
gcctgcacct caggggtgaa ttctttgcca aagtgaatgg ccagcacggt gaccagcacg  3600
ttgcccagga gctgtgggag gaagataaga ggtatgaaca tgattagcaa aagggcctag  3660
cttggactca gaataatcca gccttatccc aaccataaaa taaaagcaga atggtagctg  3720
gattgtagct gctattagca atatgaaacc tcttacatca gttacaattt atatgcagaa  3780
atatttatat gcagaaatat tgctattgcc ttaacccaga aattatcact gttattcttt  3840
agaatggtgc aaagaggcat gatacattgt atcattattg ccctgaaaga aagagattag  3900
ggaaagtatt agaaataaga taaacaaaaa agtatattaa aagaagaaag catttttaa   3960 aattacaaat gcaaaattac cctgatttgg tcaatatgtg taccctgtta cttctcccct  4020
tcctatgaca tgaacttaac catagaaaag aaggggaaag aaaacatcaa gggtcccata  4080
gactcacctt gaagttctca ggatccacat gcagcttgtc acagtgcagt tcactcagct  4140
gggcaaaggt gcccttgaga tcatccaggt gctttatggc atctcccaag gaagtcagca  4200
ccttcttgcc atgtgccttg actttggggt tgcccatgat ggcagaggca gaggacaggt  4260
tgccaaagct gtcaaagaac ctctgggtcc atgggtagaa aaccaggagc ctgtgagatt  4320
gacaagaaca gtttgacagt cagaaggtgc cacaaatcct gagaagcaac ctggactttt  4380
gccaggcaca gggtccttcc ttccctccct tgtcctggtc accagagcct accttcccag  4440
ggtttctcct ccagcatctt ccacattcac cttgtcccac aggcttgtga tagtagcctt  4500
gtcctcctct gtgaaatgac ccatggtgtc tgtttgaggt tgctagtgaa cacagttgtg  4560
tcagaagcaa atgtaagcaa tagatggctc tgccctgact tttatgccca gcctggctc   4620 ctgccctccc tgctcctggg agtagattgg ccaaccctag ggtgtggctc cacagggtga  4680
ggtctaagtg atgacagccg tacctgtcct tggctcttct ggcactggct taggagttgg  4740
acttcaaacc ctcagccctc cctctaagat atatctcttg ccccataccc atcagtacaa  4800
attgctacta aaaacatcct cctttgcaag tgtatttacg acggtatcga tgtatgtgag  4860
catgtgtcct ctaacagcac aggccttttg ccacctagct gtccaggggt gccttaaaat  4920
```

```
ggcaaacaag gtttgttttc ttttcctgtt ttcatgcctt cctcttccat atccttgttt   4980
catattaata catgtgtata gatcctaaaa atctatacac atgtattaat aaagcctgat   5040
tctgccgctt ctaggtatag aggccacctg caagataaat atttgattca caataactaa   5100
tcattctatg gcaattgata acaacaaata tatatatata tatatatata cgtatatgtg   5160
tatatatata tatatattca ggaaataata tattctagaa tatgtcacat tctgtctcag   5220
gcatccattt tctttatgat gccgtttgag gtggagtttt agtcaggtgg tcagcttctc   5280 ctttttttg ccatctgccc tgtaagcatc ctgctgggga cccagatagg agtcatcact   5340
ctaggctgag aacatctggg cacacaccct aagcctcagc atgactcatc atgactcagc   5400
attgctgtgc ttgagccaga aggtttgctt agaaggttac acagaaccag aaggcggggg   5460
tggggcactg accccgacag gggcctggcc agaactgctc atgcttggac tatgggaggt   5520
cactaatgga gacacacaga aatgtaacag gaactaaggg aattccggtg ccctgcttag   5580
gagcttaatc tttaatgaaa gctaagcttt cattaaaaaa agtctaacca gctgcattcg   5640
actttgactg cagcagctgg ttagaaggtt ctactggagg agggtcccag cccattgcta   5700
aattaacatc aggctctgag actggcagta tatctctaac agtggttgat gctatcttct   5760
ggaacttgcc tgctacattg agaccactga cccatacata ggaagcccat agctctgtcc   5820
tgaactgtta ggccactggt ccagagagtg tgcatctcct ttgatcctca taataaccct   5880
atgagataga cacaattatt actcttactt tatagatgat gatcctgaaa acataggagt   5940
caaggcactt gcccctagct gggggtatag gggagcagtc ccatgtagta gtagaatgaa   6000
aaatgctgct atgctgtgcc tcccccacct ttcccatgtc tgccctctac tcatggtcta   6060
tctctcctgg ctcctgggag tcatggactc cacccagcac caccaacctg acctaaccac   6120
ctatctgagc ctgccagcct ataacccatc tgggccctga tagctggtgg ccagccctga   6180
ccccacccca ccctccctgg aacctctgat agacacatct ggcacaccag ctcgcaaagt   6240
caccgtgagg gtcttgtgtt tgctgagtca aaattccttg aaatccaagt ccttagagac   6300
tcctgctccc aaatttacag tcatagactt cttcatggct gtctccttta tccacagaat   6360
gattcctttg cttcattgcc ccatccatct gatcctcctc atcagtgcag cacagggccc   6420
atgagcagta gctgcagagt ctcacatagg tctggcactg cctctgacat gtccgacctt   6480
aggcaaatgc ttgactcttc tgagctcgga tcccttgagc tcaggaggtc aaggctgcag   6540
tgagacatga tcttgccact gcactccagc ctggacagca gagtgaaacc ttgcctcacg   6600
aaacagaata caaaaacaaa caaacaaaaa actgctccgc aatgcgcttc cttgatgctc   6660
taccacatag gtctgggtac tttgtacaca ttatctcatt gctgttcata attgttagat   6720
taattttgta atattgatat tattcctaga aagctgaggc ctcaagatga taactttat   6780 tttctggact tgtaatagct ttctcttgta ttcaccatgt tgtaactttc ttagagtagt   6840
aacaatataa agttattgtg agttttgca aacacagcaa acacaacgac ccatatagac   6900
attgatgtga aattgtctat tgtcaattta tgggaaaaca agtatgtact ttttctacta   6960
agccattgaa acaggaataa cagaacaaga ttgaaagaat acattttccg aaattacttg   7020
agtattatac aaagacaagc acgtggacct gggaggaggg ttattgtcca tgactggtgt   7080
gtggagacaa atgcaggttt ataatagatg ggatggcatc tagcgcaatg actttgccat   7140
cacttttaga gagctcttgg gggcccagt acacaagagg ggacgcaggg tatatgtaga   7200
catctcattc ttttttcttag tgtgagaata agaaatagcca tgacctgagt ttatagacaa   7260
tgagcccttt tctctctccc actcagcagc tatgagatgg cttgccctgc ctctctacta   7320
```

```
ggctgactca ctccaaggcc cagcaatggg cagggctctg tcagggcttt gatagcacta    7380
tctgcagagc cagggccgag aagggtgga ctccagagac tctccctccc attcccgagc     7440
agggtttgct tatttatgca tttaaatgat atatttattt taaaagaaat aacaggagac    7500
tgcccagccc tggctgtgac atggaaacta tgtagaatat tttgggttcc attttttttt    7560
ccttctttca gttagaggaa aaggggctca ctgcacatac actagacaga aagtcaggag    7620
ctttgaatcc aagcctgatc atttccatgt catactgaga aagtcccccac ccttctctga   7680 gcctcagttt ctcttttat aagtaggagt ctggagtaaa tgatttccaa tggctctcat     7740
ttcaatacaa aatttccgtt tattaaatgc atgagcttcc gttactccaa gactgagaag    7800
gaaattgaac ctgagactca ttgactggca agatgtcccc agaggctctc attcagcaat    7860
aaaattctca ccttcaccca ggcccactag tgtcagattt gcatgcgtta acgcggccgc    7920
atcgatgccg tagtaccttt aagaccaatg acttacaagg cagctgtaga tcttagccac    7980 ttttaaaag aaaaggggggg actgaaggg ctaattcact cccaaagaag acaagatccc     8040
tgcaggcatt caaggccagg ctggatgtgg ctctgggcag cctgggctgc tggttgatga    8100
ccctgcacat agcaggggt tggatctgga tgagcactgt gctcctttgc aacccaggcc     8160
gttctatgat tctgtcattc taaatctctc tttcagccta aagctttttc cccgtatccc    8220
cccaggtgtc tgcaggctca aagagcagcg agaagcgttc agaggaaagc gatcccgtgc    8280
caccttcccc gtgcccgggc tgtccccgca cgctgccggc tcggggatgc gggggggagcg   8340 ccggaccgga gcggagcccc gggcggctcg ctgctgcccc ctagcggggg agggacgtaa    8400
ttacatccct gggggctttg ggggggggct gtccccgtga gctccccaga tctgcttttt    8460
gcctgtactg ggtctctctg gttagaccag atctgagcct gggagctctc tggctaacta    8520
gggaacccac tgcttaagcc tcaataaagc ttcagctgct cgagctagca gatctttttc    8580
cctctgccaa aaattatggg gacatcatga agccccttga gcatctgact tctggctaat    8640
aaaggaaatt tatttcatt gcaatagtgt gttggaattt tttgtgtctc tcactcggaa     8700
ggacatatgg gagggcaaat catttaaaac atcagaatga gtatttggtt tagagtttgg    8760
caacatatgc ccatatgctg gctgccatga acaaaggttg gctataaaga ggtcatcagt    8820
atatgaaaca gcccctgct gtccattcct tattccatag aaaagccttg acttgaggtt     8880 agatttttt tatattttgt tttgtgttat ttttttcttt aacatcccta aaattttcct    8940
tacatgtttt actagccaga ttttttcctcc tctcctgact actcccagtc atagctgtcc   9000
ctcttctctt atggagatcc ctcgacctgc agcccaagct tggcgtaatc atggtcatag    9060
ctgtttcctg tgtgaaattg ttatccgctc acaattccac acaacatacg agccggaagc    9120
ataaagtgta aagcctgggg tgcctaatga gtgagctaac tcacattaat tgcgttgcgc    9180
tcactgcccg ctttccagtc gggaaacctg tcgtgccagc ggatccgcat ctcaattagt    9240
cagcaaccat agtcccgccc ctaactccgc ccatcccgcc cctaactccg cccagttccg    9300
cccattctcc gccccatggc tgactaattt ttttatttta tgcagaggcc gaggccgcct    9360
cggcctctga gctattccag aagtagtgag gaggcttttt tggaggccta ggcttttgca    9420
aaaagctgtc gactgcagag gcctgcatgc aagcttggcg taatcatggt catagctgtt    9480
tcctgtgtga aattgttatc cgctcacaat tccacacaac atacgagccg gaagcataaa    9540
gtgtaaagcc tggggtgcct aatgagtgag ctaactcaca ttaattgcgt tgcgctcact    9600
gcccgctttc cagtcgggaa acctgtcgtg ccagctgcat taatgaatcg ccaacgcgc     9660
```

```
ggggagaggc ggtttgcgta ttgggcgctc ttccgcttcc tcgctcactg actcgctgcg    9720
ctcggtcgtt cggctgcggc gagcggtatc agctcactca aaggcggtaa tacggttatc    9780
cacagaatca ggggataacg caggaaagaa catgtgagca aaaggccagc aaaaggccag    9840
gaaccgtaaa aaggccgcgt tgctggcgtt tttccatagg ctccgccccc ctgacgagca    9900
tcacaaaaat cgacgctcaa gtcagaggtg gcgaaacccg acaggactat aaagatacca    9960
ggcgtttccc cctggaagct ccctcgtgcg ctctcctgtt ccgaccctgc cgcttaccgg    10020
atacctgtcc gcctttctcc cttcgggaag cgtggcgctt tctcatagct cacgctgtag    10080
gtatctcagt tcggtgtagg tcgttcgctc caagctgggc tgtgtgcacg aaccccccgt    10140
tcagcccgac cgctgcgcct tatccggtaa ctatcgtctt gagtccaacc cggtaagaca    10200
cgacttatcg ccactggcag cagccactgg taacaggatt agcagagcga ggtatgtagg    10260
cggtgctaca gagttcttga agtggtggcc taactacggc tacactagaa gaacagtatt    10320
tggtatctgc gctctgctga agccagttac cttcggaaaa agagttggta gctcttgatc    10380
cggcaaacaa accaccgctg gtagcggtgg ttttttgtt tgcaagcagc agattacgcg    10440
cagaaaaaaa ggatctcaag aagatccttt gatcttttct acggggtctg acgctcagtg    10500
gaacgaaaac tcacgttaag ggattttggt catgagatta tcaaaaagga tcttcaccta    10560
gatcctttta aattaaaaat gaagttttaa atcaatctaa agtatatatg agtaaacttg    10620
gtctgacagt taccaatgct taatcagtga ggcacctatc tcagcgatct gtctatttcg    10680
ttcatccata gttgcctgac tccccgtcgt gtagataact acgatacggg agggcttacc    10740
atctggcccc agtgctgcaa tgataccgcg agacccacgc tcaccggctc cagatttatc    10800
agcaataaac cagccagccg gaagggccga gcgcagaagt ggtcctgcaa ctttatccgc    10860
ctccatccag tctattaatt gttgccggga agctagagta agtagttcgc cagttaatag    10920
tttgcgcaac gttgttgcca ttgctacagg catcgtggtg tcacgctcgt cgtttggtat    10980
ggcttcattc agctccggtt cccaacgatc aaggcgagtt acatgatccc ccatgttgtg    11040
caaaaaagcg gttagctcct tcggtcctcc gatcgttgtc agaagtaagt tggccgcagt    11100
gttatcactc atggttatgg cagcactgca taattctctt actgtcatgc catccgtaag    11160
atgcttttct gtgactggtg agtactcaac caagtcattc tgagaatagt gtatgcggcg    11220
accgagttgc tcttgcccgg cgtcaatacg ggataatacc gcgccacata gcagaacttt    11280
aaaagtgctc atcattggaa aacgttcttc ggggcgaaaa ctctcaagga tcttaccgct    11340
gttgagatcc agttcgatgt aacccactcg tgcacccaac tgatcttcag catcttttac    11400
tttcaccagc gtttctgggt gagcaaaaac aggaaggcaa aatgccgcaa aaaagggaat    11460
aagggcgaca cggaaatgtt gaatactcat actcttcctt tttcaatatt attgaagcat    11520
ttatcagggt tattgtctca tgagcggata catatttgaa tgtatttaga aaaataaaca    11580
aataggggtt ccgcgcacat ttccccgaaa agtgccacct gacgtctaag aaaccattat    11640
tatcatgaca ttaacctata aaaataggcg tatcacgagg ccctttcgtc tcgcgcgttt    11700
cggtgatgac ggtgaaaacc tctgacacat gcagctcccg gagacggtca gcttgtctgt    11760
gtaagcggat gccgggagca gacaagcccg tcagggcgcg tcagcgggtg ttggcgggtg    11820
tcggggctgg cttaactatg cggcatcaga gcagattgta ctgagagtgc accatatgcg    11880
gtgtgaaata ccgcacagat gcgtaaggag aaaataccgc atcaggcgcc attcgccatt    11940
caggctcgcg aactgttggg aagggcgatc ggtgcgggcc tcttcgctat tacgccagct    12000
ggcgaaaggg ggatgtgctg caaggcgatt aagttgggta acgccagggt tttcccagtc    12060
```

```
acgacgttgt aaaacgacgg ccagtgaatt c                              12091
```

<210> SEQ ID NO 7
<211> LENGTH: 12088
<212> TYPE: DNA
<213> ORGANISM: Artificial Sequence
<220> FEATURE:
<223> OTHER INFORMATION: Synthetic: TL20c-r7SKM1/sh734-rGbGM

<400> SEQUENCE: 7

```
ggccgcctcg gccaaacagc ccttgagttt accactccct atcagtgata gagaaaagtg      60
aaagtcgagt ttaccactcc ctatcagtga tagagaaaag tgaaagtcga gtttaccact     120
ccctatcagt gatagagaaa agtgaaagtc gagtttacca ctccctatca gtgatagaga     180
aaagtgaaag tcgagtttac cagtccctat cagtgataga gaaagtgaa agtcgagttt     240
accactccct atcagtgata gagaaaagtg aaagtcgagt ttaccactcc ctatcagtga     300
tagagaaaag tgaaagtcga gctcgccatg ggaggcgtgg cctgggcggg actggggagt     360
ggcgagccct cagatcctgc atataagcag ctgcttttg cctgtactgg gtctctctgg     420
ttagaccaga tctgagcctg ggagctctct ggctaactag ggaacccact gcttaagcct     480
caataaagct tgccttgagt gcttcaagta gtgtgtgccc gtctgttgtg tgactctggt     540
aactagagat ccctcagacc cttttagtca gtgtggaaaa tctctagcag tggcgcccga     600
acagggactt gaaagcgaaa gggaaaccag aggagctctc tcgacgcagg actcggcttg     660
ctgaagcgcg cacggcaaga ggcgaggggc ggcgactggt gagtacgcca aaaattttga     720
ctagcggagg ctagaaggag agagatgggt gcgagagcgt cagtattaag cgggggagaa     780
ttagatcgcg atgggaaaaa attcggttaa ggccaggggg aaagaaaaaa tataaattaa     840
aacatatagt atgggcaagc agggagctag aacgattcgc agttaatact ggcctgttag     900
aaacatcaga aggctgtaga caaatactgg gacagctaca accatccctt cagacaggat     960
cagaagaact tagatcatta tataatacag tagcaaccct ctattgtgtg catcaaagga    1020
tagagataaa agacaccaag gaagctttag acaagataga ggaagagcaa acaaaagta    1080
agaaaaaagc acagcaagca gcaggatctt cagacctgga aattccctac aatccccaaa    1140
gtcaaggagt agtagaatct atgaataaag aattaaagaa aattatagga caggtaagag    1200
atcaggctga acatcttaag acagcagtac aaatggcagt attcatccac aattttaaaa    1260
gaaaaggggg gattgggggg tacagtgcag gggaagaat agtagacata atagcaacag    1320
acatacaaac taaagaatta caaaaacaaa ttacaaaaat tcaaaatttt cgggtttatt    1380
acagggacag cagaaatcca ctttggaaag gaccagcaaa gctcctctgg aaaggtgaag    1440
gggcagtagt aatacaagat aatagtgaca taaagtagt gccaagaaga aaagcaaaga    1500
tcattaggga ttatggaaaa cagatggcag gtgatgattg tgtggcaagt agacaggatg    1560
aggattagaa catggaaaag tttagtaaaa caccataagg aggagatatg agggacaatt    1620
ggagaagtga attatataaa tataaagtag taaaaattga accattagga gtagcaccca    1680
ccaaggcaaa gagaagagtg gtgcagagag aaaaagagc agtgggaata ggagctttgt    1740
tccttgggtt cttgggagca gcaggaagca ctatgggcgc agcgtcaatg acgctgacgg    1800
tacaggccag acaattattg tctggtatag tgcagcagca gaacaatttg ctgagggcta    1860
ttgaggcgca acagcatctg ttgcaactca gtctggggg catcaagcag ctccaggcaa    1920
gaatcctggc tgtggaaaga tacctaaagg atcaacagct cctggggatt tggggttgct    1980
```

```
ctggaaaact catttgcacc actgctgtgc cttggaatgc tagttggagt aataaatctc    2040
tggaacagat ttggaatcac acgacctgga tggagtggga cagagaaatt aacaattaca    2100
caagcttaat acactcctta attgaagaat cgcaaaacca gcaagaaaag aatgaacaag    2160
aattattgga attagataaa tgggcaagtt tgtggaattg gtttaacata acaaattggc    2220
tgtggtatat aaaattattc ataatgatag taggaggctt ggtaggttta agaatagttt    2280
ttgctgtact ttctatagtg aatagagtta ggcaggata ttcaccatta tcgtttcaga    2340
cccacctccc aaccccgagg ggaccgagct caagcttcga agcggccgca aaaaggata    2400 tgcccttgac tatgtcggac aaatagtcaa gggcatatcc tgaggtaccc aggcggcgca    2460
caagctatat aaacctgaag gaaatctcaa cttacactt aggtcaagtt acttatcgta    2520
ctagagcttc agcaggaaat ttaactaaaa tctaatttaa ccagcatagc aaatatcatt    2580
tattcccaaa atgctaaagt ttgagataaa cggacttgat ttccggctgt tttgacacta    2640
tccagaatgc cggtactatg ggtggggcag tagcccgact gcacgtcgaa cgcgtgggga    2700
tcctctagag tcgagctcgc gaggatcatc accggtgcta gccggagcca gaagcaccat    2760
aagggacatg ataagggagc cagcagacct ctgatctctt cctgaatgct aatcttaaac    2820
atcctgagga agaatgggac ttccatttgg ggtgggccta tgatagggta ataagacagt    2880
agtgaatatc aagctacaaa aagcccccctt tcaaattctt ctcagtccta acttttcata    2940
ctaagcccag tccttccaaa gcagactgtg aaagagtgat agttccggga gactagcacc    3000
ggctagccga gcttggaaca ctttcccttc attaagaacc atccttgcta ctcagctgca    3060
atcaatccag cccccaggtc ttcactgaac cttttcccat ctcttccaaa acatctgttt    3120
ctgagaagtc ctgtcctata gaggtctttc ttcccaccgg atttctccta caccatttac    3180
tcccacttgc agaactcccg tgtacaagtg tctttactgc ttttatttgc tcaacaaaat    3240
gcacatctca tataaaaata aatgaggagc atgcacacac cacaaacaca aacaggcatg    3300
cagaaataca catacacact tccctcaata taaacccttt gtggctcata tatttaaaaa    3360
gatgtaaaaa aaagagctga agaaaatcat gtgtgatctc tcagcagaat agatttatta    3420
tttgtattgc ttgcagaata aagcctatcc ttgaaagctc tgaatcatgg gcaagaggct    3480
cagtggtatc tggaggacag ggcactggcc actgcagtca ccatcttctg ccaggaagcc    3540
tgcacctcag gggtgaattc tttgccaaag tgaatggcca gcacggtgac cagcacgttg    3600
cccaggagct gtgggaggaa gataagaggt atgaacatga ttagcaaaag ggcctagctt    3660
ggactcagaa taatccagcc ttatcccaac cataaaataa aagcagaatg gtagctggat    3720
tgtagctgct attagcaata tgaaacctct tacatcagtt acaatttata tgcagaaata    3780
tttatatgca gaaatattgc tattgcctta acccagaaat tatcactgtt attctttaga    3840
atggtgcaaa gaggcatgat acattgtatc attattgccc tgaaagaaag agattaggga    3900
aagtattaga aataagataa acaaaaaagt atattaaaag aagaaagcat ttttttaaat    3960
tacaaatgca aaattaccct gatttggtca atatgtgtac cctgttactt ctcccctccc    4020
tatgacatga acttaaccat agaaaagaag gggaaagaaa acatcaaggg tcccatagac    4080
tcaccttgaa gttctcagga tccacatgca gcttgtcaca gtgcagttca ctcagctggg    4140
caaaggtgcc cttgagatca tccaggtgct ttatggcatc tcccaaggaa gtcagcacct    4200
tcttgccatg tgccttgact ttggggttgc ccatgatggc agaggcagag gacaggttgc    4260
caaagctgtc aaagaacctc tgggtccatg ggtagacaac caggagcctg tgagattgac    4320
aagaacagtt tgacagtcag aaggtgccac aaatcctgag aagcaacctg gacttttgcc    4380
```

```
aggcacaggg tccttccttc cctcccttgt cctggtcacc agagcctacc ttcccagggt    4440
ttctcctcca gcatcttcca cattcacctt gtcccacagg cttgtgatag tagccttgtc    4500
ctcctctgtg aaatgaccca tggtgtctgt ttgaggttgc tagtgaacac agttgtgtca    4560
gaagcaaatg taagcaatag atggctctgc cctgactttt atgcccagcc ctggctcctg    4620
ccctccctgc tcctgggagt agattggcca accctagggt gtggctccac agggtgaggt    4680
ctaagtgatg acagccgtac ctgtccttgg ctcttctggc actggcttag gagttggact    4740
tcaaaccctc agccctccct ctaagatata tctcttggcc ccataccatc agtacaaatt    4800
gctactaaaa acatcctcct ttgcaagtgt atttacgacg gtatcgatgt atgtgagcat    4860
gtgtcctcta acagcacagg ccttttgcca cctagctgtc caggggtgcc ttaaaatggc    4920
aaacaaggtt tgttttcttt tcctgttttc atgccttcct cttccatatc cttgtttcat    4980
attaatacat gtgtatagat cctaaaaatc tatacacatg tattaataaa gcctgattct    5040
gccgcttcta ggtatagagg ccacctgcaa gataaatatt tgattcacaa taactaatca    5100
ttctatggca attgataaca acaaatatat atatatatat atatatacgt atatgtgtat    5160
atatatatat atattcagga aataatatat tctagaatat gtcacattct gtctcaggca    5220
tccattttct ttatgatgcc gtttgaggtg gagttttagt caggtggtca gcttctcctt    5280 tttttttgcca tctgccctgt aagcatcctg ctggggaccc agataggagt catcactcta    5340
ggctgagaac atctgggcac acaccctaag cctcagcatg actcatcatg actcagcatt    5400
gctgtgcttg agccagaagg tttgcttaga aggttacaca gaaccagaag gcggggggtgg    5460 ggcactgacc ccgacagggg cctggccaga actgctcatg cttggactat gggaggtcac    5520
taatggagac acacagaaat gtaacaggaa ctaagggaat tccggtgccc tgcttaggag    5580 cttaatctttt aatgaaagct aagctttcat taaaaaaagt ctaaccagct gcattcgact    5640
ttgactgcag cagctggtta gaaggttcta ctggaggagg gtcccagccc attgctaaat    5700
taacatcagg ctctgagact ggcagtatat ctctaacagt ggttgatgct atcttctgga    5760
acttgcctgc tacattgaga ccactgaccc atacatagga agcccatagc tctgtcctga    5820
actgttaggc cactggtcca gagagtgtgc atctcctttg atcctcataa taaccctatg    5880
agatagacac aattattact cttactttat agatgatgat cctgaaaaca taggagtcaa    5940
ggcacttgcc cctagctggg ggtataggggg agcagtccca tgtagtagta gaatgaaaaa    6000
tgctgctatg ctgtgcctcc cccacctttc ccatgtctgc cctctactca tggtctatct    6060
ctcctggctc ctgggagtca tggactccac ccagcaccac caacctgacc taaccaccta    6120
tctgagcctg ccagcctata acccatctgg gccctgatag ctggtggcca gccctgaccc    6180 cacccccaccc tccctggaac ctctgataga cacatctggc acaccagctc gcaaagtcac    6240
cgtgagggtc ttgtgtttgc tgagtcaaaa ttccttgaaa tccaagtcct tagagactcc    6300
tgctcccaaa tttacagtca tagacttctt catggctgtc tcctttatcc acagaatgat    6360
tcctttgctt cattgcccca tccatctgat cctcctcatc agtgcagcac agggcccatg    6420
agcagtagct gcagagtctc acataggtct ggcactgcct ctgacatgtc cgaccttagg    6480
caaatgcttg actcttctga gctcggatcc cttgagctca ggaggtcaag gctgcagtga    6540
gacatgatct tgccactgca ctccagcctg gacagcagag tgaaaccttg cctcacgaaa    6600
cagaatacaa aaacaaacaa acaaaaaaact gctccgcaat gcgcttcctt gatgctctac    6660
cacataggtc tgggtacttt gtacacatta tctcattgct gttcataatt gttagattaa    6720
```

```
ttttgtaata ttgatattat tcctagaaag ctgaggcctc aagatgataa cttttatttt      6780
ctggacttgt aatagctttc tcttgtattc accatgttgt aactttctta gagtagtaac      6840
aatataaagt tattgtgagt ttttgcaaac acagcaaaca caacgaccca tatagacatt      6900
gatgtgaaat tgtctattgt caatttatgg gaaaacaagt atgtactttt tctactaagc      6960
cattgaaaca ggaataacag aacaagattg aaagaataca ttttccgaaa ttacttgagt      7020
attatacaaa gacaagcacg tggacctggg aggagggtta ttgtccatga ctggtgtgtg      7080
gagacaaatg caggtttata atagatggga tggcatctag cgcaatgact ttgccatcac      7140
ttttagagag ctcttggggg ccccagtaca aagaggggga cgcagggtat atgtagacat      7200
ctcattcttt ttcttagtgt gagaataaga atagccatga cctgagttta tagacaatga      7260
gcccttttct ctctcccact cagcagctat gagatggctt gccctgcctc tctactaggc      7320
tgactcactc caaggcccag caatgggcag ggctctgtca gggctttgat agcactatct      7380
gcagagccag ggccgagaag gggtggactc cagagactct ccctcccatt cccgagcagg      7440
gtttgcttat ttatgcattt aaatgatata tttattttaa aagaaataac aggagactgc      7500
ccagccctgg ctgtgacatg gaaactatgt agaatatttt gggttccatt ttttttttcct     7560 tctttcagtt agaggaaaag gggctcactg cacatacact agacagaaag tcaggagctt      7620
tgaatccaag cctgatcatt tccatgtcat actgagaaag tccccaccct tctctgagcc      7680
tcagtttctc tttttataag taggagtctg gagtaaatga tttccaatgg ctctcatttc      7740
aatacaaaat ttccgtttat taaatgcatg agcttccgtt actccaagac tgagaaggaa      7800
attgaacctg agactcattg actggcaaga tgtccccaga ggctctcatt cagcaataaa      7860
attctcacct tcacccaggc ccactagtgt cagatttgca tgcgttaacg cggccgcatc      7920
gatgccgtag tacctttaag accaatgact tacaaggcag ctgtagatct tagccacttt      7980
ttaaaagaaa agggggggact ggaagggcta attcactccc aaagaagaca agatccctgc     8040
aggcattcaa ggccaggctg gatgtggctc tgggcagcct gggctgctgg ttgatgaccc      8100
tgcacatagc aggggggttgg atctggatga gcactgtgct cctttgcaac ccaggccgtt     8160
ctatgattct gtcattctaa atctctcttt cagcctaaag ctttttcccc gtatcccccc      8220
aggtgtctgc aggctcaaag agcagcgaga agcgttcaga ggaaagcgat cccgtgccac      8280
cttccccgtg cccgggctgt ccccgcacgc tgccggctcg gggatgcggg gggagcgccg      8340
gaccggagcg gagccccggg cggctcgctg ctgccccta gcggggagg gacgtaatta       8400 catccctggg ggctttgggg ggggctgtc cccgtgagct ccccagatct gcttttgtgcc     8460 tgtactgggt ctctctggtt agaccagatc tgagcctggg agctctctgg ctaactaggg     8520
aacccactgc ttaagcctca ataaagcttc agctgtcga gctagcagat cttttttccct     8580 ctgccaaaaa ttatggggac atcatgaagc cccttgagca tctgacttct ggctaataaa      8640
ggaaatttat tttcattgca atagtgtgtt ggaatttttt gtgtctctca ctcggaagga      8700
catatgggag ggcaaatcat ttaaaacatc agaatgagta tttggtttag agtttggcaa      8760
catatgccca tatgctggct gccatgaaca aaggttggct ataaagaggt catcagtata      8820
tgaaacagcc cctgctgtc cattccttat tccatagaaa agccttgact tgaggttaga       8880
ttttttttat attttgtttt gtgttatttt tttctttaac atccctaaaa ttttccttac      8940
atgttttact agccagattt ttcctcctct cctgactact cccagtcata gctgtccctc      9000
ttctcttatg gagatccctc gacctgcagc ccaagcttgg cgtaatcatg gtcatagctg      9060
tttcctgtgt gaaattgtta tccgctcaca attccacaca acatacgagc cggaagcata      9120
```

```
aagtgtaaag cctggggtgc ctaatgagtg agctaactca cattaattgc gttgcgctca   9180
ctgcccgctt tccagtcggg aaacctgtcg tgccagcgga tccgcatctc aattagtcag   9240
caaccatagt cccgcccta actccgccca tcccgcccct aactccgccc agttccgccc   9300
attctccgcc ccatggctga ctaattttttt ttatttatgc agaggccgag gccgcctcgg   9360
cctctgagct attccagaag tagtgaggag gcttttttgg aggcctaggc ttttgcaaaa   9420
agctgtcgac tgcagaggcc tgcatgcaag cttggcgtaa tcatggtcat agctgtttcc   9480
tgtgtgaaat tgttatccgc tcacaattcc acacaacata cgagccggaa gcataaagtg   9540
taaagcctgg ggtgcctaat gagtgagcta actcacatta attgcgttgc gctcactgcc   9600
cgctttccag tcgggaaacc tgtcgtgcca gctgcattaa tgaatcggcc aacgcgcggg   9660
gagaggcggt ttgcgtattg ggcgctcttc cgcttcctcg ctcactgact cgctgcgctc   9720
ggtcgttcgg ctgcggcgag cggtatcagc tcactcaaag gcggtaatac ggttatccac   9780
agaatcaggg gataacgcag gaaagaacat gtgagcaaaa ggccagcaaa aggccaggaa   9840
ccgtaaaaag gccgcgttgc tggcgttttt ccataggctc cgcccccctg acgagcatca   9900
caaaaatcga cgctcaagtc agaggtggcg aaacccgaca ggactataaa gataccaggc   9960
gtttccccct ggaagctccc tcgtgcgctc tcctgttccg accctgccgc ttaccggata  10020
cctgtccgcc tttctccctt cgggaagcgt ggcgctttct catagctcac gctgtaggta  10080
tctcagttcg gtgtaggtcg ttcgctccaa gctgggctgt gtgcacgaac cccccgttca  10140
gcccgaccgc tgcgccttat ccggtaacta tcgtcttgag tccaacccgg taagacacga  10200
cttatcgcca ctggcagcag ccactggtaa caggattagc agagcgaggt atgtaggcgg  10260
tgctacagag ttcttgaagt ggtggcctaa ctacggctac actagaagaa cagtatttgg  10320
tatctgcgct ctgctgaagc cagttacctt cggaaaaaga gttggtagct cttgatccgg  10380
caaacaaacc accgctggta gcggtggttt tttgtttgc aagcagcaga ttacgcgcag  10440
aaaaaaagga tctcaagaag atcctttgat cttttctacg gggtctgacg ctcagtggaa  10500
cgaaaactca cgttaaggga ttttggtcat gagattatca aaaaggatct tcacctagat  10560
ccttttaaat taaaaatgaa gttttaaatc aatctaaagt atatatgagt aaacttggtc  10620
tgacagttac caatgcttaa tcagtgaggc acctatctca gcgatctgtc tatttcgttc  10680
atccatagtt gcctgactcc ccgtcgtgta gataactacg atacgggagg cttaccatc  10740 tggccccagt gctgcaatga taccgcgaga cccacgctca ccggctccag atttatcagc  10800
aataaaccag ccagccggaa gggccgagcg cagaagtggt cctgcaactt tatccgcctc  10860
catccagtct attaattgtt gccgggaagc tagagtaagt agttcgccag ttaatagttt  10920
gcgcaacgtt gttgccattg ctacaggcat cgtggtgtca cgctcgtcgt ttggtatggc  10980
ttcattcagc tccggttccc aacgatcaag gcgagttaca tgatccccca tgttgtgcaa  11040
aaaagcggtt agctccttcg gtcctccgat cgttgtcaga agtaagttgg ccgcagtgtt  11100
atcactcatg gttatggcag cactgcataa ttctcttact gtcatgccat ccgtaagatg  11160
cttttctgtg actggtgagt actcaaccaa gtcattctga atagtgta tgcggcgacc  11220 gagttgctct tgcccggcgt caatacggga taataccgcg ccacatagca gaactttaaa  11280
agtgctcatc attggaaaac gttcttcggg gcgaaaactc tcaaggatct taccgctgtt  11340
gagatccagt tcgatgtaac ccactcgtgc acccaactga tcttcagcat cttttacttt  11400
caccagcgtt tctgggtgag caaaaacagg aaggcaaaat gccgcaaaaa agggaataag  11460
```

-continued

```
ggcgacacgg aaatgttgaa tactcatact cttccttttt caatattatt gaagcattta    11520
tcagggttat tgtctcatga gcggatacat atttgaatgt atttagaaaa ataaacaaat    11580
aggggttccg cgcacatttc cccgaaaagt gccacctgac gtctaagaaa ccattattat    11640
catgacatta acctataaaa ataggcgtat cacgaggccc tttcgtctcg cgcgtttcgg    11700
tgatgacggt gaaaacctct gacacatgca gctcccggag acggtcacag cttgtctgta    11760
agcggatgcc gggagcagac aagcccgtca gggcgcgtca gcgggtgttg gcgggtgtcg    11820
gggctggctt aactatgcgg catcagagca gattgtactg agagtgcacc atatgcggtg    11880
tgaaataccg cacagatgcg taaggagaaa ataccgcatc aggcgccatt cgccattcag    11940
gctgcgcaac tgttgggaag ggcgatcggt gcgggcctct tcgctattac gccagctggc    12000
gaaaggggga tgtgctgcaa ggcgattaag ttgggtaacg ccagggtttt cccagtcacg    12060
acgttgtaaa acgacggcca gtgaattc                                       12088
```

<210> SEQ ID NO 8
<211> LENGTH: 12091
<212> TYPE: DNA
<213> ORGANISM: Artificial Sequence
<220> FEATURE:
<223> OTHER INFORMATION: Synthetic: TL20c-r7SK/sh734-rGbGM

<400> SEQUENCE: 8

```
ggccgcctcg gccaaacagc ccttgagttt accactccct atcagtgata gagaaaagtg      60
aaagtcgagt ttaccactcc ctatcagtga tagagaaaag tgaaagtcga gtttaccact     120
ccctatcagt gatagagaaa agtgaaagtc gagtttacca ctccctatca gtgatagaga     180
aaagtgaaag tcgagtttac cagtccctat cagtgataga gaaaagtgaa agtcgagttt     240
accactccct atcagtgata gagaaaagtg aaagtcgagt ttaccactcc ctatcagtga     300
tagagaaaag tgaaagtcga gctcgccatg ggaggcgtgg cctgggcggg actggggagt     360
ggcgagccct cagatcctgc atataagcag ctgcttttg cctgtactgg gtctctctgg     420
ttagaccaga tctgagcctg ggagctctct ggctaactag ggaacccact gcttaagcct     480
caataaagct tgccttgagt gcttcaagta gtgtgtgccc gtctgttgtg tgactctggt     540
aactagagat ccctcagacc cttttagtca gtgtggaaaa tctctagcag tggcgcccga     600
acagggactt gaaagcgaaa gggaaaccag aggagctctc tcgacgcagg actcggcttg     660
ctgaagcgcg cacggcaaga ggcgaggggc ggcgactggt gagtacgcca aaaattttga     720
ctagcggagg ctagaaggag agagatgggt gcgagagcgt cagtattaag cgggggagaa     780
ttagatcgcg atgggaaaaa attcggttaa ggccaggggg aaagaaaaaa tataaattaa     840
aacatatagt atgggcaagc agggagctag aacgattcgc agttaatact ggcctgttag     900
aaacatcaga aggctgtaga caaatactgg gacagctaca accatccctt cagacaggat     960
cagaagaact tagatcatta tataatacag tagcaaccct ctattgtgtg catcaaagga    1020
tagagataaa agacaccaag gaagctttag acaagataga ggaagagcaa aacaaaagta    1080
agaaaaaagc acagcaagca gcaggatctt cagacctgga aattccctac aatcccccaaa   1140 gtcaaggagt agtagaatct atgaataaag aattaaagaa aattatagga caggtaagag    1200
atcaggctga acatcttaag acagcagtac aaatggcagt attcatccac aatttaaaa     1260 gaaaggggga gattgggggg tacagtgcag gggaagaat agtagacata atagcaacag     1320
acatacaaac taaagaatta caaaaacaaa ttacaaaaat tcaaaatttt cgggtttatt     1380
acagggacag cagaaatcca ctttggaaag gaccagcaaa gctcctctgg aaaggtgaag    1440
```

```
gggcagtagt aatacaagat aatagtgaca taaaagtagt gccaagaaga aaagcaaaga    1500
tcattaggga ttatggaaaa cagatggcag gtgatgattg tgtggcaagt agacaggatg    1560
aggattagaa catggaaaag tttagtaaaa caccataagg aggagatatg agggacaatt    1620
ggagaagtga attatataaa tataaagtag taaaaattga accattagga gtagcaccca    1680
ccaaggcaaa gagaagagtg gtgcagagag aaaaaagagc agtgggaata ggagctttgt    1740
tccttgggtt cttgggagca gcaggaagca ctatgggcgc agcgtcaatg acgctgacgg    1800
tacaggccag acaattattg tctggtatag tgcagcagca gaacaatttg ctgagggcta    1860
ttgaggcgca acagcatctg ttgcaactca cagtctgggg catcaagcag ctccaggcaa    1920
gaatcctggc tgtggaaaga tacctaaagg atcaacagct cctggggatt tggggttgct    1980
ctggaaaact catttgcacc actgctgtgc cttggaatgc tagttggagt aataaatctc    2040
tggaacagat ttggaatcac acgacctgga tggagtggga cagagaaatt aacaattaca    2100
caagcttaat acactcctta attgaagaat cgcaaaacca gcaagaaaag aatgaacaag    2160
aattattgga attagataaa tgggcaagtt tgtggaattg gtttaacata acaaattggc    2220
tgtggtatat aaaattattc ataatgatag taggaggctt ggtaggttta agaatagttt    2280
ttgctgtact ttctatagtg aatagagtta ggcagggata ttcaccatta tcgtttcaga    2340
cccacctccc aaccccgagg ggaccgagct caagcttcga agcggccgca caaaaaagga    2400
tatgcccttg actatgtcgg acaaatagtc aagggcatat cctgaggtac ccaggcggcg    2460
cacaagctat ataaacctga aggaaatctc aactttacac ttaggtcaag ttacttatcg    2520
tactagagct tcagcaggaa atttaactaa aatctaattt aaccagcata gcaaatatca    2580
tttattccca aaatgctaaa gtttgagata acggacttg atttccggct gttttgacac    2640
tatccagaat gccttgcaga tgggtggggc atgctaaata ctgcacgtcg atacgcgtgg    2700
ggatcctcta gagtcgagct cgcgaggatc atcaccggtg ctagccggag ccagaagcac    2760
cataagggac atgataaggg agccagcaga cctctgatct cttcctgaat gctaatctta    2820
aacatcctga ggaagaatgg gacttccatt tggggtgggc ctatgatagg gtaataagac    2880
agtagtgaat atcaagctac aaaaagcccc ctttcaaatt cttctcagtc ctaactttc    2940 atactaagcc cagtccttcc aaagcagact gtgaaagagt gatagttccg ggagactagc    3000
accggctagc cgagcttgga acactttccc ttcattaaga accatccttg ctactcagct    3060
gcaatcaatc cagcccccag gtcttcactg aaccttttcc catctcttcc aaaacatctg    3120
tttctgagaa gtcctgtcct atagaggtct ttcttcccac cggatttctc ctacaccatt    3180
tactcccact tgcagaactc ccgtgtacaa gtgtctttac tgcttttatt tgctcaacaa    3240
aatgcacatc tcatataaaa ataaatgagg agcatgcaca caccacaaac acaaacaggc    3300
atgcagaaat acacatacac acttccctca atataaaccc tttgtggctc atatatttaa    3360
aaagatgtaa aaaaagagc tgaagaaaat catgtgtgat ctctcagcag aatagattta    3420
ttatttgtat tgcttgcaga ataaagccta tccttgaaag ctctgaatca tgggcaagag    3480
gctcagtggt atctggagga cagggcactg gccactgcag tcaccatctt ctgccaggaa    3540
gcctgcacct caggggtgaa ttcttttgcca aagtgaatgg ccagcacggt gaccagcacg    3600
ttgcccagga gctgtgggag gaagataaga ggtatgaaca tgattagcaa aagggcctag    3660
cttggactca gaataatcca gccttatccc aaccataaaa taaaagcaga atggtagctg    3720
gattgtagct gctattagca atatgaaacc tcttacatca gttacaattt atatgcagaa    3780
```

```
atatttatat gcagaaatat tgctattgcc ttaacccaga aattatcact gttattcttt    3840
agaatggtgc aaagaggcat gatacattgt atcattattg ccctgaaaga aagagattag    3900
ggaaagtatt agaaataaga taaacaaaaa agtatattaa aagaagaaag catttttaa     3960 aattacaaat gcaaaattac cctgatttgg tcaatatgtg taccctgtta cttctcccct    4020
tcctatgaca tgaacttaac catagaaaag aaggggaaag aaaacatcaa gggtcccata    4080
gactcacctt gaagttctca ggatccacat gcagcttgtc acagtgcagt tcactcagct    4140
gggcaaaggt gcccttgaga tcatccaggt gctttatggc atctcccaag gaagtcagca    4200
ccttcttgcc atgtgccttg actttggggt tgcccatgat ggcagaggca gaggacaggt    4260
tgccaaagct gtcaaagaac ctctgggtcc atgggtagac aaccaggagc ctgtgagatt    4320
gacaagaaca gtttgacagt cagaaggtgc cacaaatcct gagaagcaac ctggactttt    4380
gccaggcaca gggtccttcc ttccctccct tgtcctggtc accagagcct accttcccag    4440
ggtttctcct ccagcatctt ccacattcac cttgtcccac aggcttgtga tagtagcctt    4500
gtcctcctct gtgaaatgac ccatggtgtc tgtttgaggt tgctagtgaa cacagttgtg    4560
tcagaagcaa atgtaagcaa tagatggctc tgccctgact tttatgccca gccctggctc    4620
ctgccctccc tgctcctggg agtagattgg ccaaccctag ggtgtggctc cacagggtga    4680
ggtctaagtg atgacagccg tacctgtcct tggctcttct ggcactggct taggagttgg    4740
acttcaaacc ctcagccctc cctctaagat atatctcttg gccccatacc atcagtacaa    4800
attgctacta aaaacatcct cctttgcaag tgtatttacg acggtatcga tgtatgtgag    4860
catgtgtcct ctaacagcac aggccttttg ccacctagct gtccaggggt gccttaaaat    4920
ggcaaacaag gtttgttttc ttttcctgtt ttcatgcctt cctcttccat atccttgttt    4980
catattaata catgtgtata gatcctaaaa atctatacac atgtattaat aaagcctgat    5040
tctgccgctt ctaggtatag aggccacctg caagataaat atttgattca caataactaa    5100
tcattctatg gcaattgata acaacaaata tatatatata tatatatata cgtatatgtg    5160
tatatatata tatatattca ggaaataata tattctagaa tatgtcacat tctgtctcag    5220
gcatccattt tctttatgat gccgtttgag gtggagtttt agtcaggtgg tcagcttctc    5280 ctttttttg ccatctgccc tgtaagcatc ctgctgggga cccagatagg agtcatcact    5340
ctaggctgag aacatctggg cacacaccct aagcctcagc atgactcatc atgactcagc    5400
attgctgtgc ttgagccaga aggtttgctt agaaggttac acagaaccag aaggcggggg    5460
tggggcactg accccgacag gggcctggcc agaactgctc atgcttggac tatgggaggt    5520
cactaatgga gacacacaga aatgtaacag gaactaaggg aattccggtg ccctgcttag    5580
gagcttaatc tttaatgaaa gctaagcttt cattaaaaaa agtctaacca gctgcattcg    5640
actttgactg cagcagctgg ttagaaggtt ctactggagg agggtcccag cccattgcta    5700
aattaacatc aggctctgag actggcagta tatctctaac agtggttgat gctatcttct    5760
ggaacttgcc tgctacattg agaccactga cccatacata ggaagcccat agctctgtcc    5820
tgaactgtta ggccactggt ccagagagtg tgcatctcct ttgatcctca taataaccct    5880
atgagataga cacaattatt actcttactt tatagatgat gatcctgaaa acataggagt    5940
caaggcactt gcccctagct gggggtatag gggagcagtc ccatgtagta gtagaatgaa    6000
aaatgctgct atgctgtgcc tccccacct ttcccatgtc tgccctctac tcatggtcta    6060
tctctcctgg ctcctgggag tcatggactc cacccagcac caccaacctg acctaaccac    6120
ctatctgagc ctgccagcct ataacccatc tgggccctga tagctggtgg ccagccctga    6180
```

```
ccccacccca ccctccctgg aacctctgat agacacatct ggcacaccag ctcgcaaagt    6240
caccgtgagg gtcttgtgtt tgctgagtca aaattccttg aaatccaagt ccttagagac    6300
tcctgctccc aaatttacag tcatagactt cttcatggct gtctccttta tccacagaat    6360
gattcctttg cttcattgcc ccatccatct gatcctcctc atcagtgcag cacagggccc    6420
atgagcagta gctgcagagt ctcacatagg tctggcactg cctctgacat gtccgacctt    6480
aggcaaatgc ttgactcttc tgagctcgga tcccttgagc tcaggaggtc aaggctgcag    6540
tgagacatga tcttgccact gcactccagc ctggacagca gagtgaaacc ttgcctcacg    6600
aaacagaata caaaaacaaa caaacaaaaa actgctccgc aatgcgcttc cttgatgctc    6660
taccacatag gtctgggtac tttgtacaca ttatctcatt gctgttcata attgttagat    6720
taattttgta atattgatat tattcctaga aagctgaggc tcaagatgaa taacttttat    6780
tttctggact tgtaatagct ttctcttgta ttcaccatgt tgtaactttc ttagagtagt    6840
aacaatataa agttattgtg agtttttgca aacacagcaa acacaacgac ccatatagac    6900
attgatgtga aattgtctat tgtcaattta tgggaaaaca agtatgtact ttttctacta    6960
agccattgaa acaggaataa cagaacaaga ttgaaagaat acattttccg aaattacttg    7020
agtattatac aaagacaagc acgtggacct gggaggaggg ttattgtcca tgactggtgt    7080
gtggagacaa atgcaggttt ataatagatg ggatggcatc tagcgcaatg actttgccat    7140
cacttttaga gagctcttgg gggcccagt acacaagagg ggacgcaggg tatatgtaga    7200
catctcattc tttttcttag tgtgagaata agaaatagcca tgacctgagt ttatagacaa    7260
tgagcccttt tctctctccc actcagcagc tatgagatgg cttgccctgc ctctctacta    7320
ggctgactca ctccaaggcc cagcaatggg cagggctctg tcagggcttt gatagcacta    7380
tctgcagagc cagggccgag aagggtgga ctccagagac tctccctccc attcccgagc    7440
agggtttgct tatttatgca tttaaatgat atatttattt taaaagaaat aacaggagac    7500
tgcccagccc tggctgtgac atggaaacta tgtagaatat tttgggttcc attttttttt    7560
ccttctttca gttagaggaa aaggggctca ctgcacatac actagacaga aagtcaggag    7620
ctttgaatcc aagcctgatc atttccatgt catactgaga aagtccccac ccttctctga    7680
gcctcagttt ctcttttat aagtaggagt ctggagtaaa tgatttccaa tggctctcat    7740
ttcaatacaa aatttccgtt tattaaatgc atgagcttcc gttactccaa gactgagaag    7800
gaaattgaac ctgagactca ttgactggca agatgtcccc agaggctctc attcagcaat    7860
aaaattctca ccttcaccca ggcccactag tgtcagattt gcatgcgtta acgcggccgc    7920
atcgatgccg tagtaccttt aagaccaatg acttacaagg cagctgtaga tcttagccac    7980
tttttaaaag aaaaggggg actggaaggg ctaattcact cccaaagaag acaagatccc    8040
tgcaggcatt caaggccagg ctggatgtgg ctctgggcag cctgggctgc tggttgatga    8100
ccctgcacat agcaggggt tggatctgga tgagcactgt gctcctttgc aacccaggcc    8160
gttctatgat tctgtcattc taaatctctc tttcagccta aagcttttc cccgtatccc    8220 cccaggtgtc tgcaggctca aagagcagcg agaagcgttc agaggaaagc gatcccgtgc    8280
caccttcccc gtgcccgggc tgtccccgca cgctgccggc tcggggatgc gggggagcg    8340 ccggaccgga gcggagcccc gggcggctcg ctgctgcccc ctagcggggg agggacgtaa    8400
ttacatccct gggggctttg ggggggggct gtccccgtga gctccccaga tctgcttttt    8460
gcctgtactg ggtctctctg gttagaccag atctgagcct gggagctctc tggctaacta    8520
```

```
gggaacccac tgcttaagcc tcaataaagc ttcagctgct cgagctagca gatcttttc      8580
cctctgccaa aaattatggg gacatcatga agcccttga gcatctgact tctggctaat       8640
aaaggaaatt tattttcatt gcaatagtgt gttggaattt tttgtgtctc tcactcggaa      8700
ggacatatgg gagggcaaat catttaaaac atcagaatga gtatttggtt tagagtttgg     8760
caacatatgc ccatatgctg gctgccatga acaaaggttg gctataaaga ggtcatcagt    8820
atatgaaaca gccccctgct gtccattcct tattccatag aaaagccttg acttgaggtt    8880
agatttttt tatattttgt tttgtgttat ttttttcttt aacatcccta aaattttcct      8940
tacatgtttt actagccaga tttttcctcc tctcctgact actcccagtc atagctgtcc     9000
ctcttctctt atggagatcc ctcgacctgc agcccaagct tggcgtaatc atggtcatag     9060
ctgtttcctg tgtgaaattg ttatccgctc acaattccac acaacatacg agccggaagc    9120
ataaagtgta aagcctgggg tgcctaatga gtgagctaac tcacattaat tgcgttgcgc    9180
tcactgcccg ctttccagtc gggaaacctg tcgtgccagc ggatccgcat ctcaattagt    9240
cagcaaccat agtcccgccc ctaactccgc ccatcccgcc cctaactccg cccagttccg    9300
cccattctcc gccccatggc tgactaattt tttttattta tgcagaggcc gaggccgcct    9360
cggcctctga gctattccag aagtagtgag gaggctttt tggaggccta ggcttttgca     9420
aaaagctgtc gactgcagag gcctgcatgc aagcttggcg taatcatggt catagctgtt    9480
tcctgtgtga aattgttatc cgctcacaat tccacacaac atacgagccg aagcataaa    9540
gtgtaaagcc tggggtgcct aatgagtgag ctaactcaca ttaattgcgt tgcgctcact   9600
gcccgctttc cagtcgggaa acctgtcgtg ccagctgcat taatgaatcg gccaacgcgc   9660
ggggagaggc ggtttgcgta ttgggcgctc ttccgcttcc tcgctcactg actcgctgcg   9720
ctcggtcgtt cggctgcggc gagcggtatc agctcactca aaggcggtaa tacgttatc    9780
cacagaatca ggggataacg caggaaagaa catgtgagca aaaggccagc aaaaggccag    9840
gaaccgtaaa aaggccgcgt tgctggcgtt tttccatagg ctccgccccc ctgacgagca   9900
tcacaaaaat cgacgctcaa gtcagaggtg gcgaaacccg acaggactat aaagatacca    9960
ggcgtttccc cctggaagct ccctcgtgcg ctctcctgtt ccgaccctgc cgcttaccgg    10020
atacctgtcc gcctttctcc cttcgggaag cgtggcgctt tctcatagct cacgctgtag    10080
gtatctcagt tcggtgtagg tcgttcgctc caagctgggc tgtgtgcacg aaccccccgt   10140
tcagcccgac cgctgcgcct tatccggtaa ctatcgtctt gagtccaacc cggtaagaca   10200
cgacttatcg ccactggcag cagccactgg taacaggatt agcagagcga ggtatgtagg   10260
cggtgctaca gagttcttga agtggtggcc taactacggc tacactagaa gaacagtatt    10320
tggtatctgc gctctgctga gccagttac cttcggaaaa agagttggta gctcttgatc    10380
cggcaaacaa accaccgctg gtagcggtgg ttttttgtt tgcaagcagc agattacgcg     10440
cagaaaaaaa ggatctcaag aagatccttt gatcttttct acggggtctg acgctcagtg    10500
gaacgaaaac tcacgttaag ggattttggt catgagatta caaaaagga tcttaccta      10560
gatccttta aattaaaaat gaagttttaa atcaatctaa agtatatatg agtaaacttg      10620
gtctgacagt taccaatgct taatcagtga ggcacctatc tcagcgatct gtctatttcg    10680
ttcatccata gttgcctgac tccccgtcgt gtagataact acgatacggg agggcttacc   10740
atctggcccc agtgctgcaa tgataccgcg agacccacgc tcaccggctc cagatttatc    10800
agcaataaac cagccagccg gaagggccga gcgcagaagt ggtcctgcaa ctttatccgc    10860
ctccatccag tctattaatt gttgccggga agctagagta agtagttcgc cagttaatag    10920
```

```
tttgcgcaac gttgttgcca ttgctacagg catcgtggtg tcacgctcgt cgtttggtat    10980
ggcttcattc agctccggtt cccaacgatc aaggcgagtt acatgatccc ccatgttgtg    11040
caaaaaagcg gttagctcct tcggtcctcc gatcgttgtc agaagtaagt tggccgcagt    11100
gttatcactc atggttatgg cagcactgca taattctctt actgtcatgc catccgtaag    11160
atgcttttct gtgactggtg agtactcaac caagtcattc tgagaatagt gtatgcggcg    11220
accgagttgc tcttgcccgg cgtcaatacg ggataatacc gcgccacata gcagaacttt    11280
aaaagtgctc atcattggaa aacgttcttc ggggcgaaaa ctctcaagga tcttaccgct    11340
gttgagatcc agttcgatgt aacccactcg tgcacccaac tgatcttcag catcttttac    11400
tttcaccagc gtttctgggt gagcaaaaac aggaaggcaa atgccgcaa aaagggaat     11460 aagggcgaca cggaaatgtt gaatactcat actcttcctt tttcaatatt attgaagcat    11520
ttatcagggt tattgtctca tgagcggata catatttgaa tgtatttaga aaataaaca     11580 aataggggtt ccgcgcacat ttccccgaaa agtgccacct gacgtctaag aaaccattat    11640
tatcatgaca ttaacctata aaaataggcg tatcacgagg ccctttcgtc tcgcgcgttt    11700
cggtgatgac ggtgaaaacc tctgacacat gcagctcccg gagacggtca cagcttgtct    11760
gtaagcggat gccgggagca gacaagcccg tcagggcgcg tcagcgggtg ttggcgggtg    11820
tcggggctgg cttaactatg cggcatcaga gcagattgta ctgagagtgc accatatgcg    11880
gtgtgaaata ccgcacagat gcgtaaggag aaaataccgc atcaggcgcc attcgccatt    11940
caggctgcgc aactgttggg aagggcgatc ggtgcgggcc tcttcgctat tacgccagct    12000
ggcgaaaggg ggatgtgctg caaggcgatt aagttgggta acgccagggt tttcccagtc    12060
acgacgttgt aaaacgacgg ccagtgaatt c                                   12091

<210> SEQ ID NO 9
<211> LENGTH: 12081
<212> TYPE: DNA
<213> ORGANISM: Artificial Sequence
<220> FEATURE:
<223> OTHER INFORMATION: Synthetic: TL20c-rGbGM-7SKM1/sh734

<400> SEQUENCE: 9
ggccgcctcg gccaaacagc ccttgagttt accactccct atcagtgata gagaaaagtg      60
aaagtcgagt ttaccactcc ctatcagtga tagagaaaag tgaaagtcga gtttaccact     120
ccctatcagt gatagagaaa agtgaaagtc gagtttacca ctccctatca gtgatagaga     180
aaagtgaaag tcgagtttac cagtccctat cagtgataga gaaaagtgaa agtcgagttt     240
accactccct atcagtgata gagaaaagtg aaagtcgagt ttaccactcc ctatcagtga     300
tagagaaaag tgaaagtcga gctcgccatg ggaggcgtgg cctgggcggg actggggagt     360
ggcgagccct cagatcctgc atataagcag ctgcttttgt cctgtactgg gtctctctgg     420
ttagaccaga tctgagcctg ggagctctct ggctaactag ggaacccact gcttaagcct     480
caataaagct tgccttgagt gcttcaagta gtgtgtgccc gtctgttgtg tgactctggt     540
aactagagat ccctcagacc ctttagtca gtgtggaaaa tctctagcag tggcgcccga     600
acagggactt gaaagcgaaa gggaaaccag aggagctctc tcgacgcagg actcggcttg     660
ctgaagcgcg cacggcaaga ggcgaggggc ggcgactggt gagtacgcca aaattttga     720 ctagcggagg ctagaaggag agagatgggt gcgagagcgt cagtattaag cgggggagaa     780
ttagatcgcg atgggaaaaa attcggttaa ggccaggggg aagaaaaaa tataaattaa     840
```

```
aacatatagt atgggcaagc agggagctag aacgattcgc agttaatact ggcctgttag    900
aaacatcaga aggctgtaga caaatactgg gacagctaca accatccctt cagacaggat    960
cagaagaact tagatcatta tataatacag tagcaaccct ctattgtgtg catcaaagga   1020
tagagataaa agacaccaag gaagctttag acaagataga ggaagagcaa acaaaagta    1080
agaaaaaagc acagcaagca gcaggatctt cagacctgga aattccctac aatccccaaa   1140
gtcaaggagt agtagaatct atgaataaag aattaaagaa aattatagga caggtaagag   1200
atcaggctga acatcttaag acagcagtac aaatggcagt attcatccac aattttaaaa   1260
gaaaagggggg gattgggggg tacagtgcag gggaaagaat agtagacata atagcaacag   1320
acatacaaac taaagaatta caaaaacaaa ttacaaaaat tcaaaatttt cgggtttatt    1380
acagggacag cagaaatcca ctttggaaag gaccagcaaa gctcctctgg aaaggtgaag   1440
gggcagtagt aatacaagat aatagtgaca taaaagtagt gccaagaaga aaagcaaaga   1500
tcattaggga ttatggaaaa cagatggcag gtgatgattg tgtggcaagt agacaggatg   1560
aggattagaa catggaaaag tttagtaaaa caccataagg aggagatatg agggacaatt   1620
ggagaagtga attatataaa tataagtag taaaaattga accattagga gtagcaccca    1680
ccaaggcaaa gagaagagtg gtgcagagag aaaaaagagc agtgggaata ggagctttgt   1740
tccttgggtt cttgggagca gcaggaagca ctatgggcgc agcgtcaatg acgctgacgg   1800
tacaggccag acaattattg tctggtatag tgcagcagca gaacaatttg ctgagggcta   1860
ttgaggcgca acagcatctg ttgcaactca cagtctgggg catcaagcag ctccaggcaa   1920
gaatcctggc tgtggaaaga tacctaaagg atcaacagct cctggggatt tggggttgct   1980
ctggaaaact catttgcacc actgctgtgc cttggaatgc tagttggagt aataaatctc   2040
tggaacagat ttggaatcac acgacctgga tggagtggga cagagaaatt aacaattaca   2100
caagcttaat acactcctta attgaagaat cgcaaaacca gcaagaaaag aatgaacaag   2160
aattattgga attagataaa tgggcaagtt tgtggaattg gtttaacata acaaattggc   2220
tgtggtatat aaaattattc ataatgatag taggaggctt ggtaggttta agaatagttt   2280
ttgctgtact ttctatagtg aatagagtta ggcaggata ttcaccatta tcgtttcaga    2340
cccacctccc aaccccgagg ggaccgagct caagcttcga acgcgtgggg atcctctaga   2400
gtcgagctcg cgaggatcat caccggtgct agccggagcc agaagcacca taagggacat   2460
gataagggag ccagcagacc tctgatctct tcctgaatgc taatcttaaa catcctgagg   2520
aagaatggga cttccatttg gggtgggcct atgataggat aataagacag tagtgaatat   2580
caagctacaa aaagccccct ttcaaattct tctcagtcct aacttttcat actaagccca   2640
gtccttccaa agcagactgt gaaagagtga tagttccggg agactagcac cggctagccg   2700
agcttggaac actttccctt cattaagaac catccttgct actcagctgc aatcaatcca   2760
gcccccaggt cttcactgaa ccttttccca tctcttccaa aacatctgtt tctgagaagt   2820
cctgtcctat agaggtcttt cttcccaccg gatttctcct acaccattta ctcccacttg   2880
cagaactccc gtgtacaagt gtctttactg cttttatttg ctcaacaaaa tgcacatctc   2940
atataaaaat aaatgaggag catgcacaca ccacaaacac aaacaggcat gcagaaatac   3000
acatacacac ttccctcaat ataaaccctt tgtggctcat atatttaaaa agatgtaaaa   3060
aaaagagctg aagaaaatca tgtgtgatct ctcagcagaa tagatttatt atttgtattg   3120
cttgcagaat aaagcctatc cttgaaagct ctgaatcatg gcaagaggc tcagtggtat    3180
ctggaggaca gggcactggc cactgcagtc accatcttct gccaggaagc ctgcacctca   3240
```

```
ggggtgaatt ctttgccaaa gtgaatggcc agcacggtga ccagcacgtt gcccaggagc      3300
tgtgggagga agataagagg tatgaacatg attagcaaaa gggcctagct tggactcaga      3360
ataatccagc cttatcccaa ccataaaata aaagcagaat ggtagctgga ttgtagctgc      3420
tattagcaat atgaaacctc ttacatcagt tacaatttat atgcagaaat atttatatgc      3480
agaaatattg ctattgcctt aacccagaaa ttatcactgt tattctttag aatggtgcaa      3540
agaggcatga tacattgtat cattattgcc ctgaaagaaa gagattaggg aaagtattag      3600
aaataagata aacaaaaaag tatattaaaa gaagaaagca ttttttaaaa ttacaaatgc      3660
aaaattaccc tgatttggtc aatatgtgta ccctgttact tctcccctte ctatgacatg      3720 aacttaacca tagaaaagaa ggggaaagaa aacatcaagg gtcccataga ctcaccttga      3780
agttctcagg atccacatgc agcttgtcac agtgcagttc actcagctgg gcaaaggtgc      3840
ccttgagatc atccaggtgc tttatggcat ctcccaagga agtcagcacc ttcttgccat      3900
gtgccttgac tttgggggttg cccatgatgg cagaggcaga ggacaggttg ccaaagctgt      3960
caaagaacct ctgggtccat gggtagacaa ccaggagcct gtgagattga caagaacagt      4020
ttgacagtca gaaggtgcca caaatcctga gaagcaacct ggacttttgc caggcacagg      4080
gtccttcctt ccctcccttg tcctggtcac cagagcctac cttcccaggg tttctcctcc      4140
agcatcttcc acattcacct tgtcccacag gcttgtgata gtagccttgt cctcctctgt      4200
gaaatgaccc atggtgtctg tttgaggttg ctagtgaaca cagttgtgtc agaagcaaat      4260
gtaagcaata gatggctctg ccctgacttt tatgcccagc cctggctcct gccctccctg      4320
ctcctgggag tagattggcc aaccctaggg tgtggctcca cagggtgagg tctaagtgat      4380
gacagccgta cctgtccttg gctcttctgg cactggctta ggagttggac ttcaaaccct      4440
cagccctccc tctaagatat atctcttggc cccataccat cagtacaaat tgctactaaa      4500
aacatcctcc tttgcaagtg tatttacgac ggtatcgatg tatgtgagca tgtgtcctct      4560
aacagcacag gccttttgcc acctagctgt ccaggggtgc cttaaaatgg caaacaaggt      4620
ttgttttctt ttcctgtttt catgccttcc tcttccatat ccttgtttca tattaataca      4680
tgtgtataga tcctaaaaat ctatacacat gtattaataa agcctgattc tgccgcttct      4740
aggtatagag gccacctgca agataaatat ttgattcaca ataactaatc attctatggc      4800
aattgataac aacaaatata tatatatata tatatatacg tatatgtgta tatatatata      4860
tatattcagg aaataatata ttctagaata tgtcacattc tgtctcaggc atccattttc      4920
tttatgatgc cgtttgaggt ggagttttag tcaggtggtc agcttctcct ttttttttgcc      4980 atctgccctg taagcatcct gctggggacc cagataggag tcatcactct aggctgagaa      5040
catctgggca cacaccctaa gcctcagcat gactcatcat gactcagcat tgctgtgctt      5100
gagccagaag gtttgcttag aaggttacac agaaccagaa ggcgggggtg gggcactgac      5160
cccgacaggg gcctggccag aactgctcat gcttggacta tgggaggtca ctaatgagaa      5220
cacacagaaa tgtaacagga actaagggaa ttccggtgcc ctgcttagga gcttaatctt      5280
taatgaaagc taagctttca ttaaaaaaag tctaaccagc tgcattcgac tttgactgca      5340
gcagctggtt agaaggttct actggaggag ggtcccagcc cattgctaaa ttaacatcag      5400
gctctgagac tggcagtata tctctaacag tggttgatgc tatcttctgg aacttgcctg      5460
ctacattgag accactgacc catacatagg aagcccatag ctctgtcctg aactgttagg      5520
ccactggtcc agagagtgtg catctccttt gatcctcata ataaccctat gagatagaca      5580
```

```
caattattac tcttacttta tagatgatga tcctgaaaac ataggagtca aggcacttgc    5640
ccctagctgg gggtataggg gagcagtccc atgtagtagt agaatgaaaa atgctgctat    5700
gctgtgcctc ccccacctt cccatgtctg ccctctactc atggtctatc tctcctggct    5760
cctgggagtc atggactcca cccagcacca ccaacctgac ctaaccacct atctgagcct    5820
gccagcctat aacccatctg ggccctgata gctggtggcc agccctgacc ccaccccacc    5880
ctccctggaa cctctgatag acacatctgg cacaccagct cgcaaagtca ccgtgagggt    5940
cttgtgtttg ctgagtcaaa attccttgaa atccaagtcc ttagagactc ctgctcccaa    6000
atttacagtc atagacttct tcatggctgt ctcctttatc cacagaatga ttcctttgct    6060
tcattgcccc atccatctga tcctcctcat cagtgcagca cagggcccat gagcagtagc    6120
tgcagagtct cacataggtc tggcactgcc tctgacatgt ccgaccttag gcaaatgctt    6180
gactcttctg agctcggatc ccttgagctc aggaggtcaa ggctgcagtg agacatgatc    6240
ttgccactgc actccagcct ggacagcaga gtgaaacctt gcctcacgaa acagaataca    6300
aaaacaaaca aacaaaaaac tgctccgcaa tgcgcttcct tgatgctcta ccacataggt    6360
ctgggtactt tgtacacatt atctcattgc tgttcataat tgttagatta attttgtaat    6420
attgatatta ttcctagaaa gctgaggcct caagatgata acttttattt tctggacttg    6480
taatagcttt ctcttgtatt caccatgttg taactttctt agagtagtaa caatataaag    6540
ttattgtgag tttttgcaaa cacagcaaac acaacgaccc atatagacat tgatgtgaaa    6600
ttgtctattg tcaatttatg ggaaaacaag tatgtacttt ttctactaag ccattgaaac    6660
aggaataaca gaacaagatt gaaagaatac attttccgaa attacttgag tattatacaa    6720
agacaagcac gtggacctgg gaggagggtt attgtccatg actggtgtgt ggagacaaat    6780
gcaggtttat aatagatggg atggcatcta gcgcaatgac tttgccatca cttttagaga    6840
gctcttgggg gccccagtac acaagagggg acgcagggta tatgtagaca tctcattctt    6900
tttcttagtg tgagaataag aatagccatg acctgagttt atagacaatg agcccttttc    6960
tctctcccac tcagcagcta tgagatggct tgccctgcct ctctactagg ctgactcact    7020
ccaaggccca gcaatgggca gggctctgtc agggctttga tagcactatc tgcagagcca    7080
gggccgagaa ggggtggact ccagagactc tccctcccat tcccgagcag ggtttgctta    7140
tttatgcatt taaatgatat atttattta aagaaataa caggagactg cccagccctg    7200
gctgtgacat ggaaactatg tagaatattt tgggttccat ttttttttcc ttctttcagt    7260
tagaggaaaa ggggctcact gcacatacac tagacagaaa gtcaggagct ttgaatccaa    7320
gcctgatcat ttccatgtca tactgagaaa gtccccaccc ttctctgagc ctcagtttct    7380 cttttataa gtaggagtct ggagtaaatg atttccaatg gctctcattt caatacaaaa    7440
tttccgttta ttaaatgcat gagcttccgt tactccaaga ctgagaagga aattgaacct    7500
gagactcatt gactggcaag atgtccccag aggctctcat tcagcaataa aattctcacc    7560
ttcacccagg cccactagtg tcagatttgc atgcgttcgc gttcgacgtg cagtcgggct    7620
actgccccac ccatagtacc ggcattctgg atagtgtcaa aacagccgga aatcaagtcc    7680
gtttatctca aactttagca ttttgggaat aaatgatatt tgctatgctg gttaaattag    7740
attttagtta aatttcctgc tgaagctcta gtacgataag taacttgacc taagtgtaaa    7800
gttgagattt ccttcaggtt tatatagctt gtgcgccgcc tgggtacctc aggatatgcc    7860
cttgactatt tgtccgacat agtcaagggc atatcctttt ttgcggccgc atcgatgccg    7920
tagtaccttt aagaccaatg acttacaagg cagctgtaga tcttagccac ttttttaaaag    7980
```

```
aaaaggggggg actggaaggg ctaattcact cccaaagaag acaagatccc tgcaggcatt    8040
caaggccagg ctggatgtgg ctctgggcag cctgggctgc tggttgatga ccctgcacat    8100
agcagggggt tggatctgga tgagcactgt gctcctttgc aacccaggcc gttctatgat    8160
tctgtcattc taaatctctc tttcagccta aagcttttc cccgtatccc cccaggtgtc    8220
tgcaggctca aagagcagcg agaagcgttc agaggaaagc gatcccgtgc caccttcccc    8280
gtgcccgggc tgtccccgca cgctgccggc tcggggatgc gggggggagcg ccggaccgga    8340
gcggagcccc gggcggctcg ctgctgcccc ctagcggggg agggacgtaa ttacatccct    8400
gggggctttg gggggggggct gtccccgtga gctccccaga tctgcttttt gcctgtactg    8460
ggtctctctg gttagaccag atctgagcct gggagctctc tggctaacta gggaacccac    8520
tgcttaagcc tcaataaagc ttcagctgct cgagctagca gatcttttc cctctgccaa    8580
aaattatggg gacatcatga agcccttga gcatctgact tctggctaat aaaggaaatt    8640
tattttcatt gcaatagtgt gttggaattt tttgtgtctc tcactcggaa ggacatatgg    8700
gagggcaaat catttaaaac atcagaatga gtatttggtt tagagtttgg caacatatgc    8760
ccatatgctg gctgccatga acaaaggttg gctataaaga ggtcatcagt atatgaaaca    8820
gccccctgct gtccattcct tattccatag aaaagccttg acttgaggtt agatttttt     8880
tatattttgt tttgtgttat ttttttcttt aacatccta aaatttttcct tacatgtttt   8940
actagccaga ttttttcctcc tctcctgact actcccagtc atagctgtcc ctcttctctt    9000
atggagatcc ctcgacctgc agcccaagct tggcgtaatc atggtcatag ctgtttcctg    9060
tgtgaaattg ttatccgctc acaattccac acaacatacg agccggaagc ataaagtgta    9120
aagcctgggg tgcctaatga gtgagctaac tcacattaat tgcgttgcgc tcactgcccg    9180
ctttccagtc gggaaacctg tcgtgccagc ggatccgcat ctcaattagt cagcaaccat    9240
agtcccgccc ctaactccgc ccatcccgcc cctaactccg cccagttccg cccattctcc    9300
gccccatggc tgactaattt tttttattta tgcagaggcc gaggccgcct cggcctctga    9360
gctattccag aagtagtgag gaggcttttt tggaggccta ggcttttgca aaaagctgtc    9420
gactgcagag gcctgcatgc aagcttggcg taatcatggt catagctgtt tcctgtgtga    9480
aattgttatc cgctcacaat tccacacaac atacgagccg gaagcataaa gtgtaaagcc    9540
tggggtgcct aatgagtgag ctaactcaca ttaattgcgt tgcgctcact gcccgctttc    9600
cagtcgggaa acctgtcgtg ccagctgcat taatgaatcg gccaacgcgc ggggagaggc    9660
ggtttgcgta ttgggcgctc ttccgcttcc tcgctcactg actcgctgcg ctcggtcgtt    9720
cggctgcggc gagcggtatc agctcactca aaggcggtaa tacggttatc cacagaatca    9780
ggggataacg caggaaagaa catgtgagca aaaggccagc aaaaggccag gaaccgtaaa    9840
aaggccgcgt tgctggcgtt tttccatagg ctccgccccc ctgacgagca tcacaaaaat    9900
cgacgctcaa gtcagaggtg gcgaaacccg acaggactat aaagatacca ggcgtttccc    9960
cctggaagct ccctcgtgcg ctctcctgtt ccgaccctgc cgcttaccgg atacctgtcc   10020
gcctttctcc cttcgggaag cgtggcgctt tctcatagct cacgctgtag gtatctcagt   10080
tcggtgtagg tcgttcgctc caagctgggc tgtgtgcacg aaccccccgt tcagcccgac   10140
cgctgcgcct tatccggtaa ctatcgtctt gagtccaacc cggtaagaca cgacttatcg   10200
ccactggcag cagccactgg taacaggatt agcagagcga ggtatgtagg cggtgctaca   10260
gagttcttga agtggtggcc taactacggc tacactagaa gaacagtatt tggtatctgc   10320
```

```
gctctgctga agccagttac cttcggaaaa agagttggta gctcttgatc cggcaaacaa    10380
accaccgctg gtagcggtgg ttttttttgtt tgcaagcagc agattacgcg cagaaaaaaa    10440
ggatctcaag aagatccttt gatcttttct acggggtctg acgctcagtg aacgaaaac     10500
tcacgttaag ggattttggt catgagatta tcaaaaagga tcttcaccta gatccttta     10560
aattaaaaat gaagttttaa atcaatctaa agtatatatg agtaaacttg gtctgacagt    10620
taccaatgct taatcagtga ggcacctatc tcagcgatct gtctatttcg ttcatccata    10680
gttgcctgac tccccgtcgt gtagataact acgatacggg agggcttacc atctggcccc    10740
agtgctgcaa tgataccgcg agacccacgc tcaccggctc cagatttatc agcaataaac    10800
cagccagccg gaagggccga gcgcagaagt ggtcctgcaa ctttatccgc ctccatccag    10860
tctattaatt gttgccggga agctagagta agtagttcgc cagttaatag tttgcgcaac    10920
gttgttgcca ttgctacagg catcgtggtg tcacgctcgt cgtttggtat ggcttcattc    10980
agctccggtt cccaacgatc aaggcgagtt acatgatccc ccatgttgtg caaaaaagcg    11040
gttagctcct tcggtcctcc gatcgttgtc agaagtaagt tggccgcagt gttatcactc    11100
atggttatgg cagcactgca taattctctt actgtcatgc catccgtaag atgcttttct    11160
gtgactggtg agtactcaac caagtcattc tgagaatagt gtatgcggcg accgagttgc    11220
tcttgcccgg cgtcaatacg ggataatacc gcgccacata gcagaacttt aaaagtgctc    11280
atcattggaa aacgttcttc ggggcgaaaa ctctcaagga tcttaccgct gttgagatcc    11340
agttcgatgt aacccactcg tgcacccaac tgatcttcag catctttac tttcaccagc     11400
gtttctgggt gagcaaaaac aggaaggcaa aatgccgcaa aaaagggaat aagggcgaca    11460
cggaaatgtt gaatactcat actcttcctt tttcaatatt attgaagcat ttatcagggt    11520
tattgtctca tgagcggata catatttgaa tgtatttaga aaaataaaca aatagggggtt    11580
ccgcgcacat ttccccgaaa agtgccacct gacgtctaag aaaccattat tatcatgaca    11640
ttaacctata aaaataggcg tatcacgagg ccctttcgtc tcgcgcgttt cggtgatgac    11700
ggtgaaaacc tctgacacat gcagctcccg gagacggtca gcttgtctgt gtaagcggat    11760
gccgggagca gacaagcccg tcagggcgcg tcagcgggtg ttggcgggtg tcggggctgg    11820
cttaactatg cggcatcaga gcagattgta ctgagagtgc accatatgcg gtgtgaaata    11880
ccgcacagat gcgtaaggag aaaataccgc atcaggcgcc attcgccatt caggctgcgc    11940
aactgttggg aagggcgatc ggtgcgggcc tcttcgctat tacgccagct ggcgaaaggg    12000
ggatgtgctg caaggcgatt aagttgggta acgccagggt tttcccagtc acgacgttgt    12060
aaaacgacgg ccagtgaatt c                                              12081
```

<210> SEQ ID NO 10
<211> LENGTH: 12084
<212> TYPE: DNA
<213> ORGANISM: Artificial Sequence
<220> FEATURE:
<223> OTHER INFORMATION: Synthetic: TL20c-rGbGM-7SK/sh734

<400> SEQUENCE: 10

```
ggccgcctcg gccaaacagc ccttgagttt accactccct atcagtgata gagaaaagtg     60
aaagtcgagt ttaccactcc ctatcagtga tagagaaaag tgaaagtcga gtttaccact    120
ccctatcagt gatagagaaa agtgaaagtc gagtttacca ctccctatca gtgatagaga    180
aaagtgaaag tcgagtttac cagtccctat cagtgataga gaaaagtgaa agtcgagttt    240
accactccct atcagtgata gagaaaagtg aaagtcgagt ttaccactcc ctatcagtga    300
```

```
tagagaaaag tgaaagtcga gctcgccatg ggaggcgtgg cctgggcggg actgggagt     360 ggcgagccct cagatcctgc atataagcag ctgcttttg cctgtactgg gtctctctgg    420
ttagaccaga tctgagcctg ggagctctct ggctaactag ggaacccact gcttaagcct    480
caataaagct tgccttgagt gcttcaagta gtgtgtgccc gtctgttgtg tgactctggt    540
aactagagat ccctcagacc cttttagtca gtgtggaaaa tctctagcag tggcgcccga    600
acagggactt gaaagcgaaa gggaaaccag aggagctctc tcgacgcagg actcggcttg    660
ctgaagcgcg cacggcaaga ggcgaggggc ggcgactggt gagtacgcca aaattttga     720 ctagcggagg ctagaaggag agagatgggt gcgagagcgt cagtattaag cgggggagaa    780
ttagatcgcg atgggaaaaa attcggttaa ggccaggggg aaagaaaaaa tataaattaa    840
aacatatagt atgggcaagc agggagctag aacgattcgc agttaatact ggcctgttag    900
aaacatcaga aggctgtaga caaatactgg gacagctaca accatccctt cagacaggat    960
cagaagaact tagatcatta tataatacag tagcaaccct ctattgtgtg catcaaagga   1020
tagagataaa agacaccaag gaagctttag acaagataga ggaagagcaa acaaaagta   1080 agaaaaaagc acagcaagca gcaggatctt cagacctgga aattccctac aatccccaaa   1140
gtcaaggagt agtagaatct atgaataaag aattaaagaa aattatagga caggtaagag   1200
atcaggctga acatcttaag acagcagtac aaatggcagt attcatccac aattttaaaa   1260 gaaaagggg gattgggggg tacagtgcag gggaagaat agtagacata atagcaacag    1320
acatacaaac taagaattca caaaacaaa ttacaaaaat tcaaaatttt cgggtttatt    1380
acagggacag cagaaatcca ctttggaaag gaccagcaaa gctcctctgg aaaggtgaag   1440
gggcagtagt aatacaagat aatagtgaca taaagtagt gccaagaaga aaagcaaaga   1500
tcattaggga ttatggaaaa cagatggcag gtgatgattg tgtggcaagt agacaggatg   1560
aggattagaa catggaaaag tttagtaaaa caccataagg aggagatatg agggacaatt   1620
ggagaagtga attatataaa tataaagtag taaaaattga accattagga gtagcaccca   1680
ccaaggcaaa gagaagagtg gtgcagagag aaaaaagagc agtgggaata ggagctttgt   1740
tccttgggtt cttgggagca gcaggaagca ctatgggcgc agcgtcaatg acgctgacgg   1800
tacaggccag acaattattg tctggtatag tgcagcagca gaacaatttg ctgagggcta   1860
ttgaggcgca acagcatctg ttgcaactca cagtctgggg catcaagcag ctccaggcaa   1920
gaatcctggc tgtggaaaga tacctaaagg atcaacagct cctggggatt tggggttgct   1980
ctggaaaact catttgcacc actgctgtgc cttggaatgc tagttggagt aataaatctc   2040
tggaacagat ttggaatcac acgacctgga tggagtggga cagagaaatt aacaattaca   2100
caagcttaat acactcctta attgaagaat cgcaaaacca gcaagaaaag aatgaacaag   2160
aattattgga attagataaa tgggcaagtt tgtggaattg gtttaacata caaaattggc   2220
tgtggtatat aaaattattc ataatgatag taggaggctt ggtaggttta agaatagttt   2280
ttgctgtact ttctatagtg aatagagtta ggcagggata ttcaccatta tcgtttcaga   2340
cccacctccc aaccccgagg ggaccgagct caagcttcga acgcgtgggg atcctctaga   2400
gtcgagctcg cgaggatcat caccggtgct agccggagcc agaagcacca taaggacat    2460 gataagggag ccagcagacc tctgatctct tcctgaatgc taatcttaaa catcctgagg   2520
aagaatggga cttccatttg gggtgggcct atgataggt aataagacag tagtgaatat   2580
caagctacaa aaagccccct ttcaaattct tctcagtcct aacttttcat actaagccca   2640
```

```
gtccttccaa agcagactgt gaaagagtga tagttccggg agactagcac cggctagccg    2700
agcttggaac actttcccctt cattaagaac catccttgct actcagctgc aatcaatcca    2760
gcccccaggt cttcactgaa cctttcccca tctcttccaa aacatctgtt tctgagaagt    2820
cctgtcctat agaggtcttt cttcccaccg gatttctcct acaccattta ctcccacttg    2880
cagaactccc gtgtacaagt gtctttactg cttttatttg ctcaacaaaa tgcacatctc    2940
atataaaaat aaatgaggag catgcacaca ccacaaacac aaacaggcat gcagaaatac    3000
acatacacac ttccctcaat ataaaccctt tgtggctcat atatttaaaa agatgtaaaa    3060
aaaagagctg aagaaaatca tgtgtgatct ctcagcagaa tagatttatt atttgtattg    3120
cttgcagaat aaagcctatc cttgaaagct ctgaatcatg ggcaagaggc tcagtggtat    3180
ctggaggaca gggcactggc cactgcagtc accatcttct gccaggaagc ctgcacctca    3240
ggggtgaatt ctttgccaaa gtgaatggcc agcacggtga ccagcacgtt gcccaggagc    3300
tgtgggagga agataagagg tatgaacatg attagcaaaa gggcctagct tggactcaga    3360
ataatccagc cttatcccaa ccataaaata aaagcagaat ggtagctgga ttgtagctgc    3420
tattagcaat atgaaacctc ttacatcagt tacaatttat atgcagaaat atttatatgc    3480
agaaatattg ctattgcctt aacccagaaa ttatcactgt tattctttag aatggtgcaa    3540
agaggcatga tacattgtat cattattgcc ctgaaagaaa gagattaggg aaagtattag    3600
aaataagata aacaaaaaag tatattaaaa gaagaaagca ttttttaaaa ttacaaatgc    3660
aaaattaccc tgatttggtc aatatgtgta ccctgttact tctcccctttc ctatgacatg    3720 aacttaacca tagaaaagaa ggggaaagaa aacatcaagg gtcccataga ctcaccttga    3780
agttctcagg atccacatgc agcttgtcac agtgcagttc actcagctgg gcaaaggtgc    3840
ccttgagatc atccaggtgc tttatggcat ctcccaagga agtcagcacc ttcttgccat    3900
gtgccttgac tttggggttg cccatgatgg cagaggcaga ggacaggttg ccaaagctgt    3960
caaagaacct ctgggtccat gggtagacaa ccaggagcct gtgagattga caagaacagt    4020
ttgacagtca gaaggtgcca caaatcctga gaagcaacct ggacttttgc caggcacagg    4080
gtccttcctt ccctcccctttg tcctggtcac cagagcctac cttcccaggg tttctcctcc    4140
agcatcttcc acattcacct tgtcccacag gcttgtgata gtagccttgt cctcctctgt    4200
gaaatgaccc atggtgtctg tttgaggttg ctagtgaaca cagttgtgtc agaagcaaat    4260
gtaagcaata gatggctctg ccctgacttt tatgcccagc cctggctcct gccctccctg    4320
ctcctgggag tagattggcc aaccctaggg tgtggctcca cagggtgagg tctaagtgat    4380
gacagccgta cctgtccttg gctcttctgg cactggctta ggagttggac ttcaaaccct    4440
cagccctccc tctaagatat atctcttggc cccataccat cagtacaaat tgctactaaa    4500
aacatcctcc tttgcaagtg tatttacgac ggtatcgatg tatgtgagca tgtgtcctct    4560
aacagcacag gccttttgcc acctagctgt ccaggggtgc cttaaaatgg caaacaaggt    4620
ttgttttctt ttcctgtttt catgccttcc tcttccatat ccttgtttca tattaataca    4680
tgtgtataga tcctaaaaat ctatacacat gtattaataa agcctgattc tgccgcttct    4740
aggtatagag gccacctgca agataaatat ttgattcaca ataactaatc attctatggc    4800
aattgataac aacaaatata tatatatata tatatatacg tatatgtgta tatatatata    4860
tatattcagg aaataatata ttctagaata tgtcacattc tgtctcaggc atccatttttc    4920 tttatgatgc cgtttgaggt ggagttttag tcaggtggtc agcttctcct tttttttgcc    4980
atctgccctg taagcatcct gctggggacc cagataggag tcatcactct aggctgagaa    5040
```

```
catctgggca cacaccctaa gcctcagcat gactcatcat gactcagcat tgctgtgctt    5100
gagccagaag gtttgcttag aaggttacac agaaccagaa ggcgggggtg gggcactgac    5160
cccgacaggg gcctggccag aactgctcat gcttggacta tgggaggtca ctaatggaga    5220
cacacagaaa tgtaacagga actaagggaa ttccggtgcc ctgcttagga gcttaatctt    5280
taatgaaagc taagctttca ttaaaaaaag tctaaccagc tgcattcgac tttgactgca    5340
gcagctggtt agaaggttct actggaggag ggtcccagcc cattgctaaa ttaacatcag    5400
gctctgagac tggcagtata tctctaacag tggttgatgc tatcttctgg aacttgcctg    5460
ctacattgag accactgacc catacatagg aagcccatag ctctgtcctg aactgttagg    5520
ccactggtcc agagagtgtg catctccttt gatcctcata ataaccctat gagatagaca    5580
caattattac tcttacttta tagatgatga tcctgaaaac ataggagtca aggcacttgc    5640
ccctagctgg gggtataggg gagcagtccc atgtagtagt agaatgaaaa atgctgctat    5700
gctgtgcctc ccccaccttt cccatgtctg ccctctactc atggtctatc tctcctggct    5760
cctgggagtc atggactcca cccagcacca ccaacctgac ctaaccacct atctgagcct    5820
gccagcctat aacccatctg ggccctgata gctggtggcc agccctgacc ccacccacc    5880 ctccctggaa cctctgatag acacatctgg cacaccagct cgcaaagtca ccgtgagggt    5940
cttgtgtttg ctgagtcaaa attccttgaa atccaagtcc ttagagactc ctgctcccaa    6000
atttacagtc atagacttct tcatggctgt ctcctttatc cacagaatga ttcctttgct    6060
tcattgcccc atccatctga tcctcctcat cagtgcagca cagggcccat gagcagtagc    6120
tgcagagtct cacataggtc tggcactgcc tctgacatgt ccgaccttag gcaaatgctt    6180
gactcttctg agctcggatc ccttgagctc aggaggtcaa ggctgcagtg agacatgatc    6240
ttgccactgc actccagcct ggacagcaga gtgaaacctt gcctcacgaa acagaataca    6300
aaaacaaaca aacaaaaaac tgctccgcaa tgcgcttcct tgatgctcta ccacataggt    6360
ctgggtactt tgtacacatt atctcattgc tgttcataat tgttagatta attttgtaat    6420
attgatatta ttcctagaaa gctgaggcct caagatgata acttttatt tctggacttg    6480 taatagcttt ctcttgtatt caccatgttg aactttctt agagtagtaa caatataaag    6540
ttattgtgag ttttgcaaa cacagcaaac acaacgaccc atatagacat tgatgtgaaa    6600
ttgtctattg tcaatttatg ggaaaacaag tatgtacttt ttctactaag ccattgaaac    6660
aggaataaca gaacaagatt gaaagaatac attttccgaa attacttgag tattatacaa    6720
agacaagcac gtggacctgg gaggagggtt attgtccatg actggtgtgt ggagacaaat    6780
gcaggtttat aatagatggg atggcatcta gcgcaatgac tttgccatca cttttagaga    6840
gctcttgggg gccccagtac acaagagggg acgcagggta tatgtagaca tctcattctt    6900
tttcttagtg tgagaataag aatagccatg acctgagttt atagacaatg agccctttc    6960 tctctcccac tcagcagcta tgagatggct tgccctgcct ctctactagg ctgactcact    7020
ccaaggccca gcaatgggca gggctctgtc agggctttga tagcactatc tgcagagcca    7080
gggccgagaa ggggtggact ccagagactc tccctcccat tcccgagcag ggtttgctta    7140
tttatgcatt taaatgatat atttatttta aagaaataa caggagactg cccagccctg    7200
gctgtgacat ggaaactatg tagaatattt tgggttccat tttttttttcc ttctttcagt    7260 tagaggaaaa ggggctcact gcacatacac tagacagaaa gtcaggagct ttgaatccaa    7320
gcctgatcat ttccatgtca tactgagaaa gtccccaccc ttctctgagc ctcagtttct    7380
```

```
cttttttataa gtaggagtct ggagtaaatg atttccaatg gctctcattt caatacaaaa   7440
tttccgttta ttaaatgcat gagcttccgt tactccaaga ctgagaagga aattgaacct   7500
gagactcatt gactggcaag atgtccccag aggctctcat tcagcaataa aattctcacc   7560
ttcacccagg cccactagtg tcagatttgc atgcgttcgc gtatcgacgt gcagtattta   7620
gcatgcccca cccatctgca aggcattctg gatagtgtca aaacagccgg aaatcaagtc   7680
cgtttatctc aaactttagc attttgggaa taaatgatat ttgctatgct ggttaaatta   7740
gattttagtt aaatttcctg ctgaagctct agtacgataa gtaacttgac ctaagtgtaa   7800
agttgagatt tccttcaggt ttatatagct tgtgcgccgc ctgggtacct caggatatgc   7860
ccttgactat ttgtccgaca tagtcaaggg catatccttt tttgtgcggc cgcatcgatg   7920
ccgtagtacc tttaagacca atgacttaca aggcagctgt agatcttagc cacttttaa    7980 aagaaaaggg gggactggaa gggctaattc actcccaaag aagacaagat ccctgcaggc   8040
attcaaggcc aggctggatg tggctctggg cagcctgggc tgctggttga tgaccctgca   8100
catagcaggg ggttggatct ggatgagcac tgtgctcctt tgcaacccag gccgttctat   8160
gattctgtca ttctaaatct ctcttttcagc ctaaagcttt ttccccgtat cccccaggt   8220 gtctgcaggc tcaaagagca gcgagaagcg ttcagaggaa agcgatcccg tgccaccttc   8280
cccgtgcccg ggctgtcccc gcacgctgcc ggctcgggga tgcgggggga gcgccggacc   8340
ggagcggagc cccgggcggc tcgctgctgc cccctagcgg ggaggacg taattacatc    8400 cctgggggct ttgggggggg gctgtccccg tgagctcccc agatctgctt tttgcctgta   8460
ctgggtctct ctggttagac cagatctgag cctgggagct ctctggctaa ctagggaacc   8520
cactgcttaa gcctcaataa agcttcagct gctcgagcta gcagatcttt ttccctctgc   8580
caaaaattat ggggacatca tgaagcccct tgagcatctg acttctggct aataaaggaa   8640
atttattttc attgcaatag tgtgttggaa tttttttgtgt ctctcactcg gaaggacata   8700
tgggagggca aatcatttaa aacatcagaa tgagtatttg gtttagagtt tggcaacata   8760
tgcccatatg ctggctgcca tgaacaaagg ttggctataa agaggtcatc agtatatgaa   8820
acagccccct gctgtccatt ccttattcca tagaaaagcc ttgacttgag gttagatttt   8880
ttttatattt tgttttgtgt tattttttc tttaacatcc ctaaaatttt ccttacatgt    8940
tttactagcc agatttttcc tcctctcctg actactccca gtcatagctg tccctcttct   9000
cttatggaga tccctcgacc tgcagcccaa gcttggcgta atcatggtca tagctgtttc   9060
ctgtgtgaaa ttgttatccg ctcacaattc cacacaacat acgagccgga agcataaagt   9120
gtaaagcctg gggtgcctaa tgagtgagct aactcacatt aattgcgttg cgctcactgc   9180
ccgcttccca gtcgggaaac ctgtcgtgcc agcggatccg catctcaatt agtcagcaac   9240
catagtcccg cccctaactc cgcccatccc gcccctaact ccgcccagtt ccgcccattc   9300
tccgccccat ggctgactaa ttttttttat ttatgcagag gccgaggccg cctcggcctc   9360
tgagctattc cagaagtagt gaggaggctt ttttggaggc ctaggctttt gcaaaaagct   9420
gtcgactgca gaggcctgca tgcaagcttg gcgtaatcat ggtcatagct gtttcctgtg   9480
tgaaattgtt atccgctcac aattccacac aacatacgag ccggaagcat aaagtgtaaa   9540
gcctggggtg cctaatgagt gagctaactc acattaattg cgttgcgctc actgcccgct   9600
ttccagtcgg gaaacctgtc gtgccagctg cattaatgaa tcggccaacg cgcggggaga   9660
ggcggtttgc gtattgggcg ctcttccgct tcctcgctca ctgactcgct gcgctcggtc   9720
gttcggctgc ggcgagcggt atcagctcac tcaaaggcgg taatacggtt atccacagaa   9780
```

```
tcagggGata acgcaggaaa gaacatgtga gcaaaaggcc agcaaaaggc caggaaccgt    9840
aaaaaggccg cgttgctggc gtttttccat aggctccgcc cccctgacga gcatcacaaa    9900
aatcgacgct caagtcagag gtggcgaaac ccgacaggac tataaagata ccaggcgttt    9960
ccccctggaa gctccctcgt gcgctctcct gttccgaccc tgccgcttac cggatacctg   10020
tccgcctttc tcccttcggg aagcgtggcg ctttctcata gctcacgctg taggtatctc   10080
agttcggtgt aggtcgttcg ctccaagctg ggctgtgtgc acgaaccccc cgttcagccc   10140
gaccgctgcg ccttatccgg taactatcgt cttgagtcca acccggtaag acacgactta   10200
tcgccactgg cagcagccac tggtaacagg attagcagag cgaggtatgt aggcggtgct   10260
acagagttct tgaagtggtg gcctaactac ggctacacta agaacagt atttggtatc    10320 tgcgctctgc tgaagccagt taccttcgga aaagagttg gtagctcttg atccggcaaa    10380
caaaccaccg ctggtagcgg tggttttttt gtttgcaagc agcagattac gcgcagaaaa   10440
aaaggatctc aagaagatcc tttgatcttt tctacgggt ctgacgctca gtggaacgaa    10500
aactcacgtt aagggatttt ggtcatgaga ttatcaaaaa ggatcttcac ctagatcctt   10560
ttaaattaaa aatgaagttt taaatcaatc taaagtatat atgagtaaac ttggtctgac   10620
agttaccaat gcttaatcag tgaggcacct atctcagcga tctgtctatt tcgttcatcc   10680
atagttgcct gactccccgt cgtgtagata actacgatac ggagggctt accatctggc    10740 cccagtgctg caatgatacc gcgagaccca cgctcaccgg ctccagattt atcagcaata   10800
aaccagccag ccggaagggc cgagcgcaga agtggtcctg caactttatc cgcctccatc   10860
cagtctatta attgttgccg ggaagctaga gtaagtagtt cgccagttaa tagtttgcgc   10920
aacgttgttg ccattgctac aggcatcgtg gtgtcacgct cgtcgtttgg tatggcttca   10980
ttcagctccg gttcccaacg atcaaggcga gttacatgat cccccatgtt gtgcaaaaaa   11040
gcggttagct ccttcggtcc tccgatcgtt gtcagaagta agttggccgc agtgttatca   11100
ctcatggtta tggcagcact gcataattct cttactgtca tgccatccgt aagatgcttt   11160
tctgtgactg gtgagtactc aaccaagtca ttctgagaat agtgtatgcg gcgaccgagt   11220
tgctcttgcc cggcgtcaat acgggataat accgcgccac atagcagaac tttaaaagtg   11280
ctcatcattg gaaaacgttc ttcggggcga aaactctcaa ggatcttacc gctgttgaga   11340
tccagttcga tgtaacccac tcgtgcaccc aactgatctt cagcatcttt tactttcacc   11400
agcgtttctg ggtgagcaaa aacaggaagg caaaatgccg caaaaaaggg aataagggcg   11460
acacggaaat gttgaatact catactcttc ctttttcaat attattgaag catttatcag   11520
ggttattgtc tcatgagcgg atacatattt gaatgtattt agaaaaataa acaaataggg   11580
gttccgcgca catttccccg aaaagtgcca cctgacgtct aagaaaccat tattatcatg   11640
acattaacct ataaaaatag gcgtatcacg aggccctttc gtctcgcgcg tttcggtgat   11700
gacggtgaaa acctctgaca catgcagctc ccggagacgg tcacagcttg tctgtaagcg   11760
gatgccggga gcagacaagc ccgtcagggc gcgtcagcgg gtgttggcgg gtgtcggggc   11820
tggcttaact atgcggcatc agagcagatt gtactgagag tgcaccatat gcggtgtgaa   11880
ataccgcaca gatgcgtaag gagaaaatac cgcatcaggc gccattcgcc attcaggctg   11940
cgcaactgtt gggaagggcg atcggtgcgg gcctcttcgc tattacgcca gctggcgaaa   12000
gggggatgtg ctgcaaggcg attaagttgg gtaacgccag ggttttccca gtcacgacgt   12060
tgtaaaacga cggccagtga attc                                         12084
```

<210> SEQ ID NO 11
<211> LENGTH: 12081
<212> TYPE: DNA
<213> ORGANISM: Artificial Sequence
<220> FEATURE:
<223> OTHER INFORMATION: Synthetic: TL20c-rGbGM-r7SKM1/sh734

<400> SEQUENCE: 11

| | | | | | |
|---|---|---|---|---|---|
| ggccgcctcg | gccaaacagc | ccttgagttt | accactccct | atcagtgata | gagaaaagtg | 60 |
| aaagtcgagt | ttaccactcc | ctatcagtga | tagagaaaag | tgaaagtcga | gtttaccact | 120 |
| ccctatcagt | gatagagaaa | agtgaaagtc | gagtttacca | ctccctatca | gtgatagaga | 180 |
| aaagtgaaag | tcgagtttac | cagtccctat | cagtgataga | gaaaagtgaa | agtcgagttt | 240 |
| accactccct | atcagtgata | gagaaaagtg | aaagtcgagt | ttaccactcc | ctatcagtga | 300 |
| tagagaaaag | tgaaagtcga | gctcgccatg | ggaggcgtgg | cctgggcggg | actggggagt | 360 |
| ggcgagccct | cagatcctgc | atataagcag | ctgcttttg | cctgtactgg | gtctctctgg | 420 |
| ttagaccaga | tctgagcctg | ggagctctct | ggctaactag | ggaacccact | gcttaagcct | 480 |
| caataaagct | tgccttgagt | gcttcaagta | gtgtgtgccc | gtctgttgtg | tgactctggt | 540 |
| aactagagat | ccctcagacc | cttttagtca | gtgtggaaaa | tctctagcag | tggcgcccga | 600 |
| acagggactt | gaaagcgaaa | gggaaaccag | aggagctctc | tcgacgcagg | actcggcttg | 660 |
| ctgaagcgcg | cacggcaaga | ggcgaggggc | ggcgactggt | gagtacgcca | aaattttga | 720 |
| ctagcggagg | ctagaaggag | agagatgggt | gcgagagcgt | cagtattaag | cgggggagaa | 780 |
| ttagatcgcg | atgggaaaaa | attcggttaa | ggccaggggg | aaagaaaaaa | tataaattaa | 840 |
| aacatatagt | atgggcaagc | agggagctag | aacgattcgc | agttaatact | ggcctgttag | 900 |
| aaacatcaga | aggctgtaga | caaatactgg | gacagctaca | accatccctt | cagacaggat | 960 |
| cagaagaact | tagatcatta | tataatacag | tagcaaccct | ctattgtgtg | catcaaagga | 1020 |
| tagagataaa | agacaccaag | gaagctttag | acaagataga | ggaagagcaa | aacaaaagta | 1080 |
| agaaaaaagc | acagcaagca | gcaggatctt | cagacctgga | aattccctac | aatccccaaa | 1140 |
| gtcaaggagt | agtagaatct | atgaataaag | aattaaagaa | aattatagga | caggtaagag | 1200 |
| atcaggctga | acatcttaag | acagcagtac | aaatggcagt | attcatccac | aattttaaaa | 1260 |
| gaaaaggggg | gattgggggg | tacagtgcag | gggaagaat | agtagacata | atagcaacag | 1320 |
| acatacaaac | taaagaatta | caaaaacaaa | ttacaaaaat | tcaaaatttt | cgggtttatt | 1380 |
| acagggacag | cagaaatcca | ctttggaaag | gaccagcaaa | gctcctctgg | aaaggtgaag | 1440 |
| gggcagtagt | aatacaagat | aatagtgaca | taaaagtagt | gccaagaaga | aaagcaaaga | 1500 |
| tcattaggga | ttatggaaaa | cagatggcag | gtgatgattg | tgtggcaagt | agacaggatg | 1560 |
| aggattagaa | catggaaaag | tttagtaaaa | caccataagg | aggagatatg | agggacaatt | 1620 |
| ggagaagtga | attatataaa | tataaagtag | taaaaattga | accattagga | gtagcaccca | 1680 |
| ccaaggcaaa | gagaagagtg | gtgcagagag | aaaaagagc | agtgggaata | ggagctttgt | 1740 |
| tccttgggtt | cttgggagca | gcaggaagca | ctatgggcgc | agcgtcaatg | acgctgacgg | 1800 |
| tacaggccag | acaattattg | tctggtatag | tgcagcagca | gaacaatttg | ctgagggcta | 1860 |
| ttgaggcgca | acagcatctg | ttgcaactca | gtctggggg | catcaagcag | ctccaggcaa | 1920 |
| gaatcctggc | tgtggaaaga | tacctaaagg | atcaacagct | cctggggatt | tggggttgct | 1980 |
| ctggaaaact | catttgcacc | actgctgtgc | cttggaatgc | tagttggagt | aataaatctc | 2040 |
| tggaacagat | ttggaatcac | acgacctgga | tggagtggga | cagagaaatt | aacaattaca | 2100 |

```
caagcttaat acactcctta attgaagaat cgcaaaacca gcaagaaaag aatgaacaag    2160
aattattgga attagataaa tgggcaagtt tgtggaattg gtttaacata acaaattggc    2220
tgtggtatat aaaattattc ataatgatag taggaggctt ggtaggttta agaatagttt    2280
ttgctgtact ttctatagtg aatagagtta ggcaggata ttcaccatta tcgtttcaga    2340
cccacctccc aaccccgagg ggaccgagct caagcttcga acgcgtgggg atcctctaga    2400
gtcgagctcg cgaggatcat caccggtgct agccggagcc agaagcacca taagggacat    2460
gataagggag ccagcagacc tctgatctct tcctgaatgc taatcttaaa catcctgagg    2520
aagaatggga cttccatttg gggtgggcct atgatagggt aataagacag tagtgaatat    2580
caagctacaa aaagccccct ttcaaattct tctcagtcct aacttttcat actaagccca    2640
gtccttccaa agcagactgt gaaagagtga tagttccggg agactagcac cggctagccg    2700
agcttggaac actttcctt cattaagaac catccttgct actcagctgc aatcaatcca    2760
gcccccaggt cttcactgaa ccttttccca tctcttccaa aacatctgtt tctgagaagt    2820
cctgtcctat agaggtcttt cttcccaccg gatttctcct acaccattta ctcccacttg    2880
cagaactccc gtgtacaagt gtctttactg cttttatttg ctcaacaaaa tgcacatctc    2940
atataaaaat aaatgaggag catgcacaca ccacaaacac aaacaggcat gcagaaatac    3000
acatacacac ttccctcaat ataaaccctt tgtggctcat atatttaaaa agatgtaaaa    3060
aaaagagctg aagaaaatca tgtgtgatct ctcagcagaa tagatttatt atttgtattg    3120
cttgcagaat aaagcctatc cttgaaagct ctgaatcatg ggcaagaggc tcagtggtat    3180
ctggaggaca gggcactggc cactgcagtc accatcttct gccaggaagc ctgcacctca    3240
ggggtgaatt ctttgccaaa gtgaatggcc agcacggtga ccagcacgtt gcccaggagc    3300
tgtgggagga agataagagg tatgaacatg attagcaaaa gggcctagct tggactcaga    3360
ataatccagc cttatcccaa ccataaaata aaagcagaat ggtagctgga ttgtagctgc    3420
tattagcaat atgaaacctc ttacatcagt tacaatttat atgcagaaat atttatatgc    3480
agaaatattg ctattgcctt aacccagaaa ttatcactgt tattctttag aatggtgcaa    3540
agaggcatga tacattgtat cattattgcc ctgaaagaaa gagattaggg aaagtattag    3600
aaataagata aacaaaaaag tatattaaaa gaagaaagca tttttttaaaa ttacaaatgc    3660
aaaattcccc tgatttggtc aatatgtgta ccctgttact tctccccttc ctatgacatg    3720
aacttaacca tagaaaagaa ggggaaagaa aacatcaagg gtcccataga ctcaccttga    3780
agttctcagg atccacatgc agcttgtcac agtgcagttc actcagctgg gcaaaggtgc    3840
ccttgagatc atccaggtgc tttatggcat ctcccaagga agtcagcacc ttcttgccat    3900
gtgccttgac tttggggttg cccatgatgg cagaggcaga ggacaggttg ccaaagctgt    3960
caaagaacct ctgggtccat gggtagacaa ccaggagcct gtgagattga caagaacagt    4020
ttgacagtca gaaggtgcca caaatcctga gaagcaacct ggactttgc caggcacagg    4080
gtccttcctt ccctcccttg tcctggtcac cagagcctac cttcccaggg tttctcctcc    4140
agcatcttcc acattcacct tgtcccacag gcttgtgata gtagccttgt cctcctctgt    4200
gaaatgaccc atggtgtctg tttgaggttg ctagtgaaca cagttgtgtc agaagcaaat    4260
gtaagcaata gatggctctg ccctgacttt tatgcccagc cctggctcct gccctccctg    4320
ctcctgggag tagattggcc aaccctaggg tgtggctcca cagggtgagg tctaagtgat    4380
gacagccgta cctgtccttg gctcttctgg cactggctta ggagttggac ttcaaaccct    4440
```

```
cagccctccc tctaagatat atctcttggc cccataccat cagtacaaat tgctactaaa      4500
aacatcctcc tttgcaagtg tatttacgac ggtatcgatg tatgtgagca tgtgtcctct      4560
aacagcacag gccttttgcc acctagctgt ccaggggtgc cttaaaatgg caaacaaggt      4620
ttgttttctt ttcctgtttt catgccttcc tcttccatat ccttgtttca tattaataca      4680
tgtgtataga tcctaaaaat ctatacacat gtattaataa agcctgattc tgccgcttct      4740
aggtatagag gccacctgca agataaatat ttgattcaca ataactaatc attctatggc      4800
aattgataac aacaaatata tatatatata tatatatacg tatatgtgta tatatatata      4860
tatattcagg aaataatata ttctagaata tgtcacattc tgtctcaggc atccattttc      4920
tttatgatgc cgtttgaggt ggagttttag tcaggtggtc agcttctcct ttttttttgcc     4980 atctgccctg taagcatcct gctggggacc cagataggag tcatcactct aggctgagaa      5040
catctgggca cacaccctaa gcctcagcat gactcatcat gactcagcat tgctgtgctt      5100
gagccagaag gtttgcttag aaggttacac agaaccagaa ggcgggggtg gggcactgac      5160
cccgacaggg gcctggccag aactgctcat gcttggacta tgggaggtca ctaatggaga      5220
cacacagaaa tgtaacagga actaagggaa ttccggtgcc ctgcttagga gcttaatctt      5280
taatgaaagc taagctttca ttaaaaaaag tctaaccagc tgcattcgac tttgactgca      5340
gcagctggtt agaaggttct actggaggag ggtcccagcc cattgctaaa ttaacatcag      5400
gctctgagac tggcagtata tctctaacag tggttgatgc tatcttctgg aacttgcctg      5460
ctacattgag accactgacc catacatagg aagcccatag ctctgtcctg aactgttagg      5520
ccactggtcc agagagtgtg catctccttt gatcctcata ataaccctat gagatagaca      5580
caattattac tcttacttta tagatgatga tcctgaaaac ataggagtca aggcacttgc      5640
ccctagctgg gggtataggg gagcagtccc atgtagtagt agaatgaaaa atgctgctat      5700
gctgtgcctc ccccaccttt cccatgtctg ccctctactc atggtctatc tctcctggct      5760
cctgggagtc atggactcca cccagcacca ccaacctgac ctaaccacct atctgagcct      5820
gccagcctat aacccatctg ggccctgata gctggtggcc agccctgacc ccaccccacc      5880
ctccctggaa cctctgatag acacatctgg cacaccagct cgcaaagtca ccgtgagggt      5940
cttgtgtttg ctgagtcaaa attccttgaa atccaagtcc ttagagactc ctgctcccaa      6000
atttacagtc atagacttct tcatggctgt ctcctttatc cacagaatga ttcctttgct      6060
tcattgcccc atccatctga tcctcctcat cagtgcagca cagggcccat gagcagtagc      6120
tgcagagtct cacataggtc tggcactgcc tctgacatgt ccgaccttag gcaaatgctt      6180
gactcttctg agctcggatc ccttgagctc aggaggtcaa ggctgcagtg agacatgatc      6240
ttgccactgc actccagcct ggacagcaga gtgaaacctt gcctcacgaa acagaataca      6300
aaaacaaaca aacaaaaaac tgctccgcaa tgcgcttcct tgatgctcta ccacataggt      6360
ctgggtactt tgtacacatt atctcattgc tgttcataat tgttagatta attttgtaat      6420
attgatatta ttcctagaaa gctgaggcct caagatgata acttttattt tctggacttg      6480
taatagcttt ctcttgtatt caccatgttg taactttctt agagtagtaa caatataaag      6540
ttattgtgag tttttgcaaa cacagcaaac acaacgaccc atatagacat tgatgtgaaa      6600
ttgtctattg tcaatttatg ggaaaacaag tatgtacttt ttctactaag ccattgaaac      6660
aggaataaca gaacaagatt gaaagaatac attttccgaa attacttgag tattatacaa      6720
agacaagcac gtggacctgg gaggagggtt attgtccatg actggtgtgt ggagacaaat      6780
gcaggtttat aatagatggg atggcatcta gcgcaatgac tttgccatca ctttttagaga     6840
```

```
gctcttgggg gccccagtac acaagagggg acgcagggta tatgtagaca tctcattctt     6900
tttcttagtg tgagaataag aatagccatg acctgagttt atagacaatg agcccttttc     6960
tctctcccac tcagcagcta tgagatggct tgccctgcct ctctactagg ctgactcact     7020
ccaaggccca gcaatgggca gggctctgtc agggctttga tagcactatc tgcagagcca     7080
gggccgagaa ggggtggact ccagagactc tccctcccat tcccgagcag ggtttgctta     7140
tttatgcatt taaatgatat atttatttta aagaaataa  caggagactg cccagccctg     7200
gctgtgacat ggaaactatg tagaatattt tgggttccat ttttttttcc ttctttcagt     7260
tagaggaaaa ggggctcact gcacatacac tagacagaaa gtcaggagct ttgaatccaa     7320
gcctgatcat ttccatgtca tactgagaaa gtccccaccc ttctctgagc ctcagtttct     7380 cttttttataa gtaggagtct ggagtaaatg atttccaatg gctctcattt caatacaaaa     7440
tttccgttta ttaaatgcat gagcttccgt tactccaaga ctgagaagga aattgaacct     7500
gagactcatt gactggcaag atgtcccag  aggctctcat tcagcaataa aattctcacc     7560
ttcacccagg cccactagtg tcagatttgc atgcgttcgc gtaaaaaagg atatgccctt     7620
gactatgtcg gacaaatagt caagggcata tcctgaggta cccaggcggc gcacaagcta     7680
tataaacctg aaggaaatct caactttaca cttaggtcaa gttacttatc gtactagagc     7740
ttcagcagga aatttaacta aaatctaatt taaccagcat agcaaatatc atttattccc     7800
aaaatgctaa agtttgagat aaacggactt gatttccggc tgttttgaca ctatccagaa     7860
tgccggtact atgggtgggg cagtagcccg actgcacgtc gagcggccgc atcgatgccg     7920
tagtaccttt aagaccaatg acttacaagg cagctgtaga tcttagccac ttttttaaaag    7980 aaaaggggg  actggaaggg ctaattcact cccaaagaag acaagatccc tgcaggcatt     8040
caaggccagg ctggatgtgg ctctgggcag cctgggctgc tggttgatga ccctgcacat     8100 agcaggggt  tggatctgga tgagcactgt gctcctttgc aacccaggcc gttctatgat     8160
tctgtcattc taaatctctc tttcagccta agcttttttc cccgtatccc cccaggtgtc     8220
tgcaggctca aagagcagcg agaagcgttc agaggaaagc gatcccgtgc caccttcccc     8280
gtgcccgggc tgtccccgca cgctgccggc tcggggatgg gggggagcg  ccggaccgga     8340 gcggagcccc gggcggctcg ctgctgcccc ctagcggggg agggacgtaa ttacatccct     8400
gggggctttg ggggggggct gtccccgtga gctcccccaga tctgcttttt gcctgtactg    8460
ggtctctctg gttagaccag atctgagcct gggagctctc tggctaacta gggaacccac     8520
tgcttaagcc tcaataaagc ttcagctgct cgagctagca gatcttttc  cctctgccaa     8580 aaattatggg gacatcatga agccccttga gcatctgact tctggctaat aaaggaaatt     8640 tatttttcatt gcaatagtgt gttggaattt tttgtgtctc tcactcggaa ggacatatgg     8700
gagggcaaat catttaaaac atcagaatga gtatttggtt tagagtttgg caacatatgc     8760
ccatatgctg gctgccatga acaaaggttg gctataaaga ggtcatcagt atatgaaaca     8820
gccccctgct gtccattcct tattccatag aaaagccttg acttgaggtt agattttttt     8880
tatattttgt tttgtgttat ttttttcttt aacatcccta aaattttcct tacatgtttt     8940
actagccaga ttttttcctcc tctcctgact actcccagtc atagctgtcc ctcttctctt     9000
atggagatcc ctcgacctgc agcccaagct tggcgtaatc atggtcatag ctgtttcctg     9060
tgtgaaattg ttatccgctc acaattccac acaacatacg agccgaagc  ataaagtgta     9120 aagcctgggg tgcctaatga gtgagctaac tcacattaat tgcgttgcgc tcactgcccg     9180
```

```
ctttccagtc gggaaacctg tcgtgccagc ggatccgcat ctcaattagt cagcaaccat      9240
agtcccgccc ctaactccgc ccatcccgcc cctaactccg cccagttccg cccattctcc      9300
gccccatggc tgactaattt tttttattta tgcagaggcc gaggccgcct cggcctctga      9360
gctattccag aagtagtgag gaggcttttt tggaggccta ggcttttgca aaaagctgtc      9420
gactgcagag gcctgcatgc aagcttggcg taatcatggt catagctgtt tcctgtgtga      9480
aattgttatc cgctcacaat tccacacaac atacgagccg gaagcataaa gtgtaaagcc      9540
tggggtgcct aatgagtgag ctaactcaca ttaattgcgt tgcgctcact gcccgctttc      9600
cagtcgggaa acctgtcgtg ccagctgcat taatgaatcg gccaacgcgc ggggagaggc      9660
ggtttgcgta ttgggcgctc ttccgcttcc tcgctcactg actcgctgcg ctcggtcgtt      9720
cggctgcggc gagcggtatc agctcactca aaggcggtaa tacggttatc cacagaatca      9780
ggggataacg caggaaagaa catgtgagca aaaggccagc aaaaggccag gaaccgtaaa      9840
aaggccgcgt tgctggcgtt tttccatagg ctccgccccc ctgacgagca tcacaaaaat      9900
cgacgctcaa gtcagaggtg gcgaaacccg acaggactat aaagatacca ggcgtttccc      9960
cctggaagct ccctcgtgcg ctctcctgtt ccgaccctgc cgcttaccgg atacctgtcc     10020
gcctttctcc cttcgggaag cgtggcgctt tctcatagct cacgctgtag gtatctcagt     10080
tcggtgtagg tcgttcgctc caagctgggc tgtgtgcacg aaccccccgt tcagcccgac     10140
cgctgcgcct tatccggtaa ctatcgtctt gagtccaacc cggtaagaca cgacttatcg     10200
ccactggcag cagccactgg taacaggatt agcagagcga ggtatgtagg cggtgctaca     10260
gagttcttga agtggtggcc taactacggc tacactagaa gaacagtatt tggtatctgc     10320
gctctgctga agccagttac cttcggaaaa agagttggta gctcttgatc cggcaaacaa     10380
accaccgctg gtagcggtgg tttttttgtt tgcaagcagc agattacgcg cagaaaaaaa     10440
ggatctcaag aagatccttt gatcttttct acggggtctg acgctcagtg gaacgaaaac     10500
tcacgttaag ggattttggt catgagatta tcaaaaagga tcttcaccta gatcctttta     10560
aattaaaaat gaagttttaa atcaatctaa agtatatatg agtaaacttg gtctgacagt     10620
taccaatgct taatcagtga ggcacctatc tcagcgatct gtctatttcg ttcatccata     10680
gttgcctgac tccccgtcgt gtagataact acgatacggg agggcttacc atctggcccc     10740
agtgctgcaa tgataccgcg agacccacgc tcaccggctc cagatttatc agcaataaac     10800
cagccagccg gaagggccga gcgcagaagt ggtcctgcaa ctttatccgc ctccatccag     10860
tctattaatt gttgccggga agctagagta agtagttcgc cagttaatag tttgcgcaac     10920
gttgttgcca ttgctacagg catcgtggtg tcacgctcgt cgtttggtat ggcttcattc     10980
agctccggtt cccaacgatc aaggcgagtt acatgatccc ccatgttgtg caaaaaagcg     11040
gttagctcct tcggtcctcc gatcgttgtc agaagtaagt tggccgcagt gttatcactc     11100
atggttatgg cagcactgca taattctctt actgtcatgc catccgtaag atgcttttct     11160
gtgactggtg agtactcaac caagtcattc tgagaatagt gtatgcggcg accgagttgc     11220
tcttgcccgg cgtcaatacg ggataatacc gcgccacata gcagaacttt aaaagtgctc     11280
atcattggaa aacgttcttc ggggcgaaaa ctctcaagga tcttaccgct gttgagatcc     11340
agttcgatgt aacccactcg tgcacccaac tgatcttcag catcttttac tttcaccagc     11400
gtttctgggt gagcaaaaac aggaaggcaa aatgccgcaa aaaagggaat aagggcgaca     11460
cggaaatgtt gaatactcat actcttcctt tttcaatatt attgaagcat ttatcagggt     11520
tattgtctca tgagcggata catatttgaa tgtatttaga aaaataaaca ataggggtt     11580
```

```
ccgcgcacat ttccccgaaa agtgccacct gacgtctaag aaaccattat tatcatgaca    11640
ttaacctata aaataggcg tatcacgagg cccttcgtc tcgcgcgttt cggtgatgac     11700
ggtgaaaacc tctgacacat gcagctcccg gagacggtca cagcttgtct gtaagcggat    11760
gccgggagca gacaagcccg tcagggcgcg tcagcgggtg ttggcgggtg tcggggctgg    11820
cttaactatg cggcatcaga gcagattgta ctgagagtgc accatatgcg gtgtgaaata    11880
ccgcacagat gcgtaaggag aaaataccgc atcaggcgcc attcgccatt caggctgcgc    11940
aactgttggg aagggcgatc ggtgcgggcc tcttcgctat tacgccagct ggcgaaaggg    12000
ggatgtgctg caaggcgatt aagttgggta acgccagggt tttcccagtc acgacgttgt    12060
aaaacgacgg ccagtgaatt c                                              12081

<210> SEQ ID NO 12
<211> LENGTH: 12084
<212> TYPE: DNA
<213> ORGANISM: Artificial Sequence
<220> FEATURE:
<223> OTHER INFORMATION: Synthetic: TL20c-rGbGM-r7SK/sh734

<400> SEQUENCE: 12
ggccgcctcg gccaaacagc ccttgagttt accactccct atcagtgata gagaaaagtg      60
aaagtcgagt ttaccactcc ctatcagtga tagagaaaag tgaaagtcga gtttaccact    120
ccctatcagt gatagagaaa agtgaaagtc gagtttacca ctccctatca gtgatagaga    180
aaagtgaaag tcgagtttac cagtccctat cagtgataga gaaaagtgaa agtcgagttt    240
accactccct atcagtgata gagaaaagtg aaagtcgagt ttaccactcc ctatcagtga    300
tagagaaaag tgaaagtcga gctcgccatg gaggcgtgg cctgggcggg actgggagt     360 ggcgagccct cagatcctgc atataagcag ctgcttttg cctgtactgg gtctctctgg    420
ttagaccaga tctgagcctg ggagctctct ggctaactag gaacccact gcttaagcct    480 caataaagct tgccttgagt gcttcaagta gtgtgtgccc gtctgttgtg tgactctggt    540
aactagagat ccctcagacc cttttagtca gtgtggaaaa tctctagcag tggcgcccga    600
acagggactt gaaagcgaaa gggaaaccag aggagctctc tcgacgcagg actcggcttg    660
ctgaagcgcg cacggcaaga ggcgaggggc ggcgactggt gagtacgcca aaattttga    720 ctagcggagg ctagaaggag agagatgggt gcgagagcgt cagtattaag cggggagaa    780 ttagatcgcg atgggaaaaa attcggttaa ggccaggggg aaagaaaaaa tataaattaa    840
aacatatagt atgggcaagc agggagctag aacgattcgc agttaatact ggcctgttag    900
aaacatcaga aggctgtaga caaatactgg gacagctaca accatcccct cagacaggat    960
cagaagaact tagatcatta tataatacag tagcaaccct ctattgtgtg catcaaagga    1020
tagagataaa agacaccaag gaagctttag acaagataga ggaagagcaa aacaaaagta    1080
agaaaaaagc acagcaagca gcaggatctt cagacctgga aattcctac aatcccaa      1140 gtcaaggagt agtagaatct atgaataaag aattaaagaa attatagga caggtaagag    1200 atcaggctga acatcttaag acagcagtac aaatggcagt attcatcac aattttaaaa   1260 gaaaaggggg gattgggggg tacagtgcag gggaaagaat agtagacata atagcaacag    1320
acatacaaac taaagaatta caaaaacaaa ttacaaaaat tcaaaatttt cgggtttatt    1380
acagggacag cagaaatcca ctttggaaag gaccagcaaa gctcctctgg aaaggtgaag    1440
gggcagtagt aatacaagat aatagtgaca taaaagtagt gccaagaaga aaagcaaaga    1500
```

```
tcattaggga ttatggaaaa cagatggcag gtgatgattg tgtggcaagt agacaggatg    1560
aggattagaa catggaaaag tttagtaaaa caccataagg aggagatatg agggacaatt    1620
ggagaagtga attatataaa tataaagtag taaaaattga accattagga gtagcaccca    1680
ccaaggcaaa gagaagagtg gtgcagagag aaaaaagagc agtgggaata ggagctttgt    1740
tccttgggtt cttgggagca gcaggaagca ctatgggcgc agcgtcaatg acgctgacgg    1800
tacaggccag acaattattg tctggtatag tgcagcagca gaacaatttg ctgagggcta    1860
ttgaggcgca acagcatctg ttgcaactca cagtctgggg catcaagcag ctccaggcaa    1920
gaatcctggc tgtggaaaga tacctaaagg atcaacagct cctggggatt tggggttgct    1980
ctggaaaact catttgcacc actgctgtgc cttggaatgc tagttggagt aataaatctc    2040
tggaacagat ttggaatcac acgacctgga tggagtggga cagagaaatt aacaattaca    2100
caagcttaat acactcctta attgaagaat cgcaaaacca gcaagaaaag aatgaacaag    2160
aattattgga attagataaa tgggcaagtt tgtggaattg gtttaacata acaaattggc    2220
tgtggtatat aaaattattc ataatgatag taggaggctt ggtaggttta agaatagttt    2280
ttgctgtact ttctatagtg aatagagtta ggcagggata ttcaccatta tcgtttcaga    2340
cccacctccc aaccccgagg ggaccgagct caagcttcga acgcgtgggg atcctctaga    2400
gtcgagctcg cgaggatcat caccggtgct agccggagcc agaagcacca taagggacat    2460
gataagggag ccagcagacc tctgatctct tcctgaatgc taatcttaaa catcctgagg    2520
aagaatggga cttccatttg gggtgggcct atgatagggt aataagacag tagtgaatat    2580
caagctacaa aaagccccct ttcaaattct tctcagtcct aacttttcat actaagccca    2640
gtccttccaa agcagactgt gaaagagtga tagttccggg agactagcac cggctagccg    2700
agcttggaac actttcccctt cattaagaac catccttgct actcagctgc aatcaatcca    2760
gcccccaggt cttcactgaa ccttttccca tctcttccaa aacatctgtt tctgagaagt    2820
cctgtcctat agaggtcttt cttcccaccg gatttctcct acaccattta ctcccacttg    2880
cagaactccc gtgtacaagt gtctttactg cttttatttg ctcaacaaaa tgcacatctc    2940
atataaaaat aaatgaggag catgcacaca ccacaaacac aaacaggcat gcagaaatac    3000
acatacacac ttccctcaat ataaacccctt tgtggctcat atatttaaaa agatgtaaaa    3060
aaaagagctg aagaaaatca tgtgtgatct ctcagcagaa tagatttatt atttgtattg    3120
cttgcagaat aaagcctatc cttgaaagct ctgaatcatg ggcaagaggc tcagtggtat    3180
ctggaggaca gggcactggc cactgcagtc accatcttct gccaggaagc ctgcacctca    3240
ggggtgaatt ctttgccaaa gtgaatggcc agcacggtga ccagcacgtt gcccaggagc    3300
tgtgggagga agataagagg tatgaacatg attagcaaaa gggcctagct tggactcaga    3360
ataatccagc cttatcccaa ccataaaata aaagcagaat ggtagctgga ttgtagctgc    3420
tattagcaat atgaaacctc ttacatcagt tacaatttat atgcagaaat atttatatgc    3480
agaaatattg ctattgcctt aacccagaaa ttatcactgt tattctttag aatggtgcaa    3540
agaggcatga tacattgtat cattattgcc ctgaaagaaa gagattaggg aaagtattag    3600
aaataagata aacaaaaaag tatattaaaa gaagaaagca ttttttaaaa ttacaaatgc    3660
aaaattaccc tgatttggtc aatatgtgta ccctgttact tctcccccttc ctatgacatg    3720 aacttaacca tagaaaagaa ggggaaagaa aacatcaagg gtcccataga ctcaccttga    3780
agttctcagg atccacatgc agcttgtcac agtgcagttc actcagctgg gcaaaggtgc    3840
ccttgagatc atccaggtgc tttatggcat ctcccaagga agtcagcacc ttcttgccat    3900
```

```
gtgccttgac tttggggttg cccatgatgg cagaggcaga ggacaggttg ccaaagctgt    3960
caaagaacct ctgggtccat gggtagacaa ccaggagcct gtgagattga caagaacagt    4020
ttgacagtca gaaggtgcca caaatcctga gaagcaacct ggacttttgc caggcacagg    4080
gtccttcctt ccctcccttg tcctggtcac cagagcctac cttcccaggg tttctcctcc    4140
agcatcttcc acattcacct tgtcccacag gcttgtgata gtagccttgt cctcctctgt    4200
gaaatgaccc atggtgtctg tttgaggttg ctagtgaaca cagttgtgtc agaagcaaat    4260
gtaagcaata gatggctctg ccctgacttt tatgcccagc cctggctcct gccctccctg    4320
ctcctgggag tagattggcc aaccctaggg tgtggctcca cagggtgagg tctaagtgat    4380
gacagccgta cctgtccttg gctcttctgg cactggctta ggagttggac ttcaaaccct    4440
cagccctccc tctaagatat atctcttggc cccataccat cagtacaaat gctactaaa    4500 aacatcctcc tttgcaagtg tatttacgac ggtatcgatg tatgtgagca tgtgtcctct    4560
aacagcacag gccttttgcc acctagctgt ccaggggtgc cttaaaatgg caaacaaggt    4620
ttgttttctt ttcctgtttt catgccttcc tcttccatat ccttgtttca tattaataca    4680
tgtgtataga tcctaaaaat ctatacacat gtattaataa agcctgattc tgccgcttct    4740
aggtatagag gccacctgca agataaatat ttgattcaca ataactaatc attctatggc    4800
aattgataac aacaaatata tatatatata tatatatacg tatatgtgta tatatatata    4860
tatattcagg aaataatata ttctagaata tgtcacattc tgtctcaggc atccattttc    4920
tttatgatgc cgtttgaggt ggagttttag tcaggtggtc agcttctcct ttttttgcc    4980 atctgccctg taagcatcct gctggggacc cagataggag tcatcactct aggctgagaa    5040
catctgggca cacaccctaa gcctcagcat gactcatcat gactcagcat tgctgtgctt    5100
gagccagaag gtttgcttag aaggttacac agaaccagaa ggcgggggtg gggcactgac    5160
cccgacaggg gcctggccag aactgctcat gcttggacta tgggaggtca ctaatggaga    5220
cacacagaaa tgtaacagga actaagggaa ttccggtgcc ctgcttagga gcttaatctt    5280
taatgaaagc taagctttca ttaaaaaaag tctaaccagc tgcattcgac tttgactgca    5340
gcagctggtt agaaggttct actggaggag ggtcccagcc cattgctaaa ttaacatcag    5400
gctctgagac tggcagtata tctctaacag tggttgatgc tatcttctgg aacttgcctg    5460
ctacattgag accactgacc catacatagg aagccctag ctctgtcctg aactgttagg    5520
ccactggtcc agagagtgtg catctccttt gatcctcata ataacctat gagatagaca    5580 caattattac tcttacttta tagatgatga tcctgaaaac ataggagtca aggcacttgc    5640
ccctagctgg gggtataggg gagcagtccc atgtagtagt agaatgaaaa atgctgctat    5700
gctgtgcctc ccccacccttt cccatgtctg ccctctactc atggtctatc tctcctggct    5760
cctgggagtc atggactcca cccagcacca ccaacctgac ctaaccacct atctgagcct    5820
gccagcctat aacccatctg ggccctgata gctggtggcc agccctgacc ccaccccacc    5880
ctccctggaa cctctgatag acacatctgg cacaccagct cgcaaagtca ccgtgagggt    5940
cttgtgtttg ctgagtcaaa attccttgaa atccaagtcc ttagagactc ctgctcccaa    6000
atttacagtc atagacttct tcatggctgt ctcctttatc cacagaatga ttcctttgct    6060
tcattgcccc atccatctga tcctcctcat cagtgcagca cagggcccat gagcagtagc    6120
tgcagagtct cacataggtc tggcactgcc tctgacatgt ccgaccttag gcaaatgctt    6180
gactcttctg agctcggatc ccttgagctc aggaggtcaa ggctgcagtg agacatgatc    6240
```

```
ttgccactgc actccagcct ggacagcaga gtgaaacctt gcctcacgaa acagaataca    6300
aaaacaaaca aacaaaaaac tgctccgcaa tgcgcttcct tgatgctcta ccacataggt    6360
ctgggtactt tgtacacatt atctcattgc tgttcataat tgttagatta attttgtaat    6420
attgatatta ttcctagaaa gctgaggcct caagatgata acttttattt tctggacttg    6480
taatagcttt ctcttgtatt caccatgttg taactttctt agagtagtaa caatataaag    6540
ttattgtgag tttttgcaaa cacagcaaac acaacgaccc atatagacat tgatgtgaaa    6600
ttgtctattg tcaatttatg ggaaaacaag tatgtacttt ttctactaag ccattgaaac    6660
aggaataaca gaacaagatt gaagaataca attttccgaa attacttgag tattatacaa    6720
agacaagcac gtggacctgg gaggagggtt attgtccatg actggtgtgt ggagacaaat    6780
gcaggtttat aatagatggg atggcatcta gcgcaatgac tttgccatca cttttagaga    6840
gctcttgggg gccccagtac acaagagggg acgcagggta tatgtagaca tctcattctt    6900
tttcttagtg tgagaataag aatagccatg acctgagttt atagacaatg agcccttttc    6960
tctctcccac tcagcagcta tgagatggct tgccctgcct ctctactagg ctgactcact    7020
ccaaggccca gcaatgggca gggctctgtc agggctttga tagcactatc tgcagagcca    7080
gggccgagaa ggggtggact ccagagactc tccctcccat tcccgagcag ggtttgctta    7140
tttatgcatt taaatgatat atttatttta aagaaataa caggagactg cccagccctg    7200
gctgtgacat ggaaactatg tagaatattt tgggttccat ttttttttcc ttctttcagt    7260
tagaggaaaa ggggctcact gcacatacac tagacagaaa gtcaggagct ttgaatccaa    7320
gcctgatcat ttccatgtca tactgagaaa gtccccaccc ttctctgagc ctcagtttct    7380
ctttttataa gtaggagtct ggagtaaatg atttccaatg gctctcattt caatacaaaa    7440
tttccgttta ttaaatgcat gagcttccgt tactccaaga ctgagaagga aattgaacct    7500
gagactcatt gactggcaag atgtccccag aggctctcat tcagcaataa aattctcacc    7560
ttcacccagg cccactagtg tcagatttgc atgcgttcgc gtacaaaaaa ggatatgccc    7620
ttgactatgt cggacaaata gtcaagggca tatcctgagg tacccaggcg gcgcacaagc    7680
tatataaacc tgaaggaaat ctcaacttta cacttaggtc aagttactta tcgtactaga    7740
gcttcagcag gaaatttaac taaaatctaa tttaaccagc atagcaaata tcatttattc    7800
ccaaaatgct aaagtttgag ataaacggac ttgatttccg gctgttttga cactatccag    7860
aatgccttgc agatgggtgg ggcatgctaa atactgcacg tcgatgcggc cgcatcgatg    7920
ccgtagtacc tttaagacca atgacttaca aggcagctgt agatcttagc cacttttaa     7980
aagaaagg gggactggaa gggctaattc actcccaaag aagacaagat ccctgcaggc     8040
attcaaggcc aggctggatg tggctctggg cagcctgggc tgctggttga tgaccctgca    8100
catagcaggg ggttggatct ggatgagcac tgtgctcctt tgcaacccag gccgttctat    8160
gattctgtca ttctaaatct ctcttttcagc ctaaagcttt ttccccgtat cccccaggt    8220
gtctgcaggc tcaaagagca gcgagaagcg ttcagaggaa agcgatcccg tgccaccttc    8280
cccgtgcccg ggctgtcccc gcacgctgcc ggctcgggga tgcgggggga gcgccggacc    8340
ggagcggagc cccgggcggc tcgctgctgc ccctagcgg ggagggacg taattacatc     8400
cctgggggct ttgggggggg gctgtcccg tgagctcccc agatctgctt tttgcctgta    8460
ctgggtctct ctggttagac cagatctgag cctgggagct ctctggctaa ctagggaacc    8520
cactgcttaa gcctcaataa agcttcagct gtctgagcta gcagatcttt ttccctctgc    8580
caaaaattat ggggacatca tgaagcccct tgagcatctg acttctggct aataaaggaa    8640
```

```
atttattttc attgcaatag tgtgttggaa ttttttgtgt ctctcactcg gaaggacata    8700
tgggagggca aatcatttaa aacatcagaa tgagtatttg gtttagagtt tggcaacata    8760
tgcccatatg ctggctgcca tgaacaaagg ttggctataa agaggtcatc agtatatgaa    8820
acagccccct gctgtccatt ccttattcca tagaaaagcc ttgacttgag gttagatttt    8880
ttttatattt tgttttgtgt tattttttc tttaacatcc ctaaaatttt ccttacatgt     8940
tttactagcc agattttcc tcctctcctg actactccca gtcatagctg tccctcttct     9000
cttatggaga tccctcgacc tgcagcccaa gcttggcgta atcatggtca tagctgtttc    9060
ctgtgtgaaa ttgttatccg ctcacaattc cacacaacat acgagccgga agcataaagt    9120
gtaaagcctg gggtgcctaa tgagtgagct aactcacatt aattgcgttg cgctcactgc    9180
ccgctttcca gtcgggaaac ctgtcgtgcc agcggatccg catctcaatt agtcagcaac    9240
catagtcccg cccctaactc cgcccatccc gcccctaact ccgcccagtt ccgcccattc    9300
tccgccccat ggctgactaa ttttttttat ttatgcagag gccgaggccg cctcggcctc    9360
tgagctattc cagaagtagt gaggaggctt ttttggaggc ctaggctttt gcaaaaagct    9420
gtcgactgca gaggcctgca tgcaagcttg gcgtaatcat ggtcatagct gtttcctgtg    9480
tgaaattgtt atccgctcac aattccacac aacatacgag ccggaagcat aaagtgtaaa    9540
gcctggggtg cctaatgagt gagctaactc acattaattg cgttgcgctc actgcccgct    9600
ttccagtcgg gaaacctgtc gtgccagctg cattaatgaa tcggccaacg cgcggggaga    9660
ggcggtttgc gtattgggcg ctcttccgct tcctcgctca ctgactcgct gcgctcggtc    9720
gttcggctgc ggcgagcggt atcagctcac tcaaaggcgg taatacggtt atccacagaa    9780
tcaggggata acgcaggaaa gaacatgtga gcaaaaggcc agcaaaaggc caggaaccgt    9840
aaaaaggccg cgttgctggc gtttttccat aggctccgcc cccctgacga gcatcacaaa    9900
aatcgacgct caagtcagag gtggcgaaac ccgacaggac tataaagata ccaggcgttt    9960
ccccctggaa gctccctcgt gcgctctcct gttccgaccc tgccgcttac cggatacctg   10020
tccgcctttc tcccttcggg aagcgtggcg ctttctcata gctcacgctg taggtatctc   10080
agttcggtgt aggtcgttcg ctccaagctg ggctgtgtgc acgaaccccc cgttcagccc   10140
gaccgctgcg ccttatccgg taactatcgt cttgagtcca acccggtaag acacgactta   10200
tcgccactgg cagcagccac tggtaacagg attagcagag cgaggtatgt aggcggtgct   10260
acagagttct tgaagtggtg gcctaactac ggctacacta agaacagtt atttggtatc    10320 tgcgctctgc tgaagccagt taccttcgga aaaagagttg gtagctcttg atccggcaaa   10380
caaaccaccg ctggtagcgg tggtttttt gtttgcaagc agcagattac gcgcagaaaa    10440
aaaggatctc aagaagatcc tttgatcttt tctacgggt ctgacgctca gtggaacgaa    10500
aactcacgtt aagggatttt ggtcatgaga ttatcaaaaa ggatcttcac ctagatcctt   10560
ttaaattaaa aatgaagttt taaatcaatc taaagtatat atgagtaaac ttggtctgac   10620
agttaccaat gcttaatcag tgaggcacct atctcagcga tctgtctatt tcgttcatcc   10680
atagttgcct gactccccgt cgtgtagata actacgatac gggagggctt accatctggc   10740
cccagtgctg caatgatacc gcgagaccca cgctcaccgg ctccagattt atcagcaata   10800
aaccagccag ccggaagggc cgagcgcaga agtggtcctg caactttatc cgcctccatc   10860
cagtctatta attgttgccg ggaagctaga gtaagtagtt cgccagttaa tagtttcgc   10920 aacgttgttg ccattgctac aggcatcgtg gtgtcacgct cgtcgtttgg tatggcttca   10980
```

```
ttcagctccg gttcccaacg atcaaggcga gttacatgat cccccatgtt gtgcaaaaaa    11040
gcggttagct ccttcggtcc tccgatcgtt gtcagaagta agttggccgc agtgttatca    11100
ctcatggtta tggcagcact gcataattct cttactgtca tgccatccgt aagatgcttt    11160
tctgtgactg gtgagtactc aaccaagtca ttctgagaat agtgtatgcg gcgaccgagt    11220
tgctcttgcc cggcgtcaat acgggataat accgcgccac atagcagaac tttaaaagtg    11280
ctcatcattg gaaaacgttc ttcggggcga aaactctcaa ggatcttacc gctgttgaga    11340
tccagttcga tgtaacccac tcgtgcaccc aactgatctt cagcatcttt tactttcacc    11400
agcgtttctg ggtgagcaaa aacaggaagg caaaatgccg caaaaaaggg aataagggcg    11460
acacggaaat gttgaatact catactcttc cttttttcaat attattgaag catttatcag    11520
ggttattgtc tcatgagcgg atacatattt gaatgtattt agaaaaataa acaaataggg    11580
gttccgcgca catttccccg aaaagtgcca cctgacgtct aagaaaccat tattatcatg    11640
acattaacct ataaaaatag gcgtatcacg aggccctttc gtctcgcgcg tttcggtgat    11700
gacggtgaaa acctctgaca catgcagctc ccggagacgg tcacagcttg tctgtaagcg    11760
gatgccggga gcagacaagc ccgtcagggc gcgtcagcgg gtgttggcgg gtgtcggggc    11820
tggcttaact atgcggcatc agagcagatt gtactgagag tgcaccatat gcggtgtgaa    11880
ataccgcaca gatgcgtaag gagaaaatac cgcatcaggc gccattcgcc attcaggctg    11940
cgcaactgtt gggaagggcg atcggtgcgg gcctcttcgc tattacgcca gctggcgaaa    12000
gggggatgtg ctgcaaggcg attaagttgg gtaacgccag ggttttccca gtcacgacgt    12060
tgtaaaacga cggccagtga attc                                          12084
```

<210> SEQ ID NO 13  
<211> LENGTH: 11779  
<212> TYPE: DNA  
<213> ORGANISM: Artificial Sequence  
<220> FEATURE:  
<223> OTHER INFORMATION: Synthetic: TL20c-rGbGM

<400> SEQUENCE: 13

```
ggccgcctcg gccaaacagc ccttgagttt accactccct atcagtgata gagaaaagtg      60
aaagtcgagt ttaccactcc ctatcagtga tagagaaaag tgaaagtcga gtttaccact     120
ccctatcagt gatagagaaa agtgaaagtc gagtttacca ctccctatca gtgatagaga     180 aagtgaaag tcgagtttac cagtccctat cagtgataga gaaaagtgaa agtcgagttt     240
accactccct atcagtgata gagaaaagtg aaagtcgagt ttaccactcc ctatcagtga     300
tagagaaaag tgaaagtcga gctcgccatg ggaggcgtgg cctgggcggg actggggagt     360
ggcgagccct cagatcctgc atataagcag ctgcttttttg cctgtactgg gtctctctgg     420
ttagaccaga tctgagcctg ggagctctct ggctaactag ggaacccact gcttaagcct     480
caataaagct tgccttgagt gcttcaagta gtgtgtgccc gtctgttgtg tgactctggt     540
aactagagat ccctcagacc cttttagtca gtgtggaaaa tctctagcag tggcgcccga     600
acagggactt gaaagcgaaa gggaaaccag aggagctctc tcgacgcagg actcggcttg     660
ctgaagcgcg cacggcaaga ggcgaggggc ggcgactggg gagtacgcca aaaattttga     720
ctagcggagg ctagaaggag agagatgggt gcgagagcgt cagtattaag cggggagaa     780 ttagatcgcg atgggaaaaa attcggttaa ggccaggggg aaagaaaaaa tataaattaa     840
aacatatagt atgggcaagc agggagctag aacgattcgc agttaatact ggcctgttag     900
aaacatcaga aggctgtaga caaatactgg gacagctaca accatcccctt cagacaggat     960
```

```
cagaagaact tagatcatta tataatacag tagcaaccct ctattgtgtg catcaaagga    1020
tagagataaa agacaccaag gaagctttag acaagataga ggaagagcaa aacaaaagta    1080
agaaaaaagc acagcaagca gcaggatctt cagacctgga aattccctac aatccccaaa    1140
gtcaaggagt agtagaatct atgaataaag aattaaagaa aattatagga caggtaagag    1200
atcaggctga acatcttaag acagcagtac aaatggcagt attcatccac aattttaaaa    1260 gaaaagggg gattgggggg tacagtgcag gggaaagaat agtagacata atagcaacag    1320
acatacaaac taaagaatta caaaaacaaa ttacaaaaat tcaaaatttt cgggtttatt    1380
acagggacag cagaaatcca ctttggaaag gaccagcaaa gctcctctgg aaaggtgaag    1440
gggcagtagt aatacaagat aatagtgaca taaaagtagt gccaagaaga aaagcaaaga    1500
tcattaggga ttatggaaaa cagatggcag gtgatgattg tgtggcaagt agacaggatg    1560
aggattagaa catggaaaag tttagtaaaa caccataagg aggagatatg agggacaatt    1620
ggagaagtga attatataaa tataaagtag taaaaattga accattagga gtagcaccca    1680
ccaaggcaaa gagaagagtg gtgcagagag aaaaaagagc agtgggaata ggagctttgt    1740
tccttgggtt cttgggagca gcaggaagca ctatgggcgc agcgtcaatg acgctgacgg    1800
tacaggccag acaattattg tctggtatag tgcagcagca gaacaatttg ctgagggcta    1860
ttgaggcgca acagcatctg ttgcaactca cagtctgggg catcaagcag ctccaggcaa    1920
gaatcctggc tgtggaaaga tacctaaagg atcaacagct cctggggatt tggggttgct    1980
ctggaaaact catttgcacc actgctgtgc cttggaatgc tagttggagt aataaatctc    2040
tggaacagat ttggaatcac acgacctgga tggagtggga cagagaaatt aacaattaca    2100
caagcttaat acactcctta attgaagaat cgcaaaacca gcaagaaaag aatgaacaag    2160
aattattgga attagataaa tgggcaagtt tgtggaattg gtttaacata acaaattggc    2220
tgtggtatat aaaattattc ataatgatag taggaggctt ggtaggttta agaatagttt    2280
ttgctgtact ttctatagtg aatagagtta ggcagggata ttcaccatta tcgtttcaga    2340
cccacctccc aaccccgagg ggaccgagct caagcttcga acgcgtgggg atcctctaga    2400
gtcgagctcg cgaggatcat caccggtgct agccggagcc agaagcacca taagggacat    2460
gataagggag ccagcagacc tctgatctct cctgaatgc taatcttaaa catcctgagg    2520
aagaatggga cttccatttg gggtgggcct atgatagggt aataagacag tagtgaatat    2580
caagctacaa aaagccccct ttcaaattct tctcagtcct aacttttcat actaagccca    2640
gtccttccaa agcagactgt gaaagagtga tagttccggg agactagcac cggctagccg    2700
agcttggaac actttccctt cattaagaac catccttgct actcagctgc aatcaatcca    2760 gccccccaggt cttcactgaa cctttttccca tctcttccaa aacatctgtt tctgagaagt    2820
cctgtcctat agaggtcttt cttcccaccg gatttctcct acaccattta ctcccacttg    2880
cagaactccc gtgtacaagt gtctttactg cttttatttg ctcaacaaaa tgcacatctc    2940
atataaaaat aaatgaggag catgcacaca ccacaaacac aaacaggcat gcagaaatac    3000
acatacacac ttccctcaat ataaacccctt tgtggctcat atatttaaaa agatgtaaaa    3060
aaaagagctg aagaaaatca tgtgtgatct ctcagcagaa tagattttatt atttgtattg    3120 cttgcagaat aaagcctatc cttgaaagct ctgaatcatg ggcaagaggc tcagtggtat    3180
ctggaggaca gggcactggc cactgcagtc accatcttct gccaggaagc ctgcacctca    3240
ggggtgaatt cttttgccaaa gtgaatggcc agcacggtga ccagcacgtt gcccaggagc    3300
```

```
tgtgggagga agataagagg tatgaacatg attagcaaaa gggcctagct tggactcaga    3360
ataatccagc cttatcccaa ccataaaata aaagcagaat ggtagctgga ttgtagctgc    3420
tattagcaat atgaaacctc ttacatcagt tacaatttat atgcagaaat atttatatgc    3480
agaaatattg ctattgcctt aacccagaaa ttatcactgt tattctttag aatggtgcaa    3540
agaggcatga tacattgtat cattattgcc ctgaaagaaa gagattaggg aaagtattag    3600
aaataagata aacaaaaaag tatattaaaa gaagaaagca tttttttaaaa ttacaaatgc    3660
aaaattaccc tgatttggtc aatatgtgta ccctgttact tctccccttc ctatgacatg    3720
aacttaacca tagaaaagaa ggggaaagaa aacatcaagg gtcccataga ctcaccttga    3780
agttctcagg atccacatgc agcttgtcac agtgcagttc actcagctgg gcaaaggtgc    3840
ccttgagatc atccaggtgc tttatggcat ctcccaagga agtcagcacc ttcttgccat    3900
gtgccttgac tttggggttg cccatgatgg cagaggcaga ggacaggttg ccaaagctgt    3960
caaagaacct ctgggtccat gggtagacaa ccaggagcct gtgagattga caagaacagt    4020
ttgacagtca gaaggtgcca caaatcctga gaagcaacct ggacttttgc caggcacagg    4080
gtccttcctt ccctcccttg tcctggtcac cagagcctac cttcccaggg tttctcctcc    4140
agcatcttcc acattcacct tgtcccacag gcttgtgata gtagccttgt cctcctctgt    4200
gaaatgaccc atggtgtctg tttgaggttg ctagtgaaca cagttgtgtc agaagcaaat    4260
gtaagcaata gatggctctg ccctgacttt tatgcccagc cctggctcct gcctccctg    4320
ctcctgggag tagattggcc aaccctaggg tgtggctcca cagggtgagg tctaagtgat    4380
gacagccgta cctgtccttg gctcttctgg cactggctta ggagttggac ttcaaaccct    4440
cagccctccc tctaagatat atctcttggc cccataccat cagtacaaat gctactaaa    4500
aacatcctcc tttgcaagtg tatttacgac ggtatcgatg tatgtgagca tgtgtcctct    4560
aacagcacag gccttttgcc acctagctgt ccaggggtgc cttaaaatgg caaacaaggt    4620
ttgttttctt ttcctgtttt catgccttcc tcttccatat ccttgtttca tattaataca    4680
tgtgtataga tcctaaaaat ctatacacat gtattaataa agcctgattc tgccgcttct    4740
aggtatagag gccacctgca agataaatat ttgattcaca ataactaatc attctatggc    4800
aattgataac aacaaatata tatatatata tatatacg tatatgtgta tatatata    4860
tatattcagg aaataatata ttctagaata tgtcacattc tgtctcaggc atccatttc    4920
tttatgatgc cgtttgaggt ggagttttag tcaggtggtc agcttctcct tttttttgcc    4980
atctgccctg taagcatcct gctggggacc cagataggag tcatcactct aggctgagaa    5040
catctgggca cacaccctaa gcctcagcat gactcatcat gactcagcat tgctgtgctt    5100
gagccagaag gtttgcttag aaggttacac agaaccagaa ggcgggggtg gggcactgac    5160
cccgacaggg gcctggccag aactgctcat gcttggacta tgggaggtca ctaatggaga    5220
cacacagaaa tgtaacagga actaagggaa ttccggtgcc ctgcttagga gcttaatctt    5280
taatgaaagc taagctttca ttaaaaaaag tctaaccagc tgcattcgac tttgactgca    5340
gcagctggtt agaaggttct actggaggag ggtcccagcc cattgctaaa ttaacatcag    5400
gctctgagac tggcagtata tctctaacag tggttgatgc tatcttctgg aacttgcctg    5460
ctacattgag accactgacc catacatagg aagcccatag ctctgtcctg aactgttagg    5520
ccactggtcc agagagtgtg catctccttt gatcctcata ataaccctat gagatagaca    5580
caattattac tcttacttta tagatgatga tcctgaaaac ataggagtca aggcacttgc    5640
ccctagctgg gggtataggg gagcagtccc atgtagtagt agaatgaaaa atgctgctat    5700
```

```
gctgtgcctc cccaccttt cccatgtctg ccctctactc atggtctatc tctcctggct    5760
cctgggagtc atggactcca cccagcacca ccaacctgac ctaaccacct atctgagcct    5820
gccagcctat aacccatctg ggccctgata gctggtggcc agccctgacc ccaccccacc    5880
ctccctggaa cctctgatag acacatctgg cacaccagct cgcaaagtca ccgtgagggt    5940
cttgtgtttg ctgagtcaaa attccttgaa atccaagtcc ttagagactc ctgctcccaa    6000
atttacagtc atagacttct tcatggctgt ctcctttatc cacagaatga ttcctttgct    6060
tcattgcccc atccatctga tcctcctcat cagtgcagca cagggcccat gagcagtagc    6120
tgcagagtct cacataggtc tggcactgcc tctgacatgt ccgaccttag gcaaatgctt    6180
gactcttctg agctcggatc ccttgagctc aggaggtcaa ggctgcagtg agacatgatc    6240
ttgccactgc actccagcct ggacagcaga gtgaaacctt gcctcacgaa acagaataca    6300
aaaacaaaca aacaaaaaac tgctccgcaa tgcgcttcct tgatgctcta ccacataggt    6360
ctgggtactt tgtacacatt atctcattgc tgttcataat tgttagatta attttgtaat    6420
attgatatta ttcctagaaa gctgaggcct caagatgata acttttattt tctggacttg    6480
taatagcttt ctcttgtatt caccatgttg taactttctt agagtagtaa caatataaag    6540
ttattgtgag tttttgcaaa cacagcaaac acaacgaccc atatagacat tgatgtgaaa    6600
ttgtctattg tcaatttatg ggaaaacaag tatgtacttt ttctactaag ccattgaaac    6660
aggaataaca gaacaagatt gaaagaatac attttccgaa attacttgag tattatacaa    6720
agacaagcac gtggacctgg gaggagggtt attgtccatg actggtgtgt ggagacaaat    6780
gcaggtttat aatagatggg atggcatcta gcgcaatgac tttgccatca ctttagaga    6840 gctcttgggg gccccagtac acaagagggg acgcagggta tatgtagaca tctcattctt    6900
tttcttagtg tgagaataag aatagccatg acctgagttt atagacaatg agcccttttc    6960
tctctcccac tcagcagcta tgagatggct tgccctgcct ctctactagg ctgactcact    7020
ccaaggccca gcaatgggca gggctctgtc agggctttga tagcactatc tgcagagcca    7080
gggccgagaa ggggtggact ccagagactc tccctcccat tcccgagcag ggtttgctta    7140
tttatgcatt taaatgatat atttattta aaagaaataa caggagactg cccagccctg    7200
gctgtgacat ggaaactatg tagaatattt tgggttccat ttttttttcc ttctttcagt    7260
tagaggaaaa ggggctcact gcacatacac tagacagaaa gtcaggagct ttgaatccaa    7320
gcctgatcat ttccatgtca tactgagaaa gtccccaccc ttctctgagc ctcagtttct    7380 cttttttataa gtaggagtct ggagtaaatg atttccaatg gctctcattt caatacaaaa    7440
tttccgttta ttaaatgcat gagcttccgt tactccaaga ctgagaagga aattgaacct    7500
gagactcatt gactggcaag atgtcccag aggctctcat tcagcaataa aattctcacc    7560
ttcacccagg cccactagtg tcagatttgc atgcgttaac gcggccgcat cgatgccgta    7620
gtacctttaa gaccaatgac ttacaaggca gctgtagatc ttagccactt tttaaaagaa    7680
aaggggggac tggaagggct aattcactcc caaagaagac aagatccctg caggcattca    7740
aggccaggct ggatgtggct ctgggcagcc tgggctgctg gttgatgacc ctgcacatag    7800
cagggggttg gatctggatg agcactgtgc tcctttgcaa cccaggccgt tctatgattc    7860
tgtcattcta aatctctctt tcagcctaaa gcttttttccc cgtatccccc caggtgtctg    7920
caggctcaaa gagcagcgag aagcgttcag aggaaagcga tcccgtgcca ccttcccgt    7980 gcccgggctg tccccgcacg ctgccggctc ggggatgcgg ggggagcgcc ggaccggagc    8040
```

```
ggagccccgg gcggctcgct gctgccccct agcggggagg ggacgtaatt acatccctgg   8100
gggctttggg gggggggctgt ccccgtgagc tccccagatc tgcttttttgc ctgtactggg   8160 tctctctggt tagaccagat ctgagcctgg gagctctctg gctaactagg gaacccactg   8220
cttaagcctc aataaagctt cagctgctcg agctagcaga tcttttttccc tctgccaaaa   8280 attatgggga catcatgaag ccccttgagc atctgacttc tggctaataa aggaaattta   8340
ttttcattgc aatagtgtgt tggaattttt tgtgtctctc actcggaagg acatatggga   8400
gggcaaatca tttaaaacat cagaatgagt atttggttta gagtttggca acatatgccc   8460
atatgctggc tgccatgaac aaaggttggc tataaagagg tcatcagtat atgaaacagc   8520
cccctgctgt ccattcctta ttccatagaa aagccttgac ttgaggttag atttttttta   8580
tattttgttt tgtgttattt ttttctttaa catccctaaa attttcctta catgttttac   8640
tagccagatt tttcctcctc tcctgactac tcccagtcat agctgtccct cttctcttat   8700
ggagatccct cgacctgcag cccaagcttg gcgtaatcat ggtcatagct gtttcctgtg   8760
tgaaattgtt atccgctcac aattccacac aacatacgag ccggaagcat aaagtgtaaa   8820
gcctggggtg cctaatgagt gagctaactc acattaattg cgttgcgctc actgcccgct   8880
ttccagtcgg gaaacctgtc gtgccagcgg atccgcatct caattagtca gcaaccatag   8940
tcccgcccct aactccgccc atcccgcccc taactccgcc cagttccgcc cattctccgc   9000
cccatggctg actaattttt tttatttatg cagaggccga ggccgcctcg gcctctgagc   9060
tattccagaa gtagtgagga ggcttttttg gaggcctagg cttttgcaaa aagctgtcga   9120
ctgcagaggc ctgcatgcaa gcttggcgta atcatggtca tagctgtttc ctgtgtgaaa   9180
ttgttatccg ctcacaattc cacacaacat acgagccgga agcataaagt gtaaagcctg   9240
gggtgcctaa tgagtgagct aactcacatt aattgcgttg cgctcactgc ccgctttcca   9300
gtcgggaaac ctgtcgtgcc agctgcatta atgaatcggc caacgcgcgg ggagaggcgg   9360
tttgcgtatt gggcgctctt ccgcttcctc gctcactgac tcgctgcgct cggtcgttcg   9420
gctgcggcga gcggtatcag ctcactcaaa ggcggtaata cggttatcca cagaatcagg   9480
ggataacgca ggaaagaaca tgtgagcaaa aggccagcaa aaggccagga accgtaaaaa   9540
ggccgcgttg ctggcgtttt tccataggct ccgcccccct gacgagcatc acaaaaatcg   9600
acgctcaagt cagaggtggc gaaacccgac aggactataa agataccagg cgtttccccc   9660
tggaagctcc ctcgtgcgct ctcctgttcc gaccctgccg cttaccggat acctgtccgc   9720
ctttctccct tcgggaagcg tggcgctttc tcatagctca cgctgtaggt atctcagttc   9780
ggtgtaggtc gttcgctcca agctgggctg tgtgcacgaa ccccccgttc agcccgaccg   9840
ctgcgcctta tccggtaact atcgtcttga gtccaacccg gtaagacacg acttatcgcc   9900
actggcagca gccactggta acaggattag cagagcgagg tatgtaggcg gtgctacaga   9960
gttcttgaag tggtggccta actacggcta cactagaaga acagtatttg gtatctgcgc  10020
tctgctgaag ccagttacct tcggaaaaag agttggtagc tcttgatccg gcaaacaaac  10080
caccgctggt agcggtggtt tttttgtttg caagcagcag attacgcgca gaaaaaaagg  10140
atctcaagaa gatcctttga tcttttctac ggggtctgac gctcagtgga acgaaaactc  10200
acgttaaggg attttggtca tgagattatc aaaaaggatc ttcacctaga tccttttaaa  10260
ttaaaaatga agttttaaat caatctaaag tatatatgag taaacttggt ctgacagtta  10320
ccaatgctta atcagtgagg cacctatctc agcgatctgt ctatttcgtt catccatagt  10380
tgcctgactc cccgtcgtgt agataactac gatacgggag ggcttaccat ctggccccag  10440
```

```
tgctgcaatg ataccgcgag acccacgctc accggctcca gatttatcag caataaacca    10500
gccagccgga agggccgagc gcagaagtgg tcctgcaact ttatccgcct ccatccagtc    10560
tattaattgt tgccgggaag ctagagtaag tagttcgcca gttaatagtt tgcgcaacgt    10620
tgttgccatt gctacaggca tcgtggtgtc acgctcgtcg tttggtatgg cttcattcag    10680
ctccggttcc caacgatcaa ggcgagttac atgatccccc atgttgtgca aaaaagcggt    10740
tagctccttc ggtcctccga tcgttgtcag aagtaagttg gccgcagtgt tatcactcat    10800
ggttatggca gcactgcata attctcttac tgtcatgcca tccgtaagat gcttttctgt    10860
gactggtgag tactcaacca agtcattctg agaatagtgt atgcggcgac cgagttgctc    10920
ttgcccggcg tcaatacggg ataataccgc gccacatagc agaactttaa aagtgctcat    10980
cattggaaaa cgttcttcgg ggcgaaaact ctcaaggatc ttaccgctgt tgagatccag    11040
ttcgatgtaa cccactcgtg cacccaactg atcttcagca tcttttactt tcaccagcgt    11100
ttctgggtga gcaaaaacag gaaggcaaaa tgccgcaaaa aagggaataa gggcgacacg    11160
gaaatgttga atactcatac tcttcctttt tcaatattat tgaagcattt atcagggtta    11220
ttgtctcatg agcggataca tatttgaatg tatttagaaa aataaacaaa taggggttcc    11280
gcgcacattt ccccgaaaag tgccacctga cgtctaagaa accattatta tcatgacatt    11340
aacctataaa aataggcgta tcacgaggcc ctttcgtctc gcgcgtttcg gtgatgacgg    11400
tgaaaacctc tgacacatgc agctcccgga gacggtcaca gcttgtctgt aagcggatgc    11460
cgggagcaga caagcccgtc agggcgcgtc agcgggtgtt ggcgggtgtc ggggctggct    11520
taactatgcg gcatcagagc agattgtact gagagtgcac catatgcggt gtgaaatacc    11580
gcacagatgc gtaaggagaa aataccgcat caggcgccat cgccattca ggctgcgcaa     11640
ctgttgggaa gggcgatcgg tgcgggcctc ttcgctatta cgccagctgg cgaaagggggg   11700
atgtgctgca aggcgattaa gttgggtaac gccagggttt cccagtcac gacgttgtaa     11760
aacgacggcc agtgaattc                                                 11779
```

<210> SEQ ID NO 14
<211> LENGTH: 11678
<212> TYPE: DNA
<213> ORGANISM: Artificial Sequence
<220> FEATURE:
<223> OTHER INFORMATION: Synthetic: TL20d-7SKM1/sh734-rGbGM

<400> SEQUENCE: 14

```
ggccgcctcg gccaaacagc ccttgagttt accactccct atcagtgata gagaaaagtg     60
aaagtcgagt ttaccactcc ctatcagtga tagagaaaag tgaaagtcga gtttaccact    120
ccctatcagt gatagagaaa agtgaaagtc gagtttacca ctccctatca gtgatagaga    180
aaagtgaaag tcgagtttac cagtccctat cagtgataga gaaaagtgaa agtcgagttt    240
accactccct atcagtgata gagaaaagtg aaagtcgagt ttaccactcc ctatcagtga    300
tagagaaaag tgaaagtcga gctcgccatg ggaggcgtgg cctgggcggg actggggagt    360
ggcgagccct cagatcctgc atataagcag ctgcttttg cctgtactgg gtctctctgg    420
ttagaccaga tctgagcctg ggagctctct ggctaactag gaacccact gcttaagcct    480
caataaagct tgccttgagt gcttcaagta gtgtgtgccc gtctgttgtg tgactctggt    540
aactagagat ccctcagacc cttttagtca gtgtggaaaa tctctagcag tggcgcccga    600
acagggactt gaaagcgaaa gggaaaccag aggagctctc tcgacgcagg actcggcttg    660
```

```
ctgaagcgcg cacggcaaga ggcgaggggc ggcgactggt gagtacgcca aaaatttga     720
ctagcggagg ctagaaggag agagatgggt gcgagagcgt cagtattaag cgggggagaa    780
ttagatcgcg atgggaaaaa attcggttaa ggccaggggg aaagaaaaaa tataaattaa    840
aacatatagt atgggcaagc agggagctag aacgattcgc agttaatact ggcctgttag    900
aaacatcaga aggctgtaga caaatactgg gacagctaca accatccctt cagacaggat    960
cagaagaact tagatcatta tataatacag tagcaaccct ctattgtgtg catcaaagga   1020
tagagataaa agacaccaag gaagctttag acaagataga ggaagagcaa acaaaagta    1080
agaaaaaagc acagcaagca gcaggatctt cagacctgga aattccctac aatccccaaa   1140
gtcaaggagt agtagaatct atgaataaag aattaaagaa aattatagga caggtaagag   1200
atcaggctga acatcttaag acagcagtac aaatggcagt attcatccac aattttaaaa   1260
gaaaaggggg gattgggggg tacagtgcag gggaagaat agtagacata atagcaacag    1320
acatacaaac taaagaatta caaaacaaa ttacaaaaat tcaaaatttt cgggtttatt    1380
acagggacag cagaaatcca ctttggaaag gaccagcaaa gctcctctgg aaaggtgaag   1440
gggcagtagt aatacaagat aatagtgaca taaagtagt gccaagaaga aaagcaaaga   1500
tcattaggga ttatgaaaaa cagatggcag gtgatgattg tgtggcaagt agacaggatg   1560
aggattagaa catggaaaag tttagtaaaa caccataagg aggagatatg agggacaatt   1620
ggagaagtga attatataaa tataaagtag taaaaattga accattagga gtagcaccca   1680
ccaaggcaaa gagaagagtg gtgcagagag aaaaaagagc agtgggaata ggagctttgt   1740
tccttgggtt cttgggagca gcaggaagca ctatgggcgc agcgtcaatg acgctgacgg   1800
tacaggccag acaattattg tctggtatag tgcagcagca gaacaatttg ctgagggcta   1860
ttgaggcgca acagcatctg ttgcaactca cagtctgggg catcaagcag ctccaggcaa   1920
gaatcctggc tgtggaaaga tacctaaagg atcaacagct cctggggatt tggggttgct   1980
ctggaaaact catttgcacc actgctgtgc cttggaatgc tagttggagt aataaatctc   2040
tggaacagat ttggaatcac acgacctgga tggagtggga cagagaaatt aacaattaca   2100
caagcttaat acactcctta attgaagaat cgcaaaacca gcaagaaaag aatgaacaag   2160
aattattgga attagataaa tgggcaagtt tgtggaattg gtttaacata acaaattggc   2220
tgtggtatat aaaattattc ataatgatag taggaggctt ggtaggttta agaatagttt   2280
ttgctgtact ttctatagtg aatagagtta ggcagggata ttcaccatta tcgtttcaga   2340
cccacctccc aaccccgagg ggaccgagct caagcttcga agcggccgct cgacgtgcag   2400
tcgggctact gcccccaccca tagtaccggc attctggata gtgtcaaaac agccggaaat   2460
caagtccgtt tatctcaaac tttagcattt tgggaataaa tgatatttgc tatgctggtt   2520
aaattagatt ttagttaaat ttcctgctga agctctagta cgataagtaa cttgacctaa   2580
gtgtaaagtt gagatttcct tcaggtttat atagcttgtg cgccgcctgg gtacctcagg   2640
atatgcccct gactatttgt ccgacatagt caagggcata tccttttta cgcgtgggga   2700
tcctctagag tcgagctcgc gaggatcatc accggtgcta gccggagcca gaagcaccat   2760
aagggacatg ataagggagc cagcagacct ctgatctctt cctgaatgct aatcttaaac   2820
atcctgagga agaatgggac ttccatttgg ggtgggccta tgatagggta ataagacagt   2880
agtgaatatc aagctacaaa aagcccccct tcaaattctt ctcagtccta acttttcata   2940
ctaagcccag tccttccaaa gcagactgtg aagagtgat agttccggga gactagcacc   3000
ggctagccga gcttggaaca cttttccttc attaagaacc atccttgcta ctcagctgca   3060
```

| | |
|---|---|
| atcaatccag cccccaggtc ttcactgaac cttttcccat ctcttccaaa acatctgttt | 3120 |
| ctgagaagtc ctgtcctata gaggtctttc ttcccaccgg atttctccta caccatttac | 3180 |
| tcccacttgc agaactcccg tgtacaagtg tctttactgc ttttatttgc tcaacaaaat | 3240 |
| gcacatctca tataaaaata aatgaggagc atgcacacac cacaaacaca acaggcatg | 3300 |
| cagaaataca catacacact tccctcaata taaacccttt gtggctcata tatttaaaaa | 3360 |
| gatgtaaaaa aaagagctga agaaaatcat gtgtgatctc tcagcagaat agatttatta | 3420 |
| tttgtattgc ttgcagaata aagcctatcc ttgaaagctc tgaatcatgg gcaagaggct | 3480 |
| cagtggtatc tggaggacag ggcactggcc actgcagtca ccatcttctg ccaggaagcc | 3540 |
| tgcacctcag gggtgaattc tttgccaaag tgaatggcca gcacggtgac cagcacgttg | 3600 |
| cccaggagct gtgggaggaa gataagaggt atgaacatga ttagcaaaag ggcctagctt | 3660 |
| ggactcagaa taatccagcc ttatcccaac cataaaataa aagcagaatg gtagctggat | 3720 |
| tgtagctgct attagcaata tgaaacctct tacatcagtt acaatttata tgcagaaata | 3780 |
| tttatatgca gaaatattgc tattgcctta acccagaaat tatcactgtt attctttaga | 3840 |
| atggtgcaaa gaggcatgat acattgtatc attattgccc tgaaagaaag agattaggga | 3900 |
| aagtattaga aataagataa acaaaaaagt atattaaaag aagaaagcat tttttaaaat | 3960 |
| tacaaatgca aaattaccct gatttggtca atatgtgtac cctgttactt ctccccttcc | 4020 |
| tatgacatga acttaaccat agaaaagaag gggaaagaaa acatcaaggg tcccatagac | 4080 |
| tcaccttgaa gttctcagga tccacatgca gcttgtcaca gtgcagttca ctcagctggg | 4140 |
| caaaggtgcc cttgagatca tccaggtgct ttatggcatc tcccaaggaa gtcagcacct | 4200 |
| tcttgccatg tgccttgact ttggggttgc ccatgatggc agaggcagag gacaggttgc | 4260 |
| caaagctgtc aaagaacctc tgggtccatg ggtagacaac caggagcctg tgagattgac | 4320 |
| aagaacagtt tgacagtcag aaggtgccac aaatcctgag aagcaacctg gacttttgcc | 4380 |
| aggcacaggg tccttccttc cctcccttgt cctggtcacc agagcctacc ttcccagggt | 4440 |
| ttctcctcca gcatcttcca cattcacctt gtcccacagg cttgtgatag tagccttgtc | 4500 |
| ctcctctgtg aaatgaccca tggtgtctgt ttgaggttgc tagtgaacac agttgtgtca | 4560 |
| gaagcaaatg taagcaatag atggctctgc cctgactttt atgcccagcc ctggctcctg | 4620 |
| ccctccctgc tcctgggagt agattggcca accctagggt gtggctccac agggtgaggt | 4680 |
| ctaagtgatg acagccgtac ctgtccttgg ctcttctggc actggcttag gagttggact | 4740 |
| tcaaaccctc agccctccct ctaagatata tctcttggcc ccataccatc agtacaaatt | 4800 |
| gctactaaaa acatcctcct ttgcaagtgt atttacgacg gtatcgatgt atgtgagcat | 4860 |
| gtgtcctcta acagcacagg ccttttgcca cctagctgtc caggggtgcc ttaaaatggc | 4920 |
| aaacaaggtt tgttttcttt tcctgttttc atgccttcct cttccatatc cttgtttcat | 4980 |
| attaatacat gtgtatagat cctaaaaatc tatacacatg tattaataaa gcctgattct | 5040 |
| gccgcttcta ggtatagagg ccacctgcaa gataaatatt tgattcacaa taactaatca | 5100 |
| ttctatggca attgataaca acaaatatat atatatatat atatatacgt atatgtgtat | 5160 |
| atatatatat atattcagga aataatatat tctagaatat gtcacattct gtctcaggca | 5220 |
| tccatttct ttatgatgcc gtttgaggtg gagtttagt caggtggtca gcttctcctt | 5280 |
| ttttttgcca tctgccctgt aagcatcctg ctggggaccc agataggagt catcactcta | 5340 |
| ggctgagaac atctgggcac acaccctaag cctcagcatg actcatcatg actcagcatt | 5400 |

```
gctgtgcttg agccagaagg tttgcttaga aggttacaca gaaccagaag gcgggggtgg   5460
ggcactgacc ccgacagggg cctggccaga actgctcatg cttggactat gggaggtcac   5520
taatggagac acacagaaat gtaacaggaa ctaagggaat tccggtgccc tgcttaggag   5580
cttaatcttt aatgaaagct aagctttcat taaaaaagt ctaaccagct gcattcgact    5640
ttgactgcag cagctggtta aaggttcta ctggaggagg gtcccagccc attgctaaat    5700
taacatcagg ctctgagact ggcagtatat ctctaacagt ggttgatgct atcttctgga   5760
acttgcctgc tacattgaga ccactgaccc atacatagga agcccatagc tctgtcctga   5820
actgttaggc cactggtcca gagagtgtgc atctcctttg atcctcataa taaccctatg   5880
agatagacac aattattact cttactttat agatgatgat cctgaaaaca taggagtcaa   5940
ggcacttgcc cctagctggg ggtataggg agcagtccca tgtagtagta gaatgaaaaa    6000
tgctgctatg ctgtgcctcc cccacctttc ccatgtctgc cctctactca tggtctatct   6060
ctcctggctc ctgggagtca tggactccac ccagcaccac caacctgacc taaccaccta   6120
tctgagcctg ccagcctata acccatctgg gccctgatag ctggtggcca gccctgaccc   6180
caccccaccc tccctggaac ctctgataga cacatctggc acaccagctc gcaaagtcac   6240
cgtgagggtc ttgtgtttgc tgagtcaaaa ttccttgaaa tccaagtcct tagagactcc   6300
tgctcccaaa tttacagtca tagcttctt catggctgtc tcctttatcc acagaatgat    6360
tcctttgctt cattgcccca tccatctgat cctcctcatc agtgcagcac agggcccatg   6420
agcagtagct gcagagtctc acataggtct ggcactgcct ctgacatgtc cgaccttagg   6480
caaatgcttg actcttctga gctcggatcc cttgagctca ggaggtcaag gctgcagtga   6540
gacatgatct tgccactgca ctccagcctg acagcagag tgaaaccttg cctcacgaaa    6600
cagaatacaa aaacaaacaa acaaaaaact gctccgcaat gcgcttcctt gatgctctac   6660
cacataggtc tgggtacttt gtacacatta tctcattgct gttcataatt gttagattaa   6720
ttttgtaata ttgatattat tcctagaaag ctgaggcctc aagatgataa cttttatttt   6780
ctggacttgt aatagctttc tcttgtattc accatgttgt aactttctta gagtagtaac   6840
aatataaagt tattgtgagt ttttgcaaac acagcaaaca caacgaccca tatagacatt   6900
gatgtgaaat tgtctattgt caatttatgg gaaaacaagt atgtactttt tctactaagc   6960
cattgaaaca ggaataacag aacaagattg aagaataca ttttccgaaa ttacttgagt    7020
attatacaaa gacaagcacg tggacctggg aggagggtta ttgtccatga ctggtgtgtg   7080
gagacaaatg caggtttata atagatggga tggcatctag cgcaatgact ttgccatcac   7140
ttttagagag ctcttgggg ccccagtaca caagagggga cgcagggtat atgtagacat    7200
ctcattcttt ttcttagtgt gagaataaga atagccatga cctgagttta tagacaatga   7260
gcccttttct ctctcccact cagcagctat gagatggctt gccctgcctc tctactaggc   7320
tgactcactc caaggcccag caatgggcag ggctctgtca gggctttgat agcactatct   7380
gcagagccag ggccgagaag gggtggactc cagagactct ccctcccatt cccgagcagg   7440
gtttgcttat ttatgcattt aaatgatata tttatttaa aagaaataac aggagactgc    7500
ccagccctgg ctgtgacatg gaaactatgt agaatatttt gggttccatt ttttttttcct   7560 tctttcagtt agaggaaaag gggctcactg cacatacact agacagaaag tcaggagctt   7620
tgaatccaag cctgatcatt tccatgtcat actgagaaag tccccaccct tctctgagcc   7680
tcagtttctc tttttataag taggagtctg gagtaaatga tttccaatgg ctctcatttc   7740
aatacaaaat ttccgtttat taaatgcatg agcttccgtt actccaagac tgagaaggaa   7800
```

```
attgaacctg agactcattg actggcaaga tgtccccaga ggctctcatt cagcaataaa    7860
attctcacct tcacccaggc ccactagtgt cagatttgca tgcgttaacg cggccgcatc    7920
gatgccgtag tacctttaag accaatgact tacaaggcag ctgtagatct tagccacttt    7980
ttaaaagaaa aggggggact ggaagggcta attcactccc aaagaagaca agatagatct    8040
gcttttttgcc tgtactgggt ctctctggtt agaccagatc tgagcctggg agctctctgg    8100
ctaactaggg aacccactgc ttaagcctca ataaagcttc agctgctcga gctagcagat    8160
cttttttccct ctgccaaaaa ttatggggac atcatgaagc cccttgagca tctgacttct    8220
ggctaataaa ggaaatttat tttcattgca atagtgtgtt ggaattttttt gtgtctctca    8280
ctcggaagga catatgggag ggcaaatcat ttaaaacatc agaatgagta tttggtttag    8340
agtttggcaa catatgccca tatgctggct gccatgaaca aaggttggct ataaagaggt    8400
catcagtata tgaaacagcc ccctgctgtc cattccttat tccatagaaa agccttgact    8460
tgaggttaga ttttttttat attttgtttt gtgttatttt tttctttaac atccctaaaa    8520
ttttccttac atgttttact agccagattt ttcctcctct cctgactact cccagtcata    8580
gctgtccctc ttctcttatg gagatccctc gacctgcagc ccaagcttgg cgtaatcatg    8640
gtcatagctg tttcctgtgt gaaattgtta tccgctcaca attccacaca acatacgagc    8700
cggaagcata aagtgtaaag cctggggtgc ctaatgagtg agctaactca cattaattgc    8760
gttgcgctca ctgcccgctt tccagtcggg aaacctgtcg tgccagcgga tccgcatctc    8820
aattagtcag caaccatagt cccgccccta actccgccca tcccgcccct aactccgccc    8880
agttccgccc attctccgcc ccatggctga ctaattttt ttatttatgc agaggccgag    8940
gccgcctcgg cctctgagct attccagaag tagtgaggag gcttttttgg aggcctaggc    9000
ttttgcaaaa agctgtcgac tgcagaggcc tgcatgcaag cttggcgtaa tcatggtcat    9060
agctgtttcc tgtgtgaaat tgttatccgc tcacaattcc acacaacata cgagccggaa    9120
gcataaagtg taaagcctgg ggtgcctaat gagtgagcta actcacatta attgcgttgc    9180
gctcactgcc cgctttccag tcgggaaacc tgtcgtgcca gctgcattaa tgaatcggcc    9240
aacgcgcggg gagaggcggt ttgcgtattg ggcgctcttc cgcttcctcg ctcactgact    9300
cgctgcgctc ggtcgttcgg ctgcggcgag cggtatcagc tcactcaaag gcggtaatac    9360
ggttatccac agaatcaggg gataacgcag gaaagaacat gtgagcaaaa ggccagcaaa    9420
aggccaggaa ccgtaaaaag gccgcgttgc tggcgttttt ccataggctc cgcccccctg    9480
acgagcatca caaaaatcga cgctcaagtc agaggtggcg aaacccgaca ggactataaa    9540
gataccaggc gtttccccct ggaagctccc tcgtgcgctc tcctgttccg accctgccgc    9600
ttaccggata cctgtccgcc tttctccctt cgggaagcgt ggcgctttct catagctcac    9660
gctgtaggta tctcagttcg gtgtaggtcg ttcgctccaa gctgggctgt gtgcacgaac    9720
cccccgttca gcccgaccgc tgcgccttat ccggtaacta tcgtcttgag tccaacccgg    9780
taagacacga cttatcgcca ctggcagcag ccactggtaa caggattagc agagcgaggt    9840
atgtaggcgg tgctacagag ttcttgaagt ggtggcctaa ctacggctac actagaagaa    9900
cagtatttgg tatctgcgct ctgctgaagc cagttacctt cggaaaaaga gttggtagct    9960
cttgatccgg caaacaaacc accgctggta gcggtggttt ttttgtttgc aagcagcaga   10020
ttacgcgcag aaaaaaagga tctcaagaag atcctttgat cttttctacg ggtctgacg    10080
ctcagtggaa cgaaaactca cgttaaggga ttttggtcat gagattatca aaaaggatct   10140
```

```
tcacctagat cctttaaat taaaaatgaa gttttaaatc aatctaaagt atatatgagt    10200
aaacttggtc tgacagttac caatgcttaa tcagtgaggc acctatctca gcgatctgtc    10260
tatttcgttc atccatagtt gcctgactcc ccgtcgtgta gataactacg atacgggagg    10320
gcttaccatc tggccccagt gctgcaatga taccgcgaga cccacgctca ccggctccag    10380
atttatcagc aataaaccag ccagccggaa gggccgagcg cagaagtggt cctgcaactt    10440
tatccgcctc catccagtct attaattgtt gccgggaagc tagagtaagt agttcgccag    10500
ttaatagttt gcgcaacgtt gttgccattg ctacaggcat cgtggtgtca cgctcgtcgt    10560
ttggtatggc ttcattcagc tccggttccc aacgatcaag gcgagttaca tgatccccca    10620
tgttgtgcaa aaaagcggtt agctccttcg gtcctccgat cgttgtcaga agtaagttgg    10680
ccgcagtgtt atcactcatg gttatggcag cactgcataa ttctcttact gtcatgccat    10740
ccgtaagatg ctttctgtg actggtgagt actcaaccaa gtcattctga aatagtgta    10800 tgcggcgacc gagttgctct tgcccggcgt caatacggga taataccgcg ccacatagca    10860
gaactttaaa agtgctcatc attggaaaac gttcttcggg gcgaaaactc tcaaggatct    10920
taccgctgtt gagatccagt tcgatgtaac ccactcgtgc acccaactga tcttcagcat    10980
cttttacttt caccagcgtt tctgggtgag caaaaacagg aaggcaaaat gccgcaaaaa    11040
agggaataag ggcgacacgg aaatgttgaa tactcatact cttccttttt caatattatt    11100
gaagcattta tcaggttat tgtctcatga gcggatacat atttgaatgt atttagaaaa    11160
ataaacaaat aggggttccg cgcacatttc cccgaaaagt gccacctgac gtctaagaaa    11220
ccattattat catgacatta acctataaaa ataggcgtat cacgaggccc tttcgtctcg    11280
cgcgtttcgg tgatgacggt gaaaacctct gacacatgca gctcccggag acggtcacag    11340
cttgtctgta agcggatgcc gggagcagac aagcccgtca gggcgcgtca gcgggtgttg    11400
gcgggtgtcg ggctggctt aactatgcgg catcagagca gattgtactg agagtgcacc    11460
atatgcggtg tgaaataccg cacagatgcg taaggagaaa ataccgcatc aggcgccatt    11520
cgccattcag gctgcgcaac tgttgggaag ggcgatcgt gcgggcctct tcgctattac    11580
gccagctggc gaaaggggga tgtgctgcaa ggcgattaag ttgggtaacg ccagggtttt    11640
cccagtcacg acgttgtaaa acgacggcca gtgaattc                            11678
```

<210> SEQ ID NO 15
<211> LENGTH: 11681
<212> TYPE: DNA
<213> ORGANISM: Artificial Sequence
<220> FEATURE:
<223> OTHER INFORMATION: Synthetic: TL20d-7SK/sh734-rGbGM

<400> SEQUENCE: 15

```
ggccgcctcg gccaaacagc ccttgagttt accactccct atcagtgata gagaaaagtg      60
aaagtcgagt ttaccactcc ctatcagtga tagagaaaag tgaaagtcga gtttaccact    120
ccctatcagt gatagagaaa agtgaaagtc gagtttacca ctccctatca gtgatagaga    180
aaagtgaaag tcgagtttac cagtccctat cagtgataga aaagtgaa agtcgagttt    240 accactccct atcagtgata gagaaaagtg aaagtcgagt ttaccactcc ctatcagtga    300
tagagaaaag tgaaagtcga gctcgccatg ggaggcgtgg cctgggcggg actggggagt    360
ggcgagccct cagatcctgc atataagcag ctgcttttg cctgtactgg gtctctctgg    420
ttagaccaga tctgagcctg ggagctctct ggctaactag ggaacccact gcttaagcct    480
caataaagct tgccttgagt gcttcaagta gtgtgtgccc gtctgttgtg tgactctggt    540
```

```
aactagagat ccctcagacc cttttagtca gtgtggaaaa tctctagcag tggcgcccga    600
acagggactt gaaagcgaaa gggaaaccag aggagctctc tcgacgcagg actcggcttg    660
ctgaagcgcg cacggcaaga ggcgagggggc ggcgactggt gagtacgcca aaaattttga   720
ctagcggagg ctagaaggag agagatgggt gcgagagcgt cagtattaag cggggggagaa   780 ttagatcgcg atgggaaaaa attcggttaa ggccaggggg aaagaaaaaa tataaattaa    840
aacatatagt atgggcaagc agggagctag aacgattcgc agttaatact ggcctgttag    900
aaacatcaga aggctgtaga caaatactgg gacagctaca accatcccct cagacaggat    960
cagaagaact tagatcatta tataatacag tagcaaccct ctattgtgtg catcaaagga    1020
tagagataaa agacaccaag gaagctttag acaagataga ggaagagcaa acaaaaagta    1080
agaaaaaagc acagcaagca gcaggatctt cagacctgga aattccctac aatccccaaa    1140
gtcaaggagt agtagaatct atgaataaag aattaaagaa aattatagga caggtaagag    1200
atcaggctga acatcttaag acagcagtac aaatggcagt attcatccac aattttaaaa    1260
gaaaaggggg gattggggggg tacagtgcag gggaagaat agtagacata atagcaacag    1320
acatacaaac taagaatta caaaaacaaa ttacaaaaat tcaaaatttt cgggtttatt    1380
acagggacag cagaaatcca ctttggaaag gaccagcaaa gctcctctgg aaaggtgaag    1440
gggcagtagt aatacaagat aatagtgaca taaaagtagt gccaagaaga aaagcaaaga    1500
tcattaggga ttatggaaaa cagatggcag gtgatgattg tgtggcaagt agacaggatg    1560
aggattagaa catggaaaag tttagtaaaa caccataagg aggagatatg agggacaatt    1620
ggagaagtga attatataaa tataaagtag taaaaattga accattagga gtagcaccca    1680
ccaaggcaaa gagaagagtg gtgcagagag aaaaaagagc agtgggaata ggagctttgt    1740
tccttgggtt cttgggagca gcaggaagca ctatgggcgc agcgtcaatg acgctgacgg    1800
tacaggccag acaattattg tctggtatag tgcagcagca gaacaatttg ctgagggcta    1860
ttgaggcgca acagcatctg ttgcaactca cagtctgggg catcaagcag ctccaggcaa    1920
gaatcctggc tgtggaaaga tacctaaagg atcaacagct cctggggatt tggggttgct    1980
ctggaaaact catttgcacc actgctgtgc cttggaatgc tagttggagt aataaatctc    2040
tggaacagat ttggaatcac acgacctgga tggagtggga cagagaaatt aacaattaca    2100
caagcttaat acactcctta attgaagaat cgcaaaacca gcaagaaaag aatgaacaag    2160
aattattgga attagataaa tgggcaagtt tgtggaattg gtttaacata acaaattggc    2220
tgtggtatat aaaattattc ataatgatag taggaggctt ggtaggttta agaatagttt    2280
ttgctgtact ttctatagtg aatagagtta ggcagggata ttcaccatta tcgtttcaga    2340
cccacctccc aaccccgagg ggaccgagct caagcttcga agcggccgca tcgacgtgca    2400
gtatttagca tgccccaccc atctgcaagg cattctggat agtgtcaaaa cagccggaaa    2460
tcaagtccgt ttatctcaaa cttttagcatt tgggaataa atgatatttg ctatgctggt    2520
taaattagat tttagttaaa tttcctgctg aagctctagt acgataagta acttgaccta    2580
agtgtaaagt tgagatttcc ttcaggttta tatagcttgt gcgccgcctg ggtacctcag    2640
gatatgccct tgactatttg tccgacatag tcaagggcat atcctttttt gtacgcgtgg    2700
ggatcctcta gagtcgagct cgcgaggatc atcaccggtg ctagccggag ccagaagcac    2760
cataagggac atgataaggg agccagcaga cctctgatct cttcctgaat gctaatctta    2820
aacatcctga ggaagaatgg gacttccatt tggggtgggc ctatgatagg gtaataagac    2880
```

```
agtagtgaat atcaagctac aaaaagcccc ctttcaaatt cttctcagtc ctaactttc      2940
atactaagcc cagtccttcc aaagcagact gtgaaagagt gatagttccg ggagactagc      3000
accggctagc cgagcttgga acactttccc ttcattaaga accatccttg ctactcagct      3060
gcaatcaatc cagcccccag gtcttcactg aaccttttcc catctcttcc aaaacatctg      3120
tttctgagaa gtcctgtcct atagaggtct ttcttcccac cggatttctc ctacaccatt      3180
tactcccact gcagaactc ccgtgtacaa gtgtctttac tgctttatt tgctcaacaa       3240
aatgcacatc tcatataaaa ataaatgagg agcatgcaca caccacaaac acaaacaggc     3300
atgcagaaat acacatacac acttccctca atataaaccc tttgtggctc atatatttaa     3360
aaagatgtaa aaaaagagc tgaagaaaat catgtgtgat ctctcagcag aatagattta      3420
ttatttgtat tgcttgcaga ataaagccta tccttgaaag ctctgaatca tgggcaagag     3480
gctcagtggt atctggagga cagggcactg gccactgcag tcaccatctt ctgccaggaa     3540
gcctgcacct caggggtgaa ttctttgcca aagtgaatgg ccagcacggt gaccagcacg     3600
ttgcccagga gctgtgggag gaagataaga ggtatgaaca tgattagcaa aagggcctag    3660
cttggactca gaataatcca gccttatccc aaccataaaa taaaagcaga atggtagctg     3720
gattgtagct gctattagca atatgaaacc tcttacatca gttacaattt atatgcagaa     3780
atatttatat gcagaaatat tgctattgcc ttaacccaga aattatcact gttattcttt     3840
agaatggtgc aaagaggcat gatacattgt atcattattg ccctgaaaga aagagattag    3900
ggaaagtatt agaaataaga taaacaaaaa agtatattaa aagaagaaag cattttttaa     3960
aattacaaat gcaaaattac cctgatttgg tcaatatgtg taccctgtta cttctcccct     4020
tcctatgaca tgaacttaac catagaaaag aagggaaag aaaacatcaa gggtcccata     4080
gactcacctt gaagttctca ggatccacat gcagcttgtc acagtgcagt tcactcagct    4140
gggcaaaggt gcccttgaga tcatccaggt gctttatggc atctcccaag gaagtcagca    4200
ccttcttgcc atgtgccttg actttggggt tgcccatgat ggcagaggca gaggacaggt    4260
tgccaaagct gtcaaagaac ctctgggtcc atgggtagac aaccaggagc ctgtgagatt    4320
gacaagaaca gtttgacagt cagaaggtgc cacaaatcct gagaagcaac ctggactttt    4380
gccaggcaca gggtccttcc ttccctccct tgtcctggtc accagagcct accttcccag    4440
ggtttctcct ccagcatctt ccacattcac cttgtcccac aggcttgtga tagtagcctt    4500
gtcctcctct gtgaaatgac ccatggtgtc tgtttgaggt tgctagtgaa cacagttgtg    4560
tcagaagcaa atgtaagcaa tagatggctc tgccctgact tttatgccca gccctggctc    4620
ctgccctccc tgctcctggg agtagattgg ccaaccctag ggtgtggctc cacagggtga   4680
ggtctaagtg atgacagccg tacctgtcct tggctcttct ggcactggct taggagttgg    4740
acttcaaacc ctcagccctc cctctaagat atatctcttg gccccatacc atcagtacaa    4800
attgctacta aaaacatcct cctttgcaag tgtatttacg acggtatcga tgtatgtgag    4860
catgtgtcct ctaacagcac aggccttttg ccacctagct gtccagggt gccttaaaat    4920
ggcaaacaag gtttgttttc ttttcctgtt ttcatgcctt cctcttccat atccttgttt    4980
catattaata catgtgtata gatcctaaaa atctatacac atgtattaat aaagcctgat    5040
tctgccgctt ctaggtatag aggccacctg caagataaat atttgattca caataactaa    5100
tcattctatg gcaattgata acaacaaata tatatatata tatatatata cgtatatgtg    5160
tatatatata tatatattca ggaaataata tattctagaa tatgtcacat tctgtctcag    5220
gcatccattt tctttatgat gccgtttgag gtggagtttt agtcaggtgg tcagcttctc    5280
```

| | |
|---|---|
| cttttttttg ccatctgccc tgtaagcatc ctgctgggga cccagatagg agtcatcact | 5340 |
| ctaggctgag aacatctggg cacacaccct aagcctcagc atgactcatc atgactcagc | 5400 |
| attgctgtgc ttgagccaga aggtttgctt agaaggttac acagaaccag aaggcggggg | 5460 |
| tggggcactg accccgacag gggcctggcc agaactgctc atgcttggac tatgggaggt | 5520 |
| cactaatgga gacacacaga aatgtaacag gaactaaggg aattccggtg ccctgcttag | 5580 |
| gagcttaatc tttaatgaaa gctaagcttt cattaaaaaa agtctaacca gctgcattcg | 5640 |
| actttgactg cagcagctgg ttagaaggtt ctactggagg agggtcccag cccattgcta | 5700 |
| aattaacatc aggctctgag actggcagta tatctctaac agtggttgat gctatcttct | 5760 |
| ggaacttgcc tgctacattg agaccactga cccatacata ggaagcccat agctctgtcc | 5820 |
| tgaactgtta ggccactggt ccagagagtg tgcatctcct ttgatcctca taataaccct | 5880 |
| atgagataga cacaattatt actcttactt tatagatgat gatcctgaaa acataggagt | 5940 |
| caaggcactt gcccctagct gggggtatag gggagcagtc ccatgtagta gtagaatgaa | 6000 |
| aaatgctgct atgctgtgcc tcccccacct ttcccatgtc tgccctctac tcatggtcta | 6060 |
| tctctcctgg ctcctgggag tcatggactc cacccagcac caccaacctg acctaaccac | 6120 |
| ctatctgagc ctgccagcct ataacccatc tgggccctga tagctggtgg ccagccctga | 6180 |
| ccccacccca ccctccctgg aacctctgat agacacatct ggcacaccag ctcgcaaagt | 6240 |
| caccgtgagg gtcttgtgtt tgctgagtca aaattccttg aaatccaagt ccttagagac | 6300 |
| tcctgctccc aaatttacag tcatagactt cttcatggct gtctccttta tccacagaat | 6360 |
| gattccttg cttcattgcc ccatccatct gatcctcctc atcagtgcag cacagggccc | 6420 |
| atgagcagta gctgcagagt ctcacatagg tctggcactg cctctgacat gtccgacctt | 6480 |
| aggcaaatgc ttgactcttc tgagctcgga tcccttgagc tcaggaggtc aaggctgcag | 6540 |
| tgagacatga tcttgccact gcactccagc ctggacagca gagtgaaacc ttgcctcacg | 6600 |
| aaacagaata caaaaacaaa caaacaaaaa actgctccgc aatgcgcttc cttgatgctc | 6660 |
| taccacatag gtctgggtac tttgtacaca ttatctcatt gctgttcata attgttagat | 6720 |
| taattttgta atattgatat tattcctaga aagctgaggc ctcaagatga taacttttat | 6780 |
| tttctggact tgtaatagct ttctcttgta ttcaccatgt tgtaacttc ttagagtagt | 6840 |
| aacaatataa agttattgtg agtttttgca aacacagcaa acacaacgac ccatatagac | 6900 |
| attgatgtga aattgtctat tgtcaattta tgggaaaaca agtatgtact ttttctacta | 6960 |
| agccattgaa acaggaataa cagaacaaga ttgaaagaat acattttccg aaattacttg | 7020 |
| agtattatac aaagacaagc acgtggacct gggaggaggg ttattgtcca tgactggtgt | 7080 |
| gtggagacaa atgcaggttt ataatagatg ggatggcatc tagcgcaatg actttgccat | 7140 |
| cacttttaga gagctcttgg gggcccagt acacaagagg ggacgcaggg tatatgtaga | 7200 |
| catctcattc ttttttcttag tgtgagaata agaatagcca tgacctgagt ttatagacaa | 7260 |
| tgagcccttt tctctctccc actcagcagc tatgagatgg cttgccctgc ctctctacta | 7320 |
| ggctgactca ctccaaggcc cagcaatggg cagggctctg tcagggcttt gatagcacta | 7380 |
| tctgcagagc cagggccgag aagggtgga ctccagagac tctccctccc attcccgagc | 7440 |
| agggtttgct tatttatgca tttaaatgat atatttattt taaaagaaat aacaggagac | 7500 |
| tgcccagccc tggctgtgac atggaaacta tgtagaatat tttgggttcc attttttttt | 7560 |
| ccttctttca gttagaggaa aaggggctca ctgcacatac actagacaga aagtcaggag | 7620 |

```
ctttgaatcc aagcctgatc atttccatgt catactgaga aagtccccac ccttctctga    7680
gcctcagttt ctctttttat aagtaggagt ctggagtaaa tgatttccaa tggctctcat    7740
ttcaatacaa aatttccgtt tattaaatgc atgagcttcc gttactccaa gactgagaag    7800
gaaattgaac ctgagactca ttgactggca agatgtcccc agaggctctc attcagcaat    7860
aaaattctca ccttcaccca ggcccactag tgtcagattt gcatgcgtta acgcggccgc    7920
atcgatgccg tagtaccttt aagaccaatg acttacaagg cagctgtaga tcttagccac    7980
tttttaaaag aaaaggggg actggaaggg ctaattcact cccaagaag acaagataga     8040
tctgcttttt gcctgtactg ggtctctctg gttagaccag atctgagcct gggagctctc    8100
tggctaacta gggaacccac tgcttaagcc tcaataaagc ttcagctgct cgagctagca    8160
gatcttttc cctctgccaa aaattatggg gacatcatga agccccttga gcatctgact    8220
tctggctaat aaaggaaatt tattttcatt gcaatagtgt gttggaattt tttgtgtctc    8280
tcactcggaa ggacatatgg gagggcaaat catttaaaac atcagaatga gtatttggtt    8340
tagagtttgg caacatatgc ccatatgctg gctgccatga acaaaggttg gctataaaga    8400
ggtcatcagt atatgaaaca gcccctgct gtccattcct tattccatag aaaagccttg     8460
acttgaggtt agatttttt tatattttgt tttgtgttat tttttctttt aacatcccta     8520
aaattttcct tacatgtttt actagccaga ttttcctcc tctcctgact actcccagtc     8580
atagctgtcc ctcttctctt atggagatcc ctcgacctgc agcccaagct ggcgtaatc     8640
atggtcatag ctgtttcctg tgtgaaattg ttatccgctc acaattccac acaacatacg    8700
agccggaagc ataaagtgta aagcctgggg tgcctaatga gtgagctaac tcacattaat    8760
tgcgttgcgc tcactgcccg ctttccagtc gggaaacctg tcgtgccagc ggatccgcat    8820
ctcaattagt cagcaaccat agtcccgccc ctaactccgc ccatcccgcc ctaactccg     8880
cccagttccg cccattctcc gccccatggc tgactaattt tttttattta tgcagaggcc    8940
gaggccgcct cggcctctga gctattccag aagtagtgag gaggcttttt tggaggccta    9000
ggcttttgca aaaagctgtc gactgcagag gcctgcatgc aagcttggcg taatcatggt    9060
catagctgtt tcctgtgtga aattgttatc cgctcacaat tccacacaac atacgagccg    9120
gaagcataaa gtgtaaagcc tggggtgcct aatgagtgag ctaactcaca ttaattgcgt    9180
tgcgctcact gcccgctttc cagtcgggaa acctgtcgtg ccagctgcat taatgaatcg    9240
gccaacgcgc ggggagaggc ggtttgcgta ttgggcgctc ttccgcttcc tcgctcactg    9300
actcgctgcg ctcggtcgtt cggctgcggc gagcggtatc agctcactca aaggcggtaa    9360
tacggttatc cacagaatca ggggataacg caggaaagaa catgtgagca aaaggccagc    9420
aaaaggccag gaaccgtaaa aaggccgcgt tgctggcgtt ttttccatag gctccgcccc    9480
ctgacgagca tcacaaaaat cgacgctcaa gtcagaggtg gcgaaacccg acaggactat    9540
aaagatacca ggcgtttccc cctggaagct ccctcgtgcg ctctcctgtt ccgaccctgc    9600
cgcttaccgg atacctgtcc gcctttctcc cttcgggaag cgtggcgctt tctcatagct    9660
cacgctgtag gtatctcagt tcggtgtagg tcgttcgctc caagctgggc tgtgtgcacg    9720
aaccccccgt tcagcccgac cgctgcgcct tatccggtaa ctatcgtctt gagtccaacc    9780
cggtaagaca cgacttatcg ccactggcag cagccactgg taacaggatt agcagagcga    9840
ggtatgtagg cggtgctaca gagttcttga agtggtggcc taactacggc tacactagaa    9900
gaacagtatt tggtatctgc gctctgctga agccagttac cttcggaaaa agagttgta    9960
gctcttgatc cggcaaacaa accaccgctg gtagcggtgg ttttttttgtt tgcaagcagc   10020
```

```
agattacgcg cagaaaaaaa ggatctcaag aagatccttt gatcttttct acggggtctg    10080
acgctcagtg gaacgaaaac tcacgttaag ggattttggt catgagatta tcaaaaagga    10140
tcttcaccta gatccttta aattaaaaat gaagttttaa atcaatctaa agtatatatg    10200
agtaaacttg gtctgacagt taccaatgct taatcagtga ggcacctatc tcagcgatct    10260
gtctatttcg ttcatccata gttgcctgac tccccgtcgt gtagataact acgatacggg    10320
agggcttacc atctggcccc agtgctgcaa tgataccgcg agacccacgc tcaccggctc    10380
cagatttatc agcaataaac cagccagccg aagggccga gcgcagaagt ggtcctgcaa     10440
ctttatccgc ctccatccag tctattaatt gttgccggga agctagagta agtagttcgc    10500
cagttaatag tttgcgcaac gttgttgcca ttgctacagg catcgtggtg tcacgctcgt    10560
cgtttggtat ggcttcattc agctccggtt cccaacgatc aaggcgagtt acatgatccc    10620
ccatgttgtg caaaaaagcg gttagctcct tcggtcctcc gatcgttgtc agaagtaagt    10680
tggccgcagt gttatcactc atggttatgg cagcactgca taattctctt actgtcatgc    10740
catccgtaag atgcttttct gtgactggtg agtactcaac caagtcattc tgagaatagt    10800
gtatgcggcg accgagttgc tcttgcccgg cgtcaatacg ggataatacc gcgccacata    10860
gcagaacttt aaaagtgctc atcattggaa acgttcttc ggggcgaaaa ctctcaagga     10920
tcttaccgct gttgagatcc agttcgatgt aacccactcg tgcacccaac tgatcttcag    10980
catcttttac tttcaccagc gtttctgggt gagcaaaaac aggaaggcaa aatgccgcaa    11040
aaaagggaat aagggcgaca cggaaatgtt gaatactcat actcttcctt tttcaatatt    11100
attgaagcat ttatcagggt tattgtctca tgagcggata catatttgaa tgtatttaga    11160
aaaataaaca aataggggtt ccgcgcacat ttccccgaaa agtgccacct gacgtctaag    11220
aaaccattat tatcatgaca ttaacctata aaaataggcg tatcacgagg cccttcgtc    11280 tcgcgcgttt cggtgatgac ggtgaaaacc tctgacacat gcagctcccg gagacggtca    11340
cagcttgtct gtaagcggat gccggagca gacaagcccg tcagggcgcg tcagcgggtg    11400
ttggcgggtg tcggggctgg cttaactatg cggcatcaga gcagattgta ctgagagtgc    11460
accatatgcg gtgtgaaata ccgcacagat gcgtaaggag aaaataccgc atcaggcgcc    11520
attcgccatt caggctgcgc aactgttggg aagggcgatc ggtgcgggcc tcttcgctat    11580
tacgccagct ggcgaaaggg ggatgtgctg caaggcgatt aagttgggta acgccagggt    11640
tttcccagtc acgacgttgt aaaacgacgg ccagtgaatt c                       11681
```

<210> SEQ ID NO 16
<211> LENGTH: 11678
<212> TYPE: DNA
<213> ORGANISM: Artificial Sequence
<220> FEATURE:
<223> OTHER INFORMATION: Synthetic: TL20d-r7SKM1/sh734-rGbGM

<400> SEQUENCE: 16

```
ggccgcctcg gccaaacagc ccttgagttt accactccct atcagtgata gagaaaagtg     60
aaagtcgagt ttaccactcc ctatcagtga tagagaaaag tgaaagtcga gtttaccact    120
ccctatcagt gatagagaaa agtgaaagtc gagtttacca ctcccctatca gtgatagaga    180 aagtgaaag tcgagtttac cagtccctat cagtgataga gaaagtgaa agtcgagttt    240 accactccct atcagtgata gagaaaagtg aaagtcgagt ttaccactcc ctatcagtga    300
tagagaaaag tgaaagtcga gctcgccatg ggaggcgtgg cctgggcggg actggggagt    360
```

```
ggcgagccct cagatcctgc atataagcag ctgcttttg  cctgtactgg gtctctctgg    420
ttagaccaga tctgagcctg ggagctctct ggctaactag ggaacccact gcttaagcct    480
caataaagct tgccttgagt gcttcaagta gtgtgtgccc gtctgttgtg tgactctggt    540
aactagagat ccctcagacc cttttagtca gtgtggaaaa tctctagcag tggcgcccga    600
acagggactt gaaagcgaaa gggaaaccag aggagctctc tcgacgcagg actcggcttg    660
ctgaagcgcg cacggcaaga ggcgaggggc ggcgactggt gagtacgcca aaaattttga    720
ctagcggagg ctagaaggag agagatgggt gcgagagcgt cagtattaag cgggggagaa    780
ttagatcgcg atgggaaaaa attcggttaa ggccaggggg aaagaaaaaa tataaattaa    840
aacatatagt atgggcaagc agggagctag aacgattcgc agttaatact ggcctgttag    900
aaacatcaga aggctgtaga caaatactgg gacagctaca accatccctt cagacaggat    960
cagaagaact tagatcatta tataatacag tagcaaccct ctattgtgtg catcaaagga   1020
tagagataaa agacaccaag gaagctttag acaagataga ggaagagcaa acaaaagta    1080 agaaaaaagc acagcaagca gcaggatctt cagacctgga aattccctac aatccccaaa   1140
gtcaaggagt agtagaatct atgaataaag aattaaagaa aattatagga caggtaagag   1200
atcaggctga acatcttaag acagcagtac aaatggcagt attcatccac aattttaaaa   1260
gaaaaggggg gattgggggg tacagtgcag gggaagaat  agtagacata atagcaacag   1320
acatacaaac taaagaatta caaaaacaaa ttacaaaaat tcaaaatttt cgggtttatt   1380
acagggacag cagaaatcca ctttggaaag gaccagcaaa gctcctctgg aaaggtgaag   1440
gggcagtagt aatacaagat aatagtgaca taaagtagt  gccaagaaga aaagcaaaga   1500
tcattaggga ttatggaaaa cagatggcag gtgatgattg tgtggcaagt agacaggatg   1560
aggattagaa catggaaaag tttagtaaaa caccataagg aggagatatg agggacaatt   1620
ggagaagtga attatataaa tataaagtag taaaaattga accattagga gtagcaccca   1680
ccaaggcaaa gagaagagtg gtgcagagag aaaaagagc  agtgggaata ggagctttgt   1740
tccttgggtt cttgggagca gcaggaagca ctatgggcgc agcgtcaatg acgctgacgg   1800
tacaggccag acaattattg tctggtatag tgcagcagca gaacaatttg ctgagggcta   1860
ttgaggcgca acagcatctg ttgcaactca cagtctgggg catcaagcag ctccaggcaa   1920
gaatcctggc tgtggaaaga tacctaaagg atcaacagct cctggggatt tggggttgct   1980
ctggaaaact catttgcacc actgctgtgc cttggaatgc tagttggagt aataaatctc   2040
tggaacagat ttggaatcac acgacctgga tggagtggga cagagaaatt aacaattaca   2100
caagcttaat acactcctta attgaagaat cgcaaaacca gcaagaaaag aatgaacaag   2160
aattattgga attagataaa tgggcaagtt tgtggaattg gtttaacata acaaattggc   2220
tgtggtatat aaaattattc ataatgatag taggaggctt ggtaggttta agaatagttt   2280
ttgctgtact ttctatagtg aatagagtta ggcaggata  ttcaccatta tcgtttcaga   2340
cccacctccc aaccccgagg ggaccgagct caagcttcga agcggccgca aaaaggata   2400 tgcccttgac tatgtcggac aaatagtcaa gggcatatcc tgaggtaccc aggcggcgca   2460
caagctatat aaacctgaag gaaatctcaa ctttacactt aggtcaagtt acttatcgta   2520
ctagagcttc agcaggaaat ttaactaaaa tctaatttaa ccagcatagc aaatatcatt   2580
tattcccaaa atgctaaagt ttgagataaa cggacttgat ttccggctgt tttgacacta   2640
tccagaatgc cggtactatg ggtggggcag tagcccgact gcacgtcgaa cgcgtgggga   2700
tcctctagag tcgagctcgc gaggatcatc accggtgcta gccggagcca gaagcaccat   2760
```

```
aagggacatg ataagggagc cagcagacct ctgatctctt cctgaatgct aatcttaaac   2820
atcctgagga agaatgggac ttccatttgg ggtgggccta tgatagggta ataagacagt   2880
agtgaatatc aagctacaaa aagcccccTt tcaaattctt ctcagtccta acttttcata   2940
ctaagcccag tccttccaaa gcagactgtg aaagagtgat agttccggga gactagcacc   3000
ggctagccga gcttggaaca ctttcccttc attaagaacc atccttgcta ctcagctgca   3060
atcaatccag cccccaggtc ttcactgaac cttttcccat ctcttccaaa acatctgttt   3120
ctgagaagtc ctgtcctata gaggtctttc ttcccaccgg atttctccta caccatttac   3180
tcccacttgc agaactcccg tgtacaagtg tctttactgc ttttatttgc tcaacaaaat   3240
gcacatctca tataaaaata aatgaggagc atgcacacac cacaaacaca aacaggcatg   3300
cagaaataca catacacact tccctcaata taaacccttt gtggctcata tatttaaaaa   3360
gatgtaaaaa aaagagctga agaaaatcat gtgtgatctc tcagcagaat agatttatta   3420
tttgtattgc ttgcagaata aagcctatcc ttgaaagctc tgaatcatgg gcaagaggct   3480
cagtggtatc tggaggacag ggcactggcc actgcagtca ccatcttctg ccaggaagcc   3540
tgcacctcag gggtgaattc tttgccaaag tgaatggcca gcacggtgac cagcacgttg   3600
cccaggagct gtgggaggaa gataagaggt atgaacatga ttagcaaaag ggcctagctt   3660
ggactcagaa taatccagcc ttatcccaac cataaaataa aagcagaatg gtagctggat   3720
tgtagctgct attagcaata tgaaacctct tacatcagtt acaatttata tgcagaaata   3780
tttatatgca gaaatattgc tattgcctta acccagaaat tatcactgtt attctttaga   3840
atggtgcaaa gaggcatgat acattgtatc attattgccc tgaaagaaag agattaggga   3900
aagtattaga aataagataa acaaaaaagt atattaaaag aagaaagcat tttttaaaat   3960
tacaaatgca aaattaccct gatttggtca atatgtgtac cctgttactt ctccccttcc   4020
tatgacatga acttaaccat agaaaagaag gggaaagaaa acatcaaggg tcccatagac   4080
tcaccttgaa gttctcagga tccacatgca gcttgtcaca gtgcagttca ctcagctggg   4140
caaaggtgcc cttgagatca tccaggtgct ttatggcatc tcccaaggaa gtcagcacct   4200
tcttgccatg tgccttgact ttggggttgc ccatgatggc agaggcagag gacaggttgc   4260
caaagctgtc aaagaacctc tgggtccatg ggtagacaac caggagcctg tgagattgac   4320
aagaacagtt tgacagtcag aaggtgccac aaatcctgag aagcaacctg gacttttgcc   4380
aggcacaggg tccttccttc cctcccttgt cctggtcacc agagcctacc ttcccagggt   4440
ttctcctcca gcatcttcca cattcacctt gtcccacagg cttgtgatag tagccttgtc   4500
ctcctctgtg aaatgaccca tggtgtctgt ttgaggttgc tagtgaacac agttgtgtca   4560
gaagcaaatg taagcaatag atggctctgc cctgactttt atgcccagcc ctggctcctg   4620
ccctccctgc tcctgggagt agattggcca accctagggt gtggctccac agggtgaggt   4680
ctaagtgatg acagccgtac ctgtccttgg ctcttctggc actggcttag gagttggact   4740
tcaaaccctc agccctccct ctaagatata tctcttggcc ccataccatc agtacaaatt   4800
gctactaaaa acatcctcct ttgcaagtgt atttacgacg gtatcgatgt atgtgagcat   4860
gtgtcctcta acagcacagg ccttttgcca cctagctgtc caggggtgcc ttaaaatggc   4920
aaacaaggtt tgttttcttt tcctgttttc atgccttcct cttccatatc cttgtttcat   4980
attaatacat gtgtatagat cctaaaaatc tatacacatg tattaataaa gcctgattct   5040
gccgcttcta ggtatagagg ccacctgcaa gataaatatt tgattcacaa taactaatca   5100
```

```
ttctatggca attgataaca acaaatatat atatatatat atatatacgt atatgtgtat    5160
atatatatat atattcagga aataatatat tctagaatat gtcacattct gtctcaggca    5220
tccattttct ttatgatgcc gtttgaggtg gagttttagt caggtggtca gcttctcctt    5280 tttttttgcca tctgccctgt aagcatcctg ctggggaccc agataggagt catcactcta    5340
ggctgagaac atctgggcac acaccctaag cctcagcatg actcatcatg actcagcatt    5400
gctgtgcttg agccagaagg tttgcttaga aggttacaca gaaccagaag gcggggtgg    5460 ggcactgacc ccgacagggg cctggccaga actgctcatg cttggactat gggaggtcac    5520
taatggagac acacagaaat gtaacaggaa ctaagggaat tccggtgccc tgcttaggag    5580
cttaatcttt aatgaaagct aagctttcat taaaaaagt ctaaccagct gcattcgact    5640
ttgactgcag cagctggtta gaaggttcta ctggaggagg gtcccagccc attgctaaat    5700
taacatcagg ctctgagact ggcagtatat ctctaacagt ggttgatgct atcttctgga    5760
acttgcctgc tacattgaga ccactgaccc atacatagga agcccatagc tctgtcctga    5820
actgttaggc cactggtcca gagagtgtgc atctcctttg atcctcataa taaccctatg    5880
agatagacac aattattact cttactttat agatgatgat cctgaaaaca taggagtcaa    5940
ggcacttgcc cctagctggg ggtataggg agcagtccca tgtagtagta gaatgaaaaa    6000
tgctgctatg ctgtgcctcc cccacctttc ccatgtctgc cctctactca tggtctatct    6060
ctcctggctc ctgggagtca tggactccac ccagcaccac caacctgacc taaccaccta    6120
tctgagcctg ccagcctata acccatctgg gccctgatag ctggtggcca gccctgaccc    6180
caccccaccc tccctggaac ctctgataga cacatctggc acaccagctc gcaaagtcac    6240
cgtgagggtc ttgtgtttgc tgagtcaaaa ttccttgaaa tccaagtcct tagagactcc    6300
tgctcccaaa tttacagtca tagacttctt catggctgtc tcctttatcc acagaatgat    6360
tcctttgctt cattgcccca tccatctgat cctcctcatc agtgcagcac agggcccatg    6420
agcagtagct gcagagtctc ataggtct ggcactgcct ctgacatgtc cgacctagg     6480 caaatgcttg actcttctga gctcggatcc cttgagctca ggaggtcaag gctgcagtga    6540
gacatgatct tgccactgca ctccagcctg gacagcagag tgaaaccttg cctcacgaaa    6600
cagaatacaa aaacaaacaa acaaaaaact gctccgcaat gcgcttcctt gatgctctac    6660
cacataggtc tgggtacttt gtacacatta tctcattgct gttcataatt gttagattaa    6720
ttttgtaata ttgatattat tcctagaaag ctgaggcctc aagatgataa cttttatttt    6780
ctggacttgt aatagctttc tcttgtattc accatgttgt aactttctta gagtagtaac    6840
aatataaagt tattgtgagt ttttgcaaac acagcaaaca caacgaccca tatagacatt    6900
gatgtgaaat tgtctattgt caatttatgg gaaaacaagt atgtacttt tctactaagc    6960 cattgaaaca ggaataacag aacaagattg aaagaataca ttttccgaaa ttacttgagt    7020
attatacaaa gacaagcacg tggacctggg aggagggtta ttgtccatga ctggtgtgtg    7080
gagacaaatg caggtttata atagatggga tggcatctag cgcaatgact ttgccatcac    7140
ttttagagag ctcttggggg ccccagtaca caagagggga cgcagggtat atgtagacat    7200
ctcattcttt ttcttagtgt gagaataaga atagccatga cctgagttta tagacaatga    7260 gccctttttct ctctcccact cagcagctat gagatggctt gccctgcctc tctactaggc    7320
tgactcactc caaggcccag caatgggcag ggctctgtca gggctttgat agcactatct    7380
gcagagccag ggccgagaag gggtggactc cagagactct ccctcccatt cccgagcagg    7440
gtttgcttat ttatgcattt aaatgatata tttatttaa aagaaataac aggagactgc    7500
```

```
ccagccctgg ctgtgacatg gaaactatgt agaatatttt gggttccatt ttttttttcct   7560 tctttcagtt agaggaaaag gggctcactg cacatacact agacagaaag tcaggagctt   7620
tgaatccaag cctgatcatt tccatgtcat actgagaaag tccccaccct tctctgagcc   7680
tcagtttctc tttttataag taggagtctg gagtaaatga tttccaatgg ctctcatttc   7740
aatacaaaat ttccgtttat taaatgcatg agcttccgtt actccaagac tgagaaggaa   7800
attgaacctg agactcattg actggcaaga tgtccccaga ggctctcatt cagcaataaa   7860
attctcacct tcacccaggc ccactagtgt cagatttgca tgcgttaacg cggccgcatc   7920
gatgccgtag taccttttaag accaatgact tacaaggcag ctgtagatct tagccacttt   7980
ttaaaagaaa aggggggact ggaagggcta attcactccc aaagaagaca agatagatct   8040 gcttttttgcc tgtactgggt ctctctggtt agaccagatc tgagcctggg agctctctgg   8100
ctaactaggg aacccactgc ttaagcctca ataaagcttc agctgctcga gctagcagat   8160
ctttttccct ctgccaaaaa ttatggggac atcatgaagc cccttgagca tctgacttct   8220
ggctaataaa ggaaatttat tttcattgca atagtgtgtt ggaatttttt gtgtctctca   8280
ctcggaagga catatgggag ggcaaatcat ttaaaacatc agaatgagta tttggtttag   8340
agtttggcaa catatgccca tatgctggct gccatgaaca aaggttggct ataaagaggt   8400
catcagtata tgaaacagcc ccctgctgtc cattccttat tccatagaaa agccttgact   8460
tgaggttaga ttttttttat attttgtttt gtgttatttt tttctttaac atccctaaaa   8520
ttttccttac atgtttttact agccagattt ttcctcctct cctgactact cccagtcata   8580
gctgtccctc ttctcttatg gagatccctc gacctgcagc ccaagcttgg cgtaatcatg   8640
gtcatagctg tttcctgtgt gaaattgtta tccgctcaca attccacaca acatacgagc   8700
cggaagcata aagtgtaaag cctggggtgc ctaatgagtg agctaactca cattaattgc   8760
gttgcgctca ctgcccgctt tccagtcggg aaacctgtcg tgccagcgga tccgcatctc   8820
aattagtcag caaccatagt cccgccccta actccgccca tcccgcccct aactccgccc   8880
agttccgccc attctccgcc ccatggctga ctaatttttt ttatttatgc agaggccgag   8940
gccgcctcgg cctctgagct attccagaag tagtgaggag gcttttttgg aggcctaggc   9000
ttttgcaaaa agctgtcgac tgcagaggcc tgcatgcaag cttggcgtaa tcatggtcat   9060 agctgttttcc tgtgtgaaat tgttatccgc tcacaattcc acacaacata cgagccggaa   9120
gcataaagtg taaagcctgg ggtgcctaat gagtgagcta actcacatta attgcgttgc   9180
gctcactgcc cgctttccag tcgggaaacc tgtcgtgcca gctgcattaa tgaatcggcc   9240
aacgcgcggg gagaggcggt ttgcgtattg ggcgctcttc cgcttcctcg ctcactgact   9300
cgctgcgctc ggtcgttcgg ctgcggcgag cggtatcagc tcactcaaag gcggtaatac   9360
ggttatccac agaatcaggg gataacgcag gaaagaacat gtgagcaaaa ggccagcaaa   9420
aggccaggaa ccgtaaaaag gccgcgttgc tggcgttttt ccataggctc cgcccccctg   9480
acgagcatca caaaaatcga cgctcaagtc agaggtggcg aaacccgaca ggactataaa   9540
gataccaggc gtttccccct ggaagctccc tcgtgcgctc tcctgttccg accctgccgc   9600
ttaccggata cctgtccgcc tttctccctt cgggaagcgt ggcgctttct catagctcac   9660
gctgtaggta tctcagttcg gtgtaggtcg ttcgctccaa gctgggctgt gtgcacgaac   9720
cccccgttca gcccgaccgc tgcgccttat ccggtaacta tcgtcttgag tccaacccgg   9780
taagacacga cttatcgcca ctggcagcag ccactggtaa caggattagc agagcgaggt   9840
```

```
atgtaggcgg tgctacagag ttcttgaagt ggtggcctaa ctacggctac actagaagaa      9900
cagtatttgg tatctgcgct ctgctgaagc cagttacctt cggaaaaaga gttggtagct      9960
cttgatccgg caaacaaacc accgctggta gcggtggttt ttttgtttgc aagcagcaga     10020
ttacgcgcag aaaaaaagga tctcaagaag atcctttgat cttttctacg ggtctgacg      10080
ctcagtggaa cgaaaactca cgttaaggga ttttggtcat gagattatca aaaaggatct     10140
tcacctagat cctttttaaat taaaaatgaa gttttaaatc aatctaaagt atatatgagt    10200
aaacttggtc tgacagttac caatgcttaa tcagtgaggc acctatctca gcgatctgtc     10260
tatttcgttc atccatagtt gcctgactcc ccgtcgtgta gataactacg atacgggagg     10320
gcttaccatc tggccccagt gctgcaatga taccgcgaga cccacgctca ccggctccag     10380
atttatcagc aataaaccag ccagccggaa gggccgagcg cagaagtggt cctgcaactt     10440
tatccgcctc catccagtct attaattgtt gccgggaagc tagagtaagt agttcgccag     10500
ttaatagttt gcgcaacgtt gttgccattg ctacaggcat cgtggtgtca cgctcgtcgt     10560
ttggtatggc ttcattcagc tccggttccc aacgatcaag gcgagttaca tgatccccca    10620
tgttgtgcaa aaaagcggtt agctccttcg gtcctccgat cgttgtcaga agtaagttgg     10680
ccgcagtgtt atcactcatg gttatggcag cactgcataa ttctcttact gtcatgccat     10740
ccgtaagatg cttttctgtg actggtgagt actcaaccaa gtcattctga gaatagtgta     10800
tgcggcgacc gagttgctct tgcccggcgt caatacggga taataccgcg ccacatagca     10860
gaactttaaa agtgctcatc attggaaaac gttcttcggg gcgaaaactc tcaaggatct     10920
taccgctgtt gagatccagt tcgatgtaac ccactcgtgc acccaactga tcttcagcat     10980
cttttacttt caccagcgtt tctgggtgag caaaaacagg aaggcaaaat gccgcaaaaa     11040
agggaataag ggcgacacgg aaatgttgaa tactcatact cttcctttt  caatattatt     11100
gaagcattta tcagggttat tgtctcatga gcggatacat atttgaatgt atttagaaaa     11160
ataaacaaat aggggttccg cgcacatttc cccgaaaagt gccacctgac gtctaagaaa     11220
ccattattat catgacatta acctataaaa ataggcgtat cacgaggccc tttcgtctcg     11280
cgcgtttcgg tgatgacggt gaaaacctct gacacatgca gctcccggag acggtcacag     11340
cttgtctgta agcggatgcc gggagcagac aagcccgtca gggcgcgtca gcgggtgttg     11400
gcgggtgtcg gggctggctt aactatgcgg catcagagca gattgtactg agagtgcacc     11460
atatgcggtg tgaaataccg cacagatgcg taaggagaaa ataccgcatc aggcgccatt     11520
cgccattcag gctgcgcaac tgttgggaag ggcgatcggt gcgggcctct tcgctattac     11580
gccagctggc gaaaggggga tgtgctgcaa ggcgattaag ttgggtaacg ccagggtttt     11640
cccagtcacg acgttgtaaa acgacggcca gtgaattc                             11678
```

<210> SEQ ID NO 17
<211> LENGTH: 11681
<212> TYPE: DNA
<213> ORGANISM: Artificial Sequence
<220> FEATURE:
<223> OTHER INFORMATION: Synthetic: TL20d-r7SK/sh734-rGbGM

<400> SEQUENCE: 17

```
ggccgcctcg gccaaacagc ccttgagttt accactccct atcagtgata gagaaaagtg       60
aaagtcgagt ttaccactcc ctatcagtga tagagaaaag tgaaagtcga gtttaccact      120
ccctatcagt gatagagaaa agtgaaagtc gagtttacca ctccctatca gtgatagaga      180
aaagtgaaag tcgagtttac cagtccctat cagtgataga gaaaagtgaa agtcgagttt      240
```

```
accactccct atcagtgata gagaaaagtg aaagtcgagt ttaccactcc ctatcagtga    300
tagagaaaag tgaaagtcga gctcgccatg ggaggcgtgg cctgggcggg actggggagt    360
ggcgagccct cagatcctgc atataagcag ctgcttttg cctgtactgg gtctctctgg     420
ttagaccaga tctgagcctg ggagctctct ggctaactag ggaacccact gcttaagcct    480
caataaagct tgccttgagt gcttcaagta gtgtgtgccc gtctgttgtg tgactctggt    540
aactagagat ccctcagacc cttttagtca gtgtggaaaa tctctagcag tggcgcccga    600
acagggactt gaaagcgaaa gggaaaccag aggagctctc tcgacgcagg actcggcttg    660
ctgaagcgcg cacggcaaga ggcgaggggc ggcgactggt gagtacgcca aaattttga     720 ctagcggagg ctagaaggag agagatgggt gcgagagcgt cagtattaag cggggagaa     780 ttagatcgcg atgggaaaaa attcggttaa ggccagggg aaagaaaaa tataaattaa      840 aacatatagt atgggcaagc agggagctag aacgattcgc agttaatact ggcctgttag    900
aaacatcaga aggctgtaga caaatactgg gacagctaca accatccctt cagacaggat    960
cagaagaact tagatcatta tataatacag tagcaaccct ctattgtgtg catcaaagga    1020
tagagataaa agacaccaag gaagctttag acaagataga ggaagagcaa acaaaagta    1080 agaaaaaagc acagcaagca gcaggatctt cagacctgga aattccctac aatccccaaa    1140
gtcaaggagt agtagaatct atgaataaag aattaaagaa aattatagga caggtaagag    1200
atcaggctga acatcttaag acagcagtac aaatggcagt attcatccac aattttaaaa    1260
gaaagggggg gattgggggg tacagtgcag gggaagaat agtagacata atagcaacag    1320
acatacaaac taaagaatta caaaaacaaa ttacaaaaat tcaaaatttt cgggtttatt    1380
acagggacag cagaaatcca ctttggaaag gaccagcaaa gctcctctgg aaaggtgaag    1440
gggcagtagt aatacaagat aatagtgaca taaaagtagt gccaagaaga aaagcaaaga    1500
tcattaggga ttatggaaaa cagatggcag gtgatgattg tgtggcaagt agacaggatg    1560
aggattagaa catggaaaag tttagtaaaa caccataagg aggagatatg agggacaatt    1620
ggagaagtga attatataaa tataaagtag taaaaattga accattagga gtagcaccca    1680
ccaaggcaaa gagaagagtg gtgcagagag aaaaagagc agtgggaata ggagctttgt    1740
tccttgggtt cttgggagca gcaggaagca ctatgggcgc agcgtcaatg acgctgacgg    1800
tacaggccag acaattattg tctggtatag tgcagcagca gaacaatttg ctgagggcta    1860
ttgaggcgca acagcatctg ttgcaactca gtctggggg catcaagcag ctccaggcaa    1920
gaatcctggc tgtggaaaga tacctaaagg atcaacagct cctggggatt tggggttgct    1980
ctggaaaact catttgcacc actgctgtgc cttggaatgc tagttggagt aataaatctc    2040
tggaacagat ttggaatcac acgacctgga tggagtggga cagagaaatt aacaattaca    2100
caagcttaat acactcctta attgaagaat cgcaaaacca gcaagaaaag aatgaacaag    2160
aattattgga attagataaa tgggcaagtt tgtggaattg gtttaacata acaaattggc    2220
tgtggtatat aaaattattc ataatgatag taggaggctt ggtaggttta agaatagttt    2280
ttgctgtact ttctatagtg aatagagtta ggcagggata ttcaccatta tcgtttcaga    2340
cccacctccc aaccccgagg ggaccgagct caagcttcga gcggccgca caaaaagga     2400 tatgcccttg actatgtcgg acaaatagtc aagggcatat cctgaggtac ccaggcggcg    2460
cacaagctat ataaacctga aggaaatctc aactttacac ttaggtcaag ttacttatcg    2520
tactagagct tcagcaggaa atttaactaa aatctaattt aaccagcata gcaaatatca    2580
```

```
tttattccca aaatgctaaa gtttgagata aacggacttg atttccggct gttttgacac    2640
tatccagaat gccttgcaga tgggtggggc atgctaaata ctgcacgtcg atacgcgtgg    2700
ggatcctcta gagtcgagct cgcgaggatc atcaccggtg ctagccggag ccagaagcac    2760
cataagggac atgataaggg agccagcaga cctctgatct cttcctgaat gctaatctta    2820
aacatcctga ggaagaatgg gacttccatt tggggtgggc ctatgatagg gtaataagac    2880
agtagtgaat atcaagctac aaaaagcccc ctttcaaatt cttctcagtc ctaacttttc    2940
atactaagcc cagtccttcc aaagcagact gtgaaagagt gatagttccg ggagactagc    3000
accggctagc cgagcttgga acactttccc ttcattaaga accatccttg ctactcagct    3060
gcaatcaatc cagcccccag gtcttcactg aaccttttcc catctcttcc aaaacatctg    3120
tttctgagaa gtcctgtcct atagaggtct tcttcccac cggatttctc ctacaccatt    3180
tactcccact tgcagaactc ccgtgtacaa gtgtctttac tgcttttatt tgctcaacaa    3240
aatgcacatc tcatataaaa ataaatgagg agcatgcaca caccacaaac acaaacaggc    3300
atgcagaaat acacatacac acttccctca atataaaccc tttgtggctc atatatttaa    3360
aaagatgtaa aaaaaagagc tgaagaaaat catgtgtgat ctctcagcag aatagattta    3420
ttatttgtat tgcttgcaga ataaagccta tccttgaaag ctctgaatca tgggcaagag    3480
gctcagtggt atctggagga cagggcactg gccactgcag tcaccatctt ctgccaggaa    3540
gcctgcacct caggggtgaa ttcttttgcca aagtgaatgg ccagcacggt gaccagcacg    3600
ttgcccagga gctgtgggag gaagataaga ggtatgaaca tgattagcaa aagggcctag    3660
cttggactca gaataatcca gccttatccc aaccataaaa taaaagcaga atggtagctg    3720
gattgtagct gctattagca atatgaaacc tcttacatca gttacaattt atatgcagaa    3780
atatttatat gcagaaatat tgctattgcc ttaacccaga aattatcact gttattcttt    3840
agaatggtgc aaagaggcat gatacattgt atcattattg ccctgaaaga aagagattag    3900
ggaaagtatt agaaataaga taaacaaaaa agtatattaa aagaagaaag cattttttaa    3960
aattacaaat gcaaaattac cctgatttgg tcaatatgtg taccctgtta cttctcccct    4020
tcctatgaca tgaacttaac catagaaaag aaggggaaag aaaacatcaa gggtcccata    4080 gactcaccttt gaagttctca ggatccacat gcagcttgtc acagtgcagt tcactcagct    4140
gggcaaaggt gcccttgaga tcatccaggt gctttatggc atctcccaag gaagtcagca    4200
ccttcttgcc atgtgccttg actttggggt tgcccatgat ggcagaggca gaggacaggt    4260
tgccaaagct gtcaaagaac ctctgggtcc atgggtagac aaccaggagc ctgtgagatt    4320
gacaagaaca gtttgacagt cagaaggtgc cacaaatcct gagaagcaac ctggactttt    4380
gccaggcaca gggtccttcc ttccctccct tgtcctggtc accagagcct accttcccag    4440
ggtttctcct ccagcatctt ccacattcac cttgtcccac aggcttgtga tagtagcctt    4500
gtcctcctct gtgaaatgac ccatggtgtc tgtttgaggt tgctagtgaa cacagttgtg    4560
tcagaagcaa atgtaagcaa tagatggctc tgccctgact tttatgccca gccctggctc    4620
ctgccctccc tgctcctggg agtagattgg ccaaccctag ggtgtggctc cacagggtga    4680
ggtctaagtg atgacagccg tacctgtcct tggctcttct ggcactggct taggagttgg    4740
acttcaaacc ctcagccctc cctctaagat atatctcttg gccccatacc atcagtacaa    4800
attgctacta aaaacatcct cctttgcaag tgtatttacg acggtatcga tgtatgtgag    4860
catgtgtcct ctaacagcac aggccttttg ccacctagct gtccaggggt gccttaaaat    4920
ggcaaacaag gtttgttttc ttttcctgtt ttcatgcctt cctcttccat atccttgttt    4980
```

```
catattaata catgtgtata gatcctaaaa atctatacac atgtattaat aaagcctgat    5040
tctgccgctt ctaggtatag aggccacctg caagataaat atttgattca caataactaa    5100
tcattctatg gcaattgata acaacaaata tatatatata tatatatata cgtatatgtg    5160
tatatatata tatatattca ggaaataata tattctagaa tatgtcacat tctgtctcag    5220
gcatccattt tctttatgat gccgtttgag gtggagtttt agtcaggtgg tcagcttctc    5280
cttttttttg ccatctgccc tgtaagcatc ctgctgggga cccagatagg agtcatcact    5340
ctaggctgag aacatctggg cacacaccct aagcctcagc atgactcatc atgactcagc    5400
attgctgtgc ttgagccaga aggtttgctt agaaggttac acagaaccag aaggcggggg    5460
tggggcactg accccgacag gggcctggcc agaactgctc atgcttggac tatgggaggt    5520
cactaatgga gacacacaga aatgtaacag gaactaaggg aattccggtg ccctgcttag    5580
gagcttaatc tttaatgaaa gctaagcttt cattaaaaaa agtctaacca gctgcattcg    5640
actttgactg cagcagctgg ttagaaggtt ctactggagg agggtcccag cccattgcta    5700
aattaacatc aggctctgag actggcagta tatctctaac agtggttgat gctatcttct    5760
ggaacttgcc tgctacattg agaccactga cccatacata ggaagcccat agctctgtcc    5820
tgaactgtta ggccactggt ccagagagtg tgcatctcct ttgatcctca taataaccct    5880
atgagataga cacaattatt actcttactt tatagatgat gatcctgaaa acataggagt    5940
caaggcactt gcccctagct gggggtatag gggagcagtc ccatgtagta gtagaatgaa    6000
aaatgctgct atgctgtgcc tcccccacct ttcccatgtc tgccctctac tcatggtcta    6060
tctctcctgg ctcctgggag tcatggactc cacccagcac caccaacctg acctaaccac    6120
ctatctgagc ctgccagcct ataacccatc tgggccctga tagctggtgg ccagccctga    6180
ccccacccca ccctccctgg aacctctgat agacacatct ggcacaccag ctcgcaaagt    6240
caccgtgagg gtcttgtgtt tgctgagtca aaattccttg aaatccaagt ccttagagac    6300
tcctgctccc aaatttacag tcatagactt cttcatggct gtctccttta tccacagaat    6360
gattcctttg cttcattgcc ccatccatct gatcctcctc atcagtgcag cacagggccc    6420
atgagcagta gctgcagagt ctcacatagg tctggcactg cctctgacat gtccgacctt    6480
aggcaaatgc ttgactcttc tgagctcgga tcccttgagc tcaggaggtc aaggctgcag    6540
tgagacatga tcttgccact gcactccagc ctggacagca gagtgaaacc ttgcctcacg    6600
aaacagaata caaaaacaaa caaacaaaaa actgctccgc aatgcgcttc cttgatgctc    6660
taccacatag gtctgggtac tttgtacaca ttatctcatt gctgttcata attgttagat    6720
taattttgta atattgatat tattcctaga aagctgaggc ctcaagatga taactttttat   6780 tttctggact tgtaatagct ttctcttgta ttcaccatgt tgtaactttc ttagagtagt    6840
aacaatataa agttattgtg agttttttgca aacacagcaa acacaacgac ccatatagac    6900
attgatgtga aattgtctat tgtcaattta tgggaaaaca agtatgtact ttttctacta    6960
agccattgaa acaggaataa cagaacaaga ttgaaagaat acattttccg aaattacttg    7020
agtattatac aaagacaagc acgtggacct gggaggaggg ttattgtcca tgactggtgt    7080
gtggagacaa atgcaggttt ataatagatg ggatggcatc tagcgcaatg actttgccat    7140
cacttttaga gagctcttgg gggcccagt acacaagagg ggacgcaggg tatatgtaga    7200
catctcattc ttttttcttag tgtgagaata agaaatagcca tgacctgagt ttatagacaa    7260
tgagcccttt tctctctccc actcagcagc tatgagatgg cttgccctgc ctctctacta    7320
```

```
ggctgactca ctccaaggcc cagcaatggg cagggctctg tcagggcttt gatagcacta    7380
tctgcagagc cagggccgag aaggggtgga ctccagagac tctccctccc attcccgagc    7440
agggtttgct tatttatgca tttaaatgat atatttattt taaaagaaat aacaggagac    7500
tgcccagccc tggctgtgac atggaaacta tgtagaatat tttgggttcc atttttttt    7560
ccttctttca gttagaggaa aagggctca ctgcacatac actagacaga aagtcaggag    7620
ctttgaatcc aagcctgatc atttccatgt catactgaga aagtcccac ccttctctga    7680
gcctcagttt ctcttttat aagtaggagt ctggagtaaa tgatttccaa tggctctcat    7740
ttcaatacaa aatttccgtt tattaaatgc atgagcttcc gttactccaa gactgagaag    7800
gaaattgaac ctgagactca ttgactggca agatgtcccc agaggctctc attcagcaat    7860
aaaattctca ccttcaccca ggcccactag tgtcagattt gcatgcgtta acgcggccgc    7920
atcgatgccg tagtaccttt aagaccaatg acttacaagg cagctgtaga tcttagccac    7980
ttttaaaag aaaaggggg actggaaggg ctaattcact cccaagaag acaagataga    8040
tctgcttttt gcctgtactg ggtctctctg gttagaccag atctgagcct gggagctctc    8100
tggctaacta gggaacccac tgcttaagcc tcaataaagc ttcagctgct cgagctagca    8160
gatcttttc cctctgccaa aaattatggg gacatcatga agcccttga gcatctgact    8220
tctggctaat aaaggaaatt tattttcatt gcaatagtgt gttggaattt tttgtgtctc    8280
tcactcggaa ggacatatgg gagggcaaat catttaaaac atcagaatga gtatttggtt    8340
tagagtttgg caacatatgc ccatatgctg gctgccatga acaaaggttg gctataaaga    8400
ggtcatcagt atatgaaaca gccccctgct gtccattcct tattccatag aaaagccttg    8460
acttgaggtt agatttttt tatatttgt tttgtgttat ttttttcttt aacatcccta    8520
aaatttttcct tacatgtttt actagccaga ttttcctcc tctcctgact actcccagtc    8580
atagctgtcc ctcttctctt atggagatcc ctcgacctgc agcccaagct ggcgtaatc    8640
atggtcatag ctgtttcctg tgtgaaattg ttatccgctc acaattccac acaacatacg    8700
agccggaagc ataaagtgta aagcctgggg tgcctaatga gtgagctaac tcacattaat    8760
tgcgttgcgc tcactgcccg ctttccagtc gggaaacctg tcgtgccagc ggatccgcat    8820
ctcaattagt cagcaaccat agtcccgccc ctaactccgc ccatcccgcc cctaactccg    8880
cccagttccg cccattctcc gccccatggc tgactaattt tttttattta tgcagaggcc    8940
gaggccgcct cggcctctga gctattccag aagtagtgag gaggcttttt tggaggccta    9000
ggcttttgca aaaagctgtc gactgcgag gcctgcatgc aagcttggcg taatcatggt    9060
catagctgtt tcctgtgtga aattgttatc cgctcacaat tccacacaac atacgagccg    9120
gaagcataaa gtgtaaagcc tggggtgcct aatgagtgag ctaactcaca ttaattgcgt    9180
tgcgctcact gcccgctttc cagtcgggaa acctgtcgtg ccagctgcat taatgaatcg    9240
gccaacgcgc ggggagaggc ggtttgcgta ttgggcgctc ttccgcttcc tcgctcactg    9300
actcgctgcg ctcggtcgtt cggctgcggc gagcggtatc agctcactca aaggcggtaa    9360
tacggttatc cacagaatca ggggataacg caggaaagaa catgtgagca aaaggccagc    9420
aaaaggccag gaaccgtaaa aaggccgcgt tgctggcgtt ttccatagg ctccgccccc    9480
ctgacgagca tcacaaaaat cgacgctcaa gtcagaggtg gcgaaacccg acaggactat    9540
aaagatacca ggcgtttccc cctggaagct ccctcgtgcg ctctcctgtt ccgaccctgc    9600
cgcttaccgg atacctgtcc gcctttctcc cttcgggaag cgtggcgctt tctcatagct    9660
cacgctgtag gtatctcagt tcggtgtagg tcgttcgctc caagctgggc tgtgtgcacg    9720
```

```
aaccccccgt tcagcccgac cgctgcgcct tatccggtaa ctatcgtctt gagtccaacc    9780
cggtaagaca cgacttatcg ccactggcag cagccactgg taacaggatt agcagagcga    9840
ggtatgtagg cggtgctaca gagttcttga agtggtggcc taactacggc tacactagaa    9900
gaacagtatt tggtatctgc gctctgctga agccagttac cttcggaaaa agagttggta    9960
gctcttgatc cggcaaacaa accaccgctg gtagcggtgg tttttttgtt tgcaagcagc    10020
agattacgcg cagaaaaaaa ggatctcaag aagatccttt gatcttttct acggggtctg    10080
acgctcagtg gaacgaaaac tcacgttaag ggattttggt catgagatta tcaaaaagga    10140
tcttcaccta gatcctttta aattaaaaat gaagttttaa atcaatctaa agtatatatg    10200
agtaaacttg gtctgacagt taccaatgct taatcagtga ggcacctatc tcagcgatct    10260
gtctatttcg ttcatccata gttgcctgac tccccgtcgt gtagataact acgatacggg    10320
agggcttacc atctggcccc agtgctgcaa tgataccgcg agacccacgc tcaccggctc    10380
cagatttatc agcaataaac cagccagccg aagggccga gcgcagaagt ggtcctgcaa    10440
```

*Note: The above reflects my reading; errors may exist due to low resolution. Correcting...*

```
cagatttatc agcaataaac cagccagccg aagggccga gcgcagaagt ggtcctgcaa    10440
ctttatccgc ctccatccag tctattaatt gttgccggga agctagagta agtagttcgc    10500
cagttaatag tttgcgcaac gttgttgcca ttgctacagg catcgtggtg tcacgctcgt    10560
cgtttggtat ggcttcattc agctccggtt cccaacgatc aaggcgagtt acatgatccc    10620
ccatgttgtg caaaaaagcg gttagctcct tcggtcctcc gatcgttgtc agaagtaagt    10680
tggccgcagt gttatcactc atggttatgg cagcactgca taattctctt actgtcatgc    10740
catccgtaag atgcttttct gtgactggtg agtactcaac caagtcattc tgagaatagt    10800
gtatgcggcg accgagttgc tcttgcccgg cgtcaatacg ggataatacc gcgccacata    10860
gcagaacttt aaaagtgctc atcattggaa aacgttcttc ggggcgaaaa ctctcaagga    10920
tcttaccgct gttgagatcc agttcgatgt aacccactcg tgcacccaac tgatcttcag    10980
catcttttac tttcaccagc gtttctgggt gagcaaaaac aggaaggcaa aatgccgcaa    11040
aaaagggaat aagggcgaca cggaaatgtt gaatactcat actcttcctt tttcaatatt    11100
attgaagcat ttatcagggt tattgtctca tgagcggata catatttgaa tgtatttaga    11160
aaaataaaca ataggggtt ccgcgcacat ttccccgaaa agtgccacct gacgtctaag    11220
aaaccattat tatcatgaca ttaacctata aaaataggcg tatcacgagg ccctttcgtc    11280
tcgcgcgttt cggtgatgac ggtgaaaacc tctgacacat gcagctcccg gagacggtca    11340
cagcttgtct gtaagcggat gccgggagca gacaagcccg tcagggcgcg tcagcgggtg    11400
ttggcgggtg tcgggctgg cttaactatg cggcatcaga gcagattgta ctgagagtgc    11460
accatatgcg gtgtgaaata ccgcacagat gcgtaaggag aaaataccgc atcaggcgcc    11520
attcgccatt caggctgcgc aactgttggg aagggcgatc ggtgcgggcc tcttcgctat    11580
tacgccagct ggcgaaaggg ggatgtgctg caaggcgatt aagttgggta acgccagggt    11640
tttcccagtc acgacgttgt aaaacgacgg ccagtgaatt c                       11681
```

<210> SEQ ID NO 18
<211> LENGTH: 11369
<212> TYPE: DNA
<213> ORGANISM: Artificial Sequence
<220> FEATURE:
<223> OTHER INFORMATION: Synthetic: TL20d-GbGM

<400> SEQUENCE: 18

```
ggccgcctcg gccaaacagc ccttgagttt accactccct atcagtgata gagaaaagtg     60
```

```
aaagtcgagt ttaccactcc ctatcagtga tagagaaaag tgaaagtcga gtttaccact    120
ccctatcagt gatagagaaa agtgaaagtc gagtttacca ctccctatca gtgatagaga    180
aaagtgaaag tcgagtttac cagtccctat cagtgataga gaaaagtgaa agtcgagttt    240
accactccct atcagtgata gagaaaagtg aaagtcgagt ttaccactcc ctatcagtga    300
tagagaaaag tgaaagtcga gctcgccatg ggaggcgtgg cctgggcggg actggggagt    360
ggcgagccct cagatcctgc atataagcag ctgcttttg cctgtactgg gtctctctgg    420
ttagaccaga tctgagcctg ggagctctct ggctaactag gaacccact gcttaagcct    480 caataaagct tgccttgagt gcttcaagta gtgtgtgccc gtctgttgtg tgactctggt    540
aactagagat ccctcagacc cttttagtca gtgtggaaaa tctctagcag tggcgcccga    600
acagggactt gaaagcgaaa gggaaaccag aggagctctc tcgacgcagg actcggcttg    660
ctgaagcgcg cacggcaaga ggcgaggggc ggcgactggt gagtacgcca aaattttga    720 ctagcggagg ctagaaggag agagatgggt gcgagagcgt cagtattaag cgggggagaa    780
ttagatcgcg atgggaaaaa attcggttaa ggccaggggg aaagaaaaaa tataaattaa    840
aacatatagt atgggcaagc agggagctag aacgattcgc agttaatact ggcctgttag    900
aaacatcaga aggctgtaga caaatactgg gacagctaca accatccctt cagacaggat    960
cagaagaact tagatcatta tataatacag tagcaaccct ctattgtgtg catcaaagga   1020
tagagataaa agacaccaag gaagctttag acaagataga ggaagagcaa acaaaagta    1080 agaaaaaagc acagcaagca gcaggatctt cagacctgga aattccctac aatccccaaa   1140
gtcaaggagt agtagaatct atgaataaag aattaaagaa aattatagga caggtaagag   1200
atcaggctga acatcttaag acagcagtac aaatggcagt attcatccac aattttaaaa   1260 gaaaggggg gattgggggg tacagtgcag gggaaagaat agtagacata atagcaacag   1320
acatacaaac taaagaatta caaaaacaaa ttacaaaaat tcaaaatttt cgggtttatt   1380
acagggacag cagaaatcca ctttggaaag gaccagcaaa gctcctctgg aaaggtgaag   1440
gggcagtagt aatacaagat aatagtgaca taaaagtagt gccaagaaga aaagcaaaga   1500
tcattaggga ttatgaaaaa cagatggcag gtgatgattg tgtggcaagt agacaggatg   1560
aggattagaa catggaaaag tttagtaaaa caccataagg aggagatatg agggacaatt   1620
ggagaagtga attatataaa tataaagtag taaaaattga accattagga gtagcaccca   1680
ccaaggcaaa gagaagagtg gtgcagagag aaaaaagagc agtgggaata ggagctttgt   1740
tccttgggtt cttgggagca gcaggaagca ctatgggcgc agcgtcaatg acgctgacgg   1800
tacaggccag acaattattg tctggtatag tgcagcagca gaacaatttg ctgagggcta   1860
ttgaggcgca acagcatctg ttgcaactca gtctggggg catcaagcag ctccaggcaa   1920
gaatcctggc tgtggaaaga tacctaaagg atcaacagct cctggggatt tggggttgct   1980
ctggaaaact catttgcacc actgctgtgc cttggaatgc tagttggagt aataaatctc   2040
tggaacagat ttggaatcac acgacctgga tggagtggga cagagaaatt aacaattaca   2100
caagcttaat acactcctta attgaagaat cgcaaaacca gcaagaaaag aatgaacaag   2160
aattattgga attagataaa tgggcaagtt tgtggaattg gtttaacata caaattggc    2220 tgtggtatat aaaattattc ataatgatag taggaggctt ggtaggttta agaatagttt   2280
ttgctgtact ttctatagtg aatagagtta ggcaggata ttcaccatta tcgtttcaga   2340
cccacctccc aaccccgagg ggaccgagct caagcttcga acgcgtgggg atcctctaga   2400
gtcgagctcg cgaggatcat caccggtgct agccggagcc agaagcacca taagggacat   2460
```

```
gataagggag ccagcagacc tctgatctct tcctgaatgc taatcttaaa catcctgagg    2520
aagaatggga cttccatttg gggtgggcct atgatagggt aataagacag tagtgaatat    2580
caagctacaa aaagcccoct ttcaaattct tctcagtcct aacttttcat actaagccca    2640
gtccttccaa agcagactgt gaaagagtga tagttccggg agactagcac cggctagccg    2700
agcttggaac actttccctt cattaagaac catccttgct actcagctgc aatcaatcca    2760
gcccccaggt cttcactgaa cctttttccca tctcttccaa aacatctgtt tctgagaagt    2820
cctgtcctat agaggtcttt cttcccaccg gatttctcct acaccattta ctcccacttg    2880
cagaactccc gtgtacaagt gtcttttactg ctttttatttg ctcaacaaaa tgcacatctc    2940
atataaaaat aaatgaggag catgcacaca ccacaaacac aaacaggcat gcagaaatac    3000
acatacacac ttccctcaat ataaaccctt tgtggctcat atatttaaaa agatgtaaaa    3060
aaaagagctg aagaaaatca tgtgtgatct ctcagcagaa tagatttatt atttgtattg    3120
cttgcagaat aaagcctatc cttgaaagct ctgaatcatg ggcaagaggc tcagtggtat    3180
ctggaggaca gggcactggc cactgcagtc accatcttct gccaggaagc ctgcacctca    3240
ggggtgaatt ctttgccaaa gtgaatggcc agcacggtga ccagcacgtt gcccaggagc    3300
tgtgggagga agataagagg tatgaacatg attagcaaaa gggcctagct tggactcaga    3360
ataatccagc cttatcccaa ccataaaata aaagcagaat ggtagctgga ttgtagctgc    3420
tattagcaat atgaaacctc ttacatcagt tacaatttat atgcagaaat atttatatgc    3480
agaaatattg ctattgcctt aacccagaaa ttatcactgt tattctttag aatggtgcaa    3540
agaggcatga tacattgtat cattattgcc ctgaaagaaa gagattaggg aaagtattag    3600
aaataagata aacaaaaaag tatattaaaa gaagaaagca tttttttaaaa ttacaaatgc    3660 aaaattaccc tgatttggtc aatatgtgta ccctgttact tctccccttc ctatgacatg    3720
aacttaacca tagaaaagaa ggggaaagaa aacatcaagg gtcccataga ctcaccttga    3780
agttctcagg atccacatgc agcttgtcac agtgcagttc actcagctgg gcaaaggtgc    3840
ccttgagatc atccaggtgc tttatggcat ctcccaagga agtcagcacc ttcttgccat    3900
gtgccttgac tttggggttg cccatgatgg cagaggcaga ggacaggttg ccaaagctgt    3960
caaagaacct ctgggtccat gggtagacaa ccaggagcct gtgagattga caagaacagt    4020
ttgacagtca gaaggtgcca caaatcctga gaagcaacct ggacttttgc caggcacagg    4080
gtccttcctt ccctcccttg tcctggtcac cagagcctac cttcccaggg tttctcctcc    4140
agcatcttcc acattcacct tgtcccacag gcttgtgata gtagccttgt cctcctctgt    4200
gaaatgaccc atggtgtctg tttgaggttg ctagtgaaca cagttgtgtc agaagcaaat    4260
gtaagcaata gatggctctg ccctgacttt tatgcccagc cctggctcct gcctccctg    4320 ctcctgggag tagattggcc aaccctaggg tgtggctcca cagggtgagg tctaagtgat    4380
gacagccgta cctgtccttg gctcttctgg cactggctta ggagttggac ttcaaaccct    4440
cagccctccc tctaagatat atctcttggc cccataccat cagtacaaat gctactaaa    4500 aacatcctcc tttgcaagtg tatttacgac ggtatcgatg tatgtgagca tgtgtcctct    4560
aacagcacag gccttttgcc acctagctgt ccaggggtgc cttaaaatgg caaacaaggt    4620
ttgtttctct ttcctgtttt catgccttcc tcttccatat ccttgtttca tattaataca    4680
tgtgtataga tcctaaaaat ctatacacat gtattaataa agcctgattc tgccgcttct    4740
aggtatagag gccacctgca agataaatat ttgattcaca ataactaatc attctatggc    4800
```

```
aattgataac aacaaatata tatatatata tatatatacg tatatgtgta tatatatata  4860
tatattcagg aaataatata ttctagaata tgtcacattc tgtctcaggc atccattttc  4920
tttatgatgc cgtttgaggt ggagttttag tcaggtggtc agcttctcct tttttttgcc  4980
atctgccctg taagcatcct gctgggacc  cagataggag tcatcactct aggctgagaa  5040
catctgggca cacaccctaa gcctcagcat gactcatcat gactcagcat tgctgtgctt  5100
gagccagaag gtttgcttag aaggttacac agaaccagaa ggcggggtg  gggcactgac  5160 cccgacaggg gcctggccag aactgctcat gcttggacta tgggaggtca ctaatggaga  5220
cacacagaaa tgtaacagga actaagggaa ttccggtgcc ctgcttagga gcttaatctt  5280
taatgaaagc taagctttca ttaaaaaaag tctaaccagc tgcattcgac tttgactgca  5340
gcagctggtt agaaggttct actggaggag ggtcccagcc cattgctaaa ttaacatcag  5400
gctctgagac tggcagtata tctctaacag tggttgatgc tatcttctgg aacttgcctg  5460
ctacattgag accactgacc catacatagg aagcccatag ctctgtcctg aactgttagg  5520
ccactggtcc agagagtgtg catctccttt gatcctcata ataaccctat gagatagaca  5580
caattattac tcttacttta tagatgatga tcctgaaaac ataggagtca aggcacttgc  5640
ccctagctgg gggtataggg gagcagtccc atgtagtagt agaatgaaaa atgctgctat  5700
gctgtgcctc ccccaccttt cccatgtctg ccctctactc atggtctatc tctcctggct  5760
cctgggagtc atggactcca cccagcacca ccaacctgac ctaaccacct atctgagcct  5820
gccagcctat aacccatctg ggccctgata gctggtggcc agccctgacc ccaccccacc  5880
ctccctggaa cctctgatag acacatctgg cacaccagct cgcaaagtca ccgtgagggt  5940
cttgtgtttg ctgagtcaaa attccttgaa atccaagtcc ttagagactc ctgctcccaa  6000
atttacagtc atagacttct tcatggctgt ctcctttatc cacagaatga ttcctttgct  6060
tcattgcccc atccatctga tcctcctcat cagtgcagca cagggcccat gagcagtagc  6120
tgcagagtct cacataggtc tggcactgcc tctgacatgt ccgaccttag gcaaatgctt  6180
gactcttctg agctcggatc ccttgagctc aggaggtcaa ggctgcagtg agacatgatc  6240
ttgccactgc actccagcct ggacagcaga gtgaaacctt gcctcacgaa acagaataca  6300
aaaacaaaca aacaaaaaac tgctccgcaa tgcgcttcct tgatgctcta ccacataggt  6360
ctgggtactt tgtacacatt atctcattgc tgttcataat tgttagatta attttgtaat  6420
attgatatta ttcctagaaa gctgaggcct caagatgata acttttattt tctggacttg  6480
taatagcttt ctcttgtatt caccatgttg taactttctt agagtagtaa caatataaag  6540
ttattgtgag tttttgcaaa cacagcaaac acaacgaccc atatagacat tgatgtgaaa  6600
ttgtctattg tcaatttatg ggaaaacaag tatgtacttt ttctactaag ccattgaaac  6660
aggaataaca gaacaagatt gaaagaatac attttccgaa attacttgag tattatacaa  6720
agacaagcac gtggacctgg gaggagggtt attgtccatg actggtgtgt ggagacaaat  6780
gcaggtttat aatagatggg atggcatcta gcgcaatgac tttgccatca cttttagaga  6840
gctcttgggg gccccagtac acaagagggg acgcagggta tatgtagaca tctcattctt  6900
tttcttagtg tgagaataag aatagccatg acctgagttt atagacaatg agcccttttc  6960
tctctcccac tcagcagcta tgagatggct tgccctgcct ctctactagg ctgactcact  7020
ccaaggccca gcaatgggca gggctctgtc agggctttga tagcactatc tgcagagcca  7080
gggccgagaa ggggtggact ccagagactc tccctcccat tcccgagcag ggtttgctta  7140
tttatgcatt taaatgatat atttatttta aaagaaataa caggagactg cccagccctg  7200
```

```
gctgtgacat ggaaactatg tagaatattt tgggttccat tttttttttcc ttctttcagt   7260 tagaggaaaa ggggctcact gcacatacac tagacagaaa gtcaggagct ttgaatccaa   7320
gcctgatcat ttccatgtca tactgagaaa gtccccaccc ttctctgagc ctcagtttct   7380 cttttttataa gtaggagtct ggagtaaatg atttccaatg gctctcattt caatacaaaa   7440
tttccgttta ttaaatgcat gagcttccgt tactccaaga ctgagaagga aattgaacct   7500
gagactcatt gactggcaag atgtccccag aggctctcat tcagcaataa aattctcacc   7560
ttcacccagg cccactagtg tcagatttgc atgcgttaac gcggccgcat cgatgccgta   7620 gtaccttttaa gaccaatgac ttacaaggca gctgtagatc ttagccactt tttaaaagaa   7680 aagggggggac tggaagggct aattcactcc caaagaagac aagatagatc tgcttttttgc   7740 ctgtactggg tctctctggt tagaccagat ctgagcctgg gagctctctg ctaactagg    7800 gaacccactg cttaagcctc aataaagctt cagctgctcg agctagcaga tctttttccc    7860
tctgccaaaa attatgggga catcatgaag ccccttgagc atctgacttc tggctaataa    7920
aggaaattta ttttcattgc aatagtgtgt tggaattttt tgtgtctctc actcggaagg    7980
acatatggga gggcaaatca tttaaaacat cagaatgagt atttggttta gagtttggca    8040
acatatgccc atatgctggc tgccatgaac aaaggttggc tataaagagg tcatcagtat    8100
atgaaacagc cccctgctgt ccattcctta ttccatagaa aagccttgac ttgaggttag    8160 attttttttta tatttttgttt tgtgttattt ttttctttaa catccctaaa attttcctta    8220 catgtttttac tagccagatt tttcctcctc tcctgactac tcccagtcat agctgtccct    8280
cttctcttat ggagatccct cgacctgcag cccaagcttg gcgtaatcat ggtcatagct    8340
gtttcctgtg tgaaattgtt atccgctcac aattccacac aacatacgag ccggaagcat    8400
aaagtgtaaa gcctggggtg cctaatgagt gagctaactc acattaattg cgttgcgctc    8460
actgcccgct ttccagtcgg gaaacctgtc gtgccagcgg atccgcatct caattagtca    8520
gcaaccatag tcccgcccct aactccgccc atcccgcccc taactccgcc cagttccgcc    8580
cattctccgc cccatggctg actaattttt tttatttatg cagaggccga ggccgcctcg    8640
gcctctgagc tattccagaa gtagtgagga ggcttttttg gaggcctagg cttttgcaaa    8700
aagctgtcga ctgcagaggc ctgcatgcaa gcttggcgta atcatggtca tagctgtttc    8760
ctgtgtgaaa ttgttatccg ctcacaattc cacacaacat acgagccgga agcataaagt    8820
gtaaagcctg ggtgcctaa tgagtgagct aactcacatt aattgcgttg cgctcactgc    8880
ccgctttcca gtcgggaaac ctgtcgtgcc agctgcatta atgaatcggc caacgcgcgg    8940
ggagaggcgg tttgcgtatt gggcgctctt ccgcttcctc gctcactgac tcgctgcgct    9000
cggtcgttcg gctgcggcga gcggtatcag ctcactcaaa ggcggtaata cggttatcca    9060
cagaatcagg ggataacgca ggaaagaaca tgtgagcaaa aggccagcaa aaggccagga    9120
accgtaaaaa ggccgcgttg ctggcgtttt tccataggct ccgcccccct gacgagcatc    9180
acaaaaatcg acgctcaagt cagaggtggc gaaacccgac aggactataa agataccagg    9240
cgtttccccc tggaagctcc ctcgtgcgct ctcctgttcc gaccctgccg cttaccggat    9300
acctgtccgc ctttctccct tcgggaagcg tggcgctttc tcatagctca cgctgtaggt    9360
atctcagttc ggtgtaggtc gttcgctcca agctgggctg tgtgcacgaa ccccccgttc    9420
agcccgaccg ctgcgcctta tccggtaact atcgtcttga gtccaacccg gtaagacacg    9480
acttatcgcc actggcagca gccactggta acaggattag cagagcgagg tatgtaggcg    9540
```

| | |
|---|---|
| gtgctacaga gttcttgaag tggtggccta actacggcta cactagaaga acagtatttg | 9600 |
| gtatctgcgc tctgctgaag ccagttacct tcggaaaaag agttggtagc tcttgatccg | 9660 |
| gcaaacaaac caccgctggt agcggtggtt tttttgtttg caagcagcag attacgcgca | 9720 |
| gaaaaaagg atctcaagaa gatcctttga tcttttctac ggggtctgac gctcagtgga | 9780 |
| acgaaaactc acgttaaggg attttggtca tgagattatc aaaaaggatc ttcacctaga | 9840 |
| tccttttaaa ttaaaaatga agttttaaat caatctaaag tatatatgag taaacttggt | 9900 |
| ctgacagtta ccaatgctta atcagtgagg cacctatctc agcgatctgt ctatttcgtt | 9960 |
| catccatagt tgcctgactc cccgtcgtgt agataactac gatacgggag ggcttaccat | 10020 |
| ctggccccag tgctgcaatg ataccgcgag acccacgctc accggctcca gatttatcag | 10080 |
| caataaacca gccagccgga agggccgagc gcagaagtgg tcctgcaact ttatccgcct | 10140 |
| ccatccagtc tattaattgt tgccgggaag ctagagtaag tagttcgcca gttaatagtt | 10200 |
| tgcgcaacgt tgttgccatt gctacaggca tcgtggtgtc acgctcgtcg tttggtatgg | 10260 |
| cttcattcag ctccggttcc caacgatcaa ggcgagttac atgatccccc atgttgtgca | 10320 |
| aaaaagcggt tagctccttc ggtcctccga tcgttgtcag aagtaagttg gccgcagtgt | 10380 |
| tatcactcat ggttatggca gcactgcata attctcttac tgtcatgcca tccgtaagat | 10440 |
| gcttttctgt gactggtgag tactcaacca agtcattctg agaatagtgt atgcggcgac | 10500 |
| cgagttgctc ttgcccggcg tcaatacggg ataataccgc gccacatagc agaactttaa | 10560 |
| aagtgctcat cattggaaaa cgttcttcgg ggcgaaaact ctcaaggatc ttaccgctgt | 10620 |
| tgagatccag ttcgatgtaa cccactcgtg cacccaactg atcttcagca tcttttactt | 10680 |
| tcaccagcgt ttctgggtga gcaaaaacag gaaggcaaaa tgccgcaaaa aagggaataa | 10740 |
| gggcgacacg gaaatgttga atactcatac tcttcctttt tcaatattat tgaagcattt | 10800 |
| atcagggtta ttgtctcatg agcggataca tatttgaatg tatttagaaa aataaacaaa | 10860 |
| taggggttcc gcgcacattt ccccgaaaag tgccacctga cgtctaagaa accattatta | 10920 |
| tcatgacatt aacctataaa aataggcgta tcacgaggcc ctttcgtctc gcgcgtttcg | 10980 |
| gtgatgacgg tgaaaacctc tgacacatgc agctcccgga cggtcaca gcttgtctgt | 11040 |
| aagcggatgc cgggagcaga caagcccgtc agggcgcgtc agcgggtgtt ggcgggtgtc | 11100 |
| ggggctggct taactatgcg gcatcagagc agattgtact gagagtgcac catatgcggt | 11160 |
| gtgaaatacc gcacagatgc gtaaggagaa aataccgcat caggcgccat cgccattca | 11220 |
| ggctgcgcaa ctgttgggaa gggcgatcgg tgcgggcctc ttcgctatta cgccagctgg | 11280 |
| cgaaaggggg atgtgctgca aggcgattaa gttgggtaac gccagggttt tcccagtcac | 11340 |
| gacgttgtaa aacgacggcc agtgaattc | 11369 |

<210> SEQ ID NO 19
<211> LENGTH: 11671
<212> TYPE: DNA
<213> ORGANISM: Artificial Sequence
<220> FEATURE:
<223> OTHER INFORMATION: Synthetic: TL20d-rGbGM-7SKM1/sh734

<400> SEQUENCE: 19

| | |
|---|---|
| ggccgcctcg gccaaacagc ccttgagttt accactccct atcagtgata gagaaaagtg | 60 |
| aaagtcgagt ttaccactcc ctatcagtga tagagaaaag tgaaagtcga gtttaccact | 120 |
| ccctatcagt gatagagaaa agtgaaagtc gagtttacca ctccctatca gtgatagaga | 180 |
| aaagtgaaag tcgagtttac cagtccctat cagtgataga gaaaagtgaa agtcgagttt | 240 |

```
accactccct atcagtgata gagaaaagtg aaagtcgagt ttaccactcc ctatcagtga      300
tagagaaaag tgaaagtcga gctcgccatg ggaggcgtgg cctgggcggg actggggagt      360
ggcgagccct cagatcctgc atataagcag ctgcttttg cctgtactgg gtctctctgg       420
ttagaccaga tctgagcctg ggagctctct ggctaactag ggaacccact gcttaagcct      480
caataaagct tgccttgagt gcttcaagta gtgtgtgccc gtctgttgtg tgactctggt      540
aactagagat ccctcagacc cttttagtca gtgtggaaaa tctctagcag tggcgcccga      600
acagggactt gaaagcgaaa gggaaaccag aggagctctc tcgacgcagg actcggcttg      660
ctgaagcgcg cacggcaaga ggcgaggggc ggcgactggt gagtacgcca aaaattttga      720
ctagcggagg ctagaaggag agagatgggt gcgagagcgt cagtattaag cggggggagaa     780 ttagatcgcg atgggaaaaa attcggttaa ggccaggggg aaagaaaaaa tataaattaa      840
aacatatagt atgggcaagc agggagctag aacgattcgc agttaatact ggcctgttag      900
aaacatcaga aggctgtaga caaatactgg gacagctaca accatccctt cagacaggat      960
cagaagaact tagatcatta tataatacag tagcaaccct ctattgtgtg catcaaagga     1020
tagagataaa agacaccaag gaagctttag acaagataga ggaagagcaa acaaaagta     1080 agaaaaagc acagcaagca gcaggatctt cagacctgga aattccctac aatccccaaa     1140
gtcaaggagt agtagaatct atgaataaag aattaaagaa aattatagga caggtaagag     1200
atcaggctga acatcttaag acagcagtac aaatggcagt attcatccac aattttaaaa     1260 gaaaagggg gattgggggg tacagtgcag gggaaagaat agtagacata atagcaacag       1320
acatacaaac taaagaatta caaaaacaaa ttacaaaaat tcaaaatttt cgggtttatt      1380
acagggacag cagaaatcca ctttggaaag gaccagcaaa gctcctctgg aaaggtgaag      1440
gggcagtagt aatacaagat aatagtgaca taaaagtagt gccaagaaga aaagcaaaga     1500
tcattaggga ttatggaaaa cagatggcag gtgatgattg tgtggcaagt agacaggatg      1560
aggattagaa catggaaaag tttagtaaaa caccataagg aggagatatg agggacaatt      1620
ggagaagtga attatataaa tataaagtag taaaaattga accattagga gtagcaccca      1680
ccaaggcaaa gagaagagtg gtgcagagag aaaaaagagc agtgggaata ggagctttgt     1740
tccttgggtt cttgggagca gcaggaagca ctatgggcgc agcgtcaatg acgctgacgg      1800
tacaggccag acaattattg tctggtatag tgcagcagca gaacaatttg ctgagggcta      1860
ttgaggcgca acagcatctg ttgcaactca gtctggggg catcaagcag ctccaggcaa      1920
gaatcctggc tgtggaaaga tacctaaagg atcaacagct cctggggatt tggggttgct      1980
ctggaaaact catttgcacc actgctgtgc cttggaatgc tagttggagt aataaatctc      2040
tggaacagat ttggaatcac acgacctgga tggagtggga cagagaaatt aacaattaca      2100
caagcttaat acactcctta attgaagaat cgcaaaacca gcaagaaaag aatgaacaag      2160
aattattgga attagataaa tgggcaagtt tgtggaattg gtttaacata acaaattggc      2220
tgtggtatat aaaattattc ataatgatag taggaggctt ggtaggttta agaatagttt      2280
ttgctgtact ttctatagtg aatagagtta ggcaggata ttcaccatta tcgtttcaga      2340
cccacctccc aaccccgagg ggaccgagct caagcttcga acgcgtgggg atcctctaga      2400
gtcgagctcg cgaggatcat caccggtgct agccggagcc agaagcacca taagggacat      2460
gataagggag ccagcagacc tctgatctct tcctgaatgc taatcttaaa catcctgagg      2520
aagaatggga cttccatttg gggtgggcct atgatagggt aataagacag tagtgaatat      2580
```

```
caagctacaa aaagccccct ttcaaattct tctcagtcct aacttttcat actaagccca    2640
gtccttccaa agcagactgt gaaagagtga tagttccggg agactagcac cggctagccg    2700
agcttggaac actttccctt cattaagaac catccttgct actcagctgc aatcaatcca    2760
gcccccaggt cttcactgaa cctttttccca tctcttccaa aacatctgtt tctgagaagt    2820
cctgtcctat agaggtcttt cttcccaccg gatttctcct acaccattta ctcccacttg    2880
cagaactccc gtgtacaagt gtctttactg ctttttatttg ctcaacaaaa tgcacatctc    2940
atataaaaat aaatgaggag catgcacaca ccacaaacac aaacaggcat gcagaaatac    3000
acatacacac ttccctcaat ataaacccttt tgtggctcat atatttaaaa agatgtaaaa    3060
aaagagctg aagaaaatca tgtgtgatct ctcagcagaa tagatttatt atttgtattg    3120
cttgcagaat aaagcctatc cttgaaagct ctgaatcatg ggcaagaggc tcagtggtat    3180
ctggaggaca gggcactggc cactgcagtc accatcttct gccaggaagc ctgcacctca    3240
ggggtgaatt cttttgccaaa gtgaatggcc agcacggtga ccagcacgtt gcccaggagc    3300
tgtgggagga agataagagg tatgaacatg attagcaaaa gggcctagct tggactcaga    3360
ataatccagc cttatcccaa ccataaaata aaagcagaat ggtagctgga ttgtagctgc    3420
tattagcaat atgaaacctc ttcatcagt tacaatttat atgcagaaat atttatatgc    3480
agaaatattg ctattgcctt aacccagaaa ttatcactgt tattctttag aatggtgcaa    3540
agaggcatga tacattgtat cattattgcc ctgaaagaaa gagattaggg aaagtattag    3600
aaataagata aacaaaaaag tatattaaaa gaagaaagca ttttttaaaa ttacaaatgc    3660
aaaattaccc tgatttggtc aatatgtgta ccctgttact tctccccttc ctatgacatg    3720
aacttaacca tagaaaagaa ggggaaagaa aacatcaagg gtcccataga ctcaccttga    3780
agttctcagg atccacatgc agcttgtcac agtgcagttc actcagctgg gcaaaggtgc    3840
ccttgagatc atccaggtgc tttatggcat ctcccaagga agtcagcacc ttcttgccat    3900
gtgccttgac tttggggttg cccatgatgg cagaggcaga ggacaggttg ccaaagctgt    3960
caaagaacct ctgggtccat gggtagacaa ccaggagcct gtgagattga caagaacagt    4020
ttgacagtca gaaggtgcca caaatcctga gaagcaacct ggacttttgc caggcacagg    4080
gtccttcctt ccctcccttg tcctggtcac cagagcctac cttcccaggg tttctcctcc    4140
agcatcttcc acattcacct tgtcccacag gcttgtgata gtagccttgt cctcctctgt    4200
gaaatgaccc atggtgtctg tttgaggttg ctagtgaaca cagttgtgtc agaagcaaat    4260
gtaagcaata gatggctctg ccctgacttt tatgcccagc cctggctcct gccctccctg    4320
ctcctgggag tagattggcc aaccctaggg tgtggctcca cagggtgagg tctaagtgat    4380
gacagccgta cctgtccttg gctcttctgg cactggctta ggagttggac ttcaaaccct    4440
cagccctccc tctaagatat atctcttggc cccataccat cagtacaaat tgctactaaa    4500
aacatcctcc tttgcaagtg tatttacgac ggtatcgatg tatgtgagca tgtgtcctct    4560
aacagcacag gccttttgcc acctagctgt ccagggtgc cttaaaatgg caaacaaggt    4620
ttgttttctt ttcctgtttt catgccttcc tcttccatat ccttgtttca tattaataca    4680
tgtgtataga tcctaaaaat ctatacacat gtattaataa agcctgattc tgccgcttct    4740
aggtatagag gccacctgca agataaatat ttgattcaca ataactaatc attctatggc    4800
aattgataac aacaaatata tatatatata tatatacg tatatgtgta tatatatata    4860
tatattcagg aaataatata ttctagaata tgtcacattc tgtctcaggc atccatttc    4920
tttatgatgc cgtttgaggt ggagtttag tcaggtggtc agcttctcct ttttttttgcc    4980
```

| | |
|---|---|
| atctgccctg taagcatcct gctggggacc cagataggag tcatcactct aggctgagaa | 5040 |
| catctgggca cacaccctaa gcctcagcat gactcatcat gactcagcat tgctgtgctt | 5100 |
| gagccagaag gtttgcttag aaggttacac agaaccagaa ggcggggtg gggcactgac | 5160 |
| cccgacaggg gcctggccag aactgctcat gcttggacta tgggaggtca ctaatgagaa | 5220 |
| cacacagaaa tgtaacagga actaagggaa ttccggtgcc ctgcttagga gcttaatctt | 5280 |
| taatgaaagc taagctttca ttaaaaaaag tctaaccagc tgcattcgac tttgactgca | 5340 |
| gcagctggtt agaaggttct actggaggag ggtcccagcc cattgctaaa ttaacatcag | 5400 |
| gctctgagac tggcagtata tctctaacag tggttgatgc tatcttctgg aacttgcctg | 5460 |
| ctacattgag accactgacc catacatagg aagcccatag ctctgtcctg aactgttagg | 5520 |
| ccactggtcc agagagtgtg catctccttt gatcctcata ataacccctat gagatagaca | 5580 |
| caattattac tcttacttta tagatgatga tcctgaaaac ataggagtca aggcacttgc | 5640 |
| ccctagctgg gggtataggg gagcagtccc atgtagtagt agaatgaaaa atgctgctat | 5700 |
| gctgtgcctc ccccaccttt cccatgtctg ccctctactc atggtctatc tctcctggct | 5760 |
| cctgggagtc atggactcca cccagcacca ccaacctgac ctaaccaccct atctgagcct | 5820 |
| gccagcctat aacccatctg ggccctgata gctggtggcc agccctgacc ccaccccacc | 5880 |
| ctccctggaa cctctgatag acacatctgg cacaccagct cgcaaagtca ccgtgagggt | 5940 |
| cttgtgtttg ctgagtcaaa attccttgaa atccaagtcc ttagagactc ctgctcccaa | 6000 |
| atttacagtc atagacttct tcatggctgt ctcctttatc cacagaatga ttcctttgct | 6060 |
| tcattgcccc atccatctga tcctcctcat cagtgcagca cagggcccat gagcagtagc | 6120 |
| tgcagagtct cacataggtc tggcactgcc tctgacatgt ccgaccttag gcaaatgctt | 6180 |
| gactcttctg agctcggatc ccttgagctc aggaggtcaa ggctgcagtg agacatgatc | 6240 |
| ttgccactgc actccagcct ggacagcaga gtgaaacctt gcctcacgaa acagaataca | 6300 |
| aaaacaaaca aacaaaaaac tgctccgcaa tgcgcttcct tgatgctcta ccacataggt | 6360 |
| ctgggtactt tgtacacatt atctcattgc tgttcataat tgttagatta attttgtaat | 6420 |
| attgatatta ttcctagaaa gctgaggcct caagatgata acttttattt tctggacttg | 6480 |
| taatagcttt ctcttgtatt caccatgttg taactttctt agagtagtaa caatataaag | 6540 |
| ttattgtgag tttttgcaaa cacagcaaac acaacgaccc atatagacat tgatgtgaaa | 6600 |
| ttgtctattg tcaatttatg ggaaaacaag tatgtacttt ttctactaag ccattgaaac | 6660 |
| aggaataaca gaacaagatt gaaagaatac attttccgaa attacttgag tattatacaa | 6720 |
| agacaagcac gtggacctgg gaggaggggtt attgtccatg actggtgtgt ggagacaaat | 6780 |
| gcaggtttat aatagatggg atggcatcta gcgcaatgac tttgccatca cttttagaga | 6840 |
| gctcttgggg gccccagtac acaagagggg acgcagggta tatgtagaca tctcattctt | 6900 |
| tttcttagtg tgagaataag aatagccatg acctgagttt atagacaatg agcccttttc | 6960 |
| tctctcccac tcagcagcta tgagatggct tgccctgcct ctctactagg ctgactcact | 7020 |
| ccaaggccca gcaatgggca gggctctgtc agggctttga tagcactatc tgcagagcca | 7080 |
| gggccgagaa ggggtggact ccagagactc tccctcccat tcccgagcag ggtttgctta | 7140 |
| tttatgcatt taaatgatat atttatttta aaagaaataa caggagactg cccagccctg | 7200 |
| gctgtgacat ggaaactatg tagaatattt tgggttccat tttttttcc ttctttcagt | 7260 |
| tagaggaaaa ggggctcact gcacatacac tagacagaaa gtcaggagct ttgaatccaa | 7320 |

```
gcctgatcat ttccatgtca tactgagaaa gtccccaccc ttctctgagc ctcagtttct    7380 cttttttataa gtaggagtct ggagtaaatg atttccaatg gctctcattt caatacaaaa   7440
tttccgttta ttaaatgcat gagcttccgt tactccaaga ctgagaagga aattgaacct    7500
gagactcatt gactggcaag atgtcccag aggctctcat tcagcaataa aattctcacc     7560
ttcacccagg cccactagtg tcagatttgc atgcgttcgc gttcgacgtg cagtcgggct    7620
actgccccac ccatagtacc ggcattctgg atagtgtcaa acagccgga aatcaagtcc     7680 gtttatctca aactttagca ttttgggaat aaatgatatt tgctatgctg gttaaattag   7740 atttagtta aatttcctgc tgaagctcta gtacgataag taacttgacc taagtgtaaa    7800
gttgagattt ccttcaggtt tatatagctt gtgcgccgcc tgggtacctc aggatatgcc   7860
cttgactatt tgtccgacat agtcaagggc atatcctttt ttgcggccgc atcgatgccg   7920
tagtaccttt aagaccaatg acttacaagg cagctgtaga tcttagccac tttttaaaag   7980 aaaaggggg actggaaggg ctaattcact cccaaagaag acaagataga tctgcttttt    8040
gcctgtactg ggtctctctg gttagaccag atctgagcct gggagctctc tggctaacta   8100
gggaacccac tgcttaagcc tcaataaagc ttcagctgct cgagctagca gatcttttc    8160 cctctgccaa aaattatggg gacatcatga agccccttga gcatctgact tctggctaat   8220
aaaggaaatt tattttcatt gcaatagtgt gttggaattt tttgtgtctc tcactcggaa   8280
ggacatatgg gagggcaaat catttaaaac atcagaatga gtatttggtt tagagtttgg   8340
caacatatgc ccatatgctg gctgccatga caaaggttg gctataaaga ggtcatcagt    8400
atatgaaaca gccccctgct gtccattcct tattccatag aaaagccttg acttgaggtt   8460 agatttttt tatattttgt tttgtgttat ttttttcttt aacatcccta aaattttcct    8520
tacatgtttt actagccaga ttttttcctcc tctcctgact actcccagtc atagctgtcc   8580
ctcttctctt atggagatcc ctcgacctgc agcccaagct tggcgtaatc atggtcatag   8640
ctgtttcctg tgtgaaattg ttatccgctc acaattccac acaacatacg agccggaagc   8700
ataaagtgta aagcctgggg tgcctaatga gtgagctaac tcacattaat tgcgttgcgc   8760
tcactgcccg ctttccagtc gggaaacctg tcgtgccagc ggatccgcat ctcaattagt   8820
cagcaaccat agtcccgccc ctaactccgc ccatcccgcc cctaactccg cccagttccg   8880
cccattctcc gccccatggc tgactaattt tttttattta gcagaggcc gaggccgcct    8940 cggcctctga gctattccag aagtagtgag gaggcttttt tggaggccta ggcttttgca   9000
aaaagctgtc gactgcagag gcctgcatgc aagcttggcg taatcatggt catagctgtt   9060
tcctgtgtga aattgttatc cgctcacaat tccacacaac atacgagccg gaagcataaa   9120
gtgtaaagcc tggggtgcct aatgagtgag ctaactcaca ttaattgcgt tgcgctcact   9180
gcccgctttc cagtcgggaa acctgtcgtg ccagctgcat taatgaatcg gccaacgcgc   9240
ggggagaggc ggtttgcgta ttgggcgctc ttccgcttcc tcgctcactg actcgctgcg   9300
ctcggtcgtt cggctgcggc gagcggtatc agctcactca aaggcggtaa tacggttatc   9360
cacagaatca ggggataacg caggaaagaa catgtgagca aaaggccagc aaaaggccag   9420
gaaccgtaaa aaggccgcgt tgctggcgtt tttccatagg ctccgccccc ctgacgagca   9480
tcacaaaaat cgacgctcaa gtcagaggtg gcgaaacccg acaggactat aaagatacca   9540
ggcgtttccc cctggaagct ccctcgtgcg ctctcctgtt ccgaccctgc cgcttaccgg   9600
atacctgtcc gcctttctcc cttcgggaag cgtggcgctt tctcatagct cacgctgtag   9660
gtatctcagt tcggtgtagg tcgttcgctc caagctgggc tgtgtgcacg aaccccccgt   9720
```

```
tcagcccgac cgctgcgcct tatccggtaa ctatcgtctt gagtccaacc cggtaagaca    9780
cgacttatcg ccactggcag cagccactgg taacaggatt agcagagcga ggtatgtagg    9840
cggtgctaca gagttcttga agtggtggcc taactacggc tacactagaa gaacagtatt    9900
tggtatctgc gctctgctga agccagttac cttcggaaaa agagttggta gctcttgatc    9960
cggcaaacaa accaccgctg gtagcggtgg tttttttgtt tgcaagcagc agattacgcg   10020
cagaaaaaaa ggatctcaag aagatccttt gatcttttct acggggtctg acgctcagtg   10080
gaacgaaaac tcacgttaag ggattttggt catgagatta tcaaaaagga tcttcaccta   10140
gatccttttt aattaaaaat gaagttttaa atcaatctaa agtatatatg agtaaacttg   10200
gtctgacagt taccaatgct taatcagtga ggcacctatc tcagcgatct gtctatttcg   10260
ttcatccata gttgcctgac tccccgtcgt gtagataact acgatacggg agggcttacc   10320
atctggcccc agtgctgcaa tgataccgcg agacccacgc tcaccggctc cagatttatc   10380
agcaataaac cagccagccg gaagggccga gcgcagaagt ggtcctgcaa ctttatccgc   10440
ctccatccag tctattaatt gttgccggga agctagagta agtagttcgc cagttaatag   10500
tttgcgcaac gttgttgcca ttgctacagg catcgtggtg tcacgctcgt cgtttggtat   10560
ggcttcattc agctccggtt cccaacgatc aaggcgagtt acatgatccc ccatgttgtg   10620
caaaaaagcg gttagctcct tcggtcctcc gatcgttgtc agaagtaagt tggccgcagt   10680
gttatcactc atggttatgg cagcactgca taattctctt actgtcatgc catccgtaag   10740
atgcttttct gtgactggtg agtactcaac caagtcattc tgagaatagt gtatgcggcg   10800
accgagttgc tcttgcccgg cgtcaatacg ggataatacc gcgccacata gcagaacttt   10860
aaaagtgctc atcattggaa aacgttcttc ggggcgaaaa ctctcaagga tcttaccgct   10920
gttgagatcc agttcgatgt aacccactcg tgcacccaac tgatcttcag catcttttac   10980
tttcaccagc gtttctgggt gagcaaaaac aggaaggcaa aatgccgcaa aaaagggaat   11040
aagggcgaca cggaaatgtt gaatactcat actcttcctt tttcaatatt attgaagcat   11100
ttatcagggt tattgtctca tgagcggata catatttgaa tgtatttaga aaaataaaca   11160
aataggggtt ccgcgcacat ttccccgaaa agtgccacct gacgtctaag aaaccattat   11220
tatcatgaca ttaacctata aaaataggcg tatcacgagg ccctttcgtc tcgcgcgttt   11280
cggtgatgac ggtgaaaacc tctgacacat gcagctcccg gagacggtca gcttgtct   11340
gtaagcggat gccgggagca gacaagcccg tcagggcgcg tcagcgggtg ttggcgggtg   11400
tcggggctgg cttaactatg cggcatcaga gcagattgta ctgagagtgc accatatgcg   11460
gtgtgaaata ccgcacagat gcgtaaggag aaaataccgc atcaggcgcc attcgccatt   11520
caggctgcgc aactgttggg aagggcgatc ggtgcgggcc tcttcgctat tacgccagct   11580
ggcgaaaggg ggatgtgctg caaggcgatt aagttgggta acgccagggt tttcccagtc   11640
acgacgttgt aaaacgacgg ccagtgaatt c                                  11671
```

<210> SEQ ID NO 20
<211> LENGTH: 11674
<212> TYPE: DNA
<213> ORGANISM: Artificial Sequence
<220> FEATURE:
<223> OTHER INFORMATION: Synthetic: TL20d-rGbGM-7SK/sh734

<400> SEQUENCE: 20

```
ggccgcctcg gccaaacagc ccttgagttt accactccct atcagtgata gagaaaagtg    60
```

```
aaagtcgagt ttaccactcc ctatcagtga tagagaaaag tgaaagtcga gtttaccact     120
ccctatcagt gatagagaaa agtgaaagtc gagtttacca ctccctatca gtgatagaga     180
aaagtgaaag tcgagtttac cagtccctat cagtgataga gaaaagtgaa agtcgagttt     240
accactccct atcagtgata gagaaaagtg aaagtcgagt ttaccactcc ctatcagtga     300
tagagaaaag tgaaagtcga gctcgccatg ggaggcgtgg cctgggcggg actggggagt     360
ggcgagccct cagatcctgc atataagcag ctgcttttg cctgtactgg gtctctctgg      420
ttagaccaga tctgagcctg ggagctctct ggctaactag gaacccact gcttaagcct      480 caataaagct tgccttgagt gcttcaagta gtgtgtgccc gtctgttgtg tgactctggt     540
aactagagat ccctcagacc cttttagtca gtgtggaaaa tctctagcag tggcgcccga     600
acagggactt gaaagcgaaa gggaaaccag aggagctctc tcgacgcagg actcggcttg     660
ctgaagcgcg cacggcaaga ggcgaggggc ggcgactggt gagtacgcca aaattttga     720 ctagcgagg ctagaaggag agagatgggt gcgagagcgt cagtattaag cgggggagaa      780
ttagatcgcg atgggaaaaa attcggttaa ggccaggggg aaagaaaaaa tataaattaa     840
aacatatagt atgggcaagc agggagctag aacgattcgc agttaatact ggcctgttag     900
aaacatcaga aggctgtaga caaatactgg gacagctaca accatccctt cagacaggat     960
cagaagaact tagatcatta tataatacag tagcaaccct ctattgtgtg catcaaagga    1020
tagagataaa agacaccaag gaagctttag acaagataga ggaagagcaa aacaaaagta    1080
agaaaaaagc acagcaagca gcaggatctt cagacctgga aattccctac aatccccaaa    1140
gtcaaggagt agtagaatct atgaataaag aattaaagaa aattatagga caggtaagag    1200
atcaggctga acatcttaag acagcagtac aaatggcagt attcatccac aattttaaaa    1260 gaaaggggg gattgggggg tacagtgcag gggaagaat agtagacata atagcaacag       1320
acatacaaac taaagaatta caaaaacaaa ttacaaaaat tcaaaatttt cgggtttatt    1380
acagggacag cagaaatcca ctttggaaag gaccagcaaa gctcctctgg aaaggtgaag    1440
gggcagtagt aatacaagat aatagtgaca taaaagtagt gccaagaaga aaagcaaaga    1500
tcattaggga ttatggaaaa cagatggcag gtgatgattg tgtggcaagt agacaggatg    1560
aggattagaa catggaaaag tttagtaaaa caccataagg aggagatatg agggacaatt    1620
ggagaagtga attatataaa tataaagtag taaaaattga accattagga gtagcaccca    1680
ccaaggcaaa gagaagagtg gtgcagagag aaaaaagagc agtgggaata ggagctttgt    1740
tccttgggtt cttgggagca gcaggaagca ctatgggcgc agcgtcaatg acgctgacgg    1800
tacaggccag acaattattg tctggtatag tgcagcagca gaacaatttg ctgagggcta    1860
ttgaggcgca acagcatctg ttgcaactca gtctggggg catcaagcag ctccaggcaa     1920
gaatcctggc tgtggaaaga tacctaaagg atcaacagct cctggggatt tggggttgct    1980
ctggaaaact catttgcacc actgctgtgc cttggaatgc tagttggagt aataaatctc    2040
tggaacagat ttggaatcac acgacctgga tggagtggga cagagaaatt aacaattaca    2100
caagcttaat acactcctta attgaagaat cgcaaaacca gcaagaaaag aatgaacaag    2160
aattattgga attagataaa tgggcaagtt tgtggaattg gtttaacata caaattggc     2220 tgtggtatat aaaattattc ataatgatag taggaggctt ggtaggttta agaatagttt    2280
ttgctgtact ttctatagtg aatagagtta ggcaggata ttcaccatta tcgtttcaga     2340
cccacctccc aaccccgagg ggaccgagct caagcttcga acgcgtgggg atcctctaga    2400
gtcgagctcg cgaggatcat caccggtgct agccggagcc agaagcacca taaggacat     2460
```

```
gataagggag ccagcagacc tctgatctct tcctgaatgc taatcttaaa catcctgagg   2520
aagaatggga cttccatttg gggtgggcct atgatagggt aataagacag tagtgaatat   2580
caagctacaa aaagccccct ttcaaattct tctcagtcct aacttttcat actaagccca   2640
gtccttccaa agcagactgt gaaagagtga tagttccggg agactagcac cggctagccg   2700
agcttggaac actttccctt cattaagaac catccttgct actcagctgc aatcaatcca   2760
gcccccaggt cttcactgaa ccttttccca tctcttccaa aacatctgtt tctgagaagt   2820
cctgtcctat agaggtcttt cttcccaccg gatttctcct acaccattta ctcccacttg   2880
cagaactccc gtgtacaagt gtctttactg cttttatttg ctcaacaaaa tgcacatctc   2940
atataaaaat aaatgaggag catgcacaca ccacaaacac aaacaggcat gcagaaatac   3000
acatacacac ttccctcaat ataaaccctt tgtggctcat atatttaaaa agatgtaaaa   3060 aaagagctg aagaaaatca tgtgtgatct ctcagcagaa tagatttatt atttgtattg    3120
cttgcagaat aaagcctatc cttgaaagct ctgaatcatg gcaagaggc tcagtggtat    3180 ctggaggaca gggcactggc cactgcagtc accatcttct gccaggaagc ctgcacctca   3240
ggggtgaatt ctttgccaaa gtgaatggcc agcacgtga ccagcacgtt gcccaggagc    3300
tgtgggagga agataagagg tatgaacatg attagcaaaa gggcctagct tggactcaga   3360
ataatccagc cttatcccaa ccataaaata aaagcagaat ggtagctgga ttgtagctgc   3420
tattagcaat atgaaacctc ttacatcagt tacaatttat atgcagaaat atttatatgc   3480
agaaatattg ctattgcctt aacccagaaa ttatcactgt tattctttag aatggtgcaa   3540
agaggcatga tacattgtat cattattgcc ctgaaagaaa gagattaggg aaagtattag   3600
aaataagata aacaaaaaag tatattaaaa gaagaaagca tttttaaaa ttacaaatgc    3660 aaaattaccc tgatttggtc aatatgtgta ccctgttact tctcccttc ctatgacatg    3720 aacttaacca tagaaaagaa ggggaaagaa aacatcaagg gtcccataga ctcaccttga   3780
agttctcagg atccacatgc agcttgtcac agtgcagttc actcagctgg gcaaaggtgc   3840
ccttgagatc atccaggtgc tttatggcat ctcccaagga agtcagcacc ttcttgccat   3900
gtgccttgac tttggggttg cccatgatgg cagaggcaga ggacaggttg ccaaagctgt   3960
caaagaacct ctgggtccat gggtagacaa ccaggagcct gtgagattga caagaacagt   4020
ttgacagtca gaaggtgcca caaatcctga gaagcaacct ggacttttgc caggcacagg   4080
gtccttcctt ccctcccttg tcctggtcac cagagcctac cttcccaggg tttctcctcc   4140
agcatcttcc acattcacct tgtcccacag gcttgtgata gtagccttgt cctcctctgt   4200
gaaatgaccc atggtgtctg tttgaggttg ctagtgaaca cagttgtgtc agaagcaaat   4260
gtaagcaata gatggctctg ccctgacttt tatgcccagc cctggctcct gcctccctg    4320 ctcctgggag tagattggcc aaccctaggg tgtggctcca cagggtgagg tctaagtgat   4380
gacagccgta cctgtccttg gctcttctgg cactggctta ggagttggac ttcaaaccct   4440
cagccctccc tctaagatat atctcttggc cccataccat cagtacaaat gctactaaa    4500 aacatcctcc tttgcaagtg tatttacgac ggtatcgatg tatgtgagca tgtgtcctct   4560
aacagcacag gccttttgcc acctagctgt ccagggtgc cttaaaatgg caaacaaggt    4620
ttgttttctt ttcctgtttt catgccttcc tcttccatat ccttgtttca tattaataca   4680
tgtgtataga tcctaaaaat ctatacacat gtattaataa agcctgattc tgccgcttct   4740
aggtatagag gccacctgca agataaatat ttgattcaca ataactaatc attctatggc   4800
```

```
aattgataac aacaaatata tatatatata tatatatacg tatatgtgta tatatatata    4860
tatattcagg aaataatata ttctagaata tgtcacattc tgtctcaggc atccattttc    4920
tttatgatgc cgtttgaggt ggagttttag tcaggtggtc agcttctcct ttttttttgcc   4980
atctgccctg taagcatcct gctggggacc cagataggag tcatcactct aggctgagaa    5040
catctgggca cacaccctaa gcctcagcat gactcatcat gactcagcat tgctgtgctt    5100
gagccagaag gtttgcttag aaggttacac agaaccagaa ggcgggggtg gggcactgac    5160
cccgacaggg gcctggccag aactgctcat gcttggacta tgggaggtca ctaatggaga    5220
cacacagaaa tgtaacagga actaagggaa ttccggtgcc ctgcttagga gcttaatctt    5280
taatgaaagc taagctttca ttaaaaaaag tctaaccagc tgcattcgac tttgactgca    5340
gcagctggtt agaaggttct actggaggag ggtcccagcc cattgctaaa ttaacatcag    5400
gctctgagac tggcagtata tctctaacag tggttgatgc tatcttctgg aacttgcctg    5460
ctacattgag accactgacc catacatagg aagcccatag ctctgtcctg aactgttagg    5520
ccactggtcc agagagtgtg catctccttt gatcctcata ataaccctat gagatagaca    5580
caattattac tcttacttta tagatgatga tcctgaaaac ataggagtca aggcacttgc    5640
ccctagctgg gggtataggg gagcagtccc atgtagtagt agaatgaaaa atgctgctat    5700
gctgtgcctc ccccaccttt cccatgtctg ccctctactc atggtctatc tctcctggct    5760
cctgggagtc atggactcca cccagcacca ccaacctgac ctaaccacct atctgagcct    5820
gccagcctat aacccatctg ggccctgata gctggtggcc agccctgacc ccaccccacc    5880
ctccctggaa cctctgatag acacatctgg cacaccagct cgcaaagtca ccgtgagggt    5940
cttgtgtttg ctgagtcaaa attccttgaa atccaagtcc ttagagactc ctgctcccaa    6000
atttacagtc atagacttct tcatggctgt ctcctttatc cacagaatga ttcctttgct    6060
tcattgcccc atccatctga tcctcctcat cagtgcagca cagggcccat gagcagtagc    6120
tgcagagtct cacataggtc tggcactgcc tctgacatgt ccgaccttag gcaaatgctt    6180
gactcttctg agctcggatc ccttgagctc aggaggtcaa ggctgcagtg agacatgatc    6240
ttgccactgc actccagcct ggacagcaga gtgaaacctt gcctcacgaa acagaataca    6300
aaaacaaaca aacaaaaaac tgctccgcaa tgcgcttcct tgatgctcta ccacataggt    6360
ctgggtactt tgtacacatt atctcattgc tgttcataat tgttagatta attttgtaat    6420
attgatatta ttcctagaaa gctgaggcct caagatgata acttttattt tctggacttg    6480
taatagcttt ctcttgtatt caccatgttg taactttctt agagtagtaa caatataaag    6540
ttattgtgag ttttttgcaaa cacagcaaac acaacgaccc atatagacat tgatgtgaaa    6600
ttgtctattg tcaatttatg ggaaaacaag tatgtacttt ttctactaag ccattgaaac    6660
aggaataaca gaacaagatt gaaagaatac attttccgaa attacttgag tattatacaa    6720
agacaagcac gtggacctgg gaggagggtt attgtccatg actggtgtgt ggagacaaat    6780
gcaggtttat aatagatggg atggcatcta gcgcaatgac tttgccatca cttttagaga    6840
gctcttgggg gccccagtac acaagagggg acgcagggta tatgtagaca tctcattctt    6900
tttcttagtg tgagaataag aatagccatg acctgagttt atagacaatg agccctttttc   6960
tctctcccac tcagcagcta tgagatggct tgccctgcct ctctactagg ctgactcact    7020
ccaaggccca gcaatgggca gggctctgtc agggctttga tagcactatc tgcagagcca    7080
gggccgagaa ggggtggact ccagagactc tccctcccat tcccgagcag ggtttgctta    7140
tttatgcatt taaatgatat atttatttta aagaaaataa caggagactg cccagccctg    7200
```

```
gctgtgacat ggaaactatg tagaatattt tgggttccat ttttttttcc ttctttcagt    7260
tagaggaaaa ggggctcact gcacatacac tagacagaaa gtcaggagct ttgaatccaa    7320
gcctgatcat ttccatgtca tactgagaaa gtccccaccc ttctctgagc ctcagtttct    7380 cttttttataa gtaggagtct ggagtaaatg atttccaatg gctctcattt caatacaaaa    7440
tttccgttta ttaaatgcat gagcttccgt tactccaaga ctgagaagga aattgaacct    7500
gagactcatt gactggcaag atgtccccag aggctctcat tcagcaataa aattctcacc    7560
ttcacccagg cccactagtg tcagatttgc atgcgttcgc gtatcgacgt gcagtattta    7620
gcatgcccca cccatctgca aggcattctg gatagtgtca aaacagccgg aaatcaagtc    7680
cgtttatctc aaactttagc attttgggaa taaatgatat ttgctatgct ggttaaatta    7740
gattttagtt aaatttcctg ctgaagctct agtacgataa gtaacttgac ctaagtgtaa    7800
agttgagatt tccttcaggt ttatatagct tgtgcgccgc ctgggtacct caggatatgc    7860
ccttgactat ttgtccgaca tagtcaaggg catatccttt tttgtgcggc cgcatcgatg    7920
ccgtagtacc tttaagacca atgacttaca aggcagctgt agatcttagc cacttttaa    7980 aagaaaaggg gggactggaa gggctaattc actcccaaag aagacaagat agatctgctt    8040
tttgcctgta ctgggtctct ctggttagac cagatctgag cctgggagct ctctggctaa    8100
ctagggaacc cactgcttaa gcctcaataa agcttcagct gctcgagcta gcagatcttt    8160
ttccctctgc caaaaattat ggggacatca tgaagcccct tgagcatctg acttctggct    8220
aataaaggaa atttattttc attgcaatag tgtgttggaa ttttttgtgt ctctcactcg    8280
gaaggacata tgggagggca aatcatttaa aacatcagaa tgagtatttg gtttagagtt    8340
tggcaacata tgcccatatg ctggctgcca tgaacaaagg ttggctataa agaggtcatc    8400
agtatatgaa acagccccct gctgtccatt ccttattcca tagaaaagcc ttgacttgag    8460
gttagatttt ttttatattt tgttttgtgt tatttttttc tttaacatcc ctaaaatttt    8520
ccttacatgt tttactagcc agattttttcc tcctctcctg actactccca gtcatagctg    8580
tccctcttct cttatggaga tccctcgacc tgcagcccaa gcttggcgta atcatggtca    8640
tagctgtttc ctgtgtgaaa ttgttatccg ctcacaattc cacacaacat acgagccgga    8700
agcataaagt gtaaagcctg gggtgcctaa tgagtgagct aactcacatt aattgcgttg    8760
cgctcactgc ccgctttcca gtcgggaaac ctgtcgtgcc agcggatccg catctcaatt    8820
agtcagcaac catagtcccg cccctaactc cgcccatccc gcccctaact ccgcccagtt    8880
ccgcccattc tccgccccat ggctgactaa ttttttttat ttatgcagag gccgaggccg    8940
cctcggcctc tgagctattc cagaagtagt gaggaggctt ttttggaggc ctaggctttt    9000
gcaaaaagct gtcgactgca gaggcctgca tgcaagcttg gcgtaatcat ggtcatagct    9060
gtttcctgtg tgaaattgtt atccgctcac aattccacac aacatacgag ccggaagcat    9120
aaagtgtaaa gcctggggtg cctaatgagt gagctaactc acattaattg cgttgcgctc    9180
actgcccgct ttccagtcgg gaaacctgtc gtgccagctg cattaatgaa tcggccaacg    9240
cgcggggaga ggcggtttgc gtattgggcg ctcttccgct tcctcgctca ctgactcgct    9300
gcgctcggtc gttcggctgc ggcgagcggt atcagctcac tcaaaggcgg taatacggtt    9360
atccacagaa tcaggggata acgcaggaaa gaacatgtga gcaaaaggcc agcaaaaggc    9420
caggaaccgt aaaaaggccg cgttgctggc gtttttccat aggctccgcc ccctgacga    9480 gcatcacaaa aatcgacgct caagtcagag gtggcgaaac ccgacaggac tataaagata    9540
```

```
ccaggcgttt cccccctggaa gctccctcgt gcgctctcct gttccgaccc tgccgcttac   9600
cggatacctg tccgcctttc tcccttcggg aagcgtggcg ctttctcata gctcacgctg   9660
taggtatctc agttcggtgt aggtcgttcg ctccaagctg ggctgtgtgc acgaaccccc   9720
cgttcagccc gaccgctgcg ccttatccgg taactatcgt cttgagtcca acccggtaag   9780
acacgactta tcgccactgg cagcagccac tggtaacagg attagcagag cgaggtatgt   9840
aggcggtgct acagagttct tgaagtggtg gcctaactac ggctacacta agaacagt     9900
atttggtatc tgcgctctgc tgaagccagt taccttcgga aaaagagttg gtagctcttg   9960
atccggcaaa caaccaccg ctggtagcgg tggtttttt gtttgcaagc agcagattac    10020
gcgcagaaaa aaggatctca agaagatcc tttgatcttt tctacggggt ctgacgctca   10080
gtggaacgaa aactcacgtt aagggatttt ggtcatgaga ttatcaaaaa ggatcttcac   10140
ctagatcctt ttaaattaaa aatgaagttt taaatcaatc taaagtatat atgagtaaac   10200
ttggtctgac agttaccaat gcttaatcag tgaggcacct atctcagcga tctgtctatt   10260
tcgttcatcc atagttgcct gactccccgt cgtgtagata actacgatac gggagggctt   10320
accatctggc cccagtgctg caatgatacc gcgagaccca cgctcaccgg ctccagattt   10380
atcagcaata accagccag ccggaagggc cgagcgcaga agtggtcctg caactttatc    10440
cgcctccatc cagtctatta attgttgccg ggaagctaga gtaagtagtt cgccagttaa   10500
tagtttgcgc aacgttgttg ccattgctac aggcatcgtg gtgtcacgct cgtcgtttgg   10560
tatggcttca ttcagctccg gttcccaacg atcaaggcga gttacatgat cccccatgtt   10620
gtgcaaaaaa gcggttagct ccttcggtcc tccgatcgtt gtcagaagta agttggccgc   10680
agtgttatca ctcatggtta tggcagcact gcataattct cttactgtca tgccatccgt   10740
aagatgcttt tctgtgactg gtgagtactc aaccaagtca ttctgagaat agtgtatgcg   10800
gcgaccgagt tgctcttgcc cggcgtcaat acgggataat accgcgccac atagcagaac   10860
tttaaaagtg ctcatcattg gaaaacgttc ttcggggcga aaactctcaa ggatcttacc   10920
gctgttgaga tccagttcga tgtaacccac tcgtgcaccc aactgatctt cagcatcttt   10980
tactttcacc agcgtttctg ggtgagcaaa aacaggaagg caaaatgccg caaaaaaggg   11040
aataagggcg acacggaaat gttgaatact catactcttc cttttcaat attattgaag    11100
catttatcag ggttattgtc tcatgagcgg atacatattt gaatgtattt agaaaaataa   11160
acaaataggg gttccgcgca catttccccg aaaagtgcca cctgacgtct aagaaaccat   11220
tattatcatg acattaacct ataaaaatag gcgtatcacg aggccctttc gtctcgcgcg   11280
tttcggtgat gacggtgaaa acctctgaca catgcagctc ccggagacgg tcacagcttg   11340
tctgtaagcg gatgccggga gcagacaagc ccgtcagggc gcgtcagcgg gtgttggcgg   11400
gtgtcggggc tggcttaact atgcggcatc agagcagatt gtactgagag tgcaccatat   11460
gcggtgtgaa ataccgcaca gatgcgtaag gagaaaatac cgcatcaggc gccattcgcc   11520
attcaggctg cgcaactgtt gggaagggcg atcggtgcgg gcctcttcgc tattacgcca   11580
gctggcgaaa gggggatgtg ctgcaaggcg attaagttgg gtaacgccag gttttcccca   11640
gtcacgacgt tgtaaaacga cggccagtga attc                               11674
```

<210> SEQ ID NO 21
<211> LENGTH: 11671
<212> TYPE: DNA
<213> ORGANISM: Artificial Sequence
<220> FEATURE:
<223> OTHER INFORMATION: Synthetic: TL20d-rGbGM-r7SKM1/sh734

<400> SEQUENCE: 21

```
ggccgcctcg gccaaacagc ccttgagttt accactccct atcagtgata gagaaaagtg    60
aaagtcgagt ttaccactcc ctatcagtga tagagaaaag tgaaagtcga gtttaccact   120
ccctatcagt gatagagaaa agtgaaagtc gagtttacca ctccctatca gtgatagaga   180
aaagtgaaag tcgagtttac cagtccctat cagtgataga gaaagtgaa agtcgagttt   240
accactccct atcagtgata gagaaaagtg aaagtcgagt ttaccactcc ctatcagtga   300
tagagaaaag tgaaagtcga gctcgccatg ggaggcgtgg cctgggcggg actggggagt   360
ggcgagccct cagatcctgc atataagcag ctgcttttg cctgtactgg gtctctctgg   420
ttagaccaga tctgagcctg ggagctctct ggctaactag ggaacccact gcttaagcct   480
caataaagct tgccttgagt gcttcaagta gtgtgtgccc gtctgttgtg tgactctggt   540
aactagagat ccctcagacc cttttagtca gtgtggaaaa tctctagcag tggcgcccga   600
acagggactt gaaagcgaaa gggaaaccag aggagctctc tcgacgcagg actcggcttg   660
ctgaagcgcg cacggcaaga ggcgaggggc ggcgactggt gagtacgcca aaaattttga   720
ctagcggagg ctagaaggag agagatgggt gcgagagcgt cagtattaag cgggggagaa   780
ttagatcgcg atgggaaaaa attcggttaa ggccaggggg aaagaaaaaa tataaattaa   840
aacatatagt atgggcaagc agggagctag aacgattcgc agttaatact ggcctgttag   900
aaacatcaga aggctgtaga caaatactgg gacagctaca accatccctt cagacaggat   960
cagaagaact tagatcatta tataatacag tagcaacct ctattgtgtg catcaaagga  1020
tagagataaa agacaccaag gaagctttag acaagataga ggaagagcaa acaaaagta  1080
agaaaaaagc acagcaagca gcaggatctt cagacctgga aattccctac aatcccccaaa  1140
gtcaaggagt agtagaatct atgaataaag aattaaagaa aattatagga caggtaagag  1200
atcaggctga acatcttaag acagcagtac aaatggcagt attcatccac aattttaaaa  1260
gaaaggggg gattggggggg tacagtgcag gggaaagaat agtagacata atagcaacag  1320
acatacaaac taaagaatta caaaaacaaa ttacaaaaaat tcaaaatttt cgggtttatt  1380
acagggacag cagaaatcca ctttggaaag gaccagcaaa gctcctctgg aaaggtgaag  1440
gggcagtagt aatacaagat aatagtgaca taaaagtagt gccaagaaga aaagcaaaga  1500
tcattaggga ttatgaaaaa cagatggcag gtgatgattg tgtggcaagt agacaggatg  1560
aggattagaa catggaaaag tttagtaaaa caccataagg aggagatatg agggacaatt  1620
ggagaagtga attatataaa tataaagtag taaaaattga accattagga gtagcaccca  1680
ccaaggcaaa gagaagagtg gtgcagagag aaaaaagagc agtgggaata ggagctttgt  1740
tccttgggtt cttgggagca gcaggaagca ctatgggcgc agcgtcaatg acgctgacgg  1800
tacaggccag acaattattg tctggtatag tgcagcagca gaacaatttg ctgagggcta  1860
ttgaggcgca acagcatctg ttgcaactca gtctgggg catcaagcag ctccaggcaa  1920
gaatcctggc tgtggaaaga tacctaaagg atcaacagct cctgggatt tggggttgct  1980
ctggaaaact catttgcacc actgctgtgc cttggaatgc tagttggagt aataaatctc  2040
tggaacagat ttggaatcac acgacctgga tggagtggga cagagaaatt aacaattaca  2100
caagcttaat acactcctta attgaagaat cgcaaaacca gcaagaaaag aatgaacaag  2160
aattattgga attagataaa tgggcaagtt tgtggaattg gtttaacata acaaattggc  2220
tgtggtatat aaaattattc ataatgatag taggaggctt ggtaggttta agaatagttt  2280
```

```
ttgctgtact ttctatagtg aatagagtta ggcagggata ttcaccatta tcgtttcaga     2340
cccacctccc aacccogagg ggaccgagct caagcttcga acgcgtgggg atcctctaga     2400
gtcgagctcg cgaggatcat caccggtgct agccggagcc agaagcacca taagggacat     2460
gataagggag ccagcagacc tctgatctct tcctgaatgc taatcttaaa catcctgagg     2520
aagaatggga cttccatttg gggtgggcct atgatagggt aataagacag tagtgaatat     2580
caagctacaa aaagccccct ttcaaattct tctcagtcct aacttttcat actaagccca     2640
gtccttccaa agcagactgt gaaagagtga tagttccggg agactagcac cggctagccg     2700
agcttggaac actttccctt cattaagaac catccttgct actcagctgc aatcaatcca     2760
gcccccaggt cttcactgaa ccttttccca tctcttccaa aacatctgtt tctgagaagt     2820
cctgtcctat agaggtcttt cttcccaccg gatttctcct acaccattta ctcccacttg     2880
cagaactccc gtgtacaagt gtctttactg cttttatttg ctcaacaaaa tgcacatctc     2940
atataaaaat aaatgaggag catgcacaca ccacaaacac aaacaggcat gcagaaatac     3000
acatacacac ttccctcaat ataaaccctt tgtggctcat atatttaaaa agatgtaaaa     3060
aaaagagctg aagaaaatca tgtgtgatct ctcagcagaa tagatttatt atttgtattg     3120
cttgcagaat aaagcctatc cttgaaagct ctgaatcatg gcaagagagc tcagtggtat     3180
ctggaggaca gggcactggc cactgcagtc accatcttct gccaggaagc ctgcacctca     3240
ggggtgaatt ctttgccaaa gtgaatggcc agcacggtga ccagcacgtt gcccaggagc     3300
tgtgggagga agataagagg tatgaacatg attagcaaaa gggcctagct tggactcaga     3360
ataatccagc cttatcccaa ccataaaata aaagcagaat ggtagctgga ttgtagctgc     3420
tattagcaat atgaaacctc ttacatcagt tacaatttat atgcagaaat atttatatgc     3480
agaaatattg ctattgcctt aacccagaaa ttatcactgt tattctttag aatggtgcaa     3540
agaggcatga tacattgtat cattattgcc ctgaaagaaa gagattaggg aaagtattag     3600
aaataagata aacaaaaaag tatattaaaa gaagaaagca tttttaaaa ttacaaatgc     3660 aaaattaccc tgatttggtc aatatgtgta ccctgttact tctccccttc ctatgacatg     3720
aacttaacca tagaaaagaa ggggaaagaa aacatcaagg gtcccataga ctcaccttga     3780
agttctcagg atccacatgc agcttgtcac agtgcagttc actcagctgg gcaaaggtgc     3840
ccttgagatc atccaggtgc tttatggcat ctcccaagga agtcagcacc ttcttgccat     3900
gtgccttgac tttggggttg cccatgatgg cagaggcaga ggacaggttg ccaaagctgt     3960
caaagaacct ctgggtccat gggtagacaa ccaggagcct gtgagattga caagaacagt     4020
ttgacagtca gaaggtgcca caaatcctga gaagcaacct ggacttttgc caggcacagg     4080
gtccttcctt ccctcccttg tcctggtcac cagagcctac cttcccaggg tttctcctcc     4140
agcatcttcc acattcacct tgtcccacag gcttgtgata gtagccttgt cctcctctgt     4200
gaaatgaccc atggtgtctg tttgaggttg ctagtgaaca cagttgtgtc agaagcaaat     4260
gtaagcaata gatggctctg ccctgacttt tatgcccagc cctggctcct gccctccctg     4320
ctcctgggag tagattggcc aaccctaggg tgtggctcca cagggtgagg tctaagtgat     4380
gacagccgta cctgtccttg gctcttctgg cactggctta ggagttggac ttcaaacct     4440 cagccctccc tctaagatat atctcttggc cccataccat cagtacaaat tgctactaaa     4500
aacatcctcc tttgcaagtg tatttacgac ggtatcgatg tatgtgagca tgtgtccctct    4560 aacagcacag gccttttgcc acctagctgt ccaggggtgc cttaaaatgg caaacaaggt    4620
ttgttttctt ttcctgtttt catgccttcc tcttccatat ccttgtttca tattaataca    4680
```

-continued

```
tgtgtataga tcctaaaaat ctatacacat gtattaataa agcctgattc tgccgcttct    4740
aggtatagag gccacctgca agataaatat ttgattcaca ataactaatc attctatggc    4800
aattgataac aacaaatata tatatatata tatatatacg tatatgtgta tatatatata    4860
tatattcagg aaataatata ttctagaata tgtcacattc tgtctcaggc atccattttc    4920
tttatgatgc cgtttgaggt ggagttttag tcaggtggtc agcttctcct ttttttgcc    4980 atctgccctg taagcatcct gctggggacc cagataggag tcatcactct aggctgagaa    5040
catctgggca cacaccctaa gcctcagcat gactcatcat gactcagcat tgctgtgctt    5100
gagccagaag gtttgcttag aaggttacac agaaccagaa ggcggggtg gggcactgac    5160 cccgacaggg gcctggccag aactgctcat gcttggacta tgggaggtca ctaatggaga    5220
cacacagaaa tgtaacagga actaagggaa ttccggtgcc ctgcttagga gcttaatctt    5280
taatgaaagc taagctttca ttaaaaaaag tctaaccagc tgcattcgac tttgactgca    5340
gcagctggtt agaaggttct actggaggag ggtcccagcc cattgctaaa ttaacatcag    5400
gctctgagac tggcagtata tctctaacag tggttgatgc tatcttctgg aacttgcctg    5460
ctacattgag accactgacc catacatagg aagcccatag ctctgtcctg aactgttagg    5520
ccactggtcc agagagtgtg catctccttt gatcctcata ataaccctat gagatagaca    5580
caattattac tcttacttta tagatgatga tcctgaaaac ataggagtca aggcacttgc    5640
ccctagctgg gggtataggg gagcagtccc atgtagtagt agaatgaaaa atgctgctat    5700
gctgtgcctc ccccaccttt cccatgtctg ccctctactc atggtctatc tctcctggct    5760
cctgggagtc atggactcca cccagcacca ccaacctgac ctaaccacct atctgagcct    5820
gccagcctat aacccatctg ggccctgata gctggtggcc agccctgacc ccacccacc    5880 ctccctggaa cctctgatag acacatctgg cacaccagct cgcaaagtca ccgtgagggt    5940
cttgtgtttg ctgagtcaaa attccttgaa atccaagtcc ttagagactc ctgctcccaa    6000
atttacagtc atagacttct tcatggctgt ctcctttatc cacagaatga ttcctttgct    6060
tcattgcccc atccatctga tcctcctcat cagtgcagca cagggcccat gagcagtagc    6120
tgcagagtct cacataggtc tggcactgcc tctgacatgt ccgaccttag gcaaatgctt    6180
gactcttctg agctcggatc ccttgagctc aggaggtcaa ggctgcagtg agacatgatc    6240
ttgccactgc actccagcct ggacagcaga gtgaaacctt gcctcacgaa acagaataca    6300
aaaacaaaca aacaaaaaac tgctccgcaa tgcgcttcct tgatgctcta ccacataggt    6360
ctgggtactt tgtacacatt atctcattgc tgttcataat tgttagatta attttgtaat    6420
attgatatta ttcctagaaa gctgaggcct caagatgata actttatttt tctggacttg    6480
taatagcttt ctcttgtatt caccatgttg taactttctt agagtagtaa caatataaag    6540
ttattgtgag tttttgcaaa cacagcaaac acaacgaccc atatagacat tgatgtgaaa    6600
ttgtctattg tcaatttatg ggaaaacaag tatgtacttt ttctactaag ccattgaaac    6660
aggaataaca gaacaagatt gaaagaatac attttccgaa attacttgag tattatacaa    6720
agacaagcac gtggacctgg gaggagggtt attgtccatg actggtgtgt ggagacaaat    6780
gcaggtttat aatagatggg atggcatcta gcgcaatgac tttgccatca cttttagaga    6840
gctcttgggg gccccagtac acaagagggg acgcagggta tatgtagaca tctcattctt    6900
tttcttagtg tgagaataag aatagccatg acctgagttt atagacaatg agcccttttc    6960
tctctcccac tcagcagcta tgagatggct tgccctgcct ctctactagg ctgactcact    7020
```

```
ccaaggccca gcaatgggca gggctctgtc agggctttga tagcactatc tgcagagcca    7080
gggccgagaa ggggtggact ccagagactc tccctcccat tcccgagcag ggtttgctta    7140
tttatgcatt taaatgatat atttatttta aagaaataa caggagactg cccagccctg    7200
gctgtgacat ggaaactatg tagaatattt tgggttccat ttttttttcc ttctttcagt    7260
tagaggaaaa ggggctcact gcacatacac tagacagaaa gtcaggagct ttgaatccaa    7320
gcctgatcat ttccatgtca tactgagaaa gtccccaccc ttctctgagc ctcagtttct    7380 cttttttataa gtaggagtct ggagtaaatg atttccaatg gctctcattt caatacaaaa    7440
tttccgttta ttaaatgcat gagcttccgt tactccaaga ctgagaagga aattgaacct    7500
gagactcatt gactggcaag atgtcccag aggctctcat tcagcaataa aattctcacc    7560
ttcacccagg cccactagtg tcagatttgc atgcgttcgc gtaaaaaagg atatgccctt    7620
gactatgtcg gacaaatagt caagggcata tcctgaggta cccaggcggc gcacaagcta    7680
tataaacctg aaggaaatct caactttaca cttaggtcaa gttacttatc gtactagagc    7740
ttcagcagga aatttaacta aaatctaatt taaccagcat agcaaatatc atttattccc    7800
aaaatgctaa agtttgagat aaacggactt gatttccggc tgttttgaca ctatccagaa    7860
tgccggtact atgggtgggg cagtagcccg actgcacgtc gagcggccgc atcgatgccg    7920
tagtaccttt aagaccaatg acttacaagg cagctgtaga tcttagccac ttttaaaag    7980 aaaaggggg actggaaggg ctaattcact cccaaagaag acaagataga tctgcttttt    8040
gcctgtactg ggtctctctg gttagaccag atctgagcct gggagctctc tggctaacta    8100
gggaacccac tgcttaagcc tcaataaagc ttcagctgct cgagctagca gatcttttc    8160 cctctgccaa aaattatggg gacatcatga agcccttga gcatctgact tctggctaat    8220
aaaggaaatt tattttcatt gcaatagtgt gttggaattt tttgtgtctc tcactcggaa    8280
ggacatatgg gagggcaaat catttaaaac atcagaatga gtatttggtt tagagtttgg    8340
caacatatgc ccatatgctg gctgccatga acaaaggttg gctataaaga ggtcatcagt    8400
atatgaaaca gccccctgct gtccattcct tattccatag aaaagccttg acttgaggtt    8460 agatttttt tatattttgt tttgtgttat tttttctttt aacatcccta aaattttcct    8520
tacatgtttt actagccaga ttttttcctcc tctcctgact actcccagtc atagctgtcc    8580
ctcttctctt atggagatcc ctcgacctgc agcccaagct tggcgtaatc atggtcatag    8640
ctgtttcctg tgtgaaattg ttatccgctc acaattccac acaacatacg agccggaagc    8700
ataaagtgta aagcctgggg tgcctaatga gtgagctaac tcacattaat tgcgttgcgc    8760
tcactgcccg ctttccagtc gggaaacctg tcgtgccagc ggatccgcat ctcaattagt    8820
cagcaaccat agtcccgccc ctaactccgc ccatcccgcc cctaactccg cccagttccg    8880
cccattctcc gccccatggc tgactaattt tttttattta tgcagaggcc gaggccgcct    8940
cggcctctga gctattccag aagtagtgag gaggcttttt tggaggccta ggcttttgca    9000
aaaagctgtc gactgcagag gcctgcatgc aagcttggcg taatcatggt catagctgtt    9060
tcctgtgtga aattgttatc cgctcacaat tccacacaac atacgagccg gaagcataaa    9120
gtgtaaagcc tggggtgcct aatgagtgag ctaactcaca ttaattgcgt tgcgctcact    9180
gcccgctttc cagtcgggaa acctgtcgtg ccagctgcat taatgaatcg gccaacgcgc    9240
ggggagaggc ggtttgcgta ttgggcgctc ttccgcttcc tcgctcactg actcgctgcg    9300
ctcggtcgtt cggctgcggc gagcggtatc agctcactca aaggcggtaa tacgttatc    9360 cacagaatca ggggataacg caggaaagaa catgtgagca aaaggccagc aaaaggccag    9420
```

```
gaaccgtaaa aaggccgcgt tgctggcgtt tttccatagg ctccgccccc ctgacgagca    9480
tcacaaaaat cgacgctcaa gtcagaggtg gcgaaacccg acaggactat aaagatacca    9540
ggcgtttccc cctggaagct ccctcgtgcg ctctcctgtt ccgaccctgc cgcttaccgg    9600
atacctgtcc gcctttctcc cttcgggaag cgtggcgctt tctcatagct cacgctgtag    9660
gtatctcagt tcggtgtagg tcgttcgctc caagctgggc tgtgtgcacg aaccccccgt    9720
tcagcccgac cgctgcgcct tatccggtaa ctatcgtctt gagtccaacc cggtaagaca    9780
cgacttatcg ccactggcag cagccactgg taacaggatt agcagagcga ggtatgtagg    9840
cggtgctaca gagttcttga agtggtggcc taactacggc tacactagaa gaacagtatt    9900
tggtatctgc gctctgctga agccagttac cttcggaaaa agagttggta gctcttgatc    9960
cggcaaacaa accaccgctg gtagcggtgg ttttttttgtt tgcaagcagc agattacgcg   10020
cagaaaaaaa ggatctcaag aagatccttt gatcttttct acggggtctg acgctcagtg   10080
gaacgaaaac tcacgttaag ggattttggt catgagatta tcaaaaagga tcttcaccta   10140
gatccttta aattaaaaat gaagttttaa atcaatctaa agtatatatg agtaaacttg    10200
gtctgacagt taccaatgct taatcagtga ggcacctatc tcagcgatct gtctatttcg   10260
ttcatccata gttgcctgac tccccgtcgt gtagataact acgatacggg agggcttacc   10320
atctggcccc agtgctgcaa tgataccgcg agacccacgc tcaccggctc cagatttatc   10380
agcaataaac cagccagccg aagggccga gcgcagaagt ggtcctgcaa ctttatccgc    10440
ctccatccag tctattaatt gttgccggga agctagagta agtagttcgc cagttaatag   10500
tttgcgcaac gttgttgcca ttgctacagg catcgtggtg tcacgctcgt cgtttggtat   10560
ggcttcattc agctccggtt cccaacgatc aaggcgagtt acatgatccc ccatgttgtg   10620
caaaaaagcg gttagctcct tcggtcctcc gatcgttgtc agaagtaagt tggccgcagt   10680
gttatcactc atggttatgg cagcactgca taattctctt actgtcatgc catccgtaag   10740
atgcttttct gtgactggtg agtactcaac caagtcattc tgagaatagt gtatgcggcg   10800
accgagttgc tcttgcccgg cgtcaatacg ggataatacc gcgccacata gcagaacttt   10860
aaaagtgctc atcattggaa aacgttcttc ggggcgaaaa ctctcaagga tcttaccgct   10920
gttgagatcc agttcgatgt aacccactcg tgcacccaac tgatcttcag catctttac    10980
tttcaccagc gtttctgggt gagcaaaaac aggaaggcaa aatgccgcaa aaagggaat    11040
aagggcgaca cggaaatgtt gaatactcat actcttcctt tttcaatatt attgaagcat   11100
ttatcagggt tattgtctca tgagcggata catatttgaa tgtatttaga aaataaaca    11160
aataggggtt ccgcgcacat ttccccgaaa agtgccacct gacgtctaag aaaccattat   11220
tatcatgaca ttaacctata aaaataggcg tatcacgagg ccctttcgtc tcgcgcgttt   11280
cggtgatgac ggtgaaaacc tctgacacat gcagctcccg gagacggtca gcttgtct    11340
gtaagcggat gccgggagca gacaagcccg tcagggcgcg tcagcgggtg ttggcgggtg   11400
tcggggctgg cttaactatg cggcatcaga gcagattgta ctgagagtgc accatatgcg   11460
gtgtgaaata ccgcacagat gcgtaaggag aaaataccgc atcaggcgcc attcgccatt   11520
caggctgcgc aactgttggg aagggcgatc ggtgcgggcc tcttcgctat tacgccagct   11580
ggcgaaaggg ggatgtgctg caaggcgatt aagttgggta acgccagggt tttcccagtc   11640
acgacgttgt aaaacgacgg ccagtgaatt c                                  11671
```

<210> SEQ ID NO 22

<211> LENGTH: 11674
<212> TYPE: DNA
<213> ORGANISM: Artificial Sequence
<220> FEATURE:
<223> OTHER INFORMATION: Synthetic: TL20d-rGbGM-r7SK/sh734

<400> SEQUENCE: 22

| | | | | | |
|---|---|---|---|---|---|
| ggccgcctcg | gccaaacagc | ccttgagttt | accactccct | atcagtgata | gagaaaagtg | 60 |
| aaagtcgagt | ttaccactcc | ctatcagtga | tagagaaaag | tgaaagtcga | gtttaccact | 120 |
| ccctatcagt | gatagagaaa | agtgaaagtc | gagtttacca | ctccctatca | gtgatagaga | 180 |
| aaagtgaaag | tcgagtttac | cagtccctat | cagtgataga | gaaaagtgaa | agtcgagttt | 240 |
| accactccct | atcagtgata | gagaaaagtg | aaagtcgagt | ttaccactcc | ctatcagtga | 300 |
| tagagaaaag | tgaaagtcga | gctcgccatg | ggaggcgtgg | cctgggcggg | actggggagt | 360 |
| ggcgagccct | cagatcctgc | atataagcag | ctgcttttttg | cctgtactgg | gtctctctgg | 420 |
| ttagaccaga | tctgagcctg | ggagctctct | ggctaactag | ggaacccact | gcttaagcct | 480 |
| caataaagct | tgccttgagt | gcttcaagta | gtgtgtgccc | gtctgttgtg | tgactctggt | 540 |
| aactagagat | ccctcagacc | cttttagtca | gtgtggaaaa | tctctagcag | tggcgcccga | 600 |
| acagggactt | gaaagcgaaa | gggaaaccag | aggagctctc | tcgacgcagg | actcggcttg | 660 |
| ctgaagcgcg | cacggcaaga | ggcgaggggc | ggcgactggt | gagtacgcca | aaaattttga | 720 |
| ctagcggagg | ctagaaggag | agagatgggt | gcgagagcgt | cagtattaag | cggggagaa | 780 |
| ttagatcgcg | atgggaaaaa | attcggttaa | ggccaggggg | aaagaaaaaa | tataaattaa | 840 |
| aacatatagt | atgggcaagc | agggagctag | aacgattcgc | agttaatact | ggcctgttag | 900 |
| aaacatcaga | aggctgtaga | caaatactgg | gacagctaca | accatccctt | cagacaggat | 960 |
| cagaagaact | tagatcatta | tataatacag | tagcaaccct | ctattgtgtg | catcaaagga | 1020 |
| tagagataaa | agacaccaag | gaagctttag | acaagataga | ggaagagcaa | aacaaaagta | 1080 |
| agaaaaaagc | acagcaagca | gcaggatctt | cagacctgga | aattccctac | aatccccaaa | 1140 |
| gtcaaggagt | agtagaatct | atgaataaag | aattaaagaa | aattatagga | caggtaagag | 1200 |
| atcaggctga | acatcttaag | acagcagtac | aaatggcagt | attcatccac | aattttaaaa | 1260 |
| gaaaaggggg | gattgggggg | tacagtgcag | gggaagaat | agtagacata | atagcaacag | 1320 |
| acatacaaac | taaagaatta | caaaaacaaa | ttacaaaaat | tcaaaatttt | cgggtttatt | 1380 |
| acagggacag | cagaaatcca | ctttggaaag | gaccagcaaa | gctcctctgg | aaaggtgaag | 1440 |
| gggcagtagt | aatacaagat | aatagtgaca | taaagtagt | gccaagaaga | aaagcaaaga | 1500 |
| tcattaggga | ttatggaaaa | cagatggcag | gtgatgattg | tgtggcaagt | agacaggatg | 1560 |
| aggattagaa | catggaaaag | tttagtaaaa | caccataagg | aggagatatg | agggacaatt | 1620 |
| ggagaagtga | attatataaa | tataaagtag | taaaaattga | accattagga | gtagcaccca | 1680 |
| ccaaggcaaa | gagaagagtg | gtgcagagag | aaaaaagagc | agtgggaata | ggagctttgt | 1740 |
| tccttgggtt | cttgggagca | gcaggaagca | ctatgggcgc | agcgtcaatg | acgctgacgg | 1800 |
| tacaggccag | acaattattg | tctggtatag | tgcagcagca | gaacaatttg | ctgagggcta | 1860 |
| ttgaggcgca | acagcatctg | ttgcaactca | gtctgggg | catcaagcag | ctccaggcaa | 1920 |
| gaatcctggc | tgtggaaaga | tacctaaagg | atcaacagct | cctgggatt | tggggttgct | 1980 |
| ctggaaaact | catttgcacc | actgctgtgc | cttggaatgc | tagttggagt | aataaatctc | 2040 |
| tggaacagat | ttggaatcac | acgacctgga | tggagtggga | cagagaaatt | aacaattaca | 2100 |
| caagcttaat | acactcctta | attgaagaat | cgcaaaacca | gcaagaaaag | aatgaacaag | 2160 |

```
aattattgga attagataaa tgggcaagtt tgtggaattg gtttaacata acaaattggc    2220
tgtggtatat aaaattattc ataatgatag taggaggctt ggtaggttta agaatagttt    2280
ttgctgtact ttctatagtg aatagagtta ggcagggata ttcaccatta tcgtttcaga    2340
cccacctccc aaccccgagg ggaccgagct caagcttcga acgcgtgggg atcctctaga    2400
gtcgagctcg cgaggatcat caccggtgct agccggagcc agaagcacca taagggacat    2460
gataagggag ccagcagacc tctgatctct tcctgaatgc taatcttaaa catcctgagg    2520
aagaatggga cttccatttg gggtgggcct atgatagggt aataagacag tagtgaatat    2580
caagctacaa aaagccccct ttcaaattct tctcagtcct aacttttcat actaagccca    2640
gtccttccaa agcagactgt gaaagagtga tagttccggg agactagcac cggctagccg    2700
agcttggaac actttccctt cattaagaac catccttgct actcagctgc aatcaatcca    2760
gcccccaggt cttcactgaa ccttttccca tctcttccaa aacatctgtt tctgagaagt    2820
cctgtcctat agaggtcttt cttcccaccg gatttctcct acaccattta ctcccacttg    2880
cagaactccc gtgtacaagt gtctttactg cttttatttg ctcaacaaaa tgcacatctc    2940
atataaaaat aaatgaggag catgcacaca ccacaaacac aaacaggcat gcagaaatac    3000
acatacacac ttccctcaat ataaacccct tgtggctcat atatttaaaa agatgtaaaa    3060
aaaagagctg aagaaaatca tgtgtgatct ctcagcagaa tagatttatt atttgtattg    3120
cttgcagaat aaagcctatc cttgaaagct ctgaatcatg ggcaagaggc tcagtggtat    3180
ctggaggaca gggcactggc cactgcagtc accatcttct gccaggaagc ctgcacctca    3240
ggggtgaatt ctttgccaaa gtgaatggcc agcacggtga ccagcacgtt gcccaggagc    3300
tgtgggagga agataagagg tatgaacatg attagcaaaa gggcctagct tggactcaga    3360
ataatccagc cttatcccaa ccataaaata aaagcagaat ggtagctgga ttgtagctgc    3420
tattagcaat atgaaacctc ttacatcagt tacaatttat atgcagaaat atttatatgc    3480
agaaatattg ctattgcctt aacccagaaa ttatcactgt tattctttag aatggtgcaa    3540
agaggcatga tacattgtat cattattgcc ctgaaagaaa gagattaggg aaagtattag    3600
aaataagata aacaaaaaag tatattaaaa gaagaaagca ttttttaaaa ttacaaatgc    3660
aaaattaccc tgatttggtc aatatgtgta ccctgttact tctccccttc ctatgacatg    3720
aacttaacca tagaaaagaa ggggaaagaa aacatcaagg gtcccataga ctcaccttga    3780
agttctcagg atccacatgc agcttgtcac agtgcagttc actcagctgg gcaaaggtgc    3840
ccttgagatc atccaggtgc tttatggcat ctcccaagga agtcagcacc ttcttgccat    3900
gtgccttgac tttggggttg cccatgatgg cagaggcaga ggacaggttg ccaaagctgt    3960
caaagaacct ctgggtccat gggtagacaa ccaggagcct gtgagattga caagaacagt    4020
ttgacagtca gaaggtgcca caaatcctga gaagcaacct ggacttttgc caggcacagg    4080
gtccttcctt ccctcccttg tcctggtcac cagagcctac cttcccaggg tttctcctcc    4140
agcatcttcc acattcacct tgtcccacag gcttgtgata gtagccttgt cctcctctgt    4200
gaaatgaccc atggtgtctg tttgaggttg ctagtgaaca cagttgtgtc agaagcaaat    4260
gtaagcaata gatggctctg ccctgacttt tatgcccagc cctggctcct gcctccctg     4320 ctcctgggag tagattggcc aaccctaggg tgtggctcca cagggtgagg tctaagtgat    4380
gacagccgta cctgtccttg gctcttctgg cactggctta ggagttggac ttcaaaccct    4440
cagccctccc tctaagatat atctcttggc cccataccat cagtacaaat tgctactaaa    4500
```

```
aacatcctcc tttgcaagtg tatttacgac ggtatcgatg tatgtgagca tgtgtcctct    4560
aacagcacag gcctttttgcc acctagctgt ccaggggtgc cttaaaatgg caaacaaggt    4620
ttgttttctt ttcctgtttt catgccttcc tcttccatat ccttgtttca tattaataca    4680
tgtgtataga tcctaaaaat ctatacacat gtattaataa agcctgattc tgccgcttct    4740
aggtatagag gccacctgca agataaatat ttgattcaca ataactaatc attctatggc    4800
aattgataac aacaaatata tatatatata tatatatacg tatatgtgta tatatatata    4860
tatattcagg aaataatata ttctagaata tgtcacattc tgtctcaggc atccattttc    4920
tttatgatgc cgtttgaggt ggagttttag tcaggtggtc agcttctcct ttttttttgcc    4980 atctgccctg taagcatcct gctggggacc cagataggag tcatcactct aggctgagaa    5040
catctgggca cacaccctaa gcctcagcat gactcatcat gactcagcat tgctgtgctt    5100
gagccagaag gtttgcttag aaggttacac agaaccagaa ggcgggggtg gggcactgac    5160
cccgacaggg gcctggccag aactgctcat gcttggacta tgggaggtca ctaatgagaa    5220
cacacagaaa tgtaacagga actaagggaa ttccggtgcc ctgcttagga gcttaatctt    5280
taatgaaagc taagctttca ttaaaaaaag tctaaccagc tgcattcgac tttgactgca    5340
gcagctggtt agaaggttct actggaggag ggtcccagcc cattgctaaa ttaacatcag    5400
gctctgagac tggcagtata tctctaacag tggttgatgc tatcttctgg aacttgcctg    5460
ctacattgag accactgacc catacatagg aagcccatag ctctgtcctg aactgttagg    5520
ccactggtcc agagagtgtg catctccttt gatcctcata ataaccctat gagatagaca    5580
caattattac tcttacttta tagatgatga tcctgaaaac ataggagtca aggcacttgc    5640
ccctagctgg gggtataggg gagcagtccc atgtagtagt agaatgaaaa atgctgctat    5700
gctgtgcctc ccccacccttt cccatgtctg ccctctactc atggtctatc tctcctggct    5760
cctgggagtc atggactcca cccagcacca ccaacctgac ctaaccacct atctgagcct    5820
gccagcctat aacccatctg ggccctgata gctggtggcc agccctgacc ccaccccacc    5880
ctccctggaa cctctgatag acacatctgg cacaccagct cgcaaagtca ccgtgagggt    5940
cttgtgtttg ctgagtcaaa attccttgaa atccaagtcc ttagagactc ctgctcccaa    6000
atttacagtc atagacttct tcatggctgt ctcctttatc cacagaatga ttcctttgct    6060
tcattgcccc atccatctga tcctcctcat cagtgcagca cagggcccat gagcagtagc    6120
tgcagagtct cacataggtc tggcactgcc tctgacatgt ccgaccttag gcaaatgctt    6180
gactcttctg agctcggatc ccttgagctc aggaggtcaa ggctgcagtg agacatgatc    6240
ttgccactgc actccagcct ggacagcaga gtgaaacctt gcctcacgaa acagaataca    6300
aaaacaaaca aacaaaaaac tgctccgcaa tgcgcttcct tgatgctcta ccacataggt    6360
ctgggtactt tgtacacatt atctccattgc tgttcataat tgttagatta attttgtaat    6420
attgatatta ttcctagaaa gctgaggcct caagatgata acttttattt tctggacttg    6480
taatagcttt ctcttgtatt caccatgttg taactttctt agagtagtaa caatataaag    6540
ttattgtgag ttttgcaaa cacagcaaac acaacgaccc atatagacat tgatgtgaaa    6600
ttgtctattg tcaatttatg ggaaaacaag tatgtacttt ttctactaag ccattgaaac    6660
aggaataaca gaacaagatt gaaagaatac atttttccgaa attacttgag tattatacaa    6720
agacaagcac gtggacctgg gaggagggtt attgtccatg actggtgtgt ggagacaaat    6780
gcaggtttat aatagatggg atggcatcta gcgcaatgac tttgccatca cttttagaga    6840
gctcttgggg gccccagtac acaagagggg acgcagggta tatgtagaca tctcattctt    6900
```

```
tttcttagtg tgagaataag aatagccatg acctgagttt atagacaatg agcccttttc    6960
tctctcccac tcagcagcta tgagatggct tgccctgcct ctctactagg ctgactcact    7020
ccaaggccca gcaatgggca gggctctgtc agggctttga tagcactatc tgcagagcca    7080
gggccgagaa ggggtggact ccagagactc tccctcccat tcccgagcag ggtttgctta    7140
tttatgcatt taaatgatat atttatttta aaagaaataa caggagactg cccagccctg    7200
gctgtgacat ggaaactatg tagaatattt tgggttccat ttttttttcc ttctttcagt    7260
tagaggaaaa ggggctcact gcacatacac tagacagaaa gtcaggagct ttgaatccaa    7320
gcctgatcat ttccatgtca tactgagaaa gtccccaccc ttctctgagc ctcagtttct    7380
ctttttataa gtaggagtct ggagtaaatg atttccaatg gctctcattt caatacaaaa    7440
tttccgttta ttaaatgcat gagcttccgt tactccaaga ctgagaagga aattgaacct    7500
gagactcatt gactggcaag atgtccccag aggctctcat tcagcaataa aattctcacc    7560
ttcacccagg cccactagtg tcagatttgc atgcgttcgc gtacaaaaaa ggatatgccc    7620 tgactatgt cggacaaata gtcaagggca tatcctgagg tacccaggcg gcgcacaagc    7680
tatataaacc tgaaggaaat ctcaacttta cacttaggtc aagttactta tcgtactaga    7740
gcttcagcag gaaatttaac taaaatctaa tttaaccagc atagcaaata tcatttattc    7800
ccaaaatgct aaagtttgag ataaacggac ttgatttccg gctgttttga cactatccag    7860
aatgccttgc agatgggtgg ggcatgctaa atactgcacg tcgatgcggc cgcatcgatg    7920
ccgtagtacc tttaagacca atgacttaca aggcagctgt agatcttagc cacttttttaa    7980 aagaaagggg gggactggaa gggctaattc actcccaaag aagacaagat agatctgctt    8040
tttgcctgta ctgggtctct ctggttagac cagatctgag cctgggagct ctctggctaa    8100
ctagggaacc cactgcttaa gcctcaataa agcttcagct gctcgagcta gcagatcttt    8160
ttccctctgc caaaaattat ggggacatca tgaagcccct tgagcatctg acttctggct    8220
aataaaggaa atttattttc attgcaatag tgtgttggaa ttttttgtgt ctctcactcg    8280
gaaggacata tgggagggca aatcatttaa aacatcagaa tgagtatttg gtttagagtt    8340
tggcaacata tgcccatatg ctggctgcca tgaacaaagg ttggctataa agaggtcatc    8400
agtatatgaa acagccccct gctgtccatt ccttattcca tagaaaagcc ttgacttgag    8460
gttagatttt ttttatattt tgttttgtgt tattttttc tttaacatcc ctaaaatttt    8520
ccttacatgt tttactagcc agattttttcc tcctctcctg actactccca gtcatagctg    8580
tccctcttct cttatggaga tccctcgacc tgcagcccaa gcttggcgta atcatggtca    8640
tagctgtttc ctgtgtgaaa ttgttatccg ctcacaattc cacacaacat acgagccgga    8700
agcataaagt gtaaagcctg gggtgcctaa tgagtgagct aactcacatt aattgcgttg    8760
cgctcactgc ccgctttcca gtcgggaaac ctgtcgtgcc agcggatccg catctcaatt    8820
agtcagcaac catagtcccg cccctaactc cgcccatccc gccccaactt ccgcccagtt    8880
ccgcccattc tccgccccat ggctgactaa ttttttttat ttatgcagag gccgaggccg    8940
cctcggcctc tgagctattc cagaagtagt gaggaggctt ttttggaggc ctaggctttt    9000
gcaaaaagct gtcgactgca gaggcctgca tgcaagcttg gcgtaatcat ggtcatagct    9060
gtttcctgtg tgaaattgtt atccgctcac aattccacac aacatacgag ccggaagcat    9120
aaagtgtaaa gcctggggtg cctaatgagt gagctaactc acattaattg cgttgcgctc    9180
actgcccgct ttccagtcgg gaaacctgtc gtgccagctg cattaatgaa tcggccaacg    9240
```

```
cgcggggaga ggcggtttgc gtattgggcg ctcttccgct tcctcgctca ctgactcgct   9300
gcgctcggtc gttcggctgc ggcgagcggt atcagctcac tcaaaggcgg taatacggtt   9360
atccacagaa tcaggggata acgcaggaaa gaacatgtga gcaaaaggcc agcaaaaggc   9420
caggaaccgt aaaaaggccg cgttgctggc gtttttccat aggctccgcc cccctgacga   9480
gcatcacaaa aatcgacgct caagtcagag gtggcgaaac ccgacaggac tataaagata   9540
ccaggcgttt ccccctggaa gctccctcgt gcgctctcct gttccgaccc tgccgcttac   9600
cggatacctg tccgcctttc tcccttcggg aagcgtggcg ctttctcata gctcacgctg   9660
taggtatctc agttcggtgt aggtcgttcg ctccaagctg ggctgtgtgc acgaaccccc   9720
cgttcagccc gaccgctgcg ccttatccgg taactatcgt cttgagtcca acccggtaag   9780
acacgactta tcgccactgg cagcagccac tggtaacagg attagcagag cgaggtatgt   9840
aggcggtgct acagagttct tgaagtggtg gcctaactac ggctacacta agaacagt    9900
atttggtatc tgcgctctgc tgaagccagt taccttcgga aaaagagttg gtagctcttg   9960
atccggcaaa caaccaccg ctggtagcgg tggtttttt gtttgcaagc agcagattac    10020
gcgcagaaaa aaggatctc aagaagatcc tttgatcttt tctacggggt ctgacgctca    10080
gtggaacgaa aactcacgtt aagggatttt ggtcatgaga ttatcaaaaa ggatcttcac   10140
ctagatcctt ttaaattaaa aatgaagttt taaatcaatc taaagtatat atgagtaaac   10200
ttggtctgac agttaccaat gcttaatcag tgaggcacct atctcagcga tctgtctatt   10260
tcgttcatcc atagttgcct gactccccgt cgtgtagata actacgatac gggagggctt   10320
accatctggc cccagtgctg caatgatacc gcgagaccca cgctcaccgg ctccagattt   10380
atcagcaata aaccagccag ccggaagggc cgagcgcaga agtggtcctg caactttatc   10440
cgcctccatc cagtctatta attgttgccg ggaagctaga gtaagtagtt cgccagttaa   10500
tagtttgcgc aacgttgttg ccattgctac aggcatcgtg gtgtcacgct cgtcgtttgg   10560
tatggcttca ttcagctccg gttcccaacg atcaaggcga gttacatgat cccccatgtt   10620
gtgcaaaaaa gcggttagct ccttcggtcc tccgatcgtt gtcagaagta agttggccgc   10680
agtgttatca ctcatggtta tggcagcact gcataattct cttactgtca tgccatccgt   10740
aagatgcttt tctgtgactg gtgagtactc aaccaagtca ttctgagaat agtgtatgcg   10800
gcgaccgagt tgctcttgcc cggcgtcaat acgggataat accgcgccac atagcagaac   10860
tttaaaagtg ctcatcattg gaaaacgttc ttcggggcga aaactctcaa ggatcttacc   10920
gctgttgaga tccagttcga tgtaacccac tcgtgcaccc aactgatctt cagcatcttt   10980
tactttcacc agcgtttctg ggtgagcaaa aacaggaagg caaaatgccg caaaaaaggg   11040
aataagggcg acacggaaat gttgaatact catactcttc ctttttcaat attattgaag   11100
catttatcag ggttattgtc tcatgagcgg atacatattt gaatgtattt agaaaaataa   11160
acaaataggg gttccgcgca catttccccg aaaagtgcca cctgacgtct aagaaaccat   11220
tattatcatg acattaacct ataaaaatag gcgtatcacg aggccctttc gtctcgcgcg   11280
tttcggtgat gacggtgaaa acctctgaca catgcagctc ccggagacgg tcacagcttg   11340
tctgtaagcg gatgccggga gcagacaagc ccgtcagggc gcgtcagcgg gtgttggcgg   11400
gtgtcgggc tggcttaact atgcggcatc agagcagatt gtactgagag tgcaccatat   11460
gcggtgtgaa ataccgcaca gatgcgtaag gagaaaatac cgcatcaggc gccattcgcc   11520
attcaggctg cgcaactgtt gggaagggcg atcggtgcgg gcctcttcgc tattacgcca   11580
gctggcgaaa gggggatgtg ctgcaaggcg attaagttgg gtaacgccag ggttttccca   11640
```

```
gtcacgacgt tgtaaaacga cggccagtga attc                              11674
```

```
<210> SEQ ID NO 23
<211> LENGTH: 111
<212> TYPE: RNA
<213> ORGANISM: Artificial Sequence
<220> FEATURE:
<223> OTHER INFORMATION: Synthetic: miRNA734 de novo (RNA form)

<400> SEQUENCE: 23
acccguacau auuuugugu agcucuaguu uauagucaag ggcauauccu uguguuuuuu    60
uugaaggaua ugcccuugac uauaaacuag cgcuacacuu uuucgucuug u           111
```

```
<210> SEQ ID NO 24
<211> LENGTH: 111
<212> TYPE: RNA
<213> ORGANISM: Artificial Sequence
<220> FEATURE:
<223> OTHER INFORMATION: Synthetic: miRNA211 de novo (RNA form)

<400> SEQUENCE: 24
acccguacau auuuugugu agcucuaguu auaaaucaag gucauaaccu uguguuuuuu    60
uugaagguua ugaccuugau uuauaacuag cgcuacacuu uuucgucuug u           111
```

```
<210> SEQ ID NO 25
<211> LENGTH: 166
<212> TYPE: DNA
<213> ORGANISM: Artificial Sequence
<220> FEATURE:
<223> OTHER INFORMATION: Synthetic: miRNA211-3G

<400> SEQUENCE: 25
ccggatcaac gccctaggtt tatgtttgga tgaactgaca tacgcgtatc cgtcttttaa   60
atcaaggtca taaccgtagt gaaatatata ttaaacaggt tatgaccttg atttaaaata  120
cggtaacgcg gaattcgcaa ctattttatc aattttttgc gtcgac                 166
```

```
<210> SEQ ID NO 26
<211> LENGTH: 166
<212> TYPE: DNA
<213> ORGANISM: Artificial Sequence
<220> FEATURE:
<223> OTHER INFORMATION: Synthetic: miRNA734-3G

<400> SEQUENCE: 26
ccggatcaac gccctaggtt tatgtttgga tgaactgaca tacgcgtatc cgtcttatag   60
tcaagggcat atcctgtagt gaaatatata ttaaacaagg atatgccctt gactataata  120
cggtaacgcg gaattcgcaa ctattttatc aattttttgc gtcgac                 166
```

```
<210> SEQ ID NO 27
<211> LENGTH: 56
<212> TYPE: DNA
<213> ORGANISM: Artificial Sequence
<220> FEATURE:
<223> OTHER INFORMATION: Synthetic: shHPRT 616

<400> SEQUENCE: 27
gcaggcagta taatccaaat acctgaccca tatttggatt atactgcctg cttttt       56
```

```
<210> SEQ ID NO 28
<211> LENGTH: 55
<212> TYPE: DNA
```

```
<213> ORGANISM: Artificial Sequence
<220> FEATURE:
<223> OTHER INFORMATION: Synthetic: shHPRT 211

<400> SEQUENCE: 28
ggttatgacc ttgatttata cctgacccat attaaatcaa ggtcataacc tttttt         55

<210> SEQ ID NO 29
<211> LENGTH: 56
<212> TYPE: DNA
<213> ORGANISM: Artificial Sequence
<220> FEATURE:
<223> OTHER INFORMATION: Synthetic: shHPRT 734.1

<400> SEQUENCE: 29
gggatatgcc cttgactaat acctgaccca tattagtcaa gggcatatcc cttttt         56

<210> SEQ ID NO 30
<211> LENGTH: 52
<212> TYPE: DNA
<213> ORGANISM: Artificial Sequence
<220> FEATURE:
<223> OTHER INFORMATION: Synthetic: shHPRT 734

<400> SEQUENCE: 30
aggatatgcc cttgactatt tgtccgacat agtcaagggc atatccttttt tt            52

<210> SEQ ID NO 31
<211> LENGTH: 51
<212> TYPE: RNA
<213> ORGANISM: Artificial Sequence
<220> FEATURE:
<223> OTHER INFORMATION: Synthetic: Modified sh734

<400> SEQUENCE: 31
aggauaugcc cuugacuaug cccugaccca gcauagucaa gggcauaucc u              51

<210> SEQ ID NO 32
<211> LENGTH: 248
<212> TYPE: DNA
<213> ORGANISM: Homo sapiens
<220> FEATURE:
<221> NAME/KEY: misc_feature
<223> OTHER INFORMATION: Homo sapiens cell-line HEK-293 7SK RNA promoter
      region

<400> SEQUENCE: 32
tcgacgtgca gtatttagca tgccccaccc atctgcaagg cattctggat agtgtcaaaa     60
cagccggaaa tcaagtccgt ttatctcaaa ctttagcatt ttgggaataa atgatatttg    120
ctatgctggt taaattagat tttagttaaa tttcctgctg aagctctagt acgataagta    180
acttgaccta agtgtaaagt tgagatttcc ttcaggttta tatagcttgt gcgccgcctg    240
ggtacctc                                                             248

<210> SEQ ID NO 33
<211> LENGTH: 248
<212> TYPE: DNA
<213> ORGANISM: Homo sapiens
<220> FEATURE:
<221> NAME/KEY: misc_feature
<223> OTHER INFORMATION: Homo sapiens cell-line HEK-293 7SK RNA promoter
      region with mutation 1

<400> SEQUENCE: 33
tcgacgtgca gtcgggctac tgccccaccc atagtaccgg cattctggat agtgtcaaaa     60
```

```
cagccggaaa tcaagtccgt ttatctcaaa ctttagcatt ttgggaataa atgatatttg      120
ctatgctggt taaattagat tttagttaaa tttcctgctg aagctctagt acgataagta      180
acttgaccta agtgtaaagt tgagatttcc ttcaggttta tatagcttgt gcgccgcctg      240
ggtacctc                                                                248

<210> SEQ ID NO 34
<211> LENGTH: 9
<212> TYPE: RNA
<213> ORGANISM: Artificial Sequence
<220> FEATURE:
<223> OTHER INFORMATION: Synthetic: hsa-miR-22 loop sequence

<400> SEQUENCE: 34 ccugaccca                                                                 9

<210> SEQ ID NO 35
<211> LENGTH: 9
<212> TYPE: DNA
<213> ORGANISM: Artificial Sequence
<220> FEATURE:
<223> OTHER INFORMATION: Synthetic: Hairpin loop sequence of sh734 (5 to
      3)

<400> SEQUENCE: 35 ttgtccgac                                                                 9

<210> SEQ ID NO 36
<211> LENGTH: 483
<212> TYPE: DNA
<213> ORGANISM: Artificial Sequence
<220> FEATURE:
<223> OTHER INFORMATION: Synthetic: EF1a-miRNA734-Denovo-SV40 polyA

<400> SEQUENCE: 36
ggatatcggc tccggtgccc gtcagtgggc agagcgcaca tcgcccacag tccccgagaa       60 gttggggggga ggggtcggca attgaaccgg tgcctagaga aggtggcgcg gggtaaactg      120
ggaaagtgat gtcgtgtact ggctccgcct ttttcccgag ggtgggggag aaccgtatat      180
aagtgcagta gtcgccgtga acgttctttt cgcaacgggt ttgccgccag aacacaggat      240
gacccgtaca tatttttgtg tagctctagt tataaatcaa ggtcataacc ttgtgttttt      300
tttgaaggtt atgaccttga tttataacta gcgctacact ttttcgtctt gttagaactt      360
gtttattgca gcttataatg gttacaaata aagcaatagc atcacaaatt tcacaaataa      420
agcatttttt tcactgcatt ctagttgtgg tttgtccaaa ctcatcaatg tatcttatca      480
tct                                                                     483

<210> SEQ ID NO 37
<211> LENGTH: 483
<212> TYPE: DNA
<213> ORGANISM: Artificial Sequence
<220> FEATURE:
<223> OTHER INFORMATION: Synthetic: EF1a-miRNA211-Denovo-SV40 polyA

<400> SEQUENCE: 37
ggatatcggc tccggtgccc gtcagtgggc agagcgcaca tcgcccacag tccccgagaa       60 gttggggggga ggggtcggca attgaaccgg tgcctagaga aggtggcgcg gggtaaactg      120
ggaaagtgat gtcgtgtact ggctccgcct ttttcccgag ggtgggggag aaccgtatat      180
aagtgcagta gtcgccgtga acgttctttt cgcaacgggt ttgccgccag aacacaggat      240
```

```
gacccgtaca tattttttgtg tagctctagt ttatagtcaa gggcatatcc ttgtgttttt      300
tttgaaggat atgcccttga ctataaacta gcgctacact ttttcgtctt gttagaactt      360
gtttattgca gcttataatg gttacaaata aagcaatagc atcacaaatt tcacaaataa      420
agcatttttt tcactgcatt ctagttgtgg tttgtccaaa ctcatcaatg tatcttatca      480
tct                                                                   483

<210> SEQ ID NO 38
<211> LENGTH: 537
<212> TYPE: DNA
<213> ORGANISM: Artificial Sequence
<220> FEATURE:
<223> OTHER INFORMATION: Synthetic: EF1a-miRNA734-3G-SV40 polyA

<400> SEQUENCE: 38
ggatatcggc tccggtgccc gtcagtgggc agagcgcaca tcgcccacag tccccgagaa       60
gttgggggga ggggtcggca attgaaccgg tgcctagaga aggtggcgcg gggtaaactg      120
ggaaagtgat gtcgtgtact ggctccgcct ttttcccgag ggtgggggag aaccgtatat      180
aagtgcagta gtcgccgtga acgttctttt cgcaacgggt ttgccgccag aacacaggat      240
gccggatcaa cgccctaggt ttatgtttgg atgaactgac atacgcgtat ccgtcttata      300
gtcaagggca tatccagtag tgaaatatat attaaactgg atatgccctt gactataata      360
cggtaacgcg gaattcgcaa ctattttatc aattttttgc gtcgactaga acttgtttat      420
tgcagcttat aatggttaca aataaagcaa tagcatcaca aatttcacaa ataaagcatt      480
tttttcactg cattctagtt gtggtttgtc caaactcatc aatgtatctt atcatct        537

<210> SEQ ID NO 39
<211> LENGTH: 696
<212> TYPE: DNA
<213> ORGANISM: Artificial Sequence
<220> FEATURE:
<223> OTHER INFORMATION: Synthetic: EF1a-miRNA211-3G-SV40 polyA

<400> SEQUENCE: 39
ggatatcggc tccggtgccc gtcagtgggc agagcgcaca tcgcccacag tccccgagaa       60
gttgggggga ggggtcggca attgaaccgg tgcctagaga aggtggcgcg gggtaaactg      120
ggaaagtgat gtcgtgtact ggctccgcct ttttcccgag ggtgggggag aaccgtatat      180
aagtgcagta gtcgccgtga acgttctttt cgcaacgggt ttgccgccag aacacaggcc      240
ggatcaacgc cctaggttta tgtttggatg aactgacata cgcgtatccg tctataaatc      300
aaggtcataa cctgtagtga atatatatt aaacaaggtt atgaccttga tttattacgg      360
taacgcggaa ttcgcaacta ttttatcaat tttttgcgtc gacccggatc aacgccctag      420
gtttatgttt ggatgaactg acatacgcgt atccgtctat aaatcaaggt cataacctgt      480
agtgaaatat atattaaaca aggttatgac cttgatttat tacggtaacg cggaattcgc      540
aactatttta tcaatttttt gcgtcgacaa cttgtttatt gcagcttata atggttacaa      600
ataaagcaat agcatcacaa atttcacaaa taaagcattt ttttcactgc attctagttg      660
tggtttgtcc aaactcatca atgtatctta tcatct                                696

<210> SEQ ID NO 40
<211> LENGTH: 809
<212> TYPE: DNA
<213> ORGANISM: Artificial Sequence
<220> FEATURE:
```

<223> OTHER INFORMATION: Synthetic: Left
       Arm 150-EF1a-miRNA734-Denovo-SV40 polyA-Right Arm 150

<400> SEQUENCE: 40

```
gcttcttctc tggaatcttc ttcatcatcc tcctgacaat cgataggtac ctggctgtcg    60
tccatgctgt gtttgcttta aaagccagga cggtcacctt tggggtggtg acaagtgtga   120
tcacttgggt ggtggctgtg tttgcgtctc aagcttttcg aagcggccgc ggatatcggc   180
tccggtgccc gtcagtgggc agagcgcaca tcgcccacag tccccgagaa gttgggggga   240
ggggtcggca attgaaccgg tgcctagaga aggtggcgcg gggtaaactg ggaaagtgat   300
gtcgtgtact ggctccgcct ttttcccgag ggtgggggag aaccgtatat aagtgcagta   360
gtcgccgtga acgttctttt cgcaacgggt ttgccgccag aacacaggat gacccgtaca   420
tattttgtg tagctctagt tataaatcaa ggtcataacc ttgtgttttt tttgaaggtt    480
atgaccttga tttataacta gcgctacact ttttcgtctt gttagaactt gtttattgca   540
gcttataatg gttacaaata aagcaatagc atcacaaatt tcacaaataa agcatttttt   600
tcactgcatt ctagttgtgg tttgtccaaa ctcatcaatg tatcttatca tctacgcgtc   660
caggaatcat ctttaccaga tctcaaaaag aaggtcttca ttacacctgc agctctcatt   720
ttccatacag tcagtatcaa ttctggaaga atttccagac attaaagata gtcatcttgg   780
ggctggtcct gccgctgctt gtcatggtc                                     809
```

<210> SEQ ID NO 41
<211> LENGTH: 809
<212> TYPE: DNA
<213> ORGANISM: Artificial Sequence
<220> FEATURE:
<223> OTHER INFORMATION: Synthetic: miRNA211-Denovo

<400> SEQUENCE: 41

```
gcttcttctc tggaatcttc ttcatcatcc tcctgacaat cgataggtac ctggctgtcg    60
tccatgctgt gtttgcttta aaagccagga cggtcacctt tggggtggtg acaagtgtga   120
tcacttgggt ggtggctgtg tttgcgtctc aagcttttcg aagcggccgc ggatatcggc   180
tccggtgccc gtcagtgggc agagcgcaca tcgcccacag tccccgagaa gttgggggga   240
ggggtcggca attgaaccgg tgcctagaga aggtggcgcg gggtaaactg ggaaagtgat   300
gtcgtgtact ggctccgcct ttttcccgag ggtgggggag aaccgtatat aagtgcagta   360
gtcgccgtga acgttctttt cgcaacgggt ttgccgccag aacacaggat gacccgtaca   420
tattttgtg tagctctagt ttatagtcaa gggcatatcc ttgtgttttt tttgaaggat    480
atgcccttga ctataaacta gcgctacact ttttcgtctt gttagaactt gtttattgca   540
gcttataatg gttacaaata aagcaatagc atcacaaatt tcacaaataa agcatttttt   600
tcactgcatt ctagttgtgg tttgtccaaa ctcatcaatg tatcttatca tctacgcgtc   660
caggaatcat ctttaccaga tctcaaaaag aaggtcttca ttacacctgc agctctcatt   720
ttccatacag tcagtatcaa ttctggaaga atttccagac attaaagata gtcatcttgg   780
ggctggtcct gccgctgctt gtcatggtc                                     809
```

<210> SEQ ID NO 42
<211> LENGTH: 863
<212> TYPE: DNA
<213> ORGANISM: Artificial Sequence
<220> FEATURE:
<223> OTHER INFORMATION: Synthetic: miRNA734-3G

<400> SEQUENCE: 42

```
gcttcttctc tggaatcttc ttcatcatcc tcctgacaat cgataggtac ctggctgtcg        60
tccatgctgt gtttgcttta aaagccagga cggtcacctt ggggtggtg acaagtgtga        120
tcacttgggt ggtggctgtg tttgcgtctc aagcttttcg aagcggccgc ggatatcggc       180
tccggtgccc gtcagtgggc agagcgcaca tcgcccacag tccccgagaa gttgggggga       240
ggggtcggca attgaaccgg tgcctagaga aggtggcgcg gggtaaactg ggaaagtgat       300
gtcgtgtact ggctccgcct ttttcccgag ggtgggggag aaccgtatat aagtgcagta       360
gtcgccgtga acgttctttt cgcaacgggt ttgccgccag aacacaggat gccggatcaa       420
cgccctaggt ttatgtttgg atgaactgac atacgcgtat ccgtcttata gtcaagggca       480
tatccagtag tgaaatatat attaaactgg atatgcccct gactataata cggtaacgcg       540
gaattcgcaa ctatttttatc aattttttgc gtcgactaga acttgtttat tgcagcttat      600
aatggttaca ataaagcaa tagcatcaca aatttcacaa ataaagcatt ttttcactg         660
cattctagtt gtggtttgtc caaactcatc aatgtatctt atcatctacg cgtccaggaa       720
tcatctttac cagatctcaa aaagaaggtc ttcattacac ctgcagctct catttttccat      780
acagtcagta tcaattctgg aagaatttcc agacattaaa gatagtcatc ttggggctgg       840
tcctgccgct gcttgtcatg gtc                                               863
```

<210> SEQ ID NO 43
<211> LENGTH: 1022
<212> TYPE: DNA
<213> ORGANISM: Artificial Sequence
<220> FEATURE:
<223> OTHER INFORMATION: Synthetic: miRNA211-3G

<400> SEQUENCE: 43

```
gcttcttctc tggaatcttc ttcatcatcc tcctgacaat cgataggtac ctggctgtcg        60
tccatgctgt gtttgcttta aaagccagga cggtcacctt ggggtggtg acaagtgtga        120
tcacttgggt ggtggctgtg tttgcgtctc aagcttttcg aagcggccgc ggatatcggc       180
tccggtgccc gtcagtgggc agagcgcaca tcgcccacag tccccgagaa gttgggggga       240
ggggtcggca attgaaccgg tgcctagaga aggtggcgcg gggtaaactg ggaaagtgat       300
gtcgtgtact ggctccgcct ttttcccgag ggtgggggag aaccgtatat aagtgcagta       360
gtcgccgtga acgttctttt cgcaacgggt ttgccgccag aacacaggcc ggatcaacgc       420
cctaggttta tgtttggatg aactgacata cgcgtatccg tctataaatc aaggtcataa       480
cctgtagtga atatatatt aaacaaggtt atgaccttga tttattacgg taacgcggaa        540
ttcgcaacta ttttatcaat ttttgcgtc gacccggatc aacgccctag gtttatgttt        600
ggatgaactg acatacgcgt atccgtctat aaatcaaggt cataacctgt agtgaaatat      660
atattaaaca aggttatgac cttgatttat acggtaacg cggaattcgc aactattttta       720
tcaattttt gcgtcgacaa cttgtttatt gcagcttata atggttacaa ataaagcaat        780
agcatcacaa atttcacaaa taaagcattt ttttcactgc attctagttg tggtttgtcc       840
aaactcatca atgtatctta tcatctacgc gtccaggaat catctttacc agatctcaaa       900
aagaaggtct tcattacacc tgcagctctc attttccata cagtcagtat caattctgga       960
agaatttcca gacattaaag atagtcatct tggggctggt cctgccgctg cttgtcatgg      1020
tc                                                                    1022
```

```
<210> SEQ ID NO 44
<211> LENGTH: 20
<212> TYPE: DNA
<213> ORGANISM: Artificial Sequence
<220> FEATURE:
<223> OTHER INFORMATION: Synthetic: GbGM    F   5-3

<400> SEQUENCE: 44
tgacttcctt gggagatgcc                                                     20

<210> SEQ ID NO 45
<211> LENGTH: 20
<212> TYPE: DNA
<213> ORGANISM: Artificial Sequence
<220> FEATURE:
<223> OTHER INFORMATION: Synthetic: GbGM    R   5-3

<400> SEQUENCE: 45
caaagtgaat ggccagcacg                                                     20

<210> SEQ ID NO 46
<211> LENGTH: 20
<212> TYPE: DNA
<213> ORGANISM: Artificial Sequence
<220> FEATURE:
<223> OTHER INFORMATION: Synthetic: Probe    5- 3

<400> SEQUENCE: 46
agctcctggg caacgtgctg                                                     20

<210> SEQ ID NO 47
<211> LENGTH: 6565
<212> TYPE: DNA
<213> ORGANISM: Artificial Sequence
<220> FEATURE:
<223> OTHER INFORMATION: Synthetic: PTL20c

<400> SEQUENCE: 47
ggccgcctcg gccaaacagc ccttgagttt accactccct atcagtgata gagaaaagtg         60
aaagtcgagt ttaccactcc ctatcagtga tagagaaaag tgaaagtcga gtttaccact        120
ccctatcagt gatagagaaa agtgaaagtc gagtttacca ctccctatca gtgatagaga        180
aaagtgaaag tcgagtttac cagtccctat cagtgataga gaaaagtgaa agtcgagttt        240
accactccct atcagtgata gagaaaagtg aaagtcgagt ttaccactcc ctatcagtga        300
tagagaaaag tgaaagtcga gctcgccatg ggaggcgtgg cctgggcggg actggggagt        360
ggcgagccct cagatcctgc atataagcag ctgcttttg cctgtactgg gtctctctgg         420
ttagaccaga tctgagcctg ggagctctct ggctaactag ggaacccact gcttaagcct        480
caataaagct tgccttgagt gcttcaagta gtgtgtgccc gtctgttgtg tgactctggt        540
aactagagat ccctcagacc cttttagtca gtgtggaaaa tctctagcag tggcgcccga        600
acagggactt gaaagcgaaa gggaaaccag aggagctctc tcgacgcagg actcggcttg        660
ctgaagcgcg cacggcaaga ggcgaggggc ggcgactggt gagtacgcca aaaattttga        720
ctagcggagg ctagaaggag agagatgggt gcgagagcgt cagtattaag cgggggagaa        780
ttagatcgcg atgggaaaaa attcggttaa ggccaggggg aaagaaaaaa tataaattaa        840
aacatatagt atgggcaagc agggagctag aacgattcgc agttaatact ggcctgttag        900
aaacatcaga aggctgtaga caaatactgg gacagctaca accatccctt cagacaggat        960
cagaagaact tagatcatta tataatacag tagcaaccct ctattgtgtg catcaaagga       1020
```

```
tagagataaa agacaccaag gaagctttag acaagataga ggaagagcaa aacaaaagta   1080
agaaaaaagc acagcaagca gcaggatctt cagacctgga aattccctac aatccccaaa   1140
gtcaaggagt agtagaatct atgaataaag aattaaagaa aattatagga caggtaagag   1200
atcaggctga acatcttaag acagcagtac aaatggcagt attcatccac aattttaaaa   1260
gaaaaggggg gattgggggg tacagtgcag gggaaagaat agtagacata atagcaacag   1320
acatacaaac taaagaatta caaaaacaaa ttacaaaaat tcaaaatttt cgggtttatt   1380
acagggacag cagaaatcca ctttggaaag gaccagcaaa gctcctctgg aaaggtgaag   1440
gggcagtagt aatacaagat aatagtgaca taaaagtagt gccaagaaga aaagcaaaga   1500
tcattaggga ttatggaaaa cagatggcag gtgatgattg tgtggcaagt agacaggatg   1560
aggattagaa catggaaaag tttagtaaaa caccataagg aggagatatg agggacaatt   1620
ggagaagtga attatataaa tataaagtag taaaaattga accattagga gtagcaccca   1680
ccaaggcaaa gagaagagtg gtgcagagag aaaaaagagc agtgggaata ggagctttgt   1740
tccttgggtt cttgggagca gcaggaagca ctatgggcgc agcgtcaatg acgctgacgg   1800
tacaggccag acaattattg tctggtatag tgcagcagca gaacaatttg ctgagggcta   1860
ttgaggcgca acagcatctg ttgcaactca cagtctgggg catcaagcag ctccaggcaa   1920
gaatcctggc tgtggaaaga tacctaaagg atcaacagct cctggggatt tggggttgct   1980
ctggaaaact catttgcacc actgctgtgc cttggaatgc tagttggagt aataaatctc   2040
tggaacagat ttggaatcac acgacctgga tggagtggga cagagaaatt aacaattaca   2100
caagcttaat acactcctta attgaagaat cgcaaaacca gcaagaaaag aatgaacaag   2160
aattattgga attagataaa tgggcaagtt tgtggaattg gtttaacata acaaattggc   2220
tgtggtatat aaaattattc ataatgatag taggaggctt ggtaggttta agaatagttt   2280
ttgctgtact ttctatagtg aatagagtta ggcagggata ttcaccatta tcgtttcaga   2340
cccacctccc aaccccgagg ggaccgagct caagcttcga acgcgtgcgg ccgcatcgat   2400
gccgtagtac ctttaagacc aatgacttac aaggcagctg tagatcttag ccacttttta   2460
aaagaaaagg ggggactgga agggctaatt cactcccaaa gaagacaaga tccctgcagg   2520
cattcaaggc caggctggat gtggctctgg gcagcctggg ctgctggttg atgaccctgc   2580
acatagcagg gggttggatc tggatgagca ctgtgctcct ttgcaaccca ggccgttcta   2640
tgattctgtc attctaaatc tctctttcag cctaaagctt ttttcccgta tccccccagg   2700
tgtctgcagc tcaaagagc agcgagaagc gttcagagga aagcgatccc gtgccacctt   2760
ccccgtgccc gggctgtccc cgcacgctgc cggctcgggg atgcgggggg agcgccggac   2820
cggagcggag ccccgggcgg ctcgctgctg cccctagcg ggggagggac gtaattacat   2880
ccctgggggc tttggggggg ggctgtcccc gtgagctccc cagatctgct ttttgcctgt   2940
actgggtctc tctggttaga ccagatctga gcctgggagc tctctggcta actagggaac   3000
ccactgctta agcctcaata aagcttcagc tgctcgagct agcagatctt tttccctctg   3060
ccaaaaatta tgggacatc atgaagcccc ttgagcatct gacttctggc taataaagga   3120
aatttatttt cattgcaata gtgtgttgga atttttgtg tctctcactc ggaaggacat   3180
atgggagggc aaatcattta aaacatcaga atgagtattt ggtttagagt ttggcaacat   3240
atgcccatat gctggctgcc atgaacaaag gttggctata aagaggtcat cagtatatga   3300
aacagccccc tgctgtccat tccttattcc atagaaaagc cttgacttga ggttagattt   3360
tttttatatt ttgttttgtg ttatttttt ctttaacatc cctaaaattt tccttacatg   3420
```

```
ttttactagc cagattttc ctcctctcct gactactccc agtcatagct gtccctcttc    3480
tcttatggag atccctcgac ctgcagccca agcttggcgt aatcatggtc atagctgttt    3540
cctgtgtgaa attgttatcc gctcacaatt ccacacaaca tacgagccgg aagcataaag    3600
tgtaaagcct ggggtgccta atgagtgagc taactcacat taattgcgtt gcgctcactg    3660
cccgctttcc agtcgggaaa cctgtcgtgc cagcggatcc gcatctcaat tagtcagcaa    3720
ccatagtccc gccctaact ccgcccatcc cgccctaac tccgcccagt ccgcccatt    3780
ctccgcccca tggctgacta attttttta tttatgcaga ggccgaggcc gcctcggcct    3840
ctgagctatt ccagaagtag tgaggaggct ttttggagg cctaggcttt tgcaaaaagc    3900
tgtcgactgc agaggcctgc atgcaagctt ggcgtaatca tggtcatagc tgtttcctgt    3960
gtgaaattgt tatccgctca caattccaca acatacga gccggaagca taagtgtaa    4020
agcctgggt gcctaatgag tgagctaact cacattaatt gcgttgcgct cactgcccgc    4080
tttccagtcg ggaaacctgt cgtgccagct gcattaatga atcggccaac gcgcggggag    4140
aggcggtttg cgtattgggc gctcttccgc ttcctcgctc actgactcgc tgcgctcggt    4200
cgttcggctg cggcgagcgg tatcagctca ctcaaaggcg gtaatacggt tatccacaga    4260
atcaggggat aacgcaggaa agaacatgtg agcaaaaggc cagcaaaagg ccaggaaccg    4320
taaaaaggcc gcgttgctgg cgttttccca taggctccgc ccccctgacg agcatcacaa    4380
aaatcgacgc tcaagtcaga ggtggcgaaa cccgacagga ctataaagat accaggcgtt    4440
tcccctggaa gctccctcg tgcgctctcc tgttccgacc ctgccgctta ccggatacct    4500
gtccgccttt ctcccttcgg gaagcgtggc gctttctcat agctcacgct gtaggtatct    4560
cagttcggtg taggtcgttc gctccaagct gggctgtgtg cacgaacccc ccgttcagcc    4620
cgaccgctgc gccttatccg gtaactatcg tcttgagtcc aacccggtaa gacacgactt    4680
atcgccactg gcagcagcca ctggtaacag gattagcaga gcgaggtatg taggcggtgc    4740
tacagagttc ttgaagtggt ggcctaacta cggctacact agaagaacag tatttggtat    4800
ctgcgctctg ctgaagccag ttaccttcgg aaaaagagtt ggtagctctt gatccggcaa    4860
acaaaccacc gctggtagcg tggttttttt gtttgcaag cagcagatta cgcgcagaaa    4920
aaaaggatct caagaagatc ctttgatctt ttctacgggg tctgacgctc agtggaacga    4980
aaactcacgt taagggattt tggtcatgag attatcaaaa aggatcttca cctagatcct    5040
tttaaattaa aaatgaagtt ttaaatcaat ctaaagtata tatgagtaaa cttggtctga    5100
cagttaccaa tgcttaatca gtgaggcacc tatctcagcg atctgtctat ttcgttcatc    5160
catagttgcc tgactccccg tcgtgtagat aactacgata cgggagggct taccatctgg    5220
ccccagtgct gcaatgatac cgcgagaccc acgctcaccg gctccagatt tatcagcaat    5280
aaaccagcca gccggaaggg ccgagcgcag aagtggtcct gcaactttat ccgcctccat    5340
ccagtctatt aattgttgcc gggaagctag agtaagtagt tcgccagtta atagtttgcg    5400
caacgttgtt gccattgcta caggcatcgt ggtgtcacgc tcgtcgtttg gtatggcttc    5460
attcagctcc ggttcccaac gatcaaggcg agttacatga tcccccatgt tgtgcaaaaa    5520
agcggttagc tccttcggtc ctccgatcgt tgtcagaagt aagttggccg cagtgttatc    5580
actcatggtt atggcagcac tgcataattc tcttactgtc atgccatccg taagatgctt    5640
ttctgtgact ggtgagtact caaccaagtc attctgagaa tagtgtatgc ggcgaccgag    5700
ttgctcttgc ccggcgtcaa tacgggataa taccgcgcca catagcagaa ctttaaaagt    5760
```

```
gctcatcatt ggaaaacgtt cttcggggcg aaaactctca aggatcttac cgctgttgag    5820
atccagttcg atgtaaccca ctcgtgcacc caactgatct tcagcatctt ttactttcac    5880
cagcgtttct gggtgagcaa aaacaggaag gcaaaatgcc gcaaaaaagg gaataagggc    5940
gacacggaaa tgttgaatac tcatactctt cctttttcaa tattattgaa gcatttatca    6000
gggttattgt ctcatgagcg gatacatatt tgaatgtatt tagaaaaata aacaaatagg    6060
ggttccgcgc acatttcccc gaaaagtgcc acctgacgtc taagaaacca ttattatcat    6120
gacattaacc tataaaaata ggcgtatcac gaggccctttt cgtctcgcgc gtttcggtga    6180
tgacggtgaa aacctctgac acatgcagct cccggagacg gtcacagctt gtctgtaagc    6240
ggatgccggg agcagacaag cccgtcaggg cgcgtcagcg ggtgttggcg ggtgtcgggg    6300
ctggcttaac tatgcggcat cagagcagat tgtactgaga gtgcaccata tgcggtgtga    6360
aataccgcac agatgcgtaa ggagaaaata ccgcatcagg cgccattcgc cattcaggct    6420
gcgcaactgt tgggaagggc gatcggtgcg ggcctcttcg ctattacgcc agctggcgaa    6480
agggggatgt gctgcaaggc gattaagttg ggtaacgcca gggttttccc agtcacgacg    6540
ttgtaaaacg acggccagtg aattc                                         6565
```

```
<210> SEQ ID NO 48
<211> LENGTH: 3901
<212> TYPE: DNA
<213> ORGANISM: Artificial Sequence
<220> FEATURE:
<223> OTHER INFORMATION: Synthetic: PTL20c backbone including a 400bp
      cHS4 insulator

<400> SEQUENCE: 48
ggccgcctcg gccaaacagc ccttgagttt accactccct atcagtgata gagaaaagtg      60
aaagtcgagt ttaccactcc ctatcagtga tagagaaaag tgaaagtcga gtttaccact     120
ccctatcagt gatagagaaa agtgaaagtc gagtttacca ctccctatca gtgatagaga     180 aagtgaaag tcgagtttac cagtccctat cagtgataga gaaaagtgaa agtcgagttt     240
accactccct atcagtgata gagaaaagtg aaagtcgagt ttaccactcc ctatcagtga     300
tagagaaaag tgaaagtcga gctcgccatg ggaggcgtgg cctgggcggg actggggagt     360
ggcgagccct cagatcctgc atataagcag ctgcttttg cctgtactgg gtctctctgg     420
ttagaccaga tctgagcctg ggagctctct ggctaactag ggaacccact gcttaagcct     480
caataaagct tgccttgagt gcttcaagta gtgtgtgccc gtctgttgtg tgactctggt     540
aactagagat ccctcagacc cttttagtca gtgtggaaaa tctctagcag tggcgcccga     600
acagggactt gaaagcgaaa gggaaaccag aggagctctc tcgacgcagg actcggcttg     660
ctgaagcgcg cacggcaaga ggcgaggggc ggcgactggt gagtacgcca aaaattttga     720
ctagcggagg ctagaaggag agagatgggt gcgagagcgt cagtattaag cggggagaa     780 ttagatcgcg atgggaaaaa attcggttaa ggccaggggg aaagaaaaaa tataaattaa     840
aacatatagt atgggcaagc agggagctag aacgattcgc agttaatact ggcctgttag     900
aaacatcaga aggctgtaga caaatactgg gacagctaca accatccctt cagacaggat     960
cagaagaact tagatcatta tataatacag tagcaaccct ctattgtgtg catcaaagga    1020
tagagataaa agacaccaag gaagctttag acaagataga ggaagagcaa acaaaagta    1080 agaaaaaagc acagcaagca gcaggatctt cagacctgga aattccctac aatccccaaa    1140
gtcaaggagt agtagaatct atgaataaag aattaagaa aattataggg caggtaagag    1200
```

```
atcaggctga acatcttaag acagcagtac aaatggcagt attcatccac aattttaaaa    1260
gaaaagggg  gattgggggg tacagtgcag gggaaagaat agtagacata atagcaacag    1320
acatacaaac taaagaatta caaaacaaa  ttacaaaaat tcaaaatttt cgggtttatt    1380
acagggacag cagaaatcca ctttggaaag gaccagcaaa gctcctctgg aaaggtgaag    1440
gggcagtagt aatacaagat aatagtgaca taaaagtagt gccaagaaga aaagcaaaga    1500
tcattaggga ttatggaaaa cagatggcag gtgatgattg tgtggcaagt agacaggatg    1560
aggattagaa catggaaaag tttagtaaaa caccataagg aggagatatg agggacaatt    1620
ggagaagtga attatataaa tataaagtag taaaaattga accattagga gtagcaccca    1680
ccaaggcaaa gagaagagtg gtgcagagag aaaaagagc  agtgggaata ggagctttgt    1740
tccttgggtt cttgggagca gcaggaagca ctatgggcgc agcgtcaatg acgctgacgg    1800
tacaggccag acaattattg tctggtatag tgcagcagca gaacaatttg ctgagggcta    1860
ttgaggcgca acagcatctg ttgcaactca cagtctgggg catcaagcag ctccaggcaa    1920
gaatcctggc tgtggaaaga tacctaaagg atcaacagct cctggggatt tggggttgct    1980
ctggaaaact catttgcacc actgctgtgc cttggaatgc tagttggagt aataaatctc    2040
tggaacagat ttggaatcac acgacctgga tggagtggga cagagaaatt aacaattaca    2100
caagcttaat acactcctta attgaagaat cgcaaaacca gcaagaaaag aatgaacaag    2160
aattattgga attagataaa tgggcaagtt tgtggaattg gtttaacata acaaattggc    2220
tgtggtatat aaaattattc ataatgatag taggaggctt ggtaggttta agaatagttt    2280
ttgctgtact ttctatagtg aatagagtta ggcagggata ttcaccatta tcgtttcaga    2340
cccacctccc aaccccgagg ggaccgagct caagcttcga acgcgtgcgg ccgcatcgat    2400
gccgtagtac ctttaagacc aatgacttac aaggcagctg tagatcttag ccacttttta    2460
aaagaaaagg ggggactgga agggctaatt cactcccaaa gaagacaaga tccctgcagg    2520
cattcaaggc caggctggat gtggctctgg gcagcctggg ctgctggttg atgaccctgc    2580
acatagcagg gggttggatc tggatgagca ctgtgctcct ttgcaaccca ggccgttcta    2640
tgattctgtc attctaaatc tctctttcag cctaaagctt ttccccgta  tcccccagg     2700
tgtctgcagg ctcaaagagc agcgagaagc gttcagagga aagcgatccc gtgccacctt    2760
ccccgtgccc gggctgtccc cgcacgctgc cggctcgggg atgcgggggg agcgccggac    2820
cggagcggag ccccgggcgg ctcgctgctg cccctagcg  ggggagggac gtaattacat    2880
ccctgggggc tttggggggg ggctgtcccc gtgagctccc cagatctgct ttttgcctgt    2940
actgggtctc tctggttaga ccagatctga gcctgggagc tctctggcta actagggaac    3000
ccactgctta agcctcaata aagcttcagc tgctcgagct agcagatctt tttccctctg    3060
ccaaaaatta tgggacatc  atgaagcccc ttgagcatct gacttctggc taataaagga    3120
aatttatttt cattgcaata gtgtgttgga attttttgtg tctctcactc ggaaggacat    3180
atgggagggc aaatcattta aaacatcaga atgagtattt ggtttagagt ttggcaacat    3240
atgcccatat gctggctgcc atgaacaaag gttggctata agaggtcat  cagtatatga    3300
aacagccccc tgctgtccat tccttattcc atagaaaagc cttgacttga ggttagattt    3360
ttttatatt  ttgttttgtg ttattttttt ctttaacatc cctaaaattt tccttacatg    3420
ttttactagc cagatttttc ctcctctcct gactactccc agtcatagct gtccctcttc    3480
tcttatggag atccctcgac ctgcagccca agcttggcgt aatcatggtc atagctgttt    3540
cctgtgtgaa attgttatcc gctcacaatt ccacacaaca tacgagccgg aagcataaag    3600
```

```
tgtaaagcct gggtgccta atgagtgagc taactcacat taattgcgtt gcgctcactg    3660
cccgctttcc agtcgggaaa cctgtcgtgc cagcggatcc gcatctcaat tagtcagcaa    3720
ccatagtccc gcccctaact ccgcccatcc cgccctaac tccgccagt tccgccatt       3780 ctccgcccca tggctgacta attttttta tttatgcaga ggccgaggcc gcctcggcct     3840
ctgagctatt ccagaagtag tgaggaggct ttttggagg cctaggcttt tgcaaaaagc     3900
t                                                                    3901

<210> SEQ ID NO 49
<211> LENGTH: 412
<212> TYPE: DNA
<213> ORGANISM: Artificial Sequence
<220> FEATURE:
<223> OTHER INFORMATION: Synthetic: cHS4 insulator

<400> SEQUENCE: 49
atccctgcag gcattcaagg ccaggctgga tgtggctctg gcagcctgg gctgctggtt      60 gatgaccctg cacatagcag ggggttggat ctggatgagc actgtgctcc tttgcaaccc    120
aggccgttct atgattctgt cattctaaat ctctctttca gcctaaagct ttttccccgt    180 atcccccag gtgtctgcag gctcaaagag cagcgagaag cgttcagagg aaagcgatcc    240
cgtgccacct tccccgtgcc cgggctgtcc ccgcacgctg ccggtcggg gatgcggggg    300 gagcgccgga ccggagcgga gccccgggcg gctcgctgct gcccctagc ggggaggga    360 cgtaattaca tccctggggg ctttgggggg gggctgtccc cgtgagctcc cc          412

<210> SEQ ID NO 50
<211> LENGTH: 5221
<212> TYPE: DNA
<213> ORGANISM: Artificial Sequence
<220> FEATURE:
<223> OTHER INFORMATION: Synthetic: sGbGM vector cassette

<400> SEQUENCE: 50
ggagccagaa gcaccataag ggacatgggg atcctctaga gtcgagctcg cgaggatcat     60
caccggtgct agccgataag ggagccagca gacctctgat ctcttcctga atgctaatct    120
taaacatcct gaggaagaat gggacttcca tttggggtgg gcctatgata gggtaataag    180
acagtagtga atatcaagct acaaaaagcc ccctttcaaa ttcttctcag tcctaacttt    240
tcatactaag cccagtcctt ccaaagcaga ctgtgaaaga gtgatagttc cgggagacta    300
gcaccggcta gccgagcttg gaacactttc ccttcattaa gaaccatcct tgctactcag    360
ctgcaatcaa tccagccccc aggtcttcac tgaacctttt cccatctctt ccaaaacatc    420
tgtttctgag aagtcctgtc ctatagaggt ctttcttccc accggatttc tcctacacca    480
tttactccca cttgcagaac tcccgtgtac aagtgtcttt actgctttta tttgctcaac    540
aaaatgcaca tctcatataa aaataaatga ggagcatgca caccacaa acacaaacag    600 gcatgcagaa atacacatac acacttccct caatataaac cctttgtggc tcatatattt    660
aaaaagatgt aaaaaaaaga gctgaagaaa atcatgtgtg atctctcagc agaatagatt    720
tattatttgt attgcttgca gaataaagcc tatccttgaa agctctgaat catgggcaag    780
aggctcagtg gtatctggag gacagggcac tggccactgc agtcaccatc ttctgccagg    840
aagcctgcac ctcaggggtg aattctttgc caaagtgaat ggccagcacg gtgaccagca    900
cgttgcccag gagctgtggg aggaagataa gaggtatgaa catgattagc aaaagggcct    960
```

```
agcttggact cagaataatc cagccttatc ccaaccataa aataaaagca gaatggtagc    1020
tggattgtag ctgctattag caatatgaaa cctcttacat cagttacaat ttatatgcag    1080
aaatatttat atgcagaaat attgctattg ccttaaccca gaaattatca ctgttattct    1140
ttagaatggt gcaaagaggc atgatacatt gtatcattat tgccctgaaa gaaagagatt    1200
agggaaagta ttagaaataa gataaacaaa aaagtatatt aaaagaagaa agcattttt     1260 aaaattacaa atgcaaaatt accctgattt ggtcaatatg tgtaccctgt tacttctccc    1320
cttcctatga catgaactta accatagaaa agaaggggaa agaaaacatc aagggtccca    1380
tagactcacc ttgaagttct caggatccac atgcagcttg tcacagtgca gttcactcag    1440
ctgggcaaag gtgcccttga gatcatccag gtgctttatg gcatctccca aggaagtcag    1500
caccttcttg ccatgtgcct tgactttggg gttgcccatg atggcagagg cagaggacag    1560
gttgccaaag ctgtcaaaga acctctgggt ccatgggtag acaaccagga gcctgtgaga    1620
ttgacaagaa cagtttgaca gtcagaaggt gccacaaatc ctgagaagca acctggactt    1680
ttgccaggca cagggtcctt ccttcccctcc cttgtcctgg tcaccagagc ctaccttccc    1740
agggtttctc ctccagcatc ttccacattc accttgtccc acaggcttgt gatagtagcc    1800
ttgtcctcct ctgtgaaatg acccatgtg tctgtttgag gttgctagtg aacacagttg    1860
tgtcagaagc aaatgtaagc aatagatggc tctgccctga cttttatgcc cagccctggc    1920
tcctgccctc cctgctcctg ggagtagatt ggccaaccct agggtgtggc tccacagggt    1980
gaggtctaag tgatgacagc cgtacctgtc cttggctctt ctggcactgg cttaggagtt    2040
ggacttcaaa ccctcagccc tccctctaag atatatctct tggccccata ccatcagtac    2100
aaattgctac taaaaacatc ctcctttgca agtgtattta cgacggtatc gatgtatgtg    2160
agcatgtgtc ctctaacagc acaggccttt tgccacctag ctgtccaggg gtgccttaaa    2220
atggcaaaca aggtttgttt tcttttcctg ttttcatgcc ttcctcttcc atatccttgt    2280
ttcatattaa tacatgtgta tagatcctaa aaatctatac acatgtatta ataaagcctg    2340
attctgccgc ttctaggtat agaggccacc tgcaagataa atatttgatt cacaataact    2400
aatcattcta tggcaattga taacaacaaa tatatatata tatatatata tacgtatatg    2460
tgtatatata tatatatata tatatattca ggaaataata tattctagaa tatgtcacat    2520
tctgtctcag gcatccattt tctttatgat gccgtttgag gtggagtttt agtcaggtgg    2580
tcagcttctc cttttttttg ccatctgccc tgtaagcatc ctgctgggga cccagatagg    2640
agtcatcact ctaggctgag aacatctggg cacacaccct aagcctcagc atgactcatc    2700
atgactcagc attgctgtgc ttgagccaga aggtttgctt agaaggttac acagaaccag    2760
aaggcggggg tggggcactg acccgacag gggcctggcc agaactgctc atgcttggac    2820
tatgggaggt cactaatgga gacacacaga aatgtaacag gaactaaggg aattccggtg    2880
ccctgcttag gagcttaatc tttaatgaaa gctaagcttt cattaaaaaa agtctaacca    2940
gctgcattcg actttgactg cagcagctgg ttagaaggtt ctactggagg agggtcccag    3000
cccattgcta aattaacatc aggctctgag actggcagta tatctctaac agtggttgat    3060
gctatcttct ggaacttgcc tgctacattg agaccactga cccatacata ggaagcccat    3120
agctctgtcc tgaactgtta ggccactggt ccagagagtg tgcatctcct ttgatcctca    3180
taataaccct atgagataga cacaattatt actcttactt tatagatgat gatcctgaaa    3240
acataggagt caaggcactt gccccctagct gggggtatag gggagcagtc ccatgtagta    3300
gtagaatgaa aaatgctgct atgctgtgcc tcccccacct ttcccatgtc tgccctctac    3360
```

```
tcatggtcta tctctcctgg ctcctgggag tcatggactc cacccagcac caccaacctg    3420
acctaaccac ctatctgagc ctgccagcct ataacccatc tgggccctga tagctggtgg    3480
ccagccctga ccccacccca ccctccctgg aacctctgat agacacatct ggcacaccag    3540
ctcgcaaagt caccgtgagg gtcttgtgtt tgctgagtca aaattccttg aaatccaagt    3600
ccttagagac tcctgctccc aaatttacag tcatagactt cttcatggct gtctccttta    3660
tccacagaat gattcctttg cttcattgcc ccatccatct gatcctcctc atcagtgcag    3720
cacagggccc atgagcagta gctgcagagt ctcacatagg tctggcactg cctctgacat    3780
gtccgacctt aggcaaatgc ttgactcttc tgagctcgga tcccttgagc tcaggaggtc    3840
aaggctgcag tgagacatga tcttgccact gcactccagc ctggacagca gagtgaaacc    3900
ttgcctcacg aaacagaata caaaaacaaa caaacaaaaa actgctccgc aatgcgcttc    3960
cttgatgctc taccacatag gtctgggtac tttgtacaca ttatctcatt gctgttcata    4020
attgttagat taattttgta atattgatat tattcctaga aagctgaggc tcaagatga    4080 taacttttat tttctggact tgtaatagct ttctcttgta ttcaccatgt tgtaactttc    4140
ttagagtagt aacaatataa agttattgtg agttttttgca aacacagcaa acacaacgac    4200
ccatatagac attgatgtga aattgtctat tgtcaattta tgggaaaaca agtatgtact    4260
ttttctacta agccattgaa acaggaataa cagaacaaga ttgaaagaat acattttccg    4320
aaattacttg agtattatac aaagacaagc acgtggacct gggaggaggg ttattgtcca    4380
tgactggtgt gtggagacaa atgcaggttt ataatagatg ggatggcatc tagcgcaatg    4440
actttgccat cacttttaga gagctcttgg gggcccagt acacaagagg ggacgcaggg     4500
tatatgtaga catctcattc ttttttcttag tgtgagaata agaatagcca tgacctgagt    4560
ttatagacaa tgagcccttt tctctctccc actcagcagc tatgagatgg cttgccctgc    4620
ctctctacta ggctgactca ctccaaggcc cagcaatggg cagggctctg tcagggcttt    4680
gatagcacta tctgcagagc cagggccgag aaggggtgga ctccagagac tctccctccc    4740
attcccgagc agggtttgct tatttatgca tttaaatgat atatttattt taaaagaaat    4800
aacaggagac tgcccagccc tggctgtgac atggaaacta tgtagaatat tttgggttcc    4860 atttttttt ccttctttca gttagaggaa aaggggctca ctgcacatac actagacaga     4920
aagtcaggag ctttgaatcc aagcctgatc atttccatgt catactgaga aagtccccac    4980
ccttctctga gcctcagttt ctcttttat aagtaggagt ctggagtaaa tgatttccaa     5040
tggctctcat ttcaatacaa aatttccgtt tattaaatgc atgagcttct gttactccaa    5100
gactgagaag gaaattgaac ctgagactca ttgactggca agatgtcccc agaggctctc    5160
attcagcaat aaaattctca ccttcaccca ggcccactga gtgtcagatt tgcatgcgga    5220
t                                                                    5221
```

<210> SEQ ID NO 51  
<211> LENGTH: 100  
<212> TYPE: DNA  
<213> ORGANISM: Artificial Sequence  
<220> FEATURE:  
<223> OTHER INFORMATION: Synthetic: Exon 1 (HBG17101-7152; sGbGm reverse strand 1735-1834)

<400> SEQUENCE: 51

```
cttcccaggg tttctcctcc agcatcttcc acattcacct tgtcccacag gcttgtgata     60
gtagccttgt cctcctctgt gaaatgaccc atggtgtctg                          100
```

<210> SEQ ID NO 52
<211> LENGTH: 223
<212> TYPE: DNA
<213> ORGANISM: Artificial Sequence
<220> FEATURE:
<223> OTHER INFORMATION: Synthetic: Exon 2 (HBG17323-7545; sGbGm reverse strand 1612-1320)

<400> SEQUENCE: 52
cttgaagttc tcaggatcca catgcagctt gtcacagtgc agttcactca gctgggcaaa    60
ggtgcccttg agatcatcca ggtgctttat ggcatctccc aaggaagtca gcaccttctt   120
gccatgtgcc ttgactttgg ggttgcccat gatggcagag gcagaggaca ggttgccaaa   180
gctgtcaaag aacctctggg tccatgggta gacaaccagg agc                     223

<210> SEQ ID NO 53
<211> LENGTH: 216
<212> TYPE: DNA
<213> ORGANISM: Artificial Sequence
<220> FEATURE:
<223> OTHER INFORMATION: Synthetic: Exon 3 (HBG1 8412-8627; sGbGm reverse strand 698-913)

<400> SEQUENCE: 53
gtgatctctc agcagaatag atttattatt tgtattgctt gcagaataaa gcctatcctt    60
gaaagctctg aatcatgggc aagaggctca gtggtatctg gaggacaggg cactggccac   120
tgcagtcacc atcttctgcc aggaagcctg cacctcaggg gtgaattctt tgccaaagtg   180
aatggccagc acggtgacca gcacgttgcc caggag                             216

<210> SEQ ID NO 54
<211> LENGTH: 303
<212> TYPE: DNA
<213> ORGANISM: Artificial Sequence
<220> FEATURE:
<223> OTHER INFORMATION: Synthetic: 7SK-sh734 Sequence cassette

<400> SEQUENCE: 54
atcgacgtgc agtatttagc atgccccacc catctgcaag cattctgga tagtgtcaaa     60 acagccggaa atcaagtccg tttatctcaa actttagcat tttgggaata aatgatattt   120
gctatgctgg ttaaattaga ttttagttaa atttcctgct gaagctctag tacgataagt   180
aacttgacct aagtgtaaag ttgagatttc cttcaggttt atatagcttg tgcgccgcct   240
gggtacctca ggatatgccc ttgactattt gtccgacata gtcaagggca tatccttttt   300
tgt                                                                 303

<210> SEQ ID NO 55
<211> LENGTH: 539
<212> TYPE: DNA
<213> ORGANISM: Artificial Sequence
<220> FEATURE:
<223> OTHER INFORMATION: Synthetic: sGbGm A gamma-globin sequence 5-3 complementary strand

<400> SEQUENCE: 55
cagacaccat gggtcatttc acagaggagg acaaggctac tatcacaagc ctgtgggaca    60
aggtgaatgt ggaagatgct ggaggagaaa ccctgggaag ctcctggtt gtctacccat    120 ggacccagag gttctttgac agctttggca acctgtcctc tgcctctgcc atcatgggca   180
accccaaagt caaggcacat ggcaagaagg tgctgacttc cttgggagat gccataaagc   240

```
acctggatga tctcaagggc acctttgccc agctgagtga actgcactgt gacaagctgc    300
atgtggatcc tgagaacttc aagctcctgg gcaacgtgct ggtcaccgtg ctggccattc    360
actttggcaa agaattcacc cctgaggtgc aggcttcctg gcagaagatg gtgactgcag    420
tggccagtgc cctgtcctcc agataccact gagcctcttg cccatgattc agagctttca    480
aggataggct ttattctgca agcaatacaa ataataaatc tattctgctg agagatcac     539
```

<210> SEQ ID NO 56
<211> LENGTH: 769
<212> TYPE: DNA
<213> ORGANISM: Artificial Sequence
<220> FEATURE:
<223> OTHER INFORMATION: Synthetic: REV response element (RRE)

<400> SEQUENCE: 56

```
aggaggagat atgagggaca attggagaag tgaattatat aaatataaag tagtaaaaat     60
tgaaccatta ggagtagcac ccaccaaggc aaagagaaga gtggtgcaga gagaaaaaag    120
agcagtggga ataggagctt tgttccttgg gttcttggga gcagcaggaa gcactatggg    180
cgcagcgtca atgacgctga cggtacaggc cagacaatta ttgtctggta tagtgcagca    240
gcagaacaat ttgctgaggg ctattgaggc gcaacagcat ctgttgcaac tcacagtctg    300
gggcatcaag cagctccagg caagaatcct ggctgtggaa agatacctaa aggatcaaca    360
gctcctgggg atttggggtt gctctggaaa actcatttgc accactgctg tgccttggaa    420
tgctagttgg agtaataaat ctctggaaca gatttggaat cacacgacct ggatggagtg    480
ggacagagaa attaacaatt acacaagctt aatacactcc ttaattgaag aatcgcaaaa    540
ccagcaagaa aagaatgaac aagaattatt ggaattagat aaatgggcaa gtttgtggaa    600
ttggtttaac ataacaaatt ggctgtggta tataaaatta ttcataatga tagtaggagg    660
cttggtaggt ttaagaatag ttttgctgt actttctata gtgaatagag ttaggcaggg    720
atattcacca ttatcgtttc agacccacct cccaaccccg aggggaccg                769
```

<210> SEQ ID NO 57
<211> LENGTH: 3055
<212> TYPE: DNA
<213> ORGANISM: Artificial Sequence
<220> FEATURE:
<223> OTHER INFORMATION: Synthetic: Locus Control Region

<400> SEQUENCE: 57

```
gtatgtgagc atgtgtcctc taacagcaca ggccttttgc cacctagctg tccaggggtg     60
ccttaaaatg gcaaacaagg tttgttttct tttcctgttt tcatgccttc ctcttccata    120
tccttgtttc atattaatac atgtgtatag atcctaaaaa tctatacaca tgtattaata    180
aagcctgatt ctgccgcttc taggtataga ggccacctgc aagataaata tttgattcac    240
aataactaat cattctatgg caattgataa caacaaatat atatatatat atatatatac    300
gtatatgtgt atatatatat atatattcag gaaataatat attctagaat atgtcacatt    360
ctgtctcagg catccatttt ctttatgatg ccgtttgagg tggagtttta gtcaggtggt    420
cagcttctcc tttttttgc catctgccct gtaagcatcc tgctgggac ccagatagga    480 gtcatcactc taggctgaga acatctgggc acacaccta agcctcagca tgactcatca    540
tgactcagca ttgctgtgct tgagccagaa ggtttgctta aaggttaca cagaaccaga    600 aggcggggt ggggcactga ccccgacagg ggcctggcca gaactgctca tgcttggact    660
```

```
atgggaggtc actaatggag acacacagaa atgtaacagg aactaaggga attccggtgc    720
cctgcttagg agcttaatct ttaatgaaag ctaagctttc attaaaaaaa gtctaaccag    780
ctgcattcga ctttgactgc agcagctggt tagaaggttc tactggagga gggtcccagc    840
ccattgctaa attaacatca ggctctgaga ctggcagtat atctctaaca gtggttgatg    900
ctatcttctg gaacttgcct gctacattga gaccactgac ccatacatag gaagcccata    960
gctctgtcct gaactgttag gccactggtc cagagagtgt gcatctcctt tgatcctcat   1020
aataaccccta tgagatagac acaattatta ctcttacttt atagatgatg atcctgaaaa   1080
cataggagtc aaggcacttg cccctagctg ggggtatagg ggagcagtcc catgtagtag   1140
tagaatgaaa aatgctgcta tgctgtgcct cccccacctt tcccatgtct gccctctact   1200
catggtctat ctctcctggc tcctgggagt catggactcc acccagcacc accaacctga   1260
cctaaccacc tatctgagcc tgccagccta acccatct gggccctgat agctggtggc    1320
cagccctgac cccaccccac cctccctgga acctctgata gacacatctg gcacaccagc   1380
tcgcaaagtc accgtgaggg tcttgtgttt gctgagtcaa aattccttga aatccaagtc   1440
cttagagact cctgctccca aatttacagt catagacttc ttcatggctg tctcctttat   1500
ccacagaatg attcctttgc ttcattgccc catccatctg atcctcctca tcagtgcagc   1560
acagggccca tgagcagtag ctgcagagtc tcacataggt ctggcactgc ctctgacatg   1620
tccgacctta ggcaaatgct tgactcttct gagctcggat cccttgagct caggaggtca   1680
aggctgcagt gagacatgat cttgccactg cactccagcc tggacagcag agtgaaacct   1740
tgcctcacga aacagaatac aaaaacaaac aaacaaaaaa ctgctccgca atgcgcttcc   1800
ttgatgctct accacatagg tctgggtact ttgtacacat tatctcattg ctgttcataa   1860
ttgttagatt aattttgtaa tattgatatt attcctagaa agctgaggcc tcaagatgat   1920
aacttttatt ttctggactt gtaatagctt tctcttgtat tcaccatgtt gtaactttct   1980
tagagtagta acaatataaa gttattgtga gttttttgcaa acacagcaaa cacaacgacc   2040
catatagaca ttgatgtgaa attgtctatt gtcaatttat gggaaaacaa gtatgtactt   2100
tttctactaa gccattgaaa caggaataac agaacaagat tgaaagaata cattttccga   2160
aattacttga gtattataca aagacaagca cgtggacctg ggaggagggt tattgtccat   2220
gactggtgtg tggagacaaa tgcaggttta taatagatgg gatggcatct agcgcaatga   2280
ctttgccatc acttttagag agctcttggg ggccccagta cacaagaggg gacgcagggt   2340
atatgtagac atctcattct ttttcttagt gtgagaataa gaatagccat gacctgagtt   2400
tatagacaat gagcccttttt ctctctccca ctcagcagct atgagatggc ttgccctgcc   2460
tctctactag gctgactcac tccaaggccc agcaatgggc agggctctgt cagggctttg   2520
atagcactat ctgcagagcc agggccgaga aggggtggac tccagagact ctccctccca   2580
ttcccgagca gggtttgctt atttatgcat ttaaatgata tatttatttt aaaagaaata   2640
acaggagact gcccagccct ggctgtgaca tggaaactat gtagaatatt ttgggttcca   2700
ttttttttc cttctttcag ttagaggaaa aggggctcac tgcacataca ctagacagaa   2760
agtcaggagc tttgaatcca agcctgatca tttccatgtc atactgagaa agtccccacc   2820
cttctctgag cctcagtttc tctttttata agtaggagtc tggagtaaat gatttccaat   2880
ggctctcatt tcaatacaaa atttccgttt attaaatgca tgagcttccg ttactccaag   2940
actgagaagg aaattgaacc tgagactcat tgactggcaa gatgtcccca gaggctctca   3000
ttcagcaata aaattctcac cttcacccag gcccactagt gtcagatttg catgc        3055
```

<210> SEQ ID NO 58
<211> LENGTH: 43
<212> TYPE: DNA
<213> ORGANISM: Artificial Sequence
<220> FEATURE:
<223> OTHER INFORMATION: Synthetic: Agosh 734 5-3

<400> SEQUENCE: 58
atagtcaagg gcatatcctc aagaaggata tgcccttgac tac    43

<210> SEQ ID NO 59
<211> LENGTH: 1435
<212> TYPE: DNA
<213> ORGANISM: Homo sapiens
<220> FEATURE:
<221> NAME/KEY: misc_feature
<223> OTHER INFORMATION: Homo sapiens hypoxanthine
    phosphoribosyltransferase 1 (HPRT1), mRNA

<400> SEQUENCE: 59
ggcggggcct gcttctcctc agcttcaggc ggctgcgacg agccctcagg cgaacctctc    60
ggctttcccg cgcggcgccg cctcttgctg cgcctccgcc tcctcctctg ctccgccacc   120
ggcttcctcc tcctgagcag tcagcccgcg cgccggccgg ctccgttatg gcgacccgca   180
gccctggcgt cgtgattagt gatgatgaac caggttatga ccttgattta ttttgcatac   240
ctaatcatta tgctgaggat ttggaaaggg tgtttattcc tcatggacta attatggaca   300
ggactgaacg tcttgctcga gatgtgatga aggagatggg aggccatcac attgtagccc   360
tctgtgtgct caaggggggc tataaattct ttgctgacct gctggattac atcaaagcac   420
tgaatagaaa tagtgataga tccattccta tgactgtaga tttttatcaga ctgaagagct   480 attgtaatga ccagtcaaca ggggacataa agtaattgg tggagatgat ctctcaactt   540
taactggaaa gaatgtcttg attgtggaag atataattga cactggcaaa acaatgcaga   600
cttttgcttt ccttggtcagg cagtataatc aaagatggt caaggtcgca agcttgctgg   660
tgaaaaggac cccacgaagt gttggatata agccagactt tgttggattt gaaattccag   720
acaagtttgt tgtaggatat gcccttgact ataatgaata cttcagggat ttgaatcatg   780
tttgtgtcat tagtgaaact ggaaaagcaa atacaaagc ctaagatgag agttcaagtt   840
gagtttggaa acatctggag tcctattgac atcgccagta aaattatcaa tgttctagtt   900
ctgtggccat ctgcttagta gagctttttg catgtatctt ctaagaattt tatctgtttt   960
gtactttaga aatgtcagtt gctgcattcc taaactgttt atttgcacta tgagcctata  1020
gactatcagt tccctttggg cggattgttg tttaacttgt aaatgaaaaa attctcttaa  1080
accacagcac tattgagtga aacattgaac tcatatctgt aagaaataaa gagaagtat  1140 attagttttt taattggtat tttaattttt atatatgcag gaaagaatag aagtgattga  1200
atattgttaa ttataccacc gtgtgttaga aaagtaagaa gcagtcaatt tcacatcaa  1260 agacagcatc taagaagttt tgttctgtcc tggaattatt ttagtagtgt tcagtaatg  1320 ttgactgtat tttccaactt gttcaaatta ttaccagtga atctttgtca gcagttccct  1380
tttaaatgca aatcaataaa ttcccaaaaa tttaaaaaaa aaaaaaaaa aaaaa       1435

<210> SEQ ID NO 60
<211> LENGTH: 42
<212> TYPE: DNA
<213> ORGANISM: Artificial Sequence
<220> FEATURE:

```
<223> OTHER INFORMATION: Synthetic: miRNA 451 hairpin sequence

<400> SEQUENCE: 60
aaaccgttac cattactgag tttagtaatg gtaatggttc tc                           42

<210> SEQ ID NO 61
<211> LENGTH: 23
<212> TYPE: DNA
<213> ORGANISM: Artificial Sequence
<220> FEATURE:
<223> OTHER INFORMATION: Synthetic: sgRNA candidate for knock down of
      human HPRT

<400> SEQUENCE: 61
gttatggcga cccgcagccc tgg                                               23

<210> SEQ ID NO 62
<211> LENGTH: 212
<212> TYPE: DNA
<213> ORGANISM: Artificial Sequence
<220> FEATURE:
<223> OTHER INFORMATION: Synthetic: left homology arm from target CCR5
      gene region

<400> SEQUENCE: 62
gcttcttctc tggaatcttc ttcatcatcc tcctgacaat cgataggtac ctggctgtcg       60
tccatgctgt gtttgcttta aaagccagga cggtcacctt tggggtggtg acaagtgtga      120
tcacttgggt ggtggctgtg tttgcgtctc aagcttttcg aagcggccgc ggatatcggc      180
tccggtgccc gtcagtgggc agagcgcaca tc                                   212

<210> SEQ ID NO 63
<211> LENGTH: 221
<212> TYPE: DNA
<213> ORGANISM: Artificial Sequence
<220> FEATURE:
<223> OTHER INFORMATION: Synthetic: left homology arm from target CCR5
      gene region

<400> SEQUENCE: 63
aaagcatttt tttcactgca ttctagttgt ggtttgtcca aactcatcaa tgtatcttat       60
catctacgcg tccaggaatc atctttacca gatctcaaaa agaaggtctt cattacacct      120
gcagctctca ttttccatac agtcagtatc aattctggaa gaatttccag acattaaaga      180
tagtcatctt ggggctggtc ctgccgctgc ttgtcatggt c                         221

<210> SEQ ID NO 64
<211> LENGTH: 238
<212> TYPE: DNA
<213> ORGANISM: Artificial Sequence
<220> FEATURE:
<223> OTHER INFORMATION: Synthetic: EF1a promoter

<400> SEQUENCE: 64
ggatatcggc tccggtgccc gtcagtgggc agagcgcaca tcgcccacag tccccgagaa       60
gttgggggga ggggtcggca attgaaccgg tgcctagaga aggtggcgcg ggtaaactg       120 ggaaagtgat gtcgtgtact ggctccgcct ttttcccgag ggtgggggag aaccgtatat      180
aagtgcagta gtcgccgtga acgttctttt cgcaacgggt ttgccgccag aacacagg       238

<210> SEQ ID NO 65
<211> LENGTH: 128
<212> TYPE: DNA
```

```
<213> ORGANISM: Artificial Sequence
<220> FEATURE:
<223> OTHER INFORMATION: Synthetic: SV40 promoter

<400> SEQUENCE: 65
aacttgttta ttgcagctta taatggttac aaataaagca atagcatcac aaatttcaca    60
aataaagcat ttttttcact gcattctagt tgtggtttgt ccaaactcat caatgtatct   120
tatcatct                                                            128

<210> SEQ ID NO 66
<211> LENGTH: 87
<212> TYPE: DNA
<213> ORGANISM: Artificial Sequence
<220> FEATURE:
<223> OTHER INFORMATION: Synthetic: Beta globin promoter

<400> SEQUENCE: 66
ggtgtctgtt tgaggttgct agtgaacaca gttgtgtcag aagcaaatgt aagcaataga    60
tggctctgcc ctgacttta tgcccag                                         87

<210> SEQ ID NO 67
<211> LENGTH: 111
<212> TYPE: DNA
<213> ORGANISM: Artificial Sequence
<220> FEATURE:
<223> OTHER INFORMATION: Synthetic: miRNA734 de novo (DNA form)

<400> SEQUENCE: 67
acccgtacat attttgtgt agctctagtt tatagtcaag gcatatcct tgtgtttttt      60 ttgaaggata tgcccttgac tataaactag cgctacactt tttcgtcttg t            111

<210> SEQ ID NO 68
<211> LENGTH: 111
<212> TYPE: DNA
<213> ORGANISM: Artificial Sequence
<220> FEATURE:
<223> OTHER INFORMATION: Synthetic: miRNA211 de novo (DNA form)

<400> SEQUENCE: 68
acccgtacat attttgtgt agctctagtt ataaatcaag gtcataacct tgtgtttttt     60
ttgaaggtta tgaccttgat ttataactag cgctacactt tttcgtcttg t            111

<210> SEQ ID NO 69
<211> LENGTH: 23
<212> TYPE: DNA
<213> ORGANISM: Artificial Sequence
<220> FEATURE:
<223> OTHER INFORMATION: Synthetic: sgRNA candidate for knock down of
      human HPRT

<400> SEQUENCE: 69
gcgggtcgcc ataacggagc cgg                                            23
```

COMPOSITIONS AND METHODS FOR TREATING BETA-HEMOGLOBINOPATHIES

CROSS REFERENCE TO RELATED APPLICATIONS

The present application claims the benefit of the filing date of U.S. Provisional Patent Application No. 62/653,913, filed on Apr. 6, 2018; the benefit of the filing date of U.S. Provisional Patent Application No. 62/541,931, filed on Aug. 7, 2017; and also, the benefit of the filing date of U.S. Provisional Patent Application No. 62/533,719 filed on Jul. 18, 2017, the disclosures of which are each hereby incorporated by reference herein in their entireties.

FIELD OF DISCLOSURE

This disclosure generally relates to the fields of molecular biology and, in particular, vectors and host cells transduced by vectors.

BACKGROUND OF THE DISCLOSURE

β-Hemoglobinopathies, including beta-thalassemia and sickle-cell disease (SCD), are a heterogeneous group of commonly inherited disorders affecting the function or levels of hemoglobin. SCD and β-thalassemia are the most common monogenic disorders in the world with approximately 400,000 affected births each year. Clinical manifestations typically appear several months after birth during the switch from fetal hemoglobin (HbF) to adult β-globin (HbA) and can be severe with substantial morbidity and mortality. Allogenic bone marrow transplantation is curative but limited to those patients with an appropriately matched donor. Autologous gene therapy, which utilizes a patient's own cells, is an attractive therapeutic option.

β-thalassemia is an inherited blood disorder characterized by reduced levels of functional hemoglobin. β-thalassemias are caused by mutations in hemoglobin subunit beta (hereinafter the "HBB gene"), which is believed to be inherited in an autosomal recessive fashion. β-thalassemia major, defined clinically as transfusion-dependent, is caused by reduced or absent synthesis of the beta chain of hemoglobin. The severity of the disease depends on the nature of the mutation with variable outcomes ranging from severe anemia to clinically asymptomatic individuals.

Hundreds of different mutations have been described affecting beta-globin levels via effects on a wide range of processes, including transcription, mRNA splicing/processing, RNA stability, translation, and globin peptide stability. It is believed that the low beta-globin content allows the excess alpha-globin chains to precipitate in erythroid precursors. It is further believed that the alpha-globin aggregates cause cell membrane damage and lead to early erythroid precursor death. The resultant ineffective erythropoiesis found in patients, if severe, may necessitate frequent blood transfusions.

Sickle cell anemia ("SCA") results from a single point mutation in Exon 1 of the beta-globin gene leading to the replacement of Glutamic acid with Valine at position 6 in the mutated sickled form of hemoglobin, hemoglobin S (HbS). There are other genotypes, in addition to homozygous hemoglobin S ("HbSS"), that can result in SCD. While classical SCA is often defined as homozygous HbSS, homozygous hemoglobin C ("HbSC") and thalassemia ("HbS/β$^0$") are common genotypes that have essentially the same disease manifestations. HbS polymerizes upon deoxygenation resulting in sickle-shaped red blood cells ("RBCs") that occlude microvasculature. SCD is characterized clinically by varying degree of anemia, and episodic vasoocclusive crisis leading to multi-organ damage and premature death. Besides sickling, excessive hemolysis and a state of chronic inflammation exist.

SCD patients account for approximately 75,000 USA hospitalizations per year, resulting in an estimated annual expenditure of $475 million dollars. Worldwide, SCD is second only to thalassemia in incidence of monogenic disorders, with more than 200,000 children born annually in Africa with this disease. Medical management options currently available for SCD include supportive management of vasoocclusive crisis, long-term transfusions to avoid or prevent recurrence of severe complications of SCD such as stroke or acute chest syndrome, and fetal hemoglobin (HbF) induction with hydroxyurea. A matched allogeneic hematopoietic stem cell (HSC) transplantation is believed to be curative but restricted by the availability of matched related donors and has potential serious complications. In fetal life, the gamma-globin gene (resulting in HbF; alpha$_2$gamma$_2$) is the predominant gene expressed by the beta-globin locus and the beta-globin gene expression is repressed. However, after birth, the expression of fetal gamma-globin gene decreases to negligible levels, with a concomitant increase in beta-globin expression. In adult life, fetal gamma-globin transcripts are highly silenced, i.e. gene expression is regulated to prevent or reduce expression of gamma-globin. This change of expression results in decreased HbF with a corresponding increase in HbA (alpha$_2$beta$_2$). Gamma-globin is known to have anti-sickling properties and, thus the addition of this gene is considered for gene therapy.

Hemoglobinopathies, especially SCD, are prime targets for gene therapy for a variety of reasons. Their high prevalence, significant morbidity and mortality, and the resulting high cost of lifelong palliative medical care portends that a curative therapy can greatly improve patient outcomes and significantly reduce associated medical costs. Gene therapy for β-hemoglobinopathies by ex vivo lentiviral transfer of a therapeutic β-globin gene into autologous CD34$^+$ hematopoietic stem/progenitor cells (HSPC) has been evaluated in human clinical trials for over the past 9 years. Autologous HSC transplantation based on myeloablative therapy has resulted in transfusion independence or a reduction in transfusion volumes in β-thalassemia patients greater than 12 months after gene therapy. Recently, curative response has been reported in an adolescent with SSD (see Thompson et. al., "Gene therapy in patients with transfusion-dependent Beta-Thalassemia," N Engl J Med. 2018 Apr. 19; 378(16): 1479-1493, the disclosure of which is hereby incorporated by reference herein in its entirety). Despite promising results, the majority of subjects in these trials failed to achieve levels of engraftment of gene-corrected autologous HSPC or reach a threshold level of expression of the therapeutic protein associated with clinical benefit.

BRIEF SUMMARY OF THE DISCLOSURE

Gene therapy strategies to modify human stem cells hold great promise for curing many human diseases, included hemoglobinopathies. It is believed that the engraftment of gene modified stem cells may be enhanced by engineering stem cells in which hypoxanthine guanine phosphoribosyitransferase ("HPRT") expression is knocked down, thereby enabling the selection of genetically modified cells by conferring resistance to a guanine analog antimetabolite.

In one aspect of the present disclosure is a composition including components which introduce a therapeutic gene into a hematopoietic stem cell ("HSC") which also contemporaneously decrease expression of HPRT in the HSC. In some embodiments, the composition includes a first component designed to effectuate a decrease in HPRT expression (e.g. an agent designed to knockdown HPRT or an agent designed to knockout HPRT). In some embodiments, the composition includes a second component, namely a nucleic acid encoding a therapeutic gene. In some embodiments, the composition includes a lentiviral expression vector including a first nucleic acid encoding an agent designed to knockdown the HPRT gene or otherwise effectuate a decrease in HPRT expression; and a second nucleic acid sequence encoding the therapeutic gene. In some embodiments, the lentiviral expression vector may be incorporated within a nanocapsule, such as one adapted to target HSCs. In some embodiments, the therapeutic gene is gamma globin.

In some embodiments, the first component is designed to knockdown HPRT. In some embodiments, the first component is an RNAi, such as an siRNA, a shRNA or a miRNA. In some embodiments, the first component is an antisense oligonucleotide that targets unspliced HPRT mRNA.

In some embodiments, the first component is designed to knockout HPRT. In some embodiments, the first component is a fusion protein comprising a zinc finger protein that binds to an endogenous hypoxanthine-guanine HPRT gene and a cleavage domain, wherein the fusion protein modifies the endogenous HPRT gene. In some embodiments, a single guide RNA (sgRNA) loaded with Cas9 may be used to target the CCR5 region (target sequence, 5'-GAGCAAGCTCAGTTTACACC-3') in the CCR5 gene locus (human chromosome 3) to "knock in" a Pol-II-driven shHPRT so as effectuate "knockdown expression" of HPRT (see, for example, SEQ ID NOS: 61 and 69). In some embodiments, the first component designed to knockout HPRT is included within a non-viral delivery vehicle. In some embodiments, the first component designed to knockout HPRT is included within a nanocapsule, such as a nanocapsule adapted to target HSCs. In some embodiments, the composition includes (i) a nanocapsule configured to deliver and/or release the first component designed to knockout HPRT; and (ii) a lentiviral expression vector including the second component, i.e. the nucleic acid encoding the therapeutic gene.

In another aspect of the present disclosure is an expression vector including (i) a first nucleic acid sequence encoding an RNAi, an antisense oligonucleotide, or an exon skipping agent targeting an HPRT gene; and (ii) a second nucleic acid sequence encoding a therapeutic gene. In some embodiments, the first nucleic acid encoding the RNAi encodes a small hairpin ribonucleic acid molecule ("shRNA") targeting HPRT. In some embodiments, the first nucleic acid encoding the shRNA targeting the HPRT gene has a sequence having at least 80% identity to that of SEQ ID NO: 30. In some embodiments, the first nucleic acid sequence encoding the shRNA targeting the HPRT gene has a sequence having at least 90% identity to that of SEQ ID NO: 30. In some embodiments, the first nucleic acid sequence encoding the shRNA targeting the HPRT gene has a sequence having at least 95% identity to that of SEQ ID NO: 30. In some embodiments, the first nucleic acid sequence encoding the shRNA targeting the HPRT gene has a sequence having at least 97% identity to that of SEQ ID NO: 30. In some embodiments, the first nucleic acid sequence encoding the shRNA targeting the HPRT gene has a sequence of SEQ ID NO: 30.

In some embodiments, the first nucleic acid sequence encoding the shRNA targeting the HPRT gene has a sequence having at least 80% identity to any one of SEQ ID NOS: 27-29. In some embodiments, the first nucleic acid sequence encoding the shRNA targeting the HPRT gene has a sequence having at least 90% identity to any one of SEQ ID NOS: 27-29. In some embodiments, the first nucleic acid sequence encoding the shRNA targeting the HPRT gene has a sequence having at least 95% identity to any one of SEQ ID NOS: 27-29. In some embodiments, the first nucleic acid sequence encoding the shRNA targeting the HPRT gene has a sequence having at least 97% identity to any one of SEQ ID NOS: 27-29. In some embodiments, the first nucleic acid sequence encoding the shRNA targeting the HPRT gene has a sequence of SEQ ID NO: 27. In some embodiments, the first nucleic acid sequence encoding the shRNA targeting the HPRT gene has a sequence of SEQ ID NO: 28. In some embodiments, the first nucleic acid sequence encoding the shRNA targeting the HPRT gene has a sequence of SEQ ID NO: 29.

In some embodiments, the first nucleic acid sequence encoding the shRNA targeting the HPRT gene has a sequence having at least 80% identity to that of SEQ ID NO: 31. In some embodiments, the first nucleic acid sequence encoding the shRNA targeting the HPRT gene has a sequence having at least 90% identity to that of SEQ ID NO: 31. In some embodiments, the first nucleic acid sequence encoding the shRNA targeting the HPRT gene has a sequence having at least 95% identity to that of SEQ ID NO: 31. In some embodiments, the first nucleic acid sequence encoding the shRNA targeting the HPRT gene has a sequence having at least 97% identity to that of SEQ ID NO: 31 In some embodiments, the first nucleic acid sequence encoding the shRNA targeting the HPRT gene has a sequence of SEQ ID NO: 31.

In some embodiments, the second nucleic acid encoding the therapeutic gene is one which may genetically correct sickle cell disease or β-thalassemia; or reduce symptoms thereof (including the symptoms of severe SCD). In other embodiments, the nucleic acid encoding the therapeutic gene is one which may genetically correct immune deficiencies, hereditary diseases, blood diseases (e.g. hemophilia, hemoglobin disorders), neurological diseases, and/or lysosomal storage diseases; or reduce symptoms thereof. In some embodiments, the vector is a lentiviral vector. In some embodiments, the therapeutic gene is gamma globin. In some embodiments, the second nucleic acid sequence encoding the therapeutic gene has a sequence having at least 80% identity to that of SEQ ID NO: 55. In some embodiments, the second nucleic acid sequence encoding the therapeutic gene has a sequence having at least 90% identity to that of SEQ ID NO: 55. In some embodiments, the second nucleic acid sequence encoding the therapeutic gene has a sequence having at least 95% identity to that of SEQ ID NO: 55. In some embodiments, the second nucleic acid sequence encoding the therapeutic gene has a sequence having at least 97% identity to that of SEQ ID NO: 55. In some embodiments, the second nucleic acid sequence encoding the therapeutic gene has a sequence of SEQ ID NO: 55.

In another aspect of the present disclosure is a lentiviral expression vector including a first nucleic acid sequence encoding an anti-HPRT shRNA or an anti-HPRT shRNA embedded within a microRNA; and a second nucleic acid sequence encoding a therapeutic gene. In some embodiments, the lentiviral expression vectors are suitable for transducing HSCs ex vivo. In some embodiments, the lentiviral expression vectors are suitable for producing selectable genetically modified cells, such as HSCs. In some embodiments, the HSCs transduced ex vivo may be administered to a patient in need of treatment, e.g. for the treatment of hemoglobinopathies, including beta-thalassemia and sickle-cell disease.

In some embodiments, the therapeutic gene is gamma globin gene. In some embodiments, the second nucleic acid sequence encoding the gamma globin gene is a hybrid gamma globin gene including a point mutation that confers a competitive advantage for the α-globin chain, skewing the formation of tetrameric HbF versus HbS. In some embodiments, the second nucleic acid sequence encoding the gamma-globin gene is operably linked to a beta globin promoter. In some embodiments, the second nucleic acid sequence encoding the gamma-globin gene has at least 95% sequence identity to that of SEQ ID NO: 55.

In some embodiments, the first nucleic acid sequence is operably linked to a Pol III promoter. In some embodiments, the Pol III promoter is a *Homo sapiens* cell-line HEK-293 7sk RNA promoter (see, for example, SEQ ID NO: 32). In some embodiments, the Pol III promoter is a 7sk promoter which includes a single mutation in its nucleic acid sequence as compared with SEQ ID NO: 32. In some embodiments, the Pol III promoter is a 7sk promoter which includes multiple mutations in its nucleic acid sequence as compared with SEQ ID NO: 32. In some embodiments, the Pol III promoter is a 7sk promoter which includes a deletion in its nucleic acid sequence as compared with SEQ ID NO: 32. In some embodiments, the Pol III promoter is a 7sk promoter which includes both a mutation and a deletion in its nucleic acid sequence as compared with SEQ ID NO: 32. In some embodiments, the first nucleic acid sequence is operably linked to promoter having at least 95% identity to that of SEQ ID NO: 32. In some embodiments, the first nucleic acid sequence is operably linked to promoter having at least 95% identity to that of SEQ ID NO: 33. In some embodiments, the first nucleic acid sequence is operably linked to promoter having at least 97% identity to that of SEQ ID NO: 33. In some embodiments, the first nucleic acid sequence is operably linked to promoter having at least 98% identity to that of SEQ ID NO: 33. In some embodiments, the first nucleic acid sequence is operably linked to promoter having at least 99% identity to that of SEQ ID NO: 33. In some embodiments, the first nucleic acid sequence is operably linked to a promoter having SEQ ID NO: 33. In some embodiments, the lentiviral expression vector further comprises an expression control sequence having a 5' long terminal repeat upstream of the second nucleic acid sequence, and a 3' long terminal repeat downstream of the nucleic acid encoding the gamma-globin gene.

In another aspect of the present disclosure is a vector comprising (i) a nucleic acid sequence encoding a micro-RNA based shRNA targeting a HPRT gene; and (ii) a nucleic acid sequence encoding a therapeutic gene. In some embodiments, the therapeutic gene is used to genetically correct sickle cell anemia or β-thalassemia; or reduce symptoms thereof. In some embodiments, the nucleic acid sequence encoding the micro-RNA based shRNA targeting the HPRT gene has a sequence having at least 80% identity to that of SEQ ID NO: 67. In some embodiments, the nucleic acid sequence encoding the micro-RNA based shRNA targeting the HPRT gene has a sequence having at least 90% identity to that of SEQ ID NO: 67. In some embodiments, the nucleic acid sequence encoding the micro-RNA based shRNA targeting the HPRT gene has a sequence having at least 95% identity to that of SEQ ID NO: 67. In some embodiments, the nucleic acid sequence encoding the micro-RNA based shRNA targeting the HPRT gene has a sequence of SEQ ID NO: 67.

In some embodiments, the nucleic acid sequence encoding the micro-RNA based shRNA targeting the HPRT gene has a sequence having at least 80% identity to that of SEQ ID NO: 68. In some embodiments, the nucleic acid sequence encoding the micro-RNA based shRNA targeting the HPRT gene has a sequence having at least 90% identity to that of SEQ ID NO: 68. In some embodiments, the nucleic acid sequence encoding the micro-RNA based shRNA targeting the HPRT gene has a sequence having at least 95% identity to that of SEQ ID NO: 68. In some embodiments, the nucleic acid sequence encoding the micro-RNA based shRNA targeting the HPRT gene has a sequence of SEQ ID NO: 68.

In some embodiments, the nucleic acid sequence encoding the micro-RNA based shRNA targeting the HPRT gene has a sequence having at least 80% identity to that of SEQ ID NO: 25. In some embodiments, the nucleic acid sequence encoding the micro-RNA based shRNA targeting the HPRT gene has a sequence having at least 90% identity to that of SEQ ID NO: 25. In some embodiments, the nucleic acid sequence encoding the micro-RNA based shRNA targeting the HPRT gene has a sequence having at least 95% identity to that of SEQ ID NO: 25. In some embodiments, the nucleic acid sequence encoding the micro-RNA based shRNA targeting the HPRT gene has a sequence of SEQ ID NO: 25.

In some embodiments, the nucleic acid sequence encoding the micro-RNA based shRNA targeting the HPRT gene has a sequence having at least 80% identity to that of SEQ ID NO: 26. In some embodiments, the nucleic acid sequence encoding the micro-RNA based shRNA targeting the HPRT gene has a sequence having at least 90% identity to that of SEQ ID NO: 26. In some embodiments, the nucleic acid sequence encoding the micro-RNA based shRNA targeting the HPRT gene has a sequence having at least 95% identity to that of SEQ ID NO: 26. In some embodiments, the nucleic acid sequence encoding the micro-RNA based shRNA targeting the HPRT gene has a sequence of SEQ ID NO: 26.

In another aspect of the present disclosure is a lentiviral expression vector suitable for transducing human cells (e.g. HSCs) comprising a first nucleic acid sequence operably linked to a first promoter (e.g. a Pol III promoter) and a second nucleic acid sequence operably linked to a second promoter (e.g. a Pol II promoter), wherein the first nucleic acid sequence encodes an agent that knocks down HPRT or otherwise decreases the expression of HPRT, and wherein the second nucleic acid sequence encodes a therapeutic gene. In some embodiments, the first nucleic acid sequence has at least 95% sequence identity to that of SEQ ID NO: 30. In some embodiments, the first nucleic acid sequence has at least 95% sequence identity to that of SEQ ID NO: 31. In some embodiments, the first nucleic acid sequence has the sequence of SEQ ID NO: 31. In some embodiments, the second nucleic acid encodes for gamma globin (e.g. any of SEQ ID NOS: 3 or 55). In some embodiments, the second nucleic acid sequence has at least 95% sequence identity to that of SEQ ID NO: 55. In some embodiments, the first promoter is a 7sk promoter. In some embodiments, the 7sk promoter has at least 95% sequence identity to that of SEQ ID NO: 32. In some embodiments, the second promoter is a beta globin promoter. In some embodiments, the beta globin promoter has at least 95% sequence identity to that of SEQ ID NO: 66. In some embodiments, the lentiviral expression vector has a sequence having at least 85% sequence identity to any of SEQ ID NOS: 5-22. In some embodiments, the lentiviral expression vector has a sequence having at least 90% sequence identity to any of SEQ ID NOS: 5-22. In some embodiments, the lentiviral expression vector has a sequence having at least 95% sequence identity to any of SEQ ID NOS: 5-22. In some embodiments, the lentiviral expression vector has a sequence having at least 96% sequence identity to any of SEQ ID NOS: 5-22. In some embodiments, the lentiviral expression vector has a sequence having at least 97% sequence identity to any of SEQ ID NOS: 5-22. In some embodiments, the lentiviral expression vector has a sequence having at least 98% sequence identity to any of SEQ ID NOS: 5-22. In some embodiments, the lentiviral expression vector has a sequence having at least 99% sequence identity to any of SEQ ID NOS: 5-22.

In another aspect of the present disclosure is a polynucleotide sequence including (a) a sequence encoding an shRNA targeting HPRT; (b) a sequence encoding a gamma globin gene; (c) a sequence encoding a first promoter to drive expression of the sequence encoding the shRNA targeting HPRT; (d) a sequence encoding a second promoter to drive expression of the sequence encoding the gamma globin gene; (e) a sequence encoding a central polypurine tract element; and (f) a sequence encoding a Rev response element (SEQ ID NO: 56). In some embodiments, the polynucleotide further includes a locus control region (SEQ ID NO: 57). In some embodiments, the polynucleotide sequence has at least 85% identity to any of SEQ ID NOS: 5-22. In some embodiments, the polynucleotide sequence has at least 90% identity to any of SEQ ID NOS: 5-22. In some embodiments, the polynucleotide sequence has at least 91% identity to any of SEQ ID NOS: 5-22. In some embodiments, the polynucleotide sequence has at least 92% identity to any of SEQ ID NOS: 5-22. In some embodiments, the polynucleotide sequence has at least 93% identity to any of SEQ ID NOS: 5-22. In some embodiments, the polynucleotide sequence has at least 94% identity to any of SEQ ID NOS: 5-22. In some embodiments, the polynucleotide sequence has at least 95% identity to any of SEQ ID NOS: 5-22. In some embodiments, the polynucleotide sequence has at least 96% identity to any of SEQ ID NOS: 5-22. In some embodiments, the polynucleotide sequence has at least 97% identity to any of SEQ ID NOS: 5-22. In some embodiments, the polynucleotide sequence has at least 98% identity to any of SEQ ID NOS: 5-22. In some embodiments, the polynucleotide sequence has at least 99% identity to any of SEQ ID NOS: 5-22. In some embodiments, the first promoter is a pol III promoter. In some embodiments, the first promoter is a 7sk promoter. In some embodiments, the 7sk promoter has at least 90% sequence identity to that of SEQ ID NO: 32. In some embodiments, the second promoter is a pol II promoter. In some embodiments, the second promoter is a beta-globin promoter. In some embodiments, the polynucleotide sequence includes between 11,000 and 12,750 nucleotides. In some embodiments, the polynucleotide sequence includes between 11,500 and 12,000 nucleotides.

In another aspect of the present disclosure is a pharmaceutical composition comprising a (a) a vector, such as an expression vector, including (i) a nucleic acid sequence encoding a shRNA targeting an HPRT gene; and (ii) a nucleic acid sequence encoding a therapeutic gene (e.g. a gamma-globin gene); and (b) a pharmaceutically acceptable carrier. In some embodiments, the pharmaceutical composition is formulated as an emulsion. In some embodiments, the pharmaceutical composition is formulated within micelles. In some embodiments, the pharmaceutical composition is encapsulated within a polymer. In some embodiments, the pharmaceutical composition is encapsulated within a liposome. In some embodiments, the pharmaceutical composition is encapsulated within minicells or nanocapsules.

In another aspect of the present disclosure is a method of producing genetically modified cells, comprising: contacting the cells with a first agent which "knocks down" the HPRT gene, and a second agent that introduces a therapeutic gene for expression. In some embodiments, the cells are genetically modified by contacting the cells with a lentiviral expression vector including nucleic acid sequences encoding both the first and second agents. In some embodiments, the cells are HSCs.

In another aspect of the present disclosure is a method of producing genetically modified cells, comprising: contacting the cells with a first agent which "knocks out" the HPRT gene, and a second agent that introduces a therapeutic gene for expression. In some embodiments, a non-viral delivery vehicle is utilized to introduce the first agent to the cells; and a lentiviral expression vector is utilized to introduce the second agent to the cells. In some embodiments, the non-viral delivery vehicle is a nanocapsule. In some embodiments, the cells are HSCs.

In another aspect of the present disclosure are HSCs (e.g. CD34+ HSCs) which have been transduced with an expression vector including a therapeutic gene and an agent designed to reduce HPRT expression (e.g. by knockdown or by knockout of HPRT). In some embodiments, the transduced HSCs constitute a cell therapy product which may be administered to a subject in need of treatment thereof. In some embodiments, the therapeutic gene is a gamma globin gene. In some embodiments, the gamma globin gene encodes a peptide having at least 90% sequence identity to that of SEQ ID NO: 4.

In another aspect of the present disclosure are HSCs which have been transduced with an expression vector including a nucleic acid sequence encoding a hybrid gamma globin gene (e.g. SEQ ID NOS: 3 or 55) and a nucleic acid encoding an anti-HPRT shRNA (e.g. SEQ ID NOS: 1, 2, 30 or 31). In some embodiments, the anti-HPRT shRNA is driven by a 7sk promoter (e.g. SEQ ID NOS: 32 or 33). In some embodiments, 7sk/sh734 is oriented either upstream or downstream in the sense or anti-sense direction relative to a hybrid gamma-globin cassette. In some embodiments, the transduced HSCs constitute a cell therapy product which may be administered (such as in a pharmaceutical composition including a pharmaceutically acceptable vehicle) to a subject in need of treatment thereof (e.g. a mammal; a human patient) (e.g. for the treatment of sickle cell disease).

In another aspect of the present disclosure is a method of treating a hemoglobinopathy in a patient (e.g. a human patient) in need of treatment thereof comprising (a) transducing HSCs with a lentiviral expression vector, wherein the lentiviral expression vector includes a first nucleic acid sequence encoding an anti-HPRT shRNA or an anti-HPRT shRNA embedded within a microRNA; and a second nucleic acid sequence encoding a gamma globin gene; and (b) transplanting the transduced HSCs within the patient. In some embodiments, the HSCs are autologous or allogeneic. In some embodiments, the anti-HPRT shRNA has a sequence of any of SEQ ID NOS: 30 or 31. In some embodiments, the nucleic acid encoding the gamma globin gene has a sequence of SEQ ID NO: 55. In some embodiments, the patient is pre-treated with myeloablative conditioning prior to the transplanting of the transduced HSCs administration (e.g. such as with a purine analog, including 6-thioguanine ("6TG"); with a chemotherapy agent; with radiation; with an antibody-drug conjugate, such as those described in US Patent Publication Nos. 2017/0360954 and 2018/0147294, and PCT Publication Nos. WO/2017/219025 and WO/2017/219029, the disclosures of which are each incorporated by reference herein in their entireties). In some embodiments, the transduced HSCs are selected for in vivo following the transplantation (e.g. such as with 6TG). In some embodiments, methotrexate ("MTX") or mycophenolic acid ("MPA") are administered to ameliorate any side effects of transplantation of the transduced HSCs (e.g. graft versus host disease).

It is believed that with a strategy of combined conditioning and chemoselection (such as with a purine analog), efficient and high engraftment of HPRT-deficient, gamma globin gene-containing hematopoietic stem cells can be achieved, and it is believed that such high engraftment may be accomplished with low overall toxicity. It is believed that the enhanced engraftment and chemoselection of the gene-modified HSCs, combined with lineage-specific expression of the gamma globin gene, may result in a sufficient frequency of red blood cells expressing the therapeutic gamma globin transgene, allowing for increased levels of fetal hemoglobin formation to correct for SCD and/or beta thalassemia. As a safety measure, HPRT-deficient cells can be negatively selected, such as by introducing MTX or MPA, to inhibit the enzyme dihydrofolate reductase (DHFR) in the purine de novo synthetic pathway, thus killing HPRT deficient cells.

It is further believed that HPRT-deficient HSCs can be selected in vivo using a regimen of a purine analog (e.g. 6TG) to enhance engraftment. It is also believed that the expanded gene-modified HSCs can differentiate into erythrocytes expressing the therapeutic gamma globin transgene. The gene therapy compositions described herein have the potential to not only correct SCD and beta thalassemia, but also to greatly improve on the current "gold standards" for autologous hematopoietic stem cell transplantation. Improvements may allow for (i) out-patient procedures using the gene-modified HSCs; (ii) low adverse events (AEs), including avoiding infertility associated with other clinical therapies; (iii) low dose oral administration for conditioning (as compared with high-dose IV conditioning); (iv) in vivo selection of gene-modified cells; and/or (v) low procedure mortality rate related to transplantation and conditioning.

BRIEF DESCRIPTION OF THE FIGURES

FIGS. 1A and 1B provide schematics of an expression vector according to certain embodiments of the present disclosure.

FIG. 25A illustrates GFP expression of K562 cells transfected with EF1a-GFP nanocapsules measured on day 3. FIG. 25B illustrates the live cell number measured using TC10 on days 5 and 7.

FIG. 27A shows that about 99.6% of the cells fail to express HPRT. In a control, 100% of the untransduced cells (FIG. 27B) stain positive for HPRT expression.

FIG. 31A illustrates the secondary RNA structure and minimum free energy (δG) for sh211 (see also SEQ ID NO: 28).

FIG. 31B illustrates the secondary RNA structure and minimum free energy (δG) for sh616 (see also SEQ ID NO: 27).

FIG. 36 illustrates the location and probability of transcription binding sites within the 7sk promoter and highlights the two mutated OCT transcription factor binding sites in the distal sequence enhancer (DSE). Also shown are the predicted binding sites within the promoter for the erythroid lineage transcription factors TAL-1 and GATA-1.

FIG. 37 provides the full-length Homo sapiens hypoxanthine phosphoribosyltransferase 1 (HPRT 1), mRNA_NM_000194.2 (SEQ ID NO: 59) The location of target sequences for siRNA/shRNA described are highlighted in in bold text within the coding sequence of HPRT (underlined text).

FIG. 38 illustrates a CRISPR/Cas9 gene editing strategy and sgRNA candidates for knock down of human HPRT gene expression (see SEQ ID NOS: 61 and 69).

FIG. 39 sets forth the hybrid gamma-globin sequence sGbG$^M$ and illustrates the differences shown in bold and underlined text between an aligned human endogenous gamma-globin (see SEQ ID NO: 55).

FIG. 41 illustrates the relevant transgene and regulatory sequences of the sGbG$^M$ lentivirus vector.

FIG. 49K sets forth a table providing additional data corresponding to the graphs set forth in FIG. 49J.

FIGS. 52A, 52B, and 52C illustrate a CD34$^+$ extended culture under 6TG selection followed by erythroid differentiation.

SEQUENCE LISTING

Figure 2:
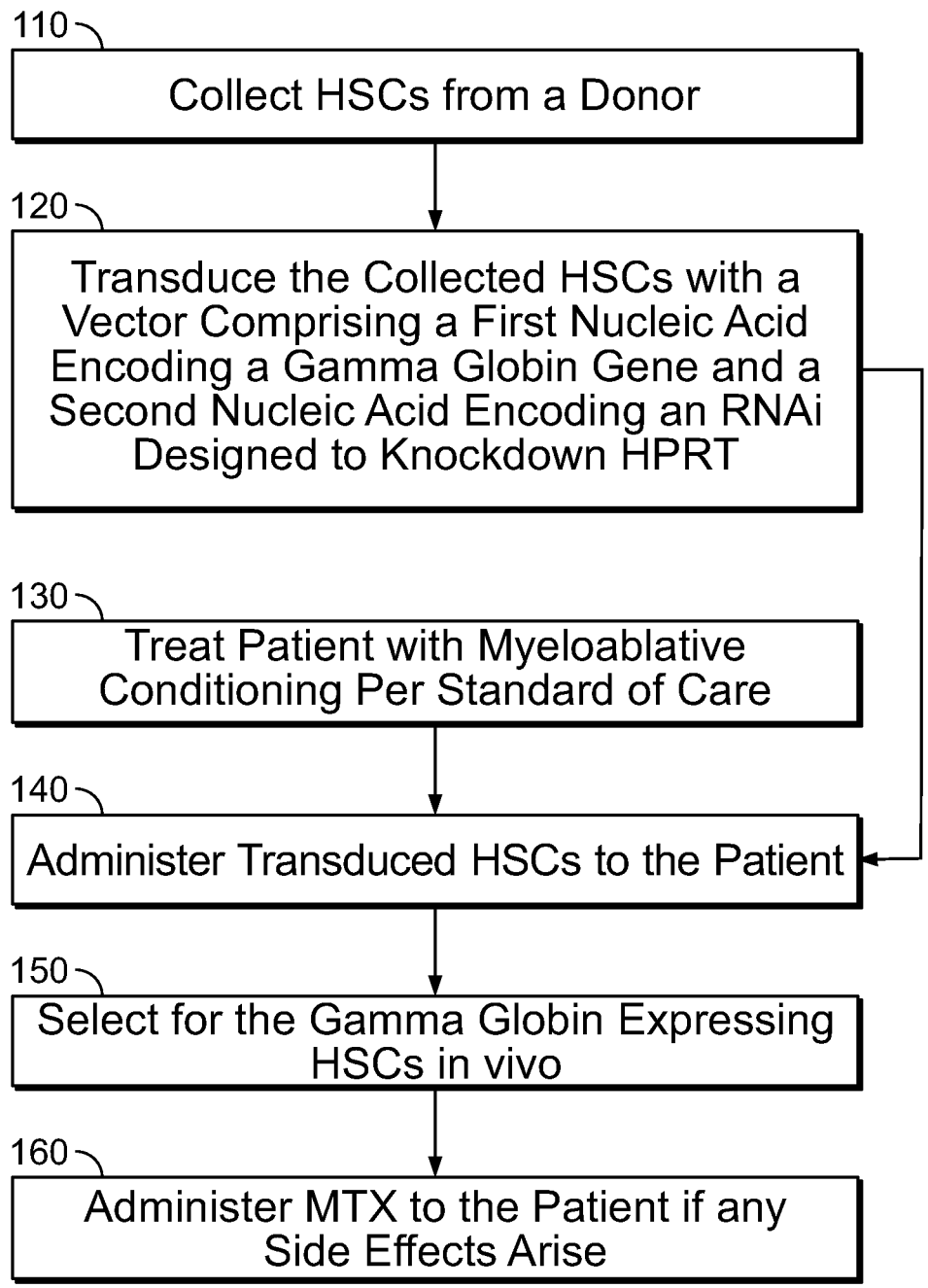
FIG. 2 sets forth a flowchart illustrating methods of treating a subject with transduced HSCs, including the steps of conditioning and chemoselection in accordance with certain embodiments of the present disclosure.
Figure 3:
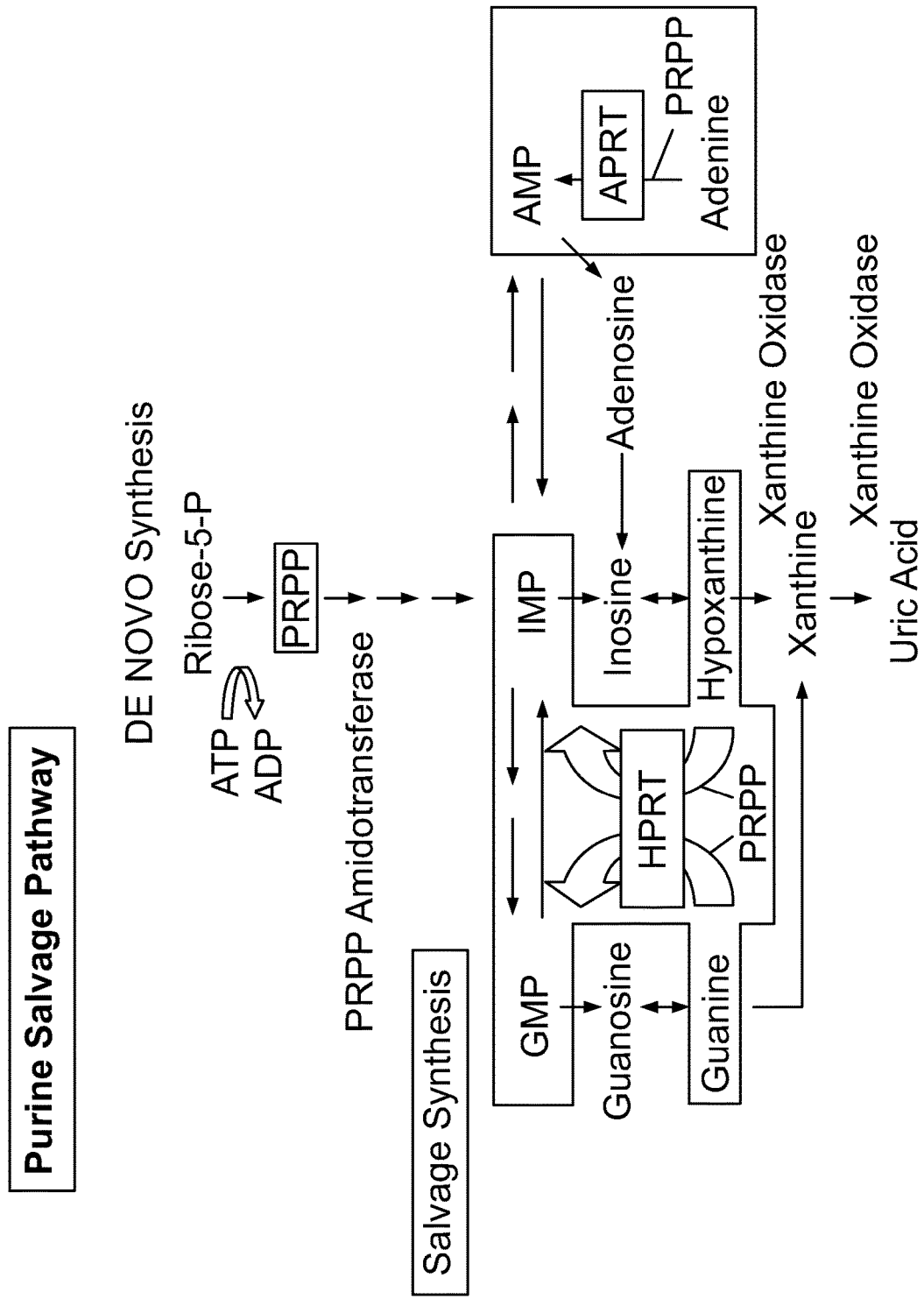
FIG. 3 illustrates the purine salvage pathway.
Figure 4:
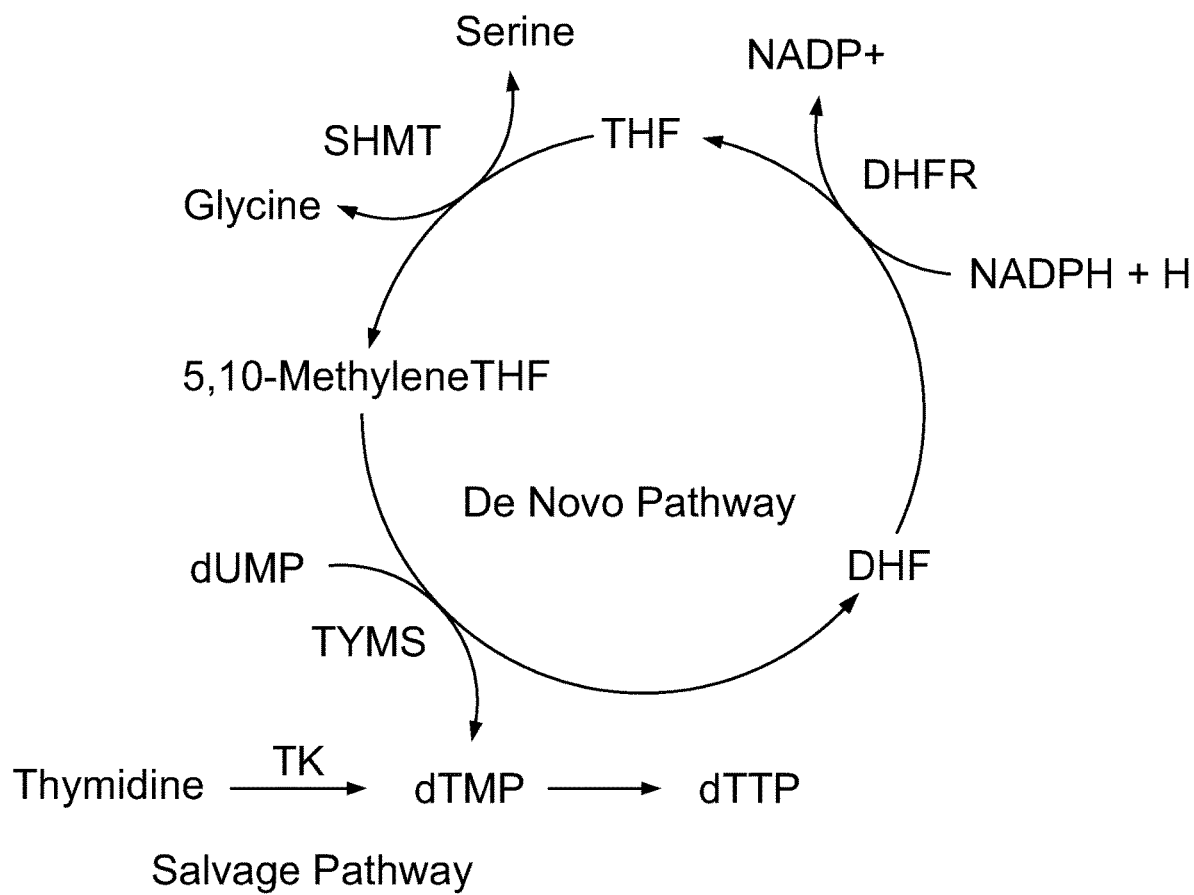
FIG. 4 illustrates the de novo path for the synthesis of dTTP.
Figure 5:
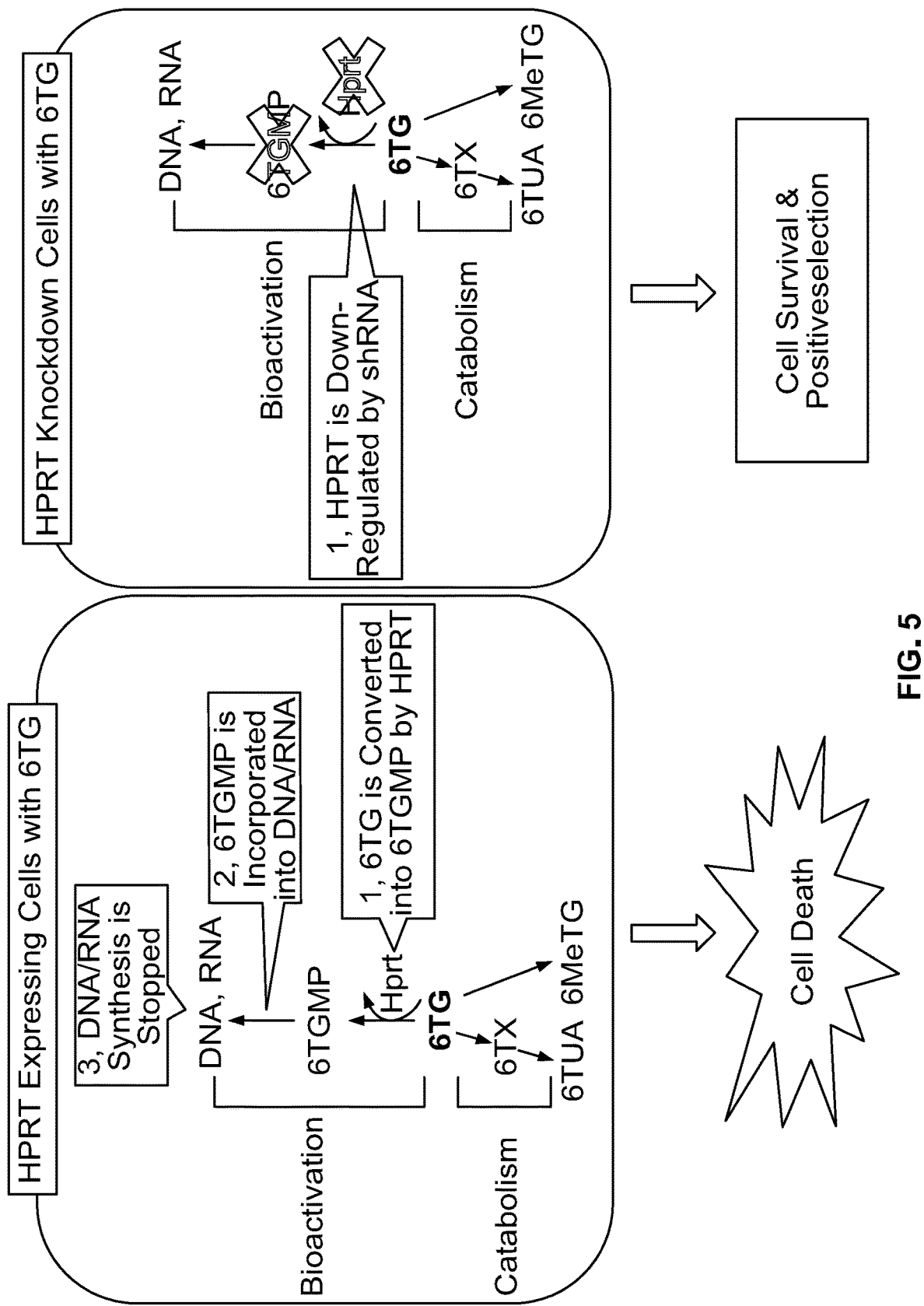
FIG. 5 illustrates a process for selecting of HPRT-deficient cells in the presence of 6TG.

The nucleic and amino acid sequences provided herein are shown using standard letter abbreviations for nucleotide bases, and three letter code for amino acids, as defined in 37 C.F.R. 1.822. The sequence listing is submitted as an ASCII text file, named "2018-07-16_Calimmune-051WO_ST25.txt" created on Jul. 16, 2018, 323 KB, which is incorporated by reference herein.

DETAILED DESCRIPTION

Definitions

It should also be understood that, unless clearly indicated to the contrary, in any methods claimed herein that include more than one step or act, the order of the steps or acts of the method is not necessarily limited to the order in which the steps or acts of the method are recited.

As used herein, the singular terms "a," "an," and "the" include plural referents unless the context clearly indicates otherwise. Similarly, the word "or" is intended to include "and" unless the context clearly indicates otherwise.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

The terms "comprising," "including," "having," and the like are used interchangeably and have the same meaning. Similarly, "comprises," "includes," "has," and the like are used interchangeably and have the same meaning. Specifically, each of the terms is defined consistent with the common United States patent law definition of "comprising" and is therefore interpreted to be an open term meaning "at least the following," and is also interpreted not to exclude additional features, limitations, aspects, etc. Thus, for example, "a device having components a, b, and c" means that the device includes at least components a, b and c. Similarly, the phrase: "a method involving steps a, b, and c" means that the method includes at least steps a, b, and c. Moreover, while the steps and processes may be outlined herein in a particular order, the skilled artisan will recognize that the ordering steps and processes may vary.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of" or "exactly one of." "Consisting essentially of," when used in the claims, shall have its ordinary meaning as used in the field of patent law.

As used herein, the terms "administer" or "administering" mean providing a composition, formulation, or specific agent to a subject (e.g. a human patient) in need of treatment, including those described herein.

As used herein, the terms "hematopoietic cell transplant" or "hematopoietic cell transplantation" refer to bone marrow transplantation, peripheral blood stem cell transplantation, umbilical vein blood transplantation, or any other source of pluripotent hematopoietic stem cells. Likewise, the terms "stem cell transplant," or "transplant," refer to a composition comprising stem cells that are in contact with (e.g. suspended in) a pharmaceutically acceptable carrier. Such compositions are capable of being administered to a subject through a catheter.

As used herein, the term "functional nucleic acid" refers to molecules having the capacity to reduce expression of a protein by directly interacting with a transcript that encodes the protein. siRNA molecules, ribozymes, and antisense nucleic acids constitute exemplary functional nucleic acids.

As used herein, the term "gene" refers broadly to any segment of DNA associated with a biological function. A gene encompasses sequences including but not limited to a coding sequence, a promoter region, a cis-regulatory sequence, a non-expressed DNA segment is a specific recognition sequence for regulatory proteins, a non-expressed DNA segment that contributes to gene expression, a DNA segment designed to have desired parameters, or combinations thereof.

As used herein, the term "gene silencing" is meant to describe the downregulation, knock-down, degradation, inhibition, suppression, repression, prevention, or decreased expression of a gene, transcript and/or polypeptide product. Gene silencing and interference also describe the prevention of translation of mRNA transcripts into a polypeptide. In some embodiments, translation is prevented, inhibited, or decreased by degrading mRNA transcripts or blocking mRNA translation.

As used herein, the term "gene expression" refers to the cellular processes by which a biologically active polypeptide is produced from a DNA sequence.

As used herein, "HPRT" is an enzyme involved in purine metabolism encoded by the HPRT1 gene. HPRT1 is located on the X chromosome, and thus is present in single copy in males. HPRT1 encodes the transferase that catalyzes the conversion of hypoxanthine to inosine monophosphate and guanine to guanosine monophosphate by transferring the 5-phosphorobosyl group from 5-phosphoribosyl 1-pyrophosphate to the purine. The enzyme functions primarily to salvage purines from degraded DNA for use in renewed purine synthesis (see also FIG. 37).

As used herein, the term "lentivirus" refers to a genus of retroviruses that are capable of infecting dividing and non-dividing cells. Several examples of lentiviruses include HIV (human immunodeficiency virus: including HIV type 1, and HIV type 2), the etiologic agent of the human acquired immunodeficiency syndrome (AIDS); visna-maedi, which causes encephalitis (visna) or pneumonia (maedi) in sheep, the caprine arthritis-encephalitis virus, which causes immune deficiency, arthritis, and encephalopathy in goats; equine infectious anemia virus, which causes autoimmune hemolytic anemia, and encephalopathy in horses; feline immunodeficiency virus (FIV), which causes immune deficiency in cats; bovine immune deficiency virus (BIV), which causes lymphadenopathy, lymphocytosis, and possibly central nervous system infection in cattle; and simian immunodeficiency virus (SIV), which causes immune deficiency and encephalopathy in sub-human primates.

As used herein, the term "lentiviral vector" is used to denote any form of a nucleic acid derived from a lentivirus and used to transfer genetic material into a cell via transduction. The term encompasses lentiviral vector nucleic acids, such as DNA and RNA, encapsulated forms of these nucleic acids, and viral particles in which the viral vector nucleic acids have been packaged.

As used herein, the terms "knock down" or "knockdown" when used in reference to an effect of RNAi on gene expression, means that the level of gene expression is inhibited, or is reduced to a level below that generally observed when examined under substantially the same conditions, but in the absence of RNAi.

As used herein, the term "knock-in" refers to the replacement of endogenous genetic material (e.g., a gene or a portion of a gene) with exogenous genetic material (i.e., a recombinant nucleic acid). The term "knock-in" as used herein also includes alterations of genetic material by introduction of one or more additional copies of the recombinant nucleic acid, with or without replacing the endogenous gene.

As used herein, the term "knock-out" refers to partial or complete suppression of the expression of an endogenous gene. This is generally accomplished by deleting a portion of the gene or by replacing a portion with a second sequence, but may also be caused by other modifications to the gene such as the introduction of stop codons, the mutation of critical amino acids, the removal of an intron junction, etc. Accordingly, a "knock-out" construct is a nucleic acid sequence, such as a DNA construct, which, when introduced into a cell, results in suppression (partial or complete) of expression of a polypeptide or protein encoded by endogenous DNA in the cell. In some embodiments, a "knockout" includes mutations such as, a point mutation, an insertion, a deletion, a frameshift, or a missense mutation As used herein, the term "minicell" refers to anucleate forms of bacterial cells, engendered by a disturbance in the coordination, during binary fission, of cell division with DNA segregation. Minicells are distinct from other small vesicles that are generated and released spontaneously in certain situations and, in contrast to minicells, are not due to specific genetic rearrangements or episomal gene expression. Minicells of the present disclosure are anucleate forms of *E. coli* or other bacterial cells, engendered by a disturbance in the coordination, during binary fission, of cell division with DNA segregation. Prokaryotic chromosomal replication is linked to normal binary fission, which involves mid-cell septum formation. In *E. coli*, for example, mutation of min genes, such as minCD, can remove the inhibition of septum formation at the cell poles during cell division, resulting in production of a normal daughter cell and an anucleate minicell. See de Boer et al., 1992; Raskin & de Boer, 1999; Hu & Lutkenhaus, 1999; Harry, 2001. Minicells are distinct from other small vesicles that are generated and released spontaneously in certain situations and, in contrast to minicells, are not due to specific genetic rearrangements or episomal gene expression. For practicing the present disclosure, it is desirable for minicells to have intact cell walls ("intact minicells"). In addition to min operon mutations, anucleate minicells also are generated following a range of other genetic rearrangements or mutations that affect septum formation, for example in the divIVB1 in *B. subtilis*. See Reeve and Cornett, 1975; Levin et al., 1992. Minicells also can be formed following a perturbation in the levels of gene expression of proteins involved in cell division/chromosome segregation. For example, overexpression of minE leads to polar division and production of minicells. Similarly, chromosome-less minicells may result from defects in chromosome segregation for example the smc mutation in *Bacillus subtilis* (Britton et al., 1998), spoOJ deletion in *B. subtilis* (Ireton et al., 1994), mukB mutation in *E. coli* (Hiraga et al., 1989), and parC mutation in *E. coli* (Stewart and D'Ari, 1992). Gene products may be supplied in trans. When over-expressed from a high-copy number plasmid, for example, CafA may enhance the rate of cell division and/or inhibit chromosome partitioning after replication (Okada et al., 1994), resulting in formation of chained cells and anucleate minicells (Wachi et al., 1989; Okada et al., 1993). Minicells can be prepared from any bacterial cell of Gram-positive or Gram-negative origin.

As used herein, the term "mutated" refers to a change in a sequence, such as a nucleotide or amino acid sequence, from a native, wild-type, standard, or reference version of the respective sequence, i.e. the non-mutated sequence. A mutated gene can result in a mutated gene product. A mutated gene product will differ from the non-mutated gene product by one or more amino acid residues. In some embodiments, a mutated gene which results in a mutated gene product can have a sequence identity of 70%, 75%, 80%, 85%, 90%, 95%, or greater to the corresponding non-mutated nucleotide sequence.

As used herein, the term "operably linked" refers to functional linkage between a nucleic acid expression control sequence (such as a promoter, signal sequence, enhancer or array of transcription factor binding sites) and a second nucleic acid sequence, wherein the expression control sequence affects transcription and/or translation of the nucleic acid corresponding to the second sequence when the appropriate molecules (e.g., transcriptional activator proteins) are bound to the expression control sequence.

As used herein, the term "retroviruses" refers to viruses having an RNA genome that is reverse transcribed by retroviral reverse transcriptase to a cDNA copy that is integrated into the host cell genome. Retroviral vectors and methods of making retroviral vectors are known in the art.

Briefly, to construct a retroviral vector, a nucleic acid encoding a gene of interest is inserted into the viral genome in the place of certain viral sequences to produce a virus that is replication-defective. In order to produce virions, a packaging cell line containing the gag, pol, and env genes but without the LTR and packaging components is constructed (Mann et al., Cell, Vol. 33:153-159, 1983). When a recombinant plasmid containing a cDNA, together with the retroviral LTR and packaging sequences, is introduced into this cell line, the packaging sequence allows the RNA transcript of the recombinant plasmid to be packaged into viral particles, which are then secreted into the culture media. The media containing the recombinant retroviruses is then collected, optionally concentrated, and used for gene transfer.

As used herein, the terms "small hairpin RNA" or "shRNA" refer to RNA molecules comprising an antisense region, a loop portion and a sense region, wherein the sense region has complementary nucleotides that base pair with the antisense region to form a duplex stem. Following post-transcriptional As used herein, the term "subject" refers to a mammal such as a human, mouse or primate. Typically, the mammal is a human (Homo sapiens).

As used herein, the term "therapeutic gene" refers to a gene that can be administered to a subject for the purpose of treating or preventing a disease.

As used herein, the terms "transduce" or "transduction" refers to the delivery of a gene(s) using a viral or retroviral vector by means of infection rather than by transfection. For example, an anti-HPRT gene carried by a retroviral vector (a modified retrovirus used as a vector for introduction of nucleic acid into cells) can be transduced into a cell through infection and provirus integration. Thus, a "transduced gene" is a gene that has been introduced into the cell via lentiviral or vector infection and provirus integration. Viral vectors (e.g., "transducing vectors") transduce genes into "target cells" or host cells.

As used herein, the terms "treatment," "treating," or "treat," with respect to a specific condition, refer to obtaining a desired pharmacologic and/or physiologic effect. The effect can be prophylactic in terms of completely or partially preventing a disease or symptom thereof and/or can be therapeutic in terms of a partial or complete cure for a disease and/or adverse effect attributable to the disease. "Treatment," as used herein, covers any treatment of a disease in a subject, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease and/or relieving one or more disease symptoms. "Treatment" can also encompass delivery of an agent or administration of a therapy in order to provide for a pharmacologic effect, even in the absence of a disease or condition. The term "treatment" is used in some embodiments to refer to administration of a compound of the present disclosure to mitigate a disease or a disorder in a host, preferably in a mammalian subject, more preferably in humans. Thus, the term "treatment" can include includes: preventing a disorder from occurring in a host, particularly when the host is predisposed to acquiring the disease but has not yet been diagnosed with the disease; inhibiting the disorder; and/or alleviating or reversing the disorder. Insofar as the methods of the present disclosure are directed to preventing disorders, it is understood that the term "prevent" does not require that the disease state be completely thwarted. Rather, as used herein, the term preventing refers to the ability of the skilled artisan to identify a population that is susceptible to disorders, such that administration of the compounds of the present disclosure can occur prior to onset of a disease. The term does not mean that the disease state must be completely avoided.

As used herein, the term "vector" refers to a nucleic acid molecule capable of mediating entry of, e.g., transferring, transporting, etc., another nucleic acid molecule into a cell. The transferred nucleic acid is generally linked to, e.g., inserted into, the vector nucleic acid molecule. A vector may include sequences that direct autonomous replication or may include sequences sufficient to allow integration into host cell DNA. As will be evident to one of ordinary skill in the art, viral vectors may include various viral components in addition to nucleic acid(s) that mediate entry of the transferred nucleic acid. Numerous vectors are known in the art including, but not limited to, linear polynucleotides, polynucleotides associated with ionic or amphiphilic compounds, plasmids, and viral vectors. Examples of viral vectors include, but are not limited to, adenoviral vectors, adeno-associated virus vectors, retroviral vectors (including lentiviral vectors), and the like.

Expression Vectors

The present disclosure provides, in some embodiments, expression vectors (e.g. lentiviral expression vectors) including at least two nucleic acid sequences for expression. In some embodiments, the nucleic acid sequences encode a nucleic acid molecule (e.g. RNA, mRNA) (e.g. a molecule which may be found in the cytoplasm of a cell, e.g. a host cell). In some embodiments, the expression vectors include a first nucleic acid sequence encoding an agent designed to knockdown the HPRT gene or otherwise effectuate a decrease in HPRT expression. In some embodiments, the expression vectors include a second nucleic acid encoding a therapeutic gene (e.g. a nucleic acid sequence encoding a gamma globin gene or a mutated gamma globin gene).

In some embodiments, the expression vector is a self-inactivating lentiviral vector. In other embodiments, the expression vector is a retroviral vector. A lentiviral genome is generally organized into a 5' long terminal repeat (LTR), the gag gene, the pol gene, the env gene, the accessory genes (nef, vif, vpr, vpu) and a 3' LTR. The viral LTR is divided into three regions called U3, R and U5. The U3 region contains the enhancer and promoter elements. The U5 region contains the polyadenylation signals. The R (repeat) region separates the U3 and U5 regions and transcribed sequences of the R region appear at both the 5' and 3' ends of the viral RNA. See, for example, "RNA Viruses: A Practical Approach" (Alan J. Cann, Ed., Oxford University Press, (2000)); O Narayan and Clements (1989) J. Gen. Virology, Vol. 70:1617-1639; Fields et al. (1990) Fundamental Virology Raven Press.; Miyoshi H, Blamer U, Takahashi M, Gage F H, Verma I M. (1998) J Virol., Vol. 72(10):8150 7, and U.S. Pat. No. 6,013,516. Examples of lentiviral vectors that have been used to infect HSCs are described in the publications which follows, each of which are hereby incorporated herein by reference in their entireties: Evans et al., Hum Gene Ther., Vol. 10:1479-1489, 1999; Case et al., Proc Natl Acad Sci USA, Vol. 96:2988-2993, 1999; Uchida et al., Proc Natl Acad Sci USA, Vol. 95:11939-11944, 1998; Miyoshi et al., Science, Vol. 283:682-686, 1999; and Sutton et al., J. Virol., Vol. 72:5781-5788, 1998.

In some embodiments, the expression vector is a modified lentivirus, and thus is able to infect both dividing and non-dividing cells. In some embodiments, the modified lentiviral genome lacks genes for lentiviral proteins required for viral replication, thus preventing undesired replication, such as replication in the target cells. In some embodiments, the required proteins for replication of the modified genome are provided in trans in the packaging cell line during production of the recombinant retrovirus or lentivirus.

In some embodiments, the expression vector comprises sequences from the 5' and 3' long terminal repeats (LTRs) of a lentivirus. In some embodiments, the vector comprises the R and U5 sequences from the 5' LTR of a lentivirus and an inactivated or self-inactivating 3' LTR from a lentivirus. In some embodiments, the LTR sequences are HIV LTR sequences.

Additional components of a lentiviral expression vector (and methods of synthesizing and/or producing such vectors) are disclosed in United States Patent Application Publication No. 2018/0112220, the disclosure of which is hereby incorporated by reference herein in its entirety.

Agents to Knockdown the HPRT Gene or Decrease its Expression

In some embodiments, the nucleic acid sequence encoding the agent designed to knockdown the HPRT gene or otherwise effectuate a decrease in its expression is an RNAi agent. In some embodiments, the RNAi agent is an shRNA, a microRNA, or a hybrid thereof. In other embodiments, the nucleic acid sequence encoding the agent designed to knockdown the HPRT gene or otherwise effectuate a decrease in its expression is an agent other than an RNAi, such as an antisense RNA, or an antisense oligonucleotide. Both RNAi agents and non-RNAi agents are described further herein.

RNAi

In some embodiments, the expression vector comprises a first nucleic acid sequence encoding a RNA interference (RNAi) agent. RNA interference is an approach for post-transcriptional silencing of gene expression by triggering degradation of homologous transcripts through a complex multistep enzymatic process, e.g. a process involving sequence-specific double-stranded small interfering RNA (siRNA). A simplified model for the RNAi pathway is based on two steps, each involving a ribonuclease enzyme. In the first step, the trigger RNA (either dsRNA or miRNA primary transcript) is processed into a short, interfering RNA (siRNA) by the RNase II enzymes Dicer and Drosha. In the second step, siRNAs are loaded into the effector complex RNA-induced silencing complex (RISC). The siRNA is unwound during RISC assembly and the single-stranded RNA hybridizes with mRNA target. It is believed that gene silencing is a result of nucleolytic degradation of the targeted mRNA by the RNase H enzyme Argonaute (Slicer). If the siRNA/mRNA duplex contains mismatches the mRNA is not cleaved. Rather, gene silencing is a result of translational inhibition.

In some embodiments, the RNAi agent is an inhibitory or silencing nucleic acid. As used herein, a "silencing nucleic acid" refers to any polynucleotide which is capable of interacting with a specific sequence to inhibit gene expression. Examples of silencing nucleic acids include RNA duplexes (e.g. siRNA, shRNA), locked nucleic acids ("LNAs"), antisense RNA, DNA polynucleotides which encode sense and/or antisense sequences of the siRNA or shRNA, DNAzymes, or ribozymes. The skilled artisan will appreciate that the inhibition of gene expression need not necessarily be gene expression from a specific enumerated sequence, and may be, for example, gene expression from a sequence controlled by that specific sequence.

While the RNAi agent may be delivered and expressed via an expression vector, it is also possible that the RNAi agent may be directly delivered through the use of a suitable nanocapsule or other non-viral delivery vehicle as described further herein. For example, an siRNA or miRNA may be "packaged" within a nanocapsule and directly delivered as noted herein.

Methods for constructing interfering RNAs are known in the art. For example, the interfering RNA can be assembled from two separate oligonucleotides, where one strand is the sense strand and the other is the antisense strand, wherein the antisense and sense strands are self-complementary (i.e., each strand comprises nucleotide sequence that is complementary to nucleotide sequence in the other strand; such as where the antisense strand and sense strand form a duplex or double stranded structure); the antisense strand comprises nucleotide sequence that is complementary to a nucleotide sequence in a target nucleic acid molecule or a portion thereof (i.e., an undesired gene) and the sense strand comprises nucleotide sequence corresponding to the target nucleic acid sequence or a portion thereof. Alternatively, interfering RNA may be assembled from a single oligonucleotide, where the self-complementary sense and antisense regions are linked by means of nucleic acid based or non-nucleic acid-based linker(s). The interfering RNA can be a polynucleotide with a duplex, asymmetric duplex, hairpin or asymmetric hairpin secondary structure, having self-complementary sense and antisense regions, wherein the antisense region comprises a nucleotide sequence that is complementary to nucleotide sequence in a separate target nucleic acid molecule or a portion thereof and the sense region having nucleotide sequence corresponding to the target nucleic acid sequence or a portion thereof. The interfering RNA can be a circular single-stranded polynucleotide having two or more loop structures and a stem comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof, and wherein the circular polynucleotide can be processed either in vivo or in vitro to generate an active siRNA molecule capable of mediating RNA interference.

In some embodiments, the interfering RNA coding region encodes a self-complementary RNA molecule having a sense region, an antisense region and a loop region. When expressed, such an RNA molecule desirably forms a "hairpin" structure and is referred to herein as an "shRNA." In some embodiments, the loop region is generally between about 2 and about 10 nucleotides in length (by way of example only, see SEQ ID NO: 35). In other embodiments, the loop region is from about 6 to about 9 nucleotides in length. In some embodiments, the sense region and the antisense region are between about 15 and about 30 nucleotides in length. Following post-transcriptional processing, the small hairpin RNA is converted into a siRNA by a cleavage event mediated by the enzyme Dicer, which is a member of the RNase III family. The siRNA is then capable of inhibiting the expression of a gene with which it shares homology. Further details are described by see Brummelkamp et al., Science 296:550-553, (2002); Lee et al, Nature Biotechnol., 20, 500-505, (2002); Miyagishi and Taira, Nature Biotechnol 20:497-500, (2002); Paddison et al. Genes & Dev. 16:948-958, (2002); Paul, Nature Biotechnol, 20, 505-508, (2002); Sui, Proc. Natl. Acad. Sd. USA, 99(6), 5515-5520, (2002); and Yu et al. Proc Natl Acad Sci USA 99:6047-6052, (2002), the disclosures of which are hereby incorporated by reference herein in their entireties.

shRNA

Figure 30A:
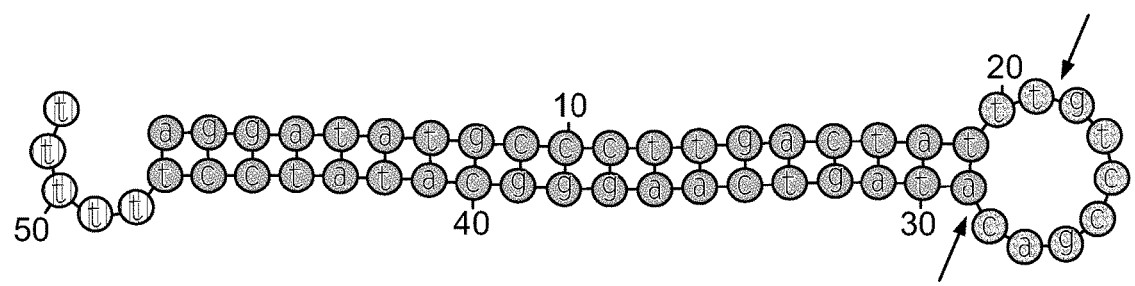
FIG. 30A illustrates the secondary structure and theoretical primary DICER cleavage sites (arrows) of sh734 (see also SEQ ID NO: 30). The secondary structure has a MFE value of about −30.9 kcal/mol.

In some embodiments, the first nucleic acid sequence encodes a shRNA targeting an HPRT gene. In some embodiments, the first nucleic acid sequence encoding a shRNA targeting an HPRT gene has a sequence having at least 80% identify to that of SEQ ID NO: 30 (referred to herein as "sh734"). In other embodiments, the first nucleic acid sequence encoding a shRNA targeting an HPRT gene has a sequence having at least 90% identify to that of SEQ ID NO: 1. In yet other embodiments the first nucleic acid sequence encoding a shRNA targeting an HPRT gene has a sequence having at least 95% identity to that of SEQ ID NO: 30. In further embodiments, the first nucleic acid sequence encoding a shRNA targeting an HPRT gene has a sequence having at least 97% identity to that of SEQ ID NO: 30. In even further embodiments, the first nucleic acid sequence encoding a shRNA targeting an HPRT gene has a sequence having at least 98% identity to that of SEQ ID NO: 30. In yet further embodiments, the first nucleic acid sequence encoding a shRNA targeting an HPRT gene has a sequence having at least 99% identity to that of SEQ ID NO: 30. In other embodiments, the first nucleic acid sequence encoding a shRNA targeting an HPRT gene has the sequence of SEQ ID NO: 30 (see also FIG. 30A).

In some embodiments, the nucleic acid sequence of SEQ ID NO: 30 may be modified. In some embodiments, modifications include: (i) the incorporation of a hsa-miR-22 loop sequence (e.g. CCUGACCCA) (SEQ ID NO: 34); (ii) the addition of a 5'-3' nucleotide spacer, such as one having two or three nucleotides (e.g. TA); (iii) a 5' start modification, such as the addition of one or more nucleotides (e.g. G); and/or (iv) the addition of two nucleotides 5' and 3' to the stem and loop (e.g. 5' A and 3' T). In general, first generation shRNAs are processed into a heterogenous mix of small RNAs, and the accumulation of precursor transcripts has been shown to induce both sequence-dependent and independent nonspecific off-target effects in vivo. Therefore, based on the current understanding of DICER processing and specificity, design rules were applied design that would optimize the structure of the sh734 and DICER processivity and efficiency. (see also Gu, S., Y. Zhang, L. Jin, Y. Huang, F. Zhang, M. C. Bassik, M. Kampmann, and M. A. Kay. 2014. Weak base pairing in both seed and 3' regions reduces RNAi off-targets and enhances si/shRNA designs. Nucleic Acids Research 42:12169-12176).

In some embodiments, the nucleic acid sequence of SEQ ID NO: 30 is modified by adding two nucleotides 5' and 3' (e.g., G and C, respectively) to the hairpin loop (SEQ ID NO: 35), thereby lengthening the guide strand from about 19 nucleotides to about 21 nucleotides in length and replacing the loop with the hsa-miR-22 loop CCUGACCCA (SEQ ID NO: 34), to provide the nucleotide sequence of SEQ ID NO: 31. In some embodiments, the nucleic acid sequence encoding a shRNA targeting an HPRT gene has a sequence having at least 90% identity to that of SEQ ID NO: 31. In other embodiments, the first nucleic acid sequence encoding a shRNA targeting an HPRT gene has a sequence having at least 95% identity to that of SEQ ID NO: 31. In other embodiments, the first nucleic acid sequence encoding a shRNA targeting an HPRT gene has a sequence having at least 97% identity to that of SEQ ID NO: 31. In other embodiments, the first nucleic acid sequence encoding a shRNA targeting an HPRT gene has a sequence having at least 98% identity to that of SEQ ID NO: 31. In other embodiments, the first nucleic acid sequence encoding a shRNA targeting an HPRT gene has a sequence having at least 99% identity to that of SEQ ID NO: 31. In yet other embodiments, the nucleic acid sequence encoding a shRNA targeting an HPRT gene has the sequence of SEQ ID NO: 31. It is believed that the shRNA encoded by SEQ ID NO: 31 achieves similar knockdown of HPRT as compared with either SEQ ID NO: 30. Likewise, it is believed that a cell rendered HPRT deficient through the knockdown of HPRT via expression of the shRNA encoded by SEQ ID NO: 31 allows for selection using a thioguanine analog (e.g. 6TG).

In some embodiments, the RNAi present within the vector encodes for a nucleic acid molecule, such as one having SEQ ID NO: 1 or SEQ ID NO: 2. In some embodiments, the nucleic acid molecules are found in the cytoplasm of a host cell. In some embodiments, the present disclosure provides for a host cell including at least one nucleic acid molecule selected from SED ID NO: 1 or SEQ ID NO: 2.

In some embodiments, the first nucleic acid sequence encoding a shRNA targeting an HPRT gene has a sequence having at least 80% identify to that of SEQ ID NO: 27 (referred to herein as "shHPRT 616"). In other embodiments, the nucleic acid sequence encoding a shRNA targeting an HPRT gene has a sequence having at least 90% identify to that of SEQ ID NO:27. In yet other embodiments, the nucleic acid sequence encoding a shRNA targeting an HPRT gene shRNA has a sequence having at least 95% identity to that of SEQ ID NO: 27. In further embodiments, the nucleic acid sequence encoding a shRNA targeting an HPRT gene has a sequence having at least 97% identity to that of SEQ ID NO: 27. In even further embodiments, the nucleic acid sequence encoding a shRNA targeting an HPRT gene has a sequence having at least 98% identity to that of SEQ ID NO: 27. In yet further embodiments, the nucleic acid sequence encoding a shRNA targeting an HPRT gene has a sequence having at least 99% identity to that of SEQ ID NO: 27. In other embodiments, the nucleic acid sequence encoding a shRNA targeting an HPRT gene has the sequence of SEQ ID NO: 27 (see also FIG. 31B).

In some embodiments, the first nucleic acid sequence encoding a shRNA targeting an HPRT gene has a sequence having at least 80% identify to that of SEQ ID NO: 28 (referred to herein as "shHPRT 211"). In other embodiments, the nucleic acid sequence encoding a shRNA targeting an HPRT gene has a sequence having at least 90% identify to that of SEQ ID NO:28. In yet other embodiments, the nucleic acid sequence encoding a shRNA targeting an HPRT gene shRNA has a sequence having at least 95% identity to that of SEQ ID NO: 28. In further embodiments, the nucleic acid sequence encoding a shRNA targeting an HPRT gene has a sequence having at least 97% identity to that of SEQ ID NO: 28. In even further embodiments, the nucleic acid sequence encoding a shRNA targeting an HPRT gene has a sequence having at least 98% identity to that of SEQ ID NO: 28. In yet further embodiments, the nucleic acid sequence encoding a shRNA targeting an HPRT gene has a sequence having at least 99% identity to that of SEQ ID NO: 28. In other embodiments, the nucleic acid sequence encoding a shRNA targeting an HPRT gene has the sequence of SEQ ID NO: 28 (see also FIG. 31A).

Figure 30B:
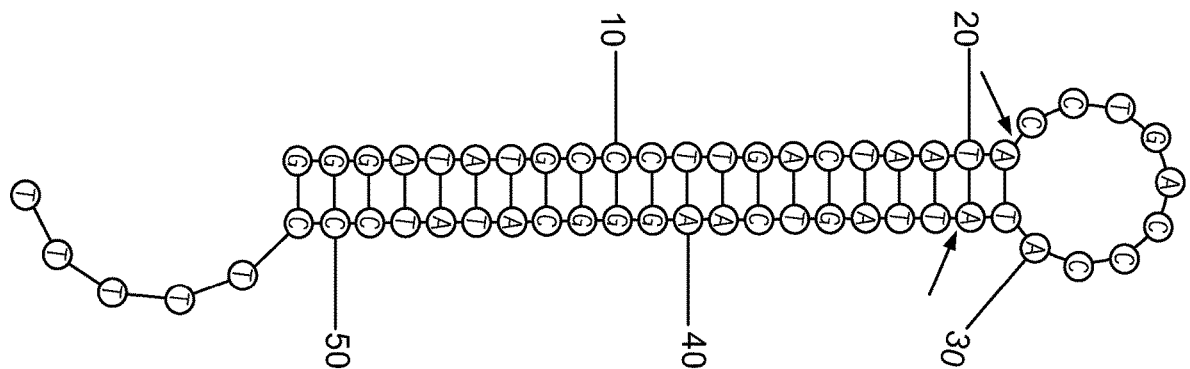
FIG. 30B illustrates a modified version of sh734 (sh734.1) (see also SEQ ID NO: 31). The secondary structure has a MFE value of −36.16 kcal/mol.

In some embodiments, the nucleic acid sequence encoding a shRNA targeting an HPRT gene has a sequence having at least 80% identify to that of SEQ ID NO: 29 (referred to herein as "shHPRT 734.1") (see also FIG. 30B). In other embodiments, the nucleic acid sequence encoding a shRNA targeting an HPRT gene has a sequence having at least 90% identify to that of SEQ ID NO:29. In yet other embodiments, the nucleic acid sequence encoding a shRNA targeting an HPRT gene shRNA has a sequence having at least 95% identity to that of SEQ ID NO: 28. In further embodiments, the nucleic acid sequence encoding a shRNA targeting an HPRT gene has a sequence having at least 97% identity to that of SEQ ID NO: 29. In even further embodiments, the nucleic acid sequence encoding a shRNA targeting an HPRT gene has a sequence having at least 98% identity to that of SEQ ID NO: 29. In yet further embodiments, the nucleic acid sequence encoding a shRNA targeting an HPRT gene has a sequence having at least 99% identity to that of SEQ ID NO: 29. In other embodiments, the nucleic acid sequence encoding a shRNA targeting an HPRT gene has the sequence of SEQ ID NO: 29 (see also FIG. 30B).

MiroRNA

MicroRNAs (miRs) are a group of non-coding RNAs which post-transcriptionally regulate the expression of their target genes. It is believed that these single stranded molecules form a miRNA-mediated silencing complex (miRISC) complex with other proteins which bind to the 3' untranslated region (UTR) of their target mRNAs so as to prevent their translation in the cytoplasm.

In some embodiments, shRNA sequences are embedded into micro-RNA secondary structures ("micro-RNA based shRNA"). In some embodiments, shRNA nucleic acid sequences targeting HPRT are embedded within micro-RNA secondary structures. In some embodiments, the micro-RNA based shRNAs target coding sequences within HPRT to achieve knockdown of HPRT expression, which is believed to be equivalent to the utilization of shRNA targeting HPRT without attendant pathway saturation and cellular toxicity or off-target effects. In some embodiments, the micro-RNA based shRNA is a de novo artificial microRNA shRNA. The production of such de novo micro-RNA based shRNAs are described by Fang, W. & Bartel, David P. The Menu of Features that Define Primary MicroRNAs and Enable De Novo Design of MicroRNA Genes. Molecular Cell 60, 131-145, the disclosure of which is hereby incorporated by reference herein in its entirety.

Figure 32A:
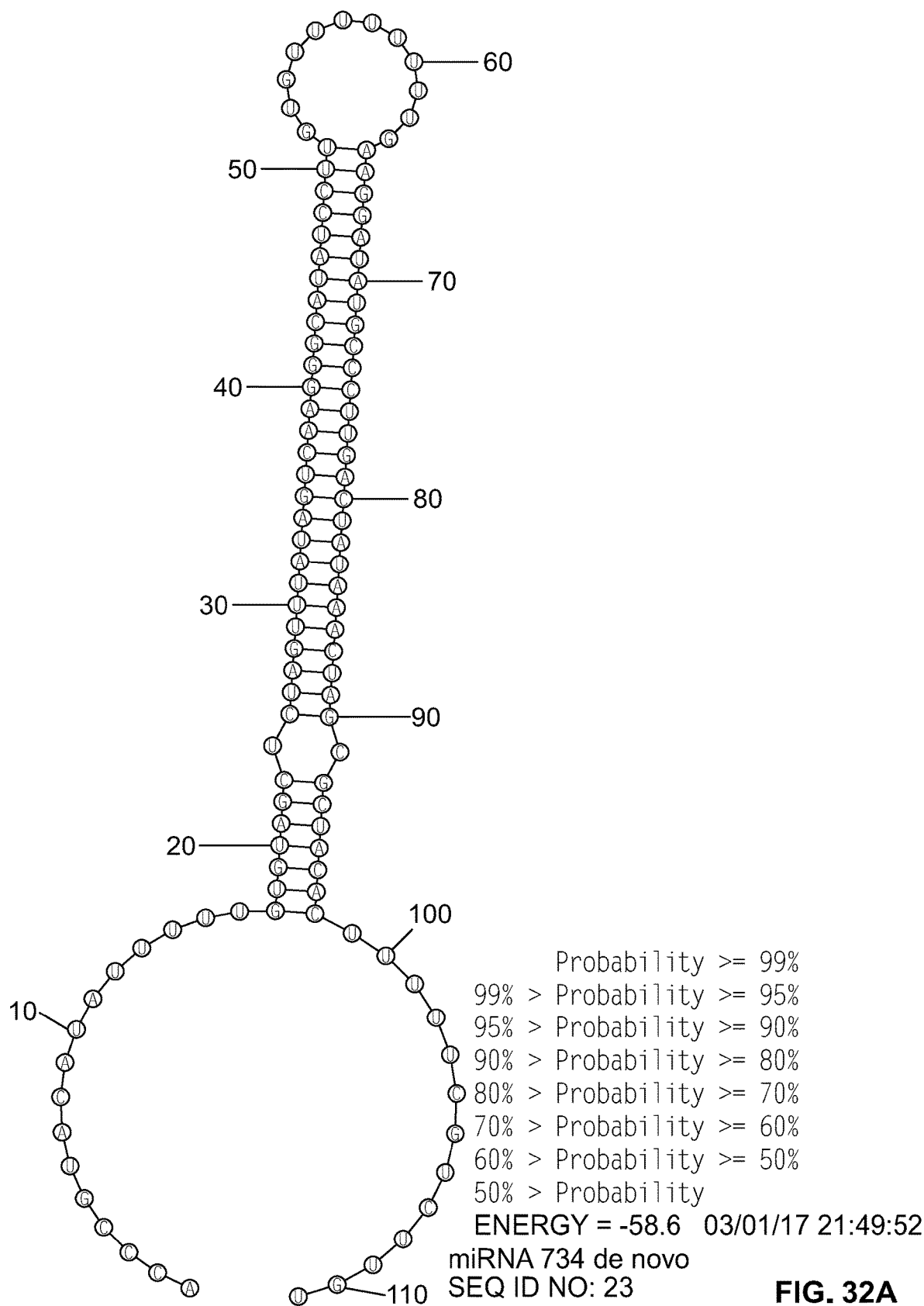
FIG. 32A illustrates the de novo design of an artificial miRNA734 (111nt). 5' and 3' DROSHA target sites and 5' and 3' Dicer cut sites are indicated by arrows in the miRNA 211 secondary structure (see also SEQ ID NO: 23).

In some embodiments, the micro-RNA based shRNA has a sequence having at least 80% identify to that of SEQ ID NO: 67. In some embodiments, the micro-RNA based shRNA has a sequence having at least 90% identify to that of SEQ ID NO: 67. In some embodiments, the micro-RNA based shRNA has a sequence having at least 95% identify to that of SEQ ID NO: 67. In some embodiments, the micro-RNA based shRNA has the sequence of SEQ ID NO: 67 ("miRNA734-Denovo") (see also FIG. 32A). The RNA form of SEQ ID NO: 67 is found at SEQ ID NO: 23.

Figure 32B:
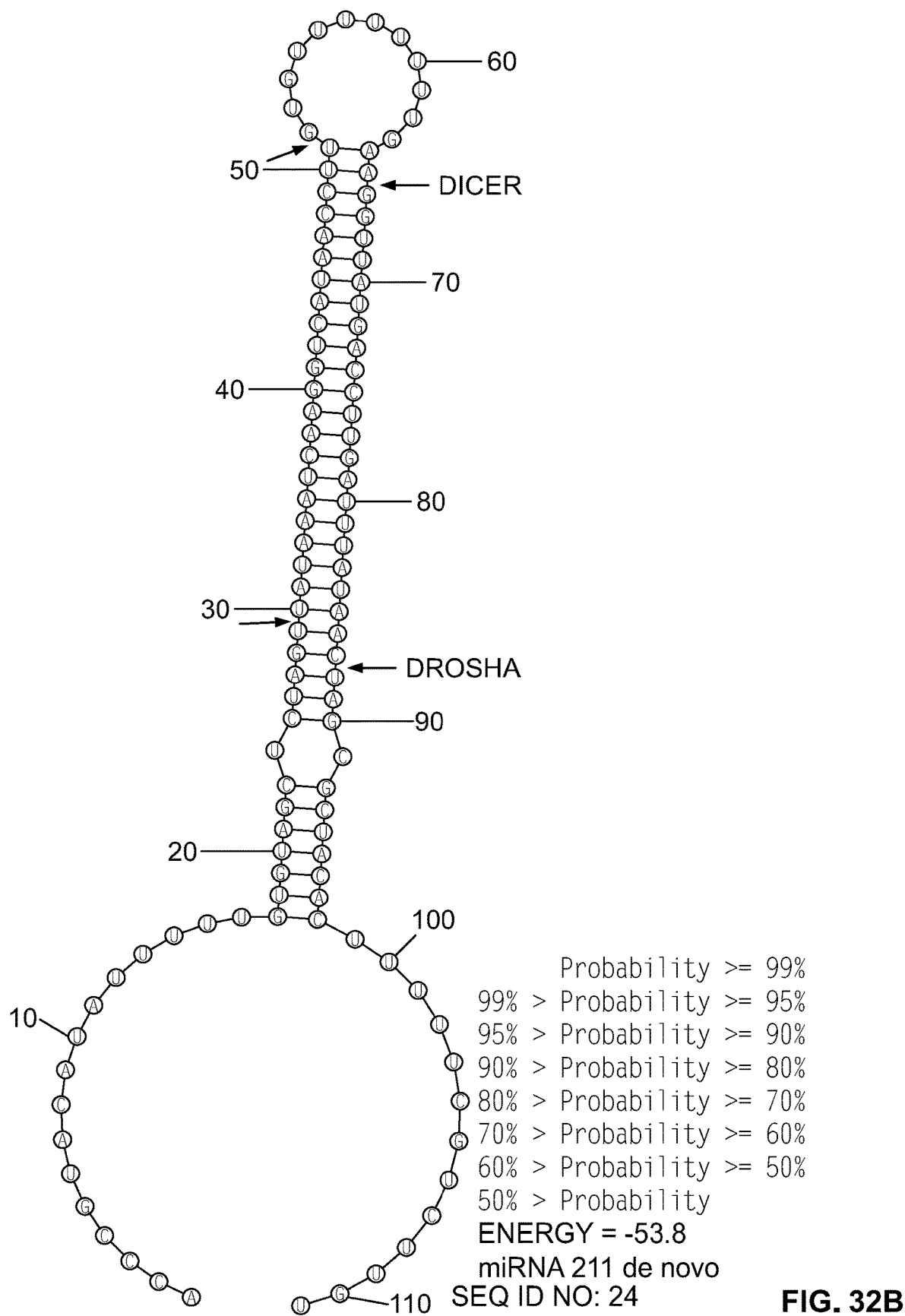
FIG. 32B illustrates the de novo design of an artificial miRNA211 (111nt) (see also SEQ ID NO: 24).

In some embodiments, the micro-RNA based shRNA has a sequence having at least 80% identify to that of SEQ ID NO: 68. In some embodiments, the micro-RNA based shRNA has a sequence having at least 90% identify to that of SEQ ID NO: 68. In some embodiments, the micro-RNA based shRNA has a sequence having at least 95% identify to that of SEQ ID NO: 68. In some embodiments, the micro-RNA based shRNA has the sequence of SEQ ID NO: 68 ("miRNA211-Denovo") (see also FIG. 32B). The RNA form of SEQ ID NO: 68 is found at SEQ ID NO: 24.

Figure 28:
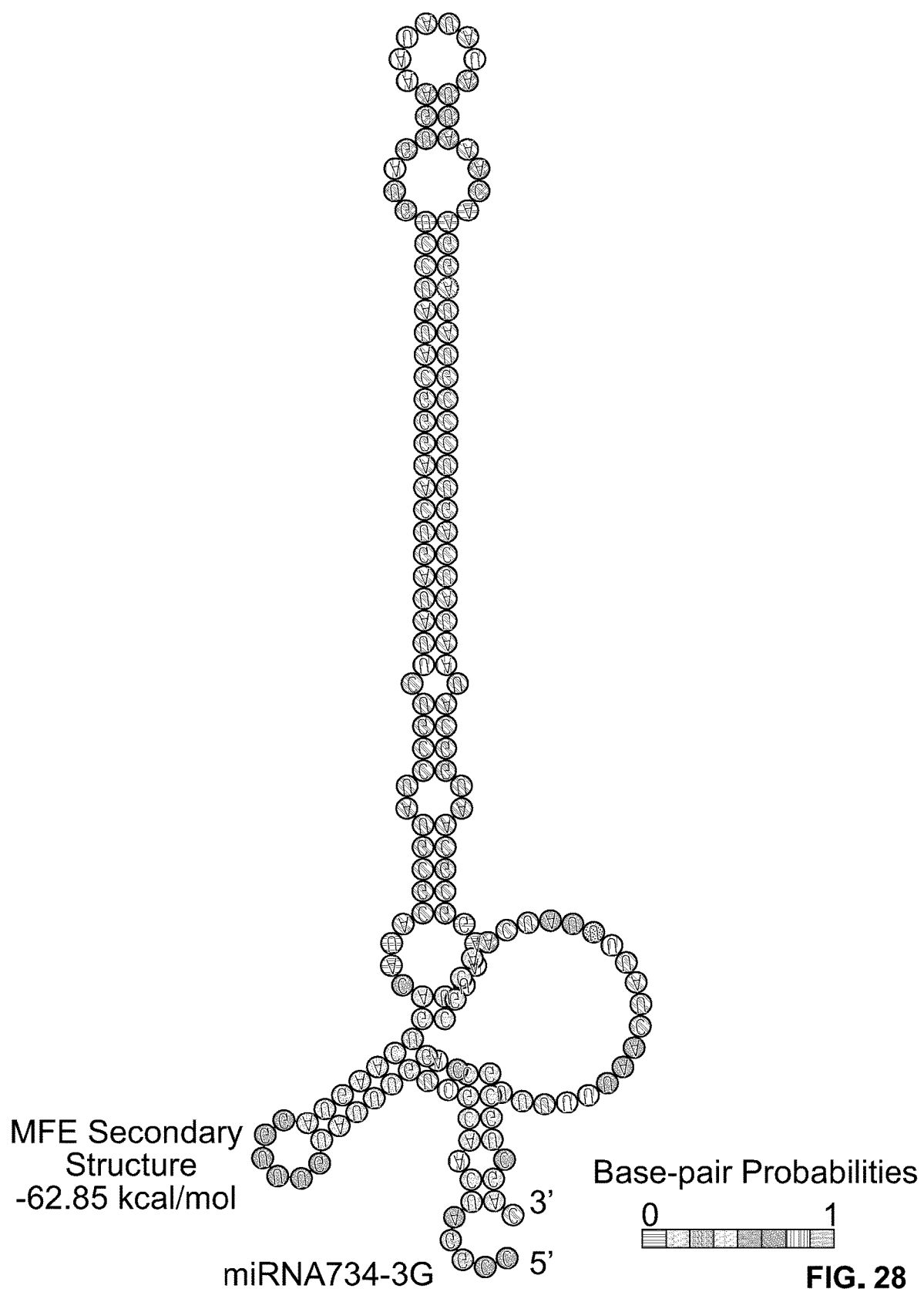
FIG. 28 illustrates a sh734 embedded in the miRNA-3G backbone, a third generation miRNA scaffold derived from the native miRNA 16-2 structure (see also SEQ ID NO: 26).
Figure 29:
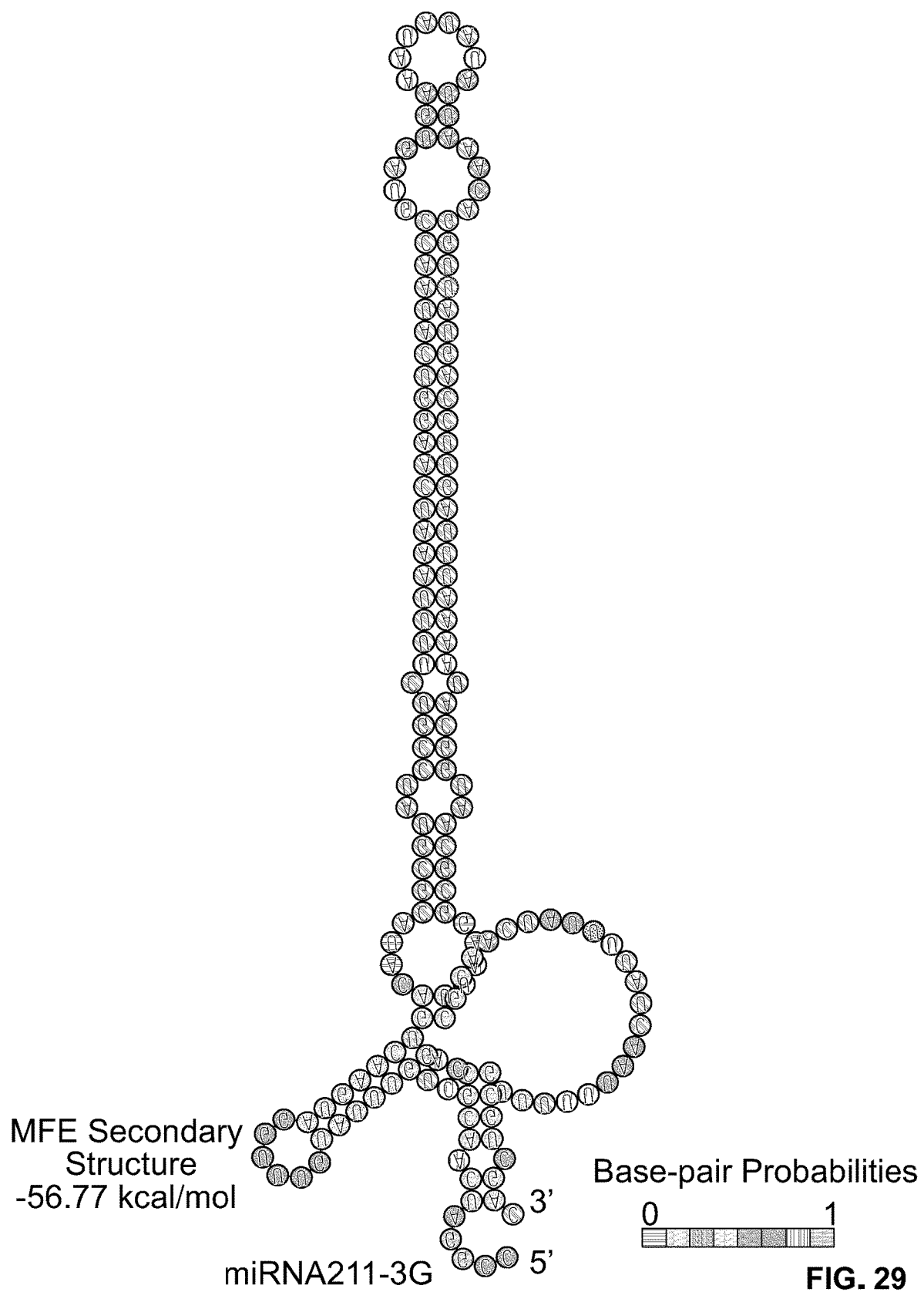
FIG. 29 illustrates the sh211 embedded in the miRNA-3G backbone, a 3rd generation miRNA scaffold derived from the native miRNA 16-2 structure (see also SEQ ID NO: 25).

In other embodiments, the micro-RNA based shRNA is a third generation miRNA scaffold modified miRNA 16-2 (hereinafter "miRNA-3G") (see, e.g. FIGS. 28 and 29). The synthesis of such miRNA-3G molecules is described by Watanabe, C., Cuellar, T. L. & Haley, B. "Quantitative evaluation of first, second, and third generation hairpin systems reveals the limit of mammalian vector-based RNAi," RNA Biology 13, 25-33 (2016), the disclosure of which is hereby incorporated by reference herein in its entirety.

In some embodiments, the miRNA-3G has a sequence having at least 80% identify to that of SEQ ID NO: 25. In some embodiments, the miRNA-3G has a sequence having at least 90% identify to that of SEQ ID NO: 25. In some embodiments, the miRNA-3G has a sequence having at least 95% identify to that of SEQ ID NO: 25. In some embodiments, the miRNA-3G has the sequence of SEQ ID NO: 25 ("miRNA211-3G") (see also FIG. 29).

In some embodiments, the miRNA-3G has a sequence having at least 80% identify to that of SEQ ID NO: 26. In some embodiments, the miRNA-3G has a sequence having at least 90% identify to that of SEQ ID NO: 26. In some embodiments, the miRNA-3G has a sequence having at least 95% identify to that of SEQ ID NO: 25. In other embodiments, the miRNA-3G has the sequence of SEQ ID NO: 26 ("miRNA734-3G") (see also FIG. 28).

Figure 33:
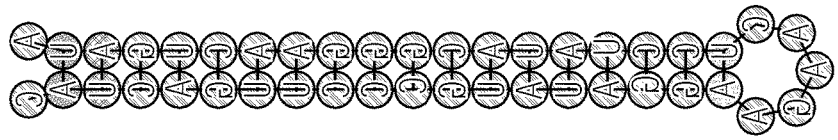
FIG. 33 illustrates the Ago-sh734 secondary structure (mimicking the human miRNA451 structure) (see also SEQ ID NO: 58).
Figure 34:
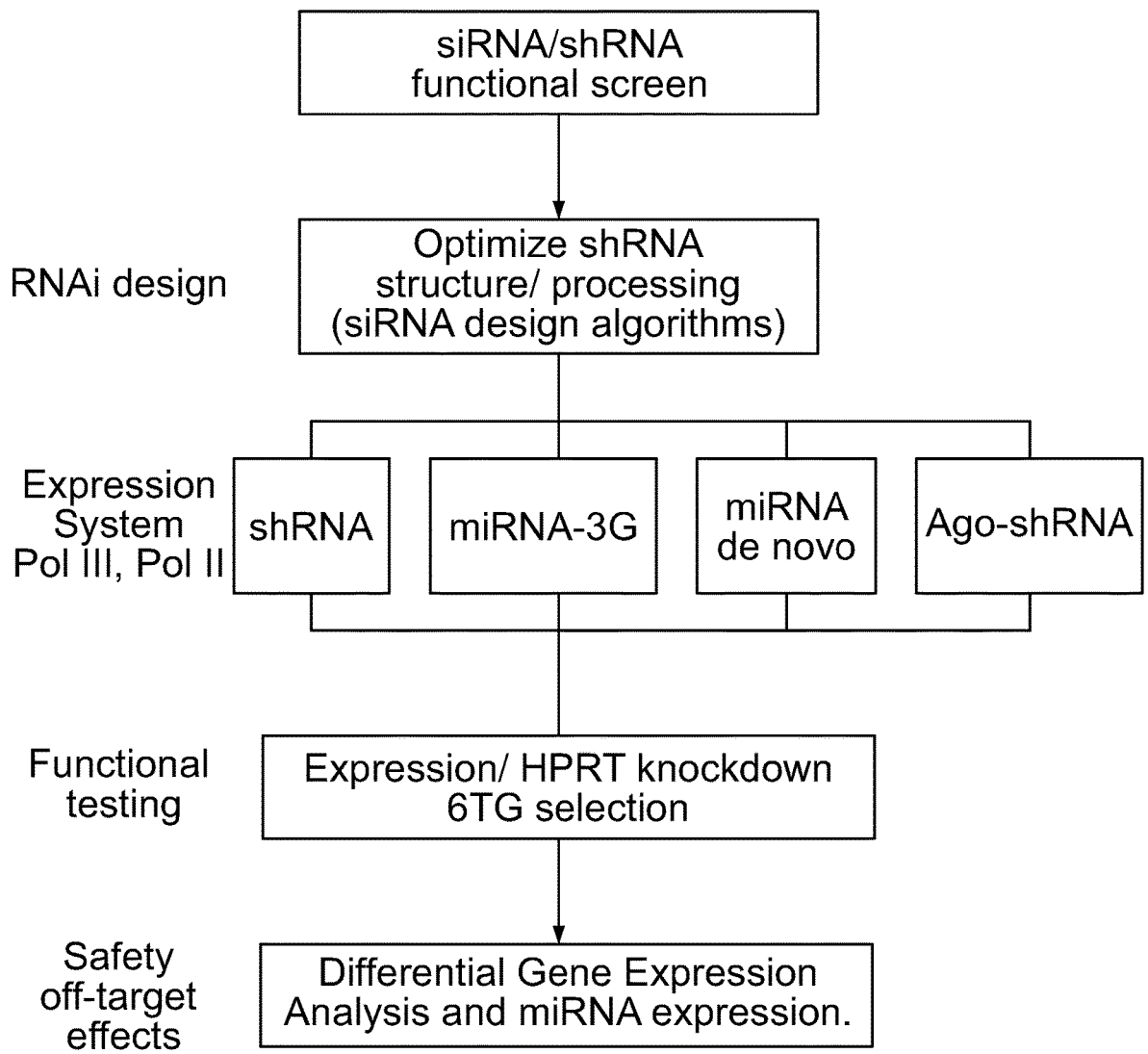
FIG. 34 sets forth a flowchart illustrating a process of four steps for RNAi design, choice of promoter and structure, functional testing and safety evaluation. In some embodiments, siRNA design algorithms are used to obtain candidates of shRNA target. Subsequently, different shRNA expression system with different promoters (Pol III or Pol II) and different shRNA designs (shRNA, $3^{rd}$-generation miRNA, miRNA de novo and dicer-independent Ago-shRNA) are designed and synthesized for functional tests and safety study. Functional tests are performed by measuring knockdown of HPRT and selection with 6-TG in transduced cell lines. Cell viability and miRNA expression are analyzed for safety evaluation. Preclinical testing and safety studies are performed in in vitro primary cells including hematopoietic stem cell and progenitor cells, and established cell lines and in in vivo murine and non-human primate models.

In some embodiments, the sh734 shRNA is adapted to mimic a miRNA-451 (see SEQ ID NO: 60) structure with a 17 nucleotide base pair stem and a 4-nucleotide loop (miR-451 regulates the drug-transporter protein P-glycoprotein). Notably, this structure does not require processing by DICER. It is believed that the pre-451 mRNA structure is cleaved by Ago2 and subsequently by poly(A)-specific ribonuclease (PARN) to generate the mature miRNA-451 structural mimic. The secondary structure for a miRNA-451-like Agosh734 sequence is shown in FIG. 33 herein (SEQ ID NO: 58). It is believed that Ago-shRNA mimics of the structure of the endogenous miR-451 and may have the advantage of being DICER independent. This is believed to restrict off target effects of passenger loading, with variable 3'-5' exonucleolytic activity (23-26nt mature) (see Herrera-Carrillo, E., and B. Berkhout. 2017. Dicer-independent processing of small RNA duplexes: mechanistic insights and applications. Nucleic Acids Res. 45:10369-10379). It is also believed that there exist advantages of utilizing alternate dicer independent processing of shRNAs, including efficient reduced off-target effects of single RNAi-active guide, no saturation of cellular RNAi Dicer machinery, and shorter RNA duplexes are less likely to trigger innate RIG-I response.

Alternatives to RNAi

As an alternative to the incorporation of a RNAi, in some embodiments, the expression vectors may include a nucleic acid sequence which encodes antisense oligonucleotides that bind sites in messenger RNA (mRNA). Antisense oligonucleotides of the present disclosure specifically hybridize with a nucleic acid encoding a protein and interfere with transcription or translation of the protein. In some embodiments, an antisense oligonucleotide targets DNA and interferes with its replication and/or transcription. In other embodiments, an antisense oligonucleotide specifically hybridizes with RNA, including pre-mRNA (i.e. precursor mRNA which is an immature single strand of mRNA), and mRNA. Such antisense oligonucleotides may affect, for example, translocation of the RNA to the site of protein translation, translation of protein from the RNA, splicing of the RNA to yield one or more mRNA species, and catalytic activity that may be engaged in or facilitated by the RNA. The overall effect of such interference is to modulate, decrease, or inhibit target protein expression.

In some embodiments, the expression vectors incorporate a nucleic acid sequence encoding for an exon skipping agent or exon skipping transgene. As used herein, the phrase "exon skipping transgene" or "exon skipping agent" refers to any nucleic acid that encodes an antisense oligonucleotide that can generate exon skipping. "Exon skipping" refers to an exon that is skipped and removed at the pre-mRNA level during protein production. It is believed that antisense oligonucleotides may interfere with splice sites or regulatory elements within an exon. This can lead to truncated, partially functional, protein despite the presence of a genetic mutation. Generally, the antisense oligonucleotides may be mutation-specific and bind to a mutation site in the pre-messenger RNA to induce exon skipping.

Exon skipping transgenes encode agents that can result in exon skipping, and such agents are antisense oligonucleotides. The antisense oligonucleotides may interfere with splice sites or regulatory elements within an exon to lead to truncated, partially functional, protein despite the presence of a genetic mutation. Additionally, the antisense oligonucleotides may be mutation-specific and bind to a mutation site in the pre-messenger RNA to induce exon skipping. Antisense oligonucleotides for exon skipping are known in the art and are generally referred to as AONs. Such AONs include small nuclear RNAs ("snRNAs"), which are a class of small RNA molecules that are confined to the nucleus and which are involved in splicing or other RNA processing reactions. Examples of antisense oligonucleotides, methods of designing them, and related production methods are disclosed, for example, in U.S. Publication Nos. 20150225718, 20150152415, 20150140639, 20150057330, 20150045415, 20140350076, 20140350067, and 20140329762, the disclosures of which are hereby incorporated by reference herein in their entireties.

In some embodiments, the expression vectors of the present disclosure include a nucleic acid which encodes an exon skipping agent which results in exon skipping during the expression of HPRT or which causes an HPRT duplication mutation (e.g. a duplication mutation in Exon 4) (see Baba S, et al. Novel mutation in HPRT1 causing a splicing error with multiple variations. Nucleosides Nucleotides Nucleic Acids. 2017 Jan. 2; 36(1):1-6, the disclosure of which is hereby incorporated by reference herein in its entirety). In some embodiments, phosphorothioate-modified antisense oligonucleotides to target sequences within the coding region of HPRT (see FIG. 38) can bind mRNA transcripts and inhibit translation of functional protein. In addition to their incorporation within expression vectors, oligonucleotides may be delivered via nanocapsules, minicells, liposomes or another suitable transfection vehicle. For example, in accordance with the present disclosure, minicells may include a functional nucleic acid, e.g. a siRNA or shRNA, or an expression vector that encodes a functional nucleic acid that can be effectively packaged for in vivo delivery.

In some embodiments, HPRT may be replaced with a modified mutated sequence by spliceosome trans-splicing, thus facilitating knockdown of HPRT. In some embodiments, this (1) requires a mutated coding region to replace the coding sequence in a target RNA, (2) a 5' or 3' splice site, and/or (3) a binding domain, i.e., antisense oligonucleotide sequence, which is complementary to the target HPRT RNA. In some embodiments, all three components are required.

Therapeutic Gene

As noted herein, the expression vectors (e.g. the lentiviral expression vectors) of the present disclosure may also include a second nucleic acid sequence encoding a therapeutic gene (e.g. gamma globin), whereby the therapeutic gene may correct a defect in a target cell (e.g. HSCs). As will be understood by those in the art, the term "therapeutic gene" includes genomic sequences, cDNA sequences, and smaller engineered gene segments that express, or may be adapted to express, proteins, polypeptides, domains, fusion proteins, and mutants that maintain some or all of the therapeutic function of the full-length polypeptide encoded by the therapeutic gene. Encompassed within the definition of "therapeutic gene" is a "biologically functional equivalent" therapeutic gene. Accordingly, sequences that have about 70% sequence homology to about 99% sequence homology and any range or amount of sequence homology derivable therein, such as, for example, about 70% to about 80%, and more preferably about 85% and about 90%; or even more preferably, between about 95% and about 99%; of amino acids that are identical or functionally equivalent to the amino acids of the therapeutic gene will be sequences that are biologically functional equivalents provided the biological activity of the polypeptide is maintained.

In some embodiments, the therapeutic gene corrects a single-gene disorder. In some embodiments, the therapeutic gene is used to treat immune deficiencies, hereditary diseases, blood diseases (e.g. hemophilia, hemoglobin disorders), lysosomal storage diseases, neurological diseases, angiogenic disorders, or cancer.

In some embodiments, the therapeutic gene is a gene encoding an enzyme adenosine deaminase, a gene encoding alpha-1-antitrypsin, a gene encoding a cystic fibrosis transmembrane conductance regulator, a gene encoding the enzyme Galactose-1-phosphate uridylyltransferase, a gene encoding a clotting factor (e.g. human Factor IX), a gene encoding a lipoprotein lipase gene, one or more genes encoding the enzymes required for dopamine synthesis, a gene encoding for glial cell line-derived neurotrophic factor (GDNF), a gene encoding interleukin-2 receptor subunit gamma (IL-2RG), a gene encoding Gp91phox, a gene encoding the Wiskott-Aldrich syndrome protein, a gene encoding a globin protein, a gene encoding a mutated globin protein (e.g. one having antisickling properties, a gene encoding a mutated beta-globin, a gene encoding gamma-globin, a gene encoding an anti-CD19 antibody, etc. In other embodiments, the therapeutic gene is selected from the group consisting of a globin gene, sphingomyelinase gene, alpha-L-iduronudase gene, huntingtin gene, neurofibromin 1 gene, MLH1 gene, MSH2 gene, MSH6 gene, PMS2 gene, cystic fibrosis transmembrane conductance regulator gene, hexosaminidase A gene dystrophin gene, FMR1 gene, phenylalanine hydroxylase gene and low-density lipoprotein gene.

Examples of classes of therapeutic genes include, but are not limited to, tumor suppressor genes, genes that induce or prevent apoptosis, genes encoding enzymes, genes encoding antibodies, genes encoding hormones, genes encoding receptors, and genes encoding cytokines, chemokines, or angiogenic factors. Specific examples of therapeutic genes include, but are not limited to, Rb, CFTR, p16, p21, p27, p57, p73, C-CAM, APC, CTS-I, zacl, scFV, ras, DCC, NF-I, NF-2, WT-I, MEN-I, MEN-II, BRCA1, VHL, MMACl, FCC, MCC, BRCA2, IL-I, IL-2, IL-3, IL-4, IL-5, IL-6, IL-7, IL-8, IL-9, IL-IO, IL-11 IL-12, IL-15Rα, IL-15, IL-21, GM-CSF, G-CSF, thymidine kinase, mda7, FUS1, interferon alpha, interferon beta, interferon gamma, ADP, p53, ABLI, BLC1, BLC6, CBFAl, CBL, CSFIR, ERBA, ERBB, EBRB2, ETS1, ETS2, ETV6, FGR, FOX, FYN, HCR, HRAS, JUN, KRAS, LCK, LYN, MDM2, MLL, MYB, MYC, MYCL1, MYCN, NRAS, PIMl, PML, RET, SRC, TAL1, TCL3, YES, MADH4, RBl, TP53, WTI, TNF, BDNF, CNTF, NGF, IGF, GMF, aFGF, bFGF, NT3, NT5, ApoAI, ApoATV, ApoE, RaplA, cytosine deaminase, Fab, ScFv, BRCA2, zacl, ATM, HIC-I, DPC-4, FHIT, PTEN, INGl, NOEY1, NOEY2, OVCA1, MADR2, 53BP2, IRF-I, zacl, DBCCR-I, rks-3, COX-I, TFPI, PGS, Dp, E2F, ras, myc, neu, raf, erb, fms, trk, ret, gsp, hst, abl, E1A, p300, VEGF, FGF, thrombospondin, BAI-I, GDAIF, MCC, 41BBL, CD80, CD86, or OX40.

Other examples of therapeutic genes are the tumor suppressor genes including, but not limited to, FUS1, Gene 26 (CACNA2D2), PL6, LUCA-I (HYAL1), LUCA-2 (HYAL2), 123F2 (RASSF1), 101F6, Gene 21 (NPRL2), SEM A3, NF1, NF2, and p53.

Yet other examples of therapeutic genes are genes encoding enzymes including, but not limited to, ACP desaturase, ACP hydroxylase, ADP-glucose pyrophorylase, PDE8A (camp Phosphodiesterase), ATPase, alcohol dehydrogenase, amylase, amyloglucosidase, catalase, cellulase, cyclooxygenase, decarboxylase, dextrinase, esterase, DNA polymerase, RNA polymerase, hyaluron synthase, galactosidase, glucanase, glucose oxidase, GTPase, helicase, hemicellulase, hyaluronidase, integrase, invertase, isomerase, kinase, lactase, lipase, lipoxygenase, lyase, lysozyme, pectinesterase, a peroxidase, a phosphatase, a phospholipase, a phosphorylase, polygalacturonase, proteinase, peptidase, pullanase, recombinase, reverse transcriptase, topoisomerase or xylanase. Further examples of therapeutic genes include the genes encoding carbamoyl synthetase I, ornithine transcarbamylase, arginosuccinate synthetase, arginosuccinate lyase, arginase, fumarylacetoacetate hydrolase, phenylalanine hydroxylase, alpha-1 antitrypsin, glucose-6-phosphatase, low-density-lipoprotein receptor, porphobilinogen deaminase, factor VIII, factor IX, cystathione beta.-synthase, branched chain ketoacid decarboxylase, albumin, isovaleryl-CoA dehydrogenase, propionyl CoA carboxylase, methyl malonyl CoA mutase, glutaryl CoA dehydrogenase, insulin, beta.-glucosidase, pyruvate carboxylase, hepatic phosphorylase, phosphorylase kinase, glycine decarboxylase, H-protein, T-protein, Menkes disease copper-transporting ATPase, Wilson's disease copper-transporting ATPase, cytosine deaminase, hypoxanthine-guanine phosphoribosyltransferase, galactose-1-phosphate uridyltransferase, phenylalanine hydroxylase, glucocerbrosidase, sphingomyelinase, alpha-L-idurom'dase, glucose-6-phosphate dehydrogenase, HSV thymidine kinase, or human thymidine kinase.

Further examples of therapeutic genes include genes encoding hormones including, but not limited to, growth hormone, prolactin, placental lactogen, luteinizing hormone, follicle-stimulating hormone, chorionic gonadotropin, uiyroid-stimulating hormone, leptin, adrenocorticotropin, angiotensin I, angiotensin II, alpha-endorphin, beta-melanocyte stimulating hormone, cholecystokinin, endothelin I, galanin, gastric inhibitory peptide, glucagon, insulin, lipotropins, neurophysins, somatostatin, calcitonin, calcitonin gene related peptide, beta-calcitonin gene related peptide, hypercalcemia of malignancy factor, parathyroid hormone-related protein, parathyroid hormone-related protein, glucagon-like peptide, pancreastatin, pancreatic peptide, peptide YY, PHM, secretin, vasoactive intestinal peptide, oxytocin, vasopressin, vasotocin, enkephalinamide, metorphinamide, alpha melanocyte stimulating hormone, atrial natriuretic factor, amylin, amyloid P component, corticotropin releasing hormone, growth hormone releasing factor, luteinizing hormone-releasing hormone, neuropeptide Y, substance K, substance P, or thyrotropin releasing hormone.

Gamma-Globin Gene

In some embodiments, the expression vector comprises a nucleic acid sequence encoding a gamma-globin gene (see, e.g. FIG. 39). In some embodiments, the nucleic acid sequence encoding the gamma-globin gene has a sequence having at least 80% identity to that of SEQ ID NO: 55. In other embodiments, the nucleic acid sequence encoding the gamma-globin gene has a sequence having at least 85% identity to that of SEQ ID NO: 55. In yet other embodiments, the nucleic acid sequence encoding the gamma-globin gene has a sequence having at least 90% identity to that of SEQ ID NO: 55. In further embodiments, the nucleic acid sequence encoding the gamma-globin gene has a sequence having at least 95% identity to that of SEQ ID NO: 55. In yet further embodiments, the nucleic acid sequence encoding the gamma-globin gene has a sequence having at least 97% identity to that of SEQ ID NO: 55. In even further embodiments, the nucleic acid sequence encoding the gamma-globin gene has a sequence having at least 98% identity to that of SEQ ID NO: 55. In even further embodiments, the nucleic acid sequence encoding the gamma-globin gene has a sequence having at least 99% identity to that of SEQ ID NO: 55. It is believed that the point mutation in the gamma globin gene of SEQ ID NO: 55 encoding a G16D amino acid change in the polypeptide has an increased affinity to bind alpha globin without altering its function, thereby greatly improving the efficiency of HbF formation in RBCs and resulting in a far more efficient anti-sickling effect that will, it is believed, correct the SCD phenotype. Exons 1, 2, and 3 of the gamma globin gene are set forth as SEQ ID NOS: 51, 52, and 53, respectively.

In some embodiments, the nucleic acid sequence encoding the gamma-globin gene has a sequence having at least 90% identity to that of SEQ ID NO: 3. In other embodiments, the nucleic acid sequence encoding the gamma-globin gene has a sequence having at least 95% identity to that of SEQ ID NO: 3. In yet other embodiments, the nucleic acid sequence encoding the gamma-globin gene has a sequence having at least 97% identity to that of SEQ ID NO: 3. In yet other embodiments, the nucleic acid sequence encoding the gamma-globin gene has a sequence having at least 98% identity to that of SEQ ID NO: 3. In yet other embodiments, the nucleic acid sequence encoding the gamma-globin gene has a sequence having at least 99% identity to that of SEQ ID NO: 3.

In some embodiments, the expression vector comprises a nucleic acid which encodes for an amino acid sequence having an identity of at least about 80% to that of SEQ ID NO: 4. In other embodiments, the nucleic acid sequence encodes an amino acid having an identity of at least about 85% to that of SEQ ID NO: 4. In yet other embodiments, the nucleic acid sequence encodes an amino acid having an identity of at least about 90% to that of SEQ ID NO: 4. In further embodiments, the nucleic acid sequence encodes an amino acid having an identity of at least about 95% to that of SEQ ID NO: 4. In yet further embodiments, the nucleic acid sequence encodes an amino acid having an identity of at least about 97% to that of SEQ ID NO: 4. In even further embodiments, the nucleic acid sequence encodes an amino acid having an identity of at least about 98% to that of SEQ ID NO: 4. In even further embodiments, the nucleic acid sequence encodes an amino acid having an identity of at least about 99% to that of SEQ ID NO: 4.

Gamma globin genes, methods of their synthesis, and incorporation into vectors are described in United States Patent Publication No. 2017/0145077, the disclosure of which is hereby incorporated by reference herein in its entirety.

Therapeutic Genes for Treating Other Diseases

Yet other therapeutic genes may be incorporated into an expression, including those genes described below.

Adenosine Deaminase-Severe Combined Immunodeficiency (ADA-SCID) deficiency results in the accumulation of toxic metabolites that destroy the immune system, causing severe combined immunodeficiency (ADA-SCID), often referred to as the "bubble boy" disease. In some embodiments, the second nucleic acid of the expression vectors described herein encodes for the human ADA cDNA sequence.

Severe Combined Immunodeficiency (SCID-X1) Disease is the most common form of SCID, accounting for 40-50% of SCID cases reported worldwide. Mutations in the IL2RG gene are leads to defective expression of the common gamma chain (γc), a subunit shared by a host of cytokine receptors, including interleukin (IL)-2, 4, 7, 9, 15, and 21 receptor complexes, which play a vital role in lymphocyte development and function. In some embodiments, the second nucleic acid of the expression vectors described herein encodes the human γc cDNA sequence.

Chronic granulomatous disease (CGD) is caused by defects in the subunits (gp91phox, p22phox, p47phox, p40phox or p67phox) of the phagocyte-derived NADPH oxidase. Mutations in the CYBB gene—encoding the gp91phox subunit—are responsible for the X-linked form of CGD, which accounts for approximately 70% of patients. X-linked CGD is characterized by severe, life-threatening bacterial and fungal infections due to an impaired production of superoxide anions and other reactive oxygen intermediates by neutrophils, eosinophils, monocytes and macrophages. Another aspect of the disease is the sterile, chronic, granulomatous inflammation affecting organs such as the gut or lung, mainly caused by increased production of pro-inflammatory cytokines, delayed apoptosis of inflammatory cells and deficient secretion of anti-inflammatory mediators by activated neutrophils. The poor outcome is associated with a history of invasive fungal infection, liver abscesses and chronic granulomatous inflammation. Available therapeutic strategies include antibiotic long-life prophylaxis, IFN-γ administration, and HCT. In some embodiments, the second nucleic acid of the expression vectors described herein encodes the human subunit cDNA sequence.

Metachromatic leukodystrophy (MLD) MLD is a rare autosomal-recessive lysosomal storage disease caused by mutations in the arylsulfatase A (ARSA) gene that result in enzyme deficiency and accumulation of the undegraded substrate cerebroside 3-sulphate (sulphatide) in neural and glial cells in the central nervous system and peripheral nervous system. This accumulation of sulphatide leads to progressive demyelination and neurodegeneration. In some embodiments, the second nucleic acid of the expression vectors described herein encodes the human ARSA cDNA sequence.

Mucopolysaccharidosis I (MPS-I) or Hurler syndrome is a lysosomal storage disorder caused by a deficiency of the alpha-L-iduronidase enzyme (IDUA). The disease is characterized by inappropriate storage of glycosamminoglycans (GAGs) with accompanying organ enlargement and damage, excretion of abnormal quantities of GAGs in urine, and disrupted GAG turnover that especially affects connective tissues. Clinical manifestations include skeletal abnormalities, hepatosplenomegaly, mental retardation, and cardiovascular and respiratory dysfunction. IDUA deficiency can result in a wide range of phenotypic presentations, and MPS I Hurler (MPS IH) represents the most severe disease variant within this spectrum, characterized by a chronic, progressive, and disabling disease course involving multiple organs and the central nervous system. The disease is fatal in childhood if untreated, with death usually occurring within the first decade of life because of cardiorespiratory failure. In some embodiments, the second nucleic acid of the expression vectors described herein encodes the human cDNA of alpha-iduronidase (IDUA).

Gaucher's disease is the most common of the lysosomal storage diseases. It is an autosomal recessive lysosomal storage disease, caused by deficiency of the enzyme glucocerebrosidase (GBA), required for the degradation of glycosphingolipids. Clinical manifestations include hepatosplenomegaly, thrombocytopenia, bone disease and a bleeding diathesis, frequently resulting in presentation to haematologists. Gene therapy represents a therapeutic alternative for patients to enzyme replacement therapy and those lacking a suitable bone marrow donor. In some embodiments, the second nucleic acid of the expression vectors described herein encodes the human cDNA of the GBA gene.

Lysosomal storage diseases (LSDs) are rare inherited metabolic disorders characterized by a dysfunction in lysosomes. LSDs encompass approximately 70 genetically distinct diseases, with a collective incidence of 1:5000 live births. Examples include Fabry disease (alpha-galactosidase A deficiency), Pompe disease (α-glucosidase [GAA] deficiency), Hunter syndrome (iduronate-2-sulfatase [I2S] deficiency), Sanfilippo syndrome (deficiency in one of the enzymes needed to break down the glycosaminoglycan heparan sulfate) and Krabbe disease (gal-actocerebrosidase deficiency). Likewise, inherited metabolic disorders are one cause of metabolic disorders, and occur when a defective gene causes an enzyme deficiency. It is believed that an expression vectors of the present disclosure may be adapted to incorporate a second nucleic acid sequence which encodes a gene suitable for use in treating any of the above-identified conditions.

Pyruvate kinase deficiency (PKD) is a monogenic metabolic disease caused by mutations in the PKLR gene that leads to hemolytic anemia of variable symptomotology and that can be fatal during the neonatal period. PKD recessive inheritance trait and its curative treatment by allogeneic bone marrow transplantation provide an ideal scenario for developing gene therapy approaches. In some embodiments, the second nucleic acid of the expression vectors described herein encodes the human PKLR cDNA.

Adrenoleukodystrophy (ALD) is a rare X-linked metabolic disorder caused by mutations in the ABCD1 gene which result in a deficiency in adrenoleukodystrophy protein (ALDP) and subsequent accumulation of very long chain fatty acids (VLCFA). VLCFA accumulation occurs in plasma and all tissue types but primarily affects the adrenal cortex and white matter of the brain and spinal cord, leading to a range of clinical outcomes. The most severe form of ALD, the inflammatory cerebral phenotype known as cerebral ALD (CALD), involves a progressive destruction of myelin, the protective sheath of the nerve cells in the brain that are responsible for thinking and muscle control. Symptoms of CALD usually occur in early childhood and progress rapidly if untreated, leading to severe loss of neurological function and eventual death in most patients. In some embodiments, the second nucleic acid of the expression vectors described herein encodes the human adrenoleukodystrophy protein (ALDP).

Fanconi anemia (FA) is an inherited bone marrow failure syndrome. A defect in 1 of at least 16 DNA repair genes leads to aplasia and enhanced risk for malignancies, especially AML and MDS. Additionally, the risk for adenoma, adenocarcinomas and squamous cell carcinomas is increased. Most patients also have a short stature, various morphological abnormalities and developmental disorders. Supportive treatment includes regular transfusions of blood products and growth hormone substitution due to concomitant endocrinopathies in FA patients. HSCT in the donor-matched setting has been the only curative option and is thus an attractive option for gene therapy. Despite the heterogeneity in genes affected, more than 60% of the patients have mutations in the FANCA gene. In some embodiments, the second nucleic acid of the expression vectors described herein encodes the human FANCA cDNA.

Promoters

In some embodiments, different promoters are used to drive expression of each of the nucleic acid sequences incorporated within the disclosed expression vectors. For example, a first nucleic acid sequence encoding an RNAi (e.g. an anti-HPRT shRNA) may be expressed from a first promoter, and a second nucleic acid sequence encoding a therapeutic gene (e.g. a gamma-globin gene) may be expressed from a second promoter, wherein the first and second promoters are different. Likewise, and by way of another example, a first nucleic acid sequence encoding a micro-RNA based shRNA to downregulate HPRT may be expressed from a first promoter and a second nucleic acid sequence encoding a therapeutic gene (e.g. the gamma-globin gene) may be expressed from a second promoter, wherein the first and second promoters are different.

In some embodiments, the promoters may be constitutive promoters or inducible promoters as known to those of ordinary skill in the art. In some embodiments, the promoter includes at least a portion of an HIV LTR (e.g. TAR).

Examples of suitable promoters include, but are not limited to, RNA polymerase I (pol I), polymerase II (pol II), or polymerase III (pol III) promoters. By "RNA polymerase III promoter" or "RNA pol III promoter" or "polymerase III promoter" or "pol III promoter" it is meant any invertebrate, vertebrate, or mammalian promoter, e.g., human, murine, porcine, bovine, primate, simian, etc. that, in its native context in a cell, associates or interacts with RNA polymerase III to transcribe its operably linked gene, or any variant thereof, natural or engineered, that will interact in a selected host cell with an RNA polymerase III to transcribe an operably linked nucleic acid sequence. RNA pol III promoters suitable for use in the expression vectors of the disclosure include, but are not limited to, human U6, mouse U6, and human H1 others.

Examples of pol II promoters include, but are not limited to, Efl alpha, CMV, and ubiquitin. Other specific pol II promoters include, but are not limited to, ankyrin promoter (Sabatino D E, et al., Proc Natl Acad Sd USA. (24):13294-9 (2000)), spectrin promoter (Gallagher P G, et al., J Biol Chem. 274(10):6062-73, (2000)), transferrin receptor promoter (Marziali G, et al., Oncogene. 21(52):7933-44, (2002)), band 3/anion transporter promoter (Frazar T F, et al., Mol Cell Biol (14):4753-63, (2003)), band 4.1 promoter (Harrison P R, et al., Exp Cell Res. 155(2):321-44, (1984)), BcI-Xl promoter (Tian C, et al., Blood 15; 101(6):2235-42 (2003)), EKLF promoter (Xue L, et al., Blood. 103(11): 4078-83 (2004)). Epub 2004 Feb. 5), ADD2 promoter (Yenerel M N, et al., Exp Hematol. 33(7):758-66 (2005)), DYRK3 promoter (Zhang D, et al., Genomics 85(1): 117-30 (2005)), SOCS promoter (Sarna M K, et al., Oncogene 22(21):3221-30 (2003)), LAF promoter (To M D, et al., bit J Cancer 1; 115(4):568-74, (2005)), PSMA promoter (Zeng H, et al., JAndrol (2):215-21, (2005)), PSA promoter (Li H W, et al., Biochem Biophys Res Commun 334(4): 1287-91, (2005)), Probasin promoter (Zhang J, et al., 145(1):134-48, (2004)). Epub 2003 Sep. 18), ELAM-I promoter/E-Selectin (Walton T, et al., Anticancer Res. 18(3A):1357-60, (1998)), Synapsin promoter (Thiel G, et al., Proc Natl Acad Sd USA., 88(8):3431-5 (1988)), Willebrand factor promoter (Jahroudi N, Lynch D C. Mol Cell-5zo/.14(2):999-1008, (1994)), FLTI (Nicklin S A, et al., Hypertension 38(1):65-70, (2001)), Tau promoter (Sadot E, et al., J Mol Biol. 256(5):805-12, (1996)), Tyrosinase promoter (Lillehammer T, et al., Cancer Gene Ther. (2005)), pander promoter (Burkhardt B R, et al., Biochim Biophys Acta. (2005)), neuron-specific enolase promoter (Levy Y S, et al., J Mol Neurosci. 21(2):121-32, (2003)), hTERT promoter (Ito H, et al., Hum Gene Ther 16(6):685-98, (2005)), HRE responsive element (Chadderton N, et al., Int J Radiat Oncol Biol Phys. 62(1):2U-22, (2005)), lck promoter (Zhang D J, et al., J Immunol. 174(11):6725-31, (2005)), MHCII promoter (De Geest B R, et al., Blood. 101(7):2551-6, (2003), Epub 2002 Nov. 21), and CDl Ic promoter (Lopez-Rodriguez C, et al., J Biol Chem. 272(46):29120-6 (1997)).

In some embodiments, the promoter driving expression of the agent designed to knockdown HPRT or otherwise decrease its expression is a RNA pol III promoter. In some embodiments, the promoter driving expression of the agent designed to knockdown HPRT or otherwise decrease its expression is a 7sk promoter (e.g. a 7SK human 7S K RNA promoter). In some embodiments, the 7sk promoter has the sequence provided by ACCESSION AY578685 (*Homo sapiens* cell-line HEK-293 7SK RNA promoter region, complete sequence, ACCESSION AY578685).

Figure 35:
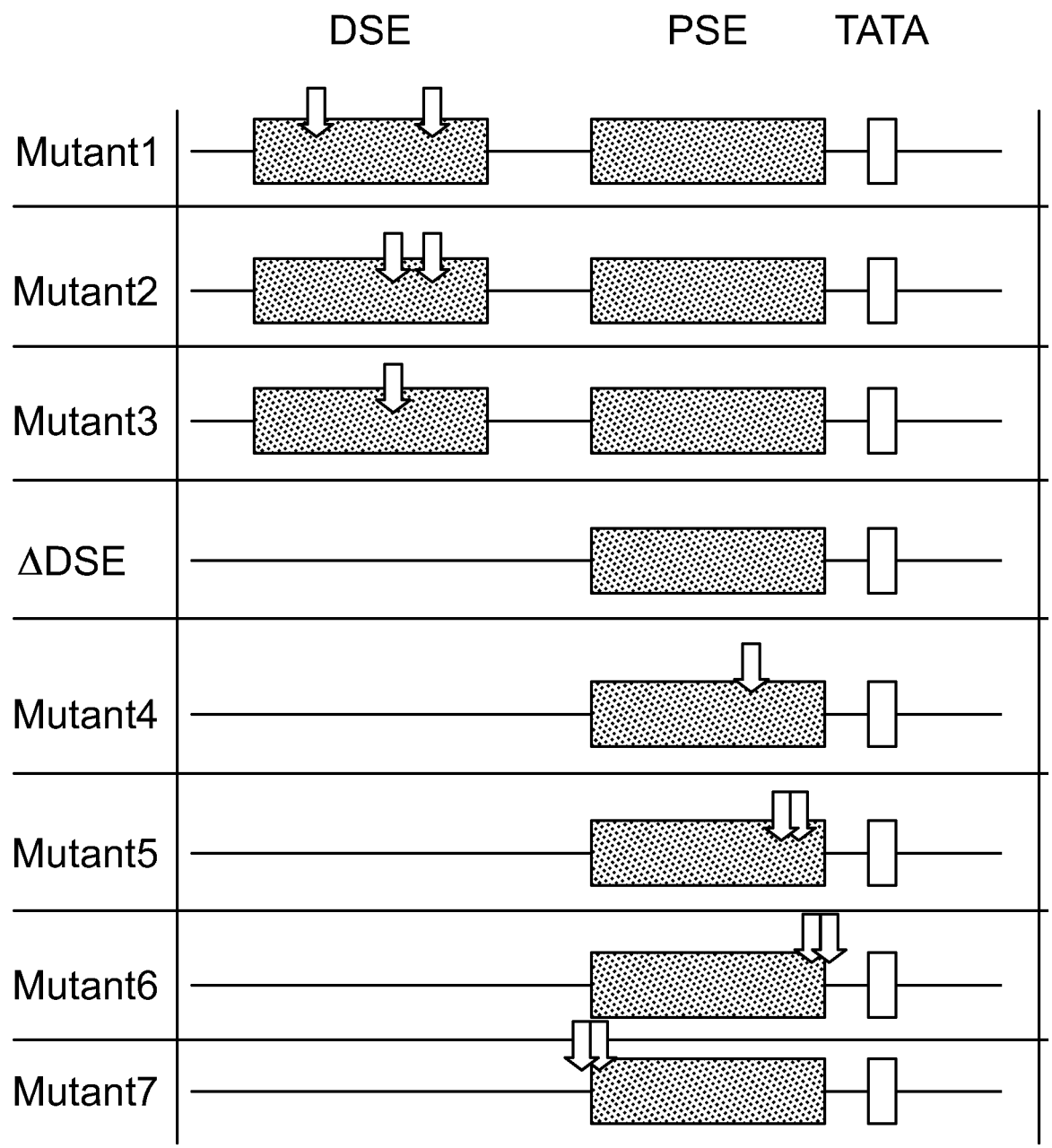
FIG. 35 illustrate human 7sk promoter mutations. Mutations (arrows) and deletions introduced into the cis-distal sequence enhancer (DSE) and proximal sequence enhancer (PSE) elements (long, wide boxes) in the 7sk promoter relative to the TATA box (tall, thin boxes) are illustrated.

In some embodiments, the 7sk promoter utilized comprises at least one mutation and/or deletion in its nucleic acid sequence in comparison to the 7sk promoter (see FIGS. 35 and 36). In other embodiments, the 7sk promoter comprises multiple mutations and/or deletions in its nucleic acid sequence in comparison to the 7sk promoter (ACCESSION AY578685). In yet other embodiments, the 7sk promoter has 95% identity to the sequence of SEQ ID NO: 32. In yet further embodiments, the 7sk promoter has the sequence of SEQ ID NO: 32. It is believed that the 7sk promoter expressed the shRNA to HPRT at a moderate level and was more effective than other Pol III promoters, e.g. U6 and H1. It is believed that the introduction of allowed for the modulation of the expression of shRNA to HPRT at therapeutic levels.

In some embodiments, the 7sk promoter has a sequence having at least 95% identity to that of SEQ ID NOS: 32. In some embodiments, the 7sk promoter has a sequence having at least 96% identity to that of SEQ ID NOS: 32. In some embodiments, the 7sk promoter has a sequence having at least 97% identity to that of SEQ ID NOS: 32. In some embodiments, the 7sk promoter has a sequence having at least 98% identity to that of SEQ ID NOS: 32. In some embodiments, the 7sk promoter has a sequence having at least 99% identity to that of SEQ ID NOS: 32. In some embodiments, the 7sk promoter has the sequence set forth in SEQ ID NOS: 32.

In some embodiments, functional mutations or deletions in the 7sk promoter are made in cis-regulatory elements to regulate expression levels of the promoter-driven transgene, including sh734 (see SEQ ID NO: 33). (see Boyd, D. C., Turner, P. C., Watkins, N. J., Gerster, T. & Murphy, S. Functional Redundancy of Promoter Elements Ensures Efficient Transcription of the Human 7SK Gene in vivo. *Journal of Molecular Biology* 253, 677-690 (1995). The mutations described are used to establish the correlation between sh734 expression levels driven by the Pol III promoter and to introduce functionality to undergo stable selection in the presence of 6TG therapy and long-term stability and safety. The location of 7sk promoter mutations are depicted in FIG. 35. The 7skM1 Oct binding site mutations in the distal sequence enhancer (DSE) and predicted TAL-1 and GATA-1 binding sites are shown in FIG. 36.

In some embodiments, the 7sk promoter has a sequence having at least 95% identity to that of SEQ ID NOS: 33. In some embodiments, the 7sk promoter has a sequence having at least 96% identity to that of SEQ ID NOS: 33. In some embodiments, the 7sk promoter has a sequence having at least 97% identity to that of SEQ ID NOS: 33. In some embodiments, the 7sk promoter has a sequence having at least 98% identity to that of SEQ ID NOS: 33. In some embodiments, the 7sk promoter has a sequence having at least 99% identity to that of SEQ ID NOS: 32. In some embodiments, the 7sk promoter has the sequence set forth in SEQ ID NOS: 33.

In some embodiments, the promoter that drives expression of a nucleic acid sequence encoding a therapeutic gene is a H1 promoter, a U6 promoter, or a mutant 7SK promoter. In some embodiments, the promoter that drives expression of a nucleic acid sequence encoding gamma-globin is a beta-globin promoter, such as illustrated in FIGS. 1A and 1B. In some embodiments, the beta-globin promoter is the wild-type human beta-globin promoter. In other embodiments, the beta globin promoter has a nucleic acid sequence having at least 90% sequence identity to that of SEQ ID NO: 66. In other embodiments, the beta globin promoter has a nucleic acid sequence having at least 95% sequence identity to that of SEQ ID NO: 66. In other embodiments, the beta globin promoter has a nucleic acid sequence having at least 99% sequence identity to that of SEQ ID NO: 66. In yet other embodiments, the beta globin promoter has the nucleic acid sequence of SEQ ID NO: 66. It is believed that the beta globin promoter is advantageous since it is subject to the normal regulation of the human beta-globin promoter expressed in red blood cells.

In other embodiments, the promoter is a tissue specific promoter. Several non-limiting examples of tissue specific promoters that may be used include lck (see, for example, Garvin et al., Mol. Cell Biol. 8:3058-3064, (1988)) and Takadera et al., Mol. Cell Biol. 9:2173-2180, (1989)), myogenin (Yee et al., Genes and Development 7:1277-1289 (1993), and thyl (Gundersen et al., Gene 113:207-214, (1992)).

It is also contemplated that a combination of promoters (e.g. UbC and H1 promoters) maybe used to obtain the desired expression of the therapeutic gene and/or interfering RNA. In some embodiments, the expression vector includes a Pol II promoter and a Pol III promoter, e.g. Pol II beta-globin promoter for gamma-globin expression and Pol III 7SK promoter for knockdown of HPRT. Promoters having tissue specificity are advantageous, in that they can specifically direct expression of the gene of interest and interfering RNA, thereby controlling the biological effect as desired.

Examples of Vectors Having a Nucleic Acid Encoding a shRNA Targeting an HPRT Gene and a Nucleic Acid Encoding a Gamma-Globin Gene Examples of lentiviral expression vectors designed to knockdown HPRT and cause the expression of a gamma globin are described below. Any of the recited expression vectors are suitable for transducing HSCs, such as ex vivo.

In some embodiments, the lentiviral expression vector includes (a) a sequence encoding an RNAi targeting HPRT; (b) a sequence encoding a gamma globin gene; (c) a sequence encoding a first promoter to drive expression of the sequence encoding the RNAi targeting HPRT; (d) a sequence encoding a second promoter to drive expression of the sequence encoding the gamma globin gene; and (e) a sequence encoding a central polypurine tract (cPPT); and (f) a sequence encoding a Rev response element (RRE). In some embodiments, the cPPT comprises about 85 base pairs of the Vif sequence of wild-type HIV. In some embodiments, the RRE comprises about 26 base pairs of the Rev sequence, about 25 base pairs of the tat sequence, and about 769 base pairs of the Env sequence of wild-type HIV. In some embodiments, the lentiviral vector further includes a locus control region. In some embodiments, the lentiviral vector further includes a self-inactivating long terminal repeat. Creation of a SIN LTR is achieved by inactivating the U3 region of the 3' LTR (preferably by deletion of a portion thereof, e.g. removal of a TATA sequence). The alteration is transferred to the 5' LTR after reverse transcription, thus eliminating the transcriptional unit of the LTRs in the provirus, which is believed to prevent mobilization by replication competent virus. An additional safety enhancement is provided by replacing the U3 region of the 5' LTR with a heterologous promoter to drive transcription of the viral genome during production of viral particles. In some embodiments, the lentiviral expression vector has at least 80%, at least 85%, at least 90%, at least 95%, at least 97%, at least 98%, or at least 99% sequence identity to one of SEQ ID NOS: 5-22. In some embodiments, the RNAi is an shRNA.

Figure 6:
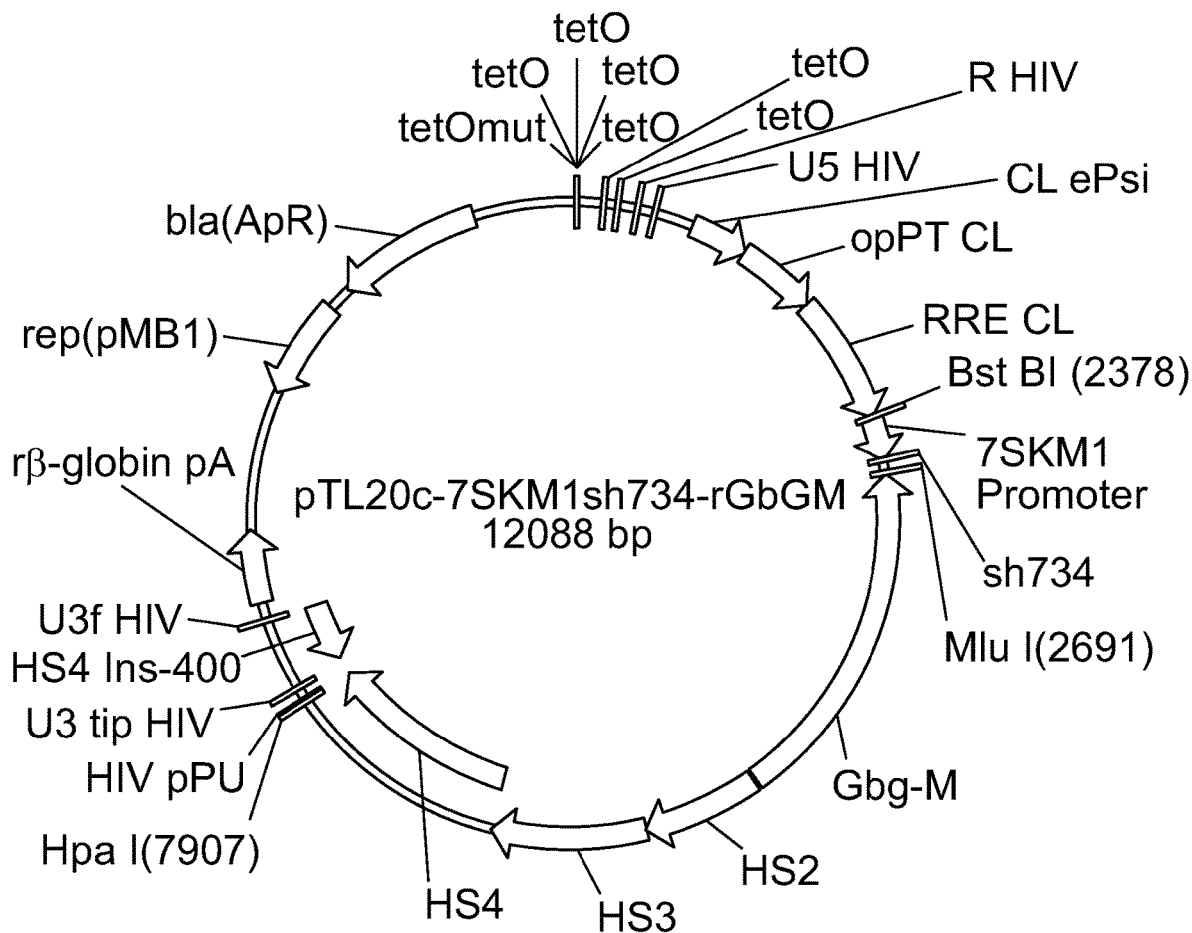
FIG. 6 provides a vector map of TL20c-7SK$^{M1}$/sh734-rGbG$^M$.

In some embodiments, the vector has a nucleic acid sequence having at least 90% sequence identity to that of SEQ ID NO: 5 (TL20c-7skM1/sh734-rGbGM). In other embodiments, the vector has a nucleic acid sequence having at least 95% sequence identity to that of SEQ ID NO: 5. In yet other embodiments, the vector has a nucleic acid sequence having at least 98% sequence identity to that of SEQ ID NO: 5. In further other embodiments, the vector has the nucleic acid sequence of SEQ ID NO: 5 (see also FIG. 6).

Figure 7:
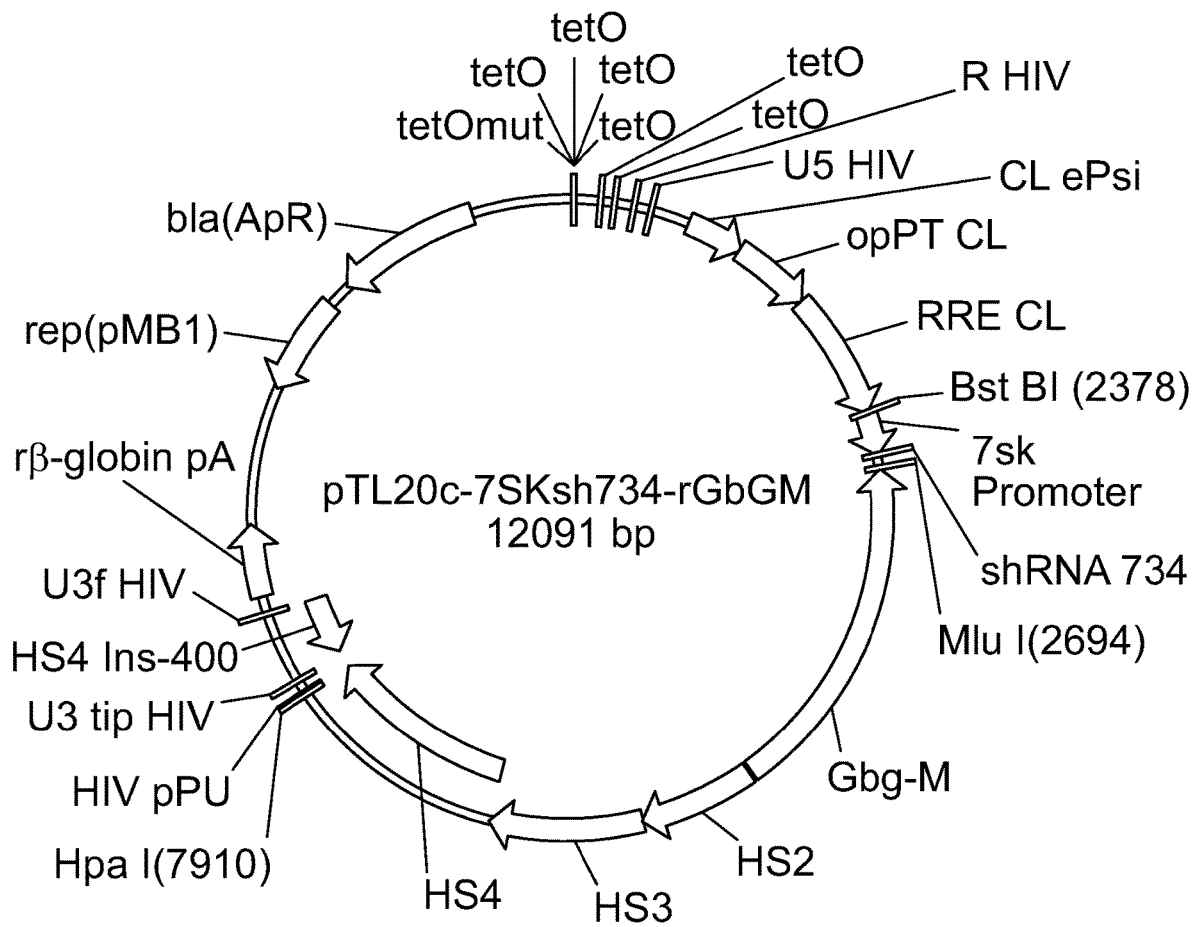
FIG. 7 provides a vector map of TL20c-7SK/sh734-rGbG$^M$.

In some embodiments, the vector has a nucleic acid sequence having at least 90% sequence identity to that of SEQ ID NO: 6 (TL20c-7sk/sh734-rGbGM). In other embodiments, the vector has a nucleic acid sequence having at least 95% sequence identity to that of SEQ ID NO: 6. In yet other embodiments, the vector has a nucleic acid sequence having at least 98% sequence identity to that of SEQ ID NO: 6. In further other embodiments, the vector has the nucleic acid sequence of SEQ ID NO: 6 (see also FIG. 7).

Figure 8:
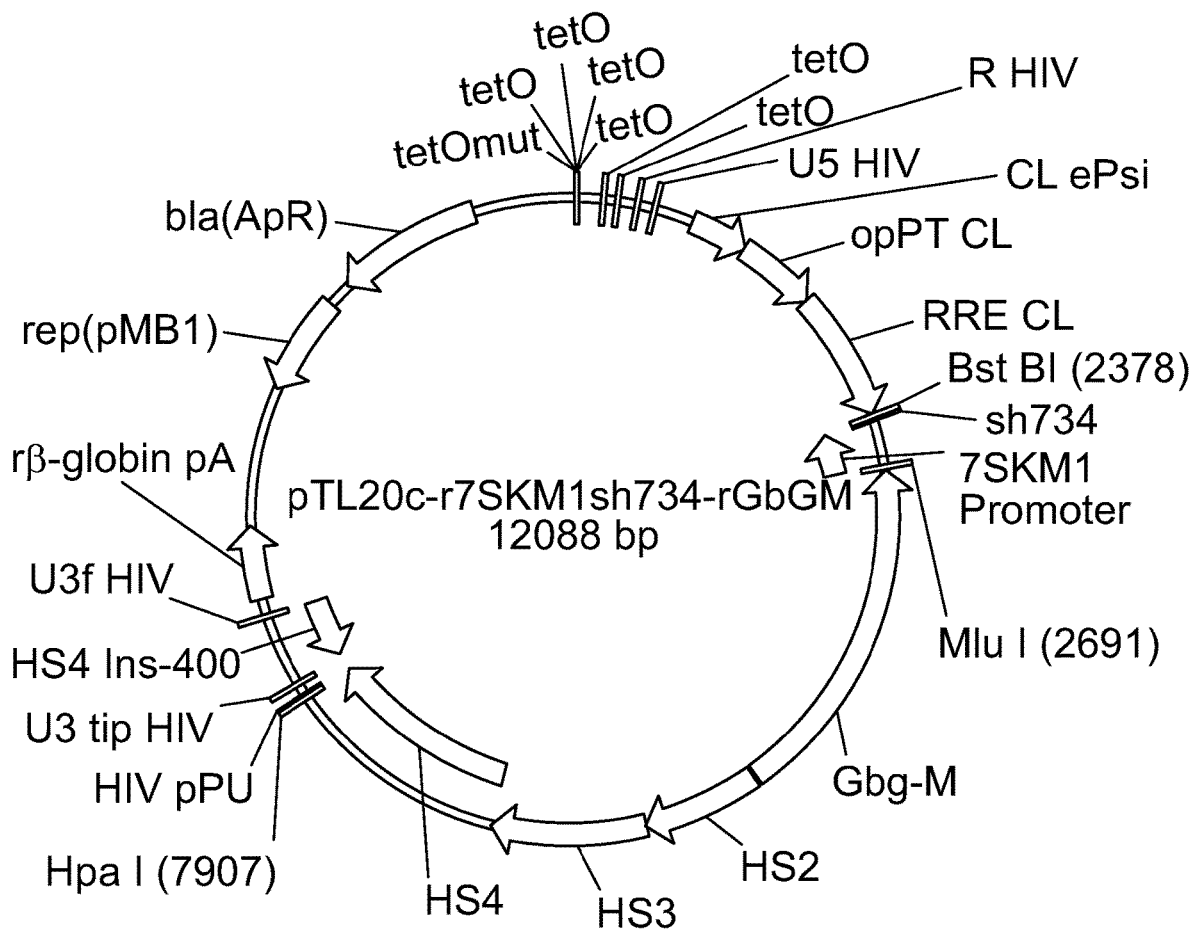
FIG. 8 provides a vector map of TL20c-r7SK$^{M1}$/sh734-rGbG$^M$.

In some embodiments, the vector has a nucleic acid sequence having at least 90% sequence identity to that of SEQ ID NO: 7 (TL20c-r7skM1/sh734-rGbGM). In other embodiments, the vector has a nucleic acid sequence having at least 95% sequence identity to that of SEQ ID NO: 7. In yet other embodiments, the vector has a nucleic acid sequence having at least 98% sequence identity to that of SEQ ID NO: 7. In further other embodiments, the vector has the nucleic acid sequence of SEQ ID NO: 7 (see also FIG. 8).

In some embodiments, the vector has a nucleic acid sequence having at least 90% sequence identity to that of SEQ ID NO: 8 (TL20c-r7sk/sh734-rGbGM). In other embodiments, the vector has a nucleic acid sequence having at least 95% sequence identity to that of SEQ ID NO: 8. In yet other embodiments, the vector has a nucleic acid sequence having at least 98% sequence identity to that of SEQ ID NO: 8. In further other embodiments, the vector has the nucleic acid sequence of SEQ ID NO: 8 (see also FIG. 9).

Figure 10:
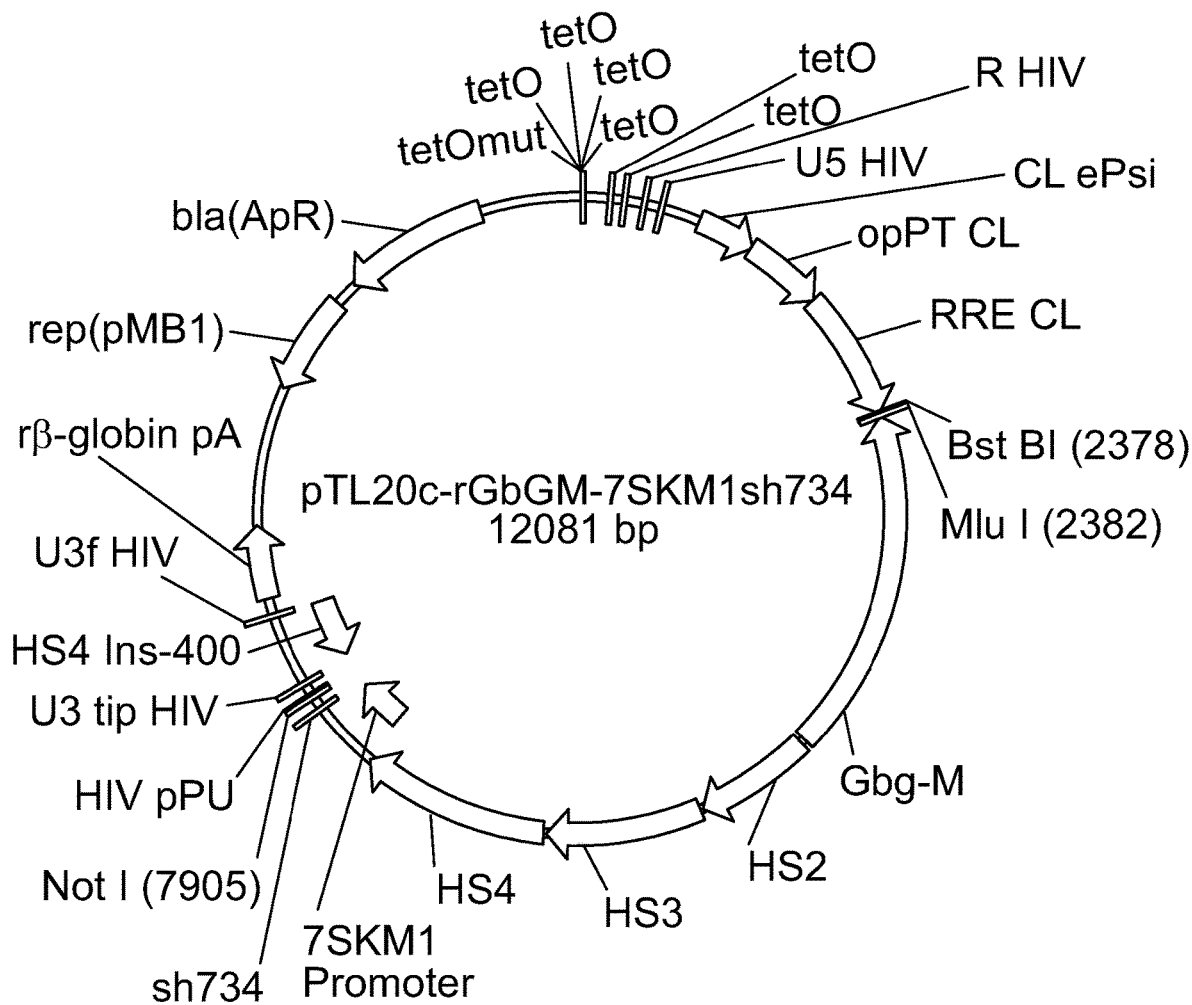
FIG. 10 provides a vector map of TL20c-rGbG$^M$-7SK$^{M1}$/sh734.

In some embodiments, the vector has a nucleic acid sequence having at least 90% sequence identity to that of SEQ ID NO: 9 (TL20c-rGbGM-7skM1/sh734). In other embodiments, the vector has a nucleic acid sequence having at least 95% sequence identity to that of SEQ ID NO: 9. In yet other embodiments, the vector has a nucleic acid sequence having at least 98% sequence identity to that of SEQ ID NO: 9. In further other embodiments, the vector has the nucleic acid sequence of SEQ ID NO: 9 (see also FIG. 10).

Figure 11:
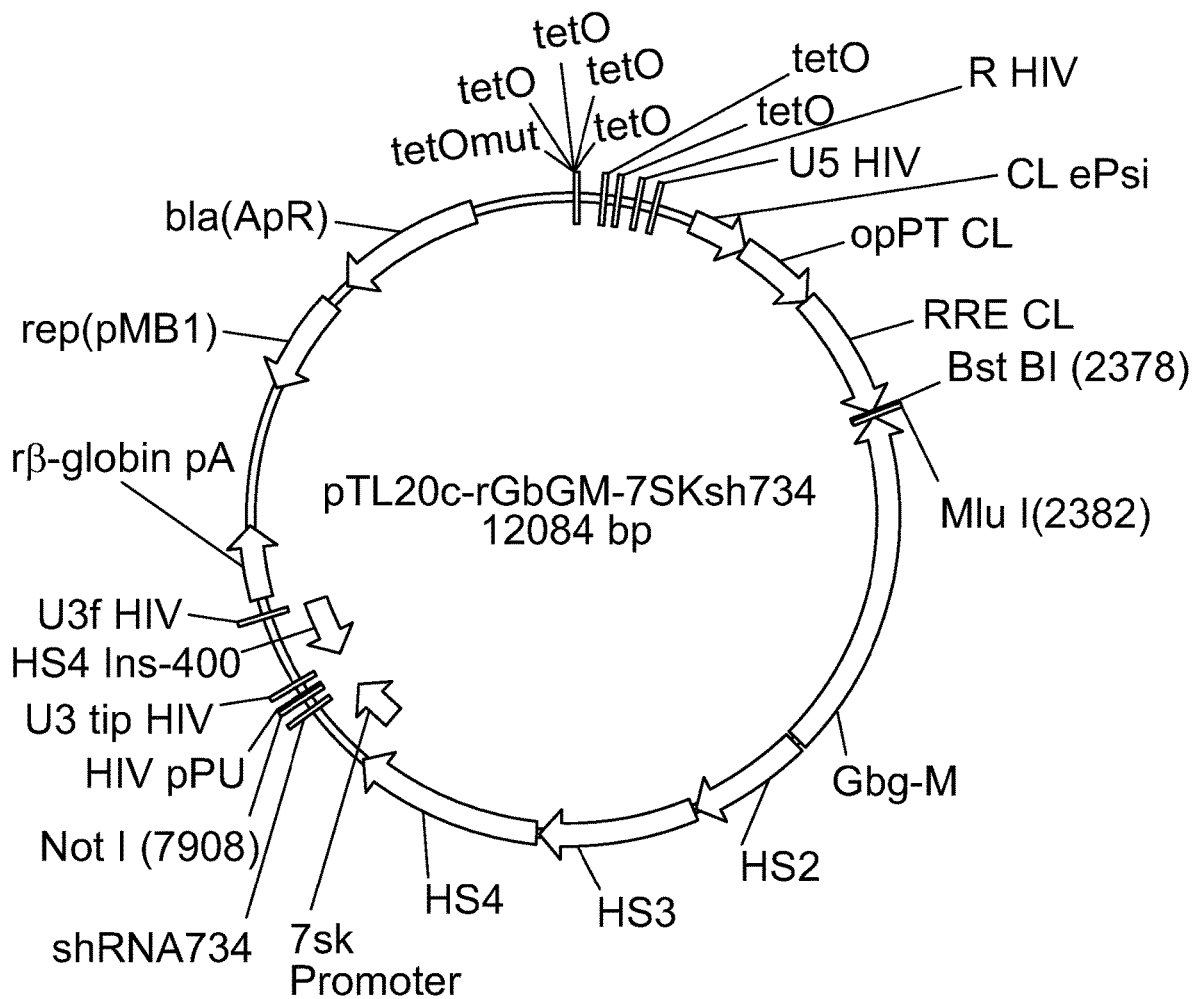
FIG. 11 provides a vector map of TL20c-rGbGM-7SK/sh734.

In some embodiments, the vector has a nucleic acid sequence having at least 90% sequence identity to that of SEQ ID NO: 10 (TL20c-rGbGM-7sk/sh734). In other embodiments, the vector has a nucleic acid sequence having at least 95% sequence identity to that of SEQ ID NO: 10. In yet other embodiments, the vector has a nucleic acid sequence having at least 98% sequence identity to that of SEQ ID NO: 10. In further other embodiments, the vector has the nucleic acid sequence of SEQ ID NO: 10 (see also FIG. 11).

Figure 12:
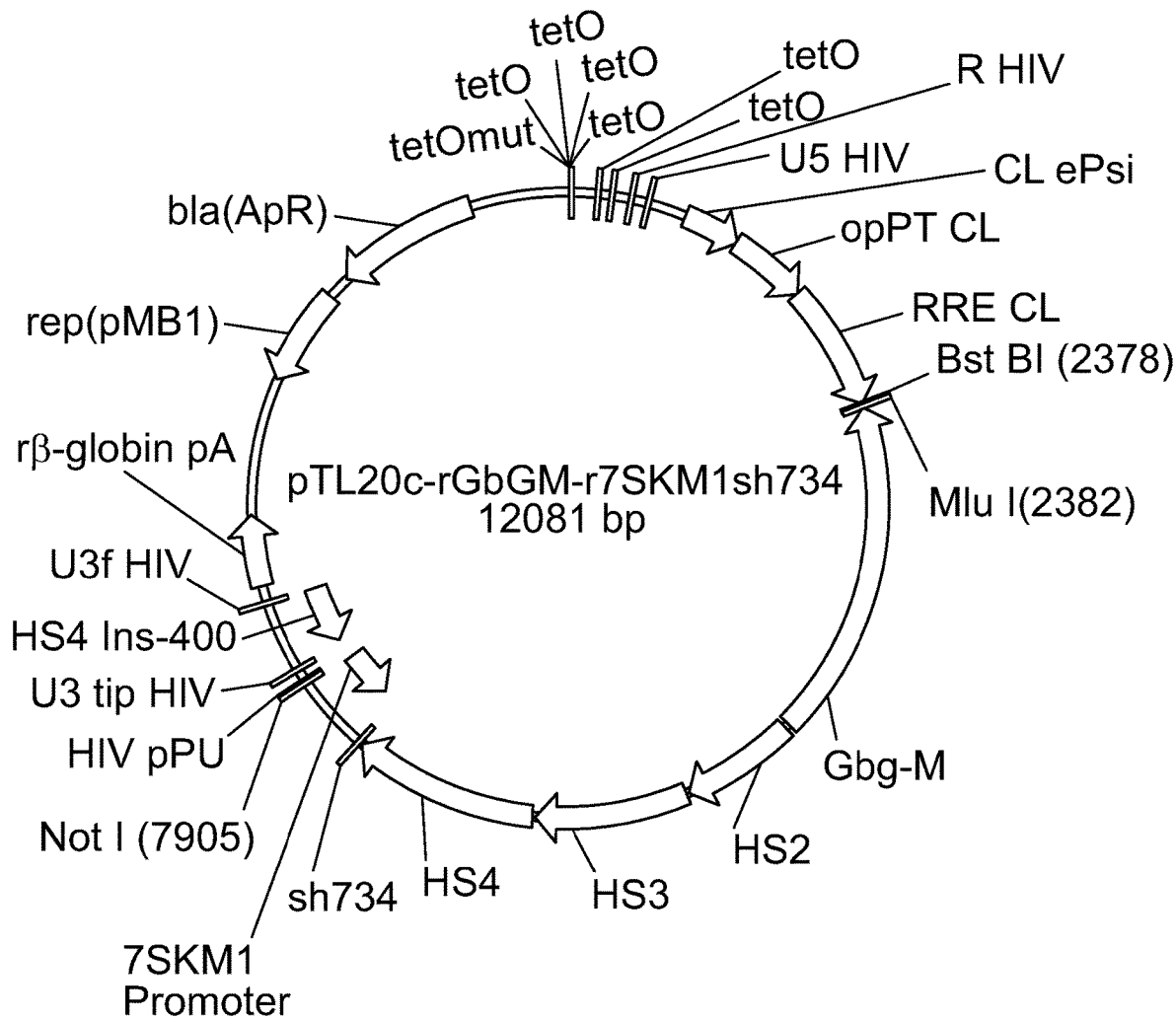
FIG. 12 provides a vector map of TL20c-rGbG$^M$-r7SK$^{M1}$/sh734.

In some embodiments, the vector has a nucleic acid sequence having at least 90% sequence identity to that of SEQ ID NO: 11 (TL20c-rGbGM-r7skM1/sh734). In other embodiments, the vector has a nucleic acid sequence having at least 95% sequence identity to that of SEQ ID NO: 11. In yet other embodiments, the vector has a nucleic acid sequence having at least 98% sequence identity to that of SEQ ID NO: 11. In further other embodiments, the vector has the nucleic acid sequence of SEQ ID NO: 11 (see also FIG. 12).

Figure 13:
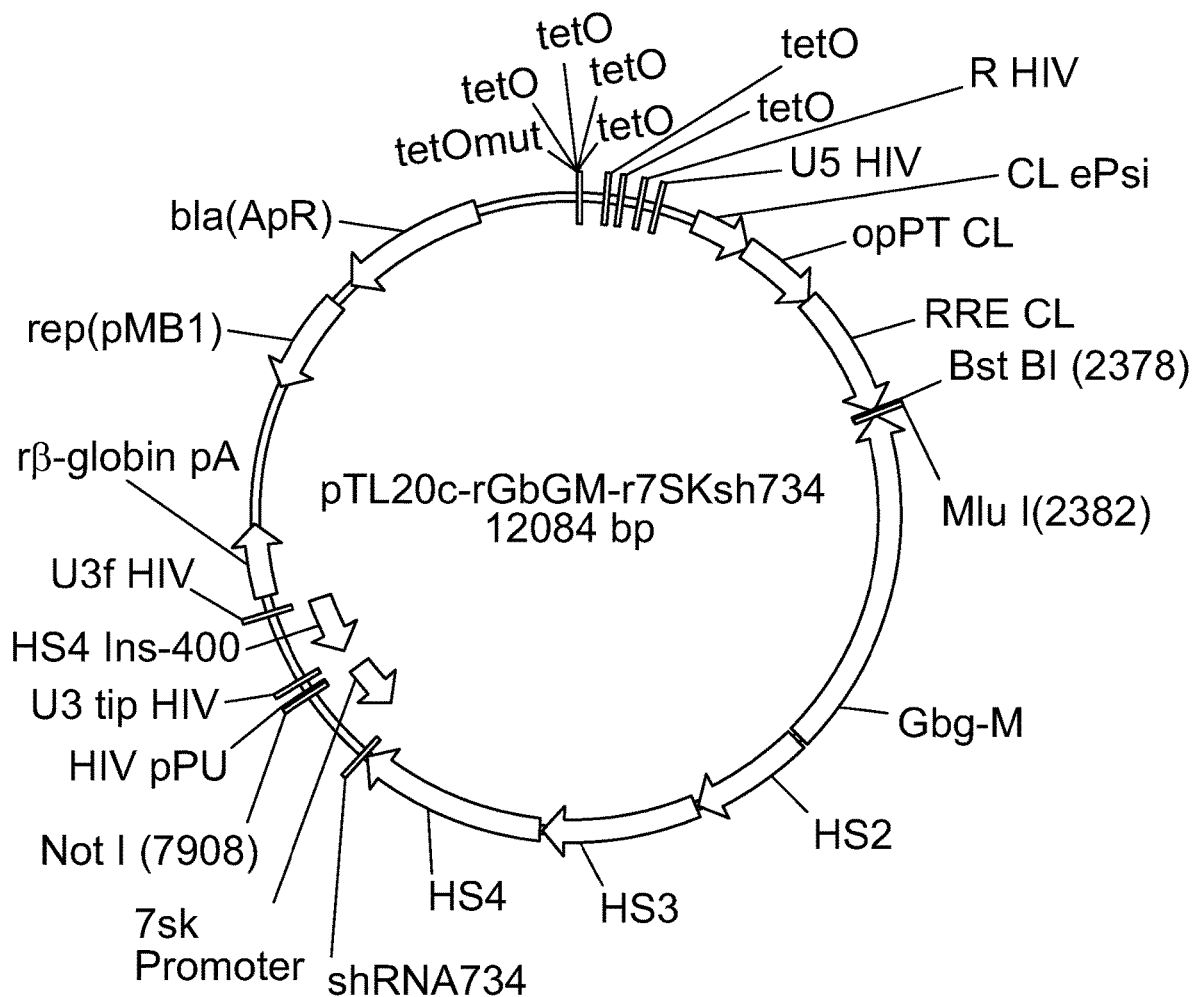
FIG. 13 provides a vector map of TL20c-rGbG$^M$-r7SK/sh734.

In some embodiments, the vector has a nucleic acid sequence having at least 90% sequence identity to that of SEQ ID NO: 12 (TL20c-rGbGM-r7sk/sh734). In other embodiments, the vector has a nucleic acid sequence having at least 95% sequence identity to that of SEQ ID NO: 12. In yet other embodiments, the vector has a nucleic acid sequence having at least 98% sequence identity to that of SEQ ID NO: 12. In further other embodiments, the vector has the nucleic acid sequence of SEQ ID NO: 12 (see also FIG. 13).

Figure 14:
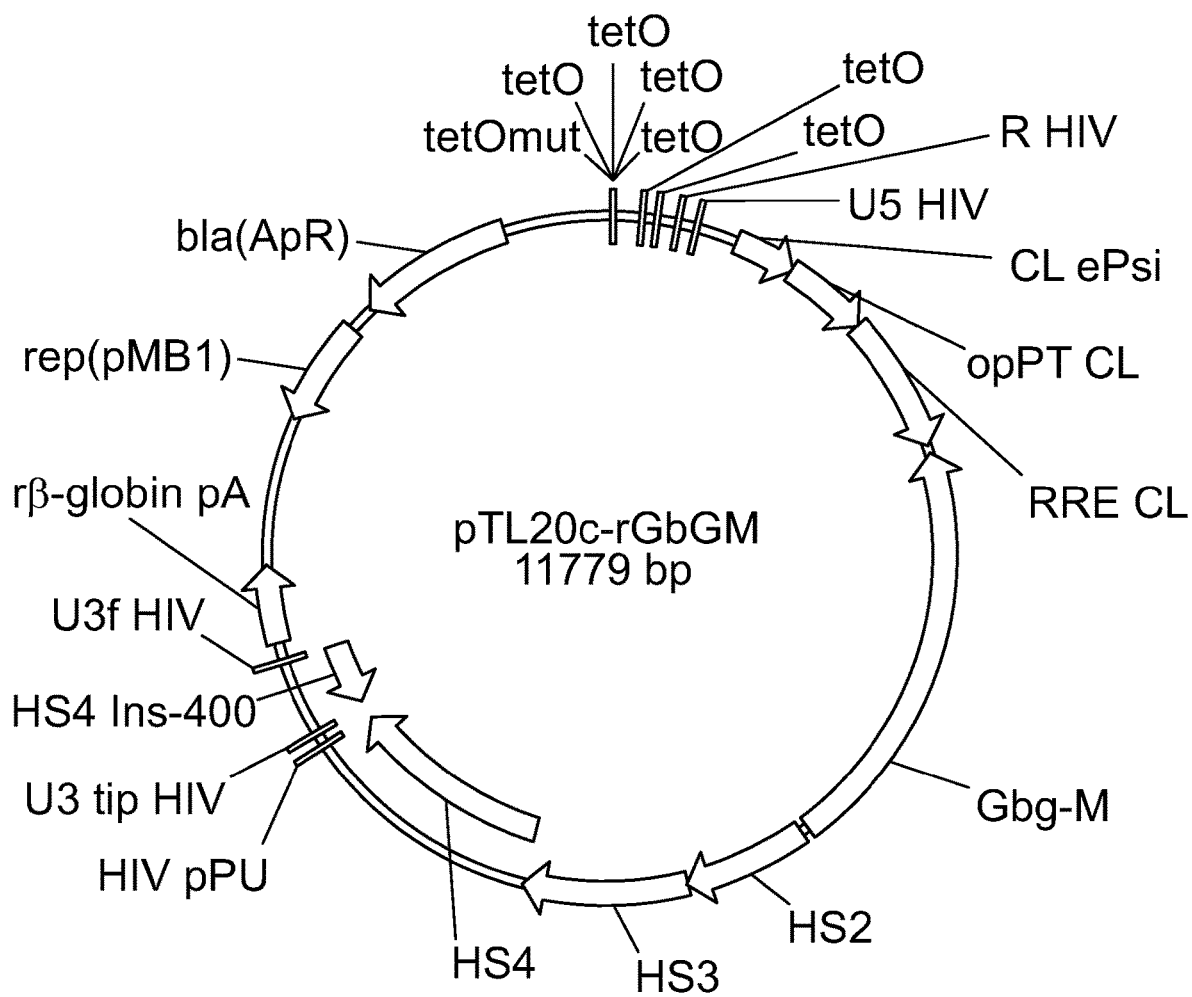
FIG. 14 provides a vector map of TL20c-rGbG$^M$.

In some embodiments, the vector has a nucleic acid sequence having at least 90% sequence identity to that of SEQ ID NO: 13 (TL20c-rGbGM). In other embodiments, the vector has a nucleic acid sequence having at least 95% sequence identity to that of SEQ ID NO: 13. In yet other embodiments, the vector has a nucleic acid sequence having at least 98% sequence identity to that of SEQ ID NO: 13. In further other embodiments, the vector has the nucleic acid sequence of SEQ ID NO: 13 (see also FIG. 14).

Figure 15:
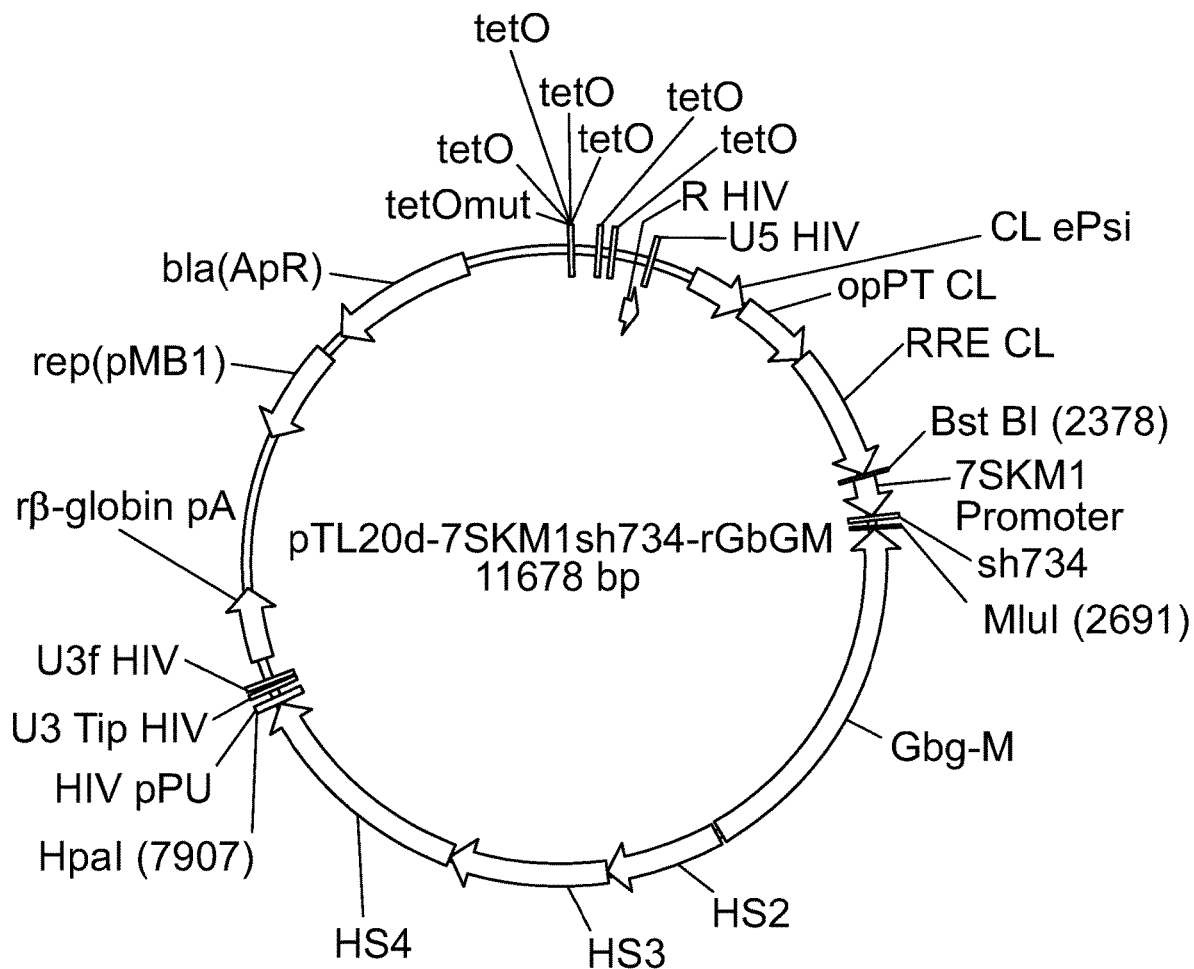
FIG. 15 provides a vector map of TL20d-7SK$^{M1}$/sh734-rGbG$^M$.

In some embodiments, the vector has a nucleic acid sequence having at least 90% sequence identity to that of SEQ ID NO: 14 (TL20d-7skM1/sh734-rGbGM). In other embodiments, the vector has a nucleic acid sequence having at least 95% sequence identity to that of SEQ ID NO: 14. In yet other embodiments, the vector has a nucleic acid sequence having at least 98% sequence identity to that of SEQ ID NO: 14. In further other embodiments, the vector has the nucleic acid sequence of SEQ ID NO: 14 (see also FIG. 15).

Figure 16:
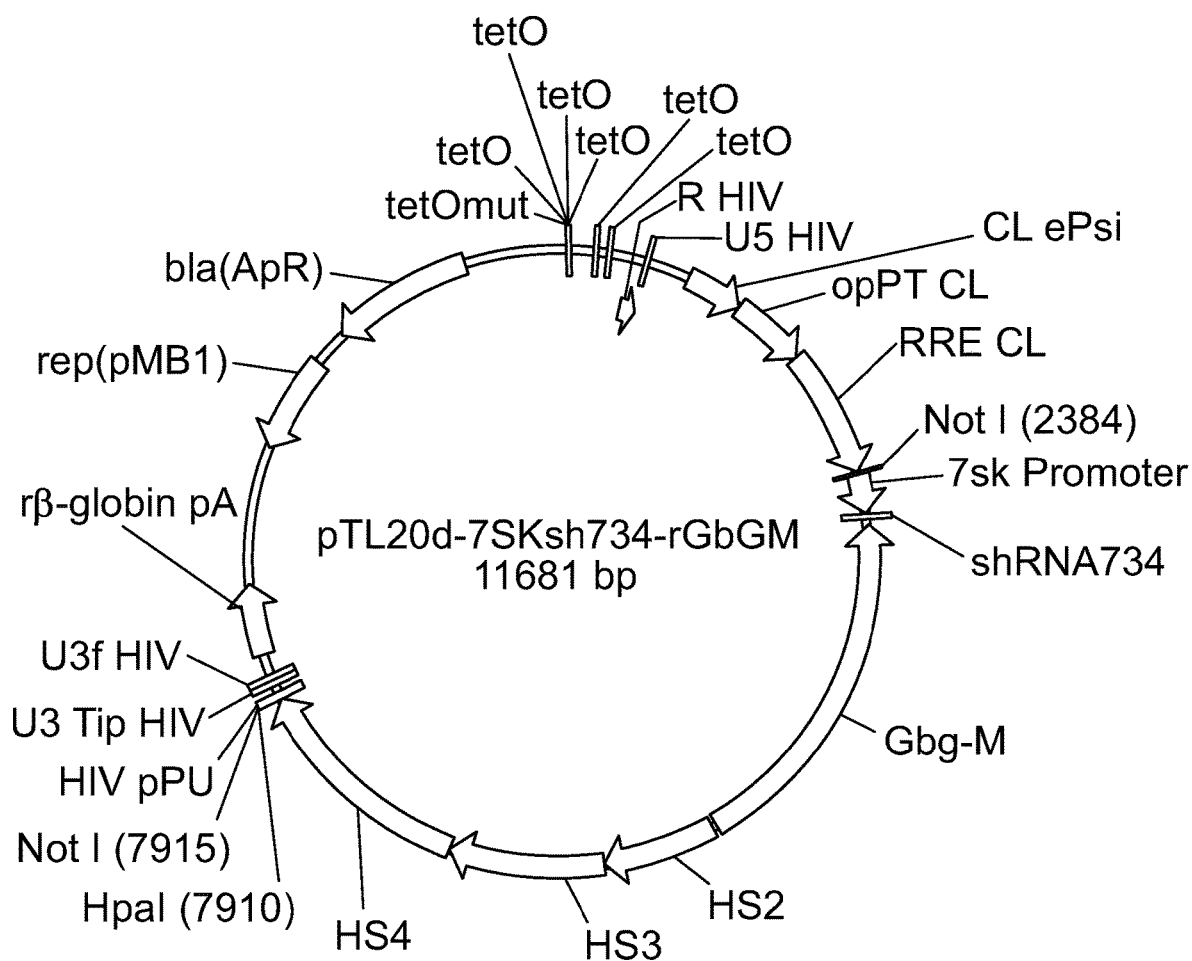
FIG. 16 provides a vector map of TL20d-7SK/sh734-rGbG$^M$.

In some embodiments, the vector has a nucleic acid sequence having at least 90% sequence identity to that of SEQ ID NO: 15 (TL20d-7sk/sh734-rGbGM). In other embodiments, the vector has a nucleic acid sequence having at least 95% sequence identity to that of SEQ ID NO: 15. In yet other embodiments, the vector has a nucleic acid sequence having at least 98% sequence identity to that of SEQ ID NO: 15. In further other embodiments, the vector has the nucleic acid sequence of SEQ ID NO: 15 (see also FIG. 16).

Figure 17:
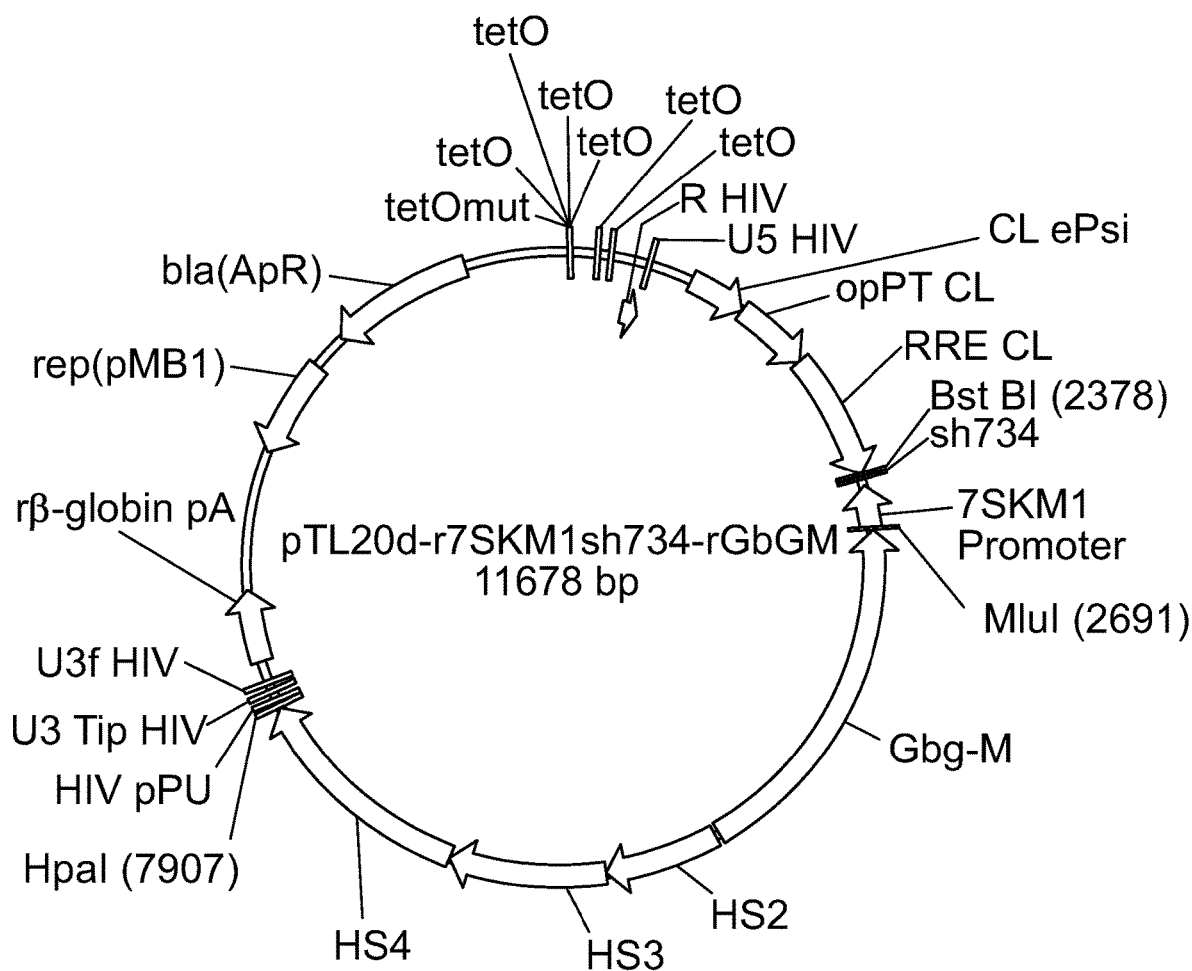
FIG. 17 provides a vector map of TL20d-r7SK$^{M1}$/sh734-rGbG$^M$.

In some embodiments, the vector has a nucleic acid sequence having at least 90% sequence identity to that of SEQ ID NO: 16 (TL20d-r7skM1/sh734-rGbGM). In other embodiments, the vector has a nucleic acid sequence having at least 95% sequence identity to that of SEQ ID NO: 16. In yet other embodiments, the vector has a nucleic acid sequence having at least 98% sequence identity to that of SEQ ID NO: 16. In further other embodiments, the vector has the nucleic acid sequence of SEQ ID NO: 16 (see also FIG. 17).

Figure 18:
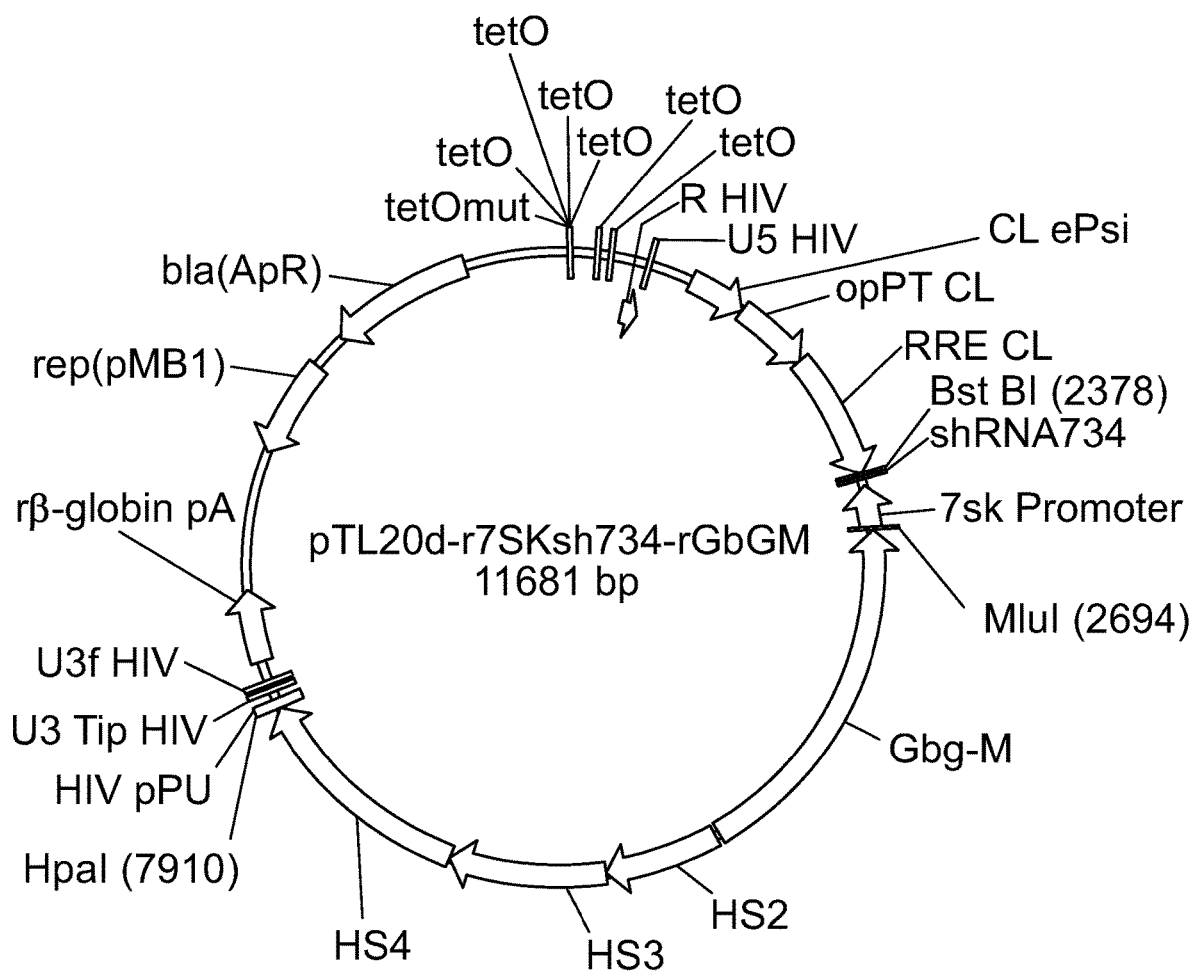
FIG. 18 provides a vector map of TL20d-r7SK/sh734-rGbG$^M$.

In some embodiments, the vector has a nucleic acid sequence having at least 90% sequence identity to that of SEQ ID NO: 17 (TL20d-r7sk/sh734-rGbGM). In other embodiments, the vector has a nucleic acid sequence having at least 95% sequence identity to that of SEQ ID NO: 17. In yet other embodiments, the vector has a nucleic acid sequence having at least 98% sequence identity to that of SEQ ID NO: 17. In further other embodiments, the vector has the nucleic acid sequence of SEQ ID NO: 17 (see also FIG. 18).

Figure 19:
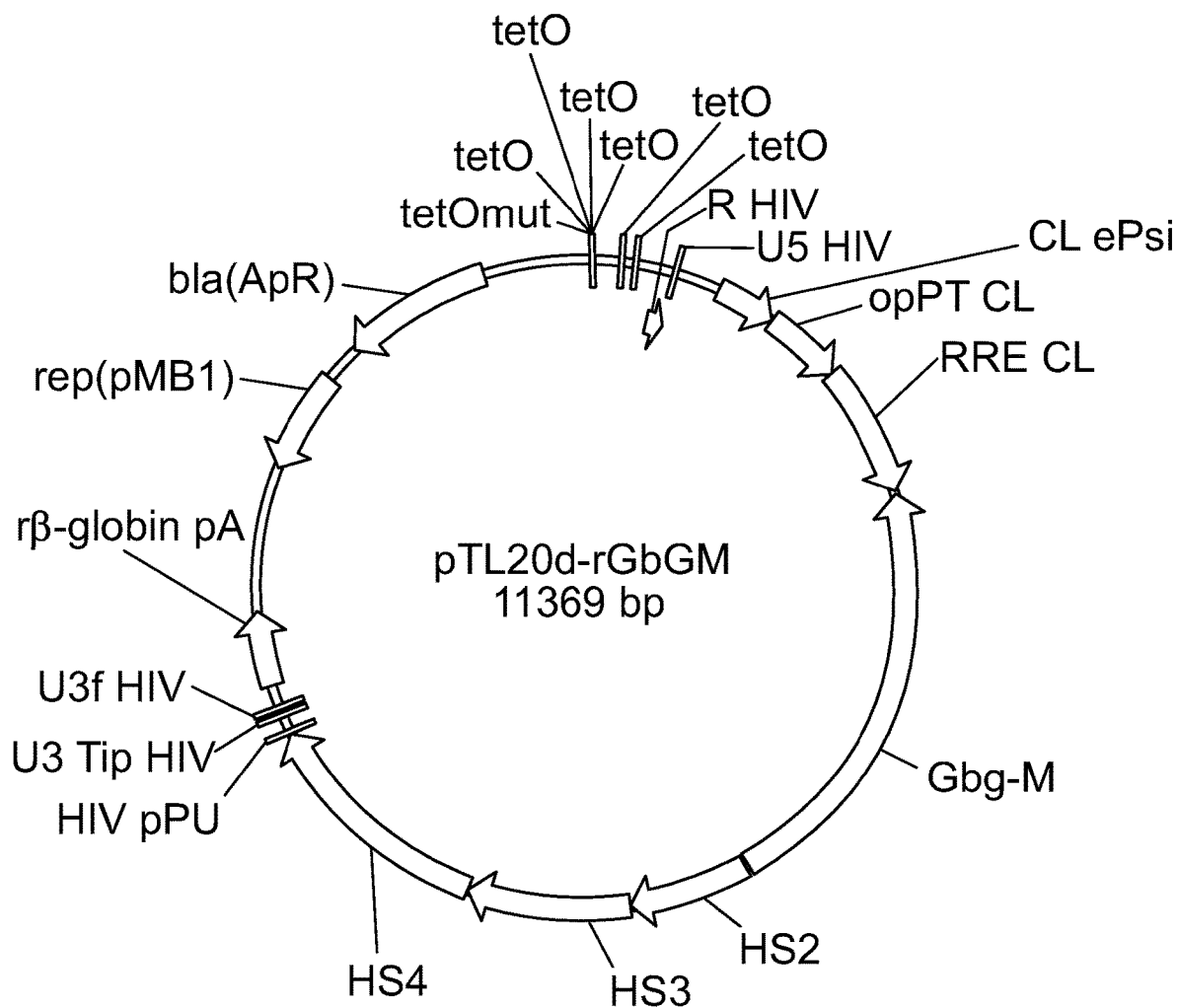
FIG. 19 provides a vector map of TL20d-rGbG$^M$.

In some embodiments, the vector has a nucleic acid sequence having at least 90% sequence identity to that of SEQ ID NO: 18 (TL20d-GbGM). In other embodiments, the vector has a nucleic acid sequence having at least 95% sequence identity to that of SEQ ID NO: 18. In yet other embodiments, the vector has a nucleic acid sequence having at least 98% sequence identity to that of SEQ ID NO: 18. In further other embodiments, the vector has the nucleic acid sequence of SEQ ID NO: 18 (see also FIG. 19).

Figure 20:
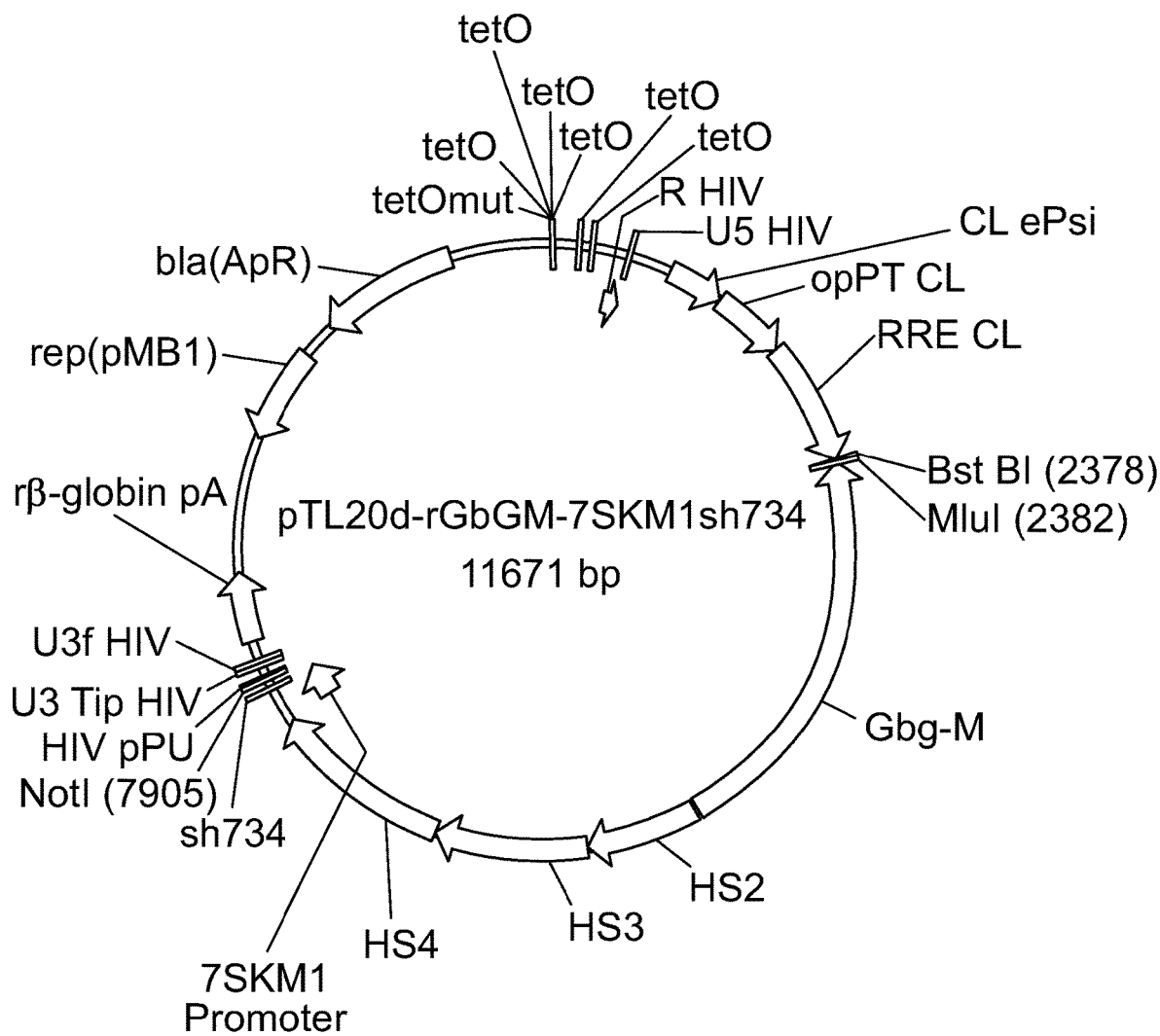
FIG. 20 provides a vector map of TL20d-rGbG$^M$-7SK$^{M1}$/sh734.

In some embodiments, the vector has a nucleic acid sequence having at least 90% sequence identity to that of SEQ ID NO: 19 (TL20d-rGbGM-7skM1/sh734). In other embodiments, the vector has a nucleic acid sequence having at least 95% sequence identity to that of SEQ ID NO: 19. In yet other embodiments, the vector has a nucleic acid sequence having at least 98% sequence identity to that of SEQ ID NO: 19. In further other embodiments, the vector has the nucleic acid sequence of SEQ ID NO: 19 (see also FIG. 20).

Figure 21:
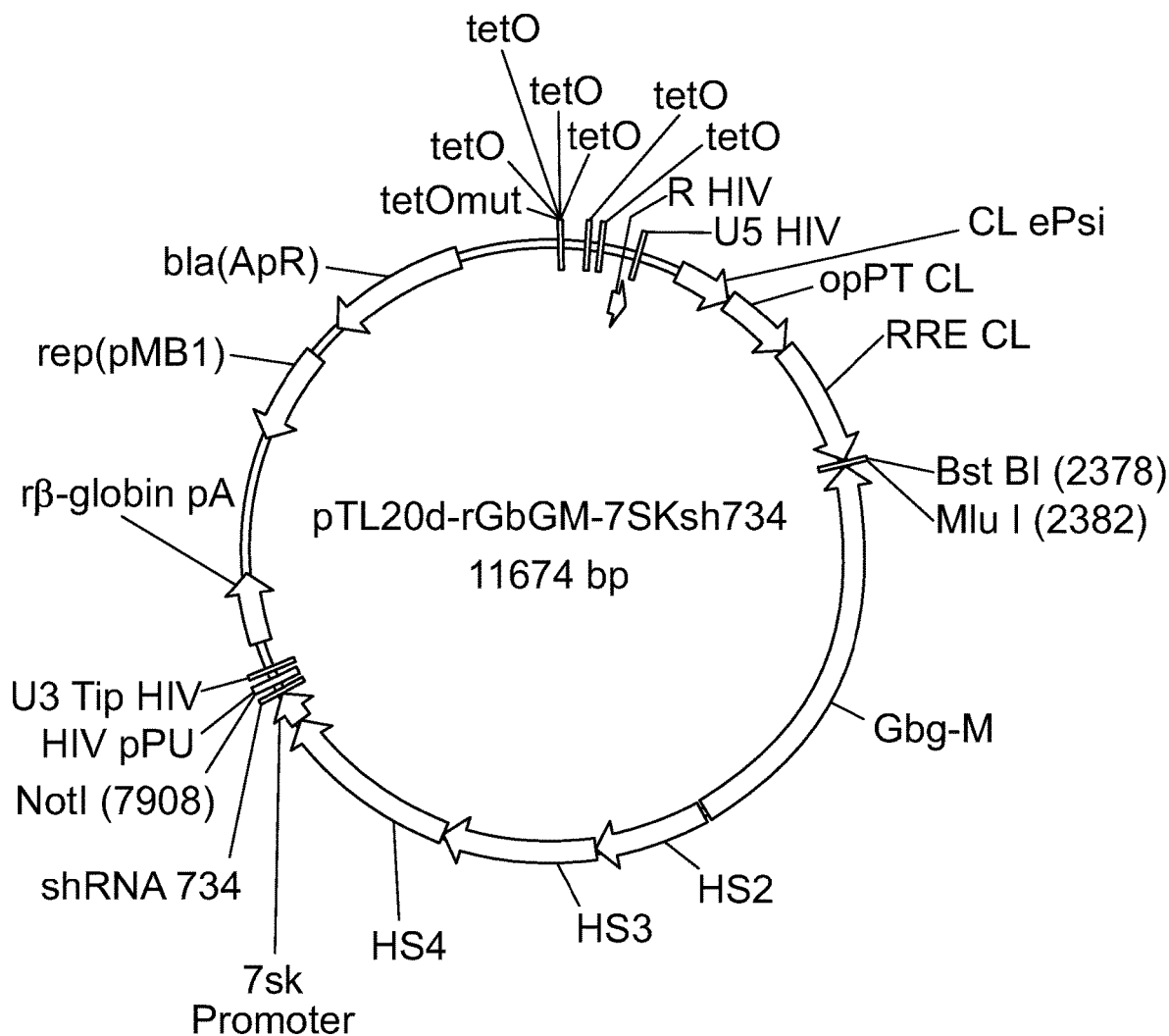
FIG. 21 provides a vector map of TL20d-GbG$^M$-7SK/sh734.

In some embodiments, the vector has a nucleic acid sequence having at least 90% sequence identity to that of SEQ ID NO: 20 (TL20d-GbGM-7sk/sh734). In other embodiments, the vector has a nucleic acid sequence having at least 95% sequence identity to that of SEQ ID NO: 20. In yet other embodiments, the vector has a nucleic acid sequence having at least 98% sequence identity to that of SEQ ID NO: 20. In further other embodiments, the vector has the nucleic acid sequence of SEQ ID NO: 20 (see also FIG. 21).

Figure 22:
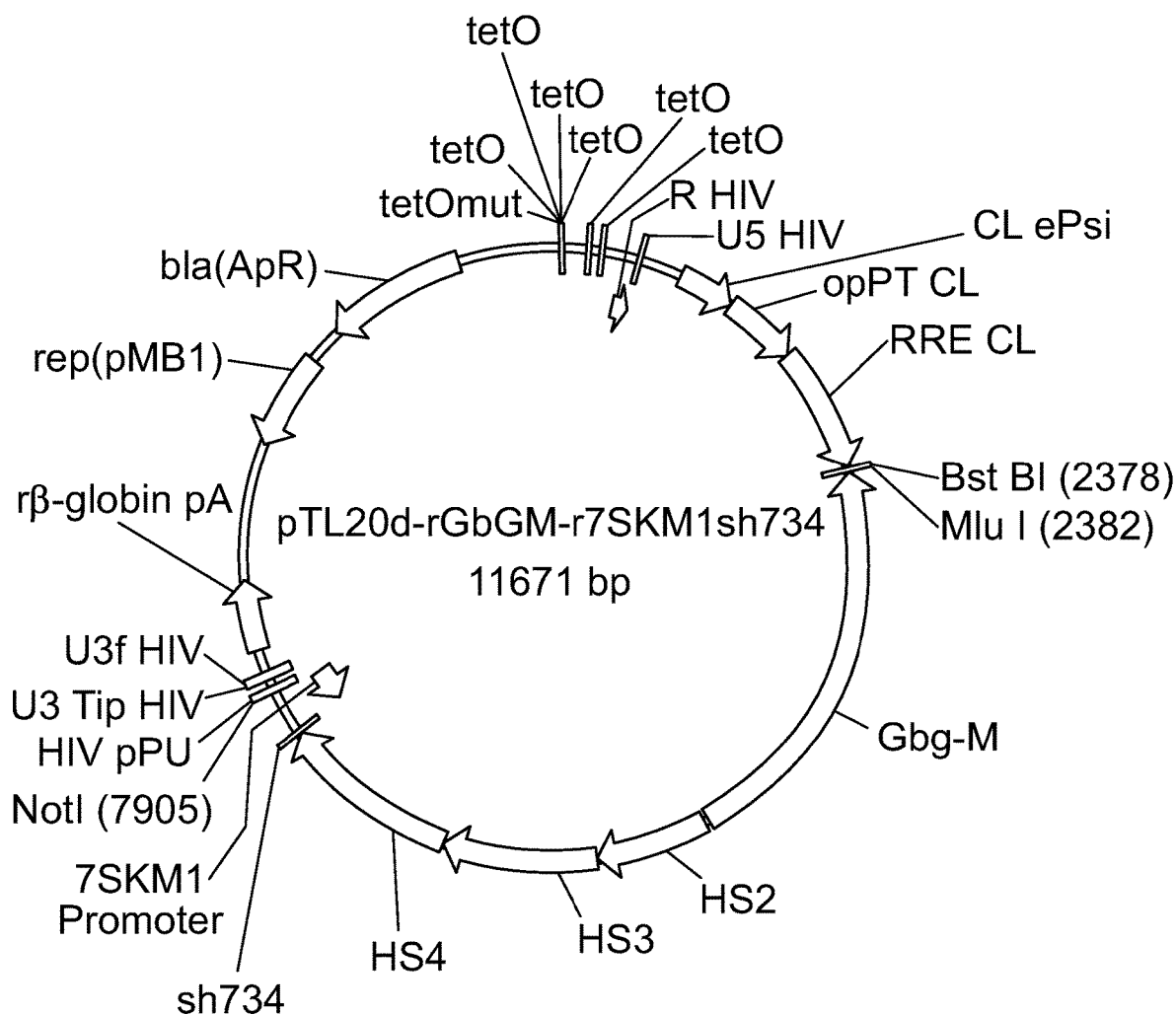
FIG. 22 provides a vector map of TL20d-rGbG$^M$-r7SK$^{M1}$/sh734.

In some embodiments, the vector has a nucleic acid sequence having at least 90% sequence identity to that of SEQ ID NO: 21 (TL20d-rGbGM-r7skM1/sh734). In other embodiments, the vector has a nucleic acid sequence having at least 95% sequence identity to that of SEQ ID NO: 21. In yet other embodiments, the vector has a nucleic acid sequence having at least 98% sequence identity to that of SEQ ID NO: 21. In further other embodiments, the vector has the nucleic acid sequence of SEQ ID NO: 21 (see also FIG. 22).

Figure 23:
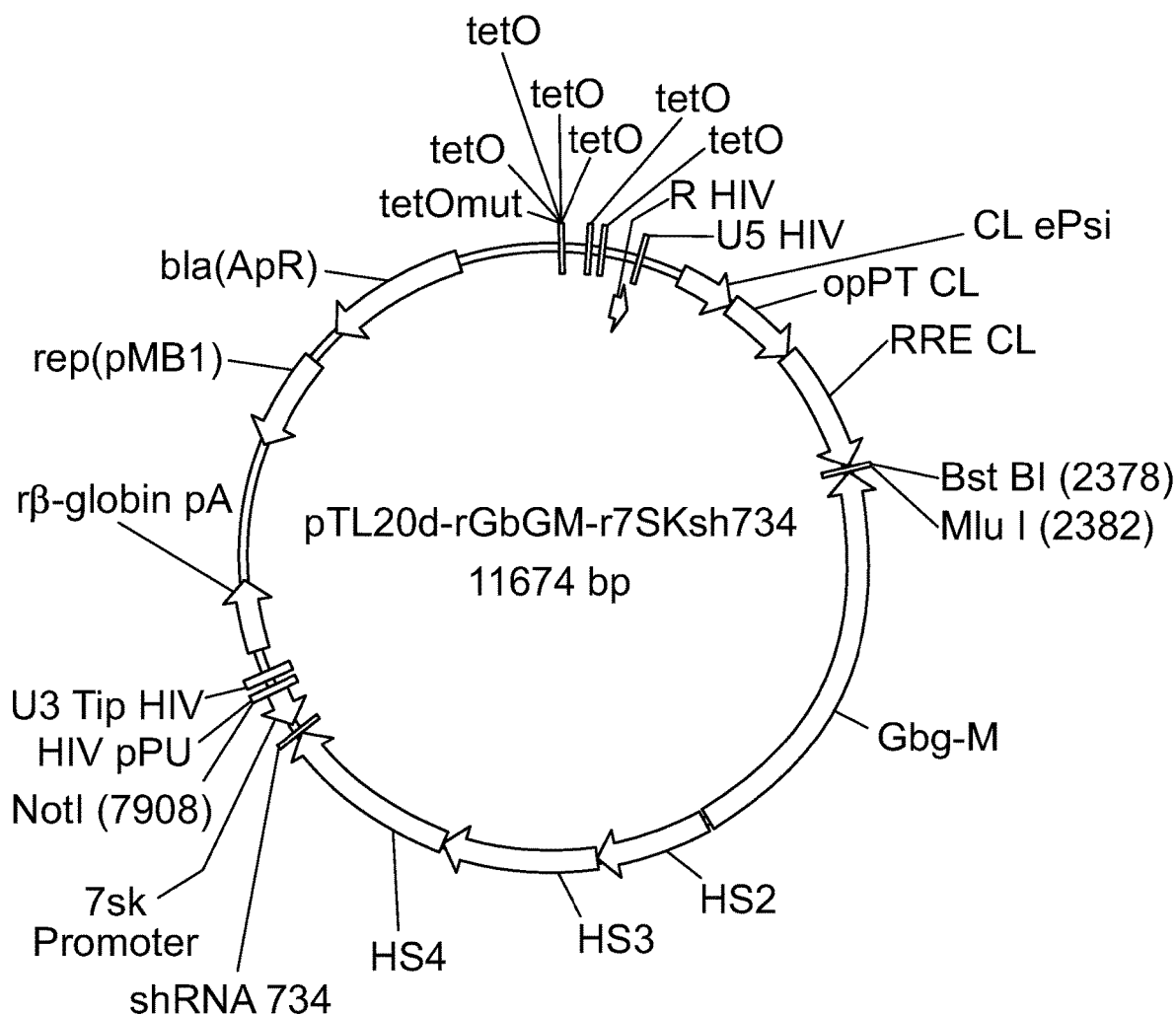
FIG. 23 provides a vector map of TL20d-rGbG$^M$-r7SK/sh734.

In some embodiments, the vector has a nucleic acid sequence having at least 90% sequence identity to that of SEQ ID NO: 22 (TL20d-rGbGM-r7sk/sh734). In other embodiments, the vector has a nucleic acid sequence having at least 95% sequence identity to that of SEQ ID NO: 22. In yet other embodiments, the vector has a nucleic acid sequence having at least 98% sequence identity to that of SEQ ID NO: 22. In further other embodiments, the vector has the nucleic acid sequence of SEQ ID NO: 22 (see also FIG. 23).

Production of Vectors

Figure 40A:
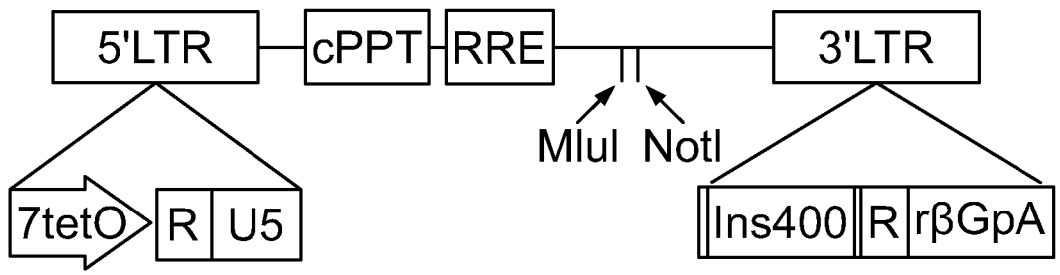
FIG. 40A provides a schematic representation of the components of the pTL20c vector.
Figure 40B:
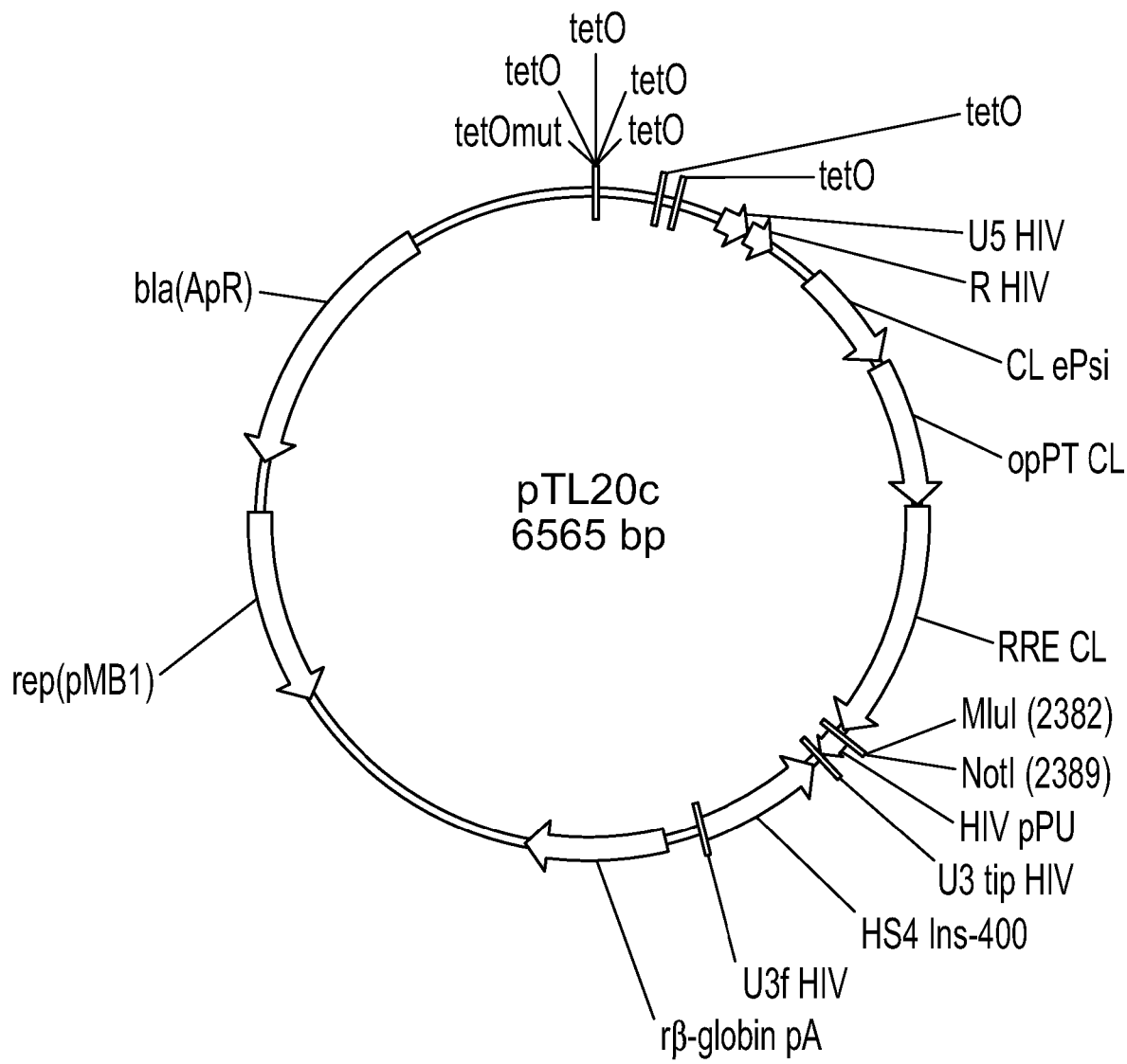
FIG. 40B illustrates a vector map for the pTL20c vector.

In some embodiments, an expression cassette, such as one having a particular transgene for expression, is inserted into expression vector, such as a lentiviral expression vector, to provide for a vector having at least one transgene for expression. For example, an expression cassette having a transgene for expression may be inserted into a pTL20c vector (SEQ ID NO: 47) (FIGS. 40A and 40B) or a pTL20d vector (i.e. PTL20c, but lacking the CHS4 insulator (SEQ ID NO: 49)) according to the methods described in in United States Patent Publication No. 2018/0112233, the disclosure of which is hereby incorporated by reference herein in its entirety. An example of inserting an expression cassette into the pTL20c vector is described at Example 1 herein.

Following insertion of the expression cassette into the expression vector, a second expression cassette is inserted into the vector having the at least one transgene for expression. For example, an expression cassette including a nucleic acid sequence to knockdown HPRT or otherwise decrease its expression may be inserted into the vector having the at least one transgene for expression. An example of inserting an expression cassette including an anti-HPRT shRNA into the vector having the at least one transgene for expression is described at Example 1 herein.

Non-Viral Delivery of Agents to Downregulate HPRT and/or to Introduce a Transgene In some embodiments, agents designed to knockdown the HPRT gene (including expression constructions including an RNAi) may be delivered through a nanocapsule other non-viral delivery vehicle. Delivery of such an agent through this method represents an alternative to effectuating downregulation of HPRT by means of an expressed RNAi or other agent from an expression vector. As described further herein, it is possible to deliver antisense RNA, oligonucleotides designed for exon skipping, or gene editing machinery by means of nanocapsules.

In general, a nanocapsule is a vesicular system that exhibits a typical core-shell structure in which active molecules are confined to a reservoir or cavity that is surrounded by a polymer membrane or coating. In some embodiments, the shell of a typical nanocapsule is made of a polymeric membrane or coating. In some embodiments, the nanocapsules are derived from a biodegradable or bioerodable polymeric material.

In some embodiments, the nanocapsule is an enzymatically degradable nanocapsule. In some embodiments, the nanocapsule consists of a single-protein core and a thin polymeric shell cross-linked by peptides. In some embodiments, a nanocapsule may be selected such that it is specifically recognizable and able to be cleaved by a protease. In some embodiments, the cleavable cross-linkers include a peptide sequence or structure that is a substrate of a protease or another enzyme.

Suitable nanocapsules includes those described in U.S. Pat. No. 9,782,357; those described in United States Patent Application Publication Nos. 2017/0354613, 2015/0071999 and 2015/035975; and those described in PCT Publication Nos. WO2016/085808, WO2017/06380, and WO2017/205541, the disclosures of which are hereby incorporated by reference herein in their entireties. Other suitable nanocapsules, their methods of synthesis, and/or methods of encapsulation, are further disclosed in United States Patent Publication No. 2011/0274682, the disclosure of which is hereby incorporated by reference herein in its entirety. Yet other suitable nanocapsules for the incorporation and delivery of agents designed to decrease expression of the HPRT gene are described in PCT Publication Nos. WO2013/138783, WO2013/033717, and WO2014/093966, the disclosures of which are hereby incorporated by reference herein in their entireties.

In some embodiments, the nanocapsules are adapted to target specific cell types (e.g. T cells, CD34 hematopoietic stem cells and progenitor cells) in vivo. For example, the nanocapsules may include one or more targeting moieties coupled to a polymer nanocapsule. In some embodiments, the targeting moiety delivers the polymer nanocapsules to a specific cell type, wherein the cell type is selected from the group comprising immune cells, blood cells, cardiac cells, lung cells, optic cells, liver cells, kidney cells, brain cells, cells of the central nervous system, cells of the peripheral nervous system, cancer cells, cells infected with viruses, stem cells, skin cells, intestinal cells, and/or auditory cells. In some embodiments, the targeting moieties are antibodies. Suitable payloads for such nanocapsules include synthetic oligonucleotides, shRNAs, miRNAs, and Ago-shRNAs targeting HPRT. In some embodiments, the payloads may be expressed in Pol III or Pol II driven promoter cassettes.

In other embodiments, agents for downregulating HPRT may be formulated within bio-nanocapsules, which are nano-size capsules produced by a genetically engineered microorganism. In some embodiments, a bio-nanocapsule is a virus protein-derived or modified virus protein-derived particle, such as a virus surface antigen particle (e.g., a hepatitis B virus surface antigen (HBsAg) particle). In other embodiments, a bio-nanocapsule is a nano-size capsule comprising a lipid bilayer membrane and a virus protein-derived or modified virus protein-derived particle such as a virus surface antigen particle. Such particles can be purified from eukaryotic cells, such as yeasts, insect cells, and mammalian cells. The size of a capsule may range from between about 10 nm to about. 500 nm. In other embodiments, the size of the capsule may range from between about 20 nm to about 250 nm. In yet other embodiments, the size of the capsule may range from between about 80 nm to about 150.

In some embodiments, a nanocapsule formulation is provided that both "corrects" a gene by "fixing" the original genetic mutation (such as by employing genome editing/engineering) and simultaneously delivering and inserting a transcription cassette encoding a mechanism to knock-down HPRT.

Antisense RNA

Antisense RNA (asRNA) is a single-stranded RNA that is complementary to a messenger RNA (mRNA) strand transcribed within a cell. Without wising to be bound by any particular theory, it is believed that antisense RNA may be introduced into a cell to inhibit translation of a complementary mRNA by base pairing to it and physically obstructing the translation machinery. Said another way, antisense RNAs are single-stranded RNA molecules that exhibit a complementary relationship to specific mRNAs.

Antisense RNAs may be utilized for gene regulation and specifically target mRNA molecules that are used for protein synthesis. The antisense RNA can physically pair and bind to the complementary mRNA, thus inhibiting the ability of the mRNA to be processed in the translation machinery. In addition to siRNA/shRNA LV delivered constructs, phosphorothioate-modified antisense oligonucleotides may be utilized to target sequences within the coding region of HPRT mRNA (see FIG. 37). These oligonucleotides can be delivered to specific cell populations and anatomic sites cells using targeted nanoparticles, as described above.

Exon Skipping

As noted herein, exon skipping may be utilized to create a defect within the HPRT gene that results in HPRT deficiency. In some embodiments, an oligonucleotide (including a modified oligonucleotide) may be delivered by means of a nanocapsule, the oligonucleotide designed to target unspliced HPRT mRNA and mediate either premature termination or skipping of an intron required for activity. An HPRT duplication mutation, e.g. e.g. a duplication mutation in Exon 4, (see Baba S, et al., "Novel mutation in HPRT1 causing a splicing error with multiple variations," Nucleosides Nucleotides Nucleic Acids. 2017 Jan. 2; 36(1): 1-6) could be introduced to cause a splicing error and functional inactivation of the HPRT protein. Replacing HPRT with a modified mutated sequence by spliceosome trans-splicing is a potential therapeutic strategy to knockdown HPRT. It is believed that this requires (1) a mutated coding region to replace the coding sequence in target RNA, (2) a 5' or 3' splice site, and (3) a binding domain, e.g., an antisense oligonucleotide sequence, which is complementary to target RNA.

The oligonucleotides may be structurally modified such that they are nuclease resistant. In some embodiments, the oligonucleotides have modified backbones or non-natural inter-nucleoside linkages. Such oligonucleotides having modified backbones include those that retain a phosphorus atom in the backbone and those that do not have a phosphorus atom in the backbone. In some embodiments, modified oligonucleotides that do not have a phosphorus atom in their inter-nucleoside backbone can also be considered to be oligonucleotides. In other embodiments, the oligonucleotides are modified such that both the sugar and the inter-nucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleo-bases are retained and are bound directly or indirectly to aza nitrogen atoms of the amide portion of the backbone. Modified oligonucleotides may also contain one or more substituted sugar moieties. Oligonucleotides may also include nucleobase (often referred to in the art simply as "base") modifications or substitutions. Certain nucleo-bases are particularly useful for increasing the binding affinity of the oligomeric compounds of the disclosure. These include, without limitation, 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. and are presently preferred base substitutions, even more particularly when combined with 2'-O-methoxyethyl sugar modifications.

Gene Editing Techniques

The present disclosure also provides compositions for the targeted insertion of a transgene (donor) including a protein-encoding sequence, for example a protein that is lacking or deficient in a subject with beta-thalassemia or sickle-cell disease. In certain embodiments, targeted integration of a corrective gene cassette into the genome of a cell is achieved using highly specific DNA binding proteins (e.g. meganucleases, ZFNs, TALENs, CRISPR/Cas systems). The gene cassettes integrated into the targeted gene may be carried on a viral or non-viral vector and/or may be integrated using one or more nucleases. Meganucleases are engineered versions of naturally occurring restriction enzymes that typically have extended DNA recognition sequences (e.g., 14-40 bp). ZFNs and TALENs are artificial fusion proteins composed of an engineered DNA binding domain fused to a nonspecific nuclease domain from the FokI restriction enzyme. Zinc finger and TALE repeat domains with customized specificities can be joined together into arrays that bind to extended DNA sequences.

In some embodiments, a CRISPR approach (described below) is utilized to knockout HPRT, combined with a "knock in" strategy to correct the SCD mutation or to convert an endogenous gamma globin promoter to beta-globin in order to, it is believed, prevent repression and allow the constitutive expression of fetal Hb in adult cells.

In some embodiments, a gene editing approach may be used to knockout HPRT. For example, isolated cells may be treated with a HPRT-targeted CRISPR/Cas9 RNP. A CRISPR/Cas system is designed to bind to a target site in a region of interest (e.g., a highly expressed gene, a disease associated gene or a safe harbor gene) in a genome, wherein the CRISPR/Cas system comprises a CRIPSR/Cas nuclease and an engineered crRNA/tracrRNA (or single guide RNA). In some embodiments, the CRISPR/Cas system recognizes a target in a HPRT gene. sgRNA candidates for knockdown of HPRT are shown in FIG. 38. Forward and reverse point accepted mutation ("PAM") sequences are listed including specificity and efficiency scores and HPRT chromosome coordinates targeted (where PAM refers to the replacement of a single amino acid in the primary structure of a protein with another single amino acid). In some embodiments, the Cas9 protein is complexed with guide RNA in a RNP (ribonucleoprotein) particle. In some embodiments, the particles further include a single-stranded DNA for targeted insertion in the disrupted HPRT locus.

Lesch-Nyhan syndrome is a rare genetic disorder of purine metabolism due to functional mutations in the HPRT gene. Mutations resulting in Lesch-Nyhan syndrome are highly heterogenous and provide functional targets for CRISPR/Cas9 and other gene editing approaches for ex vivo gene editing of T cells, Progenitor T cells, HSC and progenitor cells (Gasperini, M., G. M. Findlay, A. McKenna, J. H. Milbank, C. Lee, M. D. Zhang, D. A. Cusanovich, and J. Shendure. 2017. CRISPR/Cas9-Mediated Scanning for Regulatory Elements Required for HPRT1 Expression via Thousands of Large, Programmed Genomic Deletions. The American Journal of Human Genetics 101:192-205). A novel mutation has been identified in exon 4 of HPRT1 that is believed to cause aberrant splicing and loss of HPRT function. In some embodiments, the natural mutation could be exploited for reproducing the spicing error using a gene editing approach. (Baba, Shimpei Saito, Takashi Yamada, Yasukazu Takeshita, Eri Nomura, Noriko Yamada, Ken-ichiro Wakamatsu, Nobuaki Sasaki, Masayuki Nucleosides Nucleotides Nucleic Acids Nucleosides, Nucleotides & Nucleic Acids, 2017, Vol. 36(1), p. 1-6.

Nanocapsules targeting these specific cell-types can provide efficient in vivo delivery. Maeder M L et al. Genome-editing Technologies for Gene and Cell Therapy, Mol Ther. 2016 March; 24(3):430-46), describe various gene editing techniques, including CRISPR/Cas9 nuclease mediated methods, and these disclosures are hereby incorporated by reference herein in their entirety.

Other gene editing techniques using certain nucleases are described in U.S. Pat. Nos. 8,895,264, 9,616,090, 9,624,498, 9,650,648 and 9,22,105 and in PCT Application No. PCT/US12/61896, the disclosures of which are each hereby incorporated by reference herein in their entireties. In some embodiments, a zinc-finger protein (ZFP) that binds to a target site in an HPRT gene in a genome may be utilized, wherein the ZFP comprises one or more engineered zinc-finger binding domains. In some embodiments, ZFPs are used as a pair of zinc-finger nucleases (ZFNs) that dimerize and then cleave a target genomic region of interest, wherein the ZFNs comprise one or more engineered zinc-finger binding domains and a nuclease cleavage domain or cleavage half-domain. A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP. In some embodiments, gene editing is performed using a fusion protein comprising a zinc finger protein that binds to an endogenous hypoxanthine-guanine HPRT gene and a cleavage domain, wherein the fusion protein modifies the endogenous HPRT gene. In some embodiments, a fusion protein comprising a ZFP may be incorporated into a nanocapsule for delivery, the ZFP binding capable of binding to a target site in a region of interest in a HPRT locus.

In some embodiments, a TALE protein (Transcription activator like effector) that binds to target site in an HPRT gene in a genome may be utilized, wherein the TALE comprises one or more engineered TALE DNA binding domains. In some embodiments, the TALE is a nuclease (TALEN) that cleaves a target genomic region of interest, wherein the TALEN comprises one or more engineered TALE DNA binding domains and a nuclease cleavage domain or cleavage half-domain. Cleavage domains and cleavage half domains of ZFNs and/or TALENs can be obtained, for example, from various restriction endonucleases and/or homing endonucleases. In some embodiments, the cleavage half-domains are derived from a Type IIS restriction endonuclease (e.g., Fok I). Knockout efficiency of TAL, CRISPR/Cas9 gene editing methods and siRNA knockdown approaches resulting in loss of HPRT functional gene expression is determined by HPRT qPCR. Knockdown of HPRT expression using the miRNA211-3g is shown in FIG. 27.

In other embodiments, a vector encoding a guide RNA targeting HPRT is utilized.

In yet other embodiments, a hybrid nuclease architecture that combines a TALE with the cleavage sequence specificity of a meganuclease cleavage domain, referred to herein as a "megaTAL." In some embodiments, the megaTAL is provided by fusing minimal TAL effector domains to the N-terminus of meganuclease derived from the LAGLIDADG homing endonuclease family. In some embodiments, a megaTAL is engineered to knockout HPRT. Methods of engineering a suitable megaTAL are described by "Boissel S, Jarjour J, Astrakhan A, et al. megaTALs: A Rare-Cleaving Nuclease Architecture for Therapeutic Genome Engineering. Nucleic Acids Research. 2014; 42(4):2591-2601," the disclosure of which is hereby incorporated by reference herein in its entirety.

The nucleases, polynucleotides encoding these nucleases, donor polynucleotides and compositions comprising the proteins and/or polynucleotides described herein may be delivered in vivo or ex vivo by any suitable means. For example, methods of delivering nucleases as described herein are described, for example, in U.S. Pat. Nos. 6,453,242; 6,503,717; 6,534,261; 6,599,692; 6,607,882; 6,689,558; 6,824,978; 6,933,113; 6,979,539; 7,013,219; and 7,163,824, the disclosures of all of which are incorporated by reference herein in their entireties.

Host Cells

The present disclosure also provides a host cell comprising the novel expression vectors of the present disclosure. A "host cell" or "target cell" means a cell that is to be transformed using the methods and expression vectors of the present disclosure. In some embodiments, the host cells are mammalian cells in which the expression vector can be expressed. Suitable mammalian host cells include, but are not limited to, human cells, murine cells, non-human primate cells (e.g. rhesus monkey cells), human progenitor cells or stem cells, 293 cells, HeLa cells, D17 cells, MDCK cells, BHK cells, and Cf2Th cells. In certain embodiments, the host cell comprising an expression vector of the disclosure is a hematopoietic cell, such as hematopoietic progenitor/stem cell (e.g. CD34-positive hematopoietic progenitor/stem cell (HPSC)), a monocyte, a macrophage, a peripheral blood mononuclear cell, a CD4+T lymphocyte, a CD8+T lymphocyte, or a dendritic cell.

The hematopoietic cells (e.g. HPSC, CD4+T lymphocytes, CD8+T lymphocytes, and/or monocyte/macrophages) to be transduced with an expression vector of the disclosure can be allogeneic, autologous, or from a matched sibling. The HPSC are, in some embodiments, CD34-positive and can be isolated from the patient's bone marrow or peripheral blood. The isolated CD34-positive HPSC (and/or other hematopoietic cell described herein) is, in some embodiments, transduced with an expression vector as described herein.

In some embodiments, the host cells or transduced host cells are combined with a pharmaceutically acceptable carrier. In some embodiments, the host cells or transduced host cells are formulated with PLASMA-LYTE A (e.g. a sterile, nonpyrogenic isotonic solution for intravenous administration; where one liter of PLASMA-LYTE A has an ionic concentration of 140 mEq sodium, 5 mEq potassium, 3 mEq magnesium, 98 mEq chloride, 27 mEq acetate, and 23 mEq gluconate). In other embodiments, the host cells or transduced host cells are formulated in a solution of PLASMA-LYTE A, the solution comprising between about 8% and about 10% dimethyl sulfoxide (DMSO). In some embodiments, the less than about $2 \times 10^7$ host cells/transduced host cells are present per mL of a formulation including PLASMA-LYTE A and DMSO.

In some embodiments, the host cells are rendered substantially HPRT deficient after transduction with a vector according to the present disclosure, e.g. having at least a 50% reduction in HPRT expression. In some embodiments, the host cells include a nucleic acid molecule including at least one of SEQ ID NO: 1, SEQ ID NO: 2, or SEQ ID NO: 3.

Pharmaceutical Compositions

The present disclosure also provides for compositions, including pharmaceutical compositions, comprising one or more expression vectors and/or non-viral delivery vehicles (e.g. nanocapsules) as disclosed herein. In some embodiments, pharmaceutical compositions comprise an effective amount of at least one of the expression vectors and/or non-viral delivery vehicles as described herein and a pharmaceutically acceptable carrier. For instance, in certain embodiments, the pharmaceutical composition comprises an effective amount of an expression vector and a pharmaceutically acceptable carrier. An affective amount can be readily determined by those skilled in the art based on factors such as body size, body weight, age, health, sex of the subject, ethnicity, and viral titers.

The phrases "pharmaceutically acceptable" or "pharmacologically acceptable" refer to molecular entities and compositions that do not produce adverse, allergic, or other untoward reactions when administered to an animal or a human. For example, an expression vector may be formulated with a pharmaceutically acceptable carrier. As used herein, "pharmaceutically acceptable carrier" includes solvents, buffers, solutions, dispersion media, coatings, antibacterial and antifungal agents, isotonic and absorption delaying agents and the like acceptable for use in formulating pharmaceuticals, such as pharmaceuticals suitable for administration to humans. Methods for the formulation of compounds with pharmaceutical carriers are known in the art and are described in, for example, in Remington's Pharmaceutical Science, (17th ed. Mack Publishing Company, Easton, Pa. 1985); and Goodman & Gillman's: The Pharmacological Basis of Therapeutics (11th Edition, McGraw-Hill Professional, 2005); the disclosures of each of which are hereby incorporated herein by reference in their entirety.

In some embodiments, the pharmaceutical compositions may comprise any of the expression vectors, nanocapsules, or compositions disclosed herein in any concentration that allows the silencing nucleic acid administered to achieve a concentration in the range of from about 0.1 mg/kg to about 1 mg/kg. In some embodiments, the pharmaceutical compositions may comprise the expression vector in an amount of from about 0.1% to about 99.9% by weight. Pharmaceutically acceptable carriers suitable for inclusion within any pharmaceutical composition include water, buffered water, saline solutions such as, for example, normal saline or balanced saline solutions such as Hank's or Earle's balanced solutions), glycine, hyaluronic acid etc. The pharmaceutical composition may be formulated for parenteral administration, such as intravenous, intramuscular or subcutaneous administration. Pharmaceutical compositions for parenteral administration may comprise pharmaceutically acceptable sterile aqueous or non-aqueous solutions, dispersions, suspensions or emulsions as well as sterile powders for reconstitution into sterile injectable solutions or dispersions. Examples of suitable aqueous and non-aqueous carriers, solvents, diluents or vehicles include water, ethanol, polyols (such as glycerol, propylene glycol, polyethylene glycol, etc.), carboxymethylcellulose and mixtures thereof, vegetable oils (such as olive oil), injectable organic esters (e.g. ethyl oleate).

The pharmaceutical composition may be formulated for oral administration. Solid dosage forms for oral administration may include, for example, tablets, dragees, capsules, pills, and granules. In such solid dosage forms, the composition may comprise at least one pharmaceutically acceptable carrier such as sodium citrate and/or dicalcium phosphate and/or fillers or extenders such as starches, lactose, sucrose, glucose, mannitol, and silicic acid; binders such as carboxylmethylcellulose, alginates, gelatin, polyvinylpyrrolidone, sucrose and acacia; humectants such as glycerol; disintegrating agents such as agar-agar, calcium carbonate, potato or tapioca starch, alginic acid, silicates, and sodium carbonate; wetting agents such as acetyl alcohol, glycerol monostearate; absorbants such as kaolin and bentonite clay; and/or lubricants such as talc, calcium stearate, magnesium stearate, solid polyethylene glycol, sodium lauryl sulfate, and mixtures thereof. Liquid dosage forms for oral administration may include, for example, pharmaceutically acceptable emulsions, solutions, suspensions, syrups and elixirs. Liquid dosages may include inert diluents such as water or other solvents, solubilizing agents and/or emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (such as, for example, cottonseed oil, corn oil, germ oil, castor oil, olive oil, sesame oil), glycerol, tetrahydrofurfuryl alcohol, polyethylene glycols and fatty acid esters of sorbitan, and mixtures thereof.

The pharmaceutical compositions may comprise penetration enhancers to enhance their delivery. Penetration enhancers may include fatty acids such as oleic acid, lauric acid, capric acid, myristic acid, palmitic acid, stearic acid, linoleic acid, linolenic acid, dicaprate, reclineate, monoolein, dilaurin, caprylic acid, arachidonic acid, glyceryl 1-monocaprate, mono and di-glycerides and physiologically acceptable salts thereof. The compositions may further include chelating agents such as, for example, ethylenediaminetetraacetic acid (EDTA), citric acid, salicylates (e.g. sodium salicylate, 5-methoxysalicylate, homovanilate).

The pharmaceutical compositions may comprise any of the expression vectors disclosed herein in an encapsulated form. For example, the expression vectors may be encapsulated by biodegradable polymers such as polylactide-polyglycolide, poly(orthoesters) and poly(anhydrides), or may be encapsulated in liposomes or dispersed within a microemulsion. Liposomes may be, for example, lipofectin or lipofectamine. In another example, a composition may comprise the expression vectors disclosed herein in or on anucleated bacterial minicells (Giacalone et al, Cell Microbiology 2006, 8(10): 1624-33). The expression vectors disclosed herein may be combined with nanoparticles.

Kits

In some embodiments is a kit comprising an expression vector or a composition comprising an expression vector as described herein. The kit may include a container, where the container may be a bottle comprising the expression vector or composition in an oral or parenteral dosage form, each dosage form comprising a unit dose of the expression vector. The kit may comprise a label or the like, indicating treatment of a subject according to the methods described herein.

In some embodiments, the kit may include additional active agents. The additional active agents may be housed in a container separate from the container housing the vector or composition comprising the vector. For example, in some embodiments, the kit may comprise one or more doses of a purine analog (e.g. 6TG) and optionally instructions for dosing the purine analog for conditioning and/or chemoselection (as those steps are described further herein). In other embodiments, the kit may comprise one or more doses of MTX or MPA and optionally instructions for dosing the MTX or MPA for negative selection as described herein.

In yet other embodiments, the kit may include one or more internalizing immunotoxinss or antibody-drug conjugates, such as those described in US Patent Publication Nos. 2017/0360954 and 2018/0147294; and PCT Publication Nos. WO/2017/219025 and WO/2017/219029, the disclosures of which are each incorporated by reference herein in their entireties. In some embodiments, the kit may include an immunotoxin is selected from pseudomonas exotoxin A, deBouganin, diphtheria toxin, an amatoxin, such as α-amanitin, saporin, maytansine, a maytansinoid, an auristatin, an anthracycline, a calicheamicin, irinotecan, SN-38, a duocarmycin, a pyrrolobenzodiazepine, a pyrrolobenzodiazepine dimer, an indolinobenzodiazepine, or an indolinobenzodiazepine dimer, Ricin-A or a variant thereof. In some embodiments, the kit may include saporin.

Methods of Treatment

The methods and compositions disclosed herein are for modifying expression of a protein or correcting an aberrant gene sequence that encodes a protein expressed in a genetic disease, such as a sickle cell disease or a thalassemia. In some embodiments, the therapeutic gene provided within the vectors of the present disclosure are used to treat immune deficiencies, hereditary diseases, blood diseases (e.g. hemophilia, hemoglobin disorders), lysosomal storage diseases, neurological diseases, angiogenic disorders, or cancer. While particular reference may be made to the genetic treatment of sickle cell anemia or β-thalassemia, the present disclosure is not limited to methods of treating only those diseases. As such, in some embodiments, the method of treating immune deficiencies, hereditary diseases, blood diseases (e.g. hemophilia, hemoglobin disorders), lysosomal storage diseases, neurological diseases, angiogenic disorders, or cancer comprises (i) transducing HSCs including, autologous HSCs, allogenic HSCs, sibling matched HSCs, etc. with a vector comprising at least two nucleic acid sequences, namely a nucleic acid sequence encoding an agent to decrease HPRT expression, and a nucleic acid sequence encoding a therapeutic gene, and (ii) administering the transduced HSCs to a mammalian subject.

By way of example, an expression vector including a nucleic acid sequence encoding a gamma-globin gene (such as described herein) may be administered so as to genetically correct sickle cell disease or β-thalassemia, or reduce symptoms thereof. In some embodiments, a population of host cells transduced with an expression vector including a nucleic acid sequence encoding a gamma-globin gene may be administered so as to genetically correct sickle cell disease or β-thalassemia, or reduce symptoms thereof. It is believed that the genetic correction of HSCs with a vector encoding the gamma globin gene would result in a continuous (i.e. permanent) production of the anti-sickling HbF, thereby preventing or mitigating red blood cell sickling for the life of the subject. It is believed that this method is advantageous over currently available therapies, including its availability to all patients, particularly those who do not have a matched sibling donor, and the fact that it would be a one-time treatment, resulting in lifelong correction. It is also believed that the method is advantageously devoid of any immune side effects, and if side effects did arise, the side-effects could be mitigated by administering MTX or MPA as noted herein. It is further believed that an effective gene therapy approach will revolutionize the way SCD is treated and improve the outcomes of patients with this devastating disorder.

As noted herein, in addition to the therapeutic gene, the expression vectors of the present disclosure include an agent designed to decrease HPRT expression (e.g. a shRNA to HPRT to effect knockdown of HPRT expression), and hence provide for an in vivo chemoselection strategy that exploits the essential role that HPRT plays in metabolizing purine analogs, e.g. 6TG, into myelotoxic agents. Because HPRT-deficiency does not impair hematopoietic cell development or function, it can be removed from hematopoietic cells used for transplantation. Conditioning and chemoselection with a purine analog is discussed further herein.

In the context of the treatment of sickle cell disease or β-thalassemia (or reducing the symptoms of sickle cell disease or β-thalassemia), and with reference to FIG. 2, the treatment of a subject includes: identifying a subject in need of treatment thereof; transducing HSCs (e.g. autologous HSCs, allogenic HSCs, sibling matched HSCs) with an expression vector (e.g. a lentiviral vector) of the present disclosure (step 120); and transplanting or administering the transduced HSCs into the subject (step 140). In some embodiments, the subject in need of treatment thereof is one suffering from severe symptomatic SCD.

In some embodiments, the method of treating hemoglobinopathies comprises (i) transducing HSCs with a vector comprising at least two nucleic acid sequences, namely a nucleic acid sequence encoding a shRNA to knockdown the HPRT gene, and a nucleic acid sequence encoding a gamma globin gene, and (ii) administering the transduced HSCs to a mammalian subject. In some embodiments, the nucleic acid sequence encoding the shRNA comprises the sequence of SEQ ID NO: 30. In some embodiments, the nucleic acid sequence encoding the gamma globin gene comprises the sequence of SEQ ID NO: 55. In some embodiments, the method further comprises a step of myeloablative conditioning prior to the administration of the transduced HSCs (e.g. using a purine analog, chemotherapy, radiation therapy, treatment with one or more internalizing immunotoxins or antibody-drug conjugates, or any combination thereof). In some embodiments, the method further comprises the step of in vivo chemoselection utilizing a purine analog (e.g. 6TG) following administration of the transduced HSCs. In some embodiments, the method further comprises the step of negative selection utilizing MTX or MPA should side effects arise (e.g. GVHD).

In another aspect of the present disclosure is a method of treating hemoglobinopathies comprising administering an effective amount of a pharmaceutical composition to a mammalian subject (e.g. a human patient), wherein the pharmaceutical compositions includes an expression vector comprising at least two nucleic acid sequences, and a pharmaceutically acceptable carrier. In another aspect of the present disclosure is a method of treating hemoglobinopathies comprising administering an effective amount of a pharmaceutical composition to a mammalian subject (e.g. a human patient), wherein the pharmaceutical compositions includes a population of host cells transduced with an expression vector comprising at least two nucleic acid sequences, and a pharmaceutically acceptable carrier. In some embodiments, the expression vector is a lentiviral expression vector including a first nucleic acid encoding an RNAi to knockdown the HPRT gene; and a second nucleic acid encoding a therapeutic gene (e.g. a gamma globin gene). In some embodiments, the nucleic acid sequence encoding the gamma globin gene comprises the sequence of SEQ ID NO: 55. In some embodiments, the method further comprises a step of myeloablative conditioning prior to the administration of the transduced HSCs. In some embodiments, the method further comprises the step of in vivo chemoselection utilizing 6TG following administration of the transduced HSCs. In some embodiments, the method further comprises the step of negative selection utilizing MTX or MPA should side effects arise (e.g. GVHD).

In another aspect of the present disclosure is a method of treating severe symptomatic SCD, or reducing or ameliorating one or more symptoms of severe symptomatic SCD, comprising (i) transducing HSCs with a vector comprising at least two nucleic acid sequences, namely a nucleic acid sequence encoding a shRNA to knockdown the HPRT gene, and a nucleic acid sequence encoding a gamma globin gene, and (ii) administering the transduced HSCs to a mammalian subject. In some embodiments, the nucleic acid sequence encoding the shRNA comprises the sequence of SEQ ID NO: 30. In some embodiments, the nucleic acid sequence encoding the gamma globin gene comprises the sequence of SEQ ID NO: 55. In some embodiments, the method further comprises a step of myeloablative conditioning prior to the administration of the transduced HSCs (e.g. using a purine analog, chemotherapy, radiation therapy, treatment with one or more internalizing immunotoxins or antibody-drug conjugates, or any combination thereof). In some embodiments, the method further comprises the step of in vivo chemoselection utilizing a purine analog (e.g. 6TG) following administration of the transduced HSCs. In some embodiments, the method further comprises the step of negative selection utilizing MTX or MPA should side effects arise (e.g. GVHD). In some embodiments, treatment reduces or ameliorates at least one of acute chest syndrome, severe pain episodes, recurrent priapism, red-cell alloimmunization, and/or neurologic events.

In some embodiments, post-transplantation fetal hemoglobin exceeds at least 20%; F cells constitute at least ⅔ of the circulating red blood cells; fetal hemoglobin per F cells account for at least ⅓ of total hemoglobin in sickle red blood cells; and at least 20% gene-modified HSCs re-populate bone marrow of the subject. In some embodiments, post-transplantation fetal hemoglobin exceeds 25%, 30%, 35%, 40%, 45%, 50%, or greater. In some embodiments, post-transplantation fetal hemoglobin exceeds 55%, 60%, 65%, 70%, 75%, 80%, 85%, 90%, 95%, or greater. In some embodiments, F cells constitute at least 70%, 75%, 80%, 85%, 90%, 95%, or greater of the circulating red blood cells. In some embodiments, fetal hemoglobin per F cells account for at least ⅓ of total hemoglobin in sickle red blood cells. In some embodiments, fetal hemoglobin per F cells account for at least 40%, 45%, 50%, 55%, 60%, 65%, 70%, 75%, 80%, 85%, 90%, 95% or greater of total hemoglobin in sickle red blood cells. In some embodiments, 20%, 25%, 30%, 35%, 40%, 45%, 50%, 55%, 60%, 65%, 70%, 75%, 80%, 85%, 90%, 95%, or greater gene-modified HSCs re-populate bone marrow of the subject.

In another aspect of the present disclosure is a method of treating treat immune deficiencies, hereditary diseases, blood diseases (e.g. hemophilia, hemoglobin disorders), lysosomal storage diseases, neurological diseases, angiogenic disorders, or cancer comprising administering an effective amount of a vector to a mammalian subject, the vector comprising at least two nucleic acid sequences, namely a nucleic acid sequence encoding an RNAi to knockdown the HPRT gene, and a nucleic acid sequence encoding a therapeutic gene.

Conditioning and Chemoselection with a Purine Analog

In some embodiments, the method of treatment comprises the additional steps of (i) conditioning prior to HSC transplantation; and/or (ii) in vivo chemoselection. One or both steps may utilize a purine analog, In some embodiments, the purine analog is 6TG. It is believed that the engrafted gamma-globin gene-containing HSCs deficient in HPRT activity are highly resistant to the cytotoxic effects of the introduced purine analog. With a combined strategy of conditioning and chemoselection, efficient and high engraftment of HPRT-deficient, therapeutic gene (e.g. gamma globin gene) containing HSCs with low overall toxicity can be achieved. It is believed that resultant expression of the therapeutic gene (e.g. gamma globin gene), combined with the enhanced engraftment and chemoselection of gene-modified HSCs, can result in sufficient protein production to correct for immune deficiencies, hereditary diseases, blood diseases (e.g. hemophilia, hemoglobin disorders), lysosomal storage diseases, neurological diseases, angiogenic disorders, or cancer (and, in the case of the production of the gamma-globin protein, sufficient fetal hemoglobin formation to correct for SCD and/or beta thalassemia).

6TG is a purine analog having both anticancer and immune-suppressive activities. Thioguanine competes with hypoxanthine and guanine for the enzyme hypoxanthine-guanine phosphoribosyltransferase (HGPRTase) and is itself converted to 6-thioguanylic acid (TGMP). This nucleotide reaches high intracellular concentrations at therapeutic doses. TGMP interferes several points with the synthesis of guanine nucleotides. It inhibits de novo purine biosynthesis by pseudo-feedback inhibition of glutamine-5-phosphoribosylpyrophosphateamidotransferase—the first enzyme unique to the de novo pathway for purine ribonucleotide. TGMP also inhibits the conversion of inosinic acid (IMP) to xanthylic acid (XMP) by competition for the enzyme IMP dehydrogenase. At one-time TGMP was felt to be a significant inhibitor of ATP:GMP phosphotransferase (guanylate kinase), but recent results have shown this not to be so. Thioguanylic acid is further converted to the di- and tri-phosphates, thioguanosine diphosphate (TGDP) and thioguanosine triphosphate (TGTP) (as well as their 2'-deoxyribosyl analogues) by the same enzymes which metabolize guanine nucleotides.

As those of skill in the art will appreciate, given the inclusion of an agent designed to reduce HPRT expression, e.g. an RNAi agent to knockdown HPRT, in the vectors of the present disclosure, the resulting transduced HSCs are HPRT-deficient or substantially HPRT-deficient. As such, those HSCs that do express HPRT, i.e. HPRT wild-type cells, may be selectively depleted by administering one or more doses of 6TG. In some embodiments, 6TG may be administered for both myeloablative conditioning of HPRT-wild type recipients and for in vivo chemoselection process of donor cells. Hence, this strategy is believed to allow for the selection of gene-modified cells in vivo, i.e. for the selection of the gamma-globin containing gene-modified cells in vivo.

With reference to FIG. 2, in some embodiments, following the collection of HSCs from a donor (step 110), the HSCs are transduced with a vector according to the present disclosure (step 120). The resulting HSCs are HPRT-deficient and express the therapeutic gene, e.g. the gamma globin gene. In parallel, a patient to receive the HSCs is first treated with a myeloablative conditioning step (step 130). Following conditioning, the transduced HSCs are transplanted or administered to the patient (step 140). Therapeutic gene (e.g. gamma globin gene) containing HSCs may then be selected for (step 150) in vivo using 6TG, as discussed herein.

Myeloablative conditioning may be achieved using high-dose conditioning radiation, chemotherapy, and/or treatment with a purine analog (e.g. 6TG). In some embodiments, the HSCs are administered between about 24 and about 96 hours following treatment with the conditioning regimen. In other embodiments, the patient is treated with the HSC graft between about 24 and about 72 hours following treatment with the conditioning regimen. In yet other embodiments, the patient is treated with the HSC graft between about 24 and about 48 hours following treatment with the conditioning regimen. In some embodiments, the HSC graft comprises between about $2 \times 10^6$ cells/kg to about $15 \times 10^6$ cells/kg (body weight of patient). In some embodiments, the HSC graft comprises a minimum of $2 \times 10^6$ cells/kg, with a target of greater than $6 \times 10^6$ cells/kg. In some embodiments, at least 10% of the cells administered are transduced with a lentiviral vector as described herein. In some embodiments, at least 20% of the cells administered are transduced with a lentiviral vector as described herein. In some embodiments, at least 30% of the cells administered are transduced with a lentiviral vector as described herein. In some embodiments, at least 40% of the cells administered are transduced with a lentiviral vector as described herein. In some embodiments, at least 50% of the cells administered are transduced with a lentiviral vector as described herein.

In some embodiments, the therapeutic gene containing, HPRT-deficient HSCs are selected for in vivo using a low dose schedule of 6TG, which is believed to have minimal adverse effects on extra-hematopoietic tissues. In some embodiments, a dosage of 6TG for in vivo chemoselection ranging from between about 0.2 mg/kg/day to about 0.6 mg/kg/day is provided to a patient following introduction of the HSCs into the patient. In some embodiments, the dosage ranges from between about 0.3 mg/kg/day to about 1 mg/kg/day. In some embodiments, the dosage is up to about 2 mg/kg/day.

In some embodiments, the amount of 6TG administered per dose is based on a determination of a patient's HPRT enzyme activity. Those of ordinary skill in the art will appreciate that those presenting with higher levels of HPRT enzyme activity may be provided with doses having lower amounts of 6TG. The higher the level of HPRT the greater conversion of 6TG to toxic metabolites. Therefore, the lower dose you would need to administer to achieve the same goal.

Measurement of TPMT genotypes and/or TPMT enzyme activity before instituting 6TG conditioning may identify individuals with low or absent TPMT enzyme activity. As such, in other embodiments, the amount of 6TG administered is based on thiopurine S-methyltransferase (TPMT) levels or TPMT genotype.

In some embodiments, the dosage of 6TG for in vivo chemoselection is administered to the patient one to three times a week on a schedule with a cycle selected from the group consisting of: (i) weekly; (ii) every other week; (iii) one week of therapy followed by two, three or four weeks off; (iv) two weeks of therapy followed by one, two, three or four weeks off; (v) three weeks of therapy followed by one, two, three, four or five weeks off; (vi) four weeks of therapy followed by one, two, three, four or five weeks off; (vii) five weeks of therapy followed by one, two, three, four or five weeks off; and (viii) monthly.

In some embodiments, between about 3 and about 10 dosages of 6TG are administered to the patient over an administration period ranging from 1 week to about 4 weeks. In some embodiments, 4 or 5 dosages of 6TG are administered to the patient over a 14-day period.

Negative Selection with MTX or MPA

In addition, HPRT-deficient cells can be negatively selected by using methotrexate (MTX) to inhibit the enzyme dihydrofolate reductase (DHFR) in the purine de novo synthetic pathway. This has been developed as a safety procedure to eliminate gene-modified HSCs in case of unexpected adverse effects observed. As such, and in reference to FIG. 2, should any adverse side effects arise, a patient may be treated with MTX or mycophenolic acid (MPA) (step 160). Adverse side effects include, for example, aberrant blood counts/clonal expansion indicating insertional mutagenesis in a particular clone of cells or cytokine storm.

It is believed that MTX or MPA competitively inhibits dihydrofolate reductase (DHFR), an enzyme that participates in tetrahydrofolate (THF) synthesis. DHFR catalyzes the conversion of dihydrofolate to active tetrahydrofolate. Folic acid is needed for the de novo synthesis of the nucleoside thymidine, required for DNA synthesis. Also, folate is essential for purine and pyrimidine base biosynthesis, so synthesis will be inhibited. MTX or MPA, therefore inhibits the synthesis of DNA, RNA, thymidylates, and proteins. MTX or MPA blocks the de novo pathway by inhibiting DHFR. In HPRT−/− cell, there is no salvage or de novo pathway functional, leading to no purine synthesis, and therefore the cells die. However, the HPRT wild type cells have a functional salvage pathway, their purine synthesis takes place and the cells survive.

Given the sensitivity of the modified HSCs produced according to the present disclosure, MTX or MPA may be used to selectively eliminate HPRT-deficient cells. In some embodiments, the MTX or MPA is administered as a single dose. In some embodiments, multiple doses of the MTX or MPA are administered.

In some embodiments, an amount of MTX administered ranges from about 2 mg/m$^2$/infusion to about 100 mg/m$^2$/infusion. In some embodiments, an amount of MTX administered ranges from about 2 mg/m$^2$/infusion to about 90 mg/m$^2$/infusion. In some embodiments, an amount of MTX administered ranges from about 2 mg/m$^2$/infusion to about 80 mg/m$^2$/infusion. In some embodiments, an amount of MTX administered ranges from about 2 mg/m$^2$/infusion to about 70 mg/m$^2$/infusion. In some embodiments, an amount of MTX administered ranges from about 2 mg/m$^2$/infusion to about 60 mg/m$^2$/infusion. In some embodiments, an amount of MTX administered ranges from about 2 mg/m$^2$/infusion to about 50 mg/m$^2$/infusion. In some embodiments, an amount of MTX administered ranges from about 2 mg/m$^2$/infusion to about 40 mg/m$^2$/infusion. In some embodiments, an amount of MTX administered ranges from about 2 mg/m$^2$/infusion to about 30 mg/m$^2$/infusion. In some embodiments, an amount of MTX administered ranges from about 20 mg/m$^2$/infusion to about 20 mg/m$^2$/infusion. In some embodiments, an amount of MTX administered ranges from about 2 mg/m$^2$/infusion to about 10 mg/m$^2$/infusion. In some embodiments, an amount of MTX administered ranges from about 2 mg/m$^2$/infusion to about 8 mg/m$^2$/infusion. In other embodiments, an amount of MTX administered ranges from about 2.5 mg/m$^2$/infusion to about 7.5 mg/m$^2$/infusion. In yet other embodiments, an amount of MTX administered is about 5 mg/m$^2$/infusion. In yet further embodiments, an amount of MTX administered is about 7.5 mg/m$^2$/infusion.

In some embodiments, between 2 and 6 infusions are made, and the infusions may each comprise the same dosage or different dosages (e.g. escalating dosages, decreasing dosages, etc.). In some embodiments, the administrations may be made on a weekly basis, or a bi-monthly basis.

In some embodiments, MPA is dosed in an amount of between about 500 mg to about 1500 mg per day. In some embodiments, the dose of MPA is administered in a single bolus. In some embodiments, the dose of MPA is divided into a plurality of individual doses totaling between about 500 mg to about 1500 mg per day.

In some embodiments, an analog or derivative of MTX or MPA may be substituted for MTX or MPA. Derivatives of MTX are described in U.S. Pat. No. 5,958,928 and in PCT Publication No. WO/2007/098089, the disclosures of which are hereby incorporated by reference herein in their entireties.

Combination Therapy

Hydroxyurea, a myelosuppressive agent, is believed to raise the level of HbF and hemoglobin levels in patients. Current evidence suggests that several potential mechanisms of action by hydroxyurea may be relevant for patients with SCD, which together lead not only to HbF induction but also to additional benefits. It is believed that hydroxyurea is a potent ribonucleotide reductase (RR) inhibitor that reduces intracellular deoxynucleotide triphosphate pools and acts as an S-phase-specific agent with inhibition of DNA synthesis and eventual cellular cytotoxicity. Hydroxyurea directly inhibits the RR M2 subunit, but spontaneous regeneration of the active enzyme occurs when hydroxyurea is removed. For this reason, the in vivo effects of hydroxyurea on RR are predictably transient, resulting from the rapid absorption, metabolism, and excretion of hydroxyurea in mammalian systems. Presumably with once-daily dosing in SCD, hydroxyurea causes intermittent cytotoxic suppression of erythroid progenitors and cell stress signaling, which then affects erythropoiesis kinetics and physiology and leads to recruitment of erythroid progenitors with increased HbF levels. A remarkable attribute of hydroxyurea is the observation that treatment has multiple potential benefits for patients with SCD. Beyond HbF induction, the cytotoxic effects of hydroxyurea also reduce marrow production of neutrophils, reticulocytes and also reduce no of platelets which is an important mediator of inflammation. Additional benefits of hydroxyurea treatment include salutary effects on the circulating erythrocytes.

In another aspect of the present disclosure is a combination therapy whereby hydroxyurea is administered prior to, during, or following the administration or transplantation of transduced HSCs (described above) into a patient in need of treatment thereof. In some embodiments, hydroxyurea may be administered following the administration or transplantation of transduced HSCs on an as-needed basis, such as during a pain crisis, at the onset of acute chest syndrome, at the onset of severe or symptomatic anemia (Hb<7 g/dL), etc. In some embodiments, hydroxyurea is administered in a dose ranging from about 10 mg/kg/day to about 15 mg/kg/day, and given as a single daily dose. In some embodiments, a dose of hydroxyurea may be escalated or reduced over time.

EXAMPLES

Example 1—Production of the TL20c-rGbG$^M$-7SK/sh734 Vector

The pTL20c vector (SEQ ID NO: 47) (see FIG. 40) contains the 400 bp extended core element of the chicken hypersensitivity site 4 insulator (cHS4) (SEQ ID NO: 49) inserted in the 3'LTR in reverse orientation to the viral transcript. The cHS4 insulator contains both enhancer-blocking activity mediated by the core CTCF binding site and barrier activity mediated by VEZF1 binding sites. Additional details pertaining to the pTL20c vector, including its backbone (SEQ ID NO: 48), methods of producing producer cells lines therefrom, or harvesting viral titer are described in United States Patent Publication No. 2018/0112233, the disclosure of which is hereby incorporated by reference herein in its entirety.

The 400 bp cHS4 insulator was placed in the reverse orientation within the LTR, and combined with a 46 bp deletion that removed the residual nef sequence, which was believed to reduce the frequency of polyadenylation read-through from a lentiviral LTR 3. In addition, the rabbit β-globin polyadenylation signal was inserted downstream of the 3'LTR to provide a stronger polyadenylation signal for the vector transcript and reduce transcriptional read-through.

sGbG$^M$ Lentivirus Vector—The Gamma Globin sSIN lentivirus vector—sGbG$^M$(SEQ ID NO: 50) with relevant transgene and regulatory sequences are illustrated in FIG. 41. Exons 1, 2, and 3 are set forth in SEQ ID NOS; 41, 52, and 53, respectively. The HIV lentivirus vector is a self-inactivating (SIN) design. The U3 region of the 5'LTR (HIV enhancer/promoter) was replaced by the CMV enhancer/promoter. The U3 region of the 3'LTR contained a 400 bp deletion of the promoter enhancer, to allow a SIN design, so that it contained no viral transcriptional elements upon integration into host cells. Downstream of the 3'LTR, a bovine growth hormone poly A signal as inserted to enhance vector polyadenylation. Besides the packaging region, the vector carried approximately 350 bp of a gag gene, 540 bp of env, including the splice acceptor and rev response element, followed by 150 bp of the central polypurine tract of the pol gene downstream of the 5' LTR. The transgene expression cassette consisted of 3.2 Kb of hypersensitive sites 2, 3 and 4, derived by PCR from the genome and a modified β-globin/γ-globin hybrid gene. The hybrid globin gene was further modified using PCR and site directed mutagenesis to change all codons to γ-globin codons.

The pTL20c-sGbGM vector (FIG. 42) was constructed by inserting the sGbGM modified β-globin/γ-globin hybrid gene expression cassette (SEQ ID NO: 50) (FIG. 41) into the lentiviral pTL20c (FIG. 40) vector between MluI and NotI sites. The sequences of the transgene expression cassette consisted of 3.2 Kb of hypersensitive sites 2, 3, and 4 and a modified β-globin/γ-globin hybrid gene. The β-globin promoter and modified β-globin/γ-globin hybrid gene was inserted in reverse orientation to the viral RNA transcript in the SIN lentiviral backbone.

Figure 42A:
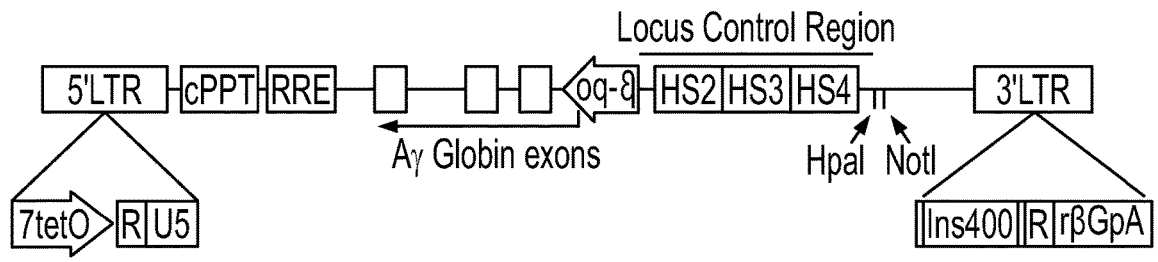
FIG. 42A provides a schematic representation of the pTL20c-sGbGM vector.
Figure 42B:
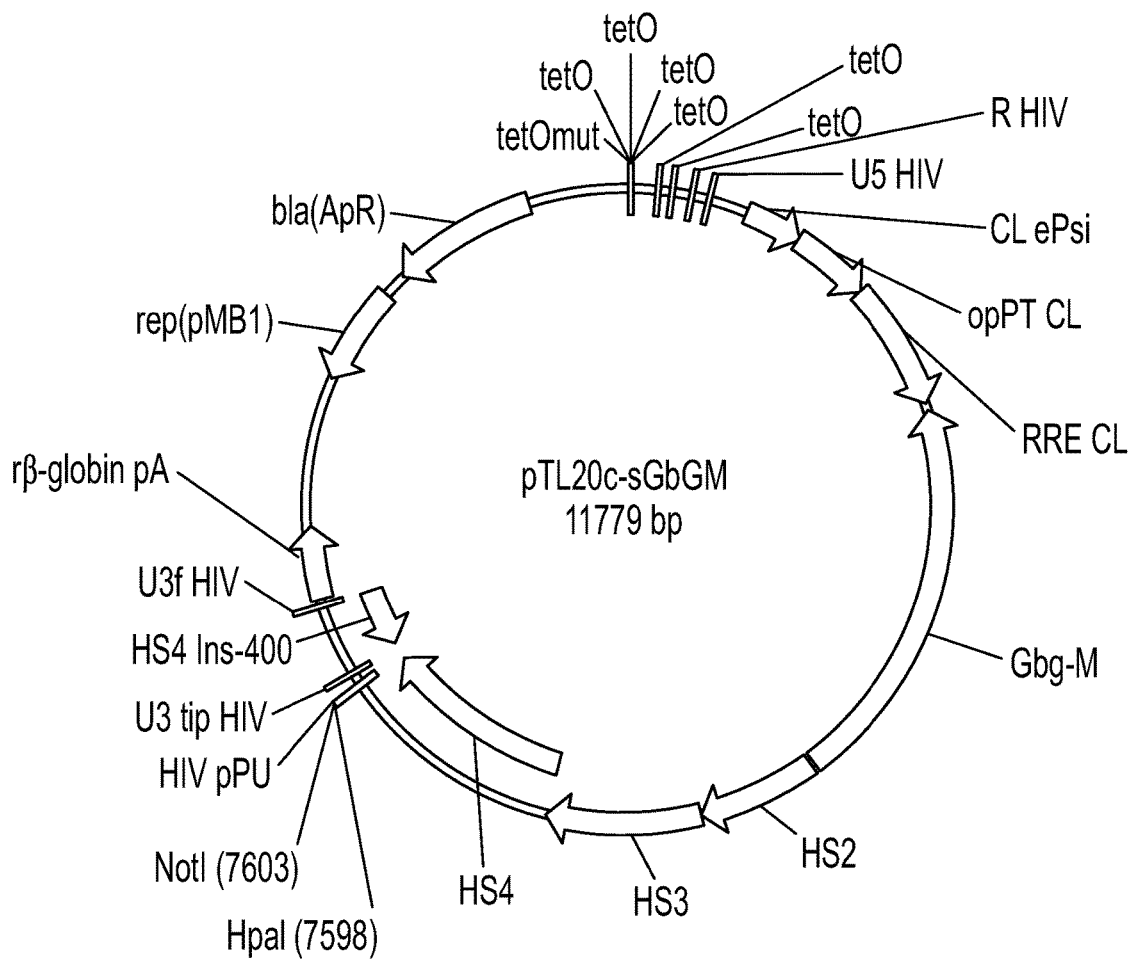
FIG. 42B illustrates a vector map for the pTL20c-sGbGM vector.
Figure 43A:
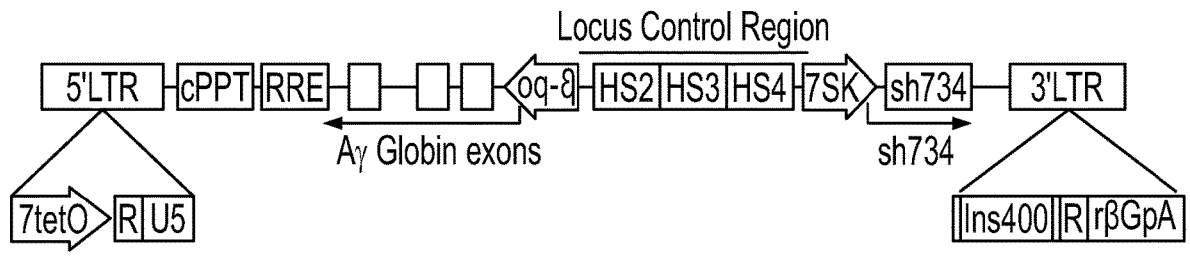
FIG. 43A provides a schematic representation of the TL20c-rGbGM-7SK/sh734 vector.
Figure 43B:
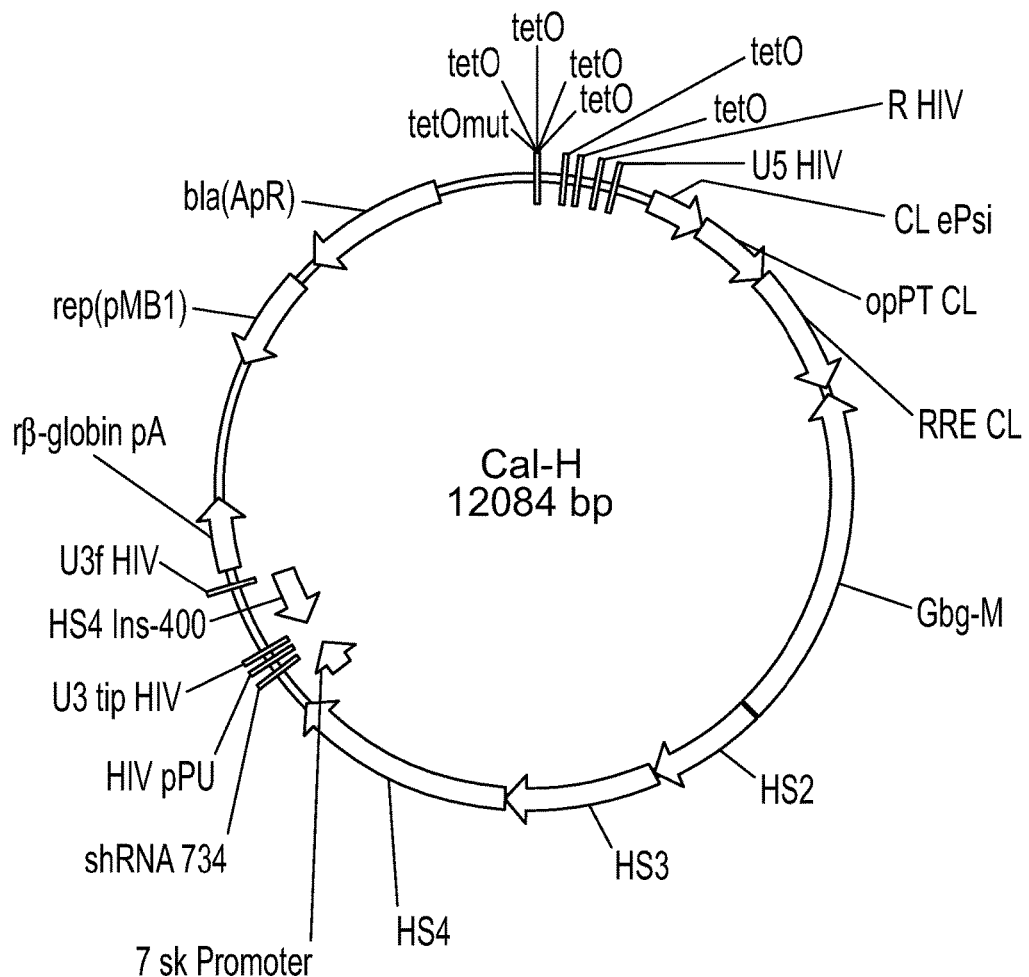
FIG. 43B illustrates a vector map for the TL20c-rGbGM-7SK/sh734 vector.

The TL20c-rGbGM-7SK/sh734 (FIG. 43) vector was constructed by inserting the short hairpin RNA (shRNA734) expression cassette (SEQ ID NO: 54) into the lentiviral pTL20c-sGbG$^M$ vector between HpaI and NotI sites (see FIG. 42). The sequence of the short hairpin RNA (shRNA734) expression cassette included the human 7sk RNA Pol III promoter (SEQ ID NO: 32) and a short hairpin RNA (shRNA734) gene (SEQ ID NO: 30).

Example 2—Pre-Clinical Testing of the TL20c-rGbGM-7SK/Sh734 Vector

Overview

The pTL20c-rGbG$^M$-7SK/sh734 dual therapeutic lentiviral vector construct was identified using a functional screen in K562 cells that compared the effect of position and orientation of the transgenes relative to each other on transgene expression and in vitro 6-TG selection. pTL20c-rGbG$^M$-7SK/sh734 transduced K562 cells selected in 6TG culture demonstrated long term stability and expression of the γ$^A$-globin transgene normalized to VCN equivalent to cells transduced with parental GbG$^M$ lentiviral vector or CAL-H that were not treated with 6TG. These findings indicated that functional expression of the sh734 and the corrective sGbG$^M$ gene driven by different promoters was mutually exclusive and that regulation of sGbG$^M$ was lineage dependent. Using an in vitro model of human erythroid differentiation, we showed that CD34+ HSCs transduced with the CAL-H lentiviral vector constitutively expressed sh734 in extended cultures at a sufficient level to knockdown the expression HPRT and confer selection of gene modified cells as determined by an increase in average vector copy number (VCN) and the frequency of transduced cells at day 14. When 6TG selected cultures were then transferred to erythroid differentiation culture conditions, the $^A$γ-Globin transgene was expressed in a lineage specific manner establishing proof of concept of sequential and coordinate regulation of transgene expression in transduced human CD34+ HSPCs. Results described herein support a clinical trial to evaluate an in vivo amplification protocol using 6TG to increase the long-term engraftment potential of CAL-H transduced CD34+ HSCs needed to achieve curative levels of total HbF and percentage of F cells for Sickle Cell Disease.

Experience to date with autologous gene therapy for thalassemia and sickle cell disease have suggested that the level of sub-myeloablative conditioning with bulsulfan doses of 12 mg/kg may be insufficient to achieve adequate donor chimerism necessary to cure disease, although estimates of mixed chimerism with gene engraftment of 30% gene modified cells might be curative. One approach to circumvent the lower efficiencies of engraftment is to apply in vivo amplification strategies. Since transduction efficiency of autologous CD34+ HSPCs can vary from 10% to 60% and an even smaller fraction of these cells are long term repopulating HSC/MPP stem cells in most cases the transduced stem cell dose is inadequate optimal. The lower efficiency is reflected in the vector copy number (VCN) that is seen in hematopoietic cell lineages after infusion. In most cases, the average VCN is significantly less than 1 per cell.

The goal of gene therapy is to offer the subject in need of treatment thereof a one-time ex-vivo correction of sickle cell HSCs with their autologous transplant and circumvent the immunological consequences such as graft rejection and graft versus host disease associated with allogeneic transplant.

Materials and Methods

HbF Infectious Titer in MEL Cells.

MEL cells were transduced by spinoculation with serial dilutions of CAL-H and sh7/GFP vector at MOI of 1 to 10 and plated at limiting dilution.

24-48 h determine % GFP positive cells

Expand and induce differentiation with 10 mM hemin and 3 mM HMBA for 3-4d.

Measure erythroblast differentiation by flow cytometry and viability/apoptosis by Annexin/7AAD staining Extract RNA. Measure sh7 and -globin expression and VCN by RT-PCR Plot fold increase -globin mRNA and -globin mRNA/VCN in transduced versus mock-transduced cells 6TG Selection and Long-term stability of CAL-H transduced K562 cells Assays to Measure Transduction Efficiency, VCN, Sh7 and γ-Globin Expression, Viability and Differentiation 1) K562 cells ($1\times10^5$ cells each condition) are transduced with 6 different vectors at 2 dilution factors at day 7.

2) The cells are reseeded into 6-well plate with additional 4 mL of fresh RPMI medium on Day 3.

3) Two cell pellets ($1\times10^6$ cells each) for DNA & RNA analysis for 13 samples including control K562 will be frozen down at day 0 (MY). Copy numbers of GbG and sh734 are analyzed.

4) $2\times10^5$ cells of control K562, 6 samples transduced at dilution factor 32 and 6 samples transduced at dilution factor 1 are reseeded in 6-well plate with 4 mL of RPMI without and with 300 nM of 6-thioguanine, respectively. $2.5\times10^6$ cells of 6 samples transduced at dilution factor 1 are made through mixing transduced and untransduced cells at ratio of 1:3. Two cell pellets ($1\times10^6$ cells each) for DNA & RNA analysis for these 6 samples will be frozen down. The medium is refreshed every 3-4 days. K562 transduced with TL20cw-7SK/sh734-GFP (dilution factor at 256 and 8) will be included as positive controls.

5) Two cell pellets ($1\times10^6$ cells each) for DNA & RNA analysis for 13 samples including control K562 will be frozen down at day 7/14/21 or even 28(MY). Copy numbers of GbG and sh734 are analyzed. The samples at day 21/28 are optional if the copy numbers of all samples are higher than 95% of expected value for day 14.

6) At day 14/21, seed $1\times10^5$ of cells of 12 samples under 6-TG selection into 12-well plate with 1 mL of RPMI without 6-TG. Run Annexin V and 7-AAD assay runs 3 days later. Use Camptothecin-treated cells and cells transduced with TL20cw-7SK/sh734-GFP (dilution factor 1) as positive control.

Objective

Given that high levels of erythroid-specific fetal-hemoglobin (gamma-globin) expression can be curative in SCD and beta-thalassemia, we assessed gene transfer efficiency (VCN), globin gene expression, erythroid differentiation, and total RBC Hb production. The K562 human erythroid leukemia cell line was used as a model of erythroid in vitro differentiation to provide evidence that (1) transferred γ-globin genes were correctly expressed and regulated as a consequence of erythroid differentiation (no expression in the undifferentiated state versus. abundant expression following differentiation); (2) that the sh734 against HPRT did not significantly alter the expression of γ-globin; and (3) that expression of the sh734 against HPRT did not significantly influenced by erythroid differentiation (high level expression in the undifferentiated state vs. similar or lower expression following differentiation).

Additional objectives for sh734 functionality/6TG selection:

Determine if comparable function of sh734+γ-globin;

Determine if comparable function of sh734±erythroid differentiation;

Determine selection and long-term stability of sh734 transduced cells; and

Determine whether sh734 does not affect cell viability or vector stability.

In Vitro Characterization

Figures 44A, 44B:
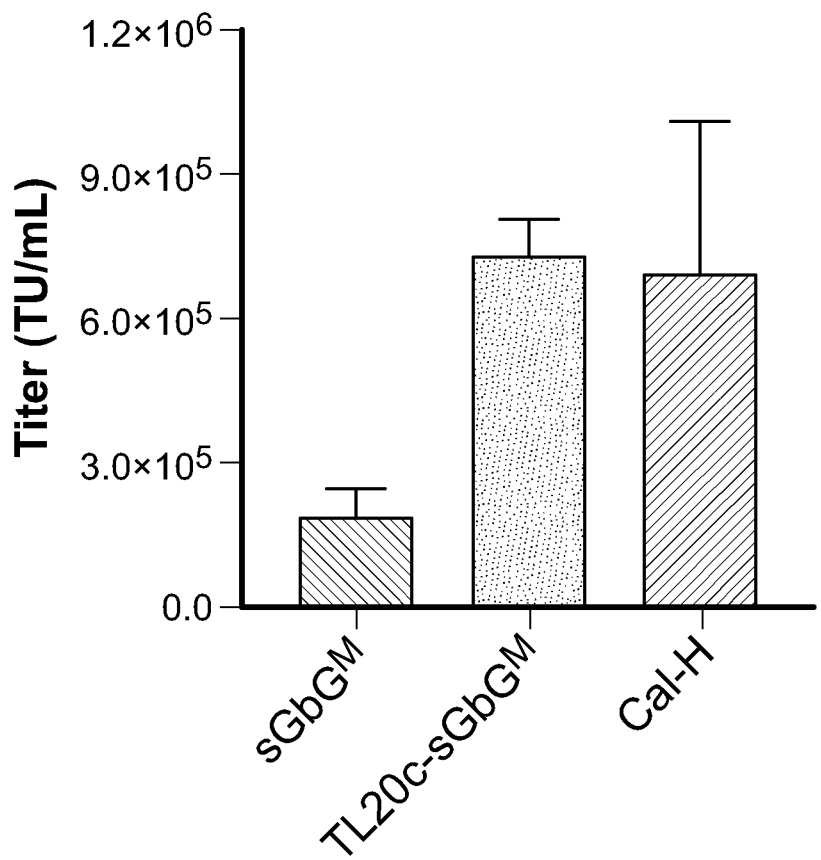
FIG. 44A illustrates that the TL20 backbone improved transduction efficiency of VSVg-pseudotyped SIN-lentivirus vectors.
FIG. 44B sets forth average titers obtained from the sGbG$^M$, pTL20c-sGbGM, and the TL20c-rGbGM-7SK/sh734 vectors.
Figure 45:
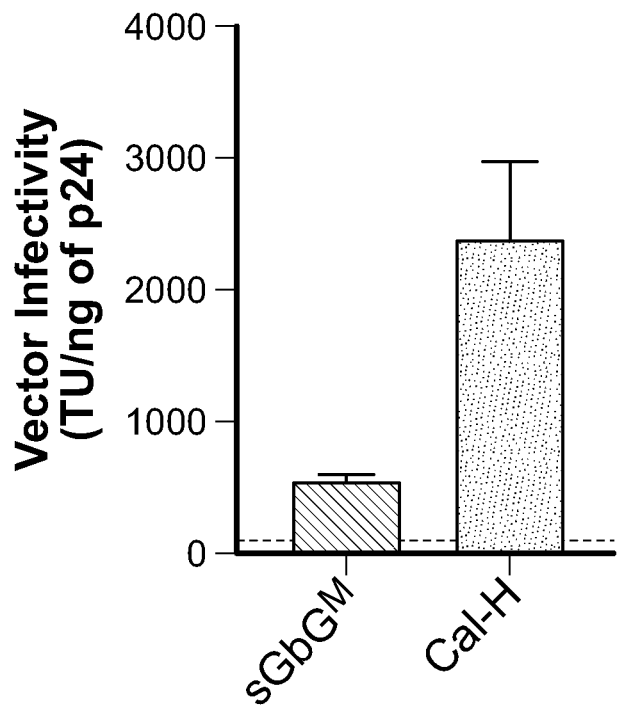
FIG. 45 sets forth the vector infectivity of the sGbG$^M$ and the sGbG$^M$-7SK/sh734 vectors.

It has been determined that the TL20c LV backbone significantly enhances the titer of the parental sGbG$^M$ lentiviral vector as illustrated in FIGS. 44A, 44B and 45. Comparable titers were obtained with the mono-vector expressing sGbG$^M$ and the dual therapeutic CAL-H vector suggesting that the expression of transgenes did not affect the titer measured as a percentage of HbF positive cells or hemoglobinization per cell as measured by the normalized MFI (data not shown). Importantly, inclusion of the 400 bp cHS4 insulator sequence in the TL20c backbone did not have an adverse effect on virus titer.

With reference to FIG. 44A, vector supernatant was generated by CaPO$_4$ mediated transient transfection of GPRG cells (see United States Patent Publication No. 2018/0112233) and stored at −80° C. All vectors were titered after 1 freeze thaw cycle. Titer (TU/mL)=% of HbF-positive cells/i 100)×dilution factor×number of cells/Volume (mL). Overall, the TL20 lentivirus vector backbone significantly improved the transduction efficiency of VSVg pseudotyped SIN-lentivirus vectors.

With regard to FIG. 45, vector stocks were produced by CaPO$_4$ transfection of GPRG cells and concentrated through a TFF system 700-fold. The vector titer was determined on MEL cells. The vector particle concentration was determined by an enzyme-linked immunosorbent assay (ELISA) specific for the HIV-1 p24 capsid protein. The values obtained were used to calculate average vector infectivity (introduction units [TU] per ng p24). Comparatively, the TL20c-rGbGM-7SK/sh734 vector provided superior vector infectivity as compared with sGbG$^M$.

Equivalent Expression and Regulation of γ-Globin sGbG$^M$ Base Construct Compared to the Sh734-Containing Construct Since levels of sh7 expression correlated well with 6TG selection in the human K562 erythroid leukemia cell line, these cell models were used to provide evidence that (1) transferred γ-globin genes were correctly expressed and regulated as a consequence of erythroid differentiation (i.e. no expression in the undifferentiated state versus abundant expression following differentiation); (2) that sh734 did not significantly alter the expression of γ-globin; and (3) that expression of sh734 did not significantly influenced by erythroid differentiation (high level expression in the undifferentiated state vs. similar or lower expression following differentiation). Since the K562 cell constitutively expressed human fetal globin and did not express adult β-globin, this was believed to be a good system to validate the specificity of specific γ-globin transgene primers and probes.

Figure 46:
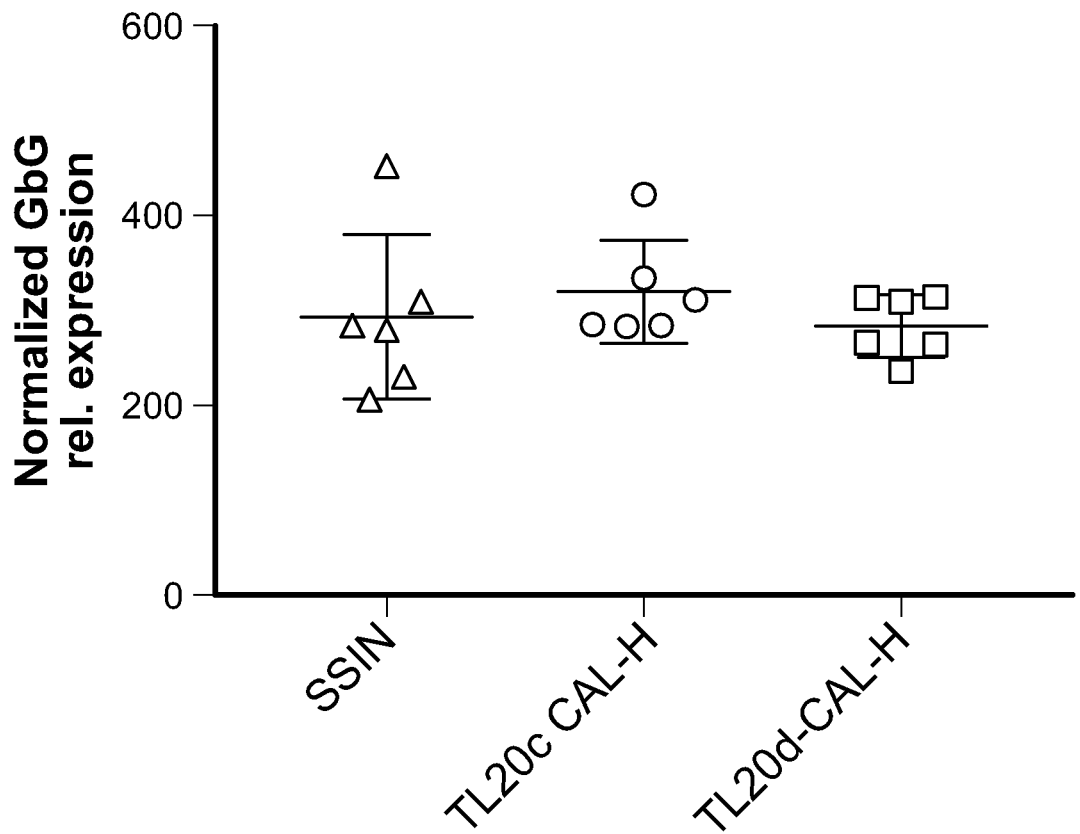
FIG. 46 illustrates the equivalent expression of sGbG$^M$ and between the monovector (pTL20c-sGbGM) and dual vector (pTL20c-sGbG$^M$-7SK/sh734).

As illustrated in FIG. 46, there was an equivalent expression of sGbG$^M$ between sGbG$^M$ (SSIN) monovector and the presently disclosed dual therapeutic TL20c-rGbGM-7SK/sh734 vector construct. MEL cells were transduced with five two-fold dilutions (1:8-1:128) of LV VCM for 3d before treating the cells with 10 μM hemin and 3 mM HMBA in the standard induction protocol. Untransduced MEL cells and parallel, transduced uninduced cultures served as a negative control. Infectious virus titer HbF was determined at day 7 by measuring the % Hu-HbF positive cells by flow cytometry. RNA was extracted from cell pellets and g-globin expression was determined by RT-PCR normalized to expression of the housekeeping gene b2M. Relative expression of g-globin normalized to Infectious Virus Titer HbF (15-25%) is plotted for each vector. Values plotted represent all biological replicates from 3 separate experiments. There was no significant difference in expression of sGbGM between the different LV transduced cells. One way ANOVA, p=0.137 and Tukeys Multiple Comparison test p>0.05.

Figure 47:
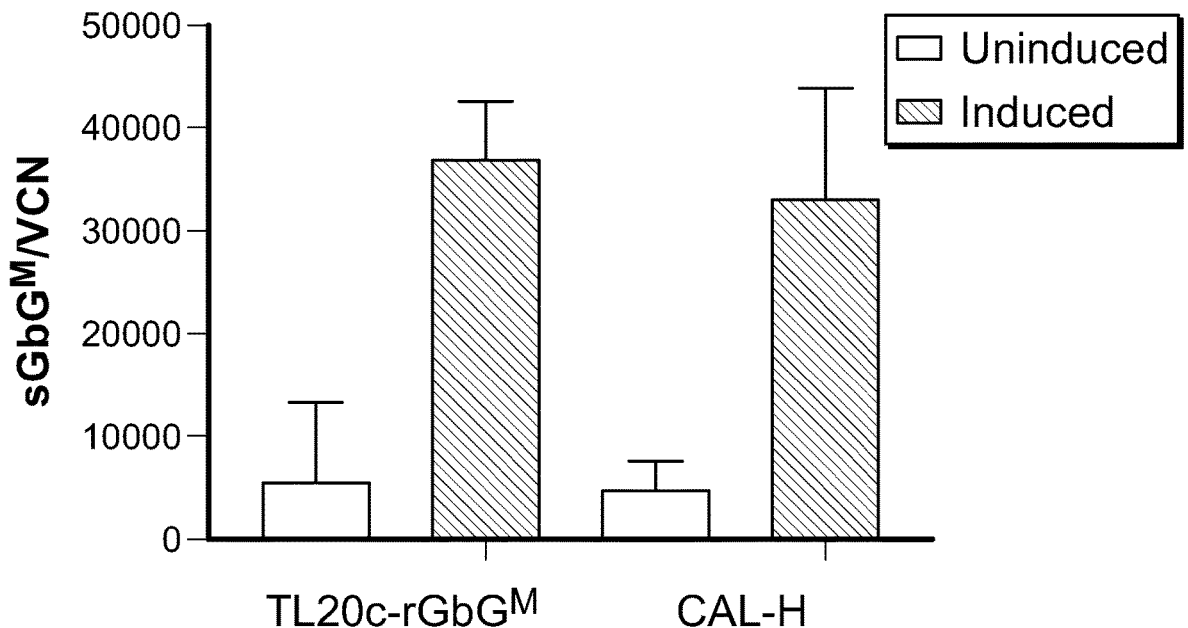
FIG. 47 illustrates the equivalent expression of the $^A$gamma-globin transgene in K562 cells transduced with the TL-20c-rGbG$^M$ vector or the TL20c-rGbGM-7SK/sh734 vector.

As shown in FIG. 47, there was a 12-fold increase in the expression of $^A$γ-globin mRNA levels in TL20c-rGbG$^M$ transduced K562 cells compared to a 7.9-fold increase in TL20c-rGbGM-7SK/sh734 transduced cells. T test at p<0.05 was not significant. In addition, all specificity controls showed no cross-reactivity of our transgene-specific γ-globin primers with endogenous fetal Hb.

More specifically, K562 cells were transduced with TL20c GbGM or CAL-H for and passaged for 39 days. Cells were harvested and cultured in medium containing 10 μM hemin and 3 mM HMBA for 3-4 days. in a standard erythroid differentiation induction protocol. Relative expression of sGbGM was measured by RT-PCR and normalized to VCN to compare treatments. There was a 12-fold increase in the expression of Ag-globin mRNA levels in TL20crGbGM transduced K562 cells compared to a 7.9-fold increase in CAL-H transduced cells (T test, p<0.05 was not significant). No GbGM expression was detected in mock transduced cells uninduced or induced and no GbGM expression was detected in K562 cells transduced with the mono-vector rsh7-GFP uninduced or induced.

Figure 48:
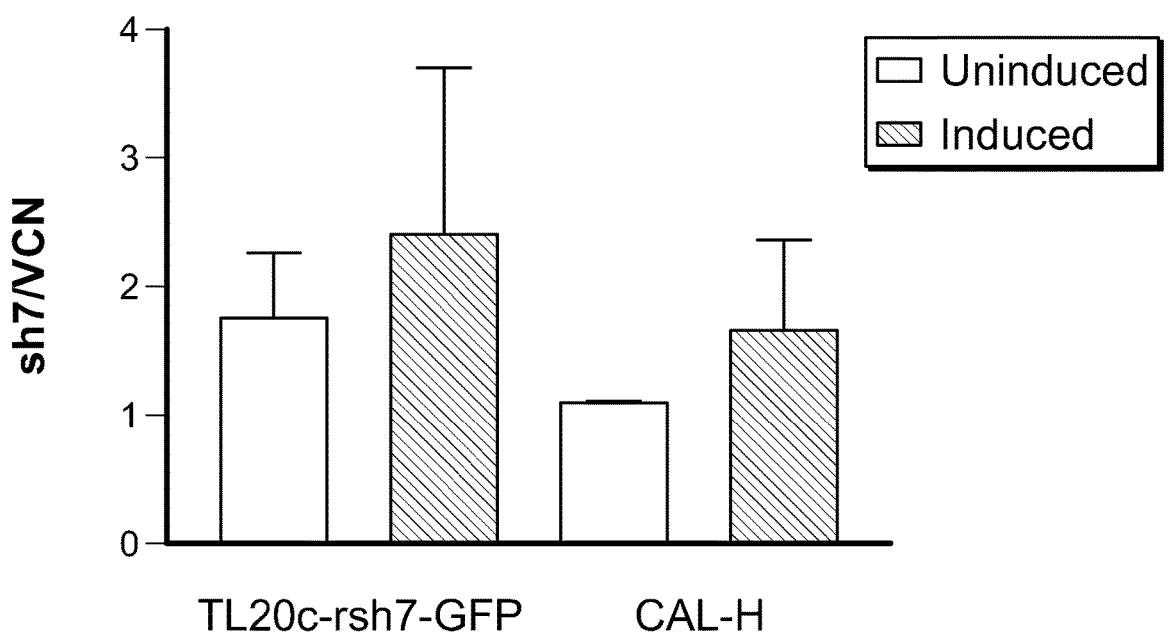
FIG. 48 illustrates that the expression of the sh7 transgene is unchanged in K562 cells during erythroid differentiation.

There is Little to No Transactivation of the Sh734 Promoter During Erythroid Differentiation Applicant has shown that the expression of the sh734 transgene remains unchanged in K562 Cells during erythroid differentiation (see FIG. 48). More specifically, K562 cells were transduced with TL20c GbGM or CAL-H for and passaged for 39d. Cells were harvested and cultured in medium containing 10 μM hemin and 3 mM HMBA for 3 to 4 days. in a standard erythroid differentiation induction protocol. Expression of sh734 was determined by RT-PCR relative to RNU38B and normalized to VCN to compare treatments. T-test was used to determine if differences in sh7 expression between groups reached significance. No significant differences were found at p<0.05. Control sh7GFP Induced and uninduced cultures p=0.69, CAL-H, p=0.226 and uninduced CAL-H vs rsh7-GFP, p=0.227. No sh734 expression was detected in the Mock and negative control TL20c-rGbGM groups.

Functional Screen of TL20 SIN LV Vectors in K562 Cells

Figure 9:
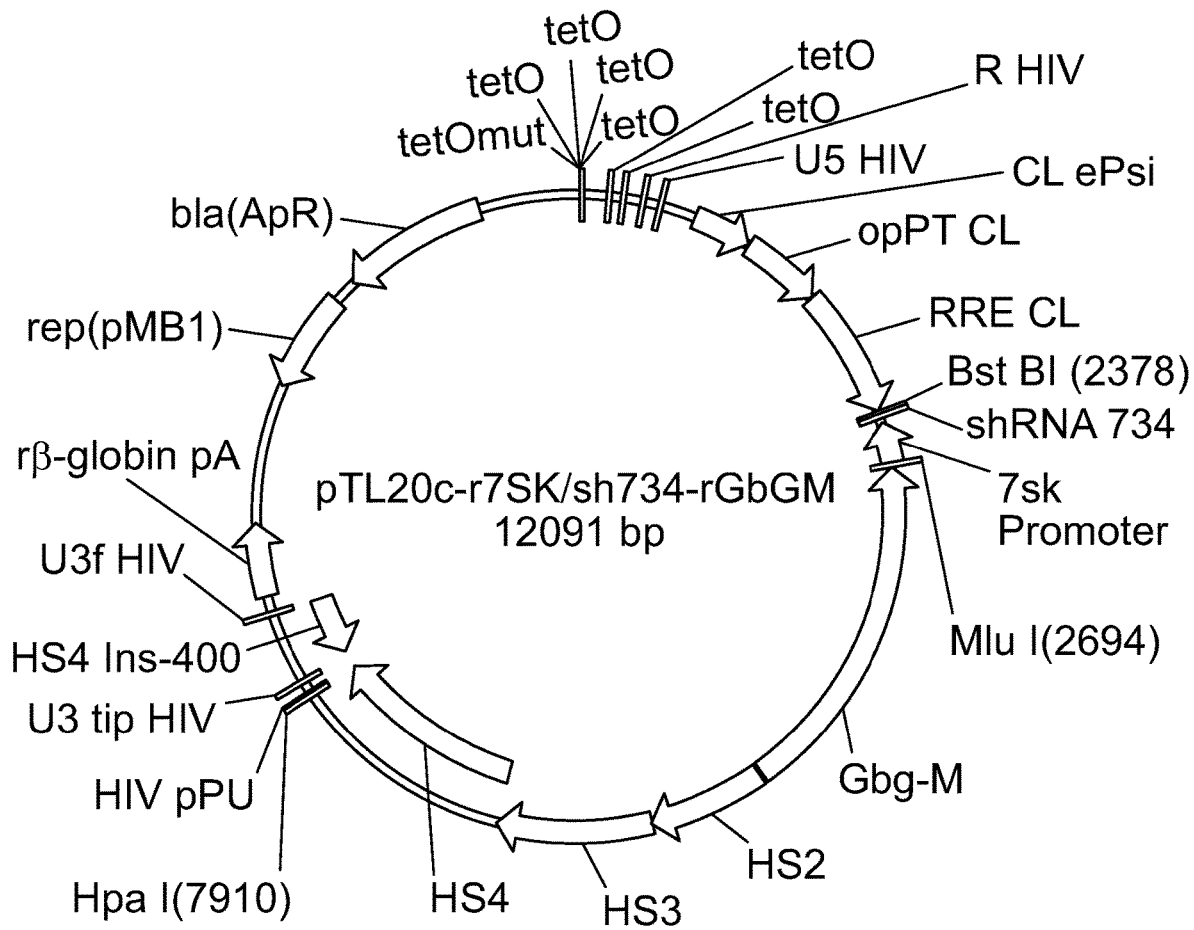
FIG. 9 provides a vector map of TL20c-r7SK/sh734-rGbG$^M$.

The TL20c-rGbGM-7SK/sh734 dual therapeutic lentiviral vector construct was identified using a functional screen in K562 cells that compared the effect of position and orientation of transgene relative to one other on transgene expression and in vitro 6-TG selection. Other dual transgene lentiviral vectors (see, e.g., SEQ ID NOS: 5 through 22) were constructed using the TL20c lentiviral vector backbone with the sh734 positioned either upstream or downstream to the GbGM cassette and in either a forward or revere orientation. TL20 self-inactivating lentiviral vectors with the cHS4 Ins-400 insulator tested included: TL20c-rGbGM-7SK/sh734 (FIG. 11), TL20c-rGbGM-r7SK/sh734 (FIG. 13), TL20c-7SK/sh734-rGbGM (FIG. 7), and TL20c-r7SK/sh734-rGbGM (FIG. 9). Other vectors tested included TL20d-rGbGM-7SK/sh734 without the cHS4 Ins-400 insulator (FIG. 21), a control sh7 reporter construct, TL20cw-7SK/sh734-UbC/GFP, and TL20c-rGbGM.

K562 cells were transduced with sh734 for 21 days before initiating 6TG treatment for 14 days (shaded areas). With reference to FIGS. 49A through 49G, vector copy number (VCN) was determined every two weeks from genomic DNA by multiplex RU5 qPCR and absolute quantitation from a standard curve using lentiviral vector (HIV-1-based LTR R-U5) target and human Apolipoprotein B (ApoB) reference sequences. Each data point represents the Mean±SD of three separate transductions (triplicate biological replicates).

TL20c-rGbGM-7SK/sh734 dual therapeutic lentiviral vector transduced K562 cells selected in 6TG culture demonstrated long term stability and expression of the gamma-globin transgene normalized to VCN equivalent to cells transduced with the parental GbGm LV vector or CAL-H transduced cells that were not treated with 6TG. These findings indicate that functional expression of the sh734 and the corrective sGbGM gene driven by separate Pol III and Pol II promoters, respectively, is mutually exclusive and that regulation of sGbGM is lineage dependent.

In this experiment, TL20c-rGbGM-r7SK/sh734, TL20c-7SK/sh734-rGbGM, and TL20c-r7SK/sh734-rGbGM lentiviral vector transduced K562 cells were only followed for two weeks post-6TG treatment. Interestingly, all dual construct vectors tested regardless of position or orientation of transgenes showed similar selection kinetics during 6TG treatment suggesting that transduced cells constitutively expressed a threshold level of sh7 that sustained HPRT knockdown allowing selection. We also observed a dose-response effect with the dual transgene self-inactivating lentiviral vectors where the VCN of 6TG treated cultures strongly correlates with sh7 expression and the dilution of virus used to transduce K562 cells (data not shown). All vectors tested showed similar expression levels of gamma-globin (relative expression GbGM/b2M) upon induction and viability (<0.5% Annexin V and 7-AAD double positive cells) (data not shown). The TL20c-rGbGM-7SK/sh734 LV vector proved most efficient in the expression of high levels of sh7, robust 6TG selection kinetics, and stability. These finding were consistent with results found in two previous experiments.

Figure 50:
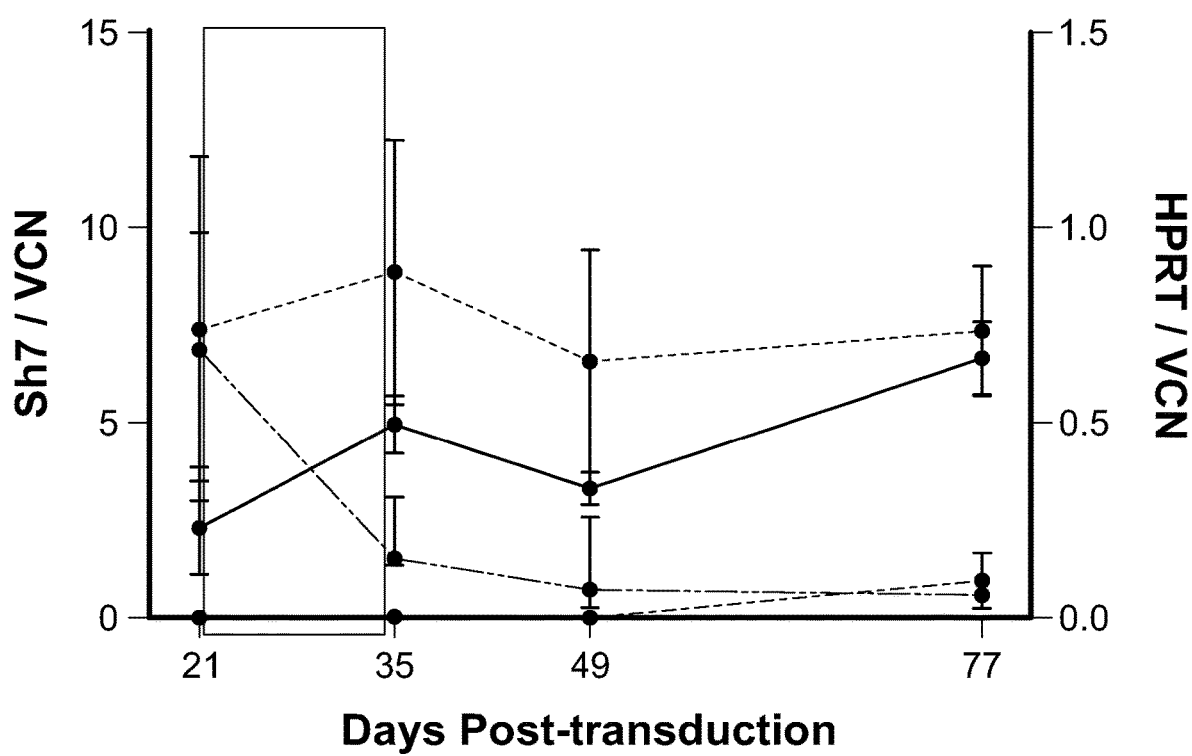
FIG. 50 illustrates that TL20c-rGbGM-7SK/sh734 transduced K562 cells expressing sh7 efficiently downregulate HPRT and confer long-term stability of 6-TG resistant cells.

With reference to FIG. 50, K562 cells were transduced with TL20c-rGbGM-7SK/sh734 or TL20c GbG$^M$21 days before initiating 6TG treatment. RNA was isolated and qRT-PCRT was performed to determine the number of copies of sh734 relative to RNU38B and normalized to VCN (relative expression/VCN). Relative expression levels of sh734 and HPRT were determined every two weeks post-transduction. The graph illustrated sh734 plotted on the left Y-axis and the percent of HPRT knockdown related to mock transduced cells (HPRT/mock×100) and normalized to VCN plotted on the right Y axis.

Figure 49A:
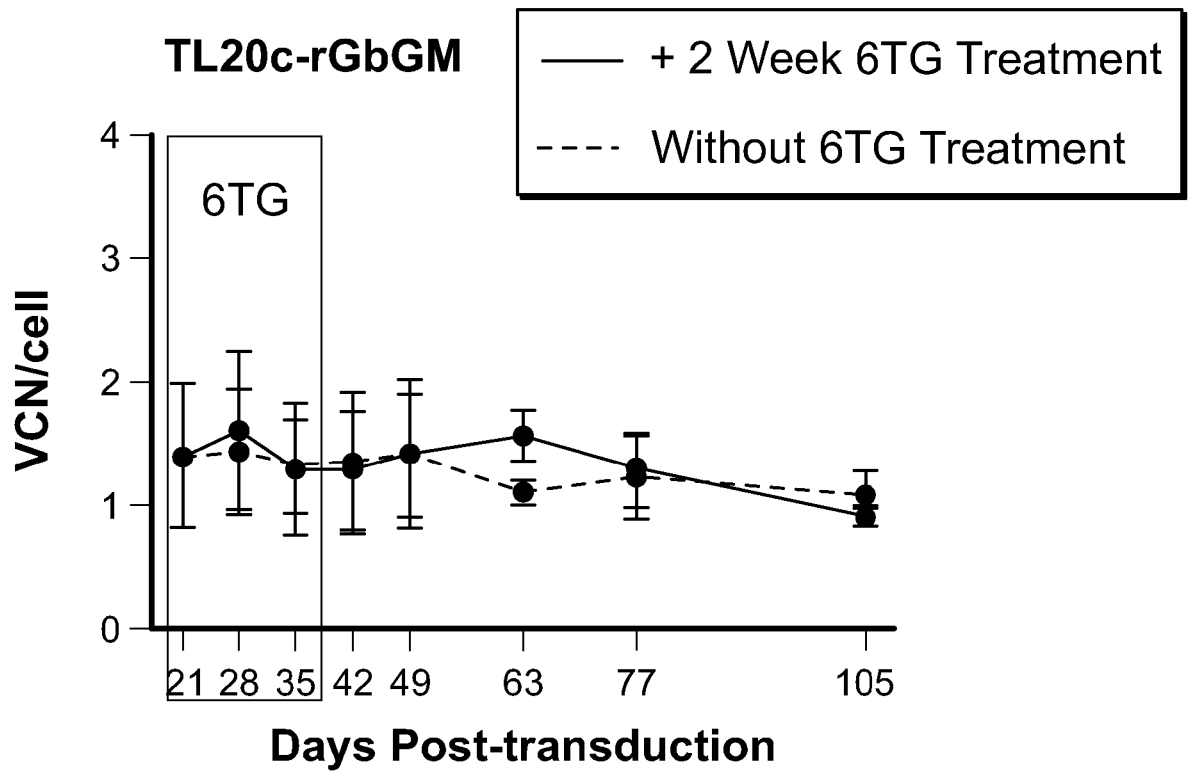
FIG. 49A sets forth a graph indicating that K562 cells transduced with the negative control GbGM mono-vector (TL20c-rGbGM) showed no increase in vector copy number during 6TG treatment.
Figure 49B:
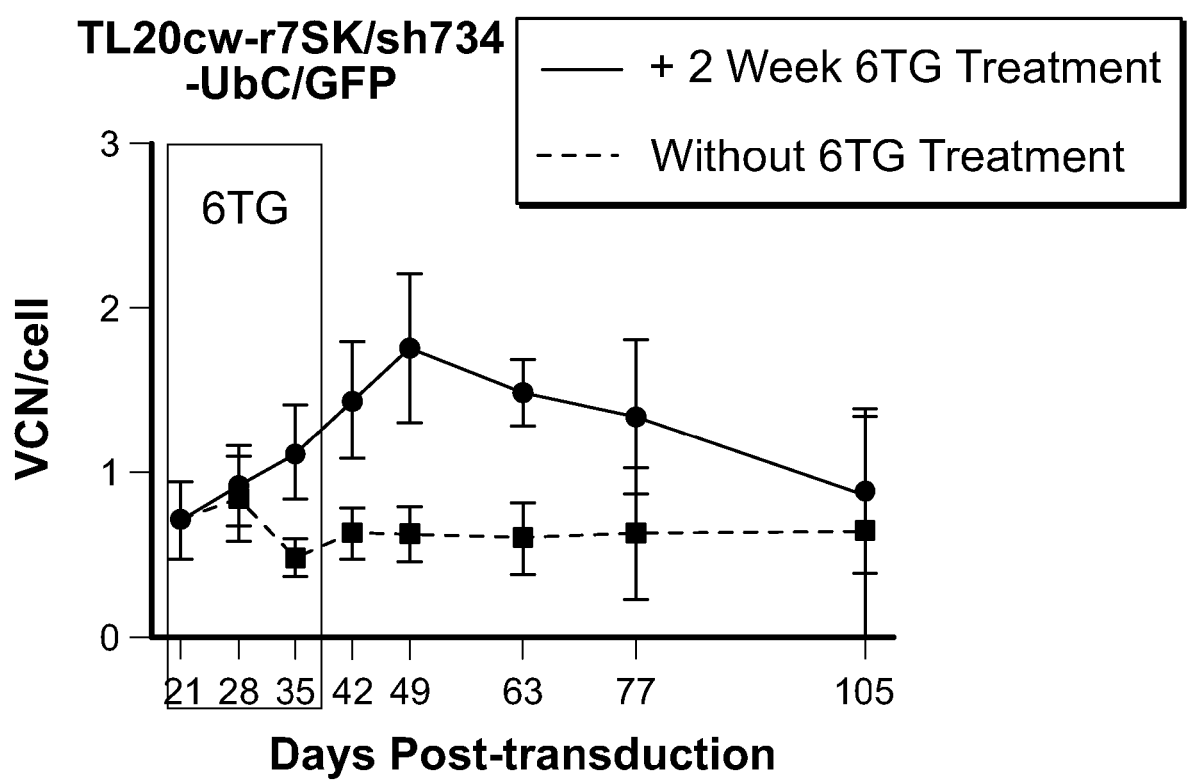
FIG. 49B sets forth a graph indicating that the control sh7 GFP reporter construct showed an increase in vector copy number during 6TG treatment which was associated with positive selection. A gradual decline in vector copy number over time was observed, despite the percentage of GFP positive cells being maintained in the culture.
Figure 49C:
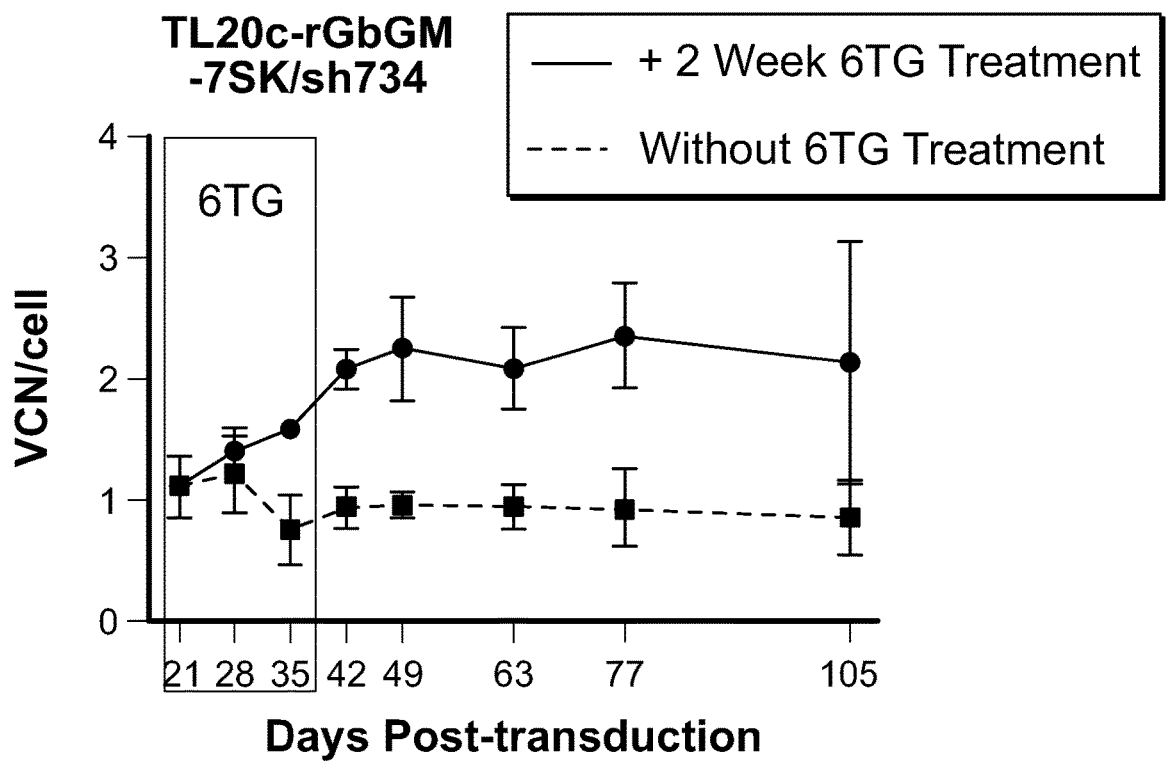
FIG. 49C provides a graph indicating the 6TG selection kinetics and stability of TL20c-rGbGM-7SK/sh734.
Figure 49D:
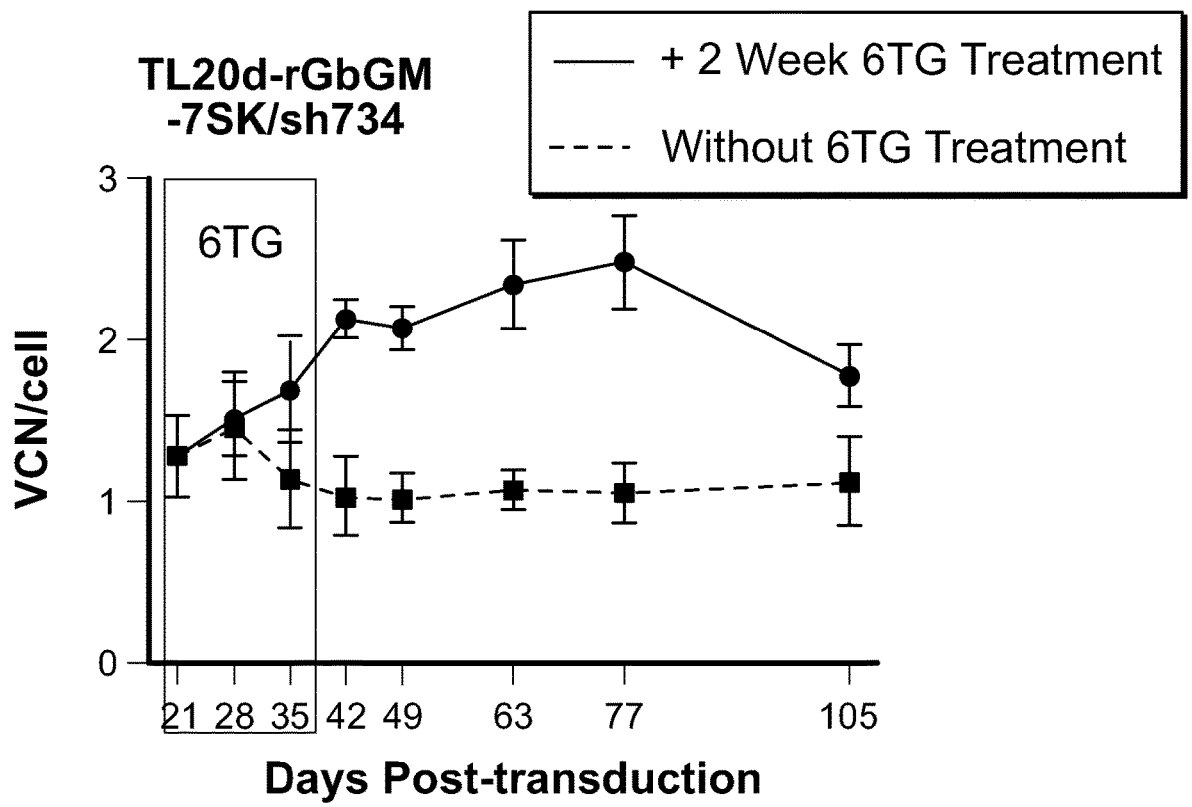
FIG. 49D provides a graph showing that removal of the cHS4 Ins-100 insulator from the TL20c-rGbGM-7SK/sh734 vector provides comparable 6TG selection kinetics and stability as compared with the TL20c-rGbGM-7SK/sh734 vector. This indicates that removal of the insulator does not adversely affect expression or result in silencing of the sh7 transgene in the lentiviral construct.
Figure 49E:
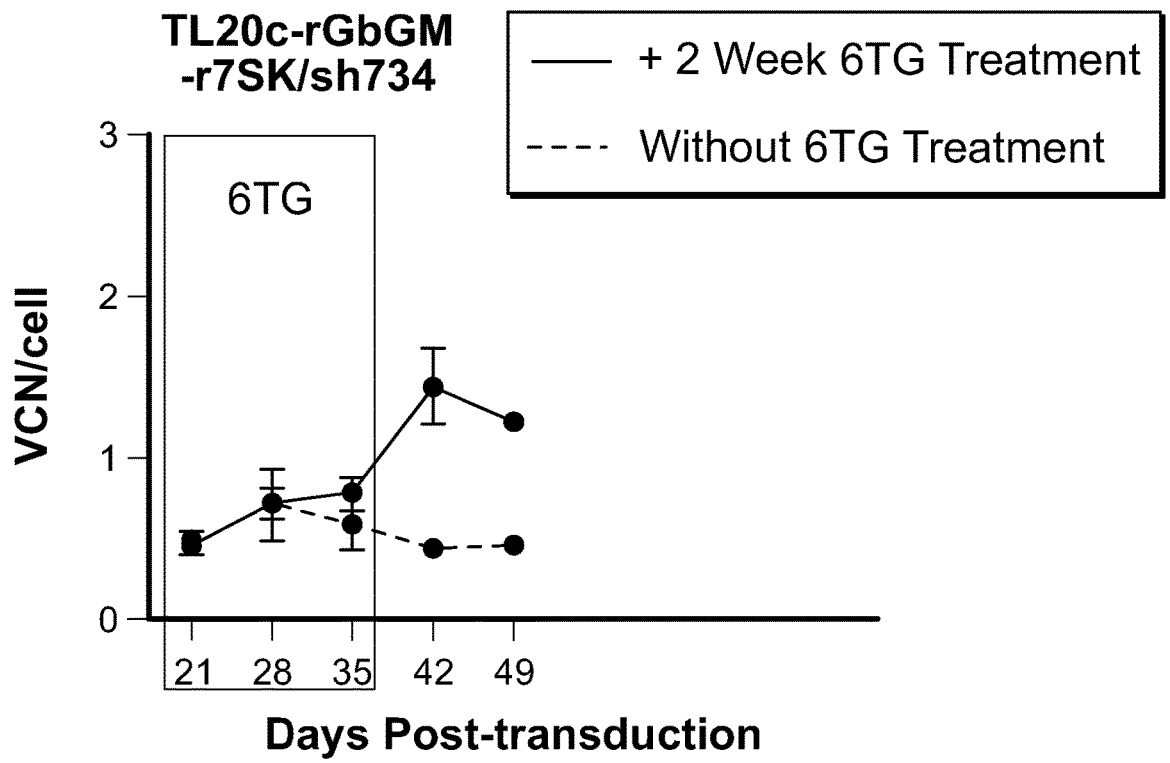
FIG. 49E provides a graph indicating the 6TG selection kinetics and stability of TL20c-rGbGM-r7SK/sh734.
Figure 49F:
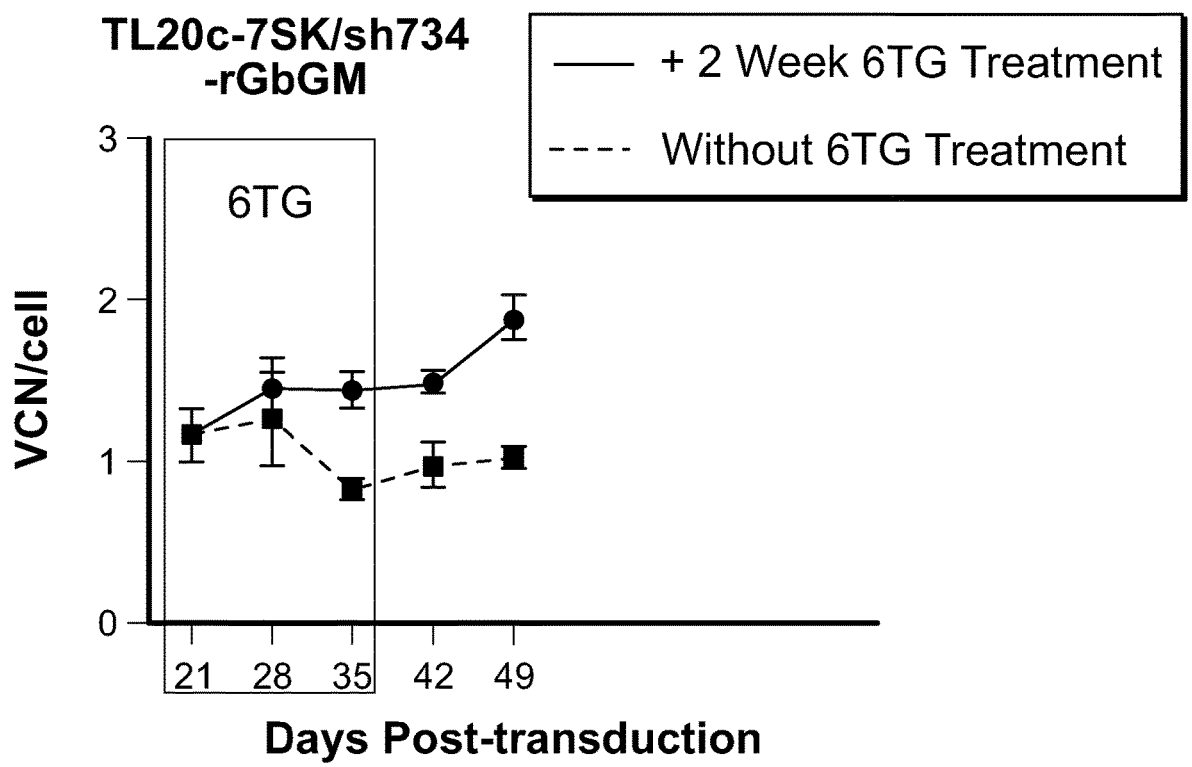
FIG. 49F provides a graph indicating the 6TG selection kinetics and stability of TL20c-rGbGM-r7SK/sh734.
Figure 49G:
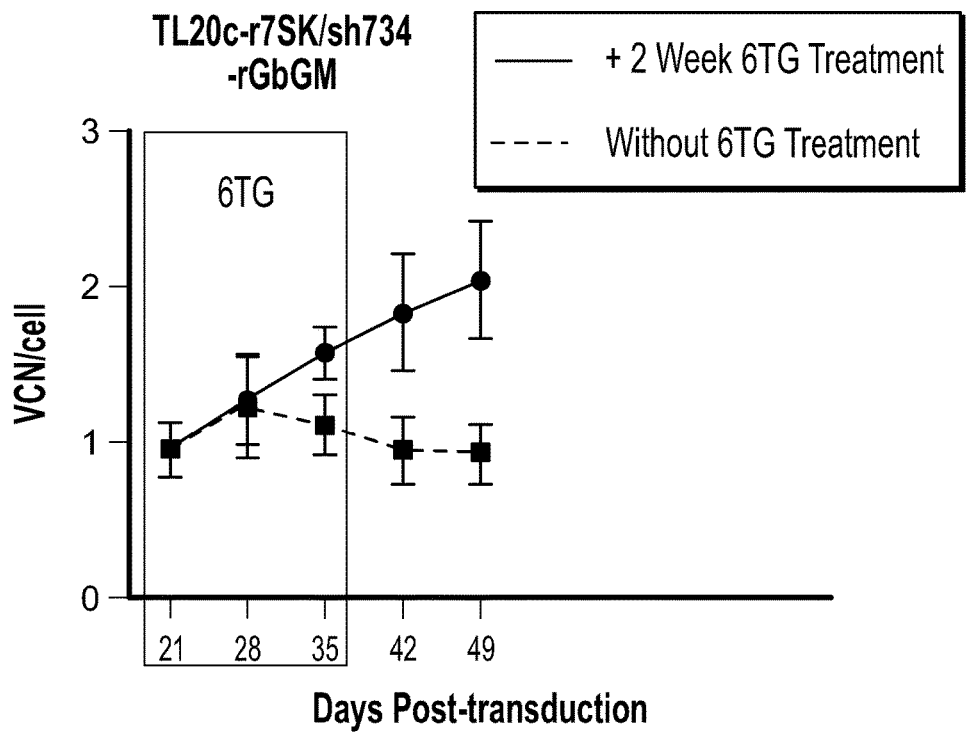
FIG. 49G provides a graph indicating the 6TG selection kinetics and stability of TL20c-r7 SK/sh734-rGbGM.
Figure 49H:
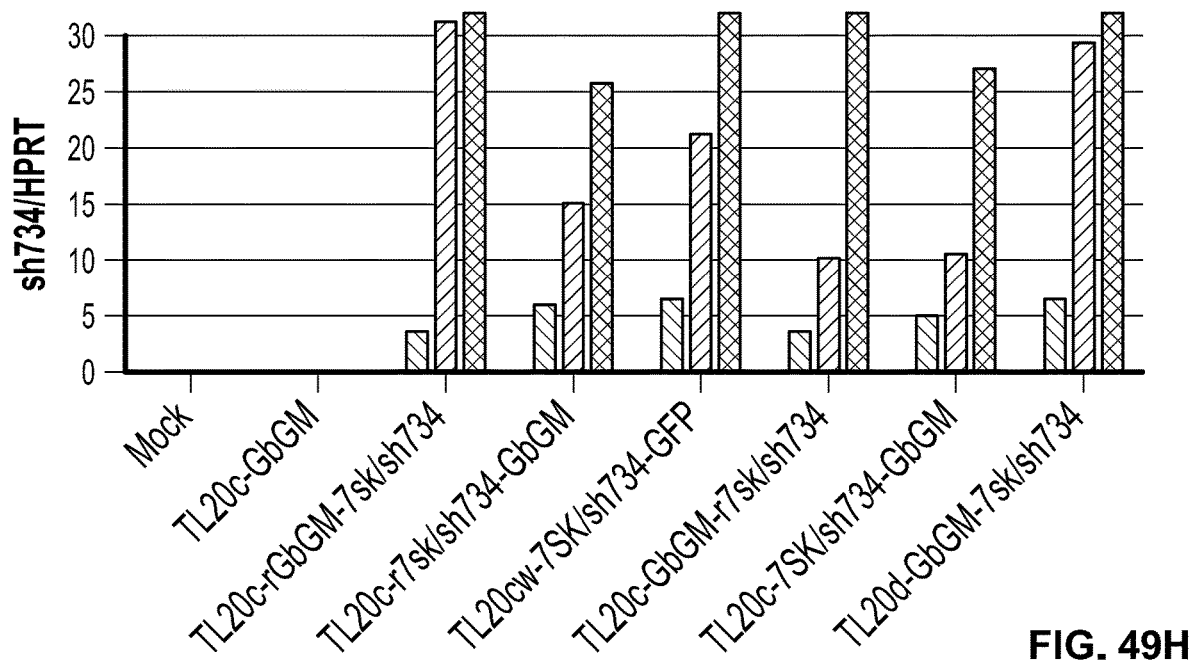
FIG. 49H shows the sh734/HPRT ratio as a measure of knockdown efficiency.
Figure 49I:
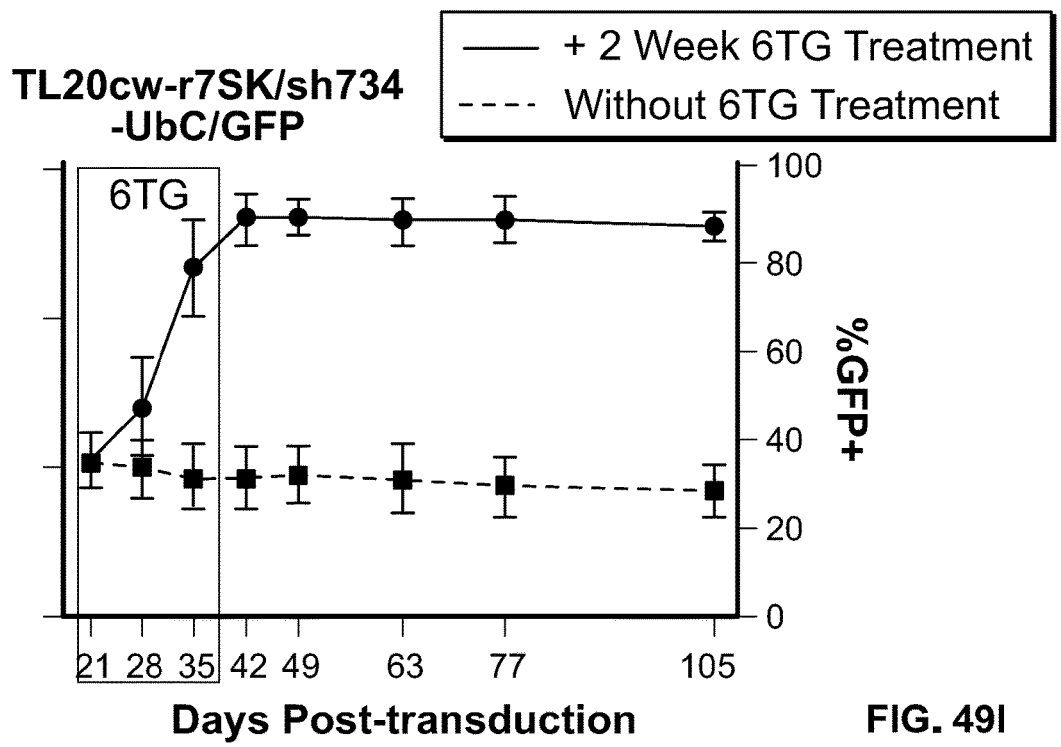
FIG. 49I illustrates that a control sh7 lentiviral vector expressing GFP showed a marked increase in sh7 gene-modified cells 14 days post 6TG treatment. At day 21, K562 cultures transduced with the sh7-GFP reporter construct were 35% GFP+ and increased to 88% GFP+ cells by day 42 following 6TG treatment. These findings suggest that sh7 is constitutively expressed in transduced K562 cells for greater than 3 months in culture at levels sufficient to maintain HPRT suppression and 6TG resistance without evidence of silencing or toxicity. Importantly, the selected cell population maintained long-term proliferative stability great than two months after discontinuation of 6TG selective pressure.
Figure 49J:
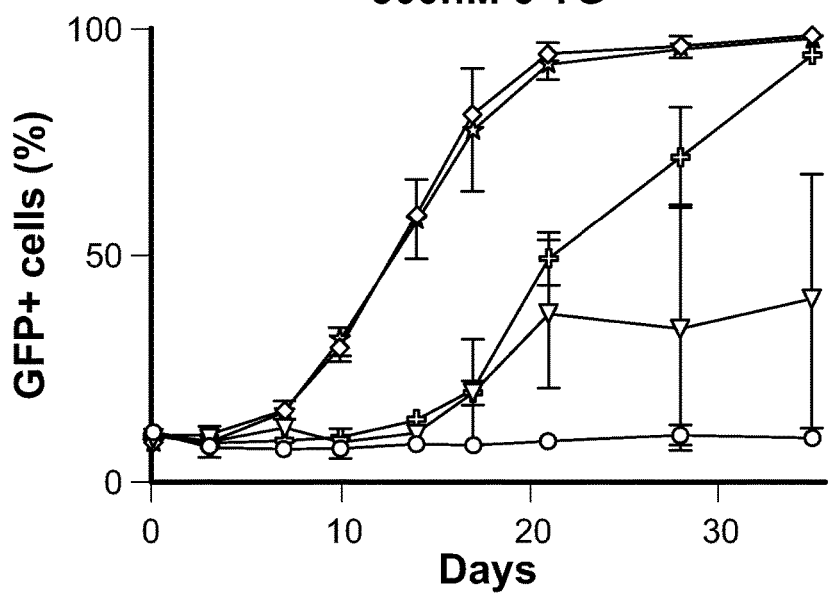
FIG. 49J illustrates the in vitro selection of K562 cells transduced with sh734-GFP reporter constructs. To establish proof of concept for LV transduced cells to express sh734 RNA and confer 6TG resistance, monitored the enrichment of gene-modified K562 GFP+ cells in cultures treated for 14d with 6TG (300 nM). The two vectors with sh734 positioned upstream of GFP in either orientation to the GFP reporter cassette in the sense orientation showed markedly faster time to enrichment of gene-modified cells compared to cultures transduced with vectors where sh734 was positioned downstream of GFP. In K562 cells, the relative level of expression of sh734/% GFP correlated with efficient knockdown of HPRT and rapid 6TG selection.
Figure 51A:
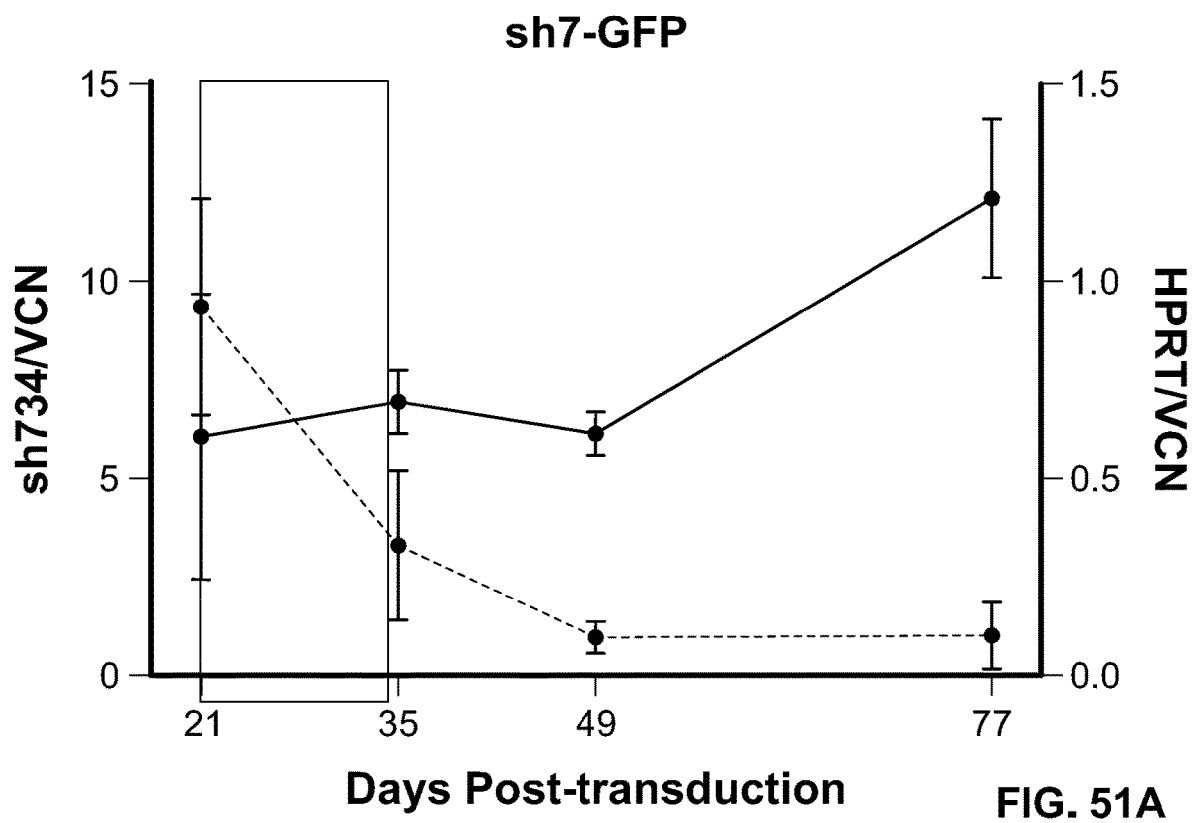
FIGS. 51A and 51B illustrate that K562 cells transduced with the TL20c-rGbGM-7SK/sh734 vector or a sh7-GFP mono-vector reporter construct exhibits similar levels of sh7 expression and kinetics of the HPRT knockdown and 6TG selection.
Figure 51B:
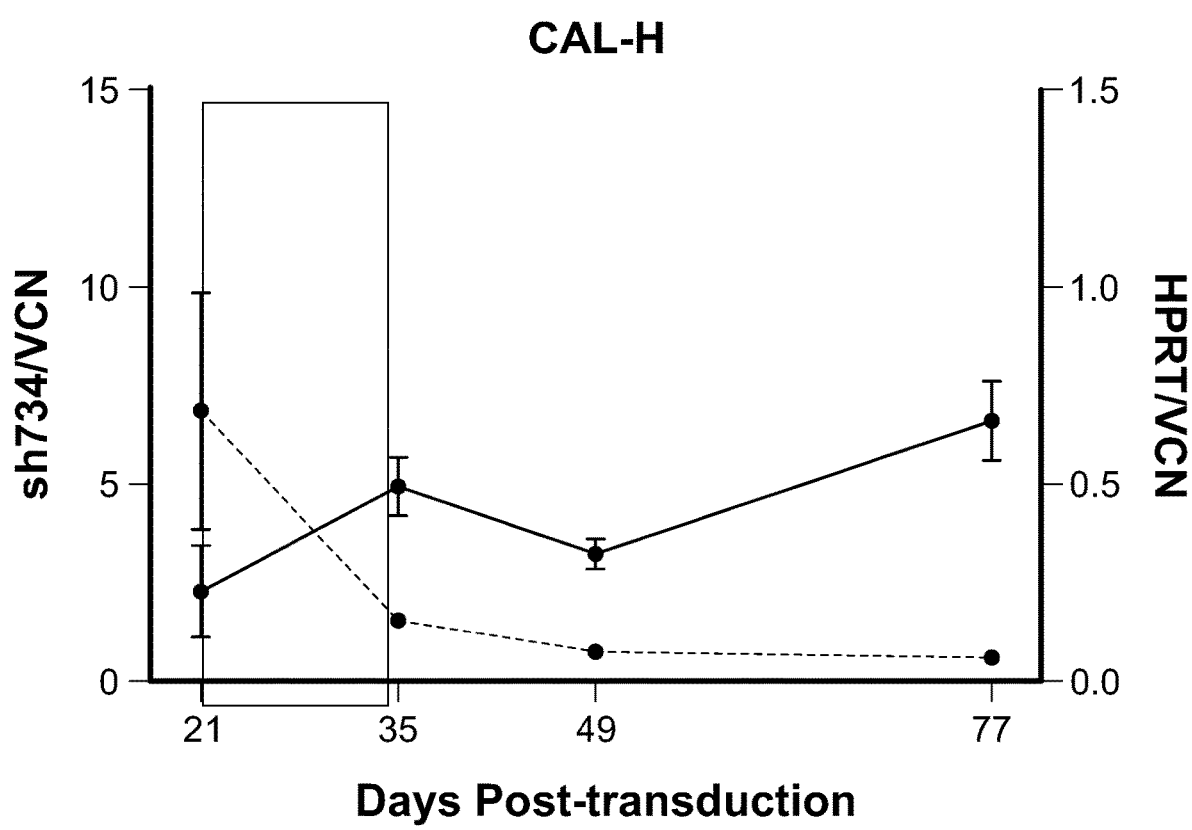
Figure 53:
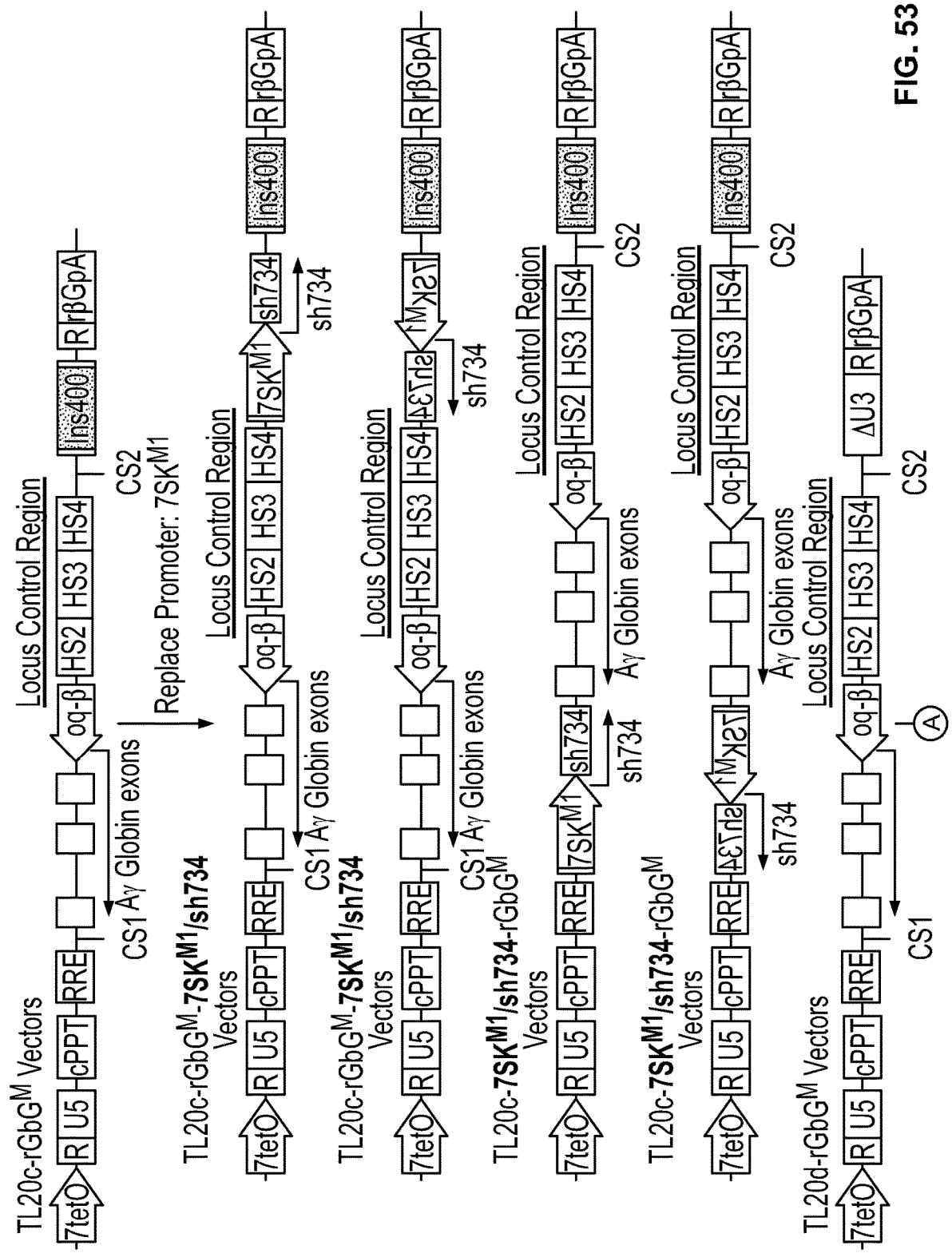
FIG. 53 illustrates constructs for a plurality of different vectors, comparatively illustrating the differences between the components of each of the vectors.

K562 cells were transduced with the sh7-GFP mono-vector reporter construct or CAL-H for 21 days before initiating 6TG. RNA was isolated, and qRT-PCR performed to determine the number of copies of sh734 relative to RNU38B and normalized to VCN (relative expression/ VCN). FIGS. 51A and 51B illustrates the percent HPRT knockdown relative to mock transduced cells (HPRT/mock× 100) normalized to VCN is plotted on the right Y axis. Overall, K562 cells transduced with the CAL-H or the sh7-GFP mono-vector reporter construct exhibited similar levels of sh734 expression and kinetics of HPRT knockdown and 6TG selection. Indeed, 6TG treatment resulted in a significant drop in HPRT levels (less than 10% of untreated cells) in cells expressing sh734. 14 days after selection, HPRT levels became undetectable in transduced cultures. 6TG selected K562 cells continued to grow and express sh734 after 3-months in culture (data not shown). These findings suggest that once resistance is established, sh734 transduced cells persist and there is little evidence of silencing in K562 cells. At day 21, K562 cultures transduced with the sh7-GFP reporter construct were 35% GFP+ and increased to 88% GFP+ cells by day 42 following 6TG treatment. With reference to FIG. 49H, the TL20c-rGbGM-7SK/sh734 LV and TL20d-rGbGM-7SK/sh734 LV vector showed rapid selection during the 2 week 6TG treatment (d35) compared to the other constructs tested.

CD34+ cells were thawed and pre-stimulated by culturing overnight $2\times10^4$ cells in 0.1 mL of SFEM II medium supplemented with SCF/Flit-3/TPO/IL-3. Pre-stimulated cells were infected with Cal-H vector at MOI=20 with spinoculation (2500 rpm and 1.5 hrs) in the presence of polybrene (6 ug/ml). The cells were taken out of centrifuge and put back in incubator for 4 hrs before exchanging to the SFEM medium supplemented with StemSpan™ CD34+ Expansion Supplement (100×) and UM171(67 nM)/SR1 (750 nM). Cells were incubated at 37° C. and 5% CO2 for 4 days. Starting from day 4, 10 mM of 6-TG stock solution was added to CD34+ cells for a final concentration at 200 nM. Fresh extended culture medium with or without 6TG was refreshed every 3-4 days. (see FIG. 52A) At day 14, VCN assay was carried out for Cal-H-transduced cells cultured in the presence of 6-TG or in the absence of 6-TG. At day 15, CD34+ cells were washed and seeded in erythroid expansion medium as SFEM II medium supplemented with erythroid expansion supplement. Fresh erythroid expansion medium was added at day 2 and 4. From day 21, erythroid medium (SFEM II medium supplemented with 10 U/mL of EPO was added every 3 days. At day 28, flow assay showed 60-80% of untransduced and transduced cells were CD235a+ (see FIG. 52B) and HbF intracellular staining showed 34.3% of Cal-H transduced cells under 6-TG selection are HbF+ compared to 15.8% in the absence of 6-TG (see FIG. 52C).

This experiment provides proof of concept for the functional regulation of CAL-H transgene expression in primitive CD34+HSPC. Functional regulation of sh7 and GbGm expression in CALH modified CD34+HSPC is shown by an increase in the average VCN following 6TG selection and a >2-fold increase in the % of HbF cells following in vitro erythroid differentiation and maturation.

CONCLUSION

The TL20c-rGbGM-7SK/sh734 dual therapeutic LV construct was identified using a functional screen in K562 cells that compared the effect of position and orientation of the transgenes relative to each other on transgene expression, long term stability and function and in vitro 6-TG selection. Infectious titer HbF and expression of the sGbG$^M$ cassette was improved when inserted in the TL20c LV backbone with the 400 bp cHS4 insulator in reverse orientation. A high-level of sh734 expression and erythroid lineage-directed gene expression in the dual therapeutic TL20c-rGbGM-7SK/sh734 vector expression was observed suggesting mutually exclusive expression of transgenes and minimum interactions between the globin gene regulatory elements and Pol III promoter. Furthermore, TL20c-rGbGM-7SK/sh734 transduced K562 cultures selected with 6TG continued to express sh734 and maintain function for more than 3-months and could be induced to differentiate toward erythroid cells and upregulate the expression of the gamma-globin transgene about 8-fold. Since transgene silencing and variability are highly dependent on vector backbone and cell type, an investigation was conducted as to whether TL20c-rGbGM-7SK/sh734 would perom as well in CD34+HSPC as it did in the K562 cell model. CD34+ HSCs were transduced with the TL20c-rGbGM-7SK/sh734 lentiviral vector and then cultured cells in medium supplemented with UM171 and SR1 to preserve the more primitive HSCs from differentiating in extended cultures treated with 6TG. After 2 weeks 6TG selected CD34 HSC cultures were transferred to erythroid differentiation medium for another 2 weeks and the percentage of HbF positive cells was measured by flow cytometry. 6TG selected cultures showed a 2-fold increase in HbF positive cells, suggesting that primitive HSCs transduced with the TL20c-rGbGM-7SK/sh734 lentiviral vector could undergo in vitro selection and express the gamma-globin in a lineage specific control.

Example 3—Design of Polymerase II (Pol-II)-Dependent shRNA for Knock Down of HPRT and its Applications for 6-TG Selection It has been well known that some polymerase III-dependent short-hairpin RNAs have overexpression issues and can induce acute cytotoxicity. Some pol III promoters, e.g. the U6, may lead to a much higher expression of short-hairpin RNAs (see Mol Ther. 2006 October; 14(4):494-504, which suggests the use of a pol II promoter driven shRNA to solve any toxicity issue), the disclosure of which is hereby incorporated by reference herein in its entirety). This is an important concern when considering the use of RNA interference (RNAi) as a potential therapeutic approach, especially in stem cell gene therapy. Here, polymerase II was used as alternative promoter to express microRNA so as to effectuate knockdown of the expression of HPRT. A CRISPR/Cas9 gene editing approach was utilized, and a Cas9 with a single guide RNA (Cas9 RNP) targeting CCR5, together with a single-stranded DNA oligonucleotide donor (ssODN) encoding an HPRT Pol II driven shRNA, was used to enable efficient replacement of the CCR5 locus with a functional HPRT miRNA. The ability to knock-in Pol II-driven shHPRT into a CCR5 region to knockdown HPRT and select for the cell line with a hairpin miroRNA expression gene under 6TG was demonstrated. For knock-in of sh211 and sh734, the obvious cytotoxicity in K562 cells was not observed.

Two types of microRNA-based shRNAs for knockdown of HPRT (Table 1) were designed. One type is a de novo design of artificial miroRNA shRNA (see Fang, W. & Bartel, David P. The Menu of Features that Define Primary MicroR-NAs and Enable De Novo Design of MicroRNA Genes. Molecular Cell 60, 131-145). Two candidates for this design were employed, including miRNA734 (111nt) (SEQ ID NO: 23 or SEQ ID NO: 67) and miRNA211(111nt) (SEQ ID NO: 24 or SEQ ID NO: 68). Another type of microRNA-based shRNA was based on a third generation miRNA scaffold modified miRNA 16-2 (miRNA-3G) (see Watanabe, C., Cuellar, T. L. & Haley, B. Quantitative evaluation of first, second, and third generation hairpin systems reveals the limit of mammalian vector-based RNAi. RNA Biology 13, 25-33 (2016)). Two further candidates were employed, including sh734 and sh211, each embedded in a miRNA 3-G (165nt) (SEQ ID NO: 25 and SEQ ID NO: 25, respectively).

Figure 24:
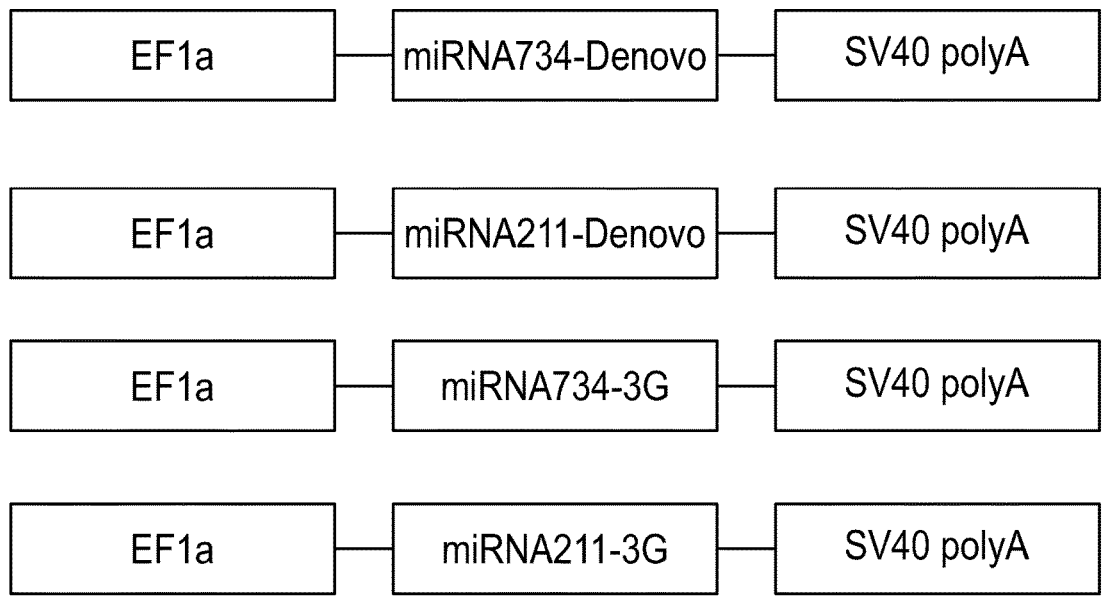
FIG. 24 provides a scheme for EF1a-driven microRNA-based shRNAs for knockdown of HPRT.
Figure 25A:
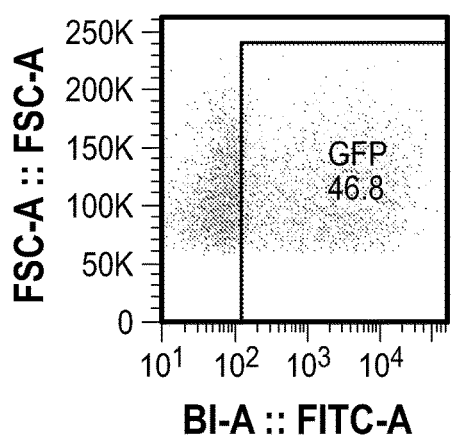
FIGS. 25A and 25B illustrate 6TG selection of K562 transiently transfected with sh734, miRNA RNA constructs delivered in nanocapsules. 1×10$^5$ of K562 cells were incubated with EF1a-GFP/EF1a-sh734-3 G/EF1a-sh211-3G/7sk-sh734 nanocapsules (200 ng of DNA) for 4 hours. 6TG was added into the culture medium to the final concentration of 1 μM on day 2.
Figure 25B:
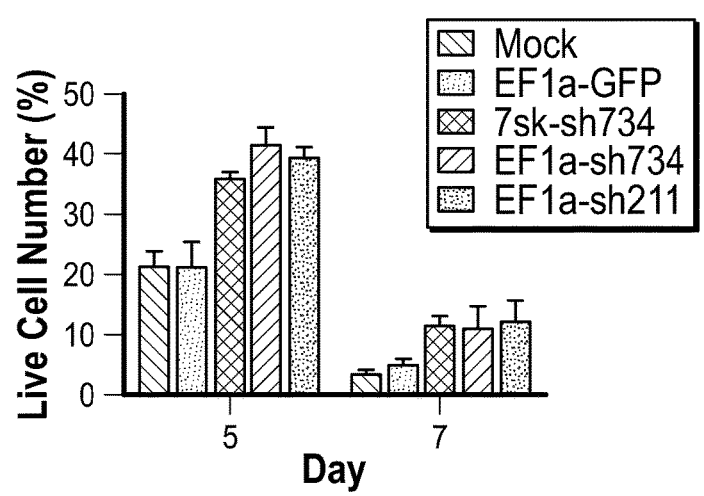

To demonstrate their biological functions, each of shRNAs having SEQ ID NOS: 23, 24, 25, and 26 were combined (each individually) with pol II promoters, namely with EF1a (SEQ ID NO: 64) and with SV40 polyA (SEQ ID NO: 65), and the corresponding DNA cassettes were synthesized to provide SEQ ID NO: 36, SEQ ID NO: 37, SEQ ID NO: 38, and SEQ ID NO:39 as set forth in Table 2 (see also FIG. 24). K562 cells were transiently transfected with nanocapsules incorporating each of the aforementioned shRNA DNA cassettes and incorporated into those cells under 6-TG selection. The cells transfected with shRNA showed resistance to 6-TG selection as demonstrated at least in FIGS. 25A and 25B. It is believed that the cells transfected with all shRNA DNA cassettes have higher survival cell number than control group under 6-TG treatment.

Figure 26:
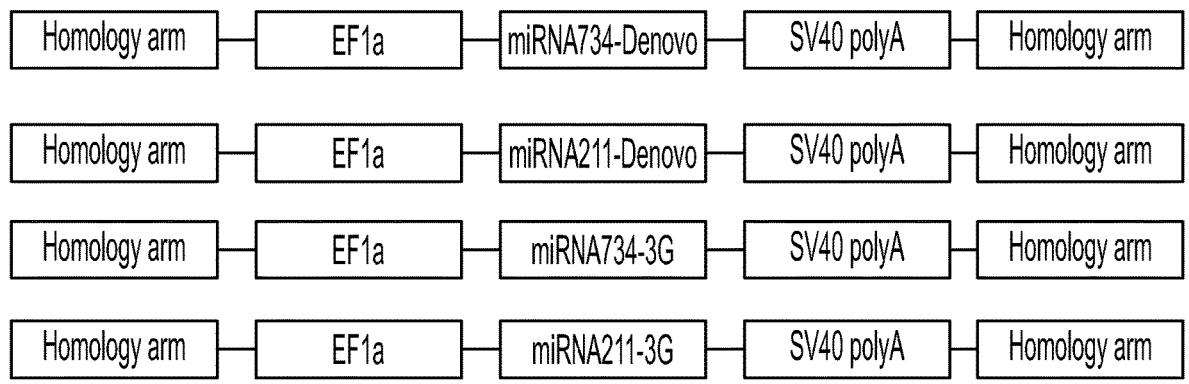
FIG. 26 provides a scheme of EF1a-driven microRNA-based shRNAs with homology arm for knock-in in CCR5 region.
Figure 27A:
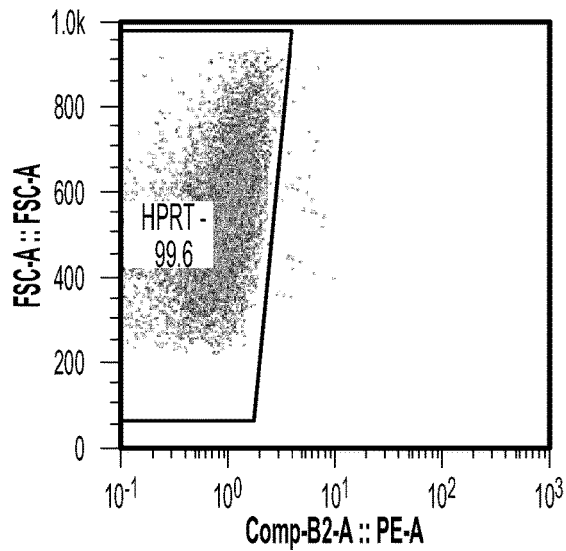
FIGS. 27A, 27B, and 27C illustrate FAC staining of control K562 cells for HPRT: Unstained (FIG. 27A), HPRT positive cells (FIG. 27B), and K562 cells with knock-in of EF1a-sh211-3G at the CCR5 locus (FIG. 27C). Gates show frequencies of cells that are HPRT negative.
Figure 27B:
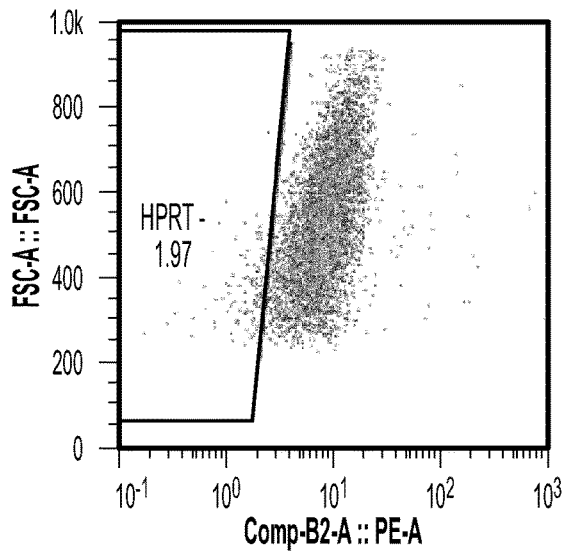
Figure 27C:
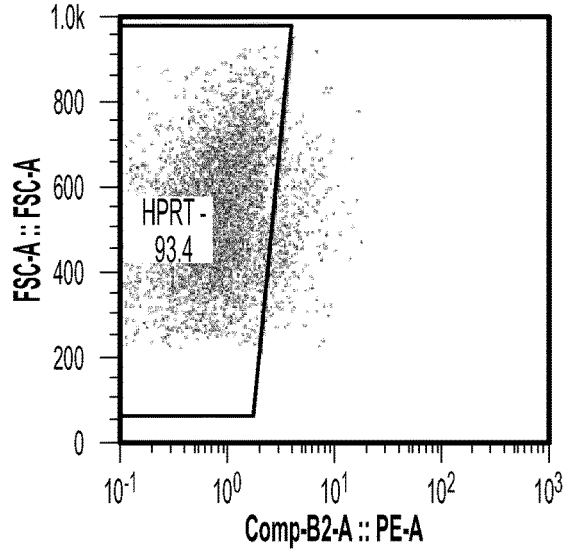

To investigate the long-term stability of the shRNAs, we also used CRIPSR technologies to knock-in shRNA-expressing cassettes into the CCR5 region to knockdown HPRT (see FIG. 26) and selected the cell line with a hairpin miroRNA expression gene under 6-TG (see also Table 3, SEQ ID NO:S 40, 41, and 42; and also, SEQ ID NOS: 62 and 63). After three weeks of 6-TG selection, HPRT staining showed K562 cells with knock-iof Pol-II-driven sh211-3G had significantly lower HPRT levels (12%) as compared with that of the control (i.e. untransduced cells) (99%) (FIGS. 27A, 27B, and 27C).

TABLE 1

Pol II-driven microRNA-based shRNAs for knockdown of HPRT.

| Name | Length (nt) | SEQ ID NO: | Sequence |
| --- | --- | --- | --- |
| miRNA734-Denovo | 111 | 23 | acccgtacatattttttgtgtagctctagtttatagtcaagggcatatcc ttgtgtttttttttgaaggatatgcccttgactataaactagcgctacac ttttttcgtcttgt |
| miRNA211-Denovo | 111 | 24 | acccgtacatattttttgtgtagctctagttataaatcaaggtcataacc ttgtgtttttttttgaaggttatgaccttgatttataactagcgctacact ttttcgtcttgt |
| miRNA734-3G | 166 | 26 | CCGGATCAACGCCCTAGGTTTATGTTTGGA TGAACTGACATACGCGTATCCGTCTTATAG TCAAGGGCATATCCTGTAGTGAAATATATA TTAAACAAGGATATGCCCTTGACTATAATA CGGTAACGCGGAATTCGCAACTATTTTATC AATTTTTTGCGTCGAC |
| miRNA211-3G | 166 | 25 | CCGGATCAACGCCCTAGGTTTATGTTTGGA TGAACTGACATACGCGTATCCGTCTTTTAA ATCAAGGTCATAACCGTAGTGAAATATAT ATTAAACAGGTTATGACCTTGATTTAAAAT ACGGTAACGCGGAATTCGCAACTATTTTAT CAATTTTTTGCGTCGAC |

TABLE 2

Sequences of EF1a-driven microRNA-based shRNAs for knockdown of HPRT.

| Name | Length (nt) | SEQ ID NO: | Sequence |
| --- | --- | --- | --- |
| EF1a-miRNA734-Denovo-SV40 polyA | 483 | 36 | ggatatcggctccggtgcccgtcagtgggcagagcgcacatcgcccacagtccccgagaagttg gggggaggggtcggcaattgaaccggtgcctagagaaggtggcgcggggtaaactgggaaag tgatgtcgtgtactggctccgccttttttcccgagggtgggggagaaccgtatataagtgcagtagtc gccgtgaacgttatttcgcaacgggtttgccgccagaacacaggatgacccgtacatattttttgtgt agctctagttataaatcaaggtcataaccttgtgtttttttttgaaggttatgaccttgatttataactagcg ctacacttttttcgtcttgttagaacttgtttattgcagcttataatggttacaaataaagcaatagcatca caaatttcacaaataaagcatttttttcactgcattctagttgtggtttgtccaaactcatcaatgtatctt atcatct |

TABLE 2-continued

Sequences of EF1a-driven microRNA-based shRNAs for knockdown of HPRT.

| Name | Length (nt) | SEQ ID NO: | Sequence |
| --- | --- | --- | --- |
| EF1a-miRNA211-Denovo-SV40 polyA | 483 | 37 | ggatatcggctccggtgcccgtcagtgggcagagcgcacatcgcccacagtccccgagaagttg<br>ggggagggggtcggcaattgaaccggtgcctagagaaggtggcgcggggtaaactgggaaag<br>tgatgtcgtgtactggctccgccttttcccgagggtgggggagaaccgtatataagtgcagtagtc<br>gccgtgaacgttatttcgcaacgggtttgccgccagaacacaggatgacccgtacatattttgtgt<br>agctctagtttatagtcaagggcatatccttgtgttttttttgaaggatatgcccttgactataaactagc<br>gctacacttttttcgtcttgttagaacttgtttattgcagcttataatggttacaaataaagcaatagcatc<br>acaaatttcacaaataaagcattttttttcactgcattctagttgtggtttgtccaaactcatcaatgtatct<br>tatcatct |
| EF1a-miRNA734-3G-SV40 polyA | 537 | 38 | ggatatcggctccggtgcccgtcagtgggcagagcgcacatcgcccacagtccccgagaagttg<br>ggggagggggtcggcaattgaaccggtgcctagagaaggtggcgcggggtaaactgggaaag<br>tgatgtcgtgtactggctccgccttttcccgagggtgggggagaaccgtatataagtgcagtagtc<br>gccgtgaacgttatttcgcaacgggtttgccgccagaacacaggatgccggatcaacgccctag<br>gtttatgtttggatgaactgacatacgcgtatccgtatagtcaagggcatatccagtagtgaaata<br>tatattaaactggatatgccatgactataatacggtaacgcggaattcgcaactattttatcaatttttt<br>gcgtcgactagaacttgtttattgcagatataatggttacaaataaagcaatagcatcacaaatttca<br>caaataaagcattttttttcactgcattctagttgtggtttgtccaaactcatcaatgtatcttatcatct |
| EF1a-miRNA211-3G-SV40 polyA | 537 | 39 | ggatatcggctccggtgcccgtcagtgggcagagcgcacatcgcccacagtccccgagaagttg<br>ggggagggggtcggcaattgaaccggtgcctagagaaggtggcgcggggtaaactgggaaag<br>tgatgtcgtgtactggctccgccttttcccgagggtgggggagaaccgtatataagtgcagtagtc<br>gccgtgaacgttatttcgcaacgggtttgccgccagaacacaggccggatcaacgccctaggttt<br>atgtttggatgaactgacatacgcgtatccgtctataaatcaaggtcataacctgtagtgaaatatata<br>ttaaacaaggttatgaccttgatttattacggtaacgcggaattcgcaactattttatcaatttttttgcgt<br>cgacccggatcaacgccctaggtttatgtttggatgaactgacatacgcgtatccgtctataaatca<br>aggtcataacctgtagtgaaatatatattaaacaaggttatgaccttgatttattacggtaacgcggaa<br>ttcgcaactattttatcaatttttttgcgtcgacaacttgtttattgcagcttataatggttacaaataaagc<br>aatagcatcacaaatttcacaaataaagcattttttttcactgcattctagttgtggtttgtccaaactcat<br>caatgtatcttatcatct |

TABLE 3 of EF1a-driven microRNA-based shRNAs with homology arm for knock-in in CCR5 region.

| Name | Length (nt) | SEQ ID NO: | Sequence |
| --- | --- | --- | --- |
| Left Arm 150-EF1a-miRNA734-Denovo-SV40 polyA-Right Arm 150 | 809 | 40 | gatatctctggaatcttcttcatcatcctcctgacaatcgataggtacctggctgtcgtccat<br>gctgtgtttgattaaaagccaggacggtcacctttggggtggtgacaagtgtgatcacttg<br>ggtggtggctgtgtttgcgtctcaagcttttcgaagcggccgcggatatcggctccggtgc<br>ccgtcagtgggcagagcgcacatcgcccacagtccccgagaagttggggggagggt<br>cggcaattgaaccggtgcctagagaaggtggcgcggggtaaactgggaaagtgatgtc<br>gtgtactggctccgccttttcccgagggtgggggagaaccgtatataagtgcagtagtcg<br>ccgtgaacgttcttttcgcaacgggtttgccgccagaacacaggatgacccgtacatatttt<br>tgtgtagctctagtttataaatcaaggtcataaccttgtgttttttttgaaggttatgaccttgattt<br>ataactagcgctacacttttttcgtcttgttagaacttgtttattgcagcttataatggttacaaat<br>aaagcaatagcatcacaaatttcacaaataaagcattttttttcactgcattctagttgtggtttg<br>tccaaactcatcaatgtatcttatcatctacgcgtccaggaatcatctttaccagatctcaaaa<br>agaaggtatcattacacctgcagctctcattttccatacagtcagtatcaattctggaagaat<br>ttccagacattaaagatagtcatcttggggctggtcctgccgctgcttgtcatggtc |
| miRNA211-Denovo | 809 | 41 | gatatctctggaatcttcttcatcatcctcctgacaatcgataggtacctggctgtcgtccat<br>gctgtgtttgattaaaagccaggacggtcacctttggggtggtgacaagtgtgatcacttg<br>ggtggtggctgtgtttgcgtctcaagcttttcgaagcggccgcggatatcggctccggtgc<br>ccgtcagtgggcagagcgcacatcgcccacagtccccgagaagttggggggagggt<br>cggcaattgaaccggtgcctagagaaggtggcgcggggtaaactgggaaagtgatgtc<br>gtgtactggctccgccttttcccgagggtgggggagaaccgtatataagtgcagtagtcg<br>ccgtgaacgttcttttcgcaacgggtttgccgccagaacacaggatgacccgtacatatttt<br>tgtgtagctctagtttatagtcaagggcatatccttgtgttttttttgaaggatatgcccttgact<br>ataaactagcgctacacttttttcgtcttgttagaacttgtttattgcagcttataatggttacaaa<br>taaagcaatagcatcacaaatttcacaaataaagcattttttttcactgcattctagttgtggttt<br>gtccaaactcatcaatgtatcttatcatctacgcgtccaggaatcatctttaccagatctcaaa<br>aagaaggtatcattacacctgcagctctcattttccatacagtcagtatcaattctggaaga<br>atttccagacattaaagatagtcatcttggggctggtcctgccgctgcttgtcatggtc |
| miRNA734-3G | 863 | 42 | gatatctctggaatcttcttcatcatcctcctgacaatcgataggtacctggctgtcgtccat<br>gctgtgtttgattaaaagccaggacggtcacctttggggtggtgacaagtgtgatcacttg<br>ggtggtggctgtgtttgcgtctcaagcttttcgaagcggccgcggatatcggctccggtgc<br>ccgtcagtgggcagagcgcacatcgcccacagtccccgagaagttggggggagggt |

TABLE 3-continued of EF1a-driven microRNA-based shRNAs with homology arm for knock-in in CCR5 region.

| Name | Length (nt) | SEQ ID NO: | Sequence |
|---|---|---|---|
| | | | cggcaattgaaccggtgcctagagaaggtggcgcggggtaaactgggaaagtgatgtc<br>gtgtactggctccgccttttccccgagggtggggagaaccgtatataagtgcagtagtcg<br>ccgtgaacgttatttcgcaacgggtttgccgccagaacacaggatgccggatcaacgcc<br>ctaggtttatgtttggatgaactgacatacgcgtatccgtcttatagtcaagggcatatccag<br>tagtgaaatatatattaaactggatatgccatgactataatacggtaacgcggaattcgcaa<br>ctattttatcaattttttgcgtcgactagaacttgtttattgcagcttataatggttacaaataaag<br>caatagcatcacaaatttcacaaataaagcattttttcactgcattctagttgtggtttgtcca<br>aactcatcaatgtatcttatcatctacgcgtccaggaatcatctttaccagatctcaaaaaga<br>aggtatcattacacctgcagctctcattttccatacagtcagtatcaattctggaagaatttcc<br>agacattaaagatagtcatcttggggctggtcctgccgctgcttgtcatggtc |
| miRNA211-3G | 863 | 43 | gatatctctggaatcttcttcatcatcctcctgacaatcgataggtacctggctgtcgtccat<br>gctgtgtttgattaaaagccaggacggtcaccttt ggggtggtgacaagtgtgatcacttg<br>ggtggtggctgtgtttgcgtctcaagcttttcgaagcggccgcggatatcggctccggtgc<br>ccgtcagtgggcagagcgcacatcgcccacagtccccgagaagttggggggaggggt<br>cggcaattgaaccggtgcctagagaaggtggcgcggggtaaactgggaaagtgatgtc<br>gtgtactggctccgccttttccccgagggtggggagaaccgtatataagtgcagtagtcg<br>ccgtgaacgttcttttcgcaacgggtttgccgccagaacacaggccggatcaacgccta<br>ggtttatgtttggatgaactgacatacgcgtatccgtctataaatcaaggtcataacctgtagt<br>gaaatatatattaaacaaggttatgaccttgatttattacggtaacgcggaattcgcaactatt<br>ttatcaattttttgcgtcgacccggatcaacgccctaggtttatgtttggatgaactgacatac<br>gcgtatccgtctataaatcaaggtcataacctgtagtgaaatatatattaaacaaggttatga<br>ccttgatttattacggtaacgcggaattcgcaactattttatcaattttttgcgtcgacaacttgt<br>ttattgcagatataatggttacaaataaagcaatagcatcacaaatttcacaaataaagcatt<br>tttttcactgcattctagttgtggtttgtccaaactcatcaatgtatcttatcatctacgcgtcca<br>ggaatcatctttaccagatctcaaaaagaaggtcttcattacacctgcagctctcattttccat<br>acagtcagtatcaattctggaagaatttccagacattaaagatagtcatcttggggctggtc<br>ctgccgctgcttgtcatggtc |

Example 4—Conditioning Prior to Hematopoietic Stem Cell Transplantation

Hematopoietic stem cell transplantation (HSCT) is widely used to treat hematological malignancies and also offers curative therapy for patients with hemoglobinopathies, congenital immunodeficiencies, and other conditions, including infectious diseases such as HIV/AIDS. However, the ability of HSCT to cure this broad range of non-malignant diseases is severely underutilized. The obstacles to using allogeneic HSCT in these diverse conditions relate primarily to the frequency of life-threatening graft-versus-host disease (GVHD), of acute complications that result from the cytotoxic effects of conditioning, such as mucositis and infections, and of long-term, irreversible complications that arise from the genotoxic effects of conditioning, such as infertility. Autologous HSCT using genetically corrected cells would avoid the risk of GVHD, but the genotoxicity of conditioning remains a substantial barrier to the development of this approach.

A promising avenue for improving the safety of conditioning is the use of drugs, such as antibodies, that are specifically targeted to HSCs and other hematopoietic cells in the bone marrow niche and that are believed to spare non-hematopoietic cells. Certain internalizing immunotoxins (also known as antibody-drug conjugates or ADCs) targeting the hematopoietic-cell-restricted CD45 receptor or the more HSC specific CD117 (c-Kit) may be used for this purpose (see, for example, US Patent Publication Nos. 2017/0360954 and 2018/0147294; and PCT Publication Nos. WO/2017/219025 and WO/2017/219029, the disclosures of which are each incorporated by reference herein in their entireties). In some embodiments, the immunotoxin is selected from pseudomonas exotoxin A, deBouganin, diphtheria toxin, an amatoxin, such as α-amanitin, saporin, maytansine, a maytansinoid, an auristatin, an anthracycline, a calicheamicin, irinotecan, SN-38, a duocarmycin, a pyrrolobenzodiazepine, a pyrrolobenzodiazepine dimer, an indolinobenzodiazepine, or an indolinobenzodiazepine dimer, Ricin-A or a variant thereof. In some embodiments, the immunotoxin is saporin, a catalytic N-glycosidase ribosome-inactivating protein that halts protein synthesis. Unlike other ricin family members, it is believed to lack a general cell entry domain and is non-toxic unless conjugated to a targeting antibody or ligand capable of receptor-mediated internalization.

In pre-clinical testing, a single dose of the immunotoxin, CD45-SAP (saporin conjugated to a CD45-targeting antibody), enabled efficient (>90%) engraftment of donor cells and full correction of a sickle-cell anemia mouse model. In contrast to irradiation, CD45-SAP completely avoided neutropenia and anemia, spared bone marrow and thymic niches, enabling rapid recovery of T and B cells, preserved anti-fungal immunity, and had minimal overall toxicity. Humanized NSG mice treated with a single dose of CD117-SAP had greater than 90% depletion of HSPCs in the bone marrow after a single administration of the ADC. These non-genotoxic conditioning methods may provide an attractive alternative to current conditioning regimens for HSCT in the treatment of non-malignant blood diseases. The improved safety of these targeted conditioning agents may extend the use of curative bone marrow transplant to patients who cannot tolerate current conditioning methods and in patients where bone marrow transplant is currently thought to be too dangerous.

In the context of the present disclosure, patients are conditioned to remove existing stem cells in the bone marrow and diseased cells, and to prevent rejection of the incoming stem cells. This process currently uses toxic agents originally developed to treat cancer, and procedures such as radiation that kill cells in a non-specific manner. To combat this harsh procedure, Applicants have developed a procedure whereby patients are treated with a combination of reduced intensity conditioning (e.g. busulfan or melphalan—both non-specific alkylating anti-cancer agents) followed by post-infusion selection of gene-modified cells, with the goal to provide HSCT as an out-patient procedure, with dramatically reduced adverse events related to the conditioning. Still, some level of non-specific chemotherapy is necessary to make space in the bone-marrow for the gene-modified cell population.

As an alternative to reduced intensity conditioning using busulfan or melphalan, antibody-drug conjugates (described above) may be used as an alternative method of conditioning, allowing for non-genotoxic bone marrow conditioning in patients prior to receiving gene therapy according to the methods described herein. Specifically, sickle cells disease or β-thalassemia patients are infused with either an anti-CD45-SAP or an anti-CD117/c-kit-SAP (or a combination of both antibodies) to "make space" in the bone marrow, followed by infusion of a modified HSC according to the methods described herein. Dosing post-infusion with 6TG could then increase the chimerism of the gene-modified cells to correct the disease. It is believed that this could potentially be done with minimal overall toxicity or adverse events to the patient.

Additional Embodiments

In another aspect of the present disclosure is a vector comprising (i) a nucleic acid sequence encoding a shRNA targeting a HPRT gene; and (ii) a nucleic acid sequence encoding a therapeutic gene. In some embodiments, the nucleic acid sequence encoding the shRNA targeting the HPRT gene has a sequence having at least 80% identity to that of SEQ ID NO: 30. In some embodiments, the nucleic acid sequence encoding the shRNA targeting the HPRT gene has a sequence having at least 90% identity to that of SEQ ID NO: 30. In some embodiments, the nucleic acid sequence encoding the shRNA targeting the HPRT gene has a sequence having at least 95% identity to that of SEQ ID NO: 30. In some embodiments, the nucleic acid sequence encoding the shRNA targeting the HPRT gene has a sequence of SEQ ID NO: 30. In some embodiments, the nucleic acid sequence encoding the therapeutic gene has a sequence having at least 80% identity to that of SEQ ID NO: 55. In some embodiments, the nucleic acid sequence encoding the therapeutic gene has a sequence having at least 90% identity to that of SEQ ID NO: 55. In some embodiments, the nucleic acid sequence encoding the therapeutic gene has a sequence having at least 95% identity to that of SEQ ID NO: 55. In some embodiments, the nucleic acid sequence encoding the therapeutic gene has the sequence of SEQ ID NO: 55. In some embodiments, the nucleic acid sequence encoding the shRNA targeting the HPRT gene is operably linked to a Pol III promoter. In some embodiments, the Pol III promoter is 7sk, or a 7sk promoter having at least one mutation or deletion. In some embodiments, the nucleic acid sequence encoding the therapeutic gene is operably linked to a Pol II promoter. In some embodiments, the nucleic acid sequence encoding the therapeutic gene is operably linked to a beta globin promoter. In some embodiments, the vector further comprises an expression control sequence having a 5' long terminal repeat upstream of the nucleic acid encoding the shRNA targeting the HPRT gene, and a 3' long terminal repeat downstream of the nucleic acid encoding the gamma-globin gene.

In another aspect of the present disclosure is a vector comprising a first nucleic acid sequence having at least 90% identity to that of SEQ ID NO: 30, and a second nucleic acid sequence having at least 90% identity to that of SEQ ID NO: 55. In some embodiments, the vector is a lentiviral vector.

In another aspect of the present disclosure is a vector comprising a first nucleic acid sequence having at least 95% identity to that of SEQ ID NO: 30, and a second nucleic acid sequence having at least 95% identity to that of SEQ ID NO: 55. In some embodiments, the vector is a lentiviral vector.

In another aspect of the present disclosure is a vector comprising a first nucleic acid sequence having at least 96% identity to that of SEQ ID NO: 30, and a second nucleic acid sequence having at least 96% identity to that of SEQ ID NO: 55. In some embodiments, the vector is a lentiviral vector.

In another aspect of the present disclosure is a vector comprising a first nucleic acid sequence having at least 97% identity to that of SEQ ID NO: 30, and a second nucleic acid sequence having at least 97% identity to that of SEQ ID NO: 55. In some embodiments, the vector is a lentiviral vector.

In another aspect of the present disclosure is a vector comprising a first nucleic acid sequence having at least 98% identity to that of SEQ ID NO: 30, and a second nucleic acid sequence having at least 98% identity to that of SEQ ID NO: 55. In some embodiments, the vector is a lentiviral vector.

In another aspect of the present disclosure is a vector comprising a first nucleic acid sequence having at least 99% identity to that of SEQ ID NO: 30, and a second nucleic acid sequence having at least 99% identity to that of SEQ ID NO: 55. In some embodiments, the vector is a lentiviral vector.

In another aspect of the present disclosure is a vector comprising a first nucleic acid sequence having SEQ ID NO: 30, and a second nucleic acid sequence having SEQ ID NO: 55. In some embodiments, the vector is a lentiviral vector.

In another aspect of the present disclosure is a composition comprising a vector comprising (i) a nucleic acid sequence encoding a shRNA targeting a HPRT gene; and (ii) a nucleic acid sequence encoding a therapeutic gene. In some embodiments, the composition further comprises a pharmaceutically acceptable carrier. In some embodiments, the nucleic acid sequence encoding the shRNA targeting the HPRT gene has a sequence having at least 95% identity to that of SEQ ID NO: 30. In some embodiments, the nucleic acid sequence encoding the shRNA targeting the HPRT gene has a sequence of SEQ ID NO: 30. In some embodiments, the nucleic acid sequence encoding the therapeutic gene has a sequence having at least 95% identity to that of SEQ ID NO: 55. In some embodiments, the nucleic acid sequence encoding the therapeutic gene has a sequence of SEQ ID NO: 55. In some embodiments, the nucleic acid sequence encoding the shRNA targeting the HPRT gene is operably linked to a Pol III promoter. In some embodiments, the nucleic acid sequence encoding the therapeutic gene is operably linked to a beta globin promoter. In some embodiments, the composition is formulated as an emulsion. In some embodiments, the composition is formulated within micelles. In some embodiments, the composition is encapsulated within a polymer. In some embodiments, the compositions are encapsulated within liposomes. In some embodiments, the compositions are encapsulated within minicells or nanocapsules.

In another aspect of the present disclosure is a cell comprising a vector comprising (i) a nucleic acid sequence encoding a shRNA targeting a HPRT gene; and (ii) a nucleic acid sequence encoding a therapeutic gene. In some embodiments, the nucleic acid sequence encoding the shRNA targeting the HPRT gene has a sequence having at least 95% identity to that of SEQ ID NO: 30. In some embodiments, the nucleic acid sequence encoding the shRNA targeting the HPRT gene has a sequence of SEQ ID NO: 30. In some embodiments, the nucleic acid sequence encoding the therapeutic gene has a sequence having at least 95% identity to that of SEQ ID NO: 55. In some embodiments, the nucleic acid sequence encoding the therapeutic gene has a sequence of SEQ ID NO: 55. In some embodiments, the nucleic acid sequence encoding the shRNA targeting the HPRT gene is operably linked to a Pol III promoter. In some embodiments, the nucleic acid sequence encoding the therapeutic gene is operably linked to a beta globin promoter.

In another aspect of the present disclosure is a cell transduced by a vector comprising (i) a nucleic acid sequence encoding a shRNA targeting a HPRT gene; and (ii) a nucleic acid sequence encoding a therapeutic gene. In some embodiments, the nucleic acid sequence encoding the shRNA targeting the HPRT gene has a sequence having at least 95% identity to that of SEQ ID NO: 30. In some embodiments, the nucleic acid sequence encoding the shRNA targeting the HPRT gene has a sequence of SEQ ID NO: 30. In some embodiments, the nucleic acid sequence encoding the therapeutic gene has a sequence having at least 95% identity to that of SEQ ID NO: 55. In some embodiments, the nucleic acid sequence encoding the therapeutic gene has a sequence of SEQ ID NO: 55. In some embodiments, the nucleic acid sequence encoding the shRNA targeting the HPRT gene is operably linked to a Pol III promoter. In some embodiments, the nucleic acid sequence encoding the therapeutic gene is operably linked to a beta globin promoter. In some embodiments, the cell is an HSC.

In another aspect of the present disclosure is a polynucleotide having at least 90% sequence identity to that of SEQ ID NO: 5.

In another aspect of the present disclosure is a recombinant plasmid comprising between about 11200 nucleotides and about 12300 nucleotides, and wherein the plasmid comprises a first nucleic acid sequence having at least 95% identity to that of SEQ ID NO: 30, and a second nucleic acid sequence having at least 95% identity to that of SEQ ID NO: 55. In some embodiments, the plasmid comprises between about 11600 nucleotides and about 12200 nucleotides. In some embodiments, the plasmid comprises between about 11600 nucleotides and about 11700 nucleotides. In some embodiments, the plasmid comprises between about 12000 nucleotides and about 12100 nucleotides.

In another aspect of the present disclosure is a lentiviral vector comprising (a) a lentiviral backbone comprising essential lentiviral sequences for integration into a target cell genome; (b) a first nucleic acid sequence having at least 95% identity to that of SEQ ID NO: 30; (c) a second nucleic acid sequence having at least 95% identity to that of SEQ ID NO: 55; (d) a first expression control element that regulates expression of the first nucleic acid; and (e) a second expression control element that regulates expression of the second nucleic acid.

In another aspect of the present disclosure is a lentiviral expression vector comprising a first nucleic acid sequence having at least 95% identity to any of SEQ ID NOS: 23-31, and a second nucleic acid sequence having SEQ ID NO: 55.

In another aspect of the present disclosure is a modified sh734 shRNA having at least one of: (i) an incorporation of an hsa-miR-22 loop sequence; (ii) an addition of a 3'-5' spacer; (iii) a 5' start modification; and/or (iv) an addition of two nucleotides 5' and 3' to the stem and loop.

In another aspect of the present disclosure is a method of co-delivering into a cell both a therapeutic gene and an interfering RNA, the interfering RNA targeting HPRT. In some embodiments, the therapeutic gene therapeutic gene encodes a gene to treat immune deficiencies, hereditary diseases, blood diseases (e.g. hemophilia, hemoglobin disorders), lysosomal storage diseases, neurological diseases, angiogenic disorders, or cancer.

In another aspect of the present disclosure is a vector comprising a first expression control sequence operably linked to a first nucleic acid sequence, the first nucleic acid sequence encoding an RNAi to knockdown HPRT; and a second expression control sequence operably linked to a second nucleic acid sequence, the second nucleic acid sequence encoding a gamma-globin gene. In some embodiments, the RNAi is an shRNA. In some embodiments, the shRNA comprises a hairpin loop sequence of SEQ ID NO: 35. In some embodiments, shRNA has at least 95% sequence identity to that of SEQ ID NO: 30. In some embodiments, the shRNA has the sequence of SEQ ID NO: 30. In some embodiments, the shRNA has at least 95% sequence identity to a nucleic acid sequence selected from the group consist of SEQ ID NO: 27, SEQ ID NO: 28, and SEQ ID NO: 29. In some embodiments, the shRNA has at least 95% sequence identity to a nucleic acid sequence selected from the group consist of SEQ ID NO: 67 and SEQ ID NO: 68. In some embodiments, the shRNA has at least 95% sequence identity to a nucleic acid sequence selected from the group consist of SEQ ID NO: 26 and SEQ ID NO: 27. In some embodiments, the shRNA has at least 95% sequence identity to that of SEQ ID NO: 59. In some embodiments, the first expression control sequence is a Pol III promoter. In some embodiments, the Pol III promoter is 7sk. In some embodiments, the 7sk promoter has at least 95% sequence identity to that of SEQ ID NO: 32. In some embodiments, 7sk promoter has the sequence of SEQ ID NO: 32. In some embodiments, 7sk promoter has the sequence of SEQ ID NO: 33. In some embodiments, the second nucleic acid encoding the gamma-globin gene has at least 95% sequence identity to that of SEQ ID NO: 55. In some embodiments, the second nucleic acid encoding the gamma-globin gene has SEQ ID NO: 55. In some embodiments, the second expression control sequence is a pol II promoter. In some embodiments, the pol II promoter is a beta-globin promoter. In some embodiments, the beta-globin promoter has at least 95% identity to that of SEQ ID NO: 66. In some embodiments, the first nucleic acid encodes a nucleic acid molecule having SEQ ID NO: 1 or SEQ ID NO: 2. In some embodiments, the second nucleic acid encodes a nucleic acid molecule having SEQ ID NO: 3. In some embodiments, the second nucleic acid encodes the amino acid sequence of SEQ ID NO: 4. In some embodiments, the vector is a self-inactivating lentiviral vector. In some embodiments, the vector has at least 95% sequence identity to any one of SEQ ID NOS: 5 to 22. In some embodiments, the vector encodes for the amino acid sequence of SEQ ID NO: 4; and encodes a nucleic acid molecule having SEQ ID NO: 1 or SEQ ID NO: 2.

In another aspect of the present disclosure is an isolated host cell include the aforementioned vector.

1. A vector comprising a first expression control sequence operably linked to a first nucleic acid sequence, the first nucleic acid sequence encoding an RNAi to knockdown HPRT; and a second expression control sequence operably linked to a second nucleic acid sequence, the second nucleic acid sequence encoding a gamma-globin gene.

2. The vector of embodiment 1, wherein the RNAi is an shRNA.

3. The vector of embodiment 2, wherein the shRNA comprises a hairpin loop sequence of SEQ ID NO: 35.

4. The vector of embodiment 2, wherein the shRNA has at least 95% sequence identity to that of SEQ ID NO: 30.

5. The vector of embodiment 4, wherein the shRNA has the sequence of SEQ ID NO: 30.

6. The vector of embodiment 2, wherein the shRNA has at least 95% sequence identity to a nucleic acid sequence selected from the group consist of SEQ ID NO: 27, SEQ ID NO: 28, and SEQ ID NO: 29.

7. The vector of embodiment 2, wherein the shRNA has at least 95% sequence identity to a nucleic acid sequence selected from the group consist of SEQ ID NO: 67 and SEQ ID NO: 68.

8. The vector of embodiment 2, wherein the shRNA has at least 95% sequence identity to a nucleic acid sequence selected from the group consist of SEQ ID NO: 26 and SEQ ID NO: 27.

9. The vector of embodiment 2, wherein the shRNA has at least 95% sequence identity to that of SEQ ID NO: 59.

10. The vector of any of the preceding embodiments, wherein the first expression control sequence is a Pol III promoter.

11. The vector of embodiment 10, wherein the Pol III promoter is 7sk.

12. The vector of embodiment 11, wherein the 7sk promoter has at least 95% sequence identity to that of SEQ ID NO: 32.

13. The vector of embodiment 12, wherein the 7sk promoter has the sequence of SEQ ID NO: 32.

14. The vector of embodiment 11, wherein the 7sk promoter has the sequence of SEQ ID NO: 33.

15. The vector of any of the preceding embodiments, wherein the second nucleic acid encoding the gamma-globin gene has at least 95% sequence identity to that of SEQ ID NO: 55.

16. The vector of any of the preceding embodiments, wherein the second nucleic acid encoding the gamma-globin gene has SEQ ID NO: 55.

17. The vector of any of the preceding embodiments, wherein the second expression control sequence is a pol II promoter.

18. The vector of embodiment 17, wherein the pol II promoter is a beta-globin promoter.

19. The vector of embodiment 18, wherein the beta-globin promoter has at least 95% identity to that of SEQ ID NO: 66.

20. The vector of any of the preceding embodiments, wherein the first nucleic acid encodes a nucleic acid molecule having SEQ ID NO: 1 or SEQ ID NO: 2.

21. The vector of any of the preceding embodiments, wherein the second nucleic acid encodes a nucleic acid molecule having SEQ ID NO: 3.

22. The vector of any of the preceding embodiments, wherein the second nucleic acid encodes a polypeptide having at least 95% identity to that of SEQ ID NO: 4.

23. The vector of any of the preceding embodiments, wherein the vector is a self-inactivating lentiviral vector.

24. The vector of any of the preceding embodiments, further comprising a cSH4 insulator.

25. The vector of embodiment 1, having at least 95% sequence identity to any one of SEQ ID NOS: 5 to 22.

26. The vector embodiment 1, wherein the second nucleic acid sequence encodes a polypeptide having at least 98% identity to that of SEQ ID NO: 4; and the first nucleic acid sequence encodes a nucleic acid molecule having at least 98% identity to of SEQ ID NO: 1 or its complement thereof.

27. A pharmaceutical composition comprising the vector of any one of embodiments 1 to 26 and a pharmaceutically acceptable carrier.

28. An isolated cell comprising the vector of any one of embodiments 1 to 26.

29. A host cell transduced with the vector according to any one of embodiments 1 to 26, wherein the host cell is substantially HPRT deficient.

30. The host cell of embodiment 29, wherein the host cell expresses the gamma-globin gene.

31. The host cell of embodiment 29, wherein the host cell is formulated with a pharmaceutically acceptable carrier.

32. The host cell of any of embodiments 29 to 31 for use in the treatment of sickle cell disease or to reduce the symptoms of sickle cell disease.

33. A method of selecting transduced cells comprising: transducing a population of cells with the vector according to any one of embodiments 1 to 26; and enriching the population of transduced cells by selecting for transduced cells with a purine analog.

34. The method of embodiment 33, wherein the purine analog is selected from the group consisting of 6TG and 6-mercaptopurin.

35. The method of 33, wherein the transduced cells are HSCs.

36. The method of 33, wherein the HSCs are allogenic HSCs.

37. The method of 33, wherein the HSCs are autologous HSCs.

38. The method of 33, wherein the HSCs are sibling matched HSCs.

39. A host cell prepared by transducing a hematopoietic stem cell with a lentiviral expression vector, the lentiviral expression vector comprising a first nucleic acid sequence encoding an anti-HPRT shRNA, and a second nucleic acid sequence encoding a gamma-globin gene.

40. The host cell of embodiment 39, wherein the lentiviral expression vector has a sequence having at least 95% identity to any of SEQ ID NOS: 5 to 22.

41. A pharmaceutical composition comprising the host cell of any of embodiments 39 and 40 and a pharmaceutically acceptable carrier.

42. A host cell comprising: (i) a nucleic acid molecule having either SEQ ID NO: 1 or SEQ ID NO: 2; and (ii) a nucleic acid molecule having SEQ ID NO: 3.

43. A method of treating sickle cell disease comprising administering the host cells of any one of embodiments 29, 30, 39, and 40 to a patient in need of treatment thereof.

44. A method of reducing the symptoms of sickle cell disease comprising administering the host cells of any one of embodiments 29, 30, 39, and 40 to a patient in need of treatment thereof.

45. A method of reducing the symptoms of severe sickle cell disease comprising administering the host cells of any one of embodiments 29, 30, 39, and 40 to a patient in need of treatment thereof.

46. A method of treating a hemoglobinopathy comprising administering the host cells of any one of embodiments 29, 30, 39, and 40 to a patient in need of treatment thereof.

47. A method of treating beta-thalassemia comprising administering the host cells of any one of embodiments 29, 30, 39, and 40 to a patient in need of treatment thereof.

48. A method of treating sickle cell disease or reducing at least one symptom of sickle cell disease in a human patient comprising: (a) transducing hematopoietic cells with a lentiviral expression vector, wherein the lentiviral expression vector comprises a first nucleic acid sequence encoding an anti-HPRT shRNA, and a second nucleic acid sequence encoding a gamma-globin gene; and (b) introducing the transduced hematopoietic cells to the human patient.

49. The method of embodiment 48, further comprising conditioning the patient prior to introducing the transduced hematopoietic cells, wherein the conditioning comprises administering chemotherapy, radiation therapy, or treatment with one or more antibody-drug conjugates.

50. The method of embodiment 48, wherein the treatment further comprises administering one or more doses of hydroxyurea following transplantation.

51. A method of increasing fetal hemoglobin levels comprising administering the host cells of any one of embodiments 29, 30, 39, and 40 to a patient in need of treatment thereof.

52. A host cell which is HPRT deficient and which expresses a polypeptide having SEQ ID NO: 4, wherein the host cell is prepared by transducing an HSC with the vector of any one of embodiments 1 to 26.

53. A host cell comprising: (i) at least one of a nucleic acid molecule having SEQ ID NO: 3 or a polypeptide having SEQ ID NO: 4; and (ii) at least one of a nucleic acid molecule having SEQ ID NO: 1 or a nucleic acid molecule having SEQ ID NO: 2.

54. The host cell of embodiment 53, wherein the host cell is prepared by contacting an HSC with the vector of any of one embodiments 1 to 26.

All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

Although the present disclosure has been described with reference to a number of illustrative embodiments, it should be understood that numerous other modifications and embodiments can be devised by those skilled in the art that will fall within the spirit and scope of the principles of this disclosure. More particularly, reasonable variations and modifications are possible in the component parts and/or arrangements of the subject combination arrangement within the scope of the foregoing disclosure, the drawings, and the appended claims without departing from the spirit of the disclosure. In addition to variations and modifications in the component parts and/or arrangements, alternative uses will also be apparent to those skilled in the art.

The invention claimed is:

1. A vector comprising a first expression control sequence operably linked to a first nucleic acid sequence, the first nucleic acid sequence encoding a shRNA targeting hypoxanthine guanine phosphoribosyltransferase (HPRT); and a second expression control sequence operably linked to a second nucleic acid sequence, the second nucleic acid sequence encoding a gamma-globin gene, wherein the second nucleic acid encoding the gamma-globin gene has the sequence of SEQ ID NO: 55.

2. The vector of claim 1, wherein the shRNA comprises a hairpin loop sequence of SEQ ID NO: 35.

3. The vector of claim 1, wherein the shRNA has the sequence of SEQ ID NO: 30.

4. The vector of claim 1, wherein the shRNA has at least 95% sequence identity to a nucleic acid sequence selected from the group consisting of SEQ ID NO: 27, SEQ ID NO: 28, and SEQ ID NO: 29.

5. The vector of claim 1, wherein the shRNA has at least 95% sequence identity to a nucleic acid sequence selected from the group consisting of SEQ ID NO: 67 and SEQ ID NO: 68.

6. The vector of claim 1, wherein the shRNA has at least 95% sequence identity to a nucleic acid sequence selected from the group consisting of SEQ ID NO: 26 and SEQ ID NO: 27.

7. The vector of claim 1, wherein the shRNA has at least 95% sequence identity to that of SEQ ID NO: 59.

8. The vector of claim 1, wherein the first expression control sequence is a Pol III promoter.

9. The vector of claim 8, wherein the Pol III promoter is 7sk.

10. The vector of claim 9, wherein the 7sk promoter has at least 95% sequence identity to that of SEQ ID NO: 32.

11. The vector of claim 9, wherein the 7sk promoter has the sequence of SEQ ID NO: 32.

12. The vector of claim 9, wherein the 7sk promoter has the sequence of SEQ ID NO: 33.

13. The vector of claim 1, wherein the second expression control sequence is a pol II promoter.

14. The vector of claim 13, wherein the pol II promoter is a beta-globin promoter.

15. The vector of claim 14, wherein the beta-globin promoter has at least 95% identity to that of SEQ ID NO: 66.

16. The vector claim 1, wherein the second nucleic acid sequence encodes a peptide having at least 95% identity to that of SEQ ID NO: 4; and the first nucleic acid sequence encodes a nucleic acid molecule having at least 95% identity to SEQ ID NO: 1 or its complement thereof.

17. The vector of claim 1, wherein the vector comprises any one of SEQ ID NOS: 5 to 22.

18. A host cell which is hypoxanthine guanine phosphoribosyitransferase (HPRT) deficient and which expresses a peptide having SEQ ID NO: 4, wherein the host cell is prepared by transducing an hematopoietic stem cell (HSC) with a vector comprising a first expression control sequence operably linked to a first nucleic acid sequence, the first nucleic acid sequence encoding a shRNA targeting HPRT; and a second expression control sequence operably linked to a second nucleic acid sequence, the second nucleic acid sequence encoding a gamma-globin gene.

19. The vector of claim 1, wherein the shRNA comprises at least 90% sequence identity to SEQ ID NO: 30.

20. The vector of claim 1, wherein the shRNA comprises at least 95% sequence identity to that of SEQ ID NO: 30.

21. The vector of claim 1, wherein the second nucleic acid encoding the gamma-globin gene comprises at least 90% identity to that of SEQ ID NO: 55.

22. The vector of claim 1, wherein the second nucleic acid encoding the gamma-globin gene comprises at least 97% identity to that of SEQ ID NO: 55.

23. A host cell which is hypoxanthine guanine phosphoribosyitransferase (HPRT) deficient and which expresses a peptide comprising at least 90% sequence identity to that of SEQ ID NO: 4, wherein the host cell is prepared by transducing an hematopoietic stem cell (HSC) with a vector comprising a first expression control sequence operably linked to a first nucleic acid sequence, the first nucleic acid sequence encoding a shRNA targeting HPRT; and a second expression control sequence operably linked to a second nucleic acid sequence, the second nucleic acid sequence encoding a gamma-globin gene.

24. The host cell of claim 23, wherein the expressed peptide comprises at least 95% sequence identity to that of SEQ ID NO: 4.

25. The host cell of claim 23, wherein the first nucleic acid encoding the shRNA targeting HPRT comprises at least 95% sequence identity to that of SEQ ID NO: 30.

26. A vector comprising a first expression control sequence operably linked to a first nucleic acid sequence, the first nucleic acid sequence encoding a shRNA targeting hypoxanthine guanine phosphoribosyltransferase (HPRT); and a second expression control sequence operably linked to a second nucleic acid sequence, the second nucleic acid sequence encoding a gamma-globin gene, wherein the second nucleic acid encoding the gamma-globin gene has at least 95% sequence identity to SEQ ID NO: 55.

27. The vector of claim 26, wherein the vector comprises SEQ ID NO: 10.

* * * * *